United States Patent
Theunissen et al.

(10) Patent No.: US 12,215,167 B2
(45) Date of Patent: Feb. 4, 2025

(54) ANTI-TISSUE FACTOR ANTIBODIES, ANTIBODY-DRUG CONJUGATES, AND RELATED METHODS

(71) Applicant: Iconic Therapeutics LLC, Palo Alto, CA (US)

(72) Inventors: Jan-Willem Theunissen, South San Francisco, CA (US); Andrew D. Avery, South San Francisco, CA (US); Allen G. Cai, South San Francisco, CA (US); Anthony Byron Cooper, South San Francisco, CA (US); Thi-Sau Migone, South San Francisco, CA (US)

(73) Assignee: ICONIC THERAPEUTICS LLC, Palo Alto, CA (US)

( * ) Notice: Subject to any disclaimer, the term of this patent is extended or adjusted under 35 U.S.C. 154(b) by 101 days.

(21) Appl. No.: 17/877,853

(22) Filed: Jul. 29, 2022

(65) Prior Publication Data
US 2023/0159657 A1   May 25, 2023

Related U.S. Application Data

(60) Division of application No. 17/458,507, filed on Aug. 26, 2021, now Pat. No. 11,447,566, which is a continuation of application No. 16/959,652, filed as application No. PCT/US2019/012427 on Jan. 4, 2019, now abandoned.

(60) Provisional application No. 62/713,797, filed on Aug. 2, 2018, provisional application No. 62/713,804, filed on Aug. 2, 2018, provisional application No. 62/646,788, filed on Mar. 22, 2018, provisional application No. 62/613,545, filed on Jan. 4, 2018, provisional application No. 62/613,564, filed on Jan. 4, 2018.

(51) Int. Cl.
| | |
|---|---|
| C07K 16/36 | (2006.01) |
| A61K 31/713 | (2006.01) |
| A61K 47/68 | (2017.01) |
| A61P 27/02 | (2006.01) |
| C12N 5/10 | (2006.01) |
| C12N 15/63 | (2006.01) |

(52) U.S. Cl.
CPC .......... *C07K 16/36* (2013.01); *A61K 31/713* (2013.01); *A61K 47/68031* (2023.08); *A61K 47/6843* (2017.08); *A61K 47/6849* (2017.08); *A61P 27/02* (2018.01); *C12N 5/10* (2013.01); *C12N 15/63* (2013.01); *C07K 2317/21* (2013.01); *C07K 2317/24* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,235,871 A | 11/1980 | Papahadjopoulos et al. |
| 4,501,728 A | 2/1985 | Geho et al. |
| 4,656,127 A | 4/1987 | Mundy |
| 4,676,980 A | 6/1987 | Segal et al. |
| 4,722,848 A | 2/1988 | Paoletti et al. |
| 4,816,567 A | 3/1989 | Cabilly et al. |
| 4,837,028 A | 6/1989 | Allen |
| 4,946,778 A | 8/1990 | Ladner et al. |
| 5,019,369 A | 5/1991 | Presant et al. |
| 5,132,405 A | 7/1992 | Huston et al. |
| 5,204,253 A | 4/1993 | Sanford et al. |
| 5,208,020 A | 5/1993 | Chari et al. |
| 5,217,879 A | 6/1993 | Huang et al. |
| 5,229,275 A | 7/1993 | Goroff |
| 5,279,833 A | 1/1994 | Rose |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,580,859 A | 12/1996 | Felgner et al. |
| 5,589,369 A | 12/1996 | Seidman et al. |
| 5,589,466 A | 12/1996 | Felgner et al. |
| 5,591,669 A | 1/1997 | Krimpenfort et al. |
| 5,622,931 A | 4/1997 | Edgington et al. |
| 5,662,907 A | 9/1997 | Kubo et al. |
| 5,814,482 A | 9/1998 | Dubensky, Jr. et al. |
| 5,843,723 A | 12/1998 | Dubensky, Jr. et al. |
| 5,849,561 A | 12/1998 | Falck-Pedersen |

(Continued)

FOREIGN PATENT DOCUMENTS

| | | |
|---|---|---|
| CA | 2705787 A1 | 6/2009 |
| CN | 103119065 A | 5/2013 |

(Continued)

OTHER PUBLICATIONS

Aalberse et al., IgG4 breaking the rules, Immunology, 2002, 105:9-19.

(Continued)

*Primary Examiner* — Michael Szperka
(74) *Attorney, Agent, or Firm* — JONES DAY

(57) ABSTRACT

Provided herein are antibodies that specifically bind to human tissue factor (TF), anti-TF antibody-drug conjugates (ADCs), and compositions comprising the antibodies or ADCs. Also provided herein are methods of making and using the antibodies or ADCs, such as therapeutic and diagnostic methods.

11 Claims, 47 Drawing Sheets
Specification includes a Sequence Listing.

(56) References Cited

U.S. PATENT DOCUMENTS

| | | |
|---|---|---|
| 5,849,589 A | 12/1998 | Tedder et al. |
| 6,015,686 A | 1/2000 | Dubensky, Jr. et al. |
| 6,037,135 A | 3/2000 | Kubo et al. |
| 6,083,716 A | 7/2000 | Nilson et al. |
| 6,090,406 A | 7/2000 | Popescu et al. |
| 6,194,551 B1 | 2/2001 | Idusogie et al. |
| 6,296,854 B1 | 10/2001 | Pushko et al. |
| 6,312,946 B1 | 11/2001 | Yeh et al. |
| 6,365,394 B1 | 4/2002 | Gao et al. |
| 6,413,935 B1 | 7/2002 | Sette et al. |
| 6,610,321 B2 | 8/2003 | Huang et al. |
| 6,737,056 B1 | 5/2004 | Presta |
| 6,783,939 B2 | 8/2004 | Olmsted et al. |
| 7,202,351 B1 | 4/2007 | Sette et al. |
| 7,285,265 B2 | 10/2007 | Vogels et al. |
| 7,291,498 B2 | 11/2007 | Roy et al. |
| 7,332,581 B2 | 2/2008 | Presta |
| 7,344,872 B2 | 3/2008 | Gao et al. |
| 7,425,328 B2 * | 9/2008 | Wang ............... A61P 35/00 424/183.1 |
| 7,435,413 B2 * | 10/2008 | Kirchhofer ........... C07K 16/36 424/139.1 |
| 7,468,181 B2 | 12/2008 | Vogels et al. |
| 7,494,647 B2 * | 2/2009 | Sato .................. A61P 9/00 435/7.1 |
| 7,531,180 B2 | 5/2009 | Polo et al. |
| 7,541,038 B2 | 6/2009 | Kovacs et al. |
| 7,557,200 B2 | 7/2009 | Wu et al. |
| 7,572,453 B2 | 8/2009 | Polo et al. |
| 7,572,628 B2 | 8/2009 | Dubensky, Jr. et al. |
| 7,605,235 B2 | 10/2009 | Anderson et al. |
| 7,732,129 B1 | 6/2010 | Zhang et al. |
| 7,744,900 B2 | 6/2010 | Dubensky, Jr. et al. |
| 7,771,979 B2 | 8/2010 | Polo et al. |
| 7,820,440 B2 | 10/2010 | Vogels et al. |
| 7,838,277 B2 | 11/2010 | Gao et al. |
| 8,052,967 B2 | 11/2011 | Vogels et al. |
| 8,093,021 B2 | 1/2012 | Hurtado et al. |
| 8,119,336 B2 | 2/2012 | Sampath et al. |
| 8,158,418 B2 | 4/2012 | Polo et al. |
| 8,216,834 B2 | 7/2012 | Colloca et al. |
| 8,252,574 B2 | 8/2012 | Mason et al. |
| 8,258,082 B2 | 9/2012 | Ladner |
| 8,647,864 B2 | 2/2014 | Polo et al. |
| 8,673,319 B2 | 3/2014 | Colloca et al. |
| 8,691,563 B2 | 4/2014 | Pushko et al. |
| 8,691,730 B2 | 4/2014 | Vasquez et al. |
| 8,722,044 B2 | 5/2014 | Almagro et al. |
| 8,951,525 B2 | 2/2015 | Almagro et al. |
| 8,999,333 B2 | 4/2015 | Almagro et al. |
| 9,017,696 B2 | 4/2015 | Draper et al. |
| 9,024,001 B2 | 5/2015 | Tang et al. |
| 9,101,572 B2 | 8/2015 | Pushko et al. |
| 9,150,641 B2 | 10/2015 | Kellenberger et al. |
| 9,150,658 B2 | 10/2015 | Verploegen et al. |
| 9,168,314 B2 * | 10/2015 | Satijn ............... A61P 35/02 |
| 9,192,661 B2 | 11/2015 | Jain et al. |
| 9,217,159 B2 | 12/2015 | Roy et al. |
| 9,234,181 B2 | 1/2016 | Tang et al. |
| 9,249,191 B2 | 2/2016 | Ueno et al. |
| 9,254,265 B2 | 2/2016 | Geall et al. |
| 9,255,126 B2 | 2/2016 | Polo et al. |
| 9,273,288 B2 | 3/2016 | Mason et al. |
| 9,295,646 B2 | 3/2016 | Brito et al. |
| 9,353,353 B2 | 5/2016 | Nabel et al. |
| 9,453,240 B2 | 9/2016 | Chamberlain et al. |
| 9,486,519 B2 | 11/2016 | Sahin et al. |
| 9,487,563 B2 | 11/2016 | Nabel et al. |
| 9,492,565 B2 | 11/2016 | Satijn et al. |
| 9,512,190 B2 | 12/2016 | Ueno et al. |
| 9,636,410 B2 | 5/2017 | Brito et al. |
| 9,714,297 B2 | 7/2017 | Verploegen et al. |
| 9,714,435 B2 | 7/2017 | Dicks et al. |
| 9,790,308 B2 | 10/2017 | Han et al. |
| 9,801,897 B2 | 10/2017 | Geall et al. |
| 10,092,636 B2 | 10/2018 | Binder |
| 10,240,128 B2 | 3/2019 | Thirion et al. |
| 10,426,824 B1 | 10/2019 | Hacohen et al. |
| 10,532,067 B2 | 1/2020 | Geall et al. |
| 10,646,587 B2 | 5/2020 | Dicks et al. |
| 11,447,566 B2 | 9/2022 | Theunissen et al. |
| 2002/0137081 A1 | 9/2002 | Bandman |
| 2003/0072767 A1 | 4/2003 | Gaiger et al. |
| 2003/0157108 A1 | 8/2003 | Presta |
| 2004/0115625 A1 | 6/2004 | Ebner |
| 2005/0123555 A1 | 6/2005 | Olmsted et al. |
| 2005/0196754 A1 | 9/2005 | Drmanac et al. |
| 2006/0104944 A1 | 5/2006 | Mousa |
| 2006/0198854 A1 | 9/2006 | Pushko |
| 2007/0031442 A1 | 2/2007 | Sewell |
| 2007/0055049 A1 | 3/2007 | Grey et al. |
| 2007/0224201 A1 | 9/2007 | Wu et al. |
| 2008/0050393 A1 | 2/2008 | Tang et al. |
| 2009/0081200 A1 | 3/2009 | Wang |
| 2009/0093050 A1 | 4/2009 | Wu et al. |
| 2009/0118181 A1 | 5/2009 | Walker et al. |
| 2009/0253184 A1 | 10/2009 | Clarke et al. |
| 2010/0041737 A1 | 2/2010 | Naldini et al. |
| 2010/0120897 A1 | 5/2010 | Hurtado et al. |
| 2010/0286070 A1 | 11/2010 | Verheyden et al. |
| 2011/0300156 A1 | 12/2011 | Verploegen et al. |
| 2012/0237528 A1 | 9/2012 | Almagro et al. |
| 2013/0011426 A1 | 1/2013 | Tureci et al. |
| 2013/0052672 A1 | 2/2013 | Varadi et al. |
| 2013/0123199 A1 | 5/2013 | Lee |
| 2013/0149375 A1 | 6/2013 | Geall |
| 2013/0171241 A1 | 7/2013 | Geall |
| 2013/0177639 A1 | 7/2013 | Geall et al. |
| 2013/0177640 A1 | 7/2013 | Geall et al. |
| 2013/0189351 A1 | 7/2013 | Geall |
| 2013/0195968 A1 | 8/2013 | Geall et al. |
| 2013/0195969 A1 | 8/2013 | Geall et al. |
| 2013/0202684 A1 | 8/2013 | Geall et al. |
| 2014/0141070 A1 | 5/2014 | Geall et al. |
| 2014/0178438 A1 | 6/2014 | Sahin et al. |
| 2014/0227346 A1 | 8/2014 | Geall et al. |
| 2014/0234304 A1 | 8/2014 | Almagro et al. |
| 2014/0242152 A1 | 8/2014 | Geall et al. |
| 2014/0248314 A1 | 9/2014 | Swanson et al. |
| 2014/0255472 A1 | 9/2014 | Geall et al. |
| 2014/0271829 A1 | 9/2014 | Lilja et al. |
| 2015/0110831 A1 | 4/2015 | Silbert et al. |
| 2015/0125465 A1 | 5/2015 | Binder et al. |
| 2015/0125477 A1 | 5/2015 | Kuttruff-Coqui et al. |
| 2015/0140068 A1 | 5/2015 | Barnett et al. |
| 2015/0307897 A1 | 10/2015 | Soden et al. |
| 2016/0074506 A1 | 3/2016 | Jain et al. |
| 2016/0199513 A1 | 7/2016 | Bancel et al. |
| 2016/0279258 A1 | 9/2016 | Valbjorn et al. |
| 2016/0289674 A1 | 10/2016 | Bancel et al. |
| 2016/0333113 A1 * | 11/2016 | Matsumura ............ A61P 43/00 |
| 2017/0136130 A1 | 5/2017 | Satijn et al. |
| 2017/0210808 A1 | 7/2017 | Rosenthal et al. |
| 2018/0044431 A1 | 2/2018 | Verploegen et al. |
| 2019/0085080 A1 | 3/2019 | Kaplan et al. |
| 2022/0257789 A1 | 8/2022 | Theunissen et al. |

FOREIGN PATENT DOCUMENTS

| | | |
|---|---|---|
| CN | 103443127 A | 12/2013 |
| CN | 112203695 A | 1/2021 |
| CN | 116322787 A | 6/2023 |
| EP | 0453082 A1 | 10/1991 |
| EP | 1069185 A1 | 1/2001 |
| EP | 2044947 A1 | 4/2009 |
| EP | 2590670 A2 | 5/2013 |
| EP | 2590676 A2 | 5/2013 |
| EP | 3115061 A1 | 1/2017 |
| FR | 2650840 A1 | 2/1991 |
| JP | 2007534295 A | 11/2007 |
| JP | 2009514895 A | 4/2009 |
| JP | 2011504724 A | 2/2011 |
| JP | 2014509856 A | 4/2014 |
| JP | 2014209917 A | 11/2014 |

(56) References Cited

FOREIGN PATENT DOCUMENTS

| | | |
|---|---|---|
| JP | 2017533886 A | 11/2017 |
| JP | 2021501776 A | 1/2021 |
| KR | 1020140019375 A | 2/2014 |
| WO | WO 1991002087 A1 | 2/1991 |
| WO | WO 1991006309 A1 | 5/1991 |
| WO | WO 1992015712 A1 | 9/1992 |
| WO | WO 1993024640 A2 | 12/1993 |
| WO | WO-9405328 A1 * | 3/1994 ......... C07K 14/745 |
| WO | WO 1994005328 A1 | 3/1994 |
| WO | WO 1995013392 A1 | 5/1995 |
| WO | WO 1996013597 A2 | 5/1996 |
| WO | WO 1996018372 A2 | 6/1996 |
| WO | WO 1999051642 A1 | 10/1999 |
| WO | WO 2001070984 A2 | 9/2001 |
| WO | WO 2001073027 A2 | 10/2001 |
| WO | WO 2003085107 A1 | 10/2003 |
| WO | WO 2004023973 A2 | 3/2004 |
| WO | WO 2004056312 A2 | 7/2004 |
| WO | WO 2005016961 A1 | 2/2005 |
| WO | WO 2007024708 A2 | 3/2007 |
| WO | WO 2007047749 A1 | 4/2007 |
| WO | WO 2007056352 A2 | 5/2007 |
| WO | WO 2008122811 A2 | 10/2008 |
| WO | WO 2008145685 A1 | 12/2008 |
| WO | WO 2009036379 A2 | 3/2009 |
| WO | WO 2009079185 A2 | 6/2009 |
| WO | WO 2009089004 A1 | 7/2009 |
| WO | WO 2010105256 A1 | 9/2010 |
| WO | WO 2011128704 A1 | 10/2011 |
| WO | WO 2011157741 A2 | 12/2011 |
| WO | WO 2012006359 A1 | 1/2012 |
| WO | WO 2012006377 A2 | 1/2012 |
| WO | WO 2012009568 A2 | 1/2012 |
| WO | WO 2012125559 A1 | 9/2012 |
| WO | WO 2012172058 A1 | 12/2012 |
| WO | WO 2012172277 A1 | 12/2012 |
| WO | WO 2013006837 A1 | 1/2013 |
| WO | WO 2014179363 A1 | 11/2014 |
| WO | WO 2016041082 A1 | 3/2016 |
| WO | WO 2016124670 A1 | 8/2016 |
| WO | WO 2017042352 A1 | 3/2017 |
| WO | WO 2017106638 A1 | 6/2017 |
| WO | WO 2018195357 A1 | 10/2018 |
| WO | WO 2019089973 A1 | 5/2019 |
| WO | WO 2019102435 A1 | 5/2019 |
| WO | WO 2019183253 A1 | 9/2019 |
| WO | WO 2021003399 A1 | 1/2021 |
| WO | WO 2022002940 A1 | 1/2022 |

OTHER PUBLICATIONS

Aarnoudse, et al., TCR Reconstitution in Jurkat Reporter cells facilitates the identification of novel tumor antigens Dy CDNA expression cloning, Int. J. Cancer, 99, pp. 7-13, (2002).

Abdulkadir et al. "Tissue factor expression and angiogenesis in human prostate carcinoma," Human Pathology, 2000, 31(4):443-447.

Abelin et al., Complementary IMAC enrichment methods for HLA-associated phosphopeptide identification by mass spectrometry. Nat Protec. Sep. 2015; 10(9):1308-1318. doi: 10.1038/nprol.2015.086. Epub Aug. 6, 2015.

Alexander et al., Development of high potency universal DR-restricted helper epitopes by modification of high affinity DR-blocking peptides, Immunity, vol. 1, Issue 9, pp. 751-761, Dec. 1994.

Anders et al., HTSeq—a Python framework to work with high-throughput sequencing data. Bioinforma. Oxf. Engl. 31, 166-169 (2015), hllps://doi.org/10.1093/bioinformatics/btu638.

Andreatta et al., Accurate pan-specific prediction of peptide-MHC class II binding affinity with improved binding core identification. Immunogenetics 67(11-12) 641-650, Nov. 2015.

Andreatta et al., Gapped sequence alignment using artificial neural networks: application to the MHC class I system. Bioinforma. Oxf. Engl. (2015). doi:10.1093/bioinformatics/blv639.

Arbabi Ghahroudi, Selection and identification of single domain antibody fragments from camel heavy-chain antibodies, FEBS Letters 414 (1997) 521-526.

Armour et al., Differential binding to human FcgRIIa and FcgRIIb receptors by human lgG wildtype and mutant antibodies, Molecular Immunology, vol. 40, Issue 9, Dec. 2003, pp. 585-593, <hllps://doi.org/10.1016/j.molimm.2003.08.004>.

Banu et al., "Building and Optimizing a Virus-specific T Cell Receptor Library for Targeted Immunotherapy in Viral Infections." Scientific Reports 4:4166, 2014.

Barbas et al., In vitro evolution of a neutralizing human antibody to human immunodeficiency virus type 1 to enhance affinity and broaden strain cross-reactivity, Proc. Nat. Acad. Sci. U.S.A., 1994, 91:3809-3813.

Barnstable et al., Production of monoclonal antibodies to group A ery 1 hrocytes, HLA and other human cell surface antigens—new tools for genetic analysis. Cell. May 1978; 14(1):9-20.

Bassani-Sternberg et al., Mass spectrometry of human leukocyte antigen class I peptidomes reveals strong effects of protein abundance and turnover on antigen presentation. Mol Cell Proteomics. Mar. 2015; 14(3):658-673. doi:10.1074/mcp.M114.042812.

Behrens et al., Antibody-Drug Conjugates (ADCs) Derived from Interchain Cysteine Cross-Linking Demonstrates improved Homogeneity and other Pharmacological Properties over Conventional Heterogeneous ADCs, Mol Pharmaceutics, 2015, 12, 11, 3986-3998 <https://doi.org/10.1021/acs.molpharmaceul.5b00432>.

Beloncle et al., "Recruilability and effect of PEEP in SARS-Cov-2-associated acute respiratory distress syndrome", Ann. Intensive Care (2020) 10:55.

Binz et al., Engineering novel binding proteins from nonimmunoglobulin domains, Nat. Biotechnol., 2005 23:1257-1268.

Bodini et al. The hidden genomic landscape of acute myeloid leukemia: subclonal structure revealed by undetected mutations. Blood 125, 600-605 (2015).

Boegel et al. HLA typing from RNA-Seq sequence reads, Genome Med. 4, 102 (2012).

Boisvert et al. A Quantitative Spatial Proteomics Analysis of Proteome Turnover in Human Cells. Mol. Cell. Proteomics 11, M111. 011429-1 (2012).

Boshart, et al., A very strong enhancer is localed upstream of an immediate early gene of human cytomegalovirus, Cell, 41:521-530 (1985), https://doi.org/10.1016/S0092-8674(85)80025-8.

Breij et al. "An antibody-drug conjugate that targets tissue factor exhibits potent therapeutic activity against a broad range of solid tumors," Cancer Research, 2014, 74(4):1214-1226.

Brennan et al., Preparation of bispecific antibodies by chemical recombination of monoclonal immunoglobulin G1 ragmenls, Science, 1985, vol. 229, Issue 4708, pp. 81-83, DOI: 10.1126/science. 3925553.

Bromberg et al., Tissue factor promotes melanoma metastasis by a pathway independent of blood coagulation, Proc. Natl. Acad. Sci. US A., vol. 92, pp. 8205-8209, Aug. 1995.

Brown et al., "Tolerance of single, but not multiple, amino acid replacements in antibody VH CDR 2: a means of minimizing B cell wastage from somatic hypermutation?", J. Immuno. May 1996, 3285-91. (Year: 1996).

Bruggemann et al., Designer mice: the production of human antibody repertoires in transgenic animals, Year in Immuno., 1993, 7:33.

Calis et al. Properties of MHC Class I Presented Peptides That Enhance Immunogenicity. PLoS Comput. Biol. 9, e1003266 (2013).

Cancer Genome Atlas Research Network. Comprehensive molecular profiling of lung adenocarcinoma. Nature 511, 543-550 (2014).

Carithers et al. A Novel Approach to High-Quality Postmortem Tissue Procurement: The GTEx Project. Biopreservation Biobanking 13, 311-319 (2015).

Carlring et al., A Novel Redox Method for rapid Production of Functional Bi-Specific Antibodies for Use in Early Pilot Studies, PloS ONE 6(7): e22533, doi:10.1371/journal.pone.0022533.

(56) References Cited

OTHER PUBLICATIONS

Carneiro-Lobo et al. "Ixolaris, a tissue factor inhibitor, blocks primary tumor growth and angiogenesis in a glioblastoma model," J Thromb Haemost, 2009, 7(11):1855-1864.

Carneiro-Lobo et al., Ixolaris, a tissue factor inhibitor, blocks primary tumor growth and angiogenesis in a glioblastoma model, Journal of Thrombosis and Haemostasis, 2009, 7:1855-1864.

Carreno et al. Cancer immunotherapy. A dendritic cell vaccine increases the breadth and diversity of melanoma heoantigen-specific T cells. Science 348, 803-808 (2015).

Carter et al., Absolute quantification of somatic DNA alterations in human cancer. Nat. Biotechnol. 30, pp. 413-421 (2012).

Chahal, et al., Dendrimer-RNA nanoparticles generate protective immunity against lethal Ebola, H1N1 influenza, and Toxoplasma gondii challenges with a single dose, PNAS, 2016 E4133-4142, www.pnas.org/cgi/doi/10.1073/pnas.1600299113.

Chari et al., Immunoconjugates Containing Novel Maytansinoids: Promising Anticancer Drugs, Cancer Research 52, 127-131, Jan. 1, 1992.

Chen et al. "Immunolocalisation of tissue factor in esophageal cancer is correlated with intratumoral angiogenesis and prognosis of the patient," Acta Histochemica, 2010, 112(3):233-239.

Chen et al., Tissue factor expression in rheumatoid synovium a potential role in pannus invasion of rheumatoid arthritis, Acta Hislochemica, 115 (2013), 692-697.

Chen et al., Tissue factor expression in rheumatoid synovium a potential role in pannus invasion of rheumatoid arthritis, Acta Histochem., 2010, 3:233-239, <https://doi.org/10.1016/j.acthis.2013.02.005>.

Chowdhury, Methods Mol. Biol., 2008, 207:179-196.

Christensen et al., Urokinase-type plasminogen activator receptor (mPAR), tissue factor (TF) and epidermal growlh factor receptor (EGFR) tumor expression patterns and prognostic value in oral cancer, BMC Cancer, 2017, 17:572, DOI 10.1186/s12885-017-3563-3.

Cibulskis et al. Sensitive detection of somatic point mutations in impure and heterogeneous cancer samples. Nat. Biotechnol. 31, 213-219 (2013).

Cieslik et al. The use of exome capture RNA-seq for highly degraded RNA with application to clinical cancer sequencing. Genome Res. 25, 1372-1381 (2015).

Cocco et al., Expression of Tissue factor in Adenocarcinoma and Squamous Cell Carcinoma of the Uterine Cervix: Implications for immunotherapy with hI-con1, a factor Vll-lgGFc chimeric protein targeting tissue factor, BMC Cancer, 2011, 11:263, http://www.biomedcentral.com/1471-2407/11/263.

Coloma et al., Design and production of novel tentravalent bispecific antibodies, Nature Biotechnol., 1997, 15:159-163.

Cooper et al., Rescue of splicing-mediated intron loss maximizes expression in lentiviral vectors containing the human ubiquitin C promoter, Nucl. Acids Res. (2015) 43 (1): 682-690.

Cornet et al., (2006) Optimal organization of a polypeptide-based candidate cancer vaccine composed of cryptic tumor peptides with enhanced immunogenicity. Vaccine 24, 2102-2109.

Cox et al., "Immunoassay Methods," in Assay Guidance Manual [Internet], Updated Dec. 24, 2014 (Cox et al., Immunoassay Methods, in Assay Guidance Manual [Internet], Updated Dec. 24, 2014 (www.ncbi.nlm.nih.gov/books/NBK92434/; accessed Sep. 29, 2015)/; accessed Sep. 29, 2015).

Del Val, Efficient processing of an antigenic sequence for presentation by MHC class I molecules depends on its neighboring residues in the protein, vol. 66, Issue 6, P1145-1153, Sep. 20, 1991, DOI:https://doi.org/10.1016/0092-8674(91)90037-Y.

Demoulins et al., Polyethylenimine-based polyplex delivery of self-replicating RNA vaccines, Nanomedicine: Nanotechnology, Biology and Medicine, vol. 12, Issue 3, Apr. 2016, pp. 711-722.

Depla et al., Rational design of a multiepitope vaccine encoding T-lymphocyte epitopes for treatment of chronic hepatitis B virus infections. Journal of Virology 82, 435-450 (2008).

Desrichard, et al., Cancer Neoantigens and Applications for Immunotherapy. Clin. Cancer Res. Off. J. Am. Assoc. Cancer Res. (2015). doi:10.1158/1078-0432.CCR-14-3175.

Duan, F. et al. Genomic and bioinformatic profiling of mutational neoepitopes reveals new rules to predict anticancer Immunogenicity. J. Exp. Med. 211, 2231-2248 (2014).

Dupuis, et al., Dendritic Cells Internalize Vaccine Adjuvant after Intramuscular Injection, Cellular Immunology, vol. 186, Issue 1, May 25, 1998, pp. 18-27, https://doi.org/10.1006/cimm.1998.1283.

Edwards et al., 2003, "The remarkable flexibility of the human antibody repertoire; isolation of over one thousand different antibodies to a single protein, BLyS," J. Mol. Biol., 334(1):103-118.

Eggers, et al., The Cleavage Preference of the Proteasome Governs the Yield of Antigenic Peptides, Journal of Experimental Medicine, vol. 182 Dec. 1995 1865-1870.

Eng et al., A deeper look into Comet—implementation and features. J. Am Soc Mass Spectrom. Nov. 2015;26 (11):1865-74. doi: 10.1007/s13361-015-1179-x. Epub Jun. 27, 2015.

Eng et al., Comet: an open-source MS/MS sequence database search tool. Proteomics. Jan. 2013;13(1):22-4. doi:10.1002/pmic.201200439. Epub Dec. 4, 2012.

Extended European Search Report for Application No. 20835557.8, received on Jul. 4, 2023, 10 pages.

Fang, et al. Stable antibody expression at therapeutic levels using the 2A peptide. Nat Biotechnol 23, 584-590 (2005).

Farina et al., Replication-Defective Vector Based on a Chimpanzee Adenovirus, Journal of Virology, Dec. 2001, p. 11603-11613.

Feck et al., "Protection of hDAF-Transgenic Porcine Endothelial Cells against Activation by Human Complement: Role of Membrane Attack Complex Introduction X," Xenotransplantation, vol. 9, Mar. 2002, pp. 97-105.

Felgner, Lipofaction A highly efficient, lipid-mediated DNA-transfaction procedure, Proc. Nall. Acad. Sci., vol. 84, p. 7413-7417, Nov. 1987.

Finco et al., Comparison of competitive ligand-binding assay and bioassay formats for the measurement of eutralizing antibodies to protein therapeutics, J. Pharm. Biomed. Anal., 2011, vol. 54, Issue 2, Jan. 2011, pp. 351-358.

Fisher et al., Biochem. J., 299:49 (Apr. 1, 1994).

Fleeton et al., Self-Replicative RNA Vaccines Elicit Protection against Influenze A Virus, Respiratory Syncytial Virus, nd a Tickbome Encephalitis Virus, Journal of Infectious Diseases 183:1395-1398 2001.

Frampton et al. Development and validation of a clinical cancer genomic profiling test based on massively parallel DNA sequencing. Nat. Biotechnol. 31, 1023-1031 (2013).

Frolov et al., Cis-acting RNA elements at the 5' end of Sindbis virus genome RNA regulate minus- and plus-strand RNA synthesis. RNA. Nov. 2001; 7(11):1638-1651.

Furney et al. SF3B1 mutations are associated with alternative splicing in uveal melanoma. Cancer Discov. (2013). doi:10.1158/2159/8290.CD-13-0330.

Gabrilovich et al., IL-12 and mutant P53 peptide-pulsed dendritic cells for the specific immunotherapy of cancer., J. Immunother Emphasis Tumor Immunol. 1996 (6):414-418.

Gaudrealut et al.,"Preclinical Pharmacology and Safety of ESBA1008, a Single-Chain Antibody Fragment, Investigated as Potential Treatment for Age Related Macular Degeneration," ARVO Annual Meeting Abstract, Mar. 2012, Investigative Opthalmology & Visual Science, vol. 53, 17 pages.

Geall, et al., Nonviral delivery of self-amplifying RNA vaccines, PNAS, 14604-14609, Sep. 4, 2012, vol. 109, No. 36, www.pnas.org/cgi/doi/10.1073/pnas.1209367109.

Goding, Monoclonal Antibodies: Principles and Practice 3rd ed. (1986) Academic Press, San Diego, CA.

Goel et al., 2004, "Plasticity within the antigen-combining site may manifest as molecular mimicry in the humoral immune response," J. Immunol., 173(12):7358-7367.

Goloman et al., HLA-DR monoclonal antibodies inhibit the proliferation of normal and chronic granulocytic leukemia myeloid progenitor cells. Br. J. Haemalol. Nov. 1982;52(3):411-420.

Graaf et al., Curr Pharm Des, 2002, 8:1391-1403.

(56) References Cited

OTHER PUBLICATIONS

Gros et al., Prospective identification of neoantigen-specific lymphocytes in the peripheral blood of melanoma patients, Nat Med. (2016) 22 (4):433-438.
Gruber et al., Efficient tumor cell lysis mediated by a bispecific single chain antibody expressed in Escherichia coli., J. Immunol., 1994, 152:5368-5374.
Guan et al. "Tissue factor expression and angiogenesis in human glioma," Clinical Biochemistry, 2002, 35(4):321-325.
Gubin, et al. "Tumor neoantigens: building a framework for personalized cancer immunotherapy," J. Clin. Invest. 125, 3413-3421 (2015).
Hawkins et al., Selection of phage antibodies by binding affinity: Mimicking affinity maturation, Journal of Molecular Biology, vol. 226, Issue 3, 1992, pp. 889-896. https://doi.org/10.1016/0022-2836(92)90639-2.
Hofer et al., An engineered selenocysteine defines a unique class of antibody derivatives, Proc. Nall. Acad. Sci. USA, 2008, 105:12451-12456.
Hofer et al., Molecularly defined antibody conjugation through a selenocysteine interface, Biochemistry, 2009, 48 (50):12047-12057.
Holliger et al., "Diabodies" Small bivalent and bispecific antibody fragments, Proc. Nall. Acad. Sci. USA, 1993, 90:6444-6448.
Holy et al., Tissue Factor in Cardiovascular Disease: Pathophysiology and Pharmacological Intervention, Adv Pharmacol, 2010, 59:259-592, <htlps://doi.org/10.1016/S1054-3589(10)59009-4>.
Hong et al., 2012, Immuno-PET of Tissue Factor in Pancreatic Cancer, J. Nucl. Med., 53(11):1748-1754.
Hoogenboom et al., By-passing immunisation: Human antibodies from synthetic repertoires of germline VH gene segments rearranged in vitro, J. Mol. Biol., 1991, 227:381-388. <htlps://doi.org/10.1016/0022-2836(92)90894-P>.
Hu et al., Immunization Delivered by Lentiviral Vectors for Cancer and Infectious Diseases, lmmunol Rev. (2011) 239 (1): 45-61, https://doi.org/10.1111/j.1600-065X.2010.00967.x.
Huang et al. "The mechanism of an inhibitory antibody on TF-initiated blood coagulation revealed by the crystal structures of human tissue factor, Fab 5G9 and TF.G9 complex," Journal of molecular biology, 1998, 275(5):873-894.
Huang, et al., The immunodominant major histocompalibility complex class I-restricted antigen of a murine colon tumor derives from an endogenous retroviral gene product, Proc. Nall. Acad. Sci., vol. 93, pp. 9730-9735, Sep. 1996, Immunology.
Hunt et al., Characterization of peptides bound to the class I MHC molecule HLA-A2.1 by mass spectrometry. Science 1992. 255: 1261-1263.
Idusogie et al., Mapping of the C1q Binding Site on Rituxan, a Chimeric Antibody with a Human lgG1 Fc, J. Immunol., 2000, 164:4178-4184.
International Searching Authority, International Search Report and Written Opinion for International Patent Application No. PCT/US2019/012427 (Pub No. WO 2019136309) mailed May 17, 2019 (14 pages).
International Searching Authority, International Search Report and Written Opinion for International Patent Application No. PCT/US2020/040711 (Pub No. WO 2021003399) mailed Dec. 15, 2020 (17 pages).
International Searching Authority, International Search Report and Written Opinion for International Patent Application No. PCT/US2021/041191 (Pub No. WO 2022011323) mailed Dec. 2, 2021 (17 pages).
Ishioka et al., Utilization of MHC class I transgenic mice for development of minigene DNA vaccines encoding multiple HLA-restricted CTL epitopes. J. Immunol 162, 3915-3925 (1999).
Jackson et al., In vitro antibody maturation. Improvement of a high affinity, neutralizing antibody against IL-1 beta., J. Immunol., 1995, 154:3310-3319.
Jakobovits et al., Analysis of homozygous mutant chimeric mice deletion of the immunoglobulin heavy-chain joining region blocks B-cell development and antibody production, Proc. Nall. Acad. Sci. U.S.A., 1993, 90:2551.
Jakobovits et al., Germ-line transmission and expression of a human-derived yeast artificial chromosome, Nature, 1993, 362:255-258.
James et al., Tetramer-guided epitope mapping reveals broad, individualized repertoires of tetanus toxin-specific CD4+ T cells and suggests HLA-based differences in epitope recognition, International Immunology, vol. 19, No. 11. pp. 1291-1301, doi:10.1093/intimm/dxm099.
Janetzki et al., Guidelines for the automated evaluation of Elispot assays. Nat Protec 10, 1098-1115 (2015).
Janeway, Jr. et al. Immunobiology—The Immune System in Health and Disease, Third Edition, 1997, Part II—The Recognition of Antigen and Part Ill—Structure of the Antibody Molecule and Immunoglobin Genes, 14 pages.
Jayaraman Maximizing the Potency of siRNA Lipid Nanoparticles for Hepatic Gene Silencing In Vivo, Angew. Chem Inl. 2012, 51, 8529-8533.
Jensen et al. "Improved Methods for Prediting Peptide Binding Affinity to MHC Class II Molecules." Immunology, 2018, doi:10.1111/imm.12889.
Johanning et al., A sindbis virus mRNA polynucleotide vector achieves prolonged and high level heterologous gene In vivo, Nucleic Acids Research, 1995, vol. 23, No. 9, 1495-1501.
Johnson et al., Molecular Determinants of Alphavirus Neurovirulence: Nucleotide and Deduced Protein Sequence Changes during Attenuation of Venezuelan Equine Encephalitis Virus. J. Gen Virol 67:1951-1960, 1986.
Jones et al., Replacing the complementarity-determining regions in a human antibody with those from a mouse, Nature, 1986, 321:522-525.
Jorgensen et al., NetMHCstab—predicting stability of peptide-MHC-I complexes; impacts for cytotoxic T lymphocyte Epitope discovery. Immunology 141, 18-26 (2014).
Jose et al., A structural and functional perspective of alphavirus replication and assembly. Future Microbiol. Sep. 2009;4(7):837-856.
Kabat et al., Unusual Distributions of Amino Acids in Complementarity-determining (Hypervariable) Segments of Heavy and Light Chains of Immunoglobulins and Their Possible Roles in Specificity of Antibody-combining Sites, J. Biol Chem, 1977, 252:6609-6616.
Kall et al., Assigning [confidence measures] significance to peptides identified by tandem mass spectrometry. Journal of Proteome Research, 7(1):29-34, Jan. 2008.
Kall et al., Nonparametric estimation of posterior error probabilities associated with peptides identified by tandem mass spectrometry. Bioinformatics, 24(16):i42-i48, Aug. 2008.
Kall et al., Semi-supervised learning for peptide identification from shotgun proteomics datasets. Nature Methods 4:923-925, Nov. 2007.
Kanda et al., Comparison of cell lines for stable production of fucose-negative antibodies with enhanced ADCC, Biotechnol. Bioeng., 2006, 94:680-688.
Kanyavuz et al., 2019, "Breaking the law: unconventional strategies for antibody diversification," Nat. Rev. Immunol., 19(6):355-368.
Kim et al. "A novel antibody-drug conjugate targeting SAIL for the treatment of hematologic malignancies," Blood cancer journal, 2015, 5(5):1-8.
Kinney et al., Nucleotide Sequence of the 26 S mRNA of the Virulent Trinidad Donkey Strain of Venezuelan Equine Encephalitis Virus and Deduced Sequence of the Encoded Structural Proteins. Virology 152 (2), 400-413. Jul. 30, 1986.
Kipriyanov et al., "Generation and Production of Engineered Antibodies," Mol Biotechnol. Jan. 2004; 26(1):39-60.
Koizume et al. "Tissue Factor—Factor VII Complex as a Key Regulator of Ovarian Cancer Phenotypes," Biomark Cancer, 2015, 7(S2):1-13.

(56) References Cited

OTHER PUBLICATIONS

Kornher, et al., Mutation detection using nucleotide analogs that alter electrophoretic mobility, Nucleic Acids Research, vol. 17, Issue 19, Oct. 11, 1989, pp. 7779-7784, https://doi.org/10.1093/nar/17.19.7779.
Kost, et al., The nucleotide sequence of the chich cytoplasmic B-actin gene, Nucleic Acids Research, vol. 11, Issue 23, Dec. 10, 1983, pp. 8287-8301, https://doi.org/10.1093/nar/11.23.8287.
Kostelny et al., Formation of a bispecific antibody by the use of leucine zippers, J. Immunol., 1992, 148:1547-1553.
Kovtun et al., Antibody-Maytansinoid Conjugates Designed to Bypass Multidrug Resistance, Cancer Res., 2010, 70:2528-2537.
Kozbor, A human hybrid myeloma for production of human monoclonal antibodies., J. Immunol., 1984, 133 (6) pp. 3001-3005.
Kreiter et al., "Mutant MHC class II epitopes drive therapeutic immune responses to cancer," Nature 520, 692-696, Apr. 2015.
Kreiter Increased antigen presentation efficiency by coupling antigens to MHC class I trafficking signals, J. Immunol 2008, 180:309-318, doi: 10.4049/jimmunol.180.1.309, http://www.jimmunol.org/contenl/180/1/309.
Krieg et al., Functional messenger RNAs are produced by SP6 in vitro transcription of cloned cDNAs, Nucleic Acids Res. Sep. 25, 1984;12(18):7057-7070.
Kuppuswamy et al., Single nucleotide primer extension to detect genetic diseases Experimental application to hemophilia B (factor IX) and cystic fibrosis genes, Proc. Natl. Acad. Sci. USA, vol. 88, pp. 1143-1174, Feb. 1991, Biochemistry.
Lam et al. Nucleotide-resolution analysis of structural variants using BreakSeq and a breakpoint library. Nat. Biotechnol. 28, 47-55 (2010).
Larsen et al. "Engineering of substrate selectivity for tissue factor. factor VIIa complex signaling through protease-activated receptor 2," The Journal of biological chemistry, 2010, 285(26):19959-19966.
Larsen et al. An integrative approach to CTL epitope prediction: a combined algorithm integrating MHC class I binding, TAP transport efficiency, and proteasomal cleavage predictions. Eur. J. Immunol. 35, 2295-2303 (2005).
LeFranc et al., IMGT unique numbering for immunoglobulin and T cell receptor variable domains and Ig superfamily V-like domains, Dev Comp Immunol, 2003, 27:55-77.
Lescar et al., 1995, "Crystal structure of a cross-reaction complex between Fab F9.13.7 and guinea fowl lysozyme," J. Biol. Chem., 270(30):18067-18076.
Li et al., RSEM: accurate transcript quantification from RNA-Seq data with or without a reference genome. BMC Bioinformatics, 12:323, Aug. 2011.
Liao-Chan et al. "Quantitative assessment of antibody internalization with novel monoclonal antibodies against Alexa fluorophores," PLoS One, 2015, 10(4):1-15.
Liepe et al., A large fraction of HLA class I ligands are proteasome-generated spliced peptides. Science, Oct. 21, 2016.
Liu et al. Athlates: accurate typing of human leukocyte antigen through exome sequencing. Nucleic Acids Res. 41, e142 (2013).
Liu et al., N-terminal Glutamate to Pyroglutamate Conversion in Vivo for Human IgG2 Antibodies, J. Biol. Chem., 2011, 286:11211-11217.
Ljungberg et al., Self-replicating alphavirus RNA vaccines, Expert Rev. Vaccines 14(2), 177-194 (2015).
Lloyd et al., 2009, "Modelling the human immune response: performance of a 1011 human antibody repertoire against a broad panel of therapeutically relevant antigens," Protein Eng. Des. Sel., 22(3):159-168 (Epub 2008).
Lo et al. "Tissue factor expression in the metaplasia-adenoma-carcinoma sequence of gastric cancer in a European population," British Journal of Cancer, 2012, 107(7):1125-1130.
Lu et al., Efficient identification of mutated cancer antigens recognized by T cells associated with durable tumor regressions, Clin Cancer Res. (2014) 20(13):3401-3410.
Lundegaard et al., State of the art and challenges in sequence based T-cell epitope prediction. Immunome Res. 6 Suppl 2, S3 (2010).
Lundstrom, Alphavirus-Based Vaccines, Viruses 2014, 6, 2392-2415, doi: 10.3390/v6062392.
Lyons et al., Influence of human COB on antigen recognition by T-cell receptor-transduced cells. Cancer Res 66, 11455-11461 (2006).
Maguire et al. SF3B1 mutations constitute a novel therapeutic target in breast cancer. J. Pathol. 235, 571-580 (2015).
Mannino & Gould-Fogerite, BioTechniques 6(7): 682-691 (1988).
Maretty et al., Bayesian transcriptome assembly. Genome Biol. 15, 501 (2014).
Marks et al., By-passing immunization: Human antibodies from V-gene libraries displayed on phage, J. Mol. Biol., 1991, 222:581-597.
Martinon et al., Induction of virus-specific cytotoxic T lymphocytes in vivo by liposome-entrapped Mrna, European Journal of Immunology vol. 23, Issue 7, Jul. 1993, https://doi.org/10.1002/eji.1830230749.
Mayor et al. HLA Typing for the Next Generation. PloS One 10, e0127153 (2015).
McGranahan et al., Allele-Specific HLA Loss and Immune Escape in Lung Cancer Evolution, Cell 171, 1259-1271.e11, (2017).
Merchant et al., An efficient route to human bispecific IgG, Nature Biotechnol., 1998, 16:677-681.
Miller et al., Design, Construction, and In Vitro Analyses of Multivalent Antibodies, J. Immunol., 2003, 170:4854-4861.
Milstein et al., (Milstein and Cuello), Hybrid hybridomas and their use in immunohistochemistry, Nature, 1983, 305:537-540.
Mommen et al., Sampling From the Proteome to the Human Leukocyte Antigen-DR (HLA-DR) Ligandome Proceeds via High Specificity. Mol Cell Proteomics 15(4): 1412-1423, Apr. 2016.
Morea et al., Antibody modeling: implications for engineering and design., Methods, 2000, 20:267-279.
Mose et al., ABRA: improved coding indel detection via assembly-based realignment. Bioinforma. Oxf. Engl. 30, 2813-2815 (2014).
Muyldermans et al., Recognition of antigens by single-domain antibody fragments: the superfluous luxury of paired domains, Trends in Biochem. Sci., 2001, 26:230-245.
Nagai, et al. (2012). Aurora kinase A-specific T-cell receptor gene transfer redirects T lymphocytes to display effective antileukemia reactivity. Blood 119, 368-376.
Ngo et al. "CNTO 859, a humanized anti-tissue factor monoclonal antibody, is a potent inhibitor of breast cancer metastasis and tumor growth in xenograft models," International journal of cancer, 2007, 120(6):1261-1267.
Nielsen et al., The role of the proteasome in generating cytotoxic T-cell epitopes: insights obtained from improved predictions of proteasomal cleavage. Immunogenetics 57, 33-41 (2005).
Nielsen, et al., NN-align—An artificial neural network-based alignment algorithm for MHC class II peptide binding prediction. BMC Bioinformatics 10:296, Sep. 2009.
Nielsen, et al., "Prediction of MHC class II binding affinity using SMM-align, a novel stabilization matrix alignment method.," BMC Bioinformatics 8:238, Jul. 2007.
Nussbaum, et al., Cleavage motifs of the yeast 20S proteasome B subunits deduced from digests of enolase 1, Proc Natl. Acad. Sci. USA, vol. 95, pp. 12504-12509, Oct. 1998, Immunology.
Nyren, et al., Solid Phase DNA Minisequencing by an Enzymatic Luminometric Inorganic Pyrophosphate Detection Assay, Analytical Biochemistry, vol. 208, Issue 1, Jan. 1993, pp. 171-175, https://doi.org/10.1006/bio.1993.1024.
Ouahabi et al., 1996, "Double long-chain amidine liposome-mediated self replicating RNA transfection," FEBS Lett., 380(1-2):108-112.
Panina-Bordignon et al., Universally immunogenic T cell epitopes: promiscuous binding to human MHC class II and promiscuous recognition by Tcells, Eur. J. Immunol. 19, 2237-2242 (1989).
Patry et al. "Tissue factor expression correlates with disease-specific survival in patients with node-negative muscle-invasive bladder cancer," International journal of cancer, 2008, 122(7):1592-1597.
Paul, Fundamental Immunology 7th ed., Ch. 5 (2013) Lippincott Williams & Wilkins, Philadelphia, PA.

(56) References Cited

OTHER PUBLICATIONS

Pearson et al., MHC class I-associated peptides derive from selective regions of the human genome. The Journal of Clinical Investigation, 2016.
Pertea et al. StringTie enables improved reconstruction of a transcriptome from RNA-seq reads. Nat. Biotechnol. 33, 290-295 (2015).
Polo et al., Stable alphavirus packaging cell lines for Sindbis virus- and Semliki Forest virus-derived vectors, Proc. Natl. Acad. Sci. vol. 96, pp. 4598-4603, Apr. 1999.
Presta, Antibody engineering, Curr. Op. Strucl. Biol., 1992, vol. 2, Issue 4, pp. 593-596.
Prezant, et al., Trapped-oligonucleotide nucleotide incorporation (TONI) assay, a simple method for screening point mutations, Human Mutation, vol. 1, Issue 2, 1992, https://doi.org/10.1002/humu.1380010212.
Pushko et al., Replicon-helper systems from attenuated Venezuelan equine encephalitis virus: expression of heterologous genes in vitro and immunization against heterologous pathogens in vivo. Virology. Dec. 22, 1997;239 (2):389-401.
Qiu et al Reviving virus based cancer vaccines by using cytomegalovirus vectors expressing modified tumor antigens, Oncoimmunology, E pub Jun. 5, 2015, vol. 5 No. 1 pp. 1-3 doi: 10.1080/2162402X.2015.1056974.
Quahabi Double long-chain amidine liposome-mediated self replicating RNA transfection, FEBS Letters 380 (1996) 108-112.
Rabia et al., "Understanding and overcoming trade—Offs between antibody affinity, specificity, stability and solubility," Biochem Eng J. Sep. 15, 2018; 137:365-374 (Year: 2018).
Rajasagi et al. Systematic identification of personal tumor-specific neoantigens in chronic lymphocytic leukemia. Blood 124, 453-462 (2014).
Regina et al. "Increased tissue factor expression is associated with reduced survival in non-small cell lung cancer and with mutations of TP53 and PTEN," Clinical Chemistry, 2009, 55(10):1834-1842.
Rheme et al., Alphaviral cytotoxicity and its implication in vector development. Exp Physiol. Jan. 2005; 90(1):45-52. Epub Nov. 12, 2004.
Riechmann et al., Reshaping human antibodies for therapy, Nature, 1988, 332:323-327, DOI:10.1038/332323a0.
Riley et al., Recent Advances in Nanomaterials for Gene Delivery—A Review. Nanomaterials 2017, 7(5), 94, doi:10.3390/nano7050094.
Ripka et al., Two chinese hamster ovary glycosylation mutants affected in the conversion of GDP-mannose to GDP-fucose, Arch. Biochem. Biophys., 1986, 249:533-545.
Rivas et al. Human genomics. Effect of predicted protein-truncating genetic variants on the human transcriptome. Science 348, 666-669 (2015).
Rizvi et al. Cancer immunology. Mutational landscape determines sensitivity to PD-1 blockade in non-small cell lung cancer. Science 348, 124-128 (2015).
Roberts et al., "Specific Viral Etiologies are Associated with Outcomes in Pediatric Acute Respiratory Distress Syndrome", Pediatr Grit Care Med. Sep. 2019; 20(9): e441-e446.
Roberts et al., Identification of novel transcripts in annotated genomes using RNA-Seq. Bioinforma. Oxf. Engl. (2011). doi:10.1093/bioinformatics/btr355.
Rodriguez, et al., DNA Immunization Ubiquitination of a Viral Protein Enhances Cytotoxic T-Lymphocyte Induction and Antiviral Protection but Abrogates Antibody Induction, Journal of Virology, Nov. 1997, p. 8497-8503, vol. 71, No. 11.
Roy et al., Assessing long-distance RNA sequence connectivity via RNA-templated DNA-DNA ligation. eLife 4, (2015).
Rudikoff et al., "Single Amino Acid Substitution Altering Antigen-Binding Specificity," Proceedings of the National Academy of Sciences, Naitonal Academy of Sciences, US., vol. 79, Mar. 1, 1982, pp. 1979-1983.
Ruf et al. "Antibody mapping of tissue factor implicates two different exon-encoded regions in function," The Biochemical journal, 1991, 278:729-733.

Sakuma et al., Lentiviral vectors: basic to translational, Biochem J. (2012) 443(3), pp. 603-618.
Sakurai et al. "Expression of Tissue Factor in Epithelial Ovarian Carcinoma Is Involved in the Development of Venous Thromboembolism," International Journal of Gynecological Cancer, 2017, 27(1):37-43.
Saunders et al. Strelka: accurate somatic small-variant calling from sequenced tumor-normal sample pairs. Bioinforma. Oxf. Engl. 28, 1811-1817 (2012).
Schier et al., Identification of functional and structural amino-acid residues by parsimonious mutagenesis, Gene, 1996, 169:147-155, DOI: 10.1016/0378-1119(95)00821-7 <htlps://www.researchgate.net/deref/htlp%3A%2F%2Fdx. doi.org%2F10.1016%2F0378-1119(95)00821-7>.
Schroeder et al., Structure and function of immunoglobulins, J. Allergy Clin. Immunol., 2010, 125:S41-52.
Schumacher et al., Neoantigens in cancer immunotherapy. Science 348, 69-74 (2015).
Shields et al., Lack of Fucose on Human lgG1 N-Linked Oligosaccharide Improves Binding to Human Fc RIII and Antibody-dependent Cellular Toxicity, J. Biol. Chem., 2002, 277:26733-26740.
Shukla et al, Comprehensive analysis of cancer-associated somatic mutations in class I HLA genes, Nat. Biotechnol. 33, pp. 1152-1158, (2015).
Siiman et al., Competitive Antibody Binding to Soluble CD16b Antigen and CD16b Antigen on Neutrophils in Whole Blood by Flow Cytometry, Cytometry, 2001, 44:30-37.
Silacci et al., Linker Length Matters, Fynomer-Fc Fusion with an Optimized Linker Displaying Picomolar IL-17A Inhibition Potency, J. Biol. Chem., 2014, 289:14392-14398.
Silva et al. "Increased tissue factor expression is an independent predictor of mortality in clear cell carcinoma of the kidney," International braz j urol : official journal of the Brazilian Society of Urology, 2014, 40(4):499-506.
Skelly et al., A powerful and flexible statistical framework for testing hypotheses of allele-specific gene expression from RNA-seq data. Genome Res. 21, 1728-1737 (2011).
Slansky et al., Enhanced Antigen-Specific Antitumor Immunity with Altered Peptide Ligands that Stabilize the MHC-Peptide-TCR Complex. Immunity, vol. 13, Issue 4, Oct. 1, 2000, pp. 529-538.
Snyder etal. Genetic basis for clinical response to CTLA-4 blockade in melanoma. N. Engl. J. Med. 371, 2189-2199 (2014).
Sokolov, Primer extension technique for the detection of single nucleotide in genomic DNA, Nucleic Acids Research, vol. 18, Issue 12, Jun. 25, 1990, p. 3671.
Song et al. CLASS: constrained transcript assembly of RNA-seq reads. BMC Bioinformatics 14 Suppl 5, S14 (2013).
Staerz et al., Hybrid hybridoma producing a bispecific monoclonal antibody that can focus effector T-cell activity, Proc. Natl. Acad. Sci. USA, 1986, 83:1453-1457.
Staerz, et al. Hybrid antibodies can target sites for attack by T cells, Nature, 1985, 314:628-631.
Stover, et al. New use of BCG for recombinant vaccines. Nature 351, 456-460 (1991) doi:10.1038/351456a0.
Strauss et al., The alphaviruses: gene expression, replication, and evolution. Microbiol Rev. Sep. 1994; 58(3): 491-562.
Strejan et al., Suppression of chronic-relapsing experimental allergic encephalomyelitis in strain-13 giunea pigs by administration of lopisone-associaled myelin basic protein, Journal of Neuroimmulogy, vol. 7, pp. 27-41, Jan. 1, 1984.
Stronen et al., Targeting of cancer neoantigens with donor-derived T cell receptor repertoires, Science. (2016) 352 (6291):1337-1341.
Stryer, 1995, Biochemistry (4th edition), W.H. Freeman and Company, pp. 18-23.
Sundberg, E., "Structural Basis of Anitbody-Antigen Interactions", Methods in Molecular Biology, Epitope Mapping Protocols, Second Edition (2009), vol. 524.
Syvanen, et al., A primer-guided nucleotide incorporation assay in the genotyping of apolipoprotein W, Genomics, vol. 8, Issue 4, Dec. 1990, pp. 684-692, https://doi.org/10.1016/0888-7543(90)90255-S.

(56) References Cited

OTHER PUBLICATIONS

Syvanen, et al., Identification of individuals by analysis of biallelic DNA markers, using PCR and sold-phase minisequencing, American Journal of Human Genetics, Jan. 1993, 52(1): 46-59.
Szoka, Jr., Comparative properties and methods of preparation of lipid vesicles (liposomes), Ann. Rev. Biophys. Bioeng. 1980, 9:467-508.
Target Capture for NextGen Sequencing—IDT. at <http://www.idtdna.com/pages/products/nextgen/target-capture> (Author, Tille should be Integrated Data Technologies Hybridization capture).
Tatsis et al., Adenoviruses as vaccine vectors, Molecular Therapy, vol. 10, Issue 4, Oct. 2004, pp. 616-629 https://doi.org/10.1016/j.ymthe.2004.07.013.
Teplyakov et al., "Crystal Structure of Tissue Factor in Complex with Antibody 10H10 Reveals the signaling Epitope," Cellular Signalling 36 (2017) 139-144.
Theunissen et al., 2018, "Treating Tissue Factor-Positive Cancers with Antibody-Drug Conjugates That Do Not Affect Blood Clotting," Mol. Cancer Ther., 17(11):2412-2426.
Theunissen et al., Methods for Studying the Cellular Response to DNA Damage: Influence of the Mre11 Complex on Chromosome Metabolism, Methods Enzymol, 2006, 409:251-284.
Todorovska et al., Design and application of diabodies, triabodies and tetrabodies for cancer targeting, J. Immunol. Methods, 2001, 248:47-66.
Tran, E. et al., Cancer immunotherapy based on mutation-specific CD4+ T cells in a patient with epithelial cancer, Science, 344:641-645 (2014).
Traunecker et al., Bispecific single chain molecules (Janusins) target cytotoxic lymphocytes on HIV infected cells, Embo J., 1991, 10:3655-3659.
Tripisciano et al., "Different Potential of Extracellular Vesicles to Support Thrombin Generation: Contributions of Phosphatidylserine, Tissue Factor, and Cellular Origin," Scientific Reports, 7:6522, Jul. 26, 2017, 11 pages.
Tutt et al., Trispecific F(ab')3 derivatives that use cooperative signaling via the TCR/CD3 complex and CO2 to activate and redirect resting cytotoxic T cells, J. Immunol., 1991, 147:60-69.
Ugozzoli, et al., Detection of specific alleles by using allele-specific primer extension followed by capture on solid support, Genetic Analysis: Biomolecular Enginnering, vol. 9, Issue 4, Aug. 1992, pp. 107-112, https://doi.org/10.1016/1050-3862(92)90049-B.
Vajdos et al., ""Comprehensive functional maps of the antigen-binding site of an anti-ErbB2 antibody obtained with shotgun scanning mutagenesis"", J_ Mol. Biol. Jul. 5, 2002, 320(2):415-428. (Year: 2002).
Vajdy, et al., Mucosal adjuvants and delivery systems for protein-, DNA- and RNA-based vaccines, Immunology & Cell Biology, vol. 82, Issue 6, 2004, https://doi.org/10.1111/j.1440-1711.2004.01288.x.
Van Allen et al., "Genomic correlates of response to CTLA-4 blockade in metastatic melanoma.," Science 350, 207-211 (2015).
Van Den Berg et al. "The relationship between tissue factor and cancer progression: insights from bench and bedside," Blood, 2012, 119(4):924-932.
Van Loo, et al., Allele-specific copy number analysis of tumors. Proc. Nall. Acad. Sci. U.S.A. 107, pp. 16910-16915, (2010).
Velders et al., Defined Flanking Spacers and Enhanced Proteolysis Is Essential for Eradication of Established Tumors by an Epitope String DNA Vaccine, The Journal of Immunology, 2001; 166:5366-5373; doi: 10.4049/immunol.166.9.5366.
Versteeg et al. "Inhibition of tissue factor signaling suppresses tumor growth," Blood, 2008, 111(1):190-199.
Vitiello et al., (1991). Analysis of the HLA-restricted influenza-specific cytotoxic T lymphocyte response in transgenic mice carrying a chimeric human-mouse class I major histocompatibility complex. J Exp Med 173, 1007-1015.
Vitting-Seerup et al., spliceR: an R package for classification of alternative splicing and prediction of coding potential from RNA-seq data. BMC Bioinformatics 15, 81 (2014).

Walter et al. Clonal architecture of secondary acute myeloid leukemia. N. Engl. J. Med. 366, 1090-1098 (2012).
Wilkerson et al. Integrated RNA and DNA sequencing improves mutation detection in low purity tumors. Nucleic Acids Res. 42, e107 (2014).
Wolff et al., Direct gene transfer into mouse muscle in vivo, Science Mar. 23, 1990: vol. 247, Issue 4949, pp. 1465-1468, DOI: 10.1126/science.1690918.
Wright et al., Effect of glycosylation on antibody function: implications for genetic engineering, TIBTECH, 1997, 15:26-32.
Wu, Targeting Genes: Delivery and Persistent Expression of a Foreign Gene Driven by Mammalian Regulatory Elements in Vivo, The Journal of Biological Chemistry, vol. 264, No. 29, Oct. 15, 1989, pp. 16985-16987.
Xu et al. RNA Compass: a dual approach for pathogen and host transcriptome analysis of RNA-seq datasets. PloS One 9, e89445 (2014).
Xu et al., Addressing polyspecificity of antibodies selected from an in vitro yeast presentation system: a FAGS-based, high-throughput selection and analytical tool, Protein Eng Des Sel., 2013, 26(10):663-670).
Yachi et al., Altered peptide ligands induce delayed CDB-T cell receptor interaction—a role for COB in distinguishing antigen quality. Immunity 25, 203-211, 2006.
Yadav, M. et al. Predicting immunogenic tumour mutations by combining mass spectrometry and exome sequencing. Nature 515, 572-576 (2014), doi:10.1038/nature14001.
Yamane-Ohnuki et al., Establishment of FUTB knockout Chinese hamster ovary cells: An ideal host cell line for producing completely defucosylated antibodies with enhanced antibody-dependent cellular cytotoxicity , Biotech. Bioeng., 2004, 87: 614-622.
Yao et al. "Tissue Factor and VEGF Expression in Prostate Carcinoma: A Tissue Microarray Study," Cancer Investigation, 2009, 27(4):430-434.
Ye et al., Pindel: a pattern growth approach to detect break points of large deletions and medium sized insertions from paired-end short reads. Bioinforma. Oxf. Engl. 25, 2865-2871 (2009).
Yeh et al. "Upregulation of tissue factor by activated Stat3 contributes to malignant pleural effusion generation via enhancing tumor metastasis and vascular permeability in lung adenocarcinoma," PLoS One, 2013, 8(9):1-14.
Yeh et al., Deterministic Diffusion Fiber Tracking Improved by Quantitative Anisotropy, PLoS One, 2013, 8:e75287.
Yoshida, et al., Splicing factor mutations and cancer. Wiley Interdiscip. Rev. RNA 5, 445-459 (2014).
Zarling et al., Identification of class I MHC-associated phosphopeptides as targets for cancer immunotherapy. Proc Natl Acad Sci USA. Oct. 3, 2006;103(40):14889-14894.
Zhang et al. "Pathological expression of tissue factor confers promising antitumor response to a novel therapeutic antibody SC1 in triple negative breast cancer and pancreatic adenocarcinoma," Oncotarget, 2017, 8(35):59086-59102.
Zhang et al. "PEAKS DB: de novo sequencing assisted database search for sensitive and accurate peptide dentification. Molecular & Cellular Proteomics," 11(4):1-8. Jan. 2, 2012.
Zhang et al. Intratumor heterogeneity in localized lung adenocarcinomas delineated by multiregion sequencing. Science 346, 256-259 (2014).
Zhou et al. A chemical genetics approach for the functional assessment of novel cancer genes. Cancer Res. (2015). doi:10.1158/0008-5472.CAN-14-2930.
Zufferey et al., Self-Inactivating Lentivirus Vector for Safe and Efficient In Vivo Gene Delivery, J. Virol. (1998) 72 (12): 9873-9880.
Gaudreault et al., 2012, "Preclinical Pharmacology and Safety of ESBA1008, a Single-chain Antibody Fragment, Investigated as Potential Treatment for Age Related Macular Degeneration," ARVO Annual Meeting Abstract, Mar. 2012, Investigative Ophthalmology & Visual Science, 53:3025 (2 pages).
Zhao et al., 2021, "Preparation of humanized anti-tissue factor antibody and its mechanism of killing colon cancer cells and

(56) References Cited

OTHER PUBLICATIONS inhibiting cell migration," Chinese Journal of Cellular and Molecular Immunology, 2:168-173, English abstract only.

* cited by examiner

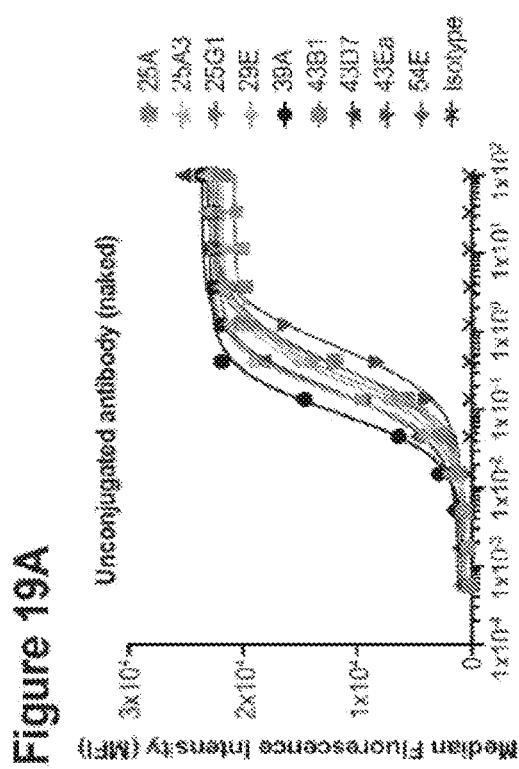
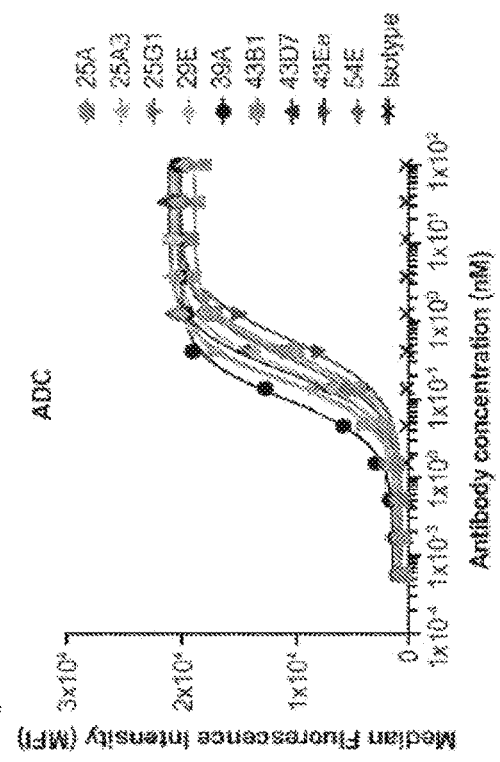

Figure 20A
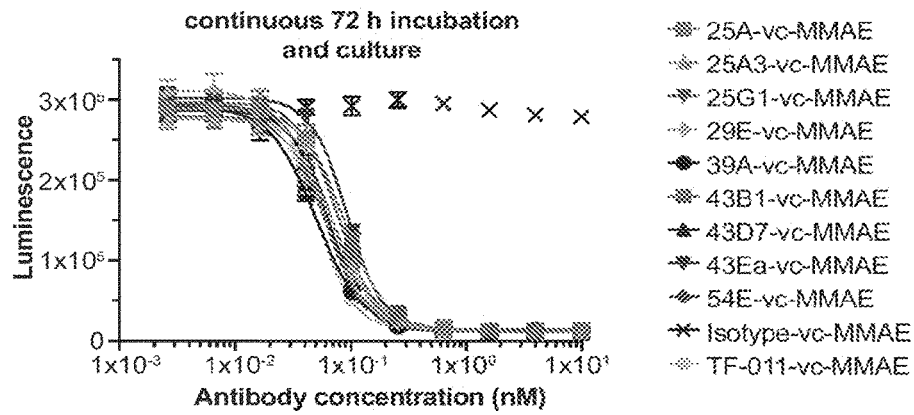
Figure 20B
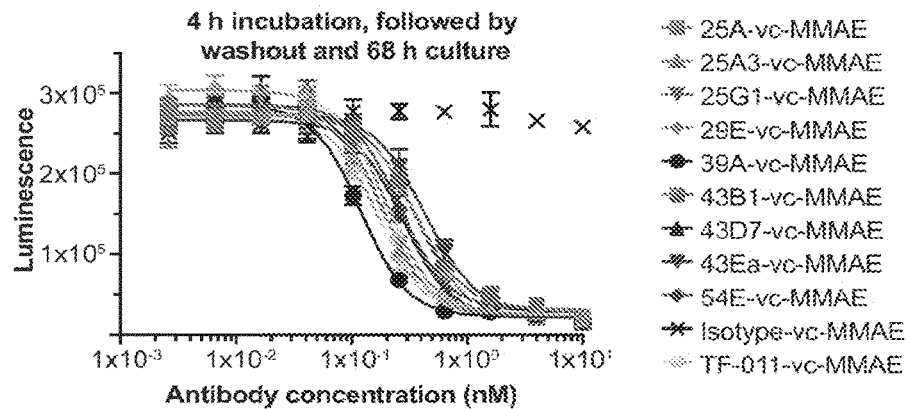
Figure 20C
|  | IC50 (nM) | |
|---|---|---|
|  | Cont. | Washout |
| 25A-vc-MMAE | 0.09 | 0.35 |
| 25A3-vc-MMAE | 0.07 | 0.19 |
| 25G1-vc-MMAE | 0.06 | 0.19 |
| 29E-vc-MMAE | 0.06 | 0.20 |
| 39A-vc-MMAE | 0.05 | 0.12 |
| 43B1-vc-MMAE | 0.08 | 0.36 |
| 43D7-vc-MMAE | 0.06 | 0.28 |
| 43Ea-vc-MMAE | 0.09 | 0.43 |
| 54E-vc-MMAE | 0.07 | 0.26 |
| Isotype-vc-MMAE | na | na |
| TF-011-vc-MMAE | 0.05 | 0.17 |

Figure 21A
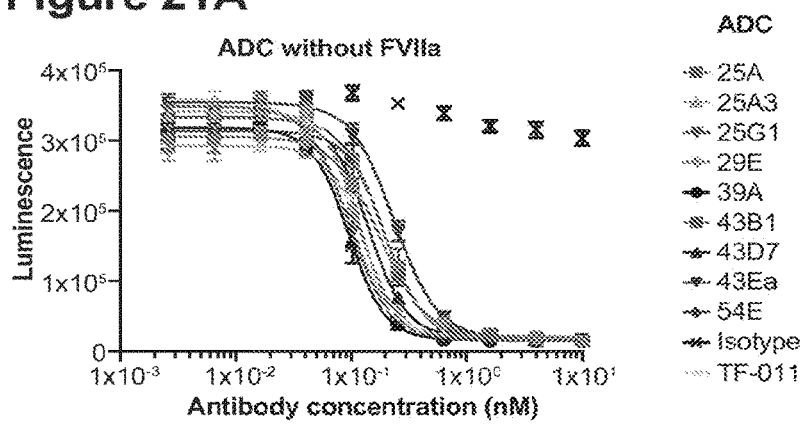
Figure 21B
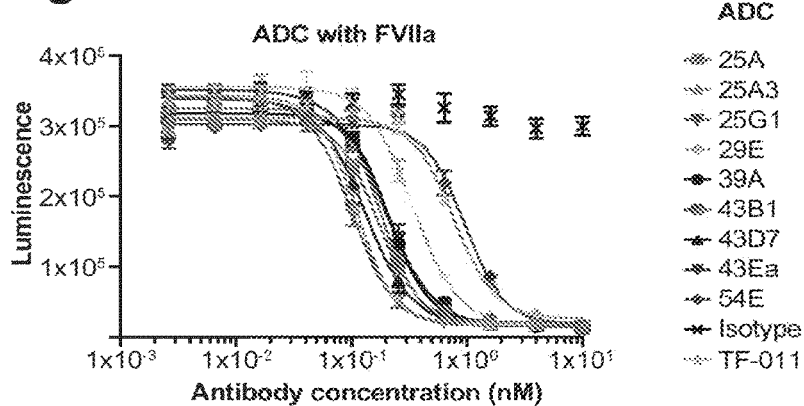
Figure 21C
| ADC | IC50 (nM) | |
|---|---|---|
| | Without FVIIa | With FVIIa |
| 25A | 0.18 | 0.17 |
| 25A3 | 0.12 | 0.11 |
| 25G1 | 0.10 | 0.10 |
| 29E | 0.13 | 0.77 |
| 39A | 0.09 | 0.22 |
| 43B1 | 0.19 | 0.19 |
| 43D7 | 0.14 | 0.13 |
| 43Ea | 0.24 | 0.19 |
| 54E | 0.20 | 0.97 |
| Isotype | na | na |
| TF-011 | 0.09 | 0.34 |

Figure 22A
| Cell line | Copy number | SEM (n) |
|---|---|---|
| A431 | $1.9 \times 10^5$ | $4.7 \times 10^4$ (8) |
| CHO | BLOQ | BLOQ (2) |
| HCT-116 | $2.2 \times 10^4$ | $6.5 \times 10^3$ (6) |
| HPAF-II | $5.7 \times 10^5$ | $4.5 \times 10^4$ (8) |
| MDA-MB-231 | $3.2 \times 10^5$ | $2.7 \times 10^4$ (7) |
| RF/6A | $7.3 \times 10^4$ | $1.7 \times 10^4$ (4) |
Figure 22B
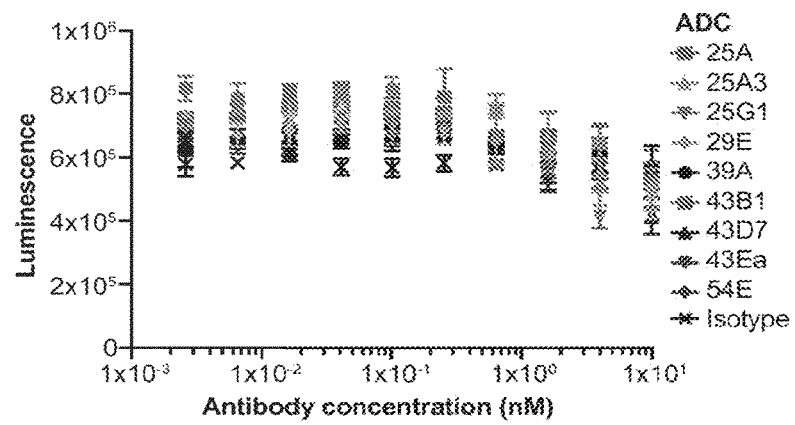
Figure 22C
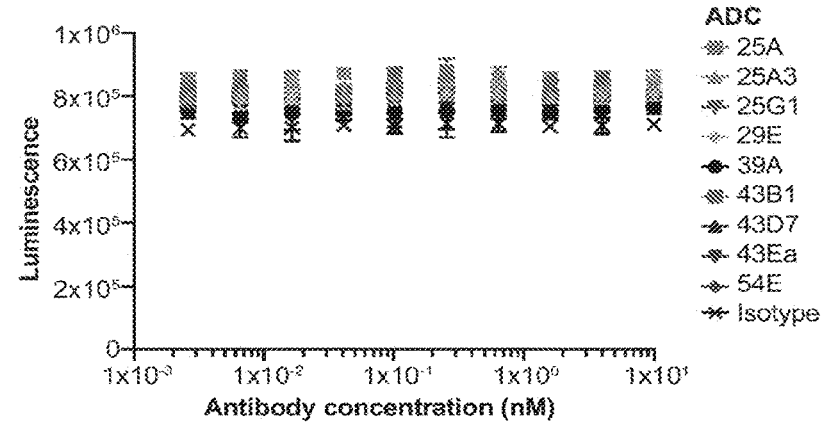

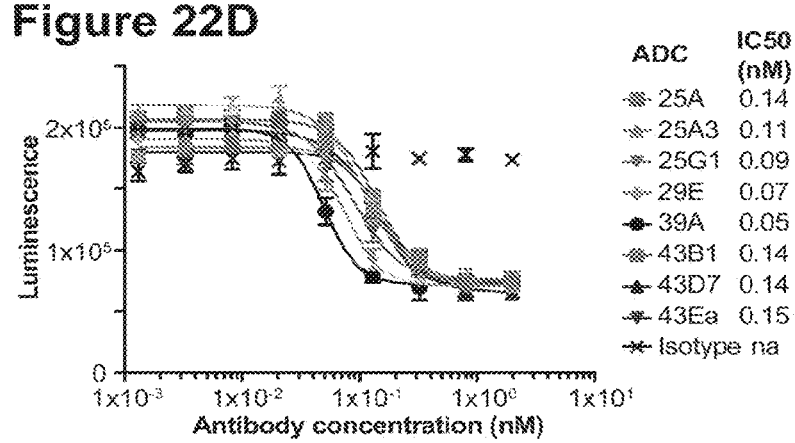
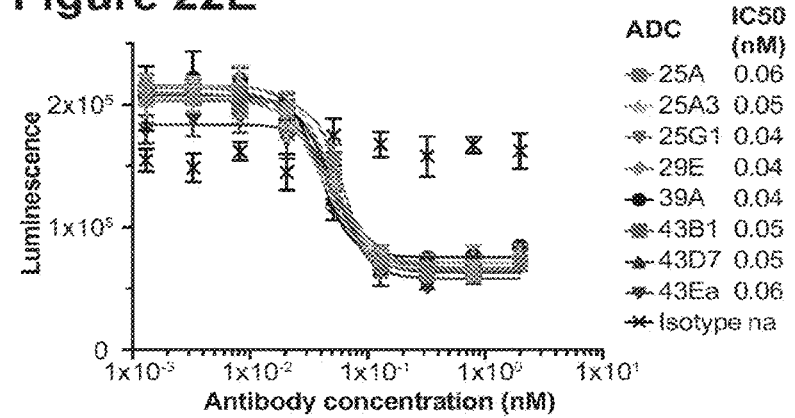

| Treatment | Donor number (#) | Copy # | SEM |
|---|---|---|---|
| no treatment | 6 | $2.4 \times 10^3$ | $4.2 \times 10^2$ |
| 3 h of cytokines | 5 | $8.7 \times 10^3$ | $7.7 \times 10^2$ |
| 6 h of cytokines | 5 | $1.2 \times 10^4$ | $8.5 \times 10^2$ |
| 20 h of cytokines | 2 | $4.6 \times 10^3$ | $2.9 \times 10^2$ |

Figure 29A
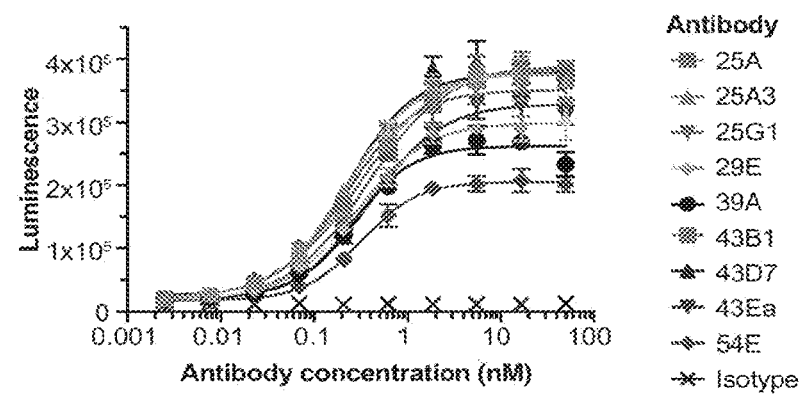
Figure 29B
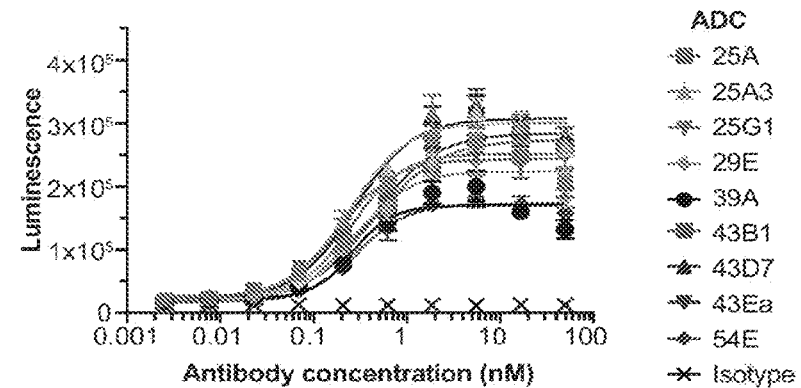
Figure 29C
| Antibody | EC50 (nM) Naked | ADC |
|---|---|---|
| 25A | 0.31 | 0.26 |
| 25A3 | 0.22 | 0.24 |
| 25G1 | 0.22 | 0.18 |
| 29E | 0.29 | 0.28 |
| 39A | 0.26 | 0.26 |
| 43B1 | 0.36 | 0.42 |
| 43D7 | 0.23 | 0.27 |
| 43Ea | 0.40 | 0.43 |
| 54E | 0.31 | 0.30 |
| Isotype | na | na |

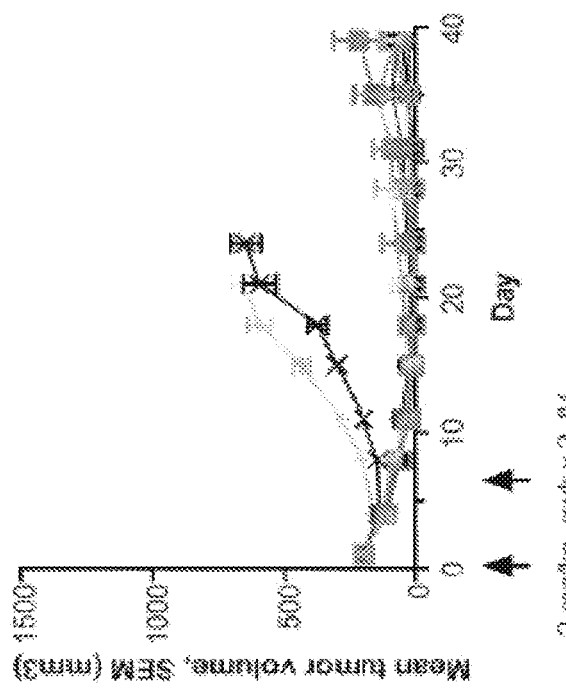
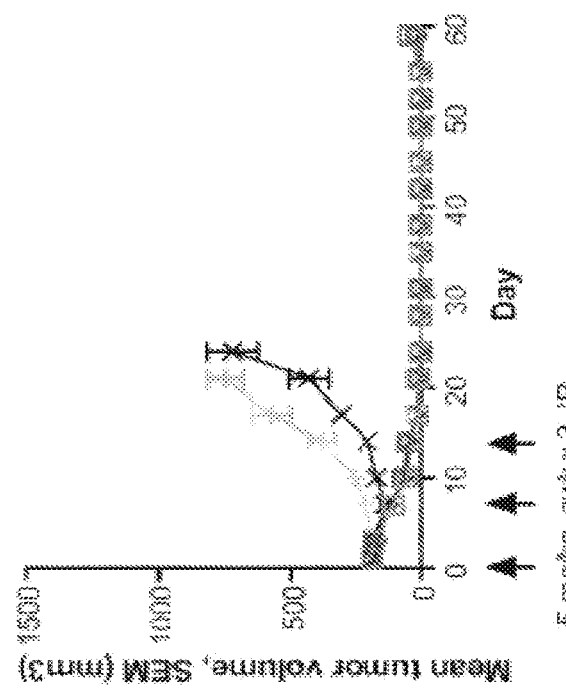
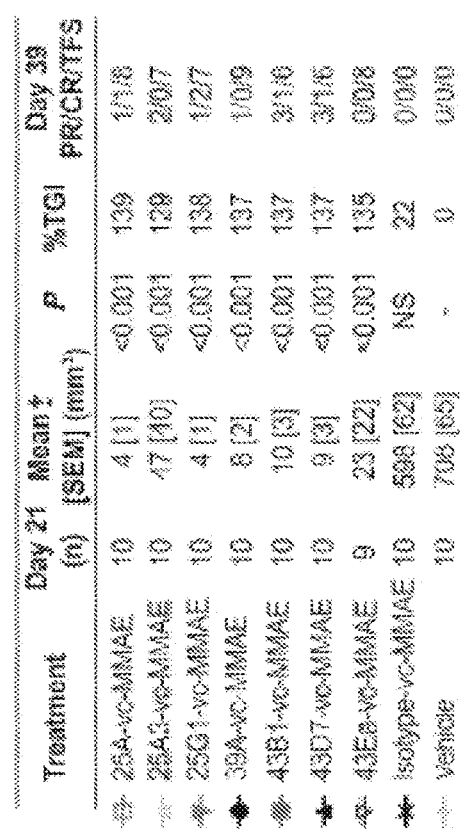

Figure 36

```
hTF     (SEQ ID NO:810)                  SGTTNTVAAYNLTWKSTNFKTILEWEPKPVNQVYTVQISTKSGDWKSKCFYTTDTECDLT   60
rTF     (SEQ ID NO:838)                  -AGTPFGKARNLTWISTDFKTILEWQPKPTNYTYTVQISDRSRNWKYKCTGTTDTECDLT   60
h1-107_r (SEQ ID NO:839)                 -AGTPFGKARNLTWISTDFKTILEWQPKPTNYTYTVQISDRSRNWKYKCTGTTDTECDLT   60
h1-77_r  (SEQ ID NO:840)                 -AGTPFGKARNLTWISTDFKTILEWQPKPTNYTYTVQISDRSRNWKYKCTGTTDTECDLT   60
h1-38_r  (SEQ ID NO:841)                 -AGTPFGKARNLTWISTDFKTILEWQPKPTNYTYTVQISDRSRNWKYKCTGTTDTECDLT   60
h39-77_r (SEQ ID NO:842)                 SGTTNTVAAYNLTWKSTNFKTILEWEPKPVNQVYTVQISDRSRNWKYKCTGTTDTECDLT   60
h78-107_r (SEQ ID NO:843)                SGTTNTVAAYNLTWKSTNFKTILEWEPKPVNQVYTVQISTKSGDWKSKCFYTTDTECDLT   60
h78-107_r.v2 (SEQ ID NO:844)             SGTTNTVAAYNLTWKSTNFKTILEWEPKPVNQVYTVQISTKSGDWKSKCFYTTDTECDLT   60
h78-93_r  (SEQ ID NO:845)                SGTTNTVAAYNLTWKSTNFKTILEWEPKPVNQVYTVQISTKSGDWRSKCFYTTDTECDLT   60
h94-107_r (SEQ ID NO:846)                SGTTNTVAAYNLTWKSTNFKTILEWEPKPVNQVYTVQISTKSGDWKSKCFYTTDTECDLT   60
h108-219_r (SEQ ID NO:847)               SGTTNTVAAYNLTWKSTNFKTILEWEPKPVNQVYTVQISTKSGDWKSKCFYTTDTECDLT   60
h108-158_r (SEQ ID NO:848)               SGTTNTVAAYNLTWKSTNFKTILEWEPKPVNQVYTVQISTKSGDWKSKCFYTTDTECDLT   60
h108-132_r (SEQ ID NO:849)               SGTTNTVAAYNLTWKSTNFKTILEWEPKPVNQVYTVQISTKSGDWKSKCFYTTDTECDLT   60
h133-158_r (SEQ ID NO:850)               SGTTNTVAAYNLTWKSTNFKTILEWEPKPVNQVYTVQISTKSGDWKSKCFYTTDTECDLT   60
h133-145_r (SEQ ID NO:851)               SGTTNTVAAYNLTWKSTNFKTILEWEPKPVNQVYTVQISTKSGDWKSKCFYTTDTECDLT   60
h133-139_r (SEQ ID NO:852)               SGTTNTVAAYNLTWKSTNFKTILEWEPKPVNQVYTVQISTKSGDWKSKCFYTTDTECDLT   60
h140-145_r (SEQ ID NO:853)               SGTTNTVAAYNLTWKSTNFKTILEWEPKPVNQVYTVQISTKSGDWKSKCFYTTDTECDLT   60
h146-158_r (SEQ ID NO:854)               SGTTNTVAAYNLTWKSTNFKTILEWEPKPVNQVYTVQISTKSGDWKSKCFYTTDTECDLT   60
h146-151_r (SEQ ID NO:855)               SGTTNTVAAYNLTWKSTNFKTILEWEPKPVNQVYTVQISTKSGDWKSKCFYTTDTECDLT   60
h152-158_r (SEQ ID NO:856)               SGTTNTVAAYNLTWKSTNFKTILEWEPKPVNQVYTVQISTKSGDWKSKCFYTTDTECDLT   60
h159-219_r (SEQ ID NO:857)               SGTTNTVAAYNLTWKSTNFKTILEWEPKPVNQVYTVQISTKSGDWKSKCFYTTDTECDLT   60
h159-189_r (SEQ ID NO:858)               SGTTNTVAAYNLTWKSTNFKTILEWEPKPVNQVYTVQISTKSGDWKSKCFYTTDTECDLT   60
h159-174_r (SEQ ID NO:859)               SGTTNTVAAYNLTWKSTNFKTILEWEPKPVNQVYTVQISTKSGDWKSKCFYTTDTECDLT   60
h159-166_r (SEQ ID NO:860)               SGTTNTVAAYNLTWKSTNFKTILEWEPKPVNQVYTVQISTKSGDWKSKCFYTTDTECDLT   60
h167-174_r (SEQ ID NO:861)               SGTTNTVAAYNLTWKSTNFKTILEWEPKPVNQVYTVQISTKSGDWKSKCFYTTDTECDLT   60
h175-189_r (SEQ ID NO:862)               SGTTNTVAAYNLTWKSTNFKTILEWEPKPVNQVYTVQISTKSGDWKSKCFYTTDTECDLT   60
h190-219_r (SEQ ID NO:863)               SGTTNTVAAYNLTWKSTNFKTILEWEPKPVNQVYTVQISTKSGDWKSKCFYTTDTECDLT   60
```

Figure 36 (continued)

```
hTF (SEQ ID NO:810)           DEIVKDVKQTYLARVFSYPAGNVEST--------GSAGEPLYENSPEFTPYLETNLGQPTIQ   114
rTF (SEQ ID NO:838)           DEIVKDVAWTYEARVLSVPWRNSTHGKETLFGTNGEEPFFTNARKFLPYRQTKIGQPVIQ   114
h1-107_r (SEQ ID NO:839)      DEIVKDVAWTYEARVLSVPWRNSTHGKETLFGTNGEEPFFTNARKFLPYRQTKLGQPTIQ   114
h1-77_r (SEQ ID NO:840)       DEIVKDVAWTYEARVLSYPAGNVEST--------GSAGEPLYENSPEFTPYLETNLGQPTIQ   114
h1-38_r (SEQ ID NO:841)       DEIVKDVNWTYEARVLSYPAGNVEST--------GSAGEPLYENSPEFTPYLETNLGQPTIQ   114
h39-77_r (SEQ ID NO:842)      DEIVKDVKQTYLARVFSYPWRNSTHG--------THGEEPFFTNARKFLPYRQTKLGQPTIQ   114
h78-107_r (SEQ ID NO:843)     DEIVKDVKQTYLARVFSVPWRNSTHGKETLFGTNGEEPFFTNARKFLPYRQTKLGQPTIQ   114
h78-107_r.v2 (SEQ ID NO:844)  DEIVKDVKQTYLARVFSVPWRNSTHGKETLFGTNGEEPPYENSPEFTPYLETNLGQPTIQ   114
h78-93_r (SEQ ID NO:845)      DEIVKDVKQTYLARVFSVPWRNSTHGKETLFGTNGEEPPYENSPEFTPYLETNLGQPTIQ   114
h94-107_r (SEQ ID NO:846)     DEIVKDVKQTYLARVFSYPAGNVEST--------GSAGEPLFTNARKFLPYRQTKLGQPVIQ   114
h108-219_r (SEQ ID NO:847)    DEIVKDVKQTYLARVFSYPAGNVEST--------GSAGEPLYENSPEFTPYLETNIGQPVIQ   113
h108-158_r (SEQ ID NO:848)    DEIVKDVKQTYLARVFSYPAGNVEST--------GSAGEPLYENSPEFTPYLETNLGQPTIQ   114
h108-132_r (SEQ ID NO:849)    DEIVKDVKQTYLARVFSYPAGNVEST--------GSAGEPLYENSPEFTPYLETNLGQPTIQ   114
h133-158_r (SEQ ID NO:850)    DEIVKDVKQTYLARVFSYPAGNVEST--------GSAGEPLYENSPEFTPYLETNLGQPTIQ   114
h133-145_r (SEQ ID NO:851)    DEIVKDVKQTYLARVFSYPAGNVEST--------GSAGEPLYENSPEFTPYLETNLGQPTIQ   114
h133-139_r (SEQ ID NO:852)    DEIVKDVKQTYLARVFSYPAGNVEST--------GSAGEPLYENSPEFTPYLETNLGQPTIQ   114
h140-145_r (SEQ ID NO:853)    DEIVKDVKQTYLARVFSYPAGNVEST--------GSAGEPLYENSPEFTPYLETNLGQPTIQ   114
h146-158_r (SEQ ID NO:854)    DEIVKDVKQTYLARVFSYPAGNVEST--------GSAGEPLYENSPEFTPYLETNLGQPTIQ   114
h146-151_r (SEQ ID NO:855)    DEIVKDVKQTYLARVFSYPAGNVEST--------GSAGEPLYENSPEFTPYLETNLGQPTIQ   114
h152-158_r (SEQ ID NO:856)    DEIVKDVKQTYLARVFSYPAGNVEST--------GSAGEPLYENSPEFTPYLETNLGQPTIQ   114
h159-219_r (SEQ ID NO:857)    DEIVKDVKQTYLARVFSYPAGNVEST--------GSAGEPLYENSPEFTPYLETNLGQPTIQ   114
h159-189_r (SEQ ID NO:858)    DEIVKDVKQTYLARVFSYPAGNVEST--------GSAGEPLYENSPEFTPYLETNLGQPTIQ   114
h159-174_r (SEQ ID NO:859)    DEIVKDVKQTYLARVFSYPAGNVEST--------GSAGEPLYENSPEFTPYLETNLGQPTIQ   114
h167-174_r (SEQ ID NO:860)    DEIVKDVKQTYLARVFSYPAGNVEST--------GSAGEPLYENSPEFTPYLETNLGQPTIQ   114
h167-174_r (SEQ ID NO:861)    DEIVKDVKQTYLARVFSYPAGNVEST--------GSAGEPLYENSPEFTPYLETNLGQPTIQ   114
h175-189_r (SEQ ID NO:862)    DEIVKDVKQTYLARVFSYPAGNVEST--------GSAGEPLYENSPEFTPYLETNLGQPTIQ   114
h190-219_r (SEQ ID NO:863)    DEIVKDVKQTYLARVFSYPAGNVEST--------GSAGEPLYENSPEFTPYLETNLGQPTIQ   114
                              ********:** ****:*  *                     *     *: *:: ****
```

| | | |
|---|---|---|
| hTF (SEQ ID NO:810) | FLIDVDKGENYCRSVQAVIPSRTVNRKSTDSPVECMGQEKGEFRE | 219 |
| rTF (SEQ ID NO:838) | FLIDVEKGVSYCFFAQAVIFSRKTNRKSPESITKCTEQWKSVLGE | 219 |
| h1-107_r (SEQ ID NO:839) | FLIDVDKGENYCFSVQAVIPSRTVNRKSTDSPVECMGQEKGEFRE | 219 |
| h1-77_r (SEQ ID NO:840) | FLIDVDKGENYCFSVQAVIPSRTVNRKSTDSPVECMGQEKGEFRE | 219 |
| h1-38_r (SEQ ID NO:841) | FLIDVDKGENYCFSVQAVIPSRTVNRKSTDSPVECMGQEKGEFRE | 219 |
| h39-77_r (SEQ ID NO:842) | FLIDVDKGENYCFSVQAVIPSRTVNRKSTDSPVECMGQEKGEFRE | 219 |
| h78-107_r (SEQ ID NO:843) | FLIDVDKGENYCFSVQAVIPSRTVNRKSTDSPVECMGQEKGEFRE | 219 |
| h78-107_r.v2 (SEQ ID NO:844) | FLIDVDKGENYCFSVQAVIPSRTVNRKSTDSPVECMGQEKGEFRE | 219 |
| h79-93_r (SEQ ID NO:845) | FLIDVDKGENYCFSVQAVIPSRTVNRKSTDSPVECMGQEKGEFRE | 219 |
| h94-107_r (SEQ ID NO:846) | FLIDVDKGENYCFSVQAVIPSRTVNRKSTDSPVECMGQEKGEFRE | 219 |
| h108-219_r (SEQ ID NO:847) | FLIDVEKGVSYCFFAQAVIFSRKTNHKSPESITKCTEQWKSVLGE | 219 |
| h108-158_r (SEQ ID NO:848) | FLIDVDKGENYCFSVQAVIPSRTVNRASTDSPVECMGQEKGEFRE | 219 |
| h108-132_r (SEQ ID NO:849) | FLIDVDKGENYCFSVQAVIPSRTVNRKSTDSPVECMGQEKGEFRE | 219 |
| h133-158_r (SEQ ID NO:850) | FLIDVDKGENYCFSVQAVIPSRTVNRKSTDSPVECMGQEKGEFRE | 219 |
| h133-145_r (SEQ ID NO:851) | FLIDVDKGENYCFSVQAVIPSRTVNRKSTDSPVECMGQEKGEFRE | 219 |
| h133-139_r (SEQ ID NO:852) | FLIDVDKGENYCFSVQAVIPSRTVNRKSTDSPVECMGQEKGEFRE | 219 |
| h140-145_r (SEQ ID NO:853) | FLIDVDKGENYCFSVQAVIPSRTVNRKSTDSPVECMGQEKGEFRE | 219 |
| h146-158_r (SEQ ID NO:854) | FLIDVEKGVSYCFFAQAVIPSRTVNRKSTDSPVECMGQEKGEFRE | 219 |
| h146-151_r (SEQ ID NO:855) | FLIDVEKGVSYCFFAQAVIPSRTVNRKSTDSPVECMGQEKGEFRE | 219 |
| h152-158_r (SEQ ID NO:856) | FLIDVDKGENYCFSVQAVIFSRKTNHKSPESITKCTEQWKSVLGE | 219 |
| h159-219_r (SEQ ID NO:857) | FLIDVDKGENYCFSVQAVIPSRTVNRKSTDSPVECMGQEKGEFRE | 219 |
| h159-189_r (SEQ ID NO:858) | FLIDVDKGENYCFSVQAVIPSRTVNRKSTDSPVECMGQEKGEFRE | 219 |
| h159-174_r (SEQ ID NO:859) | FLIDVDKGENYCFSVQAVIPSRTVNRKSTDSPVECMGQEKGEFRE | 219 |
| h159-166_r (SEQ ID NO:860) | FLIDVDKGENYCFSVQAVIPSRTVNRKSTDSPVECMGQEKGEFRE | 219 |
| h167-174_r (SEQ ID NO:861) | FLIDVDKGENYCFSVQAVIPSRTVNRKSTDSPVECMGQEKGEFRE | 219 |
| h175-189_r (SEQ ID NO:862) | FLIDVEKGVSYCFFAQAVIFSRKTNHKSPESITKCTEQWKSVLGE | 219 |
| h190-219_r (SEQ ID NO:863) | FLIDVDKGENYCFSVQAVIFSRKTNHKSPESITKCTEQWKSVLGE | 219 |

Figure 37

```
rTF    (SEQ ID NO:838)  -AGTPPGKAFNLTWISTDFKTILEWQPKPTNYTYTVQISDRSRNWKYKCTGTTDTHCDLT  59
hTF    (SEQ ID NO:810)  SGTTNTVAAYNLTWKSTNFKTILEWEPKPVNQVYTVQISTKSGDWKSKCFYTTDTECDLT  59
r141-194_h (SEQ ID NO:864) -AGTPPGKAFNLTWISTDFKTILEWQPKPTNYTYTVQISDRSRNWKYKCTGTTDTECDLT  59
                          .  ***  ::**:* :*:  ..:* * ..*: *.:* ***** rTF    (SEQ ID NO:838)  DEIVKDVNWTYEARVLSVPWRNSTHGKETLFGTHGEEPFTNARKFLPYRDFKIGQPVIQ 119
hTF    (SEQ ID NO:810)  DEIVKDVKQTYLARVFSYPAGNVEST------GSAGEPLYENSPEFTPYLNWLGQPTTQ 119
r141-194_h (SEQ ID NO:864) DEIVKDVNWTYEARVLSVPWRNSTHGKETLFGTHGEEPFTNARKFLPYRDFKIGQPVIQ 119
                          *****:   ***:* *  .  ..             **.*:   *  :***  * rTF    (SEQ ID NO:838)  KYEGGTKLKVFVKDSFTLVRANGFFLTLRQVEGNDLGYIFYRDSSTGKKTNTHTNE   179
hTF    (SEQ ID NO:810)  SFEQVGTKVNVTVEDERTLVRRNNTFISLRDVFGKDLIYTLYYWKSSSSGKKTAKTNTNE 179
r141-194_h (SEQ ID NO:864) KYEGGGTKLKVTVKDSFTLVPRNNTFISLRDVFGKDLIYTLYYWKSSSSGKKTAKTNTNE 179
                           :*: ***: *.*:*.***  .. *: **:*.*:**  * *.   .*:*: * rTF    (SEQ ID NO:838)  FLIDEKGVSYCFAQAVIFSRKTNHKSPESITKCTEQWKSVLGE           224
hTF    (SEQ ID NO:810)  FLEQVDKGENYCESVQAVIFSRTVNRKSTDSPVECMGQEKGEFRE         225
r141-194_h (SEQ ID NO:864) FLIDVDKGENYCFSVQAVIFSRKTNHKSPESITKCTEQWKSVLGE        224
                          **       .**  .:******.. ::* :*  *  *::*
```

Figure 38

```
hTF       (SEQ ID NO:810)   SGTTNTVAAWNLIWKSTNFKTILEWEPKPVNQVTVQISTKSGDWKSKCFYTTPECDLT        60
rTF       (SEQ ID NO:838)   -AGTPRGKAFNLTWISTDRKTILEWQEPKPTNYTYTVQISDRSRNWKYKCTGTDTECDLT       60
hTF_K68N  (SEQ ID NO:865)   SGTTNTVAAWNLIWKSTNFKTILEWEPKPVNQVTVQISTKSGDWKSKCFYTTDTECDLT        60
hTF_K149N (SEQ ID NO:866)   SGTTNTVAAWNLIWKSTNFKTILEWEPKPVNQVTVQISTKSGDWKSKCFYTTDTECDLT        60
hTF_N171H_T197K (SEQ ID NO:867) SGTTNTVAAWNLIWKSTNFKTILEWEPKPVNQVTVQISTKSGDWKSKCFYTTDTECDLT    60
                                 *****.******** :**********.*   . :****** .**** hTF       (SEQ ID NO:810)   DEIVKDVKQTYLARVFSYPAGNVEST------GSAGEPLYENSPEFTPYLETMLGQPTIQ     114
rTF       (SEQ ID NO:838)   DEIVKDVNWTTEAKVLSVFWRNSTNGKETLWGIHGRKKPPFTNARKFLPYRDTIKIGQPVTQ    114
hTF_K68N  (SEQ ID NO:865)   DEIVKDVNQTYLARVFSYPAGNVEST------GSAGEPLYENSPEFTPYLETMLGQPTIQ     114
hTF_K149N (SEQ ID NO:866)   DEIVKDVKQTYLARVFSYPAGNVEST------GSAGEPLYENSPEFTPYLETMLGQPTIQ     114
hTF_N171H_T197K (SEQ ID NO:867) DEIVKDVKQTYLARVFSYPAGNVEST------GSAGEPLYENSPEFTPYLETMLGQPTIQ     114
                                 ******:   *:.:**.: ..*.           *.**::****  ::::.*.:.

hTF       (SEQ ID NO:810)   SFEQVGTKVNVTVEDERTLVRRNTFLSLRDVFGKDLIYTLYYWKSSSSGKKTAKTNTNE     174
rTF       (SEQ ID NO:838)   NYEQSSRKLKVTVRDSFTLVRKAGTFLILRQVFGKDLGYTLIHYRKDSSTGRKNTISHTNE    174
hTF_K68N  (SEQ ID NO:865)   SFEQVGTKVNVTVEDERTLVRRNMFLSLRDVFGKDLIYTLYYWKSSSSGKKTAKTNTNE     174
hTF_K149N (SEQ ID NO:866)   SFEQVGTKVNVTVEDERTLVRRNMFLSLRDVFGKDLIYTLYYWKSSSSGKKTAKTNTNE     174
hTF_N171H_T197K (SEQ ID NO:867) SFEQVGTKVNVTVEDERTLVRRNMFLSRKVNRKSTDSPVECMGQEKGEFRE              174
                                 .:**..*:::** *. **:.   *:.*.** *: *:.*..  :**.:.:* hTF       (SEQ ID NO:810)   FLIPVDRGENYCFSVQAVIPSRTVNRKSTDSPVECMGQEKGEHRE                    219
rTF       (SEQ ID NO:838)   FLIDVEEKGVSICFFAQAVIFSRKTNHKSPESITKCTECQWKSVLGE                  219
hTF_K68N  (SEQ ID NO:865)   FLIPVDRGENYCFSVQAVIPSPTVNRKSTDSPVECMGQEKGEHRE                    219
hTF_K149N (SEQ ID NO:866)   FLIPVDRGENYCFSVQAVIPSPTVNRKSTDSPVECMGQEKGEFPE                    219
hTF_N171H_T197K (SEQ ID NO:867) FLIPVDRGENYCFSVQAVIPSRKVNRKSTDSPVECMGQEKGEFPE                219
                                 *****,:*  ,*** .****  .***:*:.:.::**:*.*:
```

ANTI-TISSUE FACTOR ANTIBODIES, ANTIBODY-DRUG CONJUGATES, AND RELATED METHODS

CROSS REFERENCE TO RELATED APPLICATIONS

This application is a divisional of U.S. application Ser. No. 17/458,507, filed Aug. 26, 2021, which is a continuation of U.S. application Ser. No. 16/959,652, filed Jul. 1, 2020, which is a U.S. National Phase Application of International Application No. PCT/US2019/012427, filed Jan. 4, 2019, which claims the benefit of U.S. Provisional Application Nos. 62/613,545, filed Jan. 4, 2018; 62/613,564, filed Jan. 4, 2018; 62/646,788, filed Mar. 22, 2018; 62/713,797, filed Aug. 2, 2018; and 62/713,804, filed Aug. 2, 2018, each of which is hereby incorporated by reference in its entirety.

SEQUENCE LISTING

The instant application contains a Substitute Sequence Listing which has been submitted in XML format via Patent Center and is hereby incorporated by reference in its entirety. Said Sequence Listing XML file submitted via Patent Center was created on Dec. 23, 2024, is named "14529-124-999-SUB-SL.xml", and is 823,222 bytes in size.

BACKGROUND

Blood coagulation involves a complex set of processes that result in blood clotting. Tissue factor (TF) plays an important role in these coagulation processes. TF is a cell surface receptor for the serine protease factor VIIa (FVIIa). The TF/FVIIa complex catalyzes conversion of the inactive protease factor X (FX) into the active protease factor Xa (FXa). FXa and its co-factor FVa form the prothrombinase complex, which generates thrombin from prothrombin. Thrombin converts soluble fibrinogen into insoluble strands of fibrin and catalyzes many other coagulation-related processes.

TF is over-expressed on multiple types of solid tumors. In cancer, TF/FVIIa signaling can support angiogenesis, tumor progression, and metastasis. Increased TF expression can also induce inflammation and/or angiogenesis in many other diseases, including wet age-related macular degeneration (AMD) and diabetic retinopathy.

SUMMARY

Provided herein are antibodies that specifically bind human Tissue Factor (TF), anti-TF antibody-drug conjugates, and related methods.

In one aspect, provided herein is an isolated human antibody which binds to the extracellular domain of human Tissue Factor (TF), wherein the antibody binds human TF at a human TF binding site that is distinct from a human TF binding site bound by human FVIIa.

In some embodiments, (1) the isolated antibody does not inhibit human thrombin generation as determined by thrombin generation assay (TGA) compared to a reference antibody comprising a $V_H$ sequence of SEQ ID NO:821 and a VL sequence of SEQ ID NO:822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody inhibits human thrombin generation to a lesser extent as determined by thrombin generation assay (TGA) compared to a reference antibody comprising a $V_H$ sequence of SEQ ID NO:821 and a VL sequence of SEQ ID NO:822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody allows human thrombin generation to a greater extent as determined by thrombin generation assay (TGA) compared to a reference antibody comprising a $V_H$ sequence of SEQ ID NO:821 and a $V_L$ sequence of SEQ ID NO:822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO:822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, (1) the isolated antibody allows human thrombin generation by a greater amount as determined by thrombin generation assay (TGA) compared to a reference antibody comprising a $V_H$ sequence of SEQ ID NO:821 and a $V_L$ sequence of SEQ ID NO:822, and (2) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence x[K/S]Ax[S/Y]x[S/Y/N]LEx[S/Y]; and a VL-CDR3 comprising the sequence set forth in SEQ ID NO:784.

In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the isolated antibody does not inhibit human thrombin generation as determined by thrombin generation assay (TGA) compared to a reference antibody comprising a $V_H$ sequence of SEQ ID NO:821 and a $V_L$ sequence of SEQ ID NO:822.

In some embodiments, the isolated antibody inhibits human thrombin generation to a lesser extent as determined by thrombin generation assay (TGA) compared to a reference antibody comprising a $V_H$ sequence of SEQ ID NO:821 and a $V_L$ sequence of SEQ ID NO:822.

In some embodiments, the isolated antibody allows human thrombin generation to a greater extent as determined by thrombin generation assay (TGA) compared to a reference antibody comprising a $V_H$ sequence of SEQ ID NO:821 and a $V_L$ sequence of SEQ ID NO:822.

In some embodiments, the isolated antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO:822.

In some embodiments, the isolated antibody allows human thrombin generation by a greater amount as determined by thrombin generation assay (TGA) compared to a reference antibody comprising a $V_H$ sequence of SEQ ID NO:821 and a $V_L$ sequence of SEQ ID NO:822.

In some embodiments, the antibody does not inhibit human thrombin generation as determined by thrombin generation assay (TGA). In some embodiments, the antibody does not reduce the thrombin peak on a thrombin generation curve (Peak IIa) compared to an isotype control. In some embodiments, the antibody does not increase the time from the assay start to the thrombin peak on a thrombin generation curve (ttPeak) compared to an isotype control. In some embodiments, the antibody does not decrease the endogenous thrombin potential (ETP) as determined by the area under a thrombin generation curve compared to an isotype control. In some embodiments, the antibody allows human thrombin generation as determined by thrombin generation assay (TGA). In some embodiments, the antibody maintains the thrombin peak on a thrombin generation curve (Peak IIa) compared to an isotype control. In some embodiments, the antibody maintains the time from the assay start to the thrombin peak on a thrombin generation curve (ttPeak) compared to an isotype control. In some embodiments, the antibody preserves the endogenous thrombin potential (ETP) as determined by the area under a thrombin generation curve compared to an isotype control.

In some embodiments, the antibody binds human TF at a human TF binding site that is distinct from a human TF binding site bound by human FX. In some embodiments, the antibody does not interfere with the ability of TF:FVIIa to convert FX into FXa.

In some embodiments, the antibody does not compete for binding to human TF with human FVIIa.

In some embodiments, the antibody does not inhibit human thrombin generation as determined by thrombin generation assay (TGA), allows human thrombin generation as determined by thrombin generation assay (TGA), binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not decrease the endogenous thrombin potential (ETP) as determined by the area under a thrombin generation curve compared to an isotype control, allows human thrombin generation as determined by thrombin generation assay (TGA), preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not reduce the thrombin peak on a thrombin generation curve (Peak IIa) compared to an isotype control, does not increase the time from the assay start to the thrombin peak on a thrombin generation curve (ttPeak) compared to an isotype control, does not decrease the endogenous thrombin potential (ETP) as determined by the area under a thrombin generation curve compared to an isotype control, allows human thrombin generation as determined by thrombin generation assay (TGA), maintains the thrombin peak on a thrombin generation curve (Peak IIa) compared to an isotype control, maintains the time from the assay start to the thrombin peak on a thrombin generation curve (ttPeak) compared to an isotype control, preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody inhibits FVIIa-dependent TF signaling.

In some embodiments, the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay. In some embodiments, the mutation at amino acid residue 149 of the sequence shown in SEQ ID NO:810 is K149N.

In some embodiments, the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay. In some embodiments, the mutation at amino acid residue 68 of the sequence shown in SEQ ID NO:810 is K68N.

In some embodiments, the binding between the isolated antibody and a variant TF extracellular domain comprising mutations at amino acid residues 171 and 197 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay. In some embodiments, the mutations at amino acid residues 171 and 197 of the sequence shown in SEQ ID NO:810 are N171H and T197K.

In some embodiments, the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810; the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810; the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810; and the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutation at amino acid residue 68 of the sequence shown in SEQ ID NO:810 is K68N.

In some embodiments, the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810; the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810; the binding between the isolated antibody and a variant TF extracellular domain comprising mutations at amino acid residues 171 and 197 of the sequence shown in SEQ ID NO:810 is less than 50% of the binding between the isolated antibody and the extracellular domain of TF of the sequence shown in SEQ ID NO:810; the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810; the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810; and the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; the mutation at amino acid residue 68 of the sequence shown in SEQ ID NO: 810 is K68N; and the mutations at amino acid residues 171 and 197 of the sequence shown in SEQ ID NO:810 are N171H and T197K.

In some embodiments, the antibody binds to cynomolgus TF. In some embodiments, the antibody binds to mouse TF. In some embodiments, the antibody binds to rabbit TF. In some embodiments, the antibody binds to pig TF.

In some embodiments, the antibody reduces lesion size in a swine choroidal neovascularization (CNV) model.

In some embodiments, the antibody: (a) does not inhibit human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) allows human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are NT71H and T197K.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; and (i) binds to rabbit TF.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; and (k) binds to rabbit TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; and (o) binds to rabbit TF.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; (i) binds to rabbit TF; (j) binds to pig TF; and (k) reduces lesion size in a swine choroidal neovascularization (CNV) model.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; (k) binds to rabbit TF; (l) binds to pig TF; and (m) reduces lesion size in a swine choroidal neovascularization (CNV) model.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; and (q) reduces lesion size in a swine choroidal neovascularization (CNV) model.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) reduces lesion size in a swine choroidal neovascularization (CNV) model; (r) the binding between the isolated antibody and a variant TF extracellular domain comprising a mutation at amino acid residue 149 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (s) the binding between the isolated antibody and a variant TF extracellular domain comprising a mutation at amino acid residue 68 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (t) the binding between the isolated antibody and a variant TF extracellular domain comprising mutations at amino acid residues 171 and 197 of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (u) the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (v) the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (w) the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (x) the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (y) the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (z) the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (aa) the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (bb) the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; and (cc) wherein the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) reduces lesion size in a swine choroidal neovascularization (CNV) model; (r) the binding between the isolated antibody and a variant TF extracellular domain comprising a mutation K149N of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (s) the binding between the isolated antibody and a variant TF extracellular domain comprising a mutation K68N of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (t) the binding between the isolated antibody and a variant TF extracellular domain comprising mutations N171H and T197K of the sequence shown in SEQ ID NO:810 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (u) the binding between the isolated antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (v) the binding between the isolated antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (w) the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay; (x) the binding between the isolated antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (y) the binding between the isolated antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (z) the binding between the isolated antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (aa) the binding between the isolated antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; (bb) the binding between the isolated antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay; and (cc) wherein the binding between the isolated antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody competes for binding to human TF with the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody competes for binding to human TF with the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody competes for binding to human TF with the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody binds to the same human TF epitope bound by the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain Complementary Determining Regions (CDRs) and all three light chain CDRs from: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the three heavy chain CDRs and the three light chain CDRs are determined using Kabat, Chothia, AbM, Contact, or IMGT numbering.

In some embodiments, the antibody comprises all three heavy chain Complementary Determining Regions (CDRs) and all three light chain CDRs from: the antibody designated 25A, the antibody designated 25A5-T, the antibody designated 25A3, the antibody designated 25A5, the antibody designated 25G, the antibody designated 25G1, or the antibody designated 25G9.

In some embodiments, the antibody comprises all three heavy chain Complementary Determining Regions (CDRs) and all three light chain CDRs from: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain CDRs and all three light chain CDRs from the antibody designated 25A. In some embodiments, the antibody comprises all three heavy chain CDRs and all three light chain CDRs from the antibody designated 25A3. In some embodiments, the antibody comprises all three heavy chain CDRs and all three light chain CDRs from the antibody designated 25A5. In some embodiments, the antibody comprises all three heavy chain CDRs and all three light chain CDRs from the antibody designated 25A5-T. In some embodiments, the antibody comprises all three heavy chain CDRs and all three light chain CDRs from the antibody designated 25G. In some embodiments, the antibody comprises all three heavy chain CDRs and all three light chain CDRs from the antibody designated 25G1. In some embodiments, the antibody comprises all three heavy chain CDRs and all three light chain CDRs from the antibody designated 25G9. In some embodiments, the antibody comprises all three heavy chain CDRs and all three light chain CDRs from the antibody designated 43B. In some embodiments, the antibody comprises all three heavy chain CDRs and all three light chain CDRs from the antibody designated 43B1. In some embodiments, the antibody comprises all three heavy chain CDRs and all three light chain CDRs from the antibody designated 43B7. In some embodiments, the antibody comprises all three heavy chain CDRs and all three light chain CDRs from the antibody designated 43D. In some embodiments, the antibody comprises all three heavy chain CDRs and all three light chain CDRs from the antibody designated 43D7. In some embodiments, the antibody comprises all three heavy chain CDRs and all three light chain CDRs from the antibody designated 43D8. In some embodiments, the antibody comprises all three heavy chain CDRs and all three light chain CDRs from the antibody designated 43E. In some embodiments, the antibody comprises all three heavy chain CDRs and all three light chain CDRs from the antibody designated 43Ea.

In some embodiments, the antibody comprises a $V_H$ sequence of SEQ ID NO:113 and a $V_L$ sequence of SEQ ID NO:114. In some embodiments, the antibody comprises a $V_H$ sequence of SEQ ID NO:151 and a $V_L$ sequence of SEQ ID NO:152. In some embodiments, the antibody comprises a $V_H$ sequence of SEQ ID NO:189 and a $V_L$ sequence of SEQ ID NO:190. In some embodiments, the antibody comprises a $V_H$ sequence of SEQ ID NO:836 and a $V_L$ sequence of SEQ ID NO:837. In some embodiments, the antibody comprises a $V_H$ sequence of SEQ ID NO:227 and a $V_L$ sequence of SEQ ID NO:228. In some embodiments, the antibody comprises a $V_H$ sequence of SEQ ID NO:265 and a $V_L$ sequence of SEQ ID NO:266. In some embodiments, the antibody comprises a $V_H$ sequence of SEQ ID NO:303 and a $V_L$ sequence of SEQ ID NO:304. In some embodiments, the antibody comprises a $V_H$ sequence of SEQ ID NO:455 and a $V_L$ sequence of SEQ ID NO:456. In some embodiments, the antibody comprises a $V_H$ sequence of SEQ ID NO:493 and a $V_L$ sequence of SEQ ID NO:494. In some embodiments, the antibody comprises a $V_H$ sequence of SEQ ID NO:531 and a $V_L$ sequence of SEQ ID NO:532. In some embodiments, the antibody comprises a $V_H$ sequence of SEQ ID NO:569 and a $V_L$ sequence of SEQ ID NO:570. In some embodiments, the antibody comprises a $V_H$ sequence of SEQ ID NO:607 and a $V_L$ sequence of SEQ ID NO:608. In some embodiments, the antibody comprises a $V_H$ sequence of SEQ ID NO:645 and a $V_L$ sequence of SEQ ID NO:646. In some embodiments, the antibody comprises a $V_H$ sequence of SEQ ID NO:683 and a $V_L$ sequence of SEQ ID NO:684. In some embodiments, the antibody comprises a $V_H$ sequence of SEQ ID NO:721 and a $V_L$ sequence of SEQ ID NO:722.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence x[K/S]Ax[S/Y]x[S/Y/N]LEx[S/Y]; and a VL-CDR3 comprising the sequence set forth in SEQ ID NO:784. In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877. In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883. In some embodiments, the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence GAx[S/D/F/Y]x[S/T]Rx[A/Q]x[T/N]; and a VL-CDR3 comprising the sequence set forth in SEQ ID NO:802.

In some embodiments, the antibody comprises a $V_H$ sequence of SEQ ID NO:763 and a $V_L$ sequence of SEQ ID NO:764. In some embodiments, the antibody comprises a $V_H$ sequence of SEQ ID NO:868 and a $V_L$ sequence of SEQ ID NO:869. In some embodiments, the antibody comprises a $V_H$ sequence of SEQ ID NO:870 and a $V_L$ sequence of SEQ ID NO:871. In some embodiments, the antibody comprises a $V_H$ sequence of SEQ ID NO:769 and a $V_L$ sequence of SEQ ID NO:770.

In some embodiments, the antibody comprises: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody comprises: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody consists of: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In another aspect, provided herein is an isolated antibody comprising all three heavy chain Complementary Determining Regions (CDRs) and all three light chain CDRs from: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody is human, humanized, or chimeric.

In some embodiments, the three heavy chain CDRs and the three light chain CDRs are determined using Kabat, Chothia, AbM, Contact, or IMGT numbering.

In some embodiments, the antibody comprises all three heavy chain CDRs and all three light chain CDRs from: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody comprises all three heavy chain CDRs and all three light chain CDRs from the antibody designated 25A. In some embodiments, the antibody comprises all three heavy chain CDRs and all three light chain CDRs from the antibody designated 25A3. In some embodiments, the antibody comprises all three heavy chain CDRs and all three light chain CDRs from the antibody designated 25A5. In some embodiments, the antibody comprises all three heavy chain CDRs and all three light chain CDRs from the antibody designated 25A5-T. In some embodiments, the antibody comprises all three heavy chain CDRs and all three light chain CDRs from the antibody designated 25G.

In some embodiments, the antibody comprises all three heavy chain CDRs and all three light chain CDRs from the antibody designated 25G1. In some embodiments, the antibody comprises all three heavy chain CDRs and all three light chain CDRs from the antibody designated 25G9.

In some embodiments, the antibody comprises all three heavy chain CDRs and all three light chain CDRs from: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain CDRs and all three light chain CDRs from the antibody designated 43B. In some embodiments, the antibody comprises all three heavy chain CDRs and all three light chain CDRs from the antibody designated 43B1. In some embodiments, the antibody comprises all three heavy chain CDRs and all three light chain CDRs from the antibody designated 43B7. In some embodiments, the antibody comprises all three heavy chain CDRs and all three light chain CDRs from the antibody designated 43D. In some embodiments, the antibody comprises all three heavy chain CDRs and all three light chain CDRs from the antibody designated 43D7. In some embodiments, the antibody comprises all three heavy chain CDRs and all three light chain CDRs from the antibody designated 43D8. In some embodiments, the antibody comprises all three heavy chain CDRs and all three light chain CDRs from the antibody designated 43E. In some embodiments, the antibody comprises all three heavy chain CDRs and all three light chain CDRs from the antibody designated 43Ea.

In some embodiments, the antibody comprises a $V_H$ sequence of SEQ ID NO:113 and a $V_L$ sequence of SEQ ID NO:114. In some embodiments, the antibody comprises a $V_H$ sequence of SEQ ID NO:151 and a $V_L$ sequence of SEQ ID NO:152. In some embodiments, the antibody comprises a $V_H$ sequence of SEQ ID NO:189 and a $V_L$ sequence of SEQ ID NO:190. In some embodiments, the antibody comprises a $V_H$ sequence of SEQ ID NO:836 and a $V_L$ sequence of SEQ ID NO:837. In some embodiments, the antibody comprises a $V_H$ sequence of SEQ ID NO:227 and a $V_L$ sequence of SEQ ID NO:228. In some embodiments, the antibody comprises a $V_H$ sequence of SEQ ID NO:265 and a $V_L$ sequence of SEQ ID NO:266. In some embodiments, the antibody comprises a $V_H$ sequence of SEQ ID NO:303 and a $V_L$ sequence of SEQ ID NO:304. In some embodiments, the antibody comprises a $V_H$ sequence of SEQ ID NO:455 and a $V_L$ sequence of SEQ ID NO:456. In some embodiments, the antibody comprises a $V_H$ sequence of SEQ ID NO:493 and a $V_L$ sequence of SEQ ID NO:494. In some embodiments, the antibody comprises a $V_H$ sequence of SEQ ID NO:531 and a $V_L$ sequence of SEQ ID NO:532. In some embodiments, the antibody comprises a $V_H$ sequence of SEQ ID NO:569 and a $V_L$ sequence of SEQ ID NO:570. In some embodiments, the antibody comprises a $V_H$ sequence of SEQ ID NO:607 and a $V_L$ sequence of SEQ ID NO:608. In some embodiments, the antibody comprises a $V_H$ sequence of SEQ ID NO:645 and a $V_L$ sequence of SEQ ID NO:646. In some embodiments, the antibody comprises a $V_H$ sequence of SEQ ID NO:683 and a $V_L$ sequence of SEQ ID NO:684. In some embodiments, the antibody comprises a $V_H$ sequence of SEQ ID NO:721 and a $V_L$ sequence of SEQ ID NO:722.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence x[K/S]Ax[S/Y]x[S/Y/N]LEx[S/Y]; and a VL-CDR3 comprising the sequence set forth in SEQ ID NO:784. In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877. In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883. In some embodiments, the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence GAx[S/D/F/Y]x[S/T]Rx[A/Q]x[T/N]; and a VL-CDR3 comprising the sequence set forth in SEQ ID NO:802.

In some embodiments, the antibody comprises a $V_H$ sequence of SEQ ID NO:763 and a $V_L$ sequence of SEQ ID NO:764. In some embodiments, the antibody comprises a $V_H$ sequence of SEQ ID NO:868 and a $V_L$ sequence of SEQ ID NO:869. In some embodiments, the antibody comprises a $V_H$ sequence of SEQ ID NO:870 and a $V_L$ sequence of SEQ ID NO:871. In some embodiments, the antibody comprises a $V_H$ sequence of SEQ ID NO:769 and a $V_L$ sequence of SEQ ID NO:770.

In some embodiments, the antibody comprises: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody comprises: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody consists: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In another aspect, provided herein is an isolated antibody that competes for binding to human TF with: the antibody designated 1F, the antibody designated 1G, the antibody designated 29D, the antibody designated 29E, the antibody designated 39A, or the antibody designated 54E.

In some embodiments, the antibody is human, humanized, or chimeric.

In some embodiments, the antibody inhibits FVIIa-dependent TF signaling.

In some embodiments, the antibody binds to cynomolgus TF.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; and the binding between the isolated antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the binding between the isolated antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the isolated antibody and the extracellular domain of TF of the sequence shown in SEQ ID NO:810; the binding between the isolated antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the isolated antibody and the extracellular domain of TF of the sequence shown in SEQ ID NO:810; and wherein the binding between the isolated antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the isolated antibody and the extracellular domain of TF of the sequence shown in SEQ ID NO:810, as determined by the median fluorescence intensity value of the isolated antibody relative to an isotype control in a live cell staining assay.

In some embodiments, the antibody comprises all three heavy chain Complementary Determining Regions (CDRs) and all three light chain CDRs from: the antibody designated 1F, the antibody designated 1G, the antibody designated 29D, the antibody designated 29E, the antibody designated 39A, the antibody designated 43Ea, or the antibody designated 54E. In some embodiments, the three heavy chain CDRs and the three light chain CDRs are determined using Kabat, Chothia, AbM, Contact, or IMGT numbering.

In some embodiments, the antibody comprises all three heavy chain CDRs and all three light chain CDRs from the antibody designated 1F. In some embodiments, the antibody comprises all three heavy chain CDRs and all three light chain CDRs from the antibody designated 1G. In some embodiments, the antibody comprises all three heavy chain CDRs and all three light chain CDRs from the antibody designated 29D. In some embodiments, the antibody comprises all three heavy chain CDRs and all three light chain CDRs from the antibody designated 29E. In some embodiments, the antibody comprises all three heavy chain CDRs and all three light chain CDRs from the antibody designated 39A. In some embodiments, the antibody comprises all three heavy chain CDRs and all three light chain CDRs from the antibody designated 54E.

In some embodiments, the antibody comprises a $V_H$ sequence of SEQ ID NO:37 and a $V_L$ sequence of SEQ ID NO:38. In some embodiments, the antibody comprises a $V_H$ sequence of SEQ ID NO:75 and a $V_L$ sequence of SEQ ID NO:76. In some embodiments, the antibody comprises a $V_H$ sequence of SEQ ID NO:341 and a $V_L$ sequence of SEQ ID NO:342. In some embodiments, the antibody comprises a $V_H$ sequence of SEQ ID NO:379 and a $V_L$ sequence of SEQ ID NO:380. In some embodiments, the antibody comprises a $V_H$ sequence of SEQ ID NO:417 and a $V_L$ sequence of SEQ ID NO:418. In some embodiments, the antibody comprises a $V_H$ sequence of SEQ ID NO:759 and a $V_L$ sequence of SEQ ID NO:760.

In some embodiments, the antibody comprises: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL-CDR2 comprising the sequence set forth in SEQ ID NO:777; and a VL-CDR3 comprising the sequence set forth in SEQ ID NO:778. In some embodiments, the antibody comprises: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790. In some embodiments, the antibody comprises: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796. In some embodiments, the antibody comprises: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In some embodiments, the antibody comprises a $V_H$ sequence of SEQ ID NO:761 and a $V_L$ sequence of SEQ ID NO:762. In some embodiments, the antibody comprises a $V_H$ sequence of SEQ ID NO:765 and a $V_L$ sequence of SEQ ID NO:766. In some embodiments, the antibody comprises a $V_H$ sequence of SEQ ID NO:767 and a $V_L$ sequence of SEQ ID NO:768. In some embodiments, the antibody comprises a $V_H$ sequence of SEQ ID NO:771 and a $V_L$ sequence of SEQ ID NO:772.

In some embodiments, the antibody comprises: the antibody designated 1F, the antibody designated 1G, the antibody designated 29D, the antibody designated 29E, the antibody designated 39A, or the antibody designated 54E.

In some embodiments, the antibody consists of: the antibody designated 1F, the antibody designated 1G, the antibody designated 29D, the antibody designated 29E, the antibody designated 39A, or the antibody designated 54E.

In another aspect, provided herein is an isolated antibody comprising: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL- CDR2 comprising the sequence set forth in SEQ ID NO:777; and a VL-CDR3 comprising the sequence set forth in SEQ ID NO:778.

In another aspect, provided herein is an isolated antibody comprising: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence x[K/S]Ax[S/Y]x[S/Y/N]LEx[S/Y]; and a VL-CDR3 comprising the sequence set forth in SEQ ID NO:784.

In another aspect, provided herein is an isolated antibody comprising: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790.

In another aspect, provided herein is an isolated antibody comprising: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796.

In another aspect, provided herein is an isolated antibody comprising: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence GAx[S/D/F/Y]x[S/T]Rx[A/Q]x[T/N]; and a VL-CDR3 comprising the sequence set forth in SEQ ID NO:802.

In another aspect, provided herein is an isolated antibody comprising: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In another aspect, provided herein is an isolated antibody comprising: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In another aspect, provided herein is an isolated antibody comprising: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the antibody binds to human TF with a $K_D$ of less than or equal to 50 nM, 10 nM, 5 nM, 1 nM, 0.5 nM or 0.1 nM, as measured by Octet QK384 or Biacore assay.

In some embodiments, the antibody is a monoclonal antibody.

In some embodiments, the antibody is multispecific.

In some embodiments, the antibody is a Fab, Fab', F(ab')2, Fv, scFv, (scFv)$_2$, single chain antibody molecule, dual variable domain antibody, single variable domain antibody, linear antibody, or V domain antibody.

In some embodiments, the antibody comprises a scaffold, optionally wherein the scaffold is Fc, optionally human Fc. In some embodiments, the antibody comprises a heavy chain constant region of a class selected from IgG, IgA, IgD, IgE, and IgM. In some embodiments, the antibody comprises a heavy chain constant region of the class IgG and a subclass selected from IgG1, IgG2, IgG3, and IgG4. In some embodiments, the antibody comprises a heavy chain constant region of IgG1.

In some embodiments, the Fc comprises one or more modifications, wherein the one or more modifications result in increased half-life, increased antibody-dependent cellular cytotoxicity (ADCC), increased antibody-dependent cellular phagocytosis (ADCP), increased complement-dependent cytotoxicity (CDC), or decreased effector function, compared with the Fc without the one or more modifications.

In another aspect, provided herein is an isolated antibody that competes for binding to human TF with any antibody above.

In another aspect, provided herein is an isolated antibody that binds the human TF epitope bound by any antibody above.

In another aspect, provided herein is an isolated polynucleotide or set of polynucleotides encoding any antibody above, a $V_H$ thereof, a $V_L$ thereof, a light chain thereof, a heavy chain thereof, or an antigen-binding portion thereof.

In another aspect, provided herein is a vector or set of vectors comprising the polynucleotide or set of polynucleotides above.

In another aspect, provided herein is a host cell comprising the polynucleotide or set of polynucleotides above or the vector or set of vectors above.

In another aspect, provided herein is a method of producing an antibody comprising expressing the antibody with the host cell above and isolating the expressed antibody.

In another aspect, provided herein is a pharmaceutical composition comprising any antibody above and a pharmaceutically acceptable excipient.

In another aspect, provided herein is a method of treating or preventing a disease or condition in a subject in need thereof, comprising administering to the subject an effective amount of any antibody above or the pharmaceutical composition above.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the disease or condition involves neovascularization. In some embodiments, the disease or condition involving neovascularization is age-related macular degeneration (AMD), diabetic retinopathy, or cancer. In some embodiments, the disease or condition involves vascular inflammation.

In some embodiments, the method further comprises administering one or more additional therapeutic agents to the subject. In some embodiments, the additional therapeutic agent is formulated in the same pharmaceutical composition as the antibody. In some embodiments, the additional therapeutic agent is formulated in a different pharmaceutical composition from the antibody. In some embodiments, the additional therapeutic agent is administered prior to administering the antibody. In some embodiments, the additional therapeutic agent is administered after administering the antibody. In some embodiments, the additional therapeutic agent is administered contemporaneously with the antibody.

In another aspect, provided herein is a method of detecting TF in a subject having or suspected of having a disease or condition, the method comprising: (a) receiving a sample from the subject; and (b) detecting the presence or the level of TF in the sample by contacting the sample with any antibody above.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the disease or condition involves neovascularization. In some embodiments, the disease or condition involving neovascularization is age-related macular degeneration (AMD), diabetic retinopathy, or cancer. In some embodiments, the disease or condition involves vascular inflammation.

In another aspect, provided herein is a method of detecting TF in a subject having or suspected of having a disease or condition, the method comprising: (a) administering to the subject any antibody above; and (b) detecting the presence or the level of TF in the subject.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the disease or condition involves neovascularization. In some embodiments, the disease or condition involving neovascularization is age-related macular degeneration (AMD), diabetic retinopathy, or cancer. In some embodiments, the disease or condition involves vascular inflammation.

In another aspect, provided herein is a kit comprising any antibody above or the pharmaceutical composition above and instructions for use.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody binds to the extracellular domain of human Tissue Factor (TF) at a human TF binding site that is distinct from a human TF binding site bound by human FVIIa.

In some embodiments, (1) the antibody does not inhibit human thrombin generation as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody inhibits human thrombin generation to a lesser extent as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody allows human thrombin generation to a greater extent as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, (1) the antibody allows human thrombin generation by a greater amount as determined by thrombin generation assay (TGA) compared to a reference antibody comprising a $V_H$ sequence of SEQ ID NO:821 and a $V_L$ sequence of SEQ ID NO:822, and (2) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence x[K/S]Ax[S/Y]x[S/Y/N]LEx[S/Y]; and a VL-CDR3 comprising the sequence set forth in SEQ ID NO:784.

In some embodiments, the antibody comprises: a VH-CDR1 comprising the sequence set forth in SEQ ID NO:872; a VH-CDR2 HI comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the antibody does not inhibit human thrombin generation as determined by thrombin generation assay (TGA) compared to a reference antibody comprising a $V_H$ sequence of SEQ ID NO:821 and a $V_L$ sequence of SEQ ID NO:822.

In some embodiments, the antibody inhibits human thrombin generation to a lesser extent as determined by thrombin generation assay (TGA) compared to a reference antibody comprising a $V_H$ sequence of SEQ ID NO:821 and a $V_L$ sequence of SEQ ID NO:822.

In some embodiments, the antibody allows human thrombin generation to a greater extent as determined by thrombin generation assay (TGA) compared to a reference antibody comprising a $V_H$ sequence of SEQ ID NO:821 and a $V_L$ sequence of SEQ ID NO:822.

In some embodiments, the antibody inhibits human thrombin generation by a lesser amount as determined by thrombin generation assay (TGA) compared to a reference antibody comprising a $V_H$ sequence of SEQ ID NO:821 and a $V_L$ sequence of SEQ ID NO:822.

In some embodiments, the antibody allows human thrombin generation by a greater amount as determined by thrombin generation assay (TGA) compared to a reference antibody comprising a $V_H$ sequence of SEQ ID NO:821 and a $V_L$ sequence of SEQ ID NO:822.

In some embodiments, the antibody does not inhibit human thrombin generation as determined by thrombin generation assay (TGA). In some embodiments, the antibody does not reduce the thrombin peak on a thrombin generation curve (Peak IIa) compared to an isotype control. In some embodiments, the antibody does not increase the time from the assay start to the thrombin peak on a thrombin generation curve (ttPeak) compared to an isotype control. In some embodiments, the antibody does not decrease the endogenous thrombin potential (ETP) as determined by the area under a thrombin generation curve compared to an isotype control. In some embodiments, the antibody allows human thrombin generation as determined by thrombin generation assay (TGA). In some embodiments, the antibody maintains the thrombin peak on a thrombin generation curve (Peak IIa) compared to an isotype control. In some embodiments, the antibody maintains the time from the assay start to the thrombin peak on a thrombin generation curve (ttPeak) compared to an isotype control. In some embodiments, the antibody preserves the endogenous thrombin potential (ETP) as determined by the area under a thrombin generation curve compared to an isotype control.

In some embodiments, the antibody binds human TF at a human TF binding site that is distinct from a human TF binding site bound by human FX. In some embodiments, the antibody does not interfere with the ability of TF:FVIIa to convert FX into FXa.

In some embodiments, the antibody does not compete for binding to human TF with human FVIIa.

In some embodiments, the antibody does not inhibit human thrombin generation as determined by thrombin generation assay (TGA), allows human thrombin generation as determined by thrombin generation assay (TGA), binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not decrease the endogenous thrombin potential (ETP) as determined by the area under a thrombin generation curve compared to an isotype control, allows human thrombin generation as determined by thrombin generation assay (TGA), preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody does not inhibit human thrombin generation as determined by thrombin generation assay (TGA), does not reduce the thrombin peak on a thrombin generation curve (Peak IIa) compared to an isotype control, does not increase the time from the assay start to the thrombin peak on a thrombin generation curve (ttPeak) compared to an isotype control, does not decrease the endogenous thrombin potential (ETP) as determined by the area under a thrombin generation curve compared to an isotype control, allows human thrombin generation as determined by thrombin generation assay (TGA), maintains the thrombin peak on a thrombin generation curve (Peak IIa) compared to an isotype control, maintains the time from the assay start to the thrombin peak on a thrombin generation curve (ttPeak) compared to an isotype control, preserves the endogenous thrombin potential (ETP) as determined by the area under a thrombin generation curve compared to an isotype control, binds human TF at a human TF binding site that is distinct from a human TF binding site bound by human FX, does not interfere with the ability of TF:FVIIa to convert FX into FXa, and does not compete for binding to human TF with FVIIa.

In some embodiments, the antibody inhibits FVIIa-dependent TF signaling.

In some embodiments, the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N.

In some embodiments, the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 68 of the sequence shown in SEQ ID NO:810 is K68N.

In some embodiments, the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutation at amino acid residue 68 of the sequence shown in SEQ ID NO: 810 is K68N.

In some embodiments, the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, and wherein the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO: 810 is K149N; the mutation at amino acid residue 68 of the sequence shown in SEQ ID NO: 810 is K68N; and the mutations at amino acid residues 171 and 197 of the sequence shown in SEQ ID NO:810 are N171H and T197K.

In some embodiments, the antibody binds to cynomolgus TF. In some embodiments, the antibody binds to mouse TF. In some embodiments, the antibody binds to rabbit TF. In some embodiments, the antibody binds to pig TF.

In some embodiments, the antibody: (a) does not inhibit human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) allows human thrombin generation as determined by thrombin generation assay (TGA); and (b) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); and (b) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (c) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) allows human thrombin generation as determined by thrombin generation assay (TGA); (b) binds to cynomolgus TF; (c) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and (d) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutations at amino acid residues 171 and 197 of the sequence shown in SEQ ID NO:810 are N171H and T197K.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; and (i) binds to rabbit TF.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; and (k) binds to rabbit TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; and (o) binds to rabbit TF.

In some embodiments, the antibody: (a) does not inhibit human thrombin generation as determined by thrombin generation assay (TGA); (b) allows human thrombin generation as determined by thrombin generation assay (TGA); (c) binds human TF at a human TF binding site that is distinct from a human TF binding site bound by human FX; (d) does not interfere with the ability of TF:FVIIa to convert FX into FXa; (e) does not compete for binding to human TF with FVIIa; (f) inhibits FVIIa-dependent TF signaling; (g) binds to cynomolgus TF; (h) binds to mouse TF; (i) binds to rabbit TF; and (j) binds to pig TF.

In some embodiments, the antibody: (a) does not inhibit human thrombin generation as determined by thrombin generation assay (TGA); (b) does not decrease the endogenous thrombin potential (ETP) as determined by the area under a thrombin generation curve compared to an isotype control; (c) allows human thrombin generation as determined by thrombin generation assay (TGA); (d) preserves the endogenous thrombin potential (ETP) as determined by the area under a thrombin generation curve compared to an isotype control; (e) binds human TF at a human TF binding site that is distinct from a human TF binding site bound by human FX; (f) does not interfere with the ability of TF:FVIIa to convert FX into FXa; (g) does not compete for binding to human TF with FVIIa; (h) inhibits FVIIa-dependent TF signaling; (i) binds to cynomolgus TF; (j) binds to mouse TF; (k) binds to rabbit TF; and (l) binds to pig TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; and (p) binds to pig TF.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (r) the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (s) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (bb) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody: (a) does not inhibit human thrombin generation as determined by thrombin generation assay (TGA); (b) does not reduce the thrombin peak on a thrombin generation curve (Peak IIa) compared to an isotype control; (c) does not increase the time from the assay start to the thrombin peak on a thrombin generation curve (ttPeak) compared to an isotype control; (d) does not decrease the endogenous thrombin potential (ETP) as determined by the area under a thrombin generation curve compared to an isotype control; (e) allows human thrombin generation as determined by thrombin generation assay (TGA); (f) maintains the thrombin peak on a thrombin generation curve (Peak IIa) compared to an isotype control; (g) maintains the time from the assay start to the thrombin peak on a thrombin generation curve (ttPeak) compared to an isotype control; (h) preserves the endogenous thrombin potential (ETP) as determined by the area under a thrombin generation curve compared to an isotype control; (i) binds human TF at a human TF binding site that is distinct from a human TF binding site bound by human FX; (j) does not interfere with the ability of TF:FVIIa to convert FX into FXa; (k) does not compete for binding to human TF with FVIIa; (l) inhibits FVIIa-dependent TF signaling; (m) binds to cynomolgus TF; (n) binds to mouse TF; (o) binds to rabbit TF; (p) binds to pig TF; (q) the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (r) the binding between the antibody and a variant TF extracellular domain comprising a mutation K68N of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (s) the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (bb) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody competes for binding to human TF with the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody competes for binding to human TF with the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody competes for binding to human TF with the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody binds to the same human TF epitope bound by the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody binds to the same human TF epitope bound by the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain Complementary Determining Regions (CDRs) and all three light chain CDRs from: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the three heavy chain CDRs and the three light chain CDRs are determined using Kabat, Chothia, AbM, Contact, or IMGT numbering.

In some embodiments, the antibody comprises all three heavy chain Complementary Determining Regions (CDRs)

and all three light chain CDRs from: the antibody designated 25A, the antibody designated 25A3, the antibody designated 25A5, the antibody designated 25A5-T, the antibody designated 25G, the antibody designated 25G1, or the antibody designated 25G9.

In some embodiments, the antibody comprises all three heavy chain Complementary Determining Regions (CDRs) and all three light chain CDRs from: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody comprises all three heavy chain CDRs and all three light chain CDRs from the antibody designated 25A. In some embodiments, the antibody comprises all three heavy chain CDRs and all three light chain CDRs from the antibody designated 25A3. In some embodiments, the antibody comprises all three heavy chain CDRs and all three light chain CDRs from the antibody designated 25A5. In some embodiments, the antibody comprises all three heavy chain CDRs and all three light chain CDRs from the antibody designated 25A5-T. In some embodiments, the antibody comprises all three heavy chain CDRs and all three light chain CDRs from the antibody designated 25G. In some embodiments, the antibody comprises all three heavy chain CDRs and all three light chain CDRs from the antibody designated 25G1. In some embodiments, the antibody comprises all three heavy chain CDRs and all three light chain CDRs from the antibody designated 25G9. In some embodiments, the antibody comprises all three heavy chain CDRs and all three light chain CDRs from the antibody designated 43B. In some embodiments, the antibody comprises all three heavy chain CDRs and all three light chain CDRs from the antibody designated 43B1. In some embodiments, the antibody comprises all three heavy chain CDRs and all three light chain CDRs from the antibody designated 43B7. In some embodiments, the antibody comprises all three heavy chain CDRs and all three light chain CDRs from the antibody designated 43D. In some embodiments, the antibody comprises all three heavy chain CDRs and all three light chain CDRs from the antibody designated 43D7.

In some embodiments, the antibody comprises all three heavy chain CDRs and all three light chain CDRs from the antibody designated 43D8. In some embodiments, the antibody comprises all three heavy chain CDRs and all three light chain CDRs from the antibody designated 43E. In some embodiments, the antibody comprises all three heavy chain CDRs and all three light chain CDRs from the antibody designated 43Ea.

In some embodiments, the antibody comprises a $V_H$ sequence of SEQ ID NO: 113 and a $V_L$ sequence of SEQ ID NO:114. In some embodiments, the antibody comprises a $V_H$ sequence of SEQ ID NO:151 and a $V_L$ sequence of SEQ ID NO:152. In some embodiments, the antibody comprises a $V_H$ sequence of SEQ ID NO:189 and a $V_L$ sequence of SEQ ID NO:190. In some embodiments, the antibody comprises a $V_H$ sequence of SEQ ID NO:836 and a $V_L$ sequence of SEQ ID NO:837. In some embodiments, the antibody comprises a $V_H$ sequence of SEQ ID NO:227 and a $V_L$ sequence of SEQ ID NO:228. In some embodiments, the antibody comprises a $V_H$ sequence of SEQ ID NO:265 and a $V_L$ sequence of SEQ ID NO:266. In some embodiments, the antibody comprises a $V_H$ sequence of SEQ ID NO:303 and a $V_L$ sequence of SEQ ID NO:304. In some embodiments, the antibody comprises a $V_H$ sequence of SEQ ID NO:455 and a $V_L$ sequence of SEQ ID NO:456. In some embodiments, the antibody comprises a $V_H$ sequence of SEQ ID NO:493 and a $V_L$ sequence of SEQ ID NO:494. In some embodiments, the antibody comprises a $V_H$ sequence of SEQ ID NO:531 and a $V_L$ sequence of SEQ ID NO:532. In some embodiments, the antibody comprises a $V_H$ sequence of SEQ ID NO:569 and a $V_L$ sequence of SEQ ID NO:570. In some embodiments, the antibody comprises a $V_H$ sequence of SEQ ID NO:607 and a $V_L$ sequence of SEQ ID NO:608. In some embodiments, the antibody comprises a $V_H$ sequence of SEQ ID NO:645 and a $V_L$ sequence of SEQ ID NO:646. In some embodiments, the antibody comprises a $V_H$ sequence of SEQ ID NO:683 and a $V_L$ sequence of SEQ ID NO:684. In some embodiments, the antibody comprises a $V_H$ sequence of SEQ ID NO:721 and a $V_L$ sequence of SEQ ID NO:722.

In some embodiments, the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence x[K/S]Ax[S/Y]x[S/Y/N]LEx[S/Y]; and a VL-CDR3 comprising the sequence set forth in SEQ ID NO:784. In some embodiments, the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877. In some embodiments, the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883. In some embodiments, the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence GAx[S/D/F/Y]x[S/T]Rx[A/Q]x[T/N]; and a VL-CDR3 comprising the sequence set forth in SEQ ID NO:802.

In some embodiments, the antibody comprises a $V_H$ sequence of SEQ ID NO:763 and a $V_L$ sequence of SEQ ID NO:764. In some embodiments, the antibody comprises a $V_H$ sequence of SEQ ID NO:868 and a $V_L$ sequence of SEQ ID NO:869. In some embodiments, the antibody comprises a $V_H$ sequence of SEQ ID NO:870 and a $V_L$ sequence of SEQ ID NO:871. In some embodiments, the antibody comprises a $V_H$ sequence of SEQ ID NO:769 and a $V_L$ sequence of SEQ ID NO:770.

In some embodiments, the antibody comprises: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the antibody comprises: the antibody designated 25A, the antibody designated 25A3, the antibody designated 25A5, the antibody designated 25A5-T, the antibody designated 25G, the antibody designated 25G1, or the antibody designated 25G9. In some embodiments, the antibody comprises: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In some embodiments, the antibody consists of: the antibody designated 25A, the antibody designated 25A3, the antibody designated 25A5, the antibody designated 25A5-T, the antibody designated 25G, the antibody designated 25G1, the antibody designated 25G9, the antibody designated 43B, the antibody designated 43B1, the antibody designated 43B7, the antibody designated 43D, the antibody designated 43D7, the antibody designated 43D8, the antibody designated 43E, or the antibody designated 43Ea. In some embodiments, the antibody consists of: the antibody designated 25A, the antibody designated 25A3, the antibody designated 25A5, the antibody designated 25A5-T, the antibody designated 25G, the antibody designated 25G1, or the antibody designated 25G9. In some embodiments, the antibody consists of: the antibody designated 43B, the antibody designated 43B1, the antibody designated 43B7, the antibody designated 43D, the antibody designated 43D7, the antibody designated 43D8, the antibody designated 43E, or the antibody designated 43Ea.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody competes for binding to human TF with: the antibody designated 1F, the antibody designated 1G, the antibody designated 29D, the antibody designated 29E, the antibody designated 39A, or the antibody designated 54E.

In some embodiments, the antibody inhibits FVIIa-dependent TF signaling.

In some embodiments, the antibody binds to cynomolgus TF.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; and the binding between the antibody and a human TF extracellular domain with amino acid residues 78-93 of the sequence shown in SEQ ID NO:810 replaced by rat TF extracellular domain amino acid residues 77-98 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; the binding between the antibody and a human TF extracellular domain with amino acid residues 78-107 of the sequence shown in SEQ ID NO:810 replaced by rat TF extracellular domain amino acid residues 77-112 of the sequence shown in SEQ ID NO:838 is greater than 50% of the binding between the antibody and the extracellular domain of TF of the sequence shown in SEQ ID NO:810; and the binding between the antibody and a human TF extracellular domain with amino acid residues 78-107 of the sequence shown in SEQ ID NO:810 replaced by rat TF extracellular domain amino acid residues 77-85 and 92-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the antibody comprises all three heavy chain Complementary Determining Regions (CDRs) and all three light chain CDRs from: the antibody designated 1F, the antibody designated 1G, the antibody designated 29D, the antibody designated 29E, the antibody designated 39A, the antibody designated 43Ea, or the antibody designated 54E. In some embodiments, the three heavy chain CDRs and the three light chain CDRs are determined using Kabat, Chothia, AbM, Contact, or IMGT numbering.

In some embodiments, the antibody comprises all three heavy chain CDRs and all three light chain CDRs from the antibody designated 1F. In some embodiments, the antibody comprises all three heavy chain CDRs and all three light chain CDRs from the antibody designated 1G. In some embodiments, the antibody comprises all three heavy chain CDRs and all three light chain CDRs from the antibody designated 29D. In some embodiments, the antibody comprises all three heavy chain CDRs and all three light chain CDRs from the antibody designated 29E. In some embodiments, the antibody comprises all three heavy chain CDRs and all three light chain CDRs from the antibody designated 39A. In some embodiments, the antibody comprises all three heavy chain CDRs and all three light chain CDRs from the antibody designated 54E.

In some embodiments, the antibody comprises a $V_H$ sequence of SEQ ID NO:37 and a $V_L$ sequence of SEQ ID NO:38. In some embodiments, the antibody comprises a $V_H$ sequence of SEQ ID NO:75 and a $V_L$ sequence of SEQ ID NO:76. In some embodiments, the antibody comprises a $V_H$ sequence of SEQ ID NO:341 and a $V_L$ sequence of SEQ ID NO:342. In some embodiments, the antibody comprises a $V_H$ sequence of SEQ ID NO:379 and a $V_L$ sequence of SEQ ID NO:380. In some embodiments, the antibody comprises a $V_H$ sequence of SEQ ID NO:417 and a $V_L$ sequence of SEQ ID NO:418. In some embodiments, the antibody comprises a $V_H$ sequence of SEQ ID NO:759 and a $V_L$ sequence of SEQ ID NO:760.

In some embodiments, the antibody comprises: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL-CDR2 comprising the sequence set forth in SEQ ID NO:777; and a VL-CDR3 comprising the sequence set forth in SEQ ID NO:778. In some embodiments, the antibody comprises: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790. In some embodiments, the antibody comprises: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796. In some embodiments, the antibody comprises: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In some embodiments, the antibody comprises a $V_H$ sequence of SEQ ID NO:761 and a $V_L$ sequence of SEQ ID NO:762. In some embodiments, the antibody comprises a $V_H$ sequence of SEQ ID NO:765 and a $V_L$ sequence of SEQ ID NO:766. In some embodiments, the antibody comprises a $V_H$ sequence of SEQ ID NO:767 and a $V_L$ sequence of SEQ ID NO:768. In some embodiments, the antibody comprises a $V_H$ sequence of SEQ ID NO:771 and a $V_L$ sequence of SEQ ID NO:772.

In some embodiments, the antibody comprises: the antibody designated 1F, the antibody designated 1G, the antibody designated 29D, the antibody designated 29E, the antibody designated 39A, or the antibody designated 54E. In some embodiments, the antibody consists of: the antibody designated 1F, the antibody designated 1G, the antibody designated 29D, the antibody designated 29E, the antibody designated 39A, or the antibody designated 54E.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:773; a VH-CDR2 comprising the sequence set forth in SEQ ID NO:774; a VH-CDR3 comprising the sequence set forth in SEQ ID NO:775; a VL-CDR1 comprising the sequence set forth in SEQ ID NO:776; a VL-CDR2 comprising the sequence set forth in SEQ ID NO:777; and a VL-CDR3 comprising the sequence set forth in SEQ ID NO:778.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:779; a VH-CDR2 comprising the sequence set forth in SEQ ID NO:780; a VH-CDR3 comprising the sequence set forth in SEQ ID NO:781; a VL-CDR1 comprising the sequence set forth in SEQ ID NO:782; a VL-CDR2 comprising the sequence x[K/S]Ax[S/Y]x[S/Y/N]LEx[S/Y]; and a VL-CDR3 comprising the sequence set forth in SEQ ID NO:784.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:785; a VH-CDR2 comprising the sequence set forth in SEQ ID NO:786; a VH-CDR3 comprising the sequence set forth in SEQ ID NO:787; a VL-CDR1 comprising the sequence set forth in SEQ ID NO:788; a VL-CDR2 comprising the sequence set forth in SEQ ID NO:789; and a VL-CDR3 comprising the sequence set forth in SEQ ID NO:790.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:791; a VH-CDR2 comprising the sequence set forth in SEQ ID NO:792; a VH-CDR3 comprising the sequence set forth in SEQ ID NO:793; a VL-CDR1 comprising the sequence set forth in SEQ ID NO:794; a VL-CDR2 comprising the sequence set forth in SEQ ID NO:795; and a VL-CDR3 comprising the sequence set forth in SEQ ID NO:796.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:797; a VH-CDR2 comprising the sequence set forth in SEQ ID NO:798; a VH-CDR3 comprising the sequence set forth in SEQ ID NO:799; a VL-CDR1 comprising the sequence set forth in SEQ ID NO:800; a VL-CDR2 comprising the sequence GAx[S/D/F/Y]x[S/T]Rx[A/Q]x[T/N]; and a VL-CDR3 comprising the sequence set forth in SEQ ID NO:802.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:803; a VH-CDR2 comprising the sequence set forth in SEQ ID NO:804; a VH-CDR3 comprising the sequence set forth in SEQ ID NO:805; a VL-CDR1 comprising the sequence set forth in SEQ ID NO:806; a VL-CDR2 comprising the sequence set forth in SEQ ID NO:807; and a VL-CDR3 comprising the sequence set forth in SEQ ID NO:808.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:872; a VH-CDR2 comprising the sequence set forth in SEQ ID NO:873; a VH-CDR3 comprising the sequence set forth in SEQ ID NO:874; a VL-CDR1 comprising the sequence set forth in SEQ ID NO:875; a VL-CDR2 comprising the sequence set forth in SEQ ID NO:876; and a VL-CDR3 comprising the sequence set forth in SEQ ID NO:877.

In another aspect, provided herein is an antibody-drug conjugate comprising: antibody-drug conjugate comprising: an anti-human Tissue Factor (anti-hTF) antibody, a cytotoxic agent linked to the antibody, and optionally a linker that links the antibody to the cytotoxic agent, wherein the antibody comprises: a VH-CDR1 comprising the sequence set forth in SEQ ID NO:878; a VH-CDR2 comprising the sequence set forth in SEQ ID NO:879; a VH-CDR3 comprising the sequence set forth in SEQ ID NO:880; a VL-CDR1 comprising the sequence set forth in SEQ ID NO:881; a VL-CDR2 comprising the sequence set forth in SEQ ID NO:882; and a VL-CDR3 comprising the sequence set forth in SEQ ID NO:883.

In some embodiments, the antibody is human, humanized, or chimeric.

In some embodiments, the antibody binds to human TF with a $K_D$ of less than or equal to 50 nM, 10 nM, 5 nM, 1 nM, 0.5 nM or 0.1 nM, as measured by Octet QK384 or Biacore assay.

In some embodiments, the antibody is a monoclonal antibody.

In some embodiments, the antibody is multispecific.

In some embodiments, the antibody is a Fab, Fab', F(ab')2, Fv, scFv, (scFv)$_2$, single chain antibody molecule, dual variable domain antibody, single variable domain antibody, linear antibody, or V domain antibody.

In some embodiments, the antibody comprises a scaffold, optionally wherein the scaffold is Fc, optionally human Fc. In some embodiments, the antibody comprises a heavy chain constant region of a class selected from IgG, IgA, IgD, IgE, and IgM. In some embodiments, the antibody comprises a heavy chain constant region of the class IgG and a subclass selected from IgG1, IgG2, IgG3, and IgG4. In some embodiments, the antibody comprises a heavy chain constant region of IgG1. In some embodiments, the Fc comprises one or more modifications, wherein the one or more modifications result in increased half-life, increased antibody-dependent cellular cytotoxicity (ADCC), increased antibody-dependent cellular phagocytosis (ADCP), increased complement-dependent cytotoxicity (CDC), or decreased effector function, compared with the Fc without the one or more modifications.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody competes for binding to human TF with any antibody above.

In another aspect, provided herein is an antibody-drug conjugate comprising: an anti-human Tissue Factor (anti-hTF) antibody, a cytotoxic agent linked to the antibody, and optionally a linker that links the antibody to the cytotoxic agent, wherein the antibody binds the human TF epitope bound by any antibody above.

In some embodiments, the cytotoxic agent comprises an anti-angiogenic agent, a pro-apoptotic agent, an anti-mitotic agent, an anti-kinase agent, an alkylating agent, a hormone, a hormone agonist, a hormone antagonist, a chemokine, a drug, a prodrug, a toxin, an enzyme, an antimetabolite, an antibiotic, an alkaloid, or a radioactive isotope. In some embodiments, the cytotoxic agent comprises at least one of: calicheamycin, camptothecin, carboplatin, irinotecan, SN-38, carboplatin, camptothecan, cyclophosphamide, cytarabine, dacarbazine, docetaxel, dactinomycin, daunorubicin, doxorubicin, doxorubicin, etoposide, idarubicin, topotecan, vinca alkaloid, maytansinoid, maytansinoid analog, pyrrolobenzodiazepine, taxoid, duocarmycin, dolastatin, and auristatin.

In some embodiments, the linker comprises a labile linker, an acid labile linker, a photolabile linker, a charged linker, a disulfide-containing linker, a peptidase-sensitive linker, a β-glucuronide-linker, a dimethyl linker, a thio-ether linker, or a hydrophilic linker. In some embodiments, the linker is a cleavable linker. In some embodiments, the linker is a non-cleavable linker.

In another aspect, provided herein is a pharmaceutical composition comprising any antibody-drug conjugate above and a pharmaceutically acceptable excipient.

In another aspect, provided herein is a method of treating or preventing a disease or condition in a subject in need thereof, comprising administering to the subject an effective amount of any antibody-drug conjugate above or the pharmaceutical composition above.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER−), progesterone receptors negative (PR−), and HER2 negative (HER2−) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the method further comprises administering one or more additional therapeutic agents to the subject. In some embodiments, the additional therapeutic agent is formulated in the same pharmaceutical composition as the antibody-drug conjugate.

In some embodiments, the additional therapeutic agent is formulated in a different pharmaceutical composition from the antibody-drug conjugate. In some embodiments, the additional therapeutic agent is administered prior to administering the antibody-drug conjugate. In some embodiments, the additional therapeutic agent is administered after administering the antibody-drug conjugate. In some embodiments, the additional therapeutic agent is administered contemporaneously with the antibody-drug conjugate.

In another aspect, provided herein is a method of detecting TF in a subject having or suspected of having a disease or condition, the method comprising: (a) administering to the subject any antibody-drug conjugate above; and (b) detecting the presence or the level of TF in the subject.

In some embodiments, the disease or condition is cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER–), progesterone receptors negative (PR–), and HER2 negative (HER2–) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In another aspect, provided herein is a kit comprising any antibody-drug conjugate above or the pharmaceutical composition above and instructions for use.

BRIEF DESCRIPTION OF THE DRAWINGS

These and other features, aspects, and advantages of the present invention will become better understood with regard to the following description, and accompanying drawings, where:

FIG. 1A shows the median fluorescence intensity (MFI) of antibody bound to HCT-116 cells plotted against concentrations of antibodies from groups 1, 25, and 29 and the reportable cell $EC_{50}$. FIG. 1B shows the median fluorescence intensity of antibody bound to HCT-116 cells plotted against concentrations of antibodies from groups 39, 43, and 54 and the reportable cell $EC_{50}$. The isotype control in FIG. 1B applies to both FIGS. 1A and 1B.

FIG. 2A shows the median fluorescence intensity (MFI) of antibody bound to CHO cells recombinantly expressing mouse TF (CHO-mTF) plotted against concentrations of antibodies from groups 1, 25, and 29 and the reportable cell $EC_{50}$. FIG. 2B shows the median fluorescence intensity of antibody bound to CHO-mTF cells plotted against concentrations of antibodies from groups 39, 43, and 54 and the reportable cell $EC_{50}$. The isotype control in FIG. 2B applies to both FIGS. 2A and 2B.

FIG. 3A shows Peak IIa/Thrombin generation (% Peak IIa) as measured by the Thrombin Generation Assay (TGA) without antibody incubation prior to addition of calcium and thrombin substrate in the presence of titrations of anti-TF antibodies from groups 1, 25, 29, 39, 43, and 54. FIG. 3B shows Peak IIa/Thrombin generation (% Peak IIa) as measured by the Thrombin Generation Assay (TGA) with a 10-min antibody incubation prior to addition of calcium and thrombin substrate in the presence of titrations of anti-TF antibodies from groups 1, 25, 29, 39, 43, and 54.

FIG. 4A shows the percentage of FXa conversion (% FXa) by TF:FVIIa in MDA-MB-231 cells in the presence of titrations of anti-TF antibodies from groups 1, 25, and 29. FIG. 4B shows the percentage of FXa conversion (% FXa) by TF:FVIIa in MDA-MB-231 cells in the presence of titrations of anti-TF antibodies from groups 39, 43, and 54. % FXa conversion at a reported concentration is calculated relative to an antibody-free FXa conversion reaction. The isotype control in FIG. 4B applies to both FIGS. 4A and 4B.

FIG. 5A shows the percentage of FVIIa binding (% FVIIa) in TF-positive MDA-MB-231 cells in the presence of titrations of anti-TF antibodies from groups 1, 25, and 29. FIG. 5B shows the percentage of FVIIa binding (% FVIIa) in MDA-MB-231 cells in the presence of titrations of anti-TF antibodies from groups 39, 43, and 54. % FVIIa binding at a reported concentration is calculated relative to antibody-free FVIIa binding. The isotype control in FIG. 5B applies to both FIGS. 5A and 5B.

FIG. 6A shows the concentration of IL8 (IL8 conc) in MDA-MB-231 cells in the presence of titrations of anti-TF antibodies from groups 1, 25, and 29. FIG. 6B shows the concentration of IL8 (IL8 conc) in MDA-MB-231 cells in the presence of titrations of anti-TF antibodies from groups 39, 43, and 54. The control in FIG. 6B applies to both FIGS. 6A and 6B. FIG. 6C shows the concentration of GM-CSF (GM-CSF conc) in MDA-MB-231 cells in the presence of titrations of anti-TF antibodies from groups 1, 25, and 29. FIG. 6D shows the concentration of GM-CSF (GM-CSF conc) in MDA-MB-231 cells in the presence of titrations of anti-TF antibodies from groups 39, 43, and 54. The control in FIG. 6D applies to both FIGS. 6C and 6D.

FIG. 7A shows the cell viability of TF-positive A431 cell cultures after the addition of an anti-TF antibody from groups 1, 25, and 29 and a secondary antibody against the human Fc conjugated to mono-methyl auristatin F (MMAF). FIG. 7B shows the cell viability of TF-positive A431 cell cultures after the addition of an anti-TF antibody from groups 39, 43, and 54 and a secondary antibody against the human Fc conjugated to mono-methyl auristatin F (MMAF). The isotype control in FIG. 7B applies to both FIGS. 7A and 7B.

FIG. 8A shows Peak IIa/Thrombin generation (% Peak IIa) as measured by the Thrombin Generation Assay (TGA) without antibody incubation prior to addition of calcium and thrombin substrate in the presence of titrations of anti-TF antibodies from groups 25, 39, 43, and anti-TF M1593. FIG. 8B shows Peak IIa/Thrombin generation (% Peak IIa) as measured by the Thrombin Generation Assay (TGA) with a 10-min antibody incubation prior to addition of calcium and thrombin substrate in the presence of titrations of anti-TF antibodies from groups 25, 39, 43, and anti-TF M1593.

FIG. 9A shows cell viability of TF-positive A431 cells after a 3-day incubation with titrations of anti-TF antibodies conjugated to MC-vc-PAB-MMAE (DAR of 3-4). FIG. 9B shows cell viability of TF-positive HPAF-II cells after a 4-day incubation with titrations of anti-TF antibodies conjugated to MC-vc-PAB-MMAE (DAR of 3-4).

FIG. 10A shows the efficacy of anti-TF ADCs in the A431 xenograft model. FIG. 10B shows the efficacy of anti-TF ADCs in the HPAF-II xenograft model. The arrows indicate treatments with ADC or vehicle (PBS) dosed at 5 mg/kg once per week for 3 weeks.

FIG. 12A shows the median fluorescence intensity (MFI) of antibody bound to A431 cells plotted against concentrations of antibodies from groups 1, 25, 29, 39, 43, and 54. Reportable cell $EC_{50}$'s and their 95% confidence intervals are listed. FIG. 12B shows the median fluorescence intensity of antibody bound to MDA-MB-231 cells plotted against concentrations of antibodies from groups 25, 29, 39, and 43. Reportable cell $EC_{50}$'s and their 95% confidence intervals are listed.

FIG. 13A shows the thrombin generation curves in the absence or presence of 100 nM anti-TF antibodies from groups 1, 25, and 29 and previously generated anti-TF antibodies TF-011, 5G9, and 10H10 (samples on plate 1 of Table 44). FIG. 13B shows the thrombin generation curves in the absence or presence of 100 nM anti-TF antibodies from groups 39, 43, and 54 (samples on plate 2 of Table 44). FIG. 13C shows the peak thrombin concentration in the absence or presence of titrations of anti-TF antibodies. The mean of a triplicate data set is shown. The standard deviation of the mean is listed in Table 44.

FIG. 14A shows TF:FVIIa-dependent conversion of FX into FXa on the cell surface of MDA-MB-231 cells in the absence or presence of titrations of anti-TF antibodies TF-011, 5G9 and 10H10. FIG. 14B shows FVII binding in the absence or presence of titrations of anti-TF antibodies TF-011, 5G9 and 10H10 after pre-incubation of MDA-MB-231 cells with the anti-TF antibodies. For antibodies that exhibited no less than 25% competition with FVII, the $IC_{50}$ is reported.

FIG. 15A shows percent binding of 25A3 after pre-incubation with unlabeled competitor antibodies from groups 1, 25, 29, 39, 43, and 54.

FIG. 15B shows percent binding of 25A3 after pre-incubation with unlabeled competitor antibodies TF-011, 5G9, and 10H10. The $IC_{50}$ value of antibodies that compete with 25A3 is listed.

FIG. 16A shows percent binding of 43D7 after pre-incubation with unlabeled competitor antibodies from groups 1, 25, 29, 39, 43, and 54.

FIG. 16B shows percent binding of 43D7 after pre-incubation with unlabeled competitor antibodies TF-011, 5G9, and 10H10. The $IC_{50}$ value of antibodies that compete with 43D7 is listed.

FIG. 17A shows percent binding of 39A after pre-incubation with unlabeled competitor antibodies from groups 1, 25, 29, 39, 43, and 54.

FIG. 17B shows percent binding of 39A after pre-incubation with unlabeled competitor antibodies TF-011, 5G9, and 10H10. The $IC_{50}$ value of antibodies that compete with 39A is listed.

FIG. 18A shows cell viability of TF-positive A431 cell cultures three days after titrations of anti-TF antibodies. FIG. 18B shows cell viability of TF-positive A431 cell cultures three days after titrations of anti-TF antibodies complexed with a Fab fragment against the human Fc conjugated to mono-methyl auristatin F (Fab: MMAF). The $IC_{50}$ of the anti-TF antibody Fab:MMAF complexes is listed.

FIG. 18C shows internalization of anti-TF antibodies conjugated to A488. Percent internalization of A488-conjugated anti-TF antibodies at 4 h is listed.

FIGS. 19A, 19B, and 19C show the binding of anti-TF antibodies and ADCs to human TF-positive HCT-116 cells. FIG. 19A shows the binding of anti-TF antibodies HCT-116 cells. FIG. 19B shows the binding of anti-TF ADCs to HCT-116 cells. FIG. 19C lists reportable cell $EC_{50}$'s and their 95% confidence intervals.

FIGS. 20A, 20B, and 20C show cell viability of A431 cells after titrations of anti-TF ADCs. FIG. 20A shows the cell viability after titrations of anti-TF ADCs with a continuous 72 h incubation. FIG. 20B shows the cell viability after titrations of anti-TF ADCs with a 4 h incubation followed by removal of excess ADC and culture for another 68 h. FIG. 20C lists the reportable $IC_{50}$ values of ADCs.

FIGS. 21A, 21B, and 21C show the effect of FVIIa on the in vitro efficacy of anti-TF ADCs. FIG. 21A shows the cell viability after titrations of anti-TF ADCs with a 4 h incubation followed by removal of excess ADC and culture for another 68 h in the absence of FVIIa. FIG. 21B shows the cell viability after titrations of anti-TF ADCs with a 4 h incubation followed by removal of excess ADC and culture for another 68 h in the presence of FVIIa. FIG. 21C lists the reportable $IC_{50}$ values.

FIGS. 22A, 22B, 22C, 22D, and 22E show cell viability of additional cancer cell lines after titrations of anti-TF ADCs. FIG. 22A shows the TF copy number in various cell lines with the anti-TF antibody 5G9. The standard error of the mean and the number of measurements (n) are also presented. FIG. 22B shows the cell viability of HCT-116 cells after 72 h culture in the absence or presence of titrations of anti-TF MMAE ADCs. FIG. 22C shows the cell viability of CHO cells after 72 h culture in the absence or presence of titrations of anti-TF MMAE ADCs. FIG. 22D shows the cell viability of MDA-MB-231 cells after 5-day culture in the absence or presence of titrations of anti-TF MMAE ADCs. FIG. 22E shows the cell viability of HPAF-II cells after 5-day culture in the absence or presence of titrations of anti-TF MMAE ADCs.

FIG. 23A shows staining of the microtubule network of A431 cells after treatment. FIG. 23B shows staining of the microtubule network of HPAF-II cells after treatment. Scale bar, 10 microns.

FIG. 24A shows copy numbers of surface TF on HUVECs treated with or without an inflammatory cytokine cocktail for 3, 6, or 20 h prior to analysis. FIG. 24B shows cell viability of inflammatory cytokine-treated HUVEC cultures after 4 days of culture in the presence of titrations of anti-TF or isotype-control MMAE ADCs.

FIG. 25A shows the percentage of pH3-positive cells (% pH3) with titrations of anti-TF ADCs of HUVECs in the absence of inflammatory cytokines. FIG. 25B shows the percentage of pH3-positive cells (% pH3) with titrations of anti-TF ADCs of HUVECs in the presence of inflammatory cytokines. FIG. 25C shows the percentage of pH3-positive cells (% pH3) with titrations of anti-TF ADCs of HCT-116 cells.

FIG. 26A shows the pH3 versus DNA content dot plot after treatment of 10 nM Isotype-vc-MMAE. FIG. 26B shows the pH3 versus DNA content dot plot after treatment of 10 nM 25A-vc-MMAE.

FIG. 27A shows the percentage of pH3-positive HUVECs (% pH3) in the absence or presence of 24 h of MMAE treatment. FIG. 27B shows the percentage of pH3-positive HCT-116 cells (% pH3) in the absence or presence of 24 h of MMAE treatment.

FIGS. 29A, 29B, and 29C show antibody-dependent cellular cytotoxicity (ADCC) reporter luminescence after a 6 h incubation of the reporter Jurkat cell line with TF-positive A431 cells. FIG. 29A shows the ADCC reporter luminescence in the absence or presence of titrations anti-TF antibodies. FIG. 29B shows the ADCC reporter luminescence in the absence or presence of titrations anti-TF ADCs. FIG. 29C lists the ADCC reporter luminescence $EC_{50}$ values for each anti-TF antibody or ADC.

FIGS. 30A and 30B show in vivo efficacy of anti-TF ADCs in HPAF-II xenograft model. FIG. 30A shows the mean tumor volume after weekly treatment of an anti-TF ADC at 5 mg/kg for 3 weeks. FIG. 30B shows the mean tumor volume after weekly treatment of an anti-TF ADC at 2 mg/kg for 2 weeks. The mean tumor volumes (Mean) and tumor growth inhibition (TGI) percentages on day 21 are listed. The P-values for the mean tumor volume comparison between each ADC and the vehicle control are also listed. In addition, the number of partial regression (PR), complete regression (CR), and tumor-free survivor (TFS) animals at the end of the study (day 59 for FIG. 30A and day 39 for FIG. 30B) are also listed.

FIG. 31A shows the mean tumor volume after weekly treatment of an anti-TF ADC at 4 mg/kg for 2 weeks. FIG. 31B shows the mean tumor volume after weekly treatment of an anti-TF ADC at 2 mg/kg for 2 weeks. The mean tumor volume and tumor growth inhibition on day 25 (FIG. 31A) and day 27 (FIG. 31B) are listed. The P-values for the mean tumor volume comparison between each ADC and the vehicle control are also listed. In addition, the number of partial regression (PR), complete regression (CR), and tumor-free survivor (TFS) animals at the end of the study (day 49 for FIG. 31A and day 41 for FIG. 31B) are also listed.

FIG. 33A shows the mean tumor volume in the PDX model of a head and neck carcinoma after treatment of an anti-TF ADC. FIG. 33B shows the mean tumor volume in the PDX model of an ovarian carcinoma after treatment of an anti-TF ADC. FIG. 33C shows the mean tumor volume in the PDX model of a gastric adenocarcinoma after treatment of an anti-TF ADC. The mean tumor volume and tumor growth inhibition on day 44 (FIG. 33A), day 15 (FIG. 33B), and day 25 (FIG. 33C) are listed. The P-values for the mean tumor volume comparison between each ADC and the isotype control are also listed. In addition, the number of partial responder (PR), complete responder (CR), and tumor free survivor (TFS) animals at the end of the study (day 60 for FIG. 33A and day 46 for FIGS. 33B-C) are also listed.

FIG. 34A shows the percentage change in lesion size from day 7 (baseline) to day 14 as measured by Fluorescein Angiography (FA) after intravitreal administration of anti-TF antibodies 25G9, 43D8, 1G, and 29D respectively. FIG. 34B shows the percentage change in lesion size from day 7 (baseline) to day 28 as measured by Fluorescein Angiography (FA) after intravitreal administration of anti-TF antibodies 25G9, 43D8, 1G, and 29D respectively.

FIG. 36 shows Clustal Omega alignment of chimeric TF constructs. Rat sequences are highlighted in bold. An "* (asterisk)" indicates positions which have a single, fully conserved residue. A ": (colon)" indicates conservation between groups of strongly similar properties—roughly equivalent to scoring>0.5 in the Gonnet Percent Accepted Mutation 250 matrix. A ". (period)" indicates conservation between groups of weakly similar properties—roughly equivalent to scoring=<0.5 and >0 in the Gonnet Percent Accepted Mutation 250 matrix.

FIG. 37 shows Clustal Omega alignment of chimeric TF constructs. Human sequences are highlighted in bold. An "* (asterisk)" indicates positions which have a single, fully conserved residue. A ": (colon)" indicates conservation between groups of strongly similar properties—roughly equivalent to scoring>0.5 in the Gonnet Percent Accepted Mutation 250 matrix. A ". (period)" indicates conservation between groups of weakly similar properties—roughly equivalent to scoring=<0.5 and >0 in the Gonnet Percent Accepted Mutation 250 matrix.

FIG. 38 shows Clustal Omega alignment of chimeric TF constructs. Rat sequences are highlighted in bold. An "* (asterisk)" indicates positions which have a single, fully conserved residue. A ": (colon)" indicates conservation between groups of strongly similar properties—roughly equivalent to scoring>0.5 in the Gonnet Percent Accepted Mutation 250 matrix. A ". (period)" indicates conservation between groups of weakly similar properties—roughly equivalent to scoring=<0.5 and >0 in the Gonnet Percent Accepted Mutation 250 matrix.

FIG. 39A shows the titration curves of anti-TF antibodies on human TF construct. FIG. 39B shows the titration curves of anti-TF antibodies on rat TF construct. FIG. 39C shows the titration curves of anti-TF antibodies on chimeric human-rat TF construct hTF_K68N. FIG. 39D shows the titration curves of anti-TF antibodies on chimeric human-rat TF construct hTF_K149N. FIG. 39E shows the titration curves of anti-TF antibodies on chimeric human-rat TF construct hTF_N171H_T197K. FIG. 39F shows the titration curves of anti-TF antibodies on chimeric rat-human TF construct r141-194_h.

DETAILED DESCRIPTION

1. Definitions

Figure 1A:
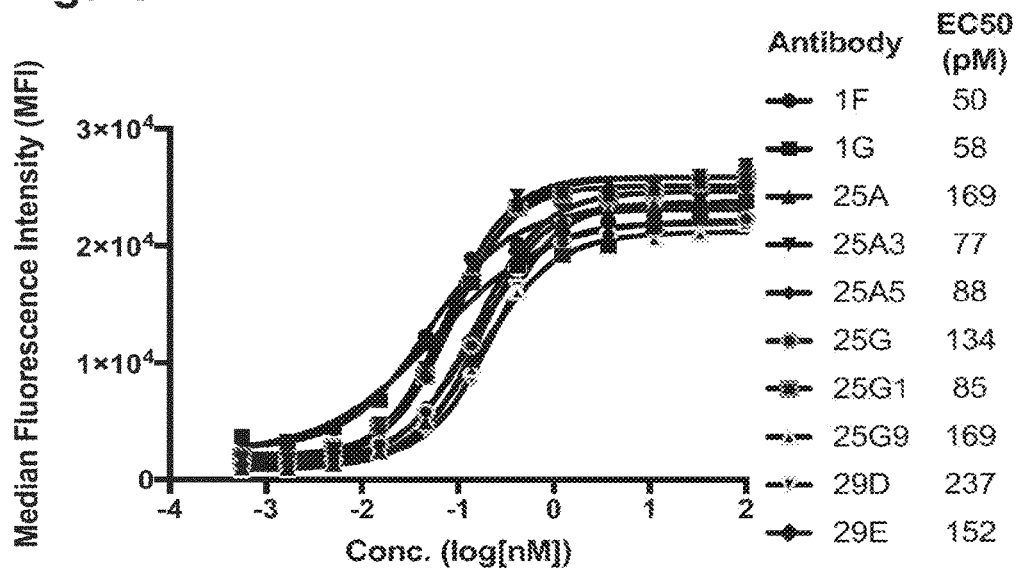
FIGS. 1A and 1B show binding of anti-TF antibodies to human TF-positive cells.

Unless otherwise defined, all terms of art, notations and other scientific terminology used herein are intended to have the meanings commonly understood by those of skill in the art. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, NY As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise. The terms "include," "such as," and the like are intended to convey inclusion without limitation, unless otherwise specifically indicated.

As used herein, the term "comprising" also specifically includes embodiments "consisting of" and "consisting essentially of" the recited elements, unless specifically indicated otherwise.

The term "about" indicates and encompasses an indicated value and a range above and below that value. In certain embodiments, the term "about" indicates the designated value+10%, +5%, or +1%. In certain embodiments, where applicable, the term "about" indicates the designated value(s)+one standard deviation of that value(s).

The terms "Tissue Factor," "TF," "platelet tissue factor," "factor III," "thromboplastin," and "CD142" are used interchangeably herein to refer to TF, or any variants (e.g., splice variants and allelic variants), isoforms, and species homologs of TF that are naturally expressed by cells, or that are expressed by cells transfected with a TF gene. In some aspects, the TF protein is a TF protein naturally expressed by a primate (e.g., a monkey or a human), a rodent (e.g., a mouse or a rat), a dog, a camel, a cat, a cow, a goat, a horse, a pig or a sheep. In some aspects, the TF protein is human TF (hTF; SEQ ID NO:809). In some aspects, the TF protein is cynomolgus TF (cTF; SEQ ID NO:813). In some aspects, the TF protein is mouse TF (mTF; SEQ ID NO:817). In some aspects, the TF protein is pig TF (pTF; SEQ ID NO:824). TF is a cell surface receptor for the serine protease factor VIIa. It is often times constitutively expressed by certain cells surrounding blood vessels and in some disease settings.

The term "antibody-drug conjugate" or "ADC" refers to a conjugate comprising an antibody conjugated to one or more cytotoxic agents, optionally through one or more linkers. The term "anti-TF antibody-drug conjugate" or "anti-TF ADC" refers to a conjugate comprising an anti-TF antibody conjugated to one or more cytotoxic agents, optionally through one or more linkers.

The term "cytotoxic agent," as used herein, refers to a substance that inhibits or prevents a cellular function and/or causes cell death or destruction. The cytotoxic agent can be an anti-angiogenic agent, a pro-apoptotic agent, an anti-mitotic agent, an anti-kinase agent, an alkylating agent, a hormone, a hormone agonist, a hormone antagonist, a chemokine, a drug, a prodrug, a toxin, an enzyme, an antimetabolite, an antibiotic, an alkaloid, or a radioactive isotope. Exemplary cytotoxic agents include calicheamycin, camptothecin, carboplatin, irinotecan, SN-38, carboplatin, camptothecan, cyclophosphamide, cytarabine, dacarbazine, docetaxel, dactinomycin, daunorubicin, doxorubicin, doxorubicin, etoposide, idarubicin, topotecan, *vinca* alkaloid, maytansinoid, maytansinoid analog, pyrrolobenzodiazepine, taxoid, duocarmycin, dolastatin, auristatin, and derivatives thereof.

A "linker" refers to a molecule that connects one composition to another, e.g., an antibody to an agent. Linkers described herein can conjugate an antibody to a cytotoxic agent. Exemplary linkers include a labile linker, an acid labile linker, a photolabile linker, a charged linker, a disulfide-containing linker, a peptidase-sensitive linker, a D-glucuronide-linker, a dimethyl linker, a thio-ether linker, and a hydrophilic linker. A linker can be cleavable or non-cleavable.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, Fundamental Immunology 7th ed., Ch. 5 (2013) Lippincott Williams & Wilkins, Philadelphia, PA Briefly, each heavy chain typically comprises a heavy chain variable region ($V_H$) and a heavy chain constant region (CH). The heavy chain constant region typically comprises three domains, abbreviated $C_{H1}$, $C_{H2}$, and $C_{H3}$. Each light chain typically comprises a light chain variable region ($V_L$) and a light chain constant region. The light chain constant region typically comprises one domain, abbreviated $C_L$.

The term "antibody" is used herein in its broadest sense and includes certain types of immunoglobulin molecules comprising one or more antigen-binding domains that specifically bind to an antigen or epitope. An antibody specifically includes intact antibodies (e.g., intact immunoglobulins), antibody fragments, and multi-specific antibodies.

The term "alternative scaffold" refers to a molecule in which one or more regions may be diversified to produce one or more antigen-binding domains that specifically bind to an antigen or epitope. In some embodiments, the antigen-binding domain binds the antigen or epitope with specificity and affinity similar to that of an antibody. Exemplary alternative scaffolds include those derived from fibronectin (e.g., Adnectins™), the β-sandwich (e.g., iMab), lipocalin (e.g., Anticalins®), EETI-II/AGRP, BPTI/LACI-D1/ITI-D2 (e.g., Kunitz domains), thioredoxin peptide aptamers, protein A (e.g., Affibody®), ankyrin repeats (e.g., DARPins), gamma-B-crystallin/ubiquitin (e.g., Affilins), CTLD3 (e.g., Tetranectins), Fynomers, and (LDLR-A module) (e.g., Avimers). Additional information on alternative scaffolds is provided in Binz et al., Nat. Biotechnol., 2005 23:1257-1268; Skerra, Current Opin. in Biotech., 2007 18:295-304; and Silacci et al., J. Biol. Chem., 2014, 289:14392-14398; each of which is incorporated by reference in its entirety.

The term "antigen-binding domain" means the portion of an antibody that is capable of specifically binding to an antigen or epitope. One example of an antigen-binding domain is an antigen-binding domain formed by a $V_H$-$V_L$ dimer of an antibody. Another example of an antigen-binding domain is an antigen-binding domain formed by diversification of certain loops from the tenth fibronectin type III domain of an Adnectin. Antigen-binding domains can be found in various contexts including antibodies and chimeric antigen receptors (CARs), for example CARs derived from antibodies or antibody fragments such as scFvs.

The terms "full length antibody," "intact antibody," and "whole antibody" are used herein interchangeably to refer to an antibody having a structure substantially similar to a naturally occurring antibody structure and having heavy chains that comprise an Fc region. For example, when used to refer to an IgG molecule, a "full length antibody" is an antibody that comprises two heavy chains and two light chains.

The term "Fc region" means the C-terminal region of an immunoglobulin heavy chain that, in naturally occurring antibodies, interacts with Fc receptors and certain proteins of the complement system. The structures of the Fc regions of various immunoglobulins, and the glycosylation sites contained therein, are known in the art. See Schroeder and Cavacini, J. Allergy Clin. Immunol., 2010, 125:S41-52, incorporated by reference in its entirety. The Fc region may be a naturally occurring Fc region, or an Fc region modified as described in the art or elsewhere in this disclosure.

The $V_H$ and $V_L$ regions may be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., Sequences of Proteins of Immunological Interest 5th ed. (1991) Public Health Service, National Institutes of Health, Bethesda, MD, incorporated by reference in its entirety.

A "Complementary Determining Region (CDR)" refers to one of three hypervariable regions (H1, H2 or H3) within the non-framework region of the immunoglobulin (Ig or antibody) $V_H$ β-sheet framework, or one of three hypervariable regions (L1, L2 or L3) within the non-framework region of the antibody $V_L$ β-sheet framework. CDRs are variable region sequences interspersed within the framework region sequences. CDRs are well recognized in the art and have been defined by, for example, Kabat as the regions of most hypervariability within the antibody variable (V) domains. See Kabat et al., J Biol Chem, 1977, 252:6609-6616 and Kabat, Adv Protein Chem, 1978, 32:1-75, each of which is incorporated by reference in its entirety. CDRs have also been defined structurally by Chothia as those residues that are not part of the conserved β-sheet framework, and thus are able to adapt different conformations. See Chothia and Lesk, J Mol Biol, 1987, 196:901-917, incorporated by reference in its entirety. Both the Kabat and Chothia nomenclatures are well known in the art. AbM, Contact and IMGT also defined CDRs. CDR positions within a canonical antibody variable domain have been determined by comparison of numerous structures. See Morea et al., Methods, 2000, 20:267-279 and Al-Lazikani et al., J Mol Biol, 1997, 273: 927-48, each of which is incorporated by reference in its entirety. Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra). Such terminology is well known to those skilled in the art.

A number of hypervariable region delineations are in use and are included herein. The Kabat CDRs are based on sequence variability and are the most commonly used. See Kabat et al. (1992) Sequences of Proteins of Immunological Interest, DIANE Publishing: 2719, incorporated by reference in its entirety. Chothia refers instead to the location of the structural loops (Chothia and Lesk, supra). The AbM hypervariable regions represent a compromise between the Kabat CDRs and Chothia structural loops, and are used by Oxford Molecular's AbM antibody modeling software. The Contact hypervariable regions are based on an analysis of the available complex crystal structures. The residues from each of these hypervariable regions are noted in Table 1.

More recently, a universal numbering system ImMunoGeneTics (IMGT) Information System™ has been developed and widely adopted. See Lefranc et al., Dev Comp Immunol, 2003, 27:55-77, incorporated by reference in its entirety. IMGT is an integrated information system specializing in immunoglobulins (IG), T cell receptors (TR) and major histocompatibility complex (MHC) of human and other vertebrates. The IMGT CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. Correspondence between the Kabat, Chothia and IMGT numbering is also well known in the art (Lefranc et al., supra). An Exemplary system, shown herein, combines Kabat and Chothia CDR definitions.

TABLE 1

|  | Exemplary (Kabat + Chothia) | Kabat | Chothia | AbM | Contact | IMGT |
| --- | --- | --- | --- | --- | --- | --- |
| VH CDR1 | 26-35 | 31-35 | 26-32 | 26-35 | 30-35 | 27-38 |
| VH CDR2 | 50-65 | 50-65 | 52a-55 | 50-58 | 47-58 | 56-65 |
| VH CDR3 | 95-102 | 95-102 | 96-101 | 95-102 | 93-101 | 105-117 |
| VL CDR1 | 24-34 | 24-34 | 26-32 | 24-34 | 30-36 | 27-38 |
| VL CDR2 | 50-56 | 50-56 | 50-52 | 50-56 | 46-55 | 56-65 |
| VL CDR3 | 89-97 | 89-97 | 91-96 | 89-97 | 89-96 | 105-117 |

The light chain from any vertebrate species can be assigned to one of two types, called kappa (κ) and lambda (λ), based on the sequence of its constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The term "constant region" or "constant domain" refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen-binding site. The constant domain contains the $C_{H1}$, $C_{H2}$ and $C_{H3}$ domains of the heavy chain and the $C_L$ domain of the light chain.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen-binding or variable region of an intact antibody. Antibody fragments include, for example, Fv fragments, Fab fragments, F(ab')$_2$ fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with ß-mercaptoethanol.

"Single-chain Fv" or "sFv" or "scFv" antibody fragments comprise a $V_H$ domain and a $V_L$ domain in a single polypeptide chain. The $V_H$ and $V_L$ are generally linked by a peptide linker. See Plückthun A. (1994). Any suitable linker may be used. In some embodiments, the linker is a (GGGGS)$_n$ (SEQ ID NO:823). In some embodiments, n=1, 2, 3, 4, 5, or 6. See Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminal of the scFv. The Fc domain may follow the $V_H$ or $V_L$, depending on the orientation of the variable domains in the scFv (i.e., $V_H$-$V_L$ or $V_L$-$V_H$). Any suitable Fc domain known in the art or described herein may be used.

The term "single domain antibody" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies.

A "multispecific antibody" is an antibody that comprises two or more different antigen-binding domains that collectively specifically bind two or more different epitopes. The two or more different epitopes may be epitopes on the same antigen (e.g., a single TF molecule expressed by a cell) or on different antigens (e.g., a TF molecule and a non-TF molecule). In some aspects, a multi-specific antibody binds two different epitopes (i.e., a "bispecific antibody"). In some aspects, a multi-specific antibody binds three different epitopes (i.e., a "trispecific antibody"). In some aspects, a multi-specific antibody binds four different epitopes (i.e., a "quadspecific antibody"). In some aspects, a multi-specific antibody binds five different epitopes (i.e., a "quintspecific antibody"). In some aspects, a multi-specific antibody binds 6, 7, 8, or more different epitopes. Each binding specificity may be present in any suitable valency. Examples of multispecific antibodies are provided elsewhere in this disclosure.

A "monospecific antibody" is an antibody that comprises one or more binding sites that specifically bind to a single epitope. An example of a monospecific antibody is a naturally occurring IgG molecule which, while divalent (i.e., having two antigen-binding domains), recognizes the same epitope at each of the two antigen-binding domains. The binding specificity may be present in any suitable valency.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human antibody (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody.

Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature*, 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" or "isolated nucleic acid" is an antibody or nucleic acid that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. In some embodiments, an isolated antibody may include an antibody in situ within recombinant cells, since at least one component of the antibody's natural environment is not present. In some aspects, an isolated antibody or isolated nucleic acid is prepared by at least one purification step. In some embodiments, an isolated antibody or isolated nucleic acid is purified to at least 80%, 85%, 90%, 95%, or 99% by weight. In some embodiments, an isolated antibody or isolated nucleic acid is purified to at least 80%, 85%, 90%, 95%, or 99% by volume. In some embodiments, an isolated antibody or isolated nucleic acid is provided as a solution comprising at least 85%, 90%, 95%, 98%, 99% to 100% antibody or nucleic acid by weight. In some embodiments, an isolated antibody or isolated nucleic acid is provided as a solution comprising at least 85%, 90%, 95%, 98%, 99% to 100% antibody or nucleic acid by volume.

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein, such as surface plasmon resonance (SPR) technology (e.g., BIACORE®) or biolayer interferometry (e.g., FORTEBIO®).

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some aspects, the affinity of a TF antibody for a non-target molecule is less than about 50% of the affinity for TF. In some aspects, the affinity of a TF antibody for a non-target molecule is less than about 40% of the affinity for TF. In some aspects, the affinity of a TF antibody for a non-target molecule is less than about 30% of the affinity for TF. In some aspects, the affinity of a TF antibody for a non-target molecule is less than about 20% of the affinity for TF. In some aspects, the affinity of a TF antibody for a non-target molecule is less than about 10% of the affinity for TF. In some aspects, the affinity of a TF antibody for a non-target molecule is less than about T % of the affinity for TF. In some aspects, the affinity of a TF antibody for a non-target molecule is less than about 0.10% of the affinity for TF.

The term "$k_d$" (sec$^{-1}$), as used herein, refers to the dissociation rate constant of a particular antibody-antigen interaction. This value is also referred to as the $k_{off}$ value.

The term "$k_a$" (M$^{-1}$×sec$^{-1}$), as used herein, refers to the association rate constant of a particular antibody-antigen interaction. This value is also referred to as the $k_{on}$ value.

The term "$K_D$" (M), as used herein, refers to the dissociation equilibrium constant of a particular antibody-antigen interaction. $K_D = k_d/k_a$. In some embodiments, the affinity of an antibody is described in terms of the $K_D$ for an interaction between such antibody and its antigen. For clarity, as known in the art, a smaller $K_D$ value indicates a higher affinity interaction, while a larger $K_D$ value indicates a lower affinity interaction.

The term "$K_A$" (M$^{-1}$), as used herein, refers to the association equilibrium constant of a particular antibody-antigen interaction. $K_A = k_a/k_d$.

An "affinity matured" antibody is an antibody with one or more alterations (e.g., in one or more CDRs or FRs) relative to a parent antibody (i.e., an antibody from which the altered antibody is derived or designed) that result in an improvement in the affinity of the antibody for its antigen, compared to the parent antibody which does not possess the alteration(s). In some embodiments, an affinity matured antibody has nanomolar or picomolar affinity for the target antigen. Affinity matured antibodies may be produced using a variety of methods known in the art. For example, Marks et al. (*Bio Technology,* 1992, 10:779-783, incorporated by reference in its entirety) describes affinity maturation by $V_H$ and $V_L$ domain shuffling. Random mutagenesis of CDR and/or framework residues is described by, for example, Barbas et al., *Proc. Nat. Acad. Sci. U.S.A.,* 1994, 91:3809-3813; Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896; each of which is incorporated by reference in its entirety.

"Fc effector functions" refer to those biological activities mediated by the Fc region of an antibody, which activities may vary depending on the antibody isotype. Examples of antibody effector functions include C1q binding to activate complement dependent cytotoxicity (CDC), Fc receptor binding to activate antibody-dependent cellular cytotoxicity (ADCC), and antibody dependent cellular phagocytosis (ADCP).

When used herein in the context of two or more antibodies, the term "competes with" or "cross-competes with" indicates that the two or more antibodies compete for binding to an antigen (e.g., TF). In one exemplary assay, TF is coated on a surface and contacted with a first TF antibody, after which a second TF antibody is added. In another exemplary assay, first a TF antibody is coated on a surface and contacted with TF, and then a second TF antibody is added. If the presence of the first TF antibody reduces binding of the second TF antibody, in either assay, then the antibodies compete with each other. The term "competes with" also includes combinations of antibodies where one antibody reduces binding of another antibody, but where no competition is observed when the antibodies are added in the reverse order. However, in some embodiments, the first and second antibodies inhibit binding of each other, regardless of the order in which they are added. In some embodiments, one antibody reduces binding of another antibody to its antigen by at least 25%, at least 50%, at least 60%, at least 70%, at least 80%, at least 85%, at least 90%, or at least 95%. A skilled artisan can select the concentrations of the antibodies used in the competition assays based on the affinities of the antibodies for TF and the valency of the antibodies. The assays described in this definition are illustrative, and a skilled artisan can utilize any suitable assay to determine if antibodies compete with each other. Suitable assays are described, for example, in Cox et al., "Immunoassay Methods," in *Assay Guidance Manual* [*Internet*], Updated Dec. 24, 2014 (www.ncbi.nlm.nih.gov/books/NBK92434/; accessed Sep. 29, 2015); Silman et al., *Cytometry*, 2001, 44:30-37; and Finco et al., *J Pharm. Biomed. Anal.*, 2011, 54:351-358; each of which is incorporated by reference in its entirety. As provided in Example 8, antibodies of group 25 and antibodies of group 43 compete with each other for binding to human TF, while antibodies from groups 1, 29, 39, and 54 do not compete for binding to human TF with antibodies of groups 25 and 43.

As used herein, an antibody that binds specifically to a human antigen is considered to bind the same antigen of mouse origin when a $K_D$ value can be measured on a ForteBio Octet with the mouse antigen. An antibody that binds specifically to a human antigen is considered to be "cross-reactive" with the same antigen of mouse origin when the $K_D$ value for the mouse antigen is no greater than 20 times the corresponding $K_D$ value for the respective human antigen. For example, the antibody M1593 described in U.S. Pat. Nos. 8,722,044, 8,951,525, and 8,999,333, each of which is herein incorporated by reference for all purposes, the humanized 5G9 antibody described in Ngo et al., 2007, *Int J Cancer*, 120(6):1261-1267, incorporated by reference in its entirety, and chimeric ALT-836 antibody described in Hong et al, 2012, *J Nucl Med*, 53(11):1748-1754, incorporated by reference in its entirety, do not bind to mouse TF. As provided in Examples 1 and 2, TF antibodies from groups 25 and 43 bind to mouse TF, e.g., the TF antibodies 25G, 25G1, 25G9, and 43D8 are cross-reactive with mouse TF.

As used herein, an antibody that binds specifically to a human antigen is considered to be "cross-reactive" with the same antigen of cynomolgus monkey origin when the $K_D$ value for the cynomolgus monkey antigen is no greater than 15 times the corresponding $K_D$ value for the respective human antigen. As provided in Example 1, all tested antibodies from groups 1, 25, 29, 39, 43, and 54 are cross-reactive with cynomolgus monkey TF.

The term "epitope" means a portion of an antigen that is specifically bound by an antibody. Epitopes frequently include surface-accessible amino acid residues and/or sugar side chains and may have specific three dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. The epitope to which an antibody binds can be determined using known techniques for epitope determination such as, for example, testing for antibody binding to TF variants with different point-mutations, or to chimeric TF variants.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, CLUSTAL OMEGA, or MUSCLE software. Those skilled in the art can determine appropriate parameters for aligning sequences, including any algorithms needed to achieve maximal alignment over the full length of the sequences being compared.

A "conservative substitution" or a "conservative amino acid substitution," refers to the substitution of an amino acid with a chemically or functionally similar amino acid. Conservative substitution tables providing similar amino acids are well known in the art. By way of example, the groups of amino acids provided in Tables 2-4 are, in some embodiments, considered conservative substitutions for one another.

TABLE 2

Selected groups of amino acids that are considered conservative substitutions for one another, in certain embodiments.

| | |
|---|---|
| Acidic Residues | D and E |
| Basic Residues | K, R, and H |
| Hydrophilic Uncharged Residues | S, T, N, and Q |
| Aliphatic Uncharged Residues | G, A, V, L, and I |
| Non-polar Uncharged Residues | C, M, and P |
| Aromatic Residues | F, Y, and W |

TABLE 3

Additional selected groups of amino acids that are considered conservative substitutions for one another, in certain embodiments.

| | |
|---|---|
| Group 1 | A, S, and T |
| Group 2 | D and E |
| Group 3 | N and Q |
| Group 4 | R and K |
| Group 5 | I, L, and M |
| Group 6 | F, Y, and W |

TABLE 4

Further selected groups of amino acids that are considered conservative substitutions for one another, in certain embodiments.

| | |
|---|---|
| Group A | A and G |
| Group B | D and E |
| Group C | N and Q |
| Group D | R, K, and H |
| Group E | I, L, M, V |
| Group F | F Y and W |
| Group G | S and T |
| Group H | C and M |

Additional conservative substitutions may be found for example in Creighton, *Proteins: Structures and Molecular*

Properties 2nd ed. (1993) W. H. Freeman & Co., New York, NY An antibody generated by making one or more conservative substitutions of amino acid residues in a parent antibody is referred to as a "conservatively modified variant."

The term "amino acid" refers to the twenty common naturally occurring amino acids. Naturally occurring amino acids include alanine (Ala; A), arginine (Ag; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which an exogenous nucleic acid has been introduced, and the progeny of such cells. Host cells include "transformants" (or "transformed cells") and "transfectants" (or "transfected cells"), which each include the primary transformed or transfected cell and progeny derived therefrom. Such progeny may not be completely identical in nucleic acid content to a parent cell, and may contain mutations.

The term "treating" (and variations thereof such as "treat" or "treatment") refers to clinical intervention in an attempt to alter the natural course of a disease or condition in a subject in need thereof. Treatment can be performed both for prophylaxis and during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

As used herein, the term "therapeutically effective amount" or "effective amount" refers to an amount of an antibody or pharmaceutical composition provided herein that, when administered to a subject, is effective to treat a disease or disorder.

As used herein, the term "subject" means a mammalian subject. Exemplary subjects include humans, monkeys, dogs, cats, mice, rats, cows, horses, camels, goats, rabbits, pigs and sheep. In certain embodiments, the subject is a human. In some embodiments the subject has a disease or condition that can be treated with an antibody provided herein. In some aspects, the disease or condition is a cancer. In some aspects, the disease or condition involves neovascularization or vascular inflammation. In certain aspects, the disease or condition involving neovascularization is age-related macular degeneration (AMD), diabetic retinopathy, or cancer.

The term "package insert" is used to refer to instructions customarily included in commercial packages of therapeutic or diagnostic products (e.g., kits) that contain information about the indications, usage, dosage, administration, combination therapy, contraindications and/or warnings concerning the use of such therapeutic or diagnostic products.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "cytostatic agent" refers to a compound or composition which arrests growth of a cell either in vitro or in vivo. In some embodiments, a cytostatic agent is an agent that reduces the percentage of cells in S phase. In some embodiments, a cytostatic agent reduces the percentage of cells in S phase by at least about 20%, at least about 40%, at least about 60%, or at least about 80%.

The term "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

The term "agonize" refers to the activation of receptor signaling to induce a biological response associated with activation of the receptor. An "agonist" is an entity that binds to and agonizes a receptor.

The term "antagonize" refers to the inhibition of receptor signaling to inhibit a biological response associated with activation of the receptor. An "antagonist" is an entity that binds to and antagonizes a receptor.

2. TF Antibodies

2.1. TF Binding

Provided herein are isolated antibodies that specifically bind to TF. In some aspects, the TF is hTF (SEQ ID NO:809). In some aspects, the TF is cTF (SEQ ID NO:813). In some aspects, the TF is mTF (SEQ ID NO:817). In some aspects, the TF is rabbit TF (SEQ ID NO:832). In some aspects, the TF is pTF (SEQ ID NO:824). In some embodiments, the antibodies provided herein specifically bind to hTF (SEQ ID NO:809), cTF (SEQ ID NO:813), mTF (SEQ ID NO:817), rabbit TF (SEQ ID NO:832), and pTF (SEQ ID NO:824). In some embodiments, the antibodies provided herein specifically bind to hTF (SEQ ID NO:809), cTF (SEQ ID NO:813), mTF (SEQ ID NO:817), and pTF (SEQ ID NO:824). In some embodiments, the antibodies provided herein specifically bind to hTF (SEQ ID NO:809), cTF (SEQ ID NO:813), and mTF (SEQ ID NO:817). In some embodiments, the antibodies provided herein specifically bind to hTF (SEQ ID NO:809) and cTF (SEQ ID NO:813). In some embodiments, the antibodies provided herein do not bind mTF (SEQ ID NO:817). In some embodiments, the antibodies provided herein do not bind pTF (SEQ ID NO:824). In some embodiments, the antibodies provided herein do not bind rabbit TF (SEQ ID NO:832).

In various embodiments, the antibodies provided herein specifically bind to the extracellular domain of human TF (SEQ ID NO:810).

In some embodiments, the binding between an antibody provided herein and a variant TF extracellular domain comprising a mutation at amino acid residue 149 of the sequence shown in SEQ ID NO:810 is less than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N.

In some embodiments, the binding between an antibody provided herein and a variant TF extracellular domain comprising a mutation at amino acid residue 68 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 68 of the sequence shown in SEQ ID NO:810 is K68N.

In some embodiments, the binding between an antibody provided herein and a variant TF extracellular domain comprising mutations at amino acid residues 171 and 197 of the sequence shown in SEQ ID NO:810 is less than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutations at amino acid residues 171 and 197 of the sequence shown in SEQ ID NO:810 are N171H and T197K.

In some embodiments, the binding between an antibody provided herein and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay.

In some embodiments, the binding between an antibody provided herein and a variant TF extracellular domain comprising a mutation at amino acid residue 149 of the sequence shown in SEQ ID NO:810 is less than 50% of the binding between the antibody provided herein and the extracellular domain of TF of the sequence shown in SEQ ID NO:810; the binding between an antibody provided herein and a variant TF extracellular domain comprising a mutation at amino acid residue 68 of the sequence shown in SEQ ID NO:810 is greater than 50% of the binding between the antibody provided herein and the extracellular domain of TF of the sequence shown in SEQ ID NO:810; the binding between an antibody provided herein and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810; and the binding between an antibody provided herein and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; and the mutation at amino acid residue 68 of the sequence shown in SEQ ID NO:810 is K68N.

In some embodiments, the binding between an antibody provided herein and a variant TF extracellular domain comprising a mutation at amino acid residue 149 of the sequence shown in SEQ ID NO:810 is less than 50% of the binding between the antibody provided herein and the extracellular domain of TF of the sequence shown in SEQ ID NO:810; the binding between an antibody provided herein and a variant TF extracellular domain comprising a mutation at amino acid residue 68 of the sequence shown in SEQ ID NO:810 is greater than 50% of the binding between the antibody provided herein and the extracellular domain of TF of the sequence shown in SEQ ID NO:810; the binding between an antibody provided herein and a variant TF extracellular domain comprising mutations at amino acid residues 171 and 197 of the sequence shown in SEQ ID NO:810 is less than 50% of the binding between the antibody provided herein and the extracellular domain of TF of the sequence shown in SEQ ID NO:810; the binding between an antibody provided herein and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810; the binding between an antibody provided herein and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810; the binding between an antibody provided herein and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810; and the binding between an antibody provided herein and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody provided herein and the extracellular domain of TF of the sequence shown in SEQ ID NO:810, as determined by the median fluorescence intensity value of the antibody relative to an isotype control in a live cell staining assay. In some embodiments, the mutation at amino acid residue 149 of the sequence shown in SEQ ID NO:810 is K149N; the mutation at amino acid residue 68 of the sequence shown in SEQ ID NO:810 is K68N; and the mutations at amino acid residues 171 and 197 of the sequence shown in SEQ ID NO:810 are N171H and T197K.

In some embodiments, the antibodies provided herein are inert in inhibiting human thrombin generation as determined by thrombin generation assay (TGA) compared to a reference antibody M1593, wherein the reference antibody M1593 comprises a $V_H$ sequence of SEQ ID NO:821 and a $V_L$ sequence of SEQ ID NO:822.

In some embodiments, the antibodies provided herein do not inhibit human thrombin generation as determined by thrombin generation assay (TGA). In certain embodiments, the antibodies provided herein allow human thrombin generation as determined by thrombin generation assay (TGA).

In some embodiments, the antibodies provided herein bind human TF at a human TF binding site that is distinct from a human TF binding site bound by human FX. In certain embodiments, the antibodies provided herein do not interfere with the ability of TF:FVIIa to convert FX into FXa.

In some embodiments, the antibodies provided herein bind human TF at a human TF binding site that is distinct from a human TF binding site bound by human FVIIa. In certain embodiments, the antibodies provided herein do not compete for binding to human TF with human FVIIa.

In some embodiments, the antibodies provided herein bind to the extracellular domain of human TF, bind human TF at a human TF binding site that is distinct from a human TF binding site bound by human FVIIa, bind human TF at a human TF binding site that is distinct from a human TF binding site bound by human FX, and allow human thrombin generation as determined by thrombin generation assay (TGA).

In some embodiments, the antibodies provided herein bind to the extracellular domain of human TF, do not inhibit human thrombin generation as determined by thrombin generation assay (TGA), do not interfere with the ability of TF:FVIIa to convert FX into FXa, and do not compete for binding to human TF with human FVIIa.

In some embodiments, the antibodies provided herein bind to the extracellular domain of human TF at a human TF binding site that is distinct from a human TF binding site bound by human FVIIa, do not inhibit human thrombin generation as determined by thrombin generation assay (TGA), allow human thrombin generation as determined by thrombin generation assay (TGA), bind to human TF at a human TF binding site that is distinct from a human TF binding site bound by human FX, do not interfere with the ability of TF:FVIIa to convert FX into FXa, and do not compete for binding to human TF with human FVIIa.

In some embodiments, the antibodies provided herein inhibit FVIIa-dependent TF signaling.

In some embodiments, the antibodies provided herein reduce lesion size in a swine choroidal neovascularization (CNV) model.

In some embodiments, the antibodies provided herein bind to the extracellular domain of human TF at a human TF binding site that is distinct from a human TF binding site bound by human FVIIa, do not inhibit human thrombin generation as determined by thrombin generation assay (TGA), allow human thrombin generation as determined by thrombin generation assay (TGA), bind to human TF at a human TF binding site that is distinct from a human TF binding site bound by human FX, do not interfere with the ability of TF:FVIIa to convert FX into FXa, do not compete for binding to human TF with human FVIIa, and bind to cynomolgus and mouse TF.

In some embodiments, the antibodies provided herein bind to the extracellular domain of human TF at a human TF binding site that is distinct from a human TF binding site bound by human FVIIa, do not inhibit human thrombin generation as determined by thrombin generation assay (TGA), allow human thrombin generation as determined by thrombin generation assay (TGA), bind to human TF at a human TF binding site that is distinct from a human TF binding site bound by human FX, do not interfere with the ability of TF:FVIIa to convert FX into FXa, do not compete for binding to human TF with human FVIIa, bind to cynomolgus, mouse, and pig TF, and reduce lesion size in a swine choroidal neovascularization (CNV) model.

In some embodiments, the antibodies provided herein bind to the extracellular domain of human TF, inhibit FVIIa-dependent TF signaling, and bind to cynomolgus TF.

2.2. Sequences of TF Antibodies 2.2.1. $V_H$ Domains

In some embodiments, an antibody provided herein comprises a $V_H$ sequence selected from SEQ ID NOs: 37, 75, 113, 151, 189, 227, 265, 303, 341, 379, 417, 455, 493, 531, 569, 607, 645, 683, 721, and 759. In some embodiments, an antibody provided herein comprises a $V_H$ sequence of SEQ ID NO:37. In some embodiments, an antibody provided herein comprises a $V_H$ sequence of SEQ ID NO: 75. In some embodiments, an antibody provided herein comprises a $V_H$ sequence of SEQ ID NO:113. In some embodiments, an antibody provided herein comprises a $V_H$ sequence of SEQ ID NO:151. In some embodiments, an antibody provided herein comprises a $V_H$ sequence of SEQ ID NO:189. In some embodiments, an antibody provided herein comprises a $V_H$ sequence of SEQ ID NO:836. In some embodiments, an antibody provided herein comprises a $V_H$ sequence of SEQ ID NO:227. In some embodiments, an antibody provided herein comprises a $V_H$ sequence of SEQ ID NO:265. In some embodiments, an antibody provided herein comprises a $V_H$ sequence of SEQ ID NO:303. In some embodiments, an antibody provided herein comprises a $V_H$ sequence of SEQ ID NO:341. In some embodiments, an antibody provided herein comprises a $V_H$ sequence of SEQ ID NO:379. In some embodiments, an antibody provided herein comprises a $V_H$ sequence of SEQ ID NO:417. In some embodiments, an antibody provided herein comprises a $V_H$ sequence of SEQ ID NO:455. In some embodiments, an antibody provided herein comprises a $V_H$ sequence of SEQ ID NO:493. In some embodiments, an antibody provided herein comprises a $V_H$ sequence of SEQ ID NO:531. In some embodiments, an antibody provided herein comprises a $V_H$ sequence of SEQ ID NO:569. In some embodiments, an antibody provided herein comprises a $V_H$ sequence of SEQ ID NO:607. In some embodiments, an antibody provided herein comprises a $V_H$ sequence of SEQ ID NO:645. In some embodiments, an antibody provided herein comprises a $V_H$ sequence of SEQ ID NO:683. In some embodiments, an antibody provided herein comprises a $V_H$ sequence of SEQ ID NO:721. In some embodiments, an antibody provided herein comprises a $V_H$ sequence of SEQ ID NO:759.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 37, 75, 113, 151, 189, 227, 265, 303, 341, 379, 417, 455, 493, 531, 569, 607, 645, 683, 721, and 759. In some embodiments, an antibody provided herein comprises a $V_H$ sequence provided in SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

2.2.2. $V_L$ Domains

In some embodiments, an antibody provided herein comprises a $V_L$ sequence selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises a $V_L$ sequence of SEQ ID NO:38. In some embodiments, an antibody provided herein comprises a $V_L$ sequence of SEQ ID NO:76. In some embodiments, an antibody provided herein comprises a $V_L$ sequence of SEQ ID NO:114. In some embodiments, an antibody provided herein comprises a $V_L$ sequence of SEQ ID NO:152. In some embodiments, an antibody provided herein comprises a $V_L$ sequence of SEQ ID NO:190. In some embodiments, an antibody provided herein comprises a $V_L$ sequence of SEQ ID NO:837. In some embodiments, an antibody provided herein comprises a $V_L$ sequence of SEQ ID NO:228. In some embodiments, an antibody provided herein comprises a $V_L$ sequence of SEQ ID NO:266. In some embodiments, an antibody provided herein comprises a $V_L$ sequence of SEQ ID NO:304. In some embodiments, an antibody provided herein comprises a $V_L$ sequence of SEQ ID NO:342. In some embodiments, an antibody provided herein comprises a $V_L$ sequence of SEQ ID NO:380. In some embodiments, an antibody provided herein comprises a $V_L$ sequence of SEQ ID NO:418. In some embodiments, an antibody provided herein comprises a $V_L$ sequence of SEQ ID NO:456. In some embodiments, an antibody provided herein comprises a $V_L$ sequence of SEQ ID NO:494. In some embodiments, an antibody provided herein comprises a $V_L$ sequence of SEQ ID NO:532. In some embodiments, an antibody provided herein comprises a $V_L$ sequence of SEQ ID NO:570. In some embodiments, an antibody provided herein comprises a $V_L$ sequence of SEQ ID NO:608. In some embodiments, an antibody provided herein comprises a $V_L$ sequence of SEQ ID NO:646. In some embodiments, an antibody provided herein comprises a $V_L$ sequence of SEQ ID NO:684. In some embodiments, an antibody provided herein comprises a $V_L$ sequence of SEQ ID NO:722. In some embodiments, an antibody provided herein comprises a $V_L$ sequence of SEQ ID NO:760.

In some embodiments, an antibody provided herein comprises a $V_L$ sequence having at least about 50%, 60%, 70%, 80%, 90%, 95%, or 99% identity to an illustrative $V_L$ sequence provided in SEQ ID NOs: 38, 76, 114, 152, 190, 228, 266, 304, 342, 380, 418, 456, 494, 532, 570, 608, 646, 684, 722, and 760. In some embodiments, an antibody provided herein comprises a $V_L$ sequence provided in SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

2.2.3. $V_H$-$V_L$ Combinations

In some embodiments, an antibody provided herein comprises a $V_H$ sequence selected from SEQ ID NOs: 37, 75, 113, 151, 189, 227, 265, 303, 341, 379, 417, 455, 493, 531, 569, 607, 645, 683, 721, and 759 and a $V_L$ sequence selected from SEQ ID NOs: 38, 76, 114, 152, 190, 228, 266, 304, 342, 380, 418, 456, 494, 532, 570, 608, 646, 684, 722, and 760.

In some embodiments, an antibody provided herein comprises a $V_H$ sequence of SEQ ID NO:37 and a $V_L$ sequence of SEQ ID NO:38. In some embodiments, an antibody provided herein comprises a $V_H$ sequence of SEQ ID NO:75 and a $V_L$ sequence of SEQ ID NO:76. In some embodiments, an antibody provided herein comprises a $V_H$ sequence of SEQ ID NO: 113 and a $V_L$ sequence of SEQ ID NO:114. In some embodiments, an antibody provided herein comprises a $V_H$ sequence of SEQ ID NO: 151 and a $V_L$ sequence of SEQ ID NO: 152. In some embodiments, an antibody provided herein comprises a $V_H$ sequence of SEQ ID NO:189 and a $V_L$ sequence of SEQ ID NO:190. In some embodiments, an antibody provided herein comprises a $V_H$ sequence of SEQ ID NO:836 and a $V_L$ sequence of SEQ ID NO:837. In some embodiments, an antibody provided herein comprises a $V_H$ sequence of SEQ ID NO:227 and a $V_L$ sequence of SEQ ID NO:228. In some embodiments, an antibody provided herein comprises a $V_H$ sequence of SEQ ID NO:265 and a $V_L$ sequence of SEQ ID NO:266. In some embodiments, an antibody provided herein comprises a $V_H$ sequence of SEQ ID NO:303 and a $V_L$ sequence of SEQ ID NO:304. In some embodiments, an antibody provided herein comprises a $V_H$ sequence of SEQ ID NO:341 and a $V_L$ sequence of SEQ ID NO:342. In some embodiments, an antibody provided herein comprises a $V_H$ sequence of SEQ ID NO:379 and a $V_L$ sequence of SEQ ID NO:380. In some embodiments, an antibody provided herein comprises a $V_H$ sequence of SEQ ID NO:417 and a $V_L$ sequence of SEQ ID NO:418. In some embodiments, an antibody provided herein comprises a $V_H$ sequence of SEQ ID NO:455 and a $V_L$ sequence of SEQ ID NO:456. In some embodiments, an antibody provided herein comprises a $V_H$ sequence of SEQ ID NO:493 and a $V_L$ sequence of SEQ ID NO:494. In some embodiments, an antibody provided herein comprises a $V_H$ sequence of SEQ ID NO:531 and a $V_L$ sequence of SEQ ID NO:532. In some embodiments, an antibody provided herein comprises a $V_H$ sequence of SEQ ID NO:569 and a $V_L$ sequence of SEQ ID NO:570. In some embodiments, an antibody provided herein comprises a $V_H$ sequence of SEQ ID NO:607 and a $V_L$ sequence of SEQ ID NO:608. In some embodiments, an antibody provided herein comprises a $V_H$ sequence of SEQ ID NO:645 and a $V_L$ sequence of SEQ ID NO:646. In some embodiments, an antibody provided herein comprises a $V_H$ sequence of SEQ ID NO:683 and a $V_L$ sequence of SEQ ID NO:684. In some embodiments, an antibody provided herein comprises a $V_H$ sequence of SEQ ID NO:721 and a $V_L$ sequence of SEQ ID NO:722. In some embodiments, an antibody provided herein comprises a $V_H$ sequence of SEQ ID NO:759 and a $V_L$ sequence of SEQ ID NO:760.

In some embodiments, an antibody provided herein comprises a $V_H$ sequence having at least about 50%, 60%, 70%, 80%, 90%, 95%, or 99% identity to an illustrative $V_H$ sequence provided in SEQ ID NOs: 37, 75, 113, 151, 189, 227, 265, 303, 341, 379, 417, 455, 493, 531, 569, 607, 645, 683, 721, and 759, and a $V_L$ sequence having at least about 50%, 60%, 70%, 80%, 90%, 95%, or 99% identity to an illustrative $V_L$ sequence provided in SEQ ID NOs: 38, 76, 114, 152, 190, 228, 266, 304, 342, 380, 418, 456, 494, 532, 570, 608, 646, 684, 722, and 760. In some embodiments, an antibody provided herein comprises a $V_H$ sequence provided in SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, 8, 9, 10, 11, 12, 13, 14, 15, 16, 17, 18, 19, 20, 21, 22, 23, 24, or 25 amino acid substitutions, and a $V_L$ sequence provided in SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

2.2.4. CDRs

In some embodiments, an antibody provided herein comprises one to three CDRs of a $V_H$ domain selected from SEQ ID NOs: 37, 75, 113, 151, 189, 227, 265, 303, 341, 379, 417, 455, 493, 531, 569, 607, 645, 683, 721, and 759. In some embodiments, an antibody provided herein comprises two to three CDRs of a $V_H$ domain selected from SEQ ID NOs: 37, 75, 113, 151, 189, 227, 265, 303, 341, 379, 417, 455, 493, 531, 569, 607, 645, 683, 721, and 759. In some embodiments, an antibody provided herein comprises three CDRs of a $V_H$ domain selected from SEQ ID NOs: 37, 75, 113, 151, 189, 227, 265, 303, 341, 379, 417, 455, 493, 531, 569, 607, 645, 683, 721, and 759. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 37, 75, 113, 151, 189, 227, 265, 303, 341, 379, 417, 455, 493, 531, 569, 607, 645, 683, 721, and 759. In some embodiments, the CDR-H1 is a CDR-H1 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, or 5 amino acid substitutions. In some embodiments, the CDR-H2 is a CDR-H2 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions. In some embodiments, the CDR-H3 is a CDR-H3 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises two to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-L1, CDR-L2, or CDR-L3 of SEQ ID NOs: 38, 76, 114, 152, 190, 228, 266, 304, 342, 380, 418, 456, 494, 532, 570, 608, 646, 684, 722, and 760. In some embodiments, the CDR-L1 is a CDR-L1 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, or 5 amino acid substitutions. In some embodiments, the CDR-L2 is a CDR-L2 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, or 8 amino acid substitutions. In some embodiments, the CDR-L3 is a CDR-L3 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises one to three CDRs of a $V_H$ domain selected from SEQ ID NOs: 37, 75, 113, 151, 189, 227, 265, 303, 341, 379, 417, 455, 493, 531, 569, 607, 645, 683, 721, and 759 and one to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises two to three CDRs of a $V_H$ domain selected from SEQ ID NOs: 37, 75, 113, 151, 189, 227, 265, 303, 341, 379, 417, 455, 493, 531, 569, 607, 645, 683, 721, and 759 and two to three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some embodiments, an antibody provided herein comprises three CDRs of a $V_H$ domain selected from SEQ ID NOs: 37, 75, 113, 151, 189, 227, 265, 303, 341, 379, 417, 455, 493, 531, 569, 607, 645, 683, 721, and 759 and three CDRs of a $V_L$ domain selected from SEQ ID NOs: 38, 76, 114, 152, 190, 228, 266, 304, 342, 380, 418, 456, 494, 532, 570, 608, 646, 684, 722, and 760. In some aspects, the CDRs are Exemplary CDRs. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, the CDRs are CDRs having at least about 50%, 75%, 80%, 85%, 90%, or 95% identity with a CDR-H1, CDR-H2, or CDR-H3 of SEQ ID NOs: 37, 75, 113, 151, 189, 227, 265, 303, 341, 379, 417, 455, 493, 531, 569, 607, 645, 683, 721, and 759 and at least about 50%, 75%, 80%, 85%, 90%, or 95% identity with a CDR-L1, CDR-L2, or CDR-L3 of SEQ ID NOs: 38, 76, 114, 152, 190, 228, 266, 304, 342, 380, 418, 456, 494, 532, 570, 608, 646, 684, 722, and 760. In some embodiments, the CDR-H1 is a CDR-H1 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, or 5 amino acid substitutions; the CDR-H2 is a CDR-H2 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions; the CDR-H3 is a CDR-H3 of a $V_H$ domain selected from SEQ ID NOs: 37, 75, 113, 151, 189, 227, 265, 303, 341, 379, 417, 455, 493, 531, 569, 607, 645, 683, 721, and 759, with up to 1, 2, 3, 4, 5, 6, 7, or 8 amino acid substitutions; the CDR-L1 is a CDR-L1 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, 5, or 6 amino acid substitutions; the CDR-L2 is a CDR-L2 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, or 4 amino acid substitutions; and the CDR-L3 is a CDR-L3 of a $V_L$ domain selected from SEQ ID NOs: 38, 76, 114, 152, 190, 228, 266, 304, 342, 380, 418, 456, 494, 532, 570, 608, 646, 684, 722, and 760, with up to 1, 2, 3, 4, or 5 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725, as determined by the Exemplary numbering system. In some aspects, the CDR-H3 has at least about 50%, 75%, 80%, 85%, 90%, or 95% identity with a CDR-H3 of SEQ ID NOs: 3, 41, 79, 117, 155, 193, 231, 269, 307, 345, 383, 421, 459, 497, 535, 573, 611, 649, 687, and 725. In some embodiments, the CDR-H3 is a CDR-H3 selected from SEQ ID NOs: 3, 41, 79, 117, 155, 193, 231, 269, 307, 345, 383, 421, 459, 497, 535, 573, 611, 649, 687, and 725, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H2 selected from SEQ ID NOs: 2, 40, 78, 116, 154, 192, 230, 268, 306, 344, 382, 420, 458, 496, 534, 572, 610, 648, 686, and 724, as determined by the Exemplary numbering system. In some aspects, the CDR-H2 has at least about 50%, 75%, 80%, 85%, 90%, or 95% identity with a CDR-H2 of SEQ ID NOs: 2, 40, 78, 116, 154, 192, 230, 268, 306, 344, 382, 420, 458, 496, 534, 572, 610, 648, 686, and 724. In some embodiments, the CDR-H2 is a CDR-H2 selected from SEQ ID NOs: 2, 40, 78, 116, 154, 192, 230, 268, 306, 344, 382, 420, 458, 496, 534, 572, 610, 648, 686, and 724, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 selected from SEQ ID NOs: 1, 39, 77, 115, 153, 191, 229, 267, 305, 343, 381, 419, 457, 495, 533, 571, 609, 647, 685, and 723, as determined by the Exemplary numbering system. In some aspects, the CDR-H1 has at least about 50%, 75%, 80%, 85%, 90%, or 95% identity with a CDR-H1 of SEQ ID NOs: 1, 39, 77, 115, 153, 191, 229, 267, 305, 343, 381, 419, 457, 495, 533, 571, 609, 647, 685, and 723. In some embodiments, the CDR-H1 is a CDR-H1 selected from SEQ ID NOs: 1, 39, 77, 115, 153, 191, 229, 267, 305, 343, 381, 419, 457, 495, 533, 571, 609, 647, 685, and 723, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725 and a CDR-H2 selected from SEQ ID NOs: 2, 40, 78, 116, 154, 192, 230, 268, 306, 344, 382, 420, 458, 496, 534, 572, 610, 648, 686, and 724. In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725, a CDR-H2 selected from SEQ ID NOs: 2, 40, 78, 116, 154, 192, 230, 268, 306, 344, 382, 420, 458, 496, 534, 572, 610, 648, 686, and 724, and a CDR-H1 selected from SEQ ID NOs: 1, 39, 77, 115, 153, 191, 229, 267, 305, 343, 381, 419, 457, 495, 533, 571, 609, 647, 685, and 723. In some embodiments, the CDR-H3 has at least about 50%, 75%, 80%, 85%, 90%, or 95% identity with a CDR-H3 of SEQ ID NOs: 3, 41, 79, 117, 155, 193, 231, 269, 307, 345, 383, 421, 459, 497, 535, 573, 611, 649, 687, and 725, the CDR-H2 has at least about 50%, 75%, 80%, 85%, 90%, or 95% identity with a CDR-H2 of SEQ ID NOs: 2, 40, 78, 116, 154, 192, 230, 268, 306, 344, 382, 420, 458, 496, 534, 572, 610, 648, 686, and 724, and the CDR-H1 has at least about 50%, 75%, 80%, 85%, 90%, or 95% identity with a CDR-H1 of SEQ ID NOs: 1, 39, 77, 115, 153, 191, 229, 267, 305, 343, 381, 419, 457, 495, 533, 571, 609, 647, 685, and 723. In some embodiments, the CDR-H3 is a CDR-H3 selected from SEQ ID NOs: 3, 41, 79, 117, 155, 193, 231, 269, 307, 345, 383, 421, 459, 497, 535, 573, 611, 649, 687, and 725, with up to 1, 2, 3, 4, 5, 6, 7, or 8 amino acid substitutions; the CDR-H2 is a CDR-H2 selected from SEQ ID NOs: 2, 40, 78, 116, 154, 192, 230, 268, 306, 344, 382, 420, 458, 496, 534, 572, 610, 648, 686, and 724, with up to 1, 2, 3, 4, 5, 6, 7, or 8 amino acid substitutions; and the CDR-H1 is a CDR-H1 selected from SEQ ID NOs: 1, 39, 77, 115, 153, 191, 229, 267, 305, 343, 381, 419, 457, 495, 533, 571, 609, 647, 685, and 723, with up to 1, 2, 3, 4, or 5 amino acid substitutions. In some aspects, the amino acid substitutions are conservative amino acid substitutions. In some embodiments, the antibody described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 selected from SEQ ID NOs: 6, 44, 82, 120, 158, 196, 234, 272, 310, 348, 386, 424, 462, 500, 538, 576, 614, 652, 690, and 728, as determined by the Exemplary numbering system. In some aspects, the CDR-L3 has at least about 50%, 75%, 80%, 85%, 90%, or 95% identity with a CDR-L3 of SEQ ID NOs: 6, 44, 82, 120, 158, 196, 234, 272, 310, 348, 386, 424, 462, 500, 538, 576, 614, 652, 690, and 728. In some embodiments, the CDR-L3 is a CDR-L3 selected from SEQ ID NOs: 6, 44, 82, 120, 158, 196, 234, 272, 310, 348, 386, 424, 462, 500, 538, 576, 614, 652, 690, and 728, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L2 selected from SEQ ID NOs: 5, 43, 81, 119, 157, 195, 233, 271, 309, 347, 385, 423, 461, 499, 537, 575, 613, 651, 689, and 727, as determined by the Exemplary numbering system. In some aspects, the CDR-L2 has at least about 50%, 75%, 80%, 85%, 90%, or 95% identity with a CDR-L2 of SEQ ID NOs: 5, 43, 81, 119, 157, 195, 233, 271, 309, 347, 385, 423, 461, 499, 537, 575, 613, 651, 689, and 727. In some embodiments, the CDR-L2 is a CDR-L2 selected from SEQ ID NOs: 5, 43, 81, 119, 157, 195, 233, 271, 309, 347, 385, 423, 461, 499, 537, 575, 613, 651, 689, and 727, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L1 selected from SEQ ID NOs: 4, 42, 80, 118, 156, 194, 232, 270, 308, 346, 384, 422, 460, 498, 536, 574, 612, 650, 688, and 726, as determined by the Exemplary numbering system. In some aspects, the CDR-L1 has at least about 50%, 75%, 80%, 85%, 90%, or 95% identity with a CDR-L1 of SEQ ID NOs: 4, 42, 80, 118, 156, 194, 232, 270, 308, 346, 384, 422, 460, 498, 536, 574, 612, 650, 688, and 726. In some embodiments, the CDR-L1 is a CDR-L1 selected from SEQ ID NOs: 4, 42, 80, 118, 156, 194, 232, 270, 308, 346, 384, 422, 460, 498, 536, 574, 612, 650, 688, and 726, with up to 1, 2, 3, 4, 5, 6, 7, or 8 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-L3 selected from SEQ ID NOs: 6, 44, 82, 120, 158, 196, 234, 272, 310, 348, 386, 424, 462, 500, 538, 576, 614, 652, 690, and 728 and a CDR-L2 selected from SEQ ID NOs: 5, 43, 81, 119, 157, 195, 233, 271, 309, 347, 385, 423, 461, 499, 537, 575, 613, 651, 689, and 727. In some embodiments, an antibody provided herein comprises a CDR-L3 selected from SEQ ID NOs: 6, 44, 82, 120, 158, 196, 234, 272, 310, 348, 386, 424, 462, 500, 538, 576, 614, 652, 690, and 728, a CDR-L2 selected from SEQ ID NOs: 5, 43, 81, 119, 157, 195, 233, 271, 309, 347, 385, 423, 461, 499, 537, 575, 613, 651, 689, and 727, and a CDR-L1 selected from SEQ ID NOs: 4, 42, 80, 118, 156, 194, 232, 270, 308, 346, 384, 422, 460, 498, 536, 574, 612, 650, 688, and 726. In some embodiments, the CDR-L3 has at least about 50%, 75%, 80%, 85%, 90%, or 95% identity with a CDR-L3 of SEQ ID NOs: 6, 44, 82, 120, 158, 196, 234, 272, 310, 348, 386, 424, 462, 500, 538, 576, 614, 652, 690, and 728, the CDR-L2 has at least about 50%, 75%, 80%, 85%, 90%, or 95% identity with a CDR-L2 of SEQ ID NOs: 5, 43, 81, 119, 157, 195, 233, 271, 309, 347, 385, 423, 461, 499, 537, 575, 613, 651, 689, and 727, and the CDR-L1 has at least about 50%, 75%, 80%, 85%, 90%, or 95% identity with a CDR-L1 of SEQ ID NOs: 4, 42, 80, 118, 156, 194, 232, 270, 308, 346, 384, 422, 460, 498, 536, 574, 612, 650, 688, and 726. In some embodiments, the CDR-L3 is a CDR-L3 selected from SEQ ID NOs: 6, 44, 82, 120, 158, 196, 234, 272, 310, 348, 386, 424, 462, 500, 538, 576, 614, 652, 690, and 728, with up to 1, 2, 3, 4, or 5 amino acid substitutions; the CDR-L2 is a CDR-L2 selected from SEQ ID NOs: 5, 43, 81, 119, 157, 195, 233, 271, 309, 347, 385, 423, 461, 499, 537, 575, 613, 651, 689, and 727, with up to 1, 2, 3, or 4 amino acid substitutions; and the CDR-L1 is a CDR-L1 selected from SEQ ID NOs: 4, 42, 80, 118, 156, 194, 232, 270, 308, 346, 384, 422, 460, 498, 536, 574, 612, 650, 688, and 726, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H3 selected from SEQ ID NOs: 3, 41, 79, 117, 155, 193, 231, 269, 307, 345, 383, 421, 459, 497, 535, 573, 611, 649, 687, and 725, a CDR-H2 selected from SEQ ID NOs: 2, 40, 78, 116, 154, 192, 230, 268, 306, 344, 382, 420, 458, 496, 534, 572, 610, 648, 686, and 724, a CDR-H1 selected from SEQ ID NOs: 1, 39, 77, 115, 153, 191, 229, 267, 305, 343, 381, 419, 457, 495, 533, 571, 609, 647, 685, and 723, a CDR-L3 selected from SEQ ID NOs: 6, 44, 82, 120, 158, 196, 234, 272, 310, 348, 386, 424, 462, 500, 538, 576, 614, 652, 690, and 728, a CDR-L2 selected from SEQ ID NOs: 5, 43, 81, 119, 157, 195, 233, 271, 309, 347, 385, 423, 461, 499, 537, 575, 613, 651, 689, and 727, and a CDR-L1 selected from SEQ ID NOs: 4, 42, 80, 118, 156, 194, 232, 270, 308, 346, 384, 422, 460, 498, 536, 574, 612, 650, 688, and 726. In some embodiments, the CDR-H3 has at least about 50%, 75%, 80%, 85%, 90%, or 95% identity with a CDR-H3 of SEQ ID NOs: 3, 41, 79, 117, 155, 193, 231, 269, 307, 345, 383, 421, 459, 497, 535, 573, 611, 649, 687, and 725, the CDR-H2 has at least about 50%, 75%, 80%, 85%, 90%, or 95% identity with a CDR-H2 of SEQ ID NOs: 2, 40, 78, 116, 154, 192, 230, 268, 306, 344, 382, 420, 458, 496, 534, 572, 610, 648, 686, and 724, the CDR-H1 has at least about 50%, 75%, 80%, 85%, 90%, or 95% identity with a CDR-H1 of SEQ ID NOs: 1, 39, 77, 115, 153, 191, 229, 267, 305, 343, 381, 419, 457, 495, 533, 571, 609, 647, 685, and 723, the CDR-L3 has at least about 50%, 75%, 80%, 85%, 90%, or 95% identity with a CDR-L3 of SEQ ID NOs: 6, 44, 82, 120, 158, 196, 234, 272, 310, 348, 386, 424, 462, 500, 538, 576, 614, 652, 690, and 728, the CDR-L2 has at least about 50%, 75%, 80%, 85%, 90%, or 95% identity with a CDR-L2 of SEQ ID NOs: 5, 43, 81, 119, 157, 195, 233, 271, 309, 347, 385, 423, 461, 499, 537, 575, 613, 651, 689, and 727, and the CDR-L1 has at least about 50%, 75%, 80%, 85%, 90%, or 95% identity with a CDR-L1 of SEQ ID NOs: 4, 42, 80, 118, 156, 194, 232, 270, 308, 346, 384, 422, 460, 498, 536, 574, 612, 650, 688, and 726. In some embodiments, the CDR-H3 is a CDR-H3 selected from SEQ ID NOs: 3, 41, 79, 117, 155, 193, 231, 269, 307, 345, 383, 421, 459, 497, 535, 573, 611, 649, 687, and 725, with up to 1, 2, 3, 4, 5, 6, 7, or 8 amino acid substitutions; the CDR-H2 is a CDR-H2 selected from SEQ ID NOs: 2, 40, 78, 116, 154, 192, 230, 268, 306, 344, 382, 420, 458, 496, 534, 572, 610, 648, 686, and 724, with up to 1, 2, 3, 4, 5, 6, 7, or 8 amino acid substitutions; the CDR-H1 is a CDR-H1 selected from SEQ ID NOs: 1, 39, 77, 115, 153, 191, 229, 267, 305, 343, 381, 419, 457, 495, 533, 571, 609, 647, 685, and 723, with up to 1, 2, 3, 4, or 5 amino acid substitutions; the CDR-L3 is a CDR-L3 selected from SEQ ID NOs: 6, 44, 82, 120, 158, 196, 234, 272, 310, 348, 386, 424, 462, 500, 538, 576, 614, 652, 690, and 728, with up to 1, 2, 3, 4, or 5 amino acid substitutions; the CDR-L2 is a CDR-L2 selected from SEQ ID NOs: 5, 43, 81, 119, 157, 195, 233, 271, 309, 347, 385, 423, 461, 499, 537, 575, 613, 651, 689, and 727, with up to 1, 2, 3, or 4 amino acid substitutions; and the CDR-L1 is a CDR-L1 selected from SEQ ID NOs: 4, 42, 80, 118, 156, 194, 232, 270, 308, 346, 384, 422, 460, 498, 536, 574, 612, 650, 688, and 726, with up to 1, 2, 3, 4, 5, or 6 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies.

In some embodiments, an antibody provided herein comprises a CDR-H1 of SEQ ID NO:1, a CDR-H2 of SEQ ID NO:2, a CDR-H3 of SEQ ID NO:3, a CDR-L1 of SEQ ID NO:4, a CDR-L2 of SEQ ID NO:5, and a CDR-L1 of SEQ ID NO:6, as determined by the Exemplary numbering system.

In some embodiments, an antibody provided herein comprises a CDR-H1 of SEQ ID NO:39, a CDR-H2 of SEQ ID NO:40, a CDR-H3 of SEQ ID NO:41, a CDR-L1 of SEQ ID NO:42, a CDR-L2 of SEQ ID NO:43, and a CDR-L1 of SEQ ID NO:44, as determined by the Exemplary numbering system.

In some embodiments, an antibody provided herein comprises a CDR-H1 of SEQ ID NO:77, a CDR-H2 of SEQ ID NO:78, a CDR-H3 of SEQ ID NO:79, a CDR-L1 of SEQ ID NO:80, a CDR-L2 of SEQ ID NO:81, and a CDR-L1 of SEQ ID NO:82, as determined by the Exemplary numbering system.

In some embodiments, an antibody provided herein comprises a CDR-H1 of SEQ ID NO:115, a CDR-H2 of SEQ ID NO:116, a CDR-H3 of SEQ ID NO:117, a CDR-L1 of SEQ ID NO:118, a CDR-L2 of SEQ ID NO:119, and a CDR-L1 of SEQ ID NO:120, as determined by the Exemplary numbering system.

In some embodiments, an antibody provided herein comprises a CDR-H1 of SEQ ID NO:153, a CDR-H2 of SEQ ID NO:154, a CDR-H3 of SEQ ID NO:155, a CDR-L1 of SEQ ID NO:156, a CDR-L2 of SEQ ID NO:157, and a CDR-L1 of SEQ ID NO:158, as determined by the Exemplary numbering system.

In some embodiments, an antibody provided herein comprises a CDR-H1 of SEQ ID NO:884, a CDR-H2 of SEQ ID NO:885, a CDR-H3 of SEQ ID NO:886, a CDR-L1 of SEQ ID NO:887, a CDR-L2 of SEQ ID NO:888, and a CDR-L1 of SEQ ID NO:889, as determined by the Exemplary numbering system.

In some embodiments, an antibody provided herein comprises a CDR-H1 of SEQ ID NO:191, a CDR-H2 of SEQ ID NO:192, a CDR-H3 of SEQ ID NO:193, a CDR-L1 of SEQ ID NO:194, a CDR-L2 of SEQ ID NO:195, and a CDR-L1 of SEQ ID NO:196, as determined by the Exemplary numbering system.

In some embodiments, an antibody provided herein comprises a CDR-H1 of SEQ ID NO:229, a CDR-H2 of SEQ ID NO:230, a CDR-H3 of SEQ ID NO:231, a CDR-L1 of SEQ ID NO:232, a CDR-L2 of SEQ ID NO:233, and a CDR-L1 of SEQ ID NO:234, as determined by the Exemplary numbering system.

In some embodiments, an antibody provided herein comprises a CDR-H1 of SEQ ID NO:267, a CDR-H2 of SEQ ID NO:268, a CDR-H3 of SEQ ID NO:269, a CDR-L1 of SEQ ID NO:270, a CDR-L2 of SEQ ID NO:271, and a CDR-L1 of SEQ ID NO:272, as determined by the Exemplary numbering system.

In some embodiments, an antibody provided herein comprises a CDR-H1 of SEQ ID NO:305, a CDR-H2 of SEQ ID NO:306, a CDR-H3 of SEQ ID NO:307, a CDR-L1 of SEQ ID NO:308, a CDR-L2 of SEQ ID NO:309, and a CDR-L1 of SEQ ID NO:310, as determined by the Exemplary numbering system.

In some embodiments, an antibody provided herein comprises a CDR-H1 of SEQ ID NO:343, a CDR-H2 of SEQ ID NO:344, a CDR-H3 of SEQ ID NO:345, a CDR-L1 of SEQ ID NO:346, a CDR-L2 of SEQ ID NO:347, and a CDR-L1 of SEQ ID NO:348, as determined by the Exemplary numbering system.

In some embodiments, an antibody provided herein comprises a CDR-H1 of SEQ ID NO:381, a CDR-H2 of SEQ ID NO:382, a CDR-H3 of SEQ ID NO:383, a CDR-L1 of SEQ ID NO:384, a CDR-L2 of SEQ ID NO:385, and a CDR-L1 of SEQ ID NO:386, as determined by the Exemplary numbering system.

In some embodiments, an antibody provided herein comprises a CDR-H1 of SEQ ID NO:419, a CDR-H2 of SEQ ID NO:420, a CDR-H3 of SEQ ID NO:421, a CDR-L1 of SEQ ID NO:422, a CDR-L2 of SEQ ID NO:423, and a CDR-L1 of SEQ ID NO:424, as determined by the Exemplary numbering system.

In some embodiments, an antibody provided herein comprises a CDR-H1 of SEQ ID NO:457, a CDR-H2 of SEQ ID NO:458, a CDR-H3 of SEQ ID NO:459, a CDR-L1 of SEQ ID NO:460, a CDR-L2 of SEQ ID NO:461, and a CDR-L1 of SEQ ID NO:462, as determined by the Exemplary numbering system.

In some embodiments, an antibody provided herein comprises a CDR-H1 of SEQ ID NO:495, a CDR-H2 of SEQ ID NO:496, a CDR-H3 of SEQ ID NO:497, a CDR-L1 of SEQ ID NO:498, a CDR-L2 of SEQ ID NO:499, and a CDR-L1 of SEQ ID NO:500, as determined by the Exemplary numbering system.

In some embodiments, an antibody provided herein comprises a CDR-H1 of SEQ ID NO:533, a CDR-H2 of SEQ ID NO:534, a CDR-H3 of SEQ ID NO:535, a CDR-L1 of SEQ ID NO:536, a CDR-L2 of SEQ ID NO:537, and a CDR-L1 of SEQ ID NO:538, as determined by the Exemplary numbering system.

In some embodiments, an antibody provided herein comprises a CDR-H1 of SEQ ID NO:571, a CDR-H2 of SEQ ID NO:572, a CDR-H3 of SEQ ID NO:573, a CDR-L1 of SEQ ID NO:574, a CDR-L2 of SEQ ID NO:575, and a CDR-L1 of SEQ ID NO:576, as determined by the Exemplary numbering system.

In some embodiments, an antibody provided herein comprises a CDR-H1 of SEQ ID NO:609, a CDR-H2 of SEQ ID NO:610, a CDR-H3 of SEQ ID NO:611, a CDR-L1 of SEQ ID NO:612, a CDR-L2 of SEQ ID NO:613, and a CDR-L1 of SEQ ID NO:614, as determined by the Exemplary numbering system.

In some embodiments, an antibody provided herein comprises a CDR-H1 of SEQ ID NO:647, a CDR-H2 of SEQ ID NO:648, a CDR-H3 of SEQ ID NO:649, a CDR-L1 of SEQ ID NO:650, a CDR-L2 of SEQ ID NO:651, and a CDR-L1 of SEQ ID NO:652, as determined by the Exemplary numbering system.

In some embodiments, an antibody provided herein comprises a CDR-H1 of SEQ ID NO:685, a CDR-H2 of SEQ ID NO:686, a CDR-H3 of SEQ ID NO:687, a CDR-L1 of SEQ ID NO:688, a CDR-L2 of SEQ ID NO:689, and a CDR-L1 of SEQ ID NO:690, as determined by the Exemplary numbering system.

In some embodiments, an antibody provided herein comprises a CDR-H1 of SEQ ID NO:723, a CDR-H2 of SEQ ID NO:724, a CDR-H3 of SEQ ID NO:725, a CDR-L1 of SEQ ID NO:726, a CDR-L2 of SEQ ID NO:727, and a CDR-L1 of SEQ ID NO:728, as determined by the Exemplary numbering system.

2.2.5. Consensus Sequences

In some embodiments, provided herein is a first family of antibodies, wherein an antibody of such family comprises the following six CDR sequences: (a) a CDR-H1 having the sequence G-F-T-F-S-$X_1$-Y-A-M-X2, wherein $X_1$ is D or S and $X_2$ is A or G (SEQ ID NO:773); (b) a CDR-H2 having the sequence $X_3$-I-S-G-S-G-G-L-T-Y-Y-A-D-S-V-K-G, wherein $X_3$ is A or T (SEQ ID NO:774); (c) a CDR-H3 having the sequence APYGYYMDV (SEQ ID NO:775); (d) a CDR-L1 having the sequence RASQSISSWLA (SEQ ID NO:776); (e) a CDR-L2 having the sequence KASSLES (SEQ ID NO:777); and (f) a CDR-L3 having the sequence QQYKSYIT (SEQ ID NO:778). In some embodiments, an antibody of such family comprises a $V_H$ sequence of SEQ ID NO:761 and a $V_L$ sequence of SEQ ID NO:762. In some embodiments, provided herein is an antibody within such first family.

In some embodiments, provided herein is a second family of antibodies, wherein an antibody of such family comprises the following six CDR sequences: (a) a CDR-H1 having the sequence G-Y-T-F-$X_1$-$X_2$-Y-G-I-S, wherein $X_1$ is D or R and $X_2$ is S or V (SEQ ID NO:779); (b) a CDR-H2 having the sequence W-$X_3$-A-P-Y-$X_4$-G-N-T-N-Y-A-Q-K-L-Q-G, wherein $X_3$ is I or V and $X_4$ is S or N (SEQ ID NO:780); (c) a CDR-H3 having the sequence D-A-G-T-Y-S-P-$X_5$-G-Y-G-M-D-V, wherein $X_5$ is F or Y (SEQ ID NO:781); (d) a CDR-L1 having the sequence $X_6$-A-S-$X_7$-S-I-$X_8$-$X_9$-W-L-A, wherein $X_6$ is R or Q, $X_7$ is Q, E, or H, $X_8$ is S, D, or N, and $X_9$ is S or N (SEQ ID NO:782); (e) a CDR-L2 having the sequence $X_{10}$-A-$X_{11}$-$X_{12}$-L-E-$X_{13}$, wherein $X_{10}$ is K or S, $X_{11}$ is S or Y, $X_{12}$ is S, Y, or N, and $X_{13}$ is S or Y; and (f) a CDR-L3 having the sequence Q-$X_{14}$-F-Q-$X_{15}$-L-P-P-F-T, wherein $X_{14}$ is Q, L, or R, and $X_{15}$ is S or K (SEQ ID NO:784). In some embodiments, an antibody of such family comprises a $V_H$ sequence of SEQ ID NO:763 and a $V_L$ sequence of SEQ ID NO:764. In some embodiments, provided herein is an antibody within such second family.

In some embodiments, provided herein is a third family of antibodies, wherein an antibody of such family comprises the following six CDR sequences: (a) a CDR-H1 having the sequence G-F-T-F-$X_1$-S-$X_2$-G-M-H, wherein $X_1$ is H or R and X$_2$ is R or Y (SEQ ID NO:785); (b) a CDR-H2 having the sequence VITYDGINKYYADSVEG (SEQ ID NO:786); (c) a CDR-H3 having the sequence DGVYYGVYDY (SEQ ID NO:787); (d) a CDR-L1 having the sequence KSSQSVLFSSNNKNYLA (SEQ ID NO:788); (e) a CDR-L2 having the sequence WASTRES (SEQ ID NO:789); and (f) a CDR-L3 having the sequence QQFHSYPLT (SEQ ID NO:790). In some embodiments, an antibody of such family comprises a V$_H$ sequence of SEQ ID NO:765 and a V$_L$ sequence of SEQ ID NO:766. In some embodiments, provided herein is an antibody within such third family.

In some embodiments, provided herein is a fourth family of antibodies, wherein an antibody of such family comprises the following six CDR sequences: (a) a CDR-H1 having the sequence GGTFSSNAIG (SEQ ID NO:791); (b) a CDR-H2 having the sequence SIIPIIGFANYAQKFQG (SEQ ID NO:792); (c) a CDR-H3 having the sequence DSGYYY-GASSFGMDV (SEQ ID NO:793); (d) a CDR-L1 having the sequence RASQSVSSNLA (SEQ ID NO:794); (e) a CDR-L2 having the sequence GASTRAT (SEQ ID NO:795); and (f) a CDR-L3 having the sequence EQYNNLPLT (SEQ ID NO:796). In some embodiments, an antibody of such family comprises a V$_H$ sequence of SEQ ID NO:767 and a V$_L$ sequence of SEQ ID NO:768. In some embodiments, provided herein is an antibody within such fourth family.

In some embodiments, provided herein is a fifth family of antibodies, wherein an antibody of such family comprises the following six CDR sequences: (a) a CDR-H1 having the sequence G-G-S-X$_1$-S-S-G-X$_2$-Y-W-S, wherein X$_1$ is I or L and X$_2$ is Q or Y (SEQ ID NO:797); (b) a CDR-H2 having the sequence E-I-X$_3$-X$_4$-S-G-S-T-R-Y-N-P-S-L-K-S, wherein X$_3$ is Y or G and X$_4$ is Y or A (SEQ ID NO:798); (c) a CDR-H3 having the sequence D-X$_5$-P-Y-Y-Y-X$_6$-G-G-Y-Y-Y-M-D-V, wherein X$_5$ is T or A and X$_6$ is E, G, or D (SEQ ID NO:799); (d) a CDR-L1 having the sequence R-A-S-X$_7$-S-V-X$_8$-SS-X$_9$-L-A, wherein X$_7$ is Q, E, or D, X$_8$ is S or D, and X$_9$ is Y or F (SEQ ID NO:800); (e) a CDR-L2 having the sequence G-A-X$_{10}$-X$_{11}$-R-X$_{12}$-X$_{13}$, wherein X$_{10}$ is S, D, F, or Y, X$_{11}$ is S or T, X$_{12}$ is A or Q, and X$_{13}$ is T or N; and (f) a CDR-L3 having the sequence Q-Q-X$_{14}$-G-V-V-P-Y-T, wherein X$_{14}$ is V, A, or D (SEQ ID NO:802). In some embodiments, an antibody of such family comprises a V$_H$ sequence of SEQ ID NO: 769 and a V$_L$ sequence of SEQ ID NO:770. In some embodiments, provided herein is an antibody within such fifth family.

In some embodiments, provided herein is a sixth family of antibodies, wherein an antibody of such family comprises the following six CDR sequences: (a) a CDR-H1 having the sequence GYTFANYYMH (SEQ ID NO:803); (b) a CDR-H2 having the sequence IINPSGGITVYAQKFQG (SEQ ID NO:804); (c) a CDR-H3 having the sequence GGSK-VAALAFDI (SEQ ID NO:805); (d) a CDR-L1 having the sequence QASQDISNSLN (SEQ ID NO:806); (e) a CDR-L2 having the sequence DASNLET (SEQ ID NO:807); and (f) a CDR-L3 having the sequence QQYNFHPLT (SEQ ID NO:808). In some embodiments, an antibody of such family comprises a V$_H$ sequence of SEQ ID NO:771 and a V$_L$ sequence of SEQ ID NO:772. In some embodiments, provided herein is an antibody within such sixth family.

In some embodiments, provided herein is a seventh family of antibodies, wherein an antibody of such family comprises the following six CDR sequences: (a) a CDR-H1 having the sequence G-Y-T-F-D-X$_1$-Y-G-I-S, wherein X$_1$ is V or A (SEQ ID NO:872); (b) a CDR-H2 having the sequence W-I-A-P-Y-X$_2$-G-N-T-N-Y-A-Q-K-L-Q-G, wherein X$_2$ is N or S (SEQ ID NO:873); (c) a CDR-H3 having the sequence D-A-G-T-Y-S-P-F-G-Y-G-M-D-V (SEQ ID NO:874); (d) a CDR-L1 having the sequence X$_3$-A-S-X$_4$-S-I-X$_5$-X$_6$-W-L-A, wherein X$_3$ is R or Q, X$_4$ is Q or E, X$_5$ is S or N, and X$_6$ is S or N (SEQ ID NO:875); (e) a CDR-L2 having the sequence K-A-X$_7$-X$_8$-L-E-X$_9$, wherein X$_7$ is S or Y, X$_8$ is S or N, and X$_9$ is S or Y (SEQ ID NO:876); and (f) a CDR-L3 having the sequence Q-X$_{10}$-F-Q-X$_{11}$-L-P-P-F-T, wherein X$_{10}$ is Q or L, and X$_{11}$ is S or K (SEQ ID NO:877). In some embodiments, an antibody of such family comprises a V$_H$ sequence of SEQ ID NO:868 and a V$_L$ sequence of SEQ ID NO:869. In some embodiments, provided herein is an antibody within such seventh family.

In some embodiments, provided herein is an eighth family of antibodies, wherein an antibody of such family comprises the following six CDR sequences: (a) a CDR-H1 having the sequence G-Y-T-F-R-S-Y-G-I-S(SEQ ID NO:878); (b) a CDR-H2 having the sequence W-V-A-P-Y-X$_1$-G-N-T-N-Y-A-Q-K-L-Q-G, wherein X$_1$ is S or N (SEQ ID NO:879); (c) a CDR-H3 having the sequence D-A-G-T-Y-S-P-Y-G-Y-G-M-D-V (SEQ ID NO:880); (d) a CDR-L1 having the sequence X$_2$-A-S-X$_3$-S-I-X$_4$-S-W-L-A, wherein X$_2$ is R or Q, X$_3$ is Q or H, X$_4$ is S or D (SEQ ID NO:881); (e) a CDR-L2 having the sequence X$_5$-A-S-X$_6$-L-E-S, wherein X$_5$ is K or S, X$_6$ is S or Y (SEQ ID NO:882); and (f) a CDR-L3 having the sequence Q-X$_7$-F-Q-S-L-P-P-F-T, wherein X$_7$ is Q, L, or R (SEQ ID NO:883). In some embodiments, an antibody of such family comprises a V$_H$ sequence of SEQ ID NO:870 and a V$_L$ sequence of SEQ ID NO:871. In some embodiments, provided herein is an antibody within such eighth family.

2.2.6. Functional Properties of Antibody Variants

As described above, and elsewhere in this disclosure, provided herein are antibody variants defined based on percent identity to an illustrative antibody sequence provided herein, or substitution of amino acid residues in comparison to an illustrative antibody sequence provided herein.

In some embodiments, a variant of an antibody provided herein has specificity for hTF. In some embodiments, a variant of an antibody provided herein has specificity for cTF. In some embodiments, a variant of an antibody provided herein has specificity for mTF. In some embodiments, a variant of an antibody provided herein has specificity for hTF and cTF. In some embodiments, a variant of an antibody provided herein has specificity for hTF and mTF. In some embodiments, a variant of an antibody provided herein has specificity for cTF and mTF. In some embodiments, a variant of an antibody provided herein has specificity for hTF, cTF and mTF.

In some embodiments, a variant of an antibody that is derived from an illustrative antibody sequence provided herein retains affinity, as measured by K$_D$, for hTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by K$_D$, for cTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by K$_D$, for mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for both hTF and cTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for both hTF and mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for both cTF and mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody. In some embodiments, a variant of an antibody that is derived from an illustrative antibody sequence provided herein retains affinity, as measured by $K_D$, for all three of hTF, cTF and mTF that is within about 1.5-fold, about 2-fold, about 3-fold, about 4-fold, about 5-fold, about 6-fold, about 7-fold, about 8-fold, about 9-fold or about 10-fold the affinity of such illustrative antibody.

In some embodiments, a variant of an antibody provided herein retains the ability to inhibit TF signaling, as measured by one or more assays or biological effects described herein. In some embodiments, a variant of an antibody provided herein retains the normal function of TF in the blood coagulation processes.

In some embodiments, a variant of an antibody provided herein competes for binding to TF with an antibody selected from 1F, 1G, 25A, 25A3, 25A5, 25A5-T, 25G, 25G1, 25G9, 29D, 29E, 39A, 43B, 43B1, 43B7, 43D, 43D7, 43D8, 43E, 43Ea, and 54E, each as provided in Table 13 of this disclosure. In some embodiments, a variant of an antibody provided herein competes for binding to TF with an antibody selected from 25A, 25A3, 25A5, 25A5-T, 25G, 25G1, and 25G9. In some embodiments, a variant of an antibody provided herein competes for binding to TF with an antibody selected from 43B, 43B1, 43B7, 43D, 43D7, 43D8, 43E, and 43Ea. In some embodiments, a variant of an antibody provided herein competes for binding to TF with an antibody selected from 25A, 25A3, 25A5, 25A5-T, 25G, 25G1, 25G9, 43B, 43B1, 43B7, 43D, 43D7, 43D8, 43E, and 43Ea. In some embodiments, a variant of an antibody provided herein competes for binding to TF with an antibody selected from 1F, 1G, 29D, 29E, 39A, or 54E.

In some embodiments, a variant of an antibody provided herein allows human thrombin generation as determined by thrombin generation assay (TGA). In some embodiments, a variant of an antibody provided herein does not inhibit human thrombin generation as determined by thrombin generation assay (TGA).

In some embodiments, a variant of an antibody provided herein binds human TF at a human TF binding site that is distinct from a human TF binding site bound by human FX. In some embodiments, a variant of an antibody provided herein does not interfere with the ability of TF:FVIIa to convert FX into FXa.

In some embodiments, a variant of an antibody provided herein binds human TF at a human TF binding site that is distinct from a human TF binding site bound by human FVIIa. In some embodiments, a variant of an antibody provided herein does not compete for binding to human TF with human FVIIa.

In some embodiments, a variant of an antibody provided herein inhibits FVIIa-dependent TF signaling.

In some embodiments, a variant of an antibody provided herein binds mouse TF (SEQ ID NO:817). In some embodiments, a variant of an antibody provided herein binds mouse TF with an affinity lower (as indicated by higher $K_D$) than the affinity of the antibody for hTF. In some embodiments, a variant of an antibody provided herein does not bind mTF.

In some embodiments, a variant of an antibody provided herein binds pig TF (SEQ ID NO:824). In some embodiments, a variant of an antibody provided herein binds pig TF with an affinity lower (as indicated by higher $K_D$) than the affinity of the antibody for hTF. In some embodiments, a variant of an antibody provided herein does not bind pTF.

In some embodiments, a variant of an antibody provided herein binds the same epitope of TF as such antibody.

2.2.7. Other Functional Properties of Antibodies

In some embodiments, an antibody provided herein has one or more of the characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; (j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, an antibody provided herein has two or more of the characteristics listed in the foregoing (a)-(dd). In some embodiments, an antibody provided herein has three or more of the characteristics listed in the foregoing (a)-(dd). In some embodiments, an antibody provided herein has four or more of the characteristics listed in the foregoing (a)-(dd). In some embodiments, an antibody provided herein has five or more of the characteristics listed in the foregoing (a)-(dd). In some embodiments, an antibody provided herein has six or more of the characteristics listed in the foregoing (a)-(dd). In some embodiments, an antibody provided herein has seven or more of the characteristics listed in the foregoing (a)-(dd). In some embodiments, an antibody provided herein has eight or more of the characteristics listed in the foregoing (a)-(dd). In some embodiments, an antibody provided herein has nine or more of the characteristics listed in the foregoing (a)-(dd). In some embodiments, an antibody provided herein has ten or more of the characteristics listed in the foregoing (a)-(dd). In some embodiments, an antibody provided herein has eleven or more of the characteristics listed in the foregoing (a)-(dd). In some embodiments, an antibody provided herein has twelve or more of the characteristics listed in the foregoing (a)-(dd). In some embodiments, an antibody provided herein has thirteen or more of the characteristics listed in the foregoing (a)-(dd). In some embodiments, an antibody provided herein has fourteen or more of the characteristics listed in the foregoing (a)-(dd). In some embodiments, an antibody provided herein has fifteen or more of the characteristics listed in the foregoing (a)-(dd). In some embodiments, an antibody provided herein has sixteen or more of the characteristics listed in the foregoing (a)-(dd). In some embodiments, an antibody provided herein has seventeen or more of the characteristics listed in the foregoing (a)-(dd). In some embodiments, an antibody provided herein has eighteen or more of the characteristics listed in the foregoing (a)-(dd). In some embodiments, an antibody provided herein has nineteen or more of the characteristics listed in the foregoing (a)-(dd). In some embodiments, an antibody provided herein has twenty or more of the characteristics listed in the foregoing (a)-(dd). In some embodiments, an antibody provided herein has twenty-one or more of the characteristics listed in the foregoing (a)-(dd). In some embodiments, an antibody provided herein has twenty-two or more of the characteristics listed in the foregoing (a)-(dd). In some embodiments, an antibody provided herein has twenty-three of the characteristics listed in the foregoing (a)-(dd). In some embodiments, an antibody provided herein has twenty-four of the characteristics listed in the foregoing (a)-(dd). In some embodiments, an antibody provided herein has twenty-five of the characteristics listed in the foregoing (a)-(dd). In some embodiments, an antibody provided herein has twenty-six of the characteristics listed in the foregoing (a)-(dd). In some embodiments, an antibody provided herein has twenty-seven of the characteristics listed in the foregoing (a)-(dd). In some embodiments, an antibody provided herein has twenty-eight of the characteristics listed in the foregoing (a)-(dd). In some embodiments, an antibody provided herein has twenty-nine of the characteristics listed in the foregoing (a)-(dd). In some embodiments, an antibody provided herein has all thirty of the characteristics listed in the foregoing (a)-(dd).

In some embodiments, an antibody provided herein has one or more of the characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; (j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation K68N of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay. In some embodiments, an antibody provided herein has two or more of the characteristics listed in the foregoing (a)-(dd). In some embodiments, an antibody provided herein has three or more of the characteristics listed in the foregoing (a)-(dd). In some embodiments, an antibody provided herein has four or more of the characteristics listed in the foregoing (a)-(dd). In some embodiments, an antibody provided herein has five or more of the characteristics listed in the foregoing (a)-(dd). In some embodiments, an antibody provided herein has six or more of the characteristics listed in the foregoing (a)-(dd). In some embodiments, an antibody provided herein has seven or more of the characteristics listed in the foregoing (a)-(dd). In some embodiments, an antibody provided herein has eight or more of the characteristics listed in the foregoing (a)-(dd). In some embodiments, an antibody provided herein has nine or more of the characteristics listed in the foregoing (a)-(dd). In some embodiments, an antibody provided herein has ten or more of the characteristics listed in the foregoing (a)-(dd). In some embodiments, an antibody provided herein has eleven or more of the characteristics listed in the foregoing (a)-(dd). In some embodiments, an antibody provided herein has twelve or more of the characteristics listed in the foregoing (a)-(dd). In some embodiments, an antibody provided herein has thirteen or more of the characteristics listed in the foregoing (a)-(dd). In some embodiments, an antibody provided herein has fourteen or more of the characteristics listed in the foregoing (a)-(dd). In some embodiments, an antibody provided herein has fifteen or more of the characteristics listed in the foregoing (a)-(dd). In some embodiments, an antibody provided herein has sixteen or more of the characteristics listed in the foregoing (a)-(dd). In some embodiments, an antibody provided herein has seventeen or more of the characteristics listed in the foregoing (a)-(dd). In some embodiments, an antibody provided herein has eighteen or more of the characteristics listed in the foregoing (a)-(dd). In some embodiments, an antibody provided herein has nineteen or more of the characteristics listed in the foregoing (a)-(dd). In some embodiments, an antibody provided herein has twenty or more of the characteristics listed in the foregoing (a)-(dd). In some embodiments, an antibody provided herein has twenty-one or more of the characteristics listed in the foregoing (a)-(dd). In some embodiments, an antibody provided herein has twenty-two or more of the characteristics listed in the foregoing (a)-(dd). In some embodiments, an antibody provided herein has twenty-three of the characteristics listed in the foregoing (a)-(dd). In some embodiments, an antibody provided herein has twenty-four of the characteristics listed in the foregoing (a)-(dd). In some embodiments, an antibody provided herein has twenty-five of the characteristics listed in the foregoing (a)-(dd). In some embodiments, an antibody provided herein has twenty-six of the characteristics listed in the foregoing (a)-(dd). In some embodiments, an antibody provided herein has twenty-seven of the characteristics listed in the foregoing (a)-(dd). In some embodiments, an antibody provided herein has twenty-eight of the characteristics listed in the foregoing (a)-(dd). In some embodiments, an antibody provided herein has twenty-nine of the characteristics listed in the foregoing (a)-(dd). In some embodiments, an antibody provided herein has all thirty of the characteristics listed in the foregoing (a)-(dd).

In some embodiments, an antibody provided herein exhibits a combination of characteristics comprising two or more of characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; (j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation at amino acid residue 68 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of characteristics comprising two or more of characteristics listed in the following (a)-(dd): (a) binds human TF at a human TF binding site that is distinct from a human TF binding site bound by human FVIIa; (b) does not inhibit human thrombin generation as determined by thrombin generation assay (TGA); (c) does not reduce the thrombin peak on a thrombin generation curve (Peak IIa) compared to an isotype control; (d) does not increase the time from the assay start to the thrombin peak on a thrombin generation curve (ttPeak) compared to an isotype control; (e) does not decrease the endogenous thrombin potential (ETP) as determined by the area under a thrombin generation curve compared to an isotype control; (f) allows human thrombin generation as determined by thrombin generation assay (TGA); (g) maintains the thrombin peak on a thrombin generation curve (Peak IIa) compared to an isotype control; (h) maintains the time from the assay start to the thrombin peak on a thrombin generation curve (ttPeak) compared to an isotype control; (i) preserves the endogenous thrombin potential (ETP) as determined by the area under a thrombin generation curve compared to an isotype control; j) binds human TF at a human TF binding site that is distinct from a human TF binding site bound by human FX; (k) does not interfere with the ability of TF:FVIIa to convert FX into FXa; (l) does not compete for binding to human TF with human FVIIa; (m) inhibits FVIIa-dependent TF signaling; (n) binds to cynomolgus TF; (o) binds to mouse TF; (p) binds to rabbit TF; (q) binds to pig TF; (r) reduces lesion size in a swine choroidal neovascularization (CNV) model; (s) the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (t) the binding between the antibody and a variant TF extracellular domain comprising a mutation K68N of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay; (u) the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; (v) the binding between the antibody and a human TF extracellular domain with amino acid residues 1-77 of the sequence shown in SEQ ID NO:810 replaced by rat TF extracellular domain amino acid residues 1-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (w) the binding between the antibody and a human TF extracellular domain with amino acid residues 39-77 of the sequence shown in SEQ ID NO:810 replaced by rat TF extracellular domain amino acid residues 38-76 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (x) the binding between the antibody and a human TF extracellular domain with amino acid residues 94-107 of the sequence shown in SEQ ID NO:810 replaced by rat TF extracellular domain amino acid residues 99-112 of the sequence shown in SEQ ID NO:838 is greater than 50% of the binding between the antibody and the extracellular domain of TF of the sequence shown in SEQ ID NO:810, as determined by the median fluorescence intensity value of the antibody relative to an isotype control in a live cell staining assay; (y) the binding between the antibody and a human TF extracellular domain with amino acid residues 146-158 of the sequence shown in SEQ ID NO:810 replaced by rat TF extracellular domain amino acid residues 151-163 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (z) the binding between the antibody and a human TF extracellular domain with amino acid residues 159-219 of the sequence shown in SEQ ID NO:810 replaced by rat TF extracellular domain amino acid residues 164-224 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (aa) the binding between the antibody and a human TF extracellular domain with amino acid residues 159-189 of the sequence shown in SEQ ID NO:810 replaced by rat TF extracellular domain amino acid residues 164-194 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (bb) the binding between the antibody and a human TF extracellular domain with amino acid residues 159-174 of the sequence shown in SEQ ID NO:810 replaced by rat TF extracellular domain amino acid residues 164-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; (cc) the binding between the antibody and a human TF extracellular domain with amino acid residues 167-174 of the sequence shown in SEQ ID NO:810 replaced by rat TF extracellular domain amino acid residues 172-179 of the sequence shown in SEQ ID NO:838 is less than 50% of the binding between the antibody and the extracellular domain of TF of the sequence shown in SEQ ID NO:810, as determined by the median fluorescence intensity value of the antibody relative to an isotype control in a live cell staining assay; and (dd) the binding between the antibody and a rat TF extracellular domain with amino acid residues 141-194 of the sequence shown in SEQ ID NO:838 replaced by human TF extracellular domain amino acid residues 136-189 of the sequence shown in SEQ ID NO:810 is greater than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); binds to cynomolgus TF; the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; does not inhibit human thrombin generation as determined by thrombin generation assay (TGA); binds to cynomolgus TF; the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); binds to cynomolgus TF; the binding between the antibody and a variant TF extracellular domain comprising a mutation at amino acid residue 149 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations at amino acid residues 171 and 197 of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

In some embodiments, an antibody provided herein exhibits a combination of the characteristics listed in the following: binds human TF at a human TF binding site that is distinct from a human TF binding site bound by human FVIIa; allows human thrombin generation as determined by thrombin generation assay (TGA); binds to cynomolgus TF; the binding between the antibody and a variant TF extracellular domain comprising a mutation K149N of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay; and the binding between the antibody and a variant TF extracellular domain comprising mutations N171H and T197K of the sequence shown in SEQ ID NO:810 is less than 50% of the binding between the antibody and the extracellular domain of TF of the sequence shown in SEQ ID NO:810, as determined by the median fluorescence intensity value of the antibody relative to an isotype control in a live cell staining assay.

2.3. Affinity and Other Properties of TF Antibodies

2.3.1. Affinity of TF Antibodies

In some embodiments, the affinity of an antibody provided herein for TF as indicated by $K_D$, is less than about 10-5 M, less than about $10^{-6}$ M, less than about $10^{-7}$ M, less than about $10^{-8}$ M, less than about $10^{-9}$ M, less than about $10^{-10}$ M, less than about $10^{-11}$ M, or less than about $10^{-12}$ M. In some embodiments, the affinity of the antibody is between about $10^{-7}$ M and $10^{-12}$ M. In some embodiments, the affinity of the antibody is between about $10^{-7}$ M and $10^{-11}$ M. In some embodiments, the affinity of the antibody is between about $10^{-7}$ M and $10^{-10}$ M. In some embodiments, the affinity of the antibody is between about $10^{-7}$ M and $10^{-9}$ M. In some embodiments, the affinity of the antibody is between about $10^{-7}$ M and $10^{-8}$ M. In some embodiments, the affinity of the antibody is between about $10^{-8}$ M and $10^{-12}$ M. In some embodiments, the affinity of the antibody is between about $10^{-8}$ M and $10^{-11}$ M. In some embodiments, the affinity of the antibody is between about $10^{-9}$ M and $10^{-11}$ M. In some embodiments, the affinity of the antibody is between about $10^{-10}$ M and $10^{-11}$ M.

In some embodiments, the $K_D$ value of an antibody provided herein for cTF is no more than 15× of the $K_D$ value of the antibody for hTF. In some embodiments, the $K_D$ value of an antibody provided herein for cTF is no more than 10× of the $K_D$ value of the antibody for hTF. In some embodiments, the $K_D$ value of an antibody provided herein for cTF is no more than 8× of the $K_D$ value of the antibody for hTF. In some embodiments, the $K_D$ value of an antibody provided herein for cTF is no more than 5× of the $K_D$ value of the antibody for hTF. In some embodiments, the $K_D$ value of an antibody provided herein for cTF is no more than 3× of the $K_D$ value of the antibody for hTF. In some embodiments, the $K_D$ value of an antibody provided herein for cTF is no more than 2× of the $K_D$ value of the antibody for hTF.

In some embodiments, the $K_D$ value of an antibody provided herein for mTF is no more than 20× of the $K_D$ value of the antibody for hTF. In some embodiments, the $K_D$ value of an antibody provided herein for mTF is no more than 15× of the $K_D$ value of the antibody for hTF. In some embodiments, the $K_D$ value of an antibody provided herein for mTF is no more than 10× of the $K_D$ value of the antibody for hTF. In some embodiments, the $K_D$ value of an antibody provided herein for mTF is no more than 5× of the $K_D$ value of the antibody for hTF. In some embodiments, the $K_D$ value of an antibody provided herein for mTF is no more than 2× of the $K_D$ value of the antibody for hTF.

In some embodiments, the affinity of an antibody provided herein for hTF as indicated by $K_D$ measured by Biacore, as set forth in Table 5 is selected from about 0.31 nM, about 6.20 nM, about 0.36 nM, about 0.08 nM, about 23.0 nM, about 0.94 nM, about 13.3 nM, about 0.47 nM, about 0.09 nM, about 1.75 nM, about 0.07 nM, about 0.14 nM, about 2.09 nM, about 0.06 nM, about 0.15 nM, about 1.46 nM, about 1.60 nM, and about 0.42 nM. In some embodiments, such affinity as indicated by $K_D$ ranges from about 23.0 nM to about 0.06 nM. In some embodiments, such is about 23.0 nM or less.

In some embodiments, the affinity of an antibody provided herein for hTF as indicated by $K_D$ measured by ForteBio, as set forth in Table 5 is selected from about 1.28 nM, about 2.20 nM, about 8.45 nM, about 1.67 nM, about 0.64 nM, about 21.9 nM, about 3.97 nM, about 35.8 nM, about 3.30 nM, about 2.32 nM, about 0.83 nM, about 2.40 nM, about 0.96 nM, about 0.86 nM, about 3.84 nM, about 1.02 nM, about 1.61 nM, about 2.52 nM, about 2.28 nM, and about 1.59 nM. In some embodiments, such affinity as indicated by $K_D$ ranges from about 35.8 nM to about 0.64 nM. In some embodiments, such $K_D$ is about 35.8 nM or less.

In some embodiments, the affinity of an antibody provided herein for cTF as indicated by $K_D$ measured by Biacore, as set forth in Table 5 is selected from about 0.26 nM, about 5.42 nM, about 0.21 nM, about 0.04 nM, about 18.0 nM, about 0.78 nM, about 16.4 nM, about 5.06 nM, about 0.08 nM, about 5.64 nM, about 0.12 nM, about 0.24 nM, about 5.66 nM, about 0.39 nM, about 5.69 nM, about 6.42 nM, and about 1.83 nM. In some embodiments, such affinity as indicated by $K_D$ ranges from about 18.0 nM to about 0.04 nM. In some embodiments, such $K_D$ is about 18.0 nM or less.

In some embodiments, the affinity of an antibody provided herein for cTF as indicated by $K_D$ measured by ForteBio, as set forth in Table 5 is selected from about 1.43 nM, about 2.70 nM, about 7.65 nM, about 1.36 nM, about 0.76 nM, about 17.5 nM, about 4.99 nM, about 42.9 nM, about 12.0 nM, about 15.0 nM, about 0.57 nM, about 3.40 nM, about 1.05 nM, about 0.94 nM, about 4.12 nM, about 1.11 nM, about 1.96 nM, about 4.07 nM, about 2.71 nM, and about 4.16 nM. In some embodiments, such affinity as indicated by $K_D$ ranges from about 42.9 nM to about 0.57 nM. In some embodiments, such $K_D$ is about 42.9 nM or less.

In some embodiments, the affinity of an antibody provided herein for mTF as indicated by $K_D$ measured by Biacore, as set forth in Table 5 is selected from about 5.4 nM, about 2.9 nM, about 21 nM, and about 2.4 nM. In some embodiments, such affinity as indicated by $K_D$ ranges from about 21 nM to about 2.4 nM. In some embodiments, such $K_D$ is about 21 nM or less.

In some embodiments, the affinity of an antibody provided herein for mTF as indicated by $K_D$ measured by ForteBio, as set forth in Table 5 is selected from about 263 nM, about 131 nM, about 188 nM, about 114 nM, about 34.2 nM, about 9.16 nM, about 161 nM, about 72.1 nM, about 360 nM, about 281 nM, about 41.4 nM, about 6.12 nM, about 121 nM, and about 140 nM. In some embodiments, such affinity as indicated by $K_D$ ranges from about 360 nM to about 6.12 nM. In some embodiments, such $K_D$ is about 360 nM or less.

Figure 1B:
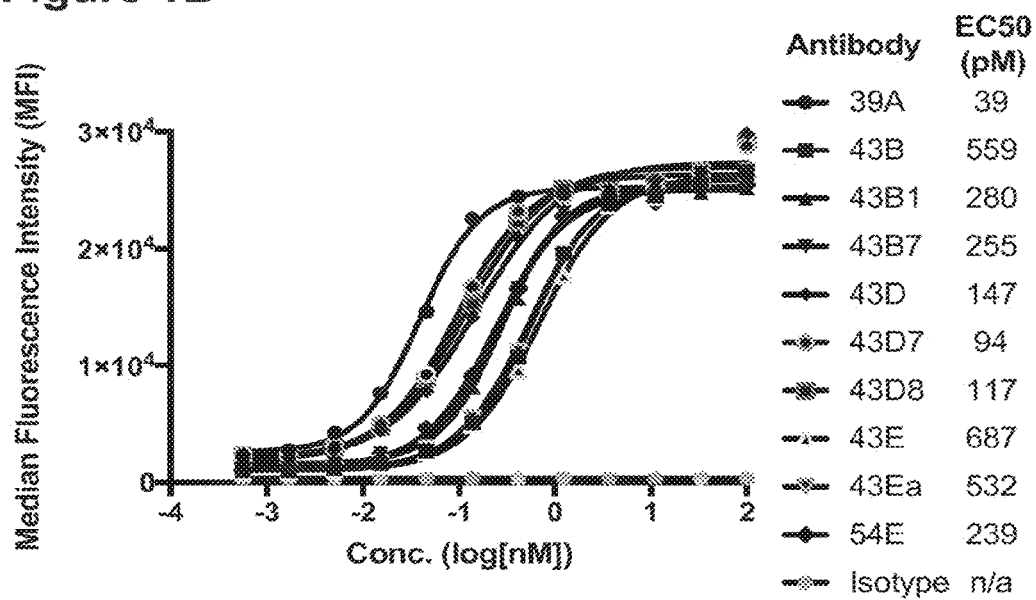

In some embodiments, the affinity of an antibody provided herein for hTF as indicated by $EC_{50}$ measured with human TF-positive HCT-116 cells, as set forth in FIGS. 1A and 1B is selected from about 50 pM, about 58 pM, about 169 pM, about 77 pM, about 88 pM, about 134 pM, about 85 pM, about 237 pM, about 152 pM, about 39 pM, about 559 pM, about 280 pM, about 255 pM, about 147 pM, about 94 pM, about 117 pM, about 687 pM, about 532 pM, and about 239 pM. In some embodiments, such affinity ranges from about 687 pM to about 39 pM. In some embodiments, such $EC_{50}$ is about 687 pM or less.

Figure 2A:
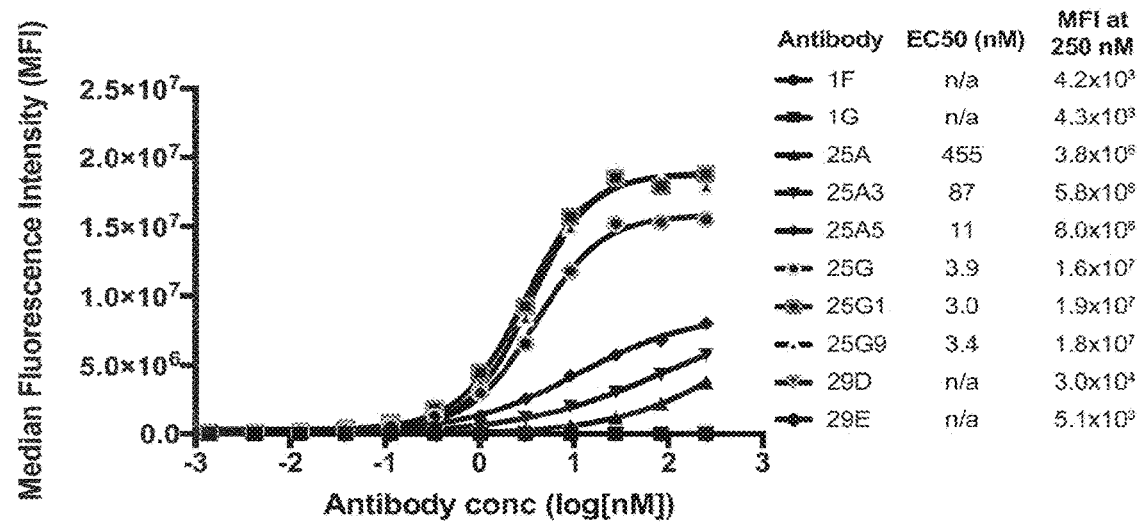
FIGS. 2A and 2B show binding of anti-TF antibodies to mouse TF-positive cells.
Figure 2B:
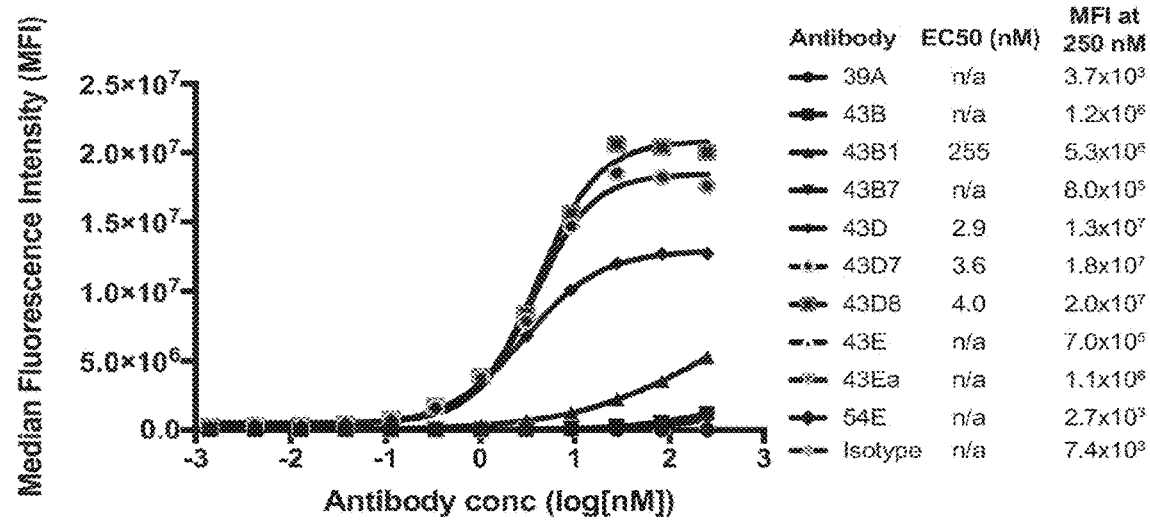

In some embodiments, the affinity of an antibody provided herein for mTF as indicated by $EC_{50}$ measured with mouse TF-positive CHO cells, as set forth in FIGS. 2A and 2B is selected from about 455 nM, about 87 nM, about 11 nM, about 3.9 nM, about 3.0 nM, about 3.4 nM, about 255 nM, about 2.9 nM, about 3.6 nM, and about 4.0 nM. In some embodiments, such affinity ranges from about 455 nM to about 2.9 nM. In some embodiments, such $EC_{50}$ is about 455 pM or less.

In some embodiments, the $K_D$ value of an antibody provided herein for pTF is no more than 20× of the $K_D$ value of the antibody for hTF. In some embodiments, the $K_D$ value of an antibody provided herein for pTF is no more than 15× of the $K_D$ value of the antibody for hTF. In some embodiments, the $K_D$ value of an antibody provided herein for pTF is no more than 10× of the $K_D$ value of the antibody for hTF. In some embodiments, the $K_D$ value of an antibody provided herein for pTF is no more than 5× of the $K_D$ value of the antibody for hTF. In some embodiments, the $K_D$ value of an antibody provided herein for pTF is no more than 2× of the $K_D$ value of the antibody for hTF.

In some embodiments, the affinity of an antibody provided herein for pTF as indicated by $K_D$ measured by Biacore, as set forth in Table 40 is 3.31 nM or 12.9 nM.

2.3.2. Thrombin Generation in the Presence of TF Antibodies

In some embodiments, the TF antibodies provided herein do not inhibit human thrombin generation as determined by thrombin generation assay (TGA). In certain embodiments, the TF antibodies provided herein allow human thrombin generation as determined by thrombin generation assay (TGA).

In some embodiments, the percent peak thrombin generation (% Peak IIa) is at least 40% in the presence of no less than 100 nM TF antibody compared to the control conditions without the antibody, as determined by thrombin generation assay (TGA). In some embodiments, the % Peak IIa is at least 50% in the presence of no less than 100 nM TF antibody compared to the control conditions without the antibody, as determined by thrombin generation assay (TGA). In some embodiments, the % Peak IIa is at least 60% in the presence of no less than 100 nM TF antibody compared to the control conditions without the antibody, as determined by thrombin generation assay (TGA). In some embodiments, the % Peak IIa is at least 70% in the presence of no less than 100 nM TF antibody compared to the control conditions without the antibody, as determined by thrombin generation assay (TGA). In some embodiments, the % Peak IIa is at least 80% in the presence of no less than 100 nM TF antibody compared to the control conditions without the antibody, as determined by thrombin generation assay (TGA). In some embodiments, the % Peak IIa is at least 90% in the presence of no less than 100 nM TF antibody compared to the control conditions without the antibody, as determined by thrombin generation assay (TGA). In some embodiments, the % Peak IIa is at least 95% in the presence of no less than 100 nM TF antibody compared to the control conditions without the antibody, as determined by thrombin generation assay (TGA). In some embodiments, the % Peak IIa is at least 99% in the presence of no less than 100 nM TF antibody compared to the control conditions without the antibody, as determined by thrombin generation assay (TGA).

In some embodiments, the % Peak IIa is at least 40% in the presence of no less than 50 nM TF antibody compared to the control conditions without the antibody, as determined by thrombin generation assay (TGA). In some embodiments, the % Peak IIa is at least 50% in the presence of no less than 50 nM TF antibody compared to the control conditions without the antibody, as determined by thrombin generation assay (TGA). In some embodiments, the % Peak IIa is at least 60% in the presence of no less than 50 nM TF antibody compared to the control conditions without the antibody, as determined by thrombin generation assay (TGA). In some embodiments, the % Peak IIa is at least 70% in the presence of no less than 50 nM TF antibody compared to the control conditions without the antibody, as determined by thrombin generation assay (TGA). In some embodiments, the % Peak IIa is at least 80% in the presence of no less than 50 nM TF antibody compared to the control conditions without the antibody, as determined by thrombin generation assay (TGA). In some embodiments, the % Peak IIa is at least 90% in the presence of no less than 50 nM TF antibody compared to the control conditions without the antibody, as determined by thrombin generation assay (TGA). In some embodiments, the % Peak IIa is at least 95% in the presence of no less than 50 nM TF antibody compared to the control conditions without the antibody, as determined by thrombin generation assay (TGA). In some embodiments, the % Peak IIa is at least 99% in the presence of no less than 50 nM TF antibody compared to the control conditions without the antibody, as determined by thrombin generation assay (TGA).

In some embodiments, the % Peak IIa is at least 60% in the presence of no less than 10 nM TF antibody compared to the control conditions without the antibody, as determined by thrombin generation assay (TGA). In some embodiments, the % Peak IIa is at least 70% in the presence of no less than 10 nM TF antibody compared to the control conditions without the antibody, as determined by thrombin generation assay (TGA). In some embodiments, the % Peak IIa is at least 80% in the presence of no less than 10 nM TF antibody compared to the control conditions without the antibody, as determined by thrombin generation assay (TGA). In some embodiments, the % Peak IIa is at least 90% in the presence of no less than 10 nM TF antibody compared to the control conditions without the antibody, as determined by thrombin generation assay (TGA). In some embodiments, the % Peak IIa is at least 95% in the presence of no less than 10 nM TF antibody compared to the control conditions without the antibody, as determined by thrombin generation assay (TGA). In some embodiments, the % Peak IIa is at least 99% in the presence of no less than 10 nM TF antibody compared to the control conditions without the antibody, as determined by thrombin generation assay (TGA).

In some embodiments, the % Peak IIa in the presence of 100 nM TF antibody, as set forth in Table 6 and Table 37 is selected from about 99%, about 100%, about 103%, about 64%, about 52%, about 87%, about 96%, about 98%, and about 53% compared to the control conditions without the antibody, as determined by thrombin generation assay (TGA) without antibody pre-incubation. In some embodiments, such % Peak IIa ranges from about 52% to about 103%. In some embodiments, such % Peak IIa is about 52% or more.

In some embodiments, the % Peak IIa in the presence of 50 nM TF antibody, as set forth in Table 6 and Table 37 is selected from about 99%, about 100%, about 103%, about 67%, about 58%, about 89%, about 96%, about 98%, about 68%, about 62%, and about 88% compared to the control conditions without the antibody, as determined by thrombin generation assay (TGA) without antibody pre-incubation. In some embodiments, such % Peak IIa ranges from about 58% to about 103%. In some embodiments, such % Peak IIa is about 58% or more.

In some embodiments, the % Peak IIa in the presence of 10 nM TF antibody, as set forth in Table 6 and Table 37 is selected from about 100%, about 99%, about 103%, about 87%, about 83%, about 95%, about 98%, about 86%, and about 96% compared to the control conditions without the antibody, as determined by thrombin generation assay (TGA) without antibody pre-incubation. In some embodiments, such % Peak IIa ranges from about 83% to about 103%. In some embodiments, such % Peak IIa is about 83% or more.

In some embodiments, the % Peak IIa in the presence of 100 nM TF antibody, as set forth in Table 7 and Table 38 is selected from about 108%, about 105%, about 111%, about 58%, about 47%, about 91%, about 103%, about 109%, about 107%, and about 45% compared to the control conditions without the antibody, as determined by thrombin generation assay (TGA) with 10 min antibody pre-incubation. In some embodiments, such % Peak IIa ranges from about 45% to about 111%. In some embodiments, such % Peak IIa is about 45% or more.

In some embodiments, the % Peak IIa in the presence of 50 nM TF antibody, as set forth in Table 7 and Table 38 is selected from about 107%, about 104%, about $1^{14}$%, about 62%, about 49%, about 87%, about 105%, about 109%, about 55%, and about 92% compared to the control conditions without the antibody, as determined by thrombin generation assay (TGA) with 10 min antibody pre-incubation. In some embodiments, such % Peak IIa ranges from about 49% to about 114%. In some embodiments, such % Peak IIa is about 49% or more.

In some embodiments, the % Peak IIa in the presence of 10 nM TF antibody, as set forth in Table 7 and Table 38 is selected from about 105%, about 114%, about 76%, about 68%, about 94%, about 108%, about 104%, about 74%, and about 93% compared to the control conditions without the antibody, as determined by thrombin generation assay (TGA) with 10 min antibody pre-incubation. In some embodiments, such % Peak IIa ranges from about 68% to about 114%. In some embodiments, such % Peak IIa is about 68% or more.

In some embodiments, the percent endogenous thrombin potential (% ETP) is at least 80% in the presence of no less than 100 nM TF antibody compared to the control conditions without the antibody, as determined by thrombin generation assay (TGA). In some embodiments, the % ETP is at least 90% in the presence of no less than 100 nM TF antibody compared to the control conditions without the antibody, as determined by thrombin generation assay (TGA). In some embodiments, the % ETP is at least 95% in the presence of no less than 100 nM TF antibody compared to the control conditions without the antibody, as determined by thrombin generation assay (TGA). In some embodiments, the % ETP is at least 99% in the presence of no less than 100 nM TF antibody compared to the control conditions without the antibody, as determined by thrombin generation assay (TGA).

In some embodiments, the % ETP is at least 80% in the presence of no less than 50 nM TF antibody compared to the control conditions without the antibody, as determined by thrombin generation assay (TGA). In some embodiments, the % ETP is at least 90% in the presence of no less than 50 nM TF antibody compared to the control conditions without the antibody, as determined by thrombin generation assay (TGA). In some embodiments, the % ETP is at least 95% in the presence of no less than 50 nM TF antibody compared to the control conditions without the antibody, as determined by thrombin generation assay (TGA). In some embodiments, the % ETP is at least 99% in the presence of no less than 50 nM TF antibody compared to the control conditions without the antibody, as determined by thrombin generation assay (TGA).

In some embodiments, the % ETP is at least 80% in the presence of no less than 10 nM TF antibody compared to the control conditions without the antibody, as determined by thrombin generation assay (TGA). In some embodiments, the % ETP is at least 90% in the presence of no less than 10 nM TF antibody compared to the control conditions without the antibody, as determined by thrombin generation assay (TGA). In some embodiments, the % ETP is at least 95% in the presence of no less than 10 nM TF antibody compared to the control conditions without the antibody, as determined by thrombin generation assay (TGA). In some embodiments, the % ETP is at least 99% in the presence of no less than 10 nM TF antibody compared to the control conditions without the antibody, as determined by thrombin generation assay (TGA).

In some embodiments, the % ETP in the presence of 100 nM TF antibody, as set forth in Table 6 and Table 37 is selected from about 108%, about 103%, about 109%, about 100%, about 96%, about 102%, about 105%, and about 92% compared to the control conditions without the antibody, as determined by thrombin generation assay (TGA) without antibody pre-incubation. In some embodiments, such % ETP ranges from about 92% to about 109%. In some embodiments, such % ETP is about 92% or more.

In some embodiments, the % ETP in the presence of 50 nM TF antibody, as set forth in Table 6 and Table 37 is selected from about 108%, about 103%, about 111%, about 101%, about 97%, about 104%, about 106%, about 93%, about 96%, and about 105% compared to the control conditions without the antibody, as determined by thrombin generation assay (TGA) without antibody pre-incubation. In some embodiments, such % ETP ranges from about 93% to about 111%. In some embodiments, such % ETP is about 93% or more.

In some embodiments, the % ETP in the presence of 10 nM TF antibody, as set forth in Table 6 and Table 37 is selected from about 106%, about 109%, about 105%, about 104%, about 107%, about 99%, about 101%, and about 102% compared to the control conditions without the antibody, as determined by thrombin generation assay (TGA) without antibody pre-incubation. In some embodiments, such % ETP ranges from about 99% to about 109%. In some embodiments, such % ETP is about 99% or more.

In some embodiments, the % ETP in the presence of 100 nM TF antibody, as set forth in Table 7 and Table 38 is selected from about 110%, about 104%, about 106%, about 98%, about 95%, about 108%, about 107%, about 96%, about 92%, and about 103% compared to the control conditions without the antibody, as determined by thrombin generation assay (TGA) with 10 min antibody pre-incubation. In some embodiments, such % ETP ranges from about 92% to about 110%. In some embodiments, such % ETP is about 92% or more.

In some embodiments, the % ETP in the presence of 50 nM TF antibody, as set forth in Table 7 and Table 38 is selected from about 110%, about 106%, about 108%, about 103%, about 96%, about 109%, about 102%, about 104%, about 94%, and about 98% compared to the control conditions without the antibody, as determined by thrombin generation assay (TGA) with 10 min antibody pre-incubation. In some embodiments, such % ETP ranges from about 94% to about 110%. In some embodiments, such % ETP is about 94% or more.

In some embodiments, the % ETP in the presence of 10 nM TF antibody, as set forth in Table 7 and Table 38 is selected from about 107%, about 106%, about 110%, about 103%, about 100%, about 105%, about 102%, and about 101% compared to the control conditions without the antibody, as determined by thrombin generation assay (TGA) with 10 min antibody pre-incubation. In some embodiments, such % ETP ranges from about 100% to about 110%. In some embodiments, such % ETP is about 100% or more.

2.3.3. FXa Conversion in the Presence of TF Antibodies

In some embodiments, the antibodies provided herein bind human TF at a human TF binding site that is distinct from a human TF binding site bound by human FX. In certain embodiments, the antibodies provided herein do not interfere with the ability of TF:FVIIa to convert FX into FXa.

In some embodiments, the percentage of FXa conversion (% FXa) is at least 75% in the presence of no less than 100 nM TF antibody compared to the control conditions without the antibody. In some embodiments, the % FXa is at least 80% in the presence of no less than 100 nM TF antibody compared to the control conditions without the antibody. In some embodiments, the % FXa is at least 85% in the presence of no less than 100 nM TF antibody compared to the control conditions without the antibody. In some embodiments, the % FXa is at least 90% in the presence of no less than 100 nM TF antibody compared to the control conditions without the antibody. In some embodiments, the % FXa is at least 95% in the presence of no less than 100 nM TF antibody compared to the control conditions without the antibody.

In some embodiments, the % FXa is at least 75% in the presence of no less than 50 nM TF antibody compared to the control conditions without the antibody. In some embodiments, the % FXa is at least 80% in the presence of no less than 50 nM TF antibody compared to the control conditions without the antibody. In some embodiments, the % FXa is at least 85% in the presence of no less than 50 nM TF antibody compared to the control conditions without the antibody. In some embodiments, the % FXa is at least 90% in the presence of no less than 50 nM TF antibody compared to the control conditions without the antibody. In some embodiments, the % FXa is at least 95% in the presence of no less than 50 nM TF antibody compared to the control conditions without the antibody.

In some embodiments, the % FXa is at least 75% in the presence of no less than 25 nM TF antibody compared to the control conditions without the antibody. In some embodiments, the % FXa is at least 80% in the presence of no less than 25 nM TF antibody compared to the control conditions without the antibody. In some embodiments, the % FXa is at least 85% in the presence of no less than 25 nM TF antibody compared to the control conditions without the antibody. In some embodiments, the % FXa is at least 90% in the presence of no less than 25 nM TF antibody compared to the control conditions without the antibody. In some embodiments, the % FXa is at least 95% in the presence of no less than 25 nM TF antibody compared to the control conditions without the antibody.

In some embodiments, the % FXa is at least 75% in the presence of no less than 12.5 nM TF antibody compared to the control conditions without the antibody. In some embodiments, the % FXa is at least 80% in the presence of no less than 12.5 nM TF antibody compared to the control conditions without the antibody. In some embodiments, the % FXa is at least 85% in the presence of no less than 12.5 nM TF antibody compared to the control conditions without the antibody. In some embodiments, % FXa is at least 90% in the presence of no less than 12.5 nM TF antibody compared to the control conditions without the antibody. In some embodiments, the % FXa is at least 95% in the presence of no less than 12.5 nM TF antibody compared to the control conditions without the antibody.

In some embodiments, the % FXa in the presence of 100 nM TF antibody, as set forth in Table 8 is selected from about 89%, about 96%, about 116%, about 108%, about 117%, about 105%, about 112%, about 106%, about 103%, about 111%, about 98%, and about 101% compared to the control conditions without the antibody. In some embodiments, such % FXa ranges from about 89% to about 117%. In some embodiments, such % FXa is about 89% or more.

In some embodiments, the % FXa in the presence of 50 nM TF antibody, as set forth in Table 8 is selected from about 94%, about 93%, about 78%, about 102%, about 99%, about 104%, about 105%, about 108%, about 107%, about 97%, and about 106% compared to the control conditions without the antibody. In some embodiments, such % FXa ranges from about 78% to about 108%. In some embodiments, such % FXa is about 78% or more.

In some embodiments, the % FXa in the presence of 25 nM TF antibody, as set forth in Table 8 is selected from about 81%, about 89%, about 85%, about 109%, about 96%, about 97%, about 108%, about 104%, about 103%, about 112%, and about 89% compared to the control conditions without the antibody. In some embodiments, such % FXa ranges from about 81% to about 112%. In some embodiments, such % FXa is about 81% or more.

In some embodiments, the % FXa in the presence of 12.5 nM TF antibody, as set forth in Table 8 is selected from about 87%, about 89%, about 82%, about 99%, about 101%, about 98%, about 113%, about 106%, about 115%, about 110%, about 120%, about 85%, and about 108% compared to the control conditions without the antibody. In some embodiments, such % FXa ranges from about 82% to about 120%. In some embodiments, such % FXa is about 82% or more.

2.3.4. FVIIa Binding in the Presence of TF Antibodies

In some embodiments, the antibodies provided herein bind human TF at a human TF binding site that is distinct from a human TF binding site bound by human FVIIa. In certain embodiments, the antibodies provided herein do not compete for binding to human TF with human FVIIa.

In some embodiments, the percentage of FVIIa binding (% FVIIa) is at least 75% in the presence of no less than 250 nM TF antibody compared to the control conditions without the antibody. In some embodiments, the % FVIIa is at least 80% in the presence of no less than 250 nM TF antibody compared to the control conditions without the antibody. In some embodiments, the % FVIIa is at least 85% in the presence of no less than 250 nM TF antibody compared to the control conditions without the antibody. In some embodiments, the % FVIIa is at least 90% in the presence of no less than 250 nM TF antibody compared to the control conditions without the antibody. In some embodiments, the % FVIIa is at least 95% in the presence of no less than 250 nM TF antibody compared to the control conditions without the antibody.

In some embodiments, the % FVIIa is at least 75% in the presence of no less than 83 nM TF antibody compared to the control conditions without the antibody. In some embodiments, the % FVIIa is at least 80% in the presence of no less than 83 nM TF antibody compared to the control conditions without the antibody. In some embodiments, the % FVIIa is at least 85% in the presence of no less than 83 nM TF antibody compared to the control conditions without the antibody. In some embodiments, the % FVIIa is at least 90% in the presence of no less than 83 nM TF antibody compared to the control conditions without the antibody. In some embodiments, the % FVIIa is at least 95% in the presence of no less than 83 nM TF antibody compared to the control conditions without the antibody.

In some embodiments, the % FVIIa is at least 75% in the presence of no less than 28 nM TF antibody compared to the control conditions without the antibody. In some embodiments, the % FVIIa is at least 80% in the presence of no less than 28 nM TF antibody compared to the control conditions without the antibody. In some embodiments, the % FVIIa is at least 85% in the presence of no less than 28 nM TF antibody compared to the control conditions without the antibody. In some embodiments, the % FVIIa is at least 90% in the presence of no less than 28 nM TF antibody compared to the control conditions without the antibody. In some embodiments, the % FVIIa is at least 95% in the presence of no less than 28 nM TF antibody compared to the control conditions without the antibody.

In some embodiments, the % FVIIa is at least 75% in the presence of no less than 9.25 nM TF antibody compared to the control conditions without the antibody. In some embodiments, the % FVIIa is at least 80% in the presence of no less than 9.25 nM TF antibody compared to the control conditions without the antibody. In some embodiments, the % FVIIa is at least 85% in the presence of no less than 9.25 nM TF antibody compared to the control conditions without the antibody. In some embodiments, the % FVIIa is at least 90% in the presence of no less than 9.25 nM TF antibody compared to the control conditions without the antibody. In some embodiments, the % FVIIa is at least 95% in the presence of no less than 9.25 nM TF antibody compared to the control conditions without the antibody.

In some embodiments, the % FVIIa in the presence of 250 nM TF antibody, as set forth in Table 9 is selected from about 98%, about 87%, about 80%, about 92%, about 95%, about 89%, about 91%, about 97%, about 94%, about 101%, and about 96% compared to the control conditions without the antibody. In some embodiments, such % FVIIa ranges from about 80% to about 101%. In some embodiments, such % FVIIa is about 80% or more.

In some embodiments, the % FVIIa in the presence of 83 nM TF antibody, as set forth in Table 9 is selected from about 97%, about 88%, about 77%, about 93%, about 94%, about 91%, about 98%, about 100%, and about 92% compared to the control conditions without the antibody. In some embodiments, such % FVIIa ranges from about 77% to about 100%. In some embodiments, such % FVIIa is about 77% or more.

In some embodiments, the % FVIIa in the presence of 28 nM TF antibody, as set forth in Table 9 is selected from about 101%, about 87%, about 79%, about 96%, about 93%, about 95%, about 98%, about 100%, about 102%, about 99%, about 92%, and about 91% compared to the control conditions without the antibody. In some embodiments, such % FVIIa ranges from about 79% to about 102%. In some embodiments, such % FVIIa is about 79% or more.

In some embodiments, the % FVIIa in the presence of 9.25 nM TF antibody, as set forth in Table 9 is selected from about 100%, about 90%, about 76%, about 97%, about 93%, about 99%, about 98%, about 102%, about 101%, and about 95% compared to the control conditions without the antibody. In some embodiments, such % FVIIa ranges from about 76% to about 102%. In some embodiments, such % FVIIa is about 76% or more.

2.3.5. FVIIa-Dependent TF Signaling in the Presence of TF Antibodies

In some embodiments, the antibodies provided herein inhibit FVIIa-dependent TF signaling. In some embodiments, the inhibition of FVIIa-dependent TF signaling is measured by the reduction of IL8. In some embodiments, the inhibition of FVIIa-dependent TF signaling is measured by the reduction of GM-CSF.

In some embodiments, the Interleukin 8 concentration (IL8 conc) is reduced by at least 70% in the presence of no less than 100 nM TF antibody compared to the control conditions without the antibody. In some embodiments, the IL8 conc is reduced by at least 80% in the presence of no less than 100 nM TF antibody compared to the control conditions without the antibody. In some embodiments, the IL8 conc is reduced by at least 90% in the presence of no less than 100 nM TF antibody compared to the control conditions without the antibody.

In some embodiments, the IL8 conc is reduced by at least 70% in the presence of no less than 40 nM TF antibody compared to the control conditions without the antibody. In some embodiments, the IL8 conc is reduced by at least 80% in the presence of no less than 40 nM TF antibody compared to the control conditions without the antibody. In some embodiments, the IL8 conc is reduced by at least 90% in the presence of no less than 40 nM TF antibody compared to the control conditions without the antibody.

In some embodiments, the IL8 conc is reduced by at least 60% in the presence of no less than 16 nM TF antibody compared to the control conditions without the antibody. In some embodiments, the IL8 conc is reduced by at least 70% in the presence of no less than 16 nM TF antibody compared to the control conditions without the antibody. In some embodiments, the IL8 conc is reduced by at least 80% in the presence of no less than 16 nM TF antibody compared to the control conditions without the antibody. In some embodiments, the IL8 conc is reduced by at least 90% in the presence of no less than 16 nM TF antibody compared to the control conditions without the antibody.

In some embodiments, the IL8 conc is reduced by at least 50% in the presence of no less than 6.4 nM TF antibody compared to the control conditions without the antibody. In some embodiments, the IL8 conc is reduced by at least 60% in the presence of no less than 6.4 nM TF antibody compared to the control conditions without the antibody. In some embodiments, the IL8 conc is reduced by at least 70% in the presence of no less than 6.4 nM TF antibody compared to the control conditions without the antibody. In some embodiments, the IL8 conc is reduced by at least 80% in the presence of no less than 6.4 nM TF antibody compared to the control conditions without the antibody. In some embodiments, the IL8 conc is reduced by at least 90% in the presence of no less than 6.4 nM TF antibody compared to the control conditions without the antibody.

In some embodiments, the Granulocyte-Macrophage Colony-Stimulating Factor concentration (GM-CSF conc) is reduced by at least 70% in the presence of no less than 100 nM TF antibody compared to the control conditions without the antibody. In some embodiments, the GM-CSF conc is reduced by at least 80% in the presence of no less than 100 nM TF antibody compared to the control conditions without the antibody. In some embodiments, the GM-CSF conc is reduced by at least 90% in the presence of no less than 100 nM TF antibody compared to the control conditions without the antibody.

In some embodiments, the GM-CSF conc is reduced by at least 70% in the presence of no less than 40 nM TF antibody compared to the control conditions without the antibody. In some embodiments, the GM-CSF conc is reduced by at least 80% in the presence of no less than 40 nM TF antibody compared to the control conditions without the antibody. In some embodiments, the GM-CSF conc is reduced by at least 90% in the presence of no less than 40 nM TF antibody compared to the control conditions without the antibody.

In some embodiments, the GM-CSF conc is reduced by at least 60% in the presence of no less than 16 nM TF antibody compared to the control conditions without the antibody. In some embodiments, the GM-CSF conc is reduced by at least 70% in the presence of no less than 16 nM TF antibody compared to the control conditions without the antibody. In some embodiments, the GM-CSF conc is reduced by at least 80% in the presence of no less than 16 nM TF antibody compared to the control conditions without the antibody. In some embodiments, the GM-CSF conc is reduced by at least 90% in the presence of no less than 16 nM TF antibody compared to the control conditions without the antibody.

In some embodiments, the GM-CSF conc is reduced by at least 50% in the presence of no less than 6.4 nM TF antibody compared to the control conditions without the antibody. In some embodiments, the GM-CSF conc is reduced by at least 60% in the presence of no less than 6.4 nM TF antibody compared to the control conditions without the antibody. In some embodiments, the GM-CSF conc is reduced by at least 70% in the presence of no less than 6.4 nM TF antibody compared to the control conditions without the antibody. In some embodiments, the GM-CSF conc is reduced by at least 80% in the presence of no less than 6.4 nM TF antibody compared to the control conditions without the antibody. In some embodiments, the GM-CSF conc is reduced by at least 90% in the presence of no less than 6.4 nM TF antibody compared to the control conditions without the antibody.

In some embodiments, the percentage of Interleukin 8 (% IL8) in the presence of 100 nM TF antibody, as set forth in Table 10 is selected from about 2%, about 9%, about 8%, about 6%, about 13%, about 1%, about 3%, about 4%, and about 5% compared to the control conditions without the antibody. In some embodiments, such % IL8 ranges from about 1% to about 13%. In some embodiments, such % IL8 is about 13% or less.

In some embodiments, the % IL8 in the presence of 40 nM TF antibody, as set forth in Table 10 is selected from about 2%, about 8%, about 7%, about 10%, about 14%, about 4%, about 5%, and about 6% compared to the control conditions without the antibody. In some embodiments, such % IL8 ranges from about 2% to about 14%. In some embodiments, such % IL8 is about 14% or less.

In some embodiments, the % IL8 in the presence of 16 nM TF antibody, as set forth in Table 10 is selected from about 2%, about 3%, about 10%, about 8%, about 7%, about 16%, about 9%, about 15%, about 5%, and about 6% compared to the control conditions without the antibody. In some embodiments, such % IL8 ranges from about 2% to about 16%. In some embodiments, such % IL8 is about 16% or less.

In some embodiments, the % IL8 in the presence of 6.4 nM TF antibody, as set forth in Table 10 is selected from about 3%, about 4%, about 11%, about 9%, about 14%, about 22%, about 12%, about 6%, about 5%, about 15%, about 21%, and about 8% compared to the control conditions without the antibody. In some embodiments, such % IL8 ranges from about 3% to about 22%. In some embodiments, such % IL8 is about 22% or less.

In some embodiments, the percentage of Granulocyte-Macrophage Colony-Stimulating Factor (% GM-CSF) in the presence of 100 nM TF antibody, as set forth in Table 11 is selected from about 6%, about 7%, about 22%, about 20%, about 12%, about 19%, about 17%, about 25%, about 5%, about 14%, about 11%, and about 10% compared to the control conditions without the antibody. In some embodiments, such % GM-CSF ranges from about 5% to about 25%. In some embodiments, such % GM-CSF is about 25% or less.

In some embodiments, the % GM-CSF in the presence of 40 nM TF antibody, as set forth in Table 11 is selected from about 6%, about 7%, about 19%, about 15%, about 18%, about 16%, about 26%, about 5%, about 13%, about 11%, and about 10% compared to the control conditions without the antibody. In some embodiments, such % GM-CSF ranges from about 5% to about 26%. In some embodiments, such % GM-CSF is about 26% or less.

In some embodiments, the % GM-CSF in the presence of 16 nM TF antibody, as set forth in Table 11 is selected from about 6%, about 7%, about 22%, about 19%, about 14%, about 32%, about 17%, about 26%, about 5%, about 12%, about 13%, about 9%, about 11%, and about 15% compared to the control conditions without the antibody. In some embodiments, such % GM-CSF ranges from about 5% to about 32%. In some embodiments, such % GM-CSF is about 32% or less.

In some embodiments, the % GM-CSF in the presence of 6.4 nM TF antibody, as set forth in Table 11 is selected from about 8%, about 9%, about 24%, about 20%, about 18%, about 39%, about 34%, about 15%, about 21%, about 16%, about 17%, and about 10% compared to the control conditions without the antibody. In some embodiments, such % GM-CSF ranges from about 8% to about 39%. In some embodiments, such % GM-CSF is about 39% or less.

2.3.6. Lesion Size Reduction in Swine Choroidal Neovascularization (CNV) Model In some embodiments, the antibodies provided herein reduce lesion size in a swine choroidal neovascularization (CNV) model. In some embodiments, the reduction in lesion size is measured by Fluorescein Angiography (FA).

In some embodiments, the lesion size in a swine CNV model is reduced by at least 5% 7 days after administration of the anti-TF antibody. In some embodiments, the lesion size in a swine CNV model is reduced by at least 10% 7 days after administration of the anti-TF antibody. In some embodiments, the lesion size in a swine CNV model is reduced by at least 20% 7 days after administration of the anti-TF antibody. In some embodiments, the lesion size in a swine CNV model is reduced by at least 40% 7 days after administration of the anti-TF antibody. In some embodiments, the lesion size in a swine CNV model is reduced by at least 60% 7 days after administration of the anti-TF antibody.

In some embodiments, the lesion size in a swine CNV model is reduced by at least 10% 21 days after administration of the anti-TF antibody. In some embodiments, the lesion size in a swine CNV model is reduced by at least 20% 21 days after administration of the anti-TF antibody. In some embodiments, the lesion size in a swine CNV model is reduced by at least 40% 21 days after administration of the anti-TF antibody. In some embodiments, the lesion size in a swine CNV model is reduced by at least 60% 21 days after administration of the anti-TF antibody. In some embodiments, the lesion size in a swine CNV model is reduced by at least 80% 21 days after administration of the anti-TF antibody.

2.4. Germlines

The antibodies provided herein may comprise any suitable $V_H$ and $V_L$ germline sequences.

In some embodiments, the $V_H$ region of an antibody provided herein is from the VH3 germline. In some embodiments, the $V_H$ region of an antibody provided herein is from the VH1 germline. In some embodiments, the $V_H$ region of an antibody provided herein is from the VH4 germline.

In some embodiments, the $V_H$ region of an antibody provided herein is from the VH3-23 germline. In some embodiments, the $V_H$ region of an antibody provided herein is from the VH1-18 germline. In some embodiments, the $V_H$ region of an antibody provided herein is from the VH3-30 germline. In some embodiments, the $V_H$ region of an antibody provided herein is from the VH1-69 germline. In some embodiments, the $V_H$ region of an antibody provided herein is from the VH4-31 germline. In some embodiments, the $V_H$ region of an antibody provided herein is from the VH4-34 germline. In some embodiments, the $V_H$ region of an antibody provided herein is from the VH1-46 germline.

In some embodiments, the $V_L$ region of an antibody provided herein is from the VK1 germline. In some embodiments, the $V_L$ region of an antibody provided herein is from the VK4 germline. In some embodiments, the $V_L$ region of an antibody provided herein is from the VK3 germline In some embodiments, the $V_L$ region of an antibody provided herein is from the VK1-05 germline. In some embodiments, the $V_L$ region of an antibody provided herein is from the VK4-01 germline. In some embodiments, the $V_L$ region of an antibody provided herein is from the VK3-15 germline. In some embodiments, the $V_L$ region of an antibody provided herein is from the VK3-20 germline. In some embodiments, the $V_L$ region of an antibody provided herein is from the VK1-33 germline.

2.5. Monospecific and Multispecific TF Antibodies

In some embodiments, the antibodies provided herein are monospecific antibodies.

In some embodiments, the antibodies provided herein are multispecific antibodies.

In some embodiments, a multispecific antibody provided herein binds more than one antigen. In some embodiments, a multispecific antibody binds two antigens. In some embodiments, a multispecific antibody binds three antigens. In some embodiments, a multispecific antibody binds four antigens. In some embodiments, a multispecific antibody binds five antigens.

In some embodiments, a multispecific antibody provided herein binds more than one epitope on a TF antigen. In some embodiments, a multispecific antibody binds two epitopes on a TF antigen. In some embodiments, a multispecific antibody binds three epitopes on a TF antigen.

Many multispecific antibody constructs are known in the art, and the antibodies provided herein may be provided in the form of any suitable multispecific suitable construct.

In some embodiments, the multispecific antibody comprises an immunoglobulin comprising at least two different heavy chain variable regions each paired with a common light chain variable region (i.e., a "common light chain antibody"). The common light chain variable region forms a distinct antigen-binding domain with each of the two different heavy chain variable regions. See Merchant et al., *Nature Biotechnol.*, 1998, 16:677-681, incorporated by reference in its entirety.

In some embodiments, the multispecific antibody comprises an immunoglobulin comprising an antibody or fragment thereof attached to one or more of the N- or C-termini of the heavy or light chains of such immunoglobulin. See Coloma and Morrison, Nature *Biotechnol.*, 1997, 15:159-163, incorporated by reference in its entirety. In some aspects, such antibody comprises a tetravalent bispecific antibody.

In some embodiments, the multispecific antibody comprises a hybrid immunoglobulin comprising at least two different heavy chain variable regions and at least two different light chain variable regions. See Milstein and Cuello, *Nature*, 1983, 305:537-540; and Staerz and Bevan, *Proc. Natl. Acad. Sci. USA*, 1986, 83:1453-1457; each of which is incorporated by reference in its entirety.

In some embodiments, the multispecific antibody comprises immunoglobulin chains with alterations to reduce the formation of side products that do not have multispecificity. In some aspects, the antibodies comprise one or more "knobs-into-holes" modifications as described in U.S. Pat. No. 5,731,168, incorporated by reference in its entirety.

In some embodiments, the multispecific antibody comprises immunoglobulin chains with one or more electrostatic modifications to promote the assembly of Fc hetero-multimers. See WO 2009/089004, incorporated by reference in its entirety.

In some embodiments, the multispecific antibody comprises a bispecific single chain molecule. See Traunecker et al., *EMBO J.*, 1991, 10:3655-3659; and Gruber et al., *J. Immunol.*, 1994, 152:5368-5374; each of which is incorporated by reference in its entirety.

In some embodiments, the multispecific antibody comprises a heavy chain variable domain and a light chain variable domain connected by a polypeptide linker, where the length of the linker is selected to promote assembly of multispecific antibodies with the desired multispecificity. For example, monospecific scFvs generally form when a heavy chain variable domain and light chain variable domain are connected by a polypeptide linker of more than 12 amino acid residues. See U.S. Pat. Nos. 4,946,778 and 5,132,405, each of which is incorporated by reference in its entirety. In some embodiments, reduction of the polypeptide linker length to less than 12 amino acid residues prevents pairing of heavy and light chain variable domains on the same polypeptide chain, thereby allowing pairing of heavy and light chain variable domains from one chain with the complementary domains on another chain. The resulting antibodies therefore have multispecificity, with the specificity of each binding site contributed by more than one polypeptide chain. Polypeptide chains comprising heavy and light chain variable domains that are joined by linkers between 3 and 12 amino acid residues form predominantly dimers (termed diabodies). With linkers between 0 and 2 amino acid residues, trimers (termed triabodies) and tetramers (termed tetrabodies) are favored. However, the exact type of oligomerization appears to depend on the amino acid residue composition and the order of the variable domain in each polypeptide chain (e.g., $V_H$-linker-$V_L$ vs. $V_L$-linker-$V_H$), in addition to the linker length. A skilled person can select the appropriate linker length based on the desired multispecificity.

In some embodiments, the multispecific antibody comprises a diabody. See Hollinger et al., *Proc. Natl. Acad. Sci. USA,* 1993, 90:6444-6448, incorporated by reference in its entirety. In some embodiments, the multispecific antibody comprises a triabody. See Todorovska et al., *J Immunol. Methods,* 2001, 248:47-66, incorporated by reference in its entirety. In some embodiments, the multispecific antibody comprises atetrabody. See id., incorporated by reference in its entirety.

In some embodiments, the multispecific antibody comprises a trispecific F(ab')$_3$ derivative. See Tutt et al. *J Immunol.,* 1991, 147:60-69, incorporated by reference in its entirety.

In some embodiments, the multispecific antibody comprises a cross-linked antibody. See U.S. Pat. No. 4,676,980; Brennan et al., *Science,* 1985, 229:81-83; Staerz, et al. *Nature,* 1985, 314:628-631; and EP 0453082; each of which is incorporated by reference in its entirety.

In some embodiments, the multispecific antibody comprises antigen-binding domains assembled by leucine zippers. See Kostelny et al., *J. Immunol.,* 1992, 148:1547-1553, incorporated by reference in its entirety.

In some embodiments, the multispecific antibody comprises complementary protein domains. In some aspects, the complementary protein domains comprise an anchoring domain (AD) and a dimerization and docking domain (DDD). In some embodiments, the AD and DDD bind to each other and thereby enable assembly of multispecific antibody structures via the "dock and lock" (DNL) approach. Antibodies of many specificities may be assembled, including bispecific antibodies, trispecific antibodies, tetraspecific antibodies, quintspecific antibodies, and hexaspecific antibodies. Multispecific antibodies comprising complementary protein domains are described, for example, in U.S. Pat. Nos. 7,521,056; 7,550,143; 7,534,866; and 7,527,787; each of which is incorporated by reference in its entirety.

In some embodiments, the multispecific antibody comprises a dual action Fab (DAF) antibody as described in U.S. Pat. Pub. No. 2008/0069820, incorporated by reference in its entirety.

In some embodiments, the multispecific antibody comprises an antibody formed by reduction of two parental molecules followed by mixing of the two parental molecules and reoxidation to assembly a hybrid structure. See Carlring et al., *PLoS One,* 2011, 6:e22533, incorporated by reference in its entirety.

In some embodiments, the multispecific antibody comprises a DVD-Ig™. A DVD-Ig™ is a dual variable domain immunoglobulin that can bind to two or more antigens. DVD-Igs™ are described in U.S. Pat. No. 7,612,181, incorporated by reference in its entirety.

In some embodiments, the multispecific antibody comprises a DART™. DARTs™ are described in Moore et al., *Blood,* 2011, 117:454-451, incorporated by reference in its entirety.

In some embodiments, the multispecific antibody comprises a DuoBody®. DuoBodies® are described in Labrijn et al., *Proc. Natl. Acad. Sci. USA,* 2013, 110:5145-5150; Gramer et al., *mAbs,* 2013, 5:962-972; and Labrijn et al., *Nature Protocols,* 2014, 9:2450-2463; each of which is incorporated by reference in its entirety.

In some embodiments, the multispecific antibody comprises an antibody fragment attached to another antibody or fragment. The attachment can be covalent or non-covalent. When the attachment is covalent, it may be in the form of a fusion protein or via a chemical linker. Illustrative examples of multispecific antibodies comprising antibody fragments attached to other antibodies include tetravalent bispecific antibodies, where an scFv is fused to the C-terminus of the $C_{H3}$ from an IgG. See Coloma and Morrison, *Nature Biotechnol.,* 1997, 15:159-163. Other examples include antibodies in which a Fab molecule is attached to the constant region of an immunoglobulin. See Miler et al., *J Immunol.,* 2003, 170:4854-4861, incorporated by reference in its entirety. Any suitable fragment may be used, including any of the fragments described herein or known in the art.

In some embodiments, the multispecific antibody comprises a CovX-Body. CovX-Bodies are described, for example, in Doppalapudi et al., *Proc. Natl. Acad. Sci. USA,* 2010, 107:22611-22616, incorporated by reference in its entirety.

In some embodiments, the multispecific antibody comprises an Fcab antibody, where one or more antigen-binding domains are introduced into an Fc region. Fcab antibodies are described in Wozniak-Knopp et al., *Protein Eng. Des. Sel.,* 2010, 23:289-297, incorporated by reference in its entirety.

In some embodiments, the multispecific antibody comprises a TandAb® antibody. TandAb® antibodies are described in Kipriyanov et al., *J Mol. Biol.,* 1999, 293:41-56 and Zhukovsky et al., *Blood,* 2013, 122:5116, each of which is incorporated by reference in its entirety.

In some embodiments, the multispecific antibody comprises a tandem Fab. Tandem Fabs are described in WO 2015/103072, incorporated by reference in its entirety.

In some embodiments, the multispecific antibody comprises a Zybody™. Zybodies™ are described in LaFleur et al., *mAbs,* 2013, 5:208-218, incorporated by reference in its entirety.

2.6. Glycosylation Variants

In certain embodiments, an antibody provided herein may be altered to increase, decrease or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to or from an antibody provided herein may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

In some embodiments, an antibody provided herein comprises a glycosylation motif that is different from a naturally occurring antibody. Any suitable naturally occurring glycosylation motif can be modified in the antibodies provided herein. The structural and glycosylation properties of immunoglobulins, for example, are known in the art and summarized, for example, in Schroeder and Cavacini, *J. Allergy Clin. Immunol.*, 2010, 125:S41-52, incorporated by reference in its entirety.

In some embodiments, an antibody provided herein comprises an IgG1 Fc region with modification to the oligosaccharide attached to asparagine 297 (Asn 297). Naturally occurring IgG1 antibodies produced by mammalian cells typically comprise a branched, biantennary oligosaccharide that is generally attached by an N-linkage to Asn 297 of the $C_{H2}$ domain of the Fc region. See Wright et al., *TIBTECH*, 1997, 15:26-32, incorporated by reference in its entirety. The oligosaccharide attached to Asn 297 may include various carbohydrates such as mannose, N-acetyl glucosamine (GlcNAc), galactose, and sialic acid, as well as a fucose attached to a GlcNAc in the "stem" of the biantennary oligosaccharide structure.

In some embodiments, the oligosaccharide attached to Asn 297 is modified to create antibodies having altered ADCC. In some embodiments, the oligosaccharide is altered to improve ADCC. In some embodiments, the oligosaccharide is altered to reduce ADCC.

In some aspects, an antibody provided herein comprises an IgG1 domain with reduced fucose content at position Asn 297 compared to a naturally occurring IgG1 domain. Such Fc domains are known to have improved ADCC. See Shields et al., *J. Biol. Chem.*, 2002, 277:26733-26740, incorporated by reference in its entirety. In some aspects, such antibodies do not comprise any fucose at position Asn 297. The amount of fucose may be determined using any suitable method, for example as described in WO 2008/077546, incorporated by reference in its entirety.

In some embodiments, an antibody provided herein comprises a bisected oligosaccharide, such as a biantennary oligosaccharide attached to the Fc region of the antibody that is bisected by GlcNAc. Such antibody variants may have reduced fucosylation and/or improved ADCC function. Examples of such antibody variants are described, for example, in WO 2003/011878; U.S. Pat. No. 6,602,684; and U.S. Pat. Pub. No. 2005/0123546; each of which is incorporated by reference in its entirety.

Other illustrative glycosylation variants which may be incorporated into the antibodies provided herein are described, for example, in U.S. Pat. Pub. Nos. 2003/0157108, 2004/0093621, 2003/0157108, 2003/0115614, 2002/0164328, 2004/0093621, 2004/0132140, 2004/0110704, 2004/0110282, 2004/0109865; International Pat. Pub. Nos. 2000/61739, 2001/29246, 2003/085119, 2003/084570, 2005/035586, 2005/035778; 2005/053742, 2002/031140; Okazaki et al., *J. Mol. Biol.*, 2004, 336:1239-1249; and Yamane-Ohnuki et al., *Biotech. Bioeng.*, 2004, 87: 614-622; each of which is incorporated by reference in its entirety.

In some embodiments, an antibody provided herein comprises an Fc region with at least one galactose residue in the oligosaccharide attached to the Fc region. Such antibody variants may have improved CDC function. Examples of such antibody variants are described, for example, in WO 1997/30087; WO 1998/58964; and WO 1999/22764; each of which is incorporated by reference in its entirety.

Examples of cell lines capable of producing defucosylated antibodies include Lec13 CHO cells, which are deficient in protein fucosylation (see Ripka et al., *Arch. Biochem. Biophys.*, 1986, 249:533-545; U.S. Pat. Pub. No. 2003/0157108; WO 2004/056312; each of which is incorporated by reference in its entirety), and knockout cell lines, such as alpha-1,6-fucosyltransferase gene or FUT8 knockout CHO cells (see Yamane-Ohnuki et al., *Biotech. Bioeng.*, 2004, 87: 614-622; Kanda et al., *Biotechnol. Bioeng.*, 2006, 94:680-688; and WO 2003/085107; each of which is incorporated by reference in its entirety).

In some embodiments, an antibody provided herein is an aglycosylated antibody. An aglycosylated antibody can be produced using any method known in the art or described herein. In some aspects, an aglycosylated antibody is produced by modifying the antibody to remove all glycosylation sites. In some aspects, the glycosylation sites are removed only from the Fc region of the antibody. In some aspects, an aglycosylated antibody is produced by expressing the antibody in an organism that is not capable of glycosylation, such as *E. coli*, or by expressing the antibody in a cell-free reaction mixture.

In some embodiments, an antibody provided herein has a constant region with reduced effector function compared to a native IgG1 antibody. In some embodiments, the affinity of a constant region of an Fc region of an antibody provided herein for Fc receptor is less than the affinity of a native IgG1 constant region for such Fc receptor.

2.7. Fc Region Amino Acid Sequence Variants

In certain embodiments, an antibody provided herein comprises an Fc region with one or more amino acid substitutions, insertions, or deletions in comparison to a naturally occurring Fc region. In some aspects, such substitutions, insertions, or deletions yield antibodies with altered stability, glycosylation, or other characteristics. In some aspects, such substitutions, insertions, or deletions yield aglycosylated antibodies.

In some aspects, the Fc region of an antibody provided herein is modified to yield an antibody with altered affinity for an Fc receptor, or an antibody that is more immunologically inert. In some embodiments, the antibody variants provided herein possess some, but not all, effector functions. Such antibodies may be useful, for example, when the half-life of the antibody is important in vivo, but when certain effector functions (e.g., complement activation and ADCC) are unnecessary or deleterious.

In some embodiments, the Fc region of an antibody provided herein is a human IgG4 Fc region comprising one or more of the hinge stabilizing mutations S228P and L235E. See Aalberse et al., *Immunology*, 2002, 105:9-19, incorporated by reference in its entirety. In some embodiments, the IgG4 Fc region comprises one or more of the following mutations: E233P, F234V, and L235A. See Armour et al., *Mol. Immunol.*, 2003, 40:585-593, incorporated by reference in its entirety. In some embodiments, the IgG4 Fc region comprises a deletion at position G236.

In some embodiments, the Fc region of an antibody provided herein is a human IgG1 Fc region comprising one or more mutations to reduce Fc receptor binding. In some aspects, the one or more mutations are in residues selected from S228 (e.g., S228A), L234 (e.g., L234A), L235 (e.g., L235A), D265 (e.g., D265A), and N297 (e.g., N297A). In some aspects, the antibody comprises a PVA236 mutation. PVA236 means that the amino acid sequence ELLG (SEQ ID NO:920), from amino acid position 233 to 236 of IgG1 or EFLG (SEQ ID NO:921) of IgG4, is replaced by PVA. See U.S. Pat. No. 9,150,641, incorporated by reference in its entirety.

In some embodiments, the Fc region of an antibody provided herein is modified as described in Armour et al., *Eur. J. Immunol.*, 1999, 29:2613-2624; WO 1999/058572; and/or U.K. Pat. App. No. 98099518; each of which is incorporated by reference in its entirety.

In some embodiments, the Fc region of an antibody provided herein is a human IgG2 Fc region comprising one or more of mutations A330S and P331S.

In some embodiments, the Fc region of an antibody provided herein has an amino acid substitution at one or more positions selected from 238, 265, 269, 270, 297, 327 and 329. See U.S. Pat. No. 6,737,056, incorporated by reference in its entirety. Such Fc mutants include Fc mutants with substitutions at two or more amino acid positions 265, 269, 270, 297 and 327, including the so-called "DANA" Fc mutant with substitution of residues 265 and 297 with alanine. See U.S. Pat. No. 7,332,581, incorporated by reference in its entirety. In some embodiments, the antibody comprises an alanine at amino acid position 265. In some embodiments, the antibody comprises an alanine at amino acid position 297.

In certain embodiments, an antibody provided herein comprises an Fc region with one or more amino acid substitutions which improve ADCC, such as a substitution at one or more of positions 298, 333, and 334 of the Fc region. In some embodiments, an antibody provided herein comprises an Fc region with one or more amino acid substitutions at positions 239, 332, and 330, as described in Lazar et al., *Proc. Natl. Acad. Sci. USA*, 2006, 103:4005-4010, incorporated by reference in its entirety.

In some embodiments, an antibody provided herein comprises one or more alterations that improves or diminishes C1q binding and/or CDC. See U.S. Pat. No. 6,194,551; WO 99/51642; and Idusogie et al., *J Immunol.*, 2000, 164:4178-4184; each of which is incorporated by reference in its entirety.

In some embodiments, an antibody provided herein comprises one or more alterations to increase half-life. Antibodies with increased half-lives and improved binding to the neonatal Fc receptor (FcRn) are described, for example, in Hinton et al., *J. Immunol.*, 2006, 176:346-356; and U.S. Pat. Pub. No. 2005/0014934; each of which is incorporated by reference in its entirety. Such Fc variants include those with substitutions at one or more of Fc region residues: 238, 250, 256, 265, 272, 286, 303, 305, 307, 311, 312, 314, 317, 340, 356, 360, 362, 376, 378, 380, 382, 413, 424, 428, and 434 of an IgG.

In some embodiments, an antibody provided herein comprises one or more Fc region variants as described in U.S. Pat. Nos. 7,371,826, 5,648,260, and 5,624,821; Duncan and Winter, *Nature*, 1988, 322:738-740; and WO 94/29351; each of which is incorporated by reference in its entirety.

2.8. Pyroglutamate

As is known in the art, both glutamate (E) and glutamine (Q) at the N-termini of recombinant proteins can cyclize spontaneously to form pyroglutamate (pE) in vitro and in vivo. See Liu et al., *J Biol. Chem.*, 2011, 286:11211-11217, incorporated by reference in its entirety.

In some embodiments, provided herein are antibodies comprising a polypeptide sequence having a pE residue at the N-terminal position. In some embodiments, provided herein are antibodies comprising a polypeptide sequence in which the N-terminal residue has been converted from Q to pE. In some embodiments, provided herein are antibodies comprising a polypeptide sequence in which the N-terminal residue has been converted from E to pE.

2.9. Cysteine Engineered Antibody Variants

In certain embodiments, provided herein are cysteine engineered antibodies, also known as "thioMAbs," in which one or more residues of the antibody are substituted with cysteine residues. In particular embodiments, the substituted residues occur at solvent accessible sites of the antibody. By substituting such residues with cysteine, reactive thiol groups are introduced at solvent accessible sites of the antibody and may be used to conjugate the antibody to other moieties, such as drug moieties or linker-drug moieties, for example, to create an immunoconjugate.

In certain embodiments, any one or more of the following residues may be substituted with cysteine: V205 of the light chain; A118 of the heavy chain Fc region; and S400 of the heavy chain Fc region. Cysteine engineered antibodies may be generated as described, for example, in U.S. Pat. No. 7,521,541, which is incorporated by reference in its entirety.

3. Anti-TF Antibody-Drug Conjugates

Provided herein are antibody-drug conjugates (ADCs) comprising an antibody that binds specifically to TF and a cytotoxic agent. In some embodiments, the cytotoxic agent is linked directly to the anti-TF antibody. In some embodiments, the cytotoxic agent is linked indirectly to the anti-TF antibody.

In some embodiments, the ADCs further comprise a linker. In some embodiments, the linker links the anti-TF antibody to the cytotoxic agent.

In some embodiments, the ADCs provided herein have a drug-antibody ratio (DAR) of 1. In some embodiments, the ADCs provided herein have a DAR of 2. In some embodiments, the ADCs provided herein have a DAR of 3. In some embodiments, the ADCs provided herein have a DAR of 4. In some embodiments, the ADCs provided herein have a DAR of 5. In some embodiments, the ADCs provided herein have a DAR of 1-2, 1-3, 1-4, 1-5, 2-3, 2-4, 2-5, 3-4, 3-5, 4-5, 1, 2, 3, 4, or 5. In some embodiments, the ADCs provided herein have a DAR greater than 5. In some embodiments, the DAR is measured by UV/vis spectroscopy, hydrophobic interaction chromatography (HIC), and/or reverse phase liquid chromatography separation with time-of-flight detection and mass characterization (RP-UPLC/Mass spectrometry).

4. Methods for Making TF Antibodies

4.1. TF Antigen Preparation

The TF antigen used for isolation of the antibodies provided herein may be intact TF or a fragment of TF. The TF antigen may be, for example, in the form of an isolated protein or a protein expressed on the surface of a cell.

In some embodiments, the TF antigen is a non-naturally occurring variant of TF, such as a TF protein having an amino acid sequence or post-translational modification that does not occur in nature.

In some embodiments, the TF antigen is truncated by removal of, for example, intracellular or membrane-spanning sequences, or signal sequences. In some embodiments, the TF antigen is fused at its C-terminus to a human IgG1 Fc domain or a polyhistidine tag.

4.2. Methods of Making Monoclonal Antibodies

Monoclonal antibodies may be obtained, for example, using the hybridoma method first described by Kohler et al., Nature, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage-display libraries (see e.g., U.S. Pat. No. 8,258,082, which is incorporated by reference in its entirety) or, alternatively, using yeast-based libraries (see e.g., U.S. Pat. No. 8,691,730, which is incorporated by reference in its entirety).

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, CA, incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, CA), and SP-2 or X63-Ag8-653 cells (available from the American Type Culture Collection, Rockville, MD). Human myeloma and mouse-human heteromyeloma cell lines also have been described for the production of human monoclonal antibodies. See e.g., Kozbor, *J Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

4.3. Methods of Making Chimeric Antibodies

Illustrative methods of making chimeric antibodies are described, for example, in U.S. Pat. No. 4,816,567; and Morrison et al., *Proc. Natl. Acad. Sci. USA*, 1984, 81:6851-6855; each of which is incorporated by reference in its entirety. In some embodiments, a chimeric antibody is made by using recombinant techniques to combine a non-human variable region (e.g., a variable region derived from a mouse, rat, hamster, rabbit, or non-human primate, such as a monkey) with a human constant region.

4.4. Methods of Making Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J. Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370; each of which is incorporated by reference in its entirety.

4.5. Methods of Making Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589,369 and 5,545,807; each of which is incorporated by reference in its entirety. Human antibodies can also be derived from phage-display libraries (see e.g., Hoogenboom et al., *J Mol. Biol.*, 1991, 227:381-388; Marks et al., *J Mol. Biol.*, 1991, 222:581-597; and U.S. Pat. Nos. 5,565,332 and 5,573,905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

4.6. Methods of Making Antibody Fragments

The antibody fragments provided herein may be made by any suitable method, including the illustrative methods described herein or those known in the art. Suitable methods include recombinant techniques and proteolytic digestion of whole antibodies. Illustrative methods of making antibody fragments are described, for example, in Hudson et al., *Nat. Med.*, 2003, 9:129-134, incorporated by reference in its entirety. Methods of making scFv antibodies are described, for example, in Pluckthun, in *The Pharmacology of Monoclonal Antibodies*, vol. 113, Rosenburg and Moore eds., Springer-Verlag, New York, pp. 269-315 (1994); WO 93/16185; and U.S. Pat. Nos. 5,571,894 and 5,587,458; each of which is incorporated by reference in its entirety.

4.7. Methods of Making Alternative Scaffolds

The alternative scaffolds provided herein may be made by any suitable method, including the illustrative methods described herein or those known in the art. For example, methods of preparing Adnectins' are described in Emanuel et al., mAbs, 2011, 3:38-46, incorporated by reference in its entirety. Methods of preparing iMabs are described in U.S. Pat. Pub. No. 2003/0215914, incorporated by reference in its entirety. Methods of preparing Anticalins® are described in Vogt and Skerra, Chem. *Biochem.*, 2004, 5:191-199, incorporated by reference in its entirety. Methods of preparing Kunitz domains are described in Wagner et al., *Biochem. & Biophys. Res. Comm.*, 1992, 186:118-1145, incorporated by reference in its entirety. Methods of preparing thioredoxin peptide aptamers are provided in Geyer and Brent, *Meth. Enzymol.*, 2000, 328:171-208, incorporated by reference in its entirety. Methods of preparing Affibodies are provided in Fernandez, Curr. Opinion in Biotech., 2004, 15:364-373, incorporated by reference in its entirety. Methods of preparing DARPins are provided in Zahnd et al., *J Mol. Biol.*, 2007, 369:1015-1028, incorporated by reference in its entirety. Methods of preparing Affilins are provided in Ebersbach et al., *J Mol. Biol.*, 2007, 372:172-185, incorporated by reference in its entirety. Methods of preparing Tetranectins are provided in Graversen et al., *J Biol. Chem.*, 2000, 275:37390-37396, incorporated by reference in its entirety. Methods of preparing Avimers are provided in Silverman et al., *Nature Biotech.*, 2005, 23:1556-1561, incorporated by reference in its entirety. Methods of preparing Fynomers are provided in Silacci et al., *J Biol. Chem.*, 2014, 289:14392-14398, incorporated by reference in its entirety.

Further information on alternative scaffolds is provided in Binz et al., Nat. *Biotechnol.*, 2005 23:1257-1268; and Skerra, *Current Opin. in Biotech.*, 2007 18:295-304, each of which is incorporated by reference in its entirety.

4.8. Methods of Making Multispecific Antibodies

The multispecific antibodies provided herein may be made by any suitable method, including the illustrative methods described herein or those known in the art. Methods of making common light chain antibodies are described in Merchant et al., *Nature Biotechnol.*, 1998, 16:677-681, incorporated by reference in its entirety. Methods of making tetravalent bispecific antibodies are described in Coloma and Morrison, Nature *Biotechnol.*, 1997, 15:159-163, incorporated by reference in its entirety. Methods of making hybrid immunoglobulins are described in Milstein and Cuello, *Nature*, 1983, 305:537-540; and Staerz and Bevan, *Proc. Natl. Acad. Sci. USA*, 1986, 83:1453-1457; each of which is incorporated by reference in its entirety. Methods of making immunoglobulins with knobs-into-holes modification are described in U.S. Pat. No. 5,731,168, incorporated by reference in its entirety. Methods of making immunoglobulins with electrostatic modifications are provided in WO 2009/089004, incorporated by reference in its entirety. Methods of making bispecific single chain antibodies are described in Traunecker et al., *EMBO J*, 1991, 10:3655-3659; and Gruber et al., *J Immunol.*, 1994, 152:5368-5374; each of which is incorporated by reference in its entirety. Methods of making single-chain antibodies, whose linker length may be varied, are described in U.S. Pat. Nos. 4,946,778 and 5,132,405, each of which is incorporated by reference in its entirety. Methods of making diabodies are described in Hollinger et al., *Proc. Natl. Acad. Sci. USA*, 1993, 90:6444-6448, incorporated by reference in its entirety. Methods of making triabodies and tetrabodies are described in Todorovska et al., *J. Immunol. Methods*, 2001, 248:47-66, incorporated by reference in its entirety. Methods of making trispecific F(ab')$_3$ derivatives are described in Tutt et al. J. *Immunol.*, 1991, 147:60-69, incorporated by reference in its entirety. Methods of making cross-linked antibodies are described in U.S. Pat. No. 4,676,980; Brennan et al., *Science*, 1985, 229:81-83; Staerz, et al. *Nature*, 1985, 314:628-631; and EP 0453082; each of which is incorporated by reference in its entirety. Methods of making antigen-binding domains assembled by leucine zippers are described in Kostelny et al., *J Immunol.*, 1992, 148:1547-1553, incorporated by reference in its entirety. Methods of making antibodies via the DNL approach are described in U.S. Pat. Nos. 7,521,056; 7,550,143; 7,534,866; and 7,527,787; each of which is incorporated by reference in its entirety. Methods of making hybrids of antibody and non-antibody molecules are described in WO 93/08829, incorporated by reference in its entirety, for examples of such antibodies. Methods of making DAF antibodies are described in U.S. Pat. Pub. No. 2008/0069820, incorporated by reference in its entirety. Methods of making antibodies via reduction and oxidation are described in Carlring et al., *PLoS One*, 2011, 6:e22533, incorporated by reference in its entirety. Methods of making DVD-Igs™ are described in U.S. Pat. No. 7,612,181, incorporated by reference in its entirety. Methods of making DART™ are described in Moore et al., *Blood*, 2011, 117: 454-451, incorporated by reference in its entirety. Methods of making DuoBodies® are described in Labrijn et al., *Proc. Natl. Acad. Sci. USA*, 2013, 110:5145-5150; Gramer et al., mAbs, 2013, 5:962-972; and Labrijn et al., *Nature Protocols*, 2014, 9:2450-2463; each of which is incorporated by reference in its entirety. Methods of making antibodies comprising scFvs fused to the C-terminus of the $C_{H3}$ from an IgG are described in Coloma and Morrison, Nature *Biotechnol.*, 1997, 15:159-163, incorporated by reference in its entirety. Methods of making antibodies in which a Fab molecule is attached to the constant region of an immunoglobulin are described in Miler et al., *J Immunol.*, 2003, 170:4854-4861, incorporated by reference in its entirety. Methods of making CovX-Bodies are described in Doppalapudi et al., *Proc. Natl. Acad. Sci. USA*, 2010, 107:22611-22616, incorporated by reference in its entirety. Methods of making Fcab antibodies are described in Wozniak-Knopp et al., *Protein Eng. Des. Sel.*, 2010, 23:289-297, incorporated by reference in its entirety. Methods of making TandAb® antibodies are described in Kipriyanov et al., *J Mol. Biol.*, 1999, 293:41-56 and Zhukovsky et al., *Blood,* 2013, 122: 5116, each of which is incorporated by reference in its entirety. Methods of making tandem Fabs are described in WO 2015/103072, incorporated by reference in its entirety. Methods of making Zybodies' are described in LaFleur et al., mAbs, 2013, 5:208-218, incorporated by reference in its entirety.

4.9. Methods of Making Variants

In some embodiments, an antibody provided herein is an affinity matured variant of a parent antibody, which may be generated, for example, using phage display-based affinity maturation techniques. Briefly, one or more CDR residues may be mutated and the variant antibodies, or portions thereof, displayed on phage and screened for affinity. Such alterations may be made in CDR "hotspots," or residues encoded by codons that undergo mutation at high frequency during the somatic maturation process (see Chowdhury, *Methods Mol. Biol.,* 2008, 207:179-196, incorporated by reference in its entirety), and/or residues that contact the antigen.

Any suitable method can be used to introduce variability into a polynucleotide sequence(s) encoding an antibody, including error-prone PCR, chain shuffling, and oligonucleotide-directed mutagenesis such as trinucleotide-directed mutagenesis (TRIM). In some aspects, several CDR residues (e.g., 4-6 residues at a time) are randomized. CDR residues involved in antigen binding may be specifically identified, for example, using alanine scanning mutagenesis or modeling. CDR-H3 and CDR-L3 in particular are often targeted for mutation.

The introduction of diversity into the variable regions and/or CDRs can be used to produce a secondary library. The secondary library is then screened to identify antibody variants with improved affinity. Affinity maturation by constructing and reselecting from secondary libraries has been described, for example, in Hoogenboom et al., *Methods in Molecular Biology,* 2001, 178:1-37, incorporated by reference in its entirety.

4.10. Vectors, Host Cells, and Recombinant Methods

Also provided are isolated nucleic acids encoding TF antibodies, vectors comprising the nucleic acids, and host cells comprising the vectors and nucleic acids, as well as recombinant techniques for the production of the antibodies.

For recombinant production of an antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include one or more of the following: a signal sequence, an origin of replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting, and any suitable host cell may be used to produce the antibodies provided herein.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), i Enterobacter, Erwinia, Klebsiella, Proteus, Salmonella (*S. typhimurium*), Serratia (*S. marcescans*), Shigella, Bacilli (*B. subtilis* and *B. licheniformis*), Pseudomonas (*P. aeruginosa*), and Streptomyces. One useful *E. coli* cloning host is *E. coli* 294, although other strains such as *E. coli* B, *E. coli* X1776, and *E. coli* W3110 are also suitable.

In addition to prokaryotes, eukaryotic microbes such as filamentous fungi or yeast are also suitable cloning or expression hosts for TF antibody-encoding vectors. *Saccharomyces cerevisiae*, or common baker's yeast, is a commonly used lower eukaryotic host microorganism. However, a number of other genera, species, and strains are available and useful, such as *Schizosaccharomyces pombe, Kluyveromyces* (*K. lactis, K. fragilis, K. bulgaricus K. wickeramii, K. waltli, K. drosophilarum, K. thermotolerans*, and *K. marxianus*), *Yarrowia, Pichia pastoris, Candida* (*C. albicans*), *Trichoderma reesia, Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells, baby hamster kidney (BHK) cells, Chinese hamster ovary (CHO), mouse sertoli cells, African green monkey kidney cells (VERO-76), and the like.

The host cells used to produce the TF antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469; or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio Technology,* 1992, 10:163-167, incorporated by reference in its entirety) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that comprise human γ1, γ2, or γ4 heavy chains (Lindmark et al., *J Immunol. Meth.*, 1983, 62:1-13, incorporated by reference in its entirety). Protein G is useful for all mouse isotypes and for human γ3 (Guss et al., *EMBO J*, 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

5. Cytotoxic Agents

In some embodiments, ADCs provided herein comprise a cytotoxic agent. The cytotoxic agents provided herein include various anti-tumor or anti-cancer agents known in the art. In some embodiments, the cytotoxic agents cause destruction of cancer cells. In some embodiments, the cytotoxic agents inhibit the growth or proliferation of cancer cells.

Suitable cytotoxic agents include anti-angiogenic agents, pro-apoptotic agents, anti-mitotic agents, anti-kinase agents, alkylating agents, hormones, hormone agonists, hormone antagonists, chemokines, drugs, prodrugs, toxins, enzymes, antimetabolites, antibiotics, alkaloids, and radioactive isotopes.

In some embodiments, the cytotoxic agent comprises at least one of: calicheamycin, camptothecin, carboplatin, irinotecan, SN-38, carboplatin, camptothecan, cyclophosphamide, cytarabine, dacarbazine, docetaxel, dactinomycin, daunorubicin, doxorubicin, doxorubicin, etoposide, idarubicin, topotecan, *vinca* alkaloid, maytansinoid, maytansinoid analog, pyrrolobenzodiazepine, taxoid, duocarmycin, dolastatin, auristatin and derivatives thereof. In certain embodiments, the cytotoxic agent is monomethyl auristatin E (MMAE).

In some embodiments, the cytotoxic agent is a diagnostic agent, such as a radioactive isotope, a metal chelator, an enzyme, a fluorescent compound, a bioluminescent compound, or a chemiluminescent compound.

In some embodiments, the cytotoxic agent is a cytotoxic payload improved safety profile, for example XMT-1267 and other cytotoxic payloads described in Trail et al., *Pharmacol Ther*, 2018, 181:126-142.

6. Linkers

In some embodiments, ADCs provided herein comprise a linker. In some embodiments, an unbound linker comprises two reactive termini: an antibody conjugation reactive termini and an cytotoxic agent conjugation reactive termini. The antibody conjugation reactive terminus of the linker can be conjugated to the antibody through a cysteine thiol or lysine amine group on the antibody, typically a thiol-reactive group such as a double bond, a leaving group such as a chloro, bromo or iodo, an R-sulfanyl group or sulfonyl group, or an amine-reactive group such as a carboxyl group. The cytotoxic agent conjugation reactive terminus of the linker can be conjugated to the cytotoxic agent through formation of an amide bond with a basic amine or carboxyl group on the cytotoxin, typically a carboxyl or basic amine group.

In some embodiments, the linker is a non-cleavable linker. In some embodiments, the linker is a cleavable linker. In some embodiments, the cytotoxic agent is released from the ADC in a cell.

Suitable linkers of ADCs include labile linkers, acid labile linkers (e.g., hydrazone linkers), photolabile linkers, charged linkers, disulfide-containing linkers, peptidase-sensitive linkers (e.g., peptide linkers comprising amino acids, for example, valine and/or citrulline such as citrulline-valine or phenylalanine-lysine), β-glucuronide-linkers (See e.g., Graaf et al., *Curr Pharm Des*, 2002, 8:1391-1403), dimethyl linkers (See e.g., Chari et al., *Cancer Research*, 1992, 52:127-131; U.S. Pat. No. 5,208,020), thio-ether linkers, or hydrophilic linkers (See e.g., Kovtun et al., *Cancer Res.*, 2010, 70:2528-2537). In certain embodiments, the cytotoxic agent is conjugated to the antibody using a valine-citrulline (vc) linker.

7. Methods for Making Antibody-Drug Conjugates

The antibody-drug conjugates (ADCs) provided herein can be made using a variety of bifunctional protein coupling agents such as BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfoSIAB, sulfo-SMCC, and sulfo-SMPB, and SVSB (succinimidyl-(4-vinylsulfone)benzoate)). For example, a ricin immunotoxin can be prepared as described in Vitetta et al., Science, 1987, 238:1098. Additionally, the ADCs can be prepared using any suitable methods as disclosed in the art, e.g., in Bioconjugate Techniques, 2nd Ed., G. T. Hermanson, ed., Elsevier, San Francisco, 2008.

In some embodiments, the ADCs are made with site-specific conjugation techniques, resulting in homogeneous drug loading and avoiding ADC subpopulations with altered antigen-binding or pharmacokinetics. In some embodiments, "thiomabs" comprising cysteine substitutions at positions on the heavy and light chains are engineered to provide reactive thiol groups that do not disrupt immunoglobulin folding and assembly or alter antigen binding (Junutula et al., *J. Immunol. Meth.,* 2008, 332: 41-52; Junutula et al., Nat. *Biotechnol.,* 2008, 26: 925-932). In some embodiments, selenocysteine is co-translationally inserted into an antibody sequence by recoding the stop codon UGA from termination to selenocysteine insertion, allowing site specific covalent conjugation at the nucleophilic selenol group of selenocysteine in the presence of the other natural amino acids (See e.g., Hofer et al., *Proc. Natl. Acad. Sci. USA,* 2008, 105: 12451-12456; Hofer et al., *Biochemistry,* 2009, 48(50): 12047-12057). In certain embodiments, ADCs were synthesized as described in Behrens et al., *Mol Pharm,* 2015, 12:3986-98.

8. Assays

A variety of assays known in the art may be used to identify and characterize anti-TF antibodies and anti-TF ADCs provided herein.

8.1. Binding, Competition, and Epitope Mapping Assays

Specific antigen-binding activity of the antibodies provided herein may be evaluated by any suitable method, including using SPR, BLI, RIA and MSD-SET, as described elsewhere in this disclosure. Additionally, antigen-binding activity may be evaluated by ELISA assays and Western blot assays.

Assays for measuring competition between two antibodies, or an antibody and another molecule (e.g., one or more ligands of TF) are described elsewhere in this disclosure and, for example, in Harlow and Lane, *Antibodies: A Laboratory Manual* ch. 14, 1988, Cold Spring Harbor Laboratory, Cold Spring Harbor, N.Y, incorporated by reference in its entirety.

Assays for mapping the epitopes to which the antibodies provided herein bind are described, for example, in Morris "Epitope Mapping Protocols," in *Methods in Molecular Biology* vol. 66, 1996, Humana Press, Totowa, N.J., incorporated by reference in its entirety. In some embodiments, the epitope is determined by peptide competition. In some embodiments, the epitope is determined by mass spectrometry. In some embodiments, the epitope is determined by crystallography.

8.2. Thrombin Generation, FXa Conversion, and TF Signaling Assays

Thrombin generation in the presence of the antibodies provided herein can be determined by the Thrombin Generation Assay (TGA), as described elsewhere in this disclosure.

Assays for measuring FXa conversion in the presence of the antibodies provided herein are described elsewhere in this disclosure.

Inhibition of TF signaling can be determined by measuring the production of a cytokine regulated by the TF signaling, such as IL8 and GM-CSF. Assays for determining the IL8 and/or GM-CSF level are provided elsewhere in this disclosure and, for example, in Hjortoe et al., *Blood,* 2004, 103:3029-3037.

8.3. Assays for Effector Functions

Effector function following treatment with the antibodies provided herein may be evaluated using a variety of in vitro and in vivo assays known in the art, including those described in Ravetch and Kinet, *Annu. Rev. Immunol.,* 1991, 9:457-492; U.S. Pat. Nos. 5,500,362, 5,821,337; Hellstrom et al., Proc. Nat'l *Acad. Sci.* USA, 1986, 83:7059-7063; Hellstrom et al., Proc. Nat'l *Acad. Sci.* USA, 1985, 82:1499-1502; Bruggemann et al., *J Exp.* Med., 1987, 166:1351-1361; Clynes et al., Proc. Nat'l *Acad. Sci.* USA, 1998, 95:652-656; WO 2006/029879; WO 2005/100402; Gazzano-Santoro et al., *J Immunol. Methods,* 1996, 202:163-171; Cragg et al., *Blood,* 2003, 101:1045-1052; Cragg et al. *Blood,* 2004, 103:2738-2743; and Petkova et al., Int'l. *Immunol.,* 2006, 18:1759-1769; each of which is incorporated by reference in its entirety.

8.4. Cytotoxicity Assays and In Vivo Studies

Assays for evaluating cytotoxicity of the antibody-drug conjugates (ADCs) provided herein are described elsewhere in this disclosure.

Xenograft studies in immune compromised mice for evaluating the in vivo efficacy of the ADCs provided herein are described elsewhere in this disclosure.

Syngeneic studies in immune competent mice for evaluating the in vivo efficacy of the ADCs are included in this disclosure.

8.5. Immunohistochemistry (IHC) Assays

Immunohistochemistry (IHC) assays for evaluating the TF expression in patient samples are described elsewhere in this disclosure.

8.6. Chimeric Construct Mapping and Epitope Binning Assays

Epitope binding differences between the anti-human TF antibodies provided herein can be determined by the chimeric TF construct mapping experiments and the epitope binning assays, as described elsewhere in this disclosure.

9. Pharmaceutical Compositions

The antibodies or ADCs provided herein can be formulated in any appropriate pharmaceutical composition and administered by any suitable route of administration. Suitable routes of administration include, but are not limited to, the intravitreal, intraarterial, intradermal, intramuscular, intraperitoneal, intravenous, nasal, parenteral, pulmonary, and subcutaneous routes.

The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

9.1. Parenteral Dosage Forms

In certain embodiments, the antibodies or ADCs provided herein are formulated as parenteral dosage forms. Parenteral dosage forms can be administered to subjects by various routes including, but not limited to, subcutaneous, intravenous (including infusions and bolus injections), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry (e.g., lyophilized) products ready to be dissolved or suspended in a pharmaceutically acceptable vehicle for injection, suspensions ready for injection, and emulsions.

10. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies or ADCs.

The amount of the antibody/ADC or composition which will be effective in the prevention or treatment of a disorder or one or more symptoms thereof can vary with the nature and severity of the disease or condition, and the route by which the antibody/ADC is administered. The frequency and dosage can also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies or ADCs provided herein are also encompassed by the dosage amounts and dose frequency schedules provided herein. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

As discussed in more detail elsewhere in this disclosure, an antibody or ADC provided herein may optionally be administered with one or more additional agents useful to prevent or treat a disease or disorder. The effective amount of such additional agents may depend on the amount of ADC present in the formulation, the type of disorder or treatment, and the other factors known in the art or described herein.

11. Therapeutic Applications

For therapeutic applications, the antibodies or ADCs of the invention are administered to a mammal, generally a human, in a pharmaceutically acceptable dosage form such as those known in the art and those discussed above. For example, the antibodies or ADCs of the invention may be administered to a human intravenously as a bolus or by continuous infusion over a period of time, by intravitreal, intramuscular, intraperitoneal, intra-cerebrospinal, subcutaneous, intra-articular, intrasynovial, intrathecal, or intratumoral routes. The antibodies or ADCs also are suitably administered by peritumoral, intralesional, or perilesional routes, to exert local as well as systemic therapeutic effects. The intraperitoneal route may be particularly useful, for example, in the treatment of ovarian tumors.

The antibodies or ADCs provided herein may be useful for the treatment of any disease or condition involving TF. In some embodiments, the disease or condition is a disease or condition that can benefit from treatment with an anti-TF antibody or ADC.

In some embodiments, the antibodies or ADCs provided herein are provided for use as a medicament. In some embodiments, the antibodies or ADCs provided herein are provided for use in the manufacture or preparation of a medicament. In some embodiments, the medicament is for the treatment of a disease or condition that can benefit from an anti-TF antibody or ADC.

In some embodiments, provided herein is a method of treating a disease or condition in a subject in need thereof by administering an effective amount of an anti-TF antibody or ADC provided herein to the subject.

In some embodiments, the disease or condition that can benefit from treatment with an anti-TF antibody or ADC is cancer. In some embodiments, the anti-TF antibodies or ADCs provided herein are provided for use as a medicament for the treatment of cancer. In some embodiments, the anti-TF antibodies or ADCs provided herein are provided for use in the manufacture or preparation of a medicament for the treatment of cancer. In some embodiments, provided herein is a method of treating cancer in a subject in need thereof by administering an effective amount of an anti-TF antibody or ADC provided herein to the subject.

TF is involved in thrombosis, metastasis, tumor growth, and/or tumor angiogenesis of various types of cancers, such as ovarian cancer (See Sakurai et al., *Int J Gynecol Cancer*, 2017, 27:37-43; Koizume et al., *Biomark Cancer*, 2015, 7:1-13; each of which is incorporated by reference in its entirety), cervical cancer (See Cocco et al., *BMC Cancer*, 2011, 11:263, incorporated by reference in its entirety), head and neck cancer (See Christensen et al., *BMC Cancer*, 2017, 17:572, incorporated by reference in its entirety), prostate cancer (See Yao et al., *Cancer Invest.*, 2009, 27:430-434; Abdulkadir et al., *Hum Pathol.*, 2009, 31:443-447; each of which is incorporated by reference in its entirety), pancreatic cancer (See Zhang et al., *Oncotarget*, 2017, 8:59086-59102, incorporated by reference in its entirety), triple negative breast cancer (See Zhang et al., *Oncotarget*, 2017, 8:59086-59102, incorporated by reference in its entirety), glioblastoma (See Guan et al., *Clin Biochem.*, 2002, 35:321-325; Carneiro-Lobo et al., *J Thromb Haemost*, 2009, 7:1855-1864; each of which is incorporated by reference in its entirety), lung cancer (See Yeh et al., *PLoS One*, 2013, 8:e75287; Regina et al., *Clin Chem.*, 2009, 55:1834-42; each of which is incorporated by reference in its entirety), gastric cancer (See Lo et al., *Br J Cancer.*, 2012, 107:1125-1130, incorporated by reference in its entirety), esophageal cancer (See Chen et al., *Acta Histochem.*, 2010, 3:233-239, incorporated by reference in its entirety), bladder cancer (See Patry et al., *Int J Cancer.*, 2008, 122:1592-1597, incorporated by reference in its entirety), melanoma (See Bromberg et al., *Proc Natl Acad Sci USA.*, 1995, 92:8205-8209, incorporated by reference in its entirety), and kidney cancer (See Silva et al., *Int Braz J Urol.*, 2014, 40:499-506, incorporated by reference in its entirety).

Any suitable cancer may be treated with the antibodies or ADCs provided herein. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER-), progesterone receptors negative (PR-), and HER2 negative (HER2-) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer. Additional information on the types of cancers that can be treated with anti-TF antibodies or ADCs is provided in van den Berg et al., *Blood*, 2012, 119:924-932, which is incorporated by reference in its entirety.

In some embodiments, provided herein is a method of delaying the onset of a cancer in a subject in need thereof by administering an effective amount of an antibody or ADC provided herein to the subject.

In some embodiments, provided herein is a method of preventing the onset of a cancer in a subject in need thereof by administering an effective amount of an antibody or ADC provided herein to the subject.

In some embodiments, provided herein is a method of reducing the size of a tumor in a subject in need thereof by administering an effective amount of an antibody or ADC provided herein to the subject.

In some embodiments, provided herein is a method of reducing the number of metastases in a subject in need thereof by administering an effective amount of an antibody or ADC provided herein to the subject.

In some embodiments, provided herein is a method for extending the period of overall survival, median survival time, or progression-free survival in a subject in need thereof by administering an effective amount of an antibody or ADC provided herein to the subject.

In some embodiments, provided herein is a method for treating a subject who has become resistant to a standard of care therapeutic by administering an effective amount of an antibody or ADC provided herein to the subject.

In some embodiments, the disease or condition that can benefit from treatment with an anti-TF antibody is a disease or condition involving neovascularization. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, the disease or condition that can benefit from treatment with an anti-TF antibody is a disease or condition involving vascular inflammation.

In some embodiments, the anti-TF antibodies provided herein are provided for use as a medicament for the treatment of a disease or condition involving neovascularization. In some embodiments, the anti-TF antibodies provided herein are provided for use in the manufacture or preparation of a medicament for the treatment of a disease or condition involving neovascularization. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, the anti-TF antibodies provided herein are provided for use as a medicament for the treatment of a disease or condition involving vascular inflammation. In some embodiments, the anti-TF antibodies provided herein are provided for use in the manufacture or preparation of a medicament for the treatment of a disease or condition involving vascular inflammation.

In some embodiments, provided herein is a method of treating a disease or condition involving neovascularization in a subject in need thereof by administering an effective amount of an anti-TF antibody provided herein to the subject. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, provided herein is a method of treating a disease or condition involving vascular inflammation in a subject in need thereof by administering an effective amount of an anti-TF antibody provided herein to the subject.

In some embodiments, provided herein is a method of delaying the onset of a disease or condition involving neovascularization in a subject in need thereof by administering an effective amount of an antibody provided herein to the subject.

In some embodiments, provided herein is a method of preventing the onset of a disease or condition involving neovascularization in a subject in need thereof by administering an effective amount of an antibody provided herein to the subject.

In some embodiments, provided herein is a method of delaying the onset of age-related macular degeneration (AMD) in a subject in need thereof by administering an effective amount of an antibody provided herein to the subject.

In some embodiments, provided herein is a method of preventing the onset of age-related macular degeneration (AMD) in a subject in need thereof by administering an effective amount of an antibody provided herein to the subject.

In some embodiments, provided herein is a method of delaying the onset of diabetic retinopathy in a subject in need thereof by administering an effective amount of an antibody provided herein to the subject.

In some embodiments, provided herein is a method of preventing the onset of diabetic retinopathy in a subject in need thereof by administering an effective amount of an antibody provided herein to the subject.

In some embodiments, provided herein is a method of delaying the onset of a disease or condition involving vascular inflammation in a subject in need thereof by administering an effective amount of an antibody provided herein to the subject.

In some embodiments, provided herein is a method of preventing the onset of a disease or condition involving vascular inflammation in a subject in need thereof by administering an effective amount of an antibody provided herein to the subject.

12. Combination Therapies

In some embodiments, an antibody or ADC provided herein is administered with at least one additional therapeutic agent. Any suitable additional therapeutic agent may be administered with an antibody or ADC provided herein. In some aspects, the additional therapeutic agent is selected from radiation, a cytotoxic agent, a chemotherapeutic agent, a cytostatic agent, an anti-hormonal agent, an immunostimulatory agent, an anti-angiogenic agent, and combinations thereof.

The additional therapeutic agent may be administered by any suitable means. In some embodiments, an antibody or ADC provided herein and the additional therapeutic agent are included in the same pharmaceutical composition. In some embodiments, an antibody or ADC provided herein and the additional therapeutic agent are included in different pharmaceutical compositions.

In embodiments where an antibody or ADC provided herein and the additional therapeutic agent are included in different pharmaceutical compositions, administration of the antibody or ADC can occur prior to, simultaneously, and/or following, administration of the additional therapeutic agent.

13. Diagnostic Methods

Also provided are methods for detecting the presence of TF on cells from a subject. Such methods may be used, for example, to predict and evaluate responsiveness to treatment with an antibody or ADC provided herein.

In some embodiments, the method can be used to detect TF in a subject having or suspected of having a disease or condition. In some embodiments, the methods comprise (a) receiving a sample from the subject; and (b) detecting the presence or the level of TF in the sample by contacting the sample with the antibody provided herein. In some embodiments, the methods comprise (a) administering to the subject the antibody provided herein; and (b) detecting the presence or the level of TF in the subject. In some embodiments, the disease or condition is a cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER-), progesterone receptors negative (PR-), and HER2 negative (HER2-) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer. In some embodiments, the disease or condition involves neovascularization. In certain embodiments, the disease or condition involving neovascularization is age-related macular degeneration (AMD). In certain embodiments, the disease or condition involving neovascularization is diabetic retinopathy. In certain embodiments, the disease or condition involving neovascularization is cancer. In some embodiments, the disease or condition involves vascular inflammation.

In some embodiments, the methods comprise (a) administering to the subject the ADC provided herein; and (b) detecting the presence or the level of TF in the subject. In some embodiments, the disease or condition is a cancer. In some embodiments, the cancer is head and neck cancer. In some embodiments, the cancer is ovarian cancer. In some embodiments, the cancer is gastric cancer. In some embodiments, the cancer is esophageal cancer. In some embodiments, the cancer is cervical cancer. In some embodiments, the cancer is prostate cancer. In some embodiments, the cancer is pancreatic cancer. In some embodiments, the cancer is estrogen receptors negative (ER-), progesterone receptors negative (PR-), and HER2 negative (HER2-) triple negative breast cancer. In some embodiments, the cancer is glioblastoma. In some embodiments, the cancer is lung cancer. In some embodiments, the cancer is bladder cancer. In some embodiments, the cancer is melanoma. In some embodiments, the cancer is kidney cancer.

In some embodiments, the antibody provided herein is conjugated with a fluorescent label. In some embodiments, the antibody provided herein is conjugated with a radioactive label. In some embodiments, the antibody provided herein is conjugated with an enzyme label.

In some embodiments, the ADC provided herein comprises a fluorescent label. In some embodiments, the ADC provided herein comprises a radioactive label. In some embodiments, the ADC provided herein comprises an enzyme label.

In some embodiments, the relative amount of TF expressed by such cells is determined. The fraction of cells expressing TF and the relative amount of TF expressed by such cells can be determined by any suitable method. In some embodiments, flow cytometry is used to make such measurements. In some embodiments, fluorescence assisted cell sorting (FACS) is used to make such measurement.

14. Kits

Also provided are kits comprising the antibodies or ADCs provided herein. The kits may be used for the treatment, prevention, and/or diagnosis of a disease or disorder, as described herein.

In some embodiments, the kit comprises a container and a label or package insert on or associated with the container. Suitable containers include, for example, bottles, vials, syringes, and IV solution bags. The containers may be formed from a variety of materials, such as glass or plastic. The container holds a composition that is by itself, or when combined with another composition, effective for treating, preventing and/or diagnosing a disease or disorder. The container may have a sterile access port. For example, if the container is an intravenous solution bag or a vial, it may have a port that can be pierced by a needle. At least one active agent in the composition is an antibody or ADC provided herein. The label or package insert indicates that the composition is used for treating the selected condition.

In some embodiments, the kit comprises (a) a first container with a first composition contained therein, wherein the first composition comprises an antibody or ADC provided herein; and (b) a second container with a second composition contained therein, wherein the second composition comprises a further therapeutic agent. The kit in this embodiment of the invention may further comprise a package insert indicating that the compositions can be used to treat a particular condition.

Alternatively, or additionally, the kit may further comprise a second (or third) container comprising a pharmaceutically-acceptable excipient. In some aspects, the excipient is a buffer. The kit may further include other materials desirable from a commercial and user standpoint, including filters, needles, and syringes.

Examples

The following are examples of methods and compositions of the invention. It is understood that various other embodiments may be practiced, given the general description provided herein.

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Generation of TF Antibodies

Human, cynomolgus monkey, and mouse TF extracellular domain (ECD) fragments were expressed as C-terminal His or Fcγ fragment fusions. Expi293 cells (ThermoFisher Scientific, Waltham, MA, USA) were transiently transfected as recommended by the manufacturer with pcDNA3.1V5-HisA (ThermoFisher Scientific) encoding human, cynomolgus, or mouse TF ECD-His6 (HHHHHH (SEQ ID NO:922)) (TF-His; SEQ ID NOs:811, 815, and 819, respectively) or pFUSE-hIgG1-Fc (Invivogen, San Diego, CA, USA) encoding human, cynomolgus or mouse TF ECD-Fc (TF-Fc; SEQ ID NOs:812, 816, and 820, respectively). For the His-tagged proteins, cell culture supernatants cleared from cells by centrifugation were preconditioned with 330 mM sodium chloride and 13.3 mM imidazole. Using recommended procedures, the TF-His6 and TF-Fc proteins were purified by affinity chromatography with a HisTrap HP and MabSelect SuRe column (GE Healthcare Bio-Sciences, Marlborough, MA, USA), respectively. FVII-Fc expressed in Expi293 was purified by affinity chromatography with a MabSelect SuRe column, followed by size exclusion chromatography. The TF-His6 and TF-Fc proteins were biotinylated with a 15× molar excess of Sulfo-NHS-SS-biotin as recommended (ThermoFisher Scientific). The non-labeled and biotinylated proteins were further purified by size exclusion chromatography using a Superdex 200 Increase 10/300 column (GE Healthcare Bio-Sciences).

Human antibodies against human TF were generated by Adimab™ yeast-based antibody presentation using the biotinylated recombinant TF proteins as screening antigens, as described below. All antibodies against human TF were evaluated for cross-reactivity with cynomolgus monkey and mouse TF. The binding activity of the antibodies to human, cynomolgus monkey, and mouse TF is shown in Table 5.

I. Library Interrogation and Selection Methodology for Isolation of Anti-TF Antibodies Naive Library Selections Eight naïve human synthetic yeast libraries each of ~$10^9$ diversity were designed, generated, and propagated as described previously (see, e.g., WO2009036379; WO2010105256; WO2012009568; Xu et al., *Protein Eng Des Sel.*, 2013, 26(10):663-70). Eight parallel selections were performed, using the eight naïve libraries for monomeric human TF selections.

For the first two rounds of selection, a magnetic bead sorting technique utilizing the Miltenyi MACS system was performed, essentially as described (Siegel et al., *J Immunol Methods*, 2004, 286(1-2):141-53). Briefly, yeast cells (~$10^{10}$ cells/library) were incubated with 10 nM of biotinylated human TF Fc-fusion antigen for 15 min at room temperature in FACS wash buffer PBS with 0.1% BSA. After washing once with 50 mL ice-cold wash buffer, the cell pellet was resuspended in 40 mL wash buffer, and 500 µl Streptavidin MicroBeads (Miltenyi Biotec, Bergisch Gladbach, Germany; Cat #130-048-101) were added to the yeast and incubated for 15 min at 4° C. Next, the yeast were pelleted, resuspended in 5 mL wash buffer, and loaded onto a MACS LS column (Miltenyi Biotec, Bergisch Gladbach, Germany; Cat. #130-042-401). After the 5 mL was loaded, the column was washed 3 times with 3 mL FACS wash buffer. The column was then removed from the magnetic field, and the yeast were eluted with 5 mL of growth media and then grown overnight.

Subsequent to the two rounds of MACS, the following four rounds of sorting were performed using flow cytometry (FACS). For the first round of FACS, approximately $5\times10^7$ yeast were pelleted, washed three times with wash buffer, and incubated with 10 nM of each the biotinylated Fc-fusion proteins of mouse and/or cynomolgus TF antigen for 10-15 min at room temperature. Yeast were then washed twice and stained with LC-FITC diluted 1:100 (Southern Biotech, Birmingham, Alabama; Cat #2062-02) and either SA-633 (Life Technologies, Grand Island, NY; Cat #S21375) diluted 1:500, or EA-PE (Sigma-Aldrich, St Louis; Cat #E4011) diluted 1:50, secondary reagents for 15 min at 4° C. After washing twice with ice-cold wash buffer, the cell pellets were resuspended in 0.4 mL wash buffer and transferred to strainer-capped sort tubes. Sorting was performed using a FACS ARIA sorter (BD Biosciences), and sort gates were determined to select for TF binding. The mouse- and cyno-selected populations from the first round of FACS were grown out and expanded through sub-culturing in selective media. The second, third, and fourth rounds of FACS involved positive sorts to enrich for TF binders and/or negative sorts to decrease the number of non-specific binders using soluble membrane proteins from CHO cells (see, e.g., WO2014179363 and Xu et al., *PEDS*, 2013, 26(10): 663-70). After the final round of sorting, yeast were plated and sequenced.

Affinity Maturation of Clones Identified in Naïve Selections

Heavy chains from the naïve outputs (described above) were used to prepare light chain diversification libraries, which were then used for additional selection rounds. In particular, heavy chain variable regions were extracted from the fourth naïve selection round outputs and transformed into a light chain library with a diversity of $1\times10^6$.

The first of selection round utilized Miltenyi MACS beads and 10 nM biotinylated human TF Fc-fusion as antigen. Subsequent to the MACS bead selections, three rounds of FACS sorting were performed as described above using cynomolgus and mouse Fc-fusion TF at 10 nM or either biotinylated Fc-fusion TF antigens or biotinylated monomeric HIS-forms of human, mouse or cynomolgus TF. Individual colonies from each FACS selection round were sequenced.

Optimization of Leads Identified from Naïve or Light Chain Diversification Selections Optimization of lead clones was carried out utilizing three maturation strategies: diversification of CDR-H1 and CDR-H2; diversification of CDR-H3 following CDR-H1 and CDR-H2 diversity pool optimization; and diversification of CDR-L3 within selected CDR-L1 and CDR-L2 diversity pools.

CDR-H1 and CDR-H2 selection: The CDR-H3s from clones selected from either naïve or light chain diversification procedure were recombined into a premade library with CDR-H1 and CDR-H2 variants of a diversity of $1 \times 10^8$ and selections were performed using biotinylated Fc-fusion cynomolgus TF antigen, biotinylated cynomolgus HIS-TF antigen, and/or biotinylated human HIS-TF. Affinity pressures were applied by using decreasing concentrations of biotinylated HIS-TF antigens (down to 1 nM) under equilibrium conditions at room temperature.

CDR-H3/CDR-H1/CDR-H2 selections: Oligos were ordered from IDT which comprised the CDR-H3 as well as a homologous flanking region on either side of the CDR-H3. Amino acid positions in the CDR-H3 were variegated via NNK diversity at two positions per oligo across the entire CDR-H3. The CDR-H3 oligos were double-stranded using primers which annealed to the flanking region of the CDR-H3. The remaining FR1 to FR3 of the heavy chain variable region was amplified from pools of antibodies with improved affinity that were isolated from the CDR-H1 and CDR-H2 diversities selected above. The library was then created by transforming the double stranded CDR-H3 oligo, the FR1 to FR3 pooled fragments, and the heavy chain expression vector into yeast already containing the light chain of the parent. Selections were performed as during previous cycles using FACS sorting. FACS rounds assessed non-specific binding, species cross-reactivity, and affinity pressure, and sorting was performed to obtain populations with the desired characteristics. Affinity pressures for these selections were performed as described above in the CDR-H1 and CDR-H2 selection.

CDR-L3/CDR-L1/CDR-L2 selections: Oligos were ordered from IDT which comprised the CDR-L3 as well as a homologous flanking region on either side of the CDR-L3. Amino acid positions in the CDR-L3 were variegated via NNK diversity at one position per oligo across the entire CDR-L3. The CDR-L3 oligos were double-stranded using primers which annealed to the flanking region of the CDR-L3. The remaining FR1 to FR3 of the light chain variable region was amplified from pools of antibodies with improved affinity that were isolated from the CDR-L1 and CDR-L2 diversities selected above. The library was then created by transforming the double stranded CDR-L3 oligo, the FR1 to FR3 pooled fragments, and the light chain expression vector into yeast already containing the heavy chain of the parent. Selections were performed as during previous cycles using FACS sorting. FACS rounds assessed non-specific binding, species cross-reactivity, and affinity pressure, and sorting was performed to obtain populations with the desired characteristics. Affinity pressures included titrations as well as incorporation of the parental Fab in antigen pre-complexation.

II. IgG and Fab Production and Purification

In order to produce sufficient amounts of selected antibodies for further characterization, the yeast clones were grown to saturation and then induced for 48 h at 30° C. with shaking. After induction, yeast cells were pelleted and the supernatants were harvested for purification. IgGs were purified using a Protein A column and eluted with acetic acid, pH 2.0. Fab fragments were generated by papain digestion and purified over CaptureSelect IgG-CH1 affinity matrix (LifeTechnologies, Cat #1943200250).

Example 2: Binding Affinity Assay

Kinetic measurements for the anti-TF antibodies were conducted on an Octet QK384 (Pall ForteBio, Fremont, CA, USA) or a Biacore (GE Healthcare Bio-Sciences).

ForteBio affinity measurements were performed generally as previously described (Estep et al., MAbs. 2013 March-April; 5(2):270-8). Briefly, ForteBio affinity measurements were performed by loading IgGs on-line onto AHC sensors. Sensors were equilibrated off-line in assay buffer for 30 min and then monitored on-line for 60 seconds for baseline establishment. Sensors with loaded IgGs were exposed to 100 nM antigen (human, cynomolgus, or mouse TF) for 3 min, afterwards they were transferred to assay buffer for 3 min for off-rate measurement. Alternatively, binding measurements were obtained by loading biotinylated TF monomer on SA sensors followed by exposure to 100 nM antibody Fab in solution. Kinetic data was analyzed and fitted using a 1:1 Langmuir binding model and the $K_D$ was calculated by dividing the $k_{off}$ by the $k_{on}$. The $K_D$ values of the TF antibodies measured by the Octet-based experiments are shown in Table 5.

For the Biacore-based measurements, the antibody was covalently coupled to a CM5 or C1 chip using an amine-coupling kit (GE Healthcare Bio-Sciences). Association between the anti-TF antibodies and a five-point three-fold titration of TF-His starting at 25 to 500 nM was measured for 300 sec. Subsequently, dissociation between the anti-TF antibody and TF-His was measured for up to 1800 sec. Kinetic data was analyzed and fitted globally using a 1:1 binding model. The $K_D$ values of the TF antibodies measured by the Biacore-based experiments are shown in Table 5.

As shown in Table 5, the affinity of the antibodies for hTF, as indicated by $K_D$, is between $10^{-7}$ M and $10^{-11}$ M. All anti-hTF antibodies are cross-reactive with cTF. In addition, all anti-hTF antibodies from groups 25 and 43 exhibit binding activity to mTF. The anti-hTF antibodies 25G, 25G1, 25G9, and 43D8 are cross-reactive with mTF. There are no other known human or humanized anti-hTF monoclonal antibodies that exhibit binding activity and cross-reactivity to mouse TF, indicating that the antibodies from groups 25 and 43 bind to a novel TF epitope.

TABLE 5

Antibody Kinetics

| Ab | Human $K_D$ (nM) [Biacore] | Cynomolgus $K_D$ (nM) [Biacore] | Mouse $K_D$ (nM) [Biacore] | Human $K_D$ (nM) [ForteBio] | Cynomolgus $K_D$ (nM) [ForteBio] | Mouse $K_D$ (nM) [ForteBio] |
|---|---|---|---|---|---|---|
| 1F | 0.31 | 0.26 | nd* | 1.28 | 1.43 | no binding* |
| 1G | nd* | nd* | nd* | 2.20 | 2.70 | nd* |
| 25A | 6.20 | 5.42 | nd* | 8.45 | 7.65 | 263 |
| 25A3 | 0.36 | 0.21 | nd* | 1.67 | 1.36 | 131 |
| 25A5 | 0.08 | 0.04 | nd* | 0.64 | 0.76 | 188 |
| 25G | 23.0 | 18.0 | nd* | 21.9 | 17.5 | 114 |
| 25G1 | 0.94 | 0.78 | 5.4 | 3.97 | 4.99 | 34.2 |
| 25G9 | 13.3 | 16.4 | 2.9 | 35.8 | 42.9 | 9.16 |
| 29D | nd* | nd* | nd* | 3.30 | 12.0 | nd |
| 29E | 0.47 | 5.06 | nd* | 2.32 | 15.0 | no binding* |
| 39A | 0.09 | 0.08 | nd* | 0.83 | 0.57 | no binding* |
| 43B | 1.75 | 5.64 | nd* | 2.40 | 3.40 | 161 |
| 43B1 | 0.07 | 0.12 | nd* | 0.96 | 1.05 | 72.1 |
| 43B7 | 0.14 | 0.24 | nd* | 0.86 | 0.94 | 360 |
| 43D | 2.09 | 5.66 | nd* | 3.84 | 4.12 | 281 |
| 43D7 | 0.06 | 0.12 | 21 | 1.02 | 1.11 | 41.4 |
| 43D8 | 0.15 | 0.39 | 2.4 | 1.61 | 1.96 | 6.12 |
| 43E | 1.46 | 5.69 | nd* | 2.52 | 4.07 | 121 |
| 43Ea | 1.60 | 6.42 | nd* | 2.28 | 2.71 | 140 |
| 54E | 0.42 | 1.83 | nd* | 1.59 | 4.16 | no binding* | no binding*: no to weak binding, with no reportable $K_D$
nd*: not determined

Example 3: Cell-Based Binding Assay

HCT116 cells with endogenous expression of human TF were obtained from the American Tissue Culture Collection (ATCC, Manassas, VA, USA) and were maintained as recommended. Flp-In-CHO cells expressing mouse TF were generated by transfection of Flp-In-CHO cells as recommended with a pcDNA5/FRT vector (ThermoFisher Scientific) encoding full-length mouse TF with a C-terminal FLAG tag. A mouse TF-positive CHO clone was isolated by limiting dilution in tissue culture-treated 96-well plates.

Cell-based antibody binding was assessed as previously described in Liao-Chan et al., *PLoS One*, 2015, 10:e0124708, which is incorporated by reference in its entirety. $1.2 \times 10^5$ cells collected with Cellstripper (Mediatech, Manassas, VA, USA) were incubated with a twelve-point 1:3 dilution titration of anti-human TF IgG1 or Fab antibody starting at 250 nM or 100 nM for 2 hr on ice. After 2 washes, cells labeled with IgG1 or Fab were incubated for 30 min on ice with 150 nM of Goat Phycoerythrin (PE) F(ab')$_2$ fragment goat anti-human IgG, Fcγ fragment specific (Jackson ImmunoResearch, West Grove, PA, USA) or FITC-labeled F(ab')$_2$ fragment goat anti-human kappa (SouthernBiotech, Birmingham, AL, USA), respectively. After 2 washes, dead cells were labeled with TO-PRO-3 Iodide (ThermoFisher Scientific) and samples were analyzed on a CytoFLEX flow cytometer (Beckman Coulter, Brea, CA, USA) or Novocyte flow cytometer (ACEA Biosciences, San Diego, CA, USA). The median fluorescence intensities (MFIs) at each dilution were plotted and cell $EC_{50}$'s were derived using a 4-parameter binding model in Prism (GraphPad, La Jolla, CA, USA). The results of binding of anti-TF antibodies to human TF-positive HCT-116 cells are shown in FIGS. 1A and 1B. The results of binding of anti-TF antibodies to CHO cells expressing mouse TF are shown in FIGS. 2A and 2B.

All anti-hTF antibodies in FIGS. 1A and 1B exhibit high affinity to human TF-positive HCT-116 cells with an $EC_{50}$ ranging from about 687 pM to about 39 pM. Antibodies from groups 25 and 43 exhibit binding to CHO cells expressing mouse TF with an $EC_{50}$ ranging from about 455 nM to about 2.9 nM, as shown in FIGS. 2A and 2B. The binding activity to mouse TF is a unique property of the anti-hTF antibodies from groups 25 and 43. This is advantageous for pre-clinical studies of these antibodies with mouse models.

Example 4: Thrombin Generation Assay (TGA)

The TGA assay was performed using the calibrated-automated-thrombogram (CAT) instrument manufactured and distributed by STAGO. The test method design was equivalent to a standard CAT assay measurement, except that the plasma source was NPP in citrate/CTI. The anti-TF antibodies were titrated at 0, 10, 50 and 100 nM and mixed with normal pooled plasma (NPP) collected in 11 mM citrate supplemented with 100 microgram/mL of corn trypsin inhibitor (citrate/CTI). Relipidated TF was added to a 96-well assay plate, followed by addition of the antibody/NPP mixture. After a 10-min incubation or directly after combining the relipidated TF with antibody/NPP, thrombin generation was initiated by the addition of calcium and the thrombin substrate. The STAGO software was used to report the following parameters: Peak IIa (highest thrombin concentration generated [nM]); Lag Time (time to IIa generation [min]); ETP (endogenous thrombin potential, area under the curve [nM x min]); and ttPeak (time to Peak IIa [min]). Percent peak thrombin generation (% Peak IIa) and percent endogenous thrombin potential (% ETP) in the presence of each antibody relative to a no antibody plasma control on the same plate were also reported.

Figure 3A:
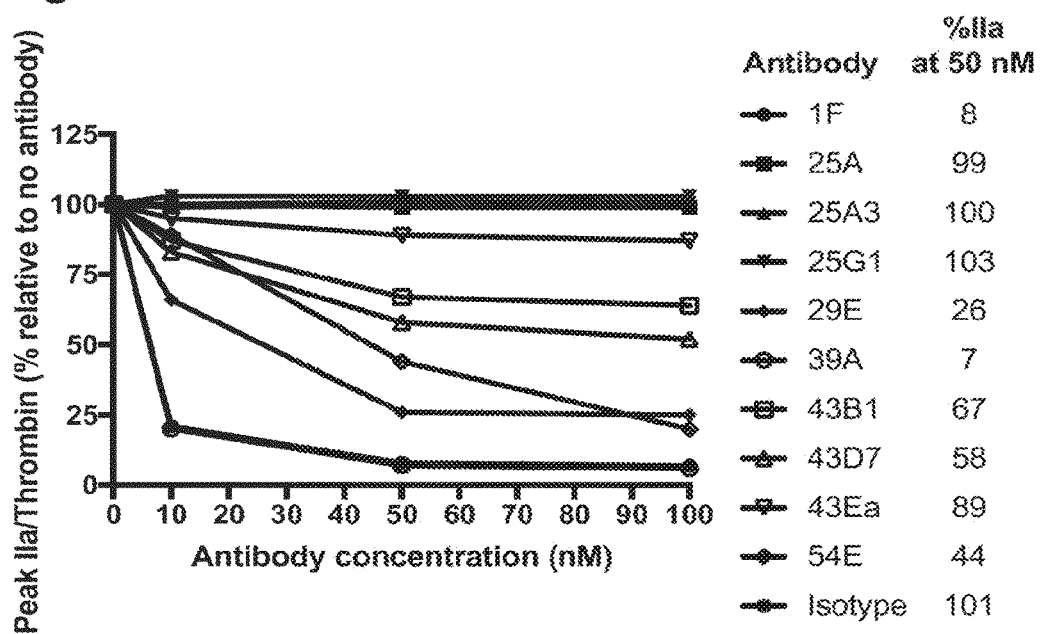
FIGS. 3A and 3B show thrombin generation in the presence of anti-TF antibody.
Figure 3B:
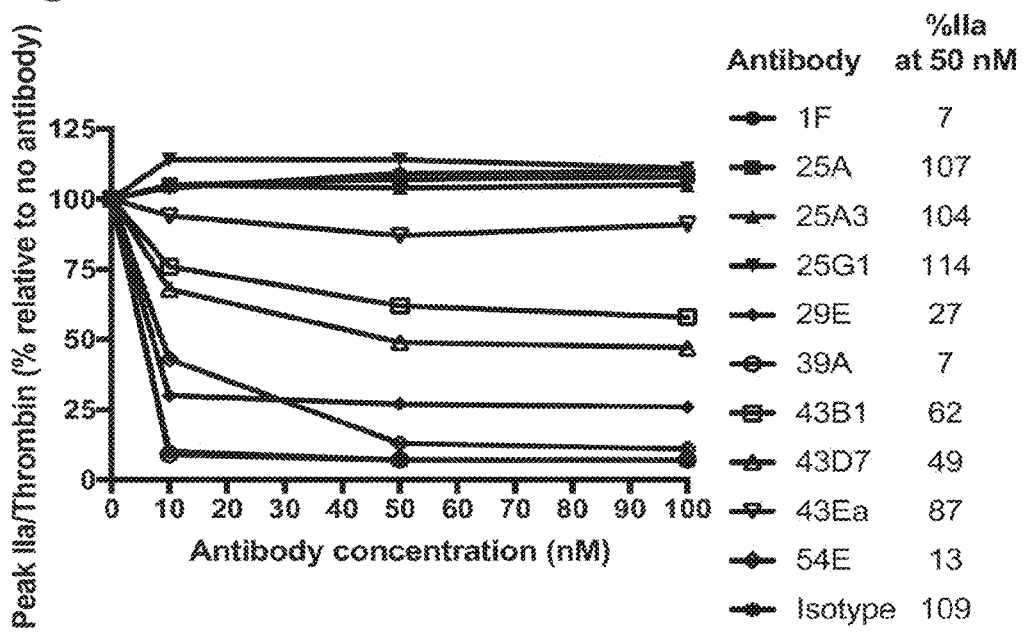

The Peak IIa, Lag Time, ETP, ttPeak, % Peak IIa, and % ETP in the presence of each antibody selected from 1F, 25A, 25A3, 25G1, 29E, 39A, 43B1, 43D7, 43Ea, and 54E without antibody incubation prior to addition of calcium and thrombin substrate are shown in Table 6. The Peak IIa, Lag Time, ETP, ttPeak, % Peak IIa, and % ETP in the presence of each antibody selected from 1F, 25A, 25A3, 25G1, 29E, 39A, 43B1, 43D7, 43Ea, and 54E with 10 min antibody incubation prior to addition of calcium and thrombin substrate are shown in Table 7. The % Peak IIa in the presence of titrations of anti-TF antibodies without antibody incubation prior to addition of calcium and thrombin substrate is plotted in FIG. 3A. The % Peak IIa in the presence of titrations of anti-TF antibodies with 10 min antibody incubation prior to addition of calcium and thrombin substrate is plotted in FIG. 3B.

The % Peak IIa is greater than 90% in the presence of antibodies from group 25, including 25A, 25A3, and 25G1. The * ETP is greater than 1000 in the presence of antibodies from group 25, including 25A, 25A3, and 25G1. The % Peak IIa is greater than 40% in the presence of antibodies from group 43, including 43B1, 43D7, and 43Ea. The % ETP is greater than 90% in the presence of antibodies from group 43, including 43B1, 43D7, and 43Ea.

This data indicates that antibodies from groups 25 and 43 allow normal thrombin generation, and therefore are not inhibitors of thrombin generation.

TABLE 6

Thrombin Generation Assay without Antibody Pre-Incubation

| Plate | Antibody | Ab conc. (nM) | Peak IIa (nM) | Lag Time (mm) | ETP (nM · min) | ttPeak (mm) | % Peak IIa | % ETP |
|---|---|---|---|---|---|---|---|---|
| 1 | 1F | 100 | 29 | 25.9 | * | 37.9 | 7 | * |
|  |  | 50 | 32 | 27.2 | * | 36.8 | 8 | * |
|  |  | 10 | 83 | 12.1 | 1395 | 19.8 | 21 | 58 |
| 1 | 25A | 100 | 398 | 4.4 | 2610 | 7.1 | 99 | 108 |
|  |  | 50 | 399 | 4.2 | 2621 | 7.1 | 99 | 108 |
|  |  | 10 | 403 | 4.1 | 2555 | 6.8 | 100 | 106 |
| 1 | 25A3 | 100 | 405 | 3.9 | 2493 | 6.5 | 100 | 103 |
|  |  | 50 | 404 | 3.9 | 2495 | 6.6 | 100 | 103 |
|  |  | 10 | 401 | 4.2 | 2550 | 7.3 | 99 | 106 |
| 1 | 25G1 | 100 | 416 | 4.5 | 2626 | 7.1 | 103 | 109 |
|  |  | 50 | 416 | 4.5 | 2680 | 7.1 | 103 | 111 |
|  |  | 10 | 417 | 4.5 | 2635 | 7.0 | 103 | 109 |
| 1 | 29E | 100 | 99 | 17.3 | * | 26.4 | 25 | * |
|  |  | 50 | 107 | 14.4 | 1747 | 22.7 | 26 | 72 |
|  |  | 10 | 266 | 5.7 | 2189 | 10.0 | 66 | 91 |
| 1 | 39A | 100 | 26 | 28.9 | * | 40.1 | 6 | * |
|  |  | 50 | 30 | 30.5 | * | 40.0 | 7 | * |
|  |  | 10 | 82 | 12.1 | 1330 | 19.6 | 20 | 55 |
| 1 | Plasma ctrl. | NA | 403 | 4.1 | 2417 | 6.8 | 100 | 100 |
| 2 | 43B1 | 100 | 221 | 5.2 | 2167 | 10.6 | 64 | 100 |
|  |  | 50 | 232 | 5.2 | 2195 | 10.3 | 67 | 101 |
|  |  | 10 | 299 | 4.9 | 2288 | 8.9 | 87 | 105 |
| 2 | 43D7 | 100 | 179 | 5.4 | 2094 | 11.8 | 52 | 96 |
|  |  | 50 | 202 | 5.3 | 2116 | 11.1 | 58 | 97 |
|  |  | 10 | 287 | 5.0 | 2263 | 9.0 | 83 | 104 |
| 2 | 43Ea | 100 | 300 | 4.6 | 2219 | 8.1 | 87 | 102 |
|  |  | 50 | 307 | 4.6 | 2234 | 8.1 | 89 | 103 |
|  |  | 10 | 328 | 5.0 | 2329 | 8.3 | 95 | 107 |
| 2 | 54E | 100 | 68 | 14.8 | 1175 | 23.9 | 20 | 54 |
|  |  | 50 | 154 | 8.9 | 2019 | 15.9 | 44 | 93 |
|  |  | 10 | 307 | 5.7 | 2307 | 9.6 | 89 | 106 |
| 2 | Isotype | 100 | 348 | 5.0 | 2415 | 8.3 | 101 | 111 |
|  |  | 50 | 347 | 5.0 | 2360 | 8.0 | 101 | 109 |
|  |  | 10 | 346 | 4.3 | 2260 | 7.6 | 100 | 104 |
| 2 | Plasma ctrl. | NA | 345 | 4.7 | 2171 | 7.8 | 100 | 100 |

* Groups with "No Tail Found" Errors when the software cannot calculate the ETP.

TABLE 7

Thrombin Generation Assay with 10 min Antibody Pre-Incubation

| Plate | Antibody | Ab conc. (nM) | Peak IIa (nM) | Lag Time (mm) | ETP (nM · min) | ttPeak (mm) | % Peak IIa | % ETP |
|---|---|---|---|---|---|---|---|---|
| 1 | 1F | 100 | 17 | 30.3 | * | 42.0 | 7 | * |
|  |  | 50 | 20 | 27.6 | * | 38.9 | 7 | * |
|  |  | 10 | 27 | 18.8 | 540 | 28.6 | 10 | 31 |
| 1 | 25A | 100 | 285 | 3.3 | 1898 | 6.7 | 108 | 110 |
|  |  | 50 | 284 | 3.3 | 1887 | 6.6 | 107 | 110 |
|  |  | 10 | 277 | 3.3 | 1842 | 6.7 | 105 | 107 |
| 1 | 25A3 | 100 | 277 | 3.1 | 1785 | 6.3 | 105 | 104 |
|  |  | 50 | 275 | 3.2 | 1824 | 6.4 | 104 | 106 |
|  |  | 10 | 278 | 3.2 | 1827 | 6.6 | 105 | 106 |
| 1 | 25G1 | 100 | 293 | 3.3 | 1827 | 6.4 | 111 | 106 |
|  |  | 50 | 301 | 3.3 | 1853 | 6.3 | 114 | 108 |
|  |  | 10 | 302 | 3.3 | 1891 | 6.3 | 114 | 110 |

TABLE 7-continued

Thrombin Generation Assay with 10 min Antibody Pre-Incubation

| Plate | Antibody | Ab conc. (nM) | Peak IIa (nM) | Lag Time (mm) | ETP (nM · min) | ttPeak (mm) | % Peak IIa | % ETP |
|---|---|---|---|---|---|---|---|---|
| 1 | 29E | 100 | 68 | 15.1 | 1098 | 25.3 | 26 | 64 |
|  |  | 50 | 70 | 14.2 | 1168 | 24.3 | 27 | 68 |
|  |  | 10 | 78 | 10.4 | 1254 | 20.2 | 30 | 73 |
| 1 | 39A | 100 | 17 | 28.0 | * | 40.2 | 7 | * |
|  |  | 50 | 17 | 28.4 | 346 | 38.9 | 7 | 20 |
|  |  | 10 | 25 | 20.8 | 482 | 30.7 | 9 | 28 |
| 1 | Plasma ctrl. | NA | 264 | 3.3 | 1720 | 6.8 | 100 | 100 |
| 2 | 43B1 | 100 | 152 | 3.2 | 1712 | 9.3 | 58 | 98 |
|  |  | 50 | 163 | 3.2 | 1797 | 9.0 | 62 | 103 |
|  |  | 10 | 200 | 3.2 | 1788 | 8.1 | 76 | 103 |
| 2 | 43D7 | 100 | 124 | 3.6 | 1656 | 10.3 | 47 | 95 |
|  |  | 50 | 128 | 3.6 | 1677 | 10.3 | 49 | 96 |
|  |  | 10 | 178 | 3.6 | 1745 | 8.8 | 68 | 100 |
| 2 | 43Ea | 100 | 239 | 2.9 | 1820 | 6.9 | 91 | 104 |
|  |  | 50 | 227 | 2.9 | 1791 | 7.1 | 87 | 103 |
|  |  | 10 | 247 | 3.2 | 1825 | 7.0 | 94 | 105 |
| 2 | 54E | 100 | 29 | 22.1 | 580 | 32.3 | 11 | 33 |
|  |  | 50 | 35 | 18.3 | 680 | 28.4 | 13 | 39 |
|  |  | 10 | 112 | 6.1 | 1530 | 13.4 | 43 | 88 |
| 2 | Isotype | 100 | 288 | 3.2 | 1888 | 6.6 | 110 | 108 |
|  |  | 50 | 285 | 3.2 | 1879 | 6.6 | 109 | 108 |
|  |  | 10 | 273 | 3.2 | 1804 | 6.6 | 104 | 104 |
| 2 | Plasma ctrl. | NA | 262 | 3.2 | 1742 | 6.9 | 100 | 100 |

* Groups with "No Tail Found" Errors when the software cannot calculate the ETP.

Example 5: FXa Conversion Assay

Figure 4A:
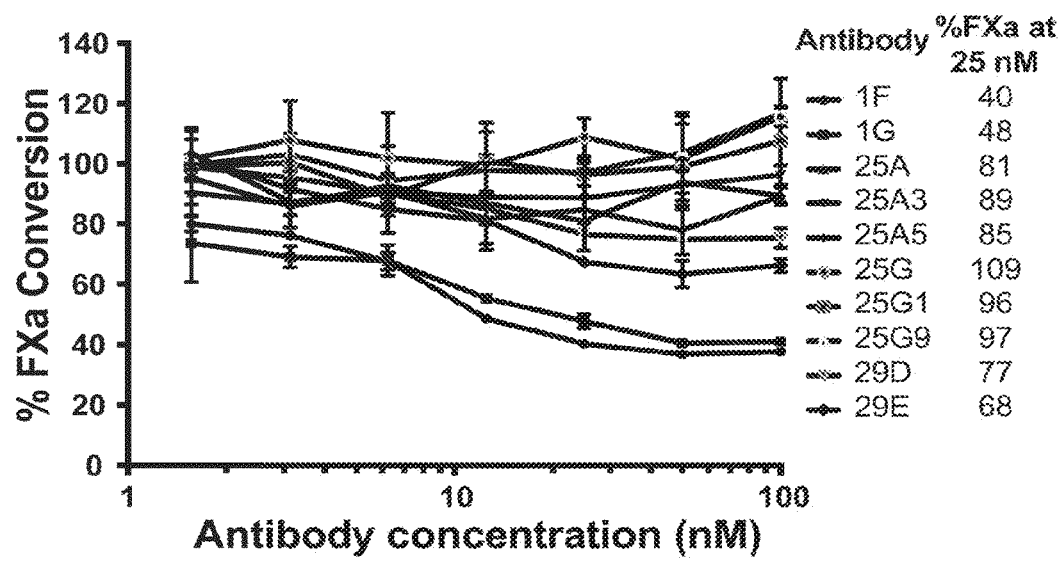
FIGS. 4A and 4B show FXa conversion in the presence of anti-TF antibody.
Figure 4B:
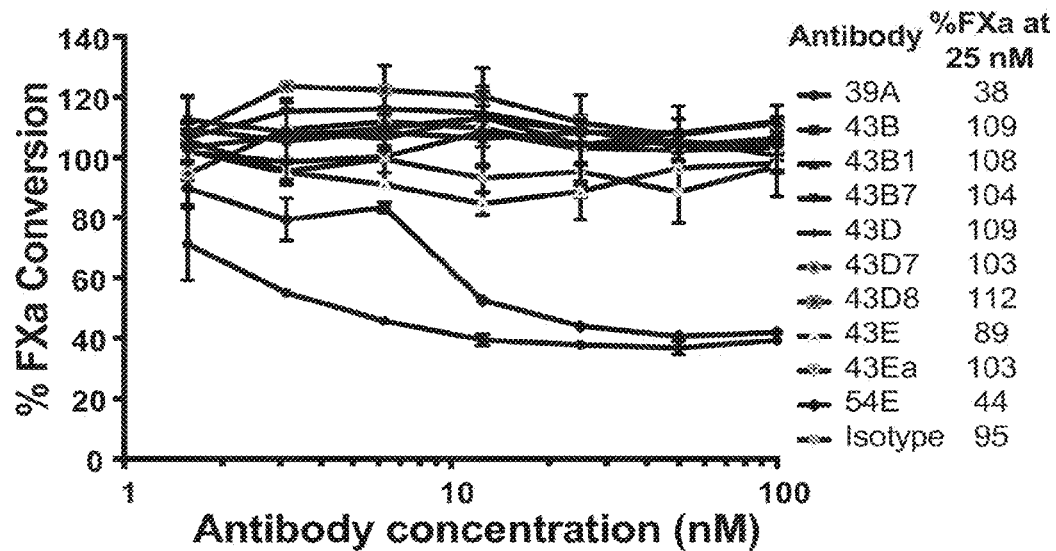

To evaluate the ability of TF:FVIIa to convert FX into FXa in the presence of human antibodies against TF, $5 \times 10^4$ MDA-MB-231 cells (ATCC, Manassas, VA, USA) were plated into tissue culture-treated black 96-well plates (Greiner Bio-One, Monroe, NC, USA). After removal of the cell culture media and addition of a final concentration of 200 nM of FX in a HEPES buffer with 1.5 mM $CaCl_2$), cells were incubated with a titration of the antibodies for 15 min at 37° C. Upon reconstitution of the binary TF:FVIIa complex with a final concentration of 20 nM of FVIIa, cells were incubated for 5 min at 37° C. After quenching the reaction with ethylenediaminetetraacetic acid (EDTA), generated FXa was measured with 50 pM of SN-7 6-amino-1-naphthalenesulfonamide-based fluorogenic substrate (Haematologic Technologies, Essex Junction, VT, USA) on an Envision plate reader equipped with an Umbelliferone 355 excitation filter, an Umbelliferone 460 emission filter, and a LANCE/DELFIA top mirror (Perkin Elmer, Waltham, MA, USA). FXa conversion percentages (% FXa) in the presence of an anti-TF antibody titration relative to a no-antibody control are summarized in Table 8 and plotted in FIGS. 4A and 4B.

The FXa conversion percentage ranges from about 78% to about 120% in presence of different concentrations of antibodies from groups 25 and 43, including 25A, 25A3, 25G, 25G1, 25G5, 25G9, 43B, 43B1, 43B7, 43D, 43D7, 43D8, 43E, and 43Ea.

This data indicates that anti-TF antibodies from groups 25 and 43 do not inhibit TF:FVIIa mediated FXa conversion from FX. This data also indicates that anti-TF antibodies from groups 25 and 43 have a human TF binding site that is distinct from the human TF binding site bound by FX.

TABLE 8

| | % FXa conversion | | | |
|---|---|---|---|---|
| | % FXa | | | |
| Antibody | 12.5 nM | 25 nM | 50 nM | 100 nM |
| 1F | 49 | 40 | 37 | 38 |
| 1G | 55 | 48 | 41 | 41 |
| 25A | 87 | 81 | 94 | 89 |
| 25A3 | 89 | 89 | 93 | 96 |
| 25A5 | 82 | 85 | 78 | 89 |
| 25G | 99 | 109 | 102 | 116 |
| 25G1 | 101 | 96 | 99 | 108 |
| 25G9 | 98 | 97 | 104 | 117 |
| 29D | 85 | 77 | 75 | 75 |
| 29E | 81 | 68 | 63 | 66 |
| 39A | 39 | 38 | 37 | 39 |
| 43B | 113 | 109 | 105 | 105 |
| 43B1 | 106 | 108 | 108 | 112 |
| 43B7 | 113 | 104 | 108 | 112 |
| 43D | 115 | 109 | 104 | 106 |
| 43D7 | 110 | 103 | 102 | 103 |
| 43D8 | 120 | 112 | 107 | 111 |
| 43E | 85 | 89 | 97 | 98 |
| 43Ea | 108 | 103 | 106 | 101 |
| 54E | 53 | 44 | 41 | 42 |
| 5G9 | 37 | 33 | 30 | 30 |
| Isotype ctrl | 93 | 95 | 89 | 97 |

Example 6: FVIIa Competition Assay

FVII-Fc conjugates were generated using Alexa Fluor 488 5-sulfo-dichlorophenol esters (ThermoFisher Scientific). Excess Alexa Fluor dye was removed from the conjugate preparations by gel filtration (ThermoFisher Scientific).

Figure 5A:
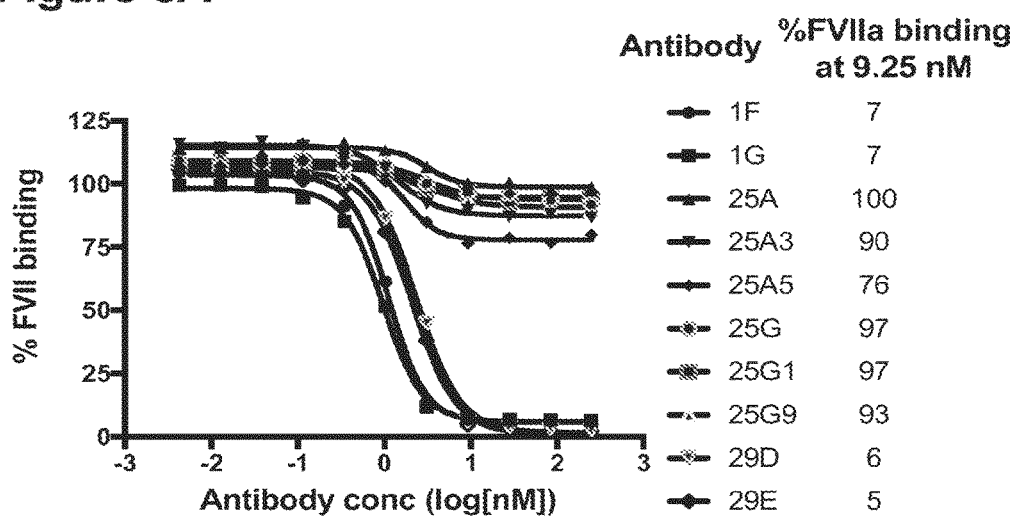
FIGS. 5A and 5B show FVIIa binding in the presence of anti-TF antibody.
Figure 5B:
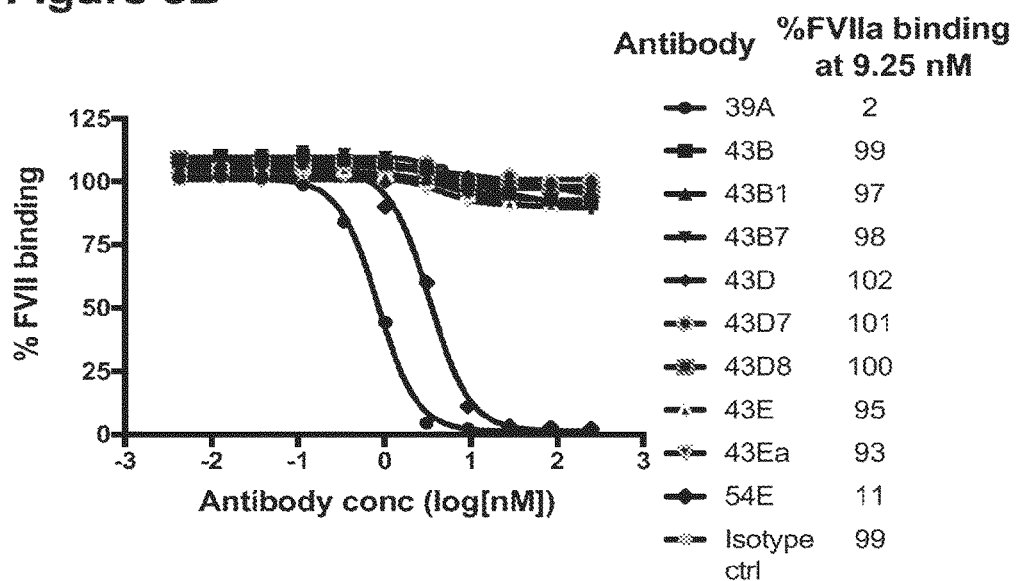

To evaluate competition between FVIIa and the human antibodies against TF, TF-positive MDA-MB-231 cells (ATCC, Manassas, VA, USA) were first incubated for 1 hr on ice with a titration of the human antibodies against TF. Subsequently, a final concentration of 20 nM of FVII-Fc conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. FVII-Fc binding was summarized with % FVII-Fc binding= [$\text{MFI}_{antibody\ labeled\ cells}$ − $\text{MFI}_{unstained}$ cells]/[$\text{MFI}_{IgG1\ control\ labeled\ cells}$ − $\text{MFI}_{unstained}$ cells]. Percentage of FVIIa binding (% FVIIa) in the presence of an anti-TF antibody titration relative to a no-antibody control is summarized in Table 9 and plotted in FIGS. 5A and 5B.

The FVIIa binding percentage ranges from about 76% to about 102% in the presence of antibodies of different concentrations from groups 25 and 43, including 25A, 25A3, 25G, 25G1, 25G5, 25G9, 43B, 43B1, 43B7, 43D, 43D7, 43D8, 43E, and 43Ea.

This data indicates that anti-TF antibodies from groups 25 and 43 do not compete for binding to human TF with FVIIa. This data also indicates that anti-TF antibodies from groups 25 and 43 have a human TF binding site that is distinct from the human TF binding site bound by FVIIa.

TABLE 9

Competition of Anti-TF Antibody with FVIIa

| Antibody | % FVIIa | | | |
|---|---|---|---|---|
| | 9.25 nM | 28 nM | 83 nM | 250 nM |
| 1F | 7 | 7 | 7 | 6 |
| 1G | 7 | 7 | 7 | 6 |
| 25A | 100 | 101 | 97 | 98 |
| 25A3 | 90 | 87 | 88 | 87 |
| 25A5 | 76 | 79 | 77 | 80 |
| 25G | 97 | 96 | 93 | 92 |
| 25G1 | 97 | 93 | 94 | 95 |
| 25G9 | 93 | 93 | 91 | 89 |
| 29D | 6 | 4 | 3 | 3 |
| 29E | 5 | 3 | 2 | 2 |
| 39A | 2 | 2 | 2 | 2 |
| 43B | 99 | 95 | 93 | 91 |
| 43B1 | 97 | 95 | 93 | 91 |
| 43B7 | 98 | 98 | 97 | 97 |
| 43D | 102 | 100 | 98 | 94 |
| 43D7 | 101 | 102 | 100 | 101 |
| 43D8 | 100 | 99 | 98 | 96 |
| 43E | 95 | 92 | 91 | 89 |
| 43Ea | 93 | 91 | 92 | 89 |
| 54E | 11 | 3 | 3 | 2 |
| Isotype | 99 | 98 | 97 | 99 |

Example 7: TF Signaling Assay

Figure 6A:
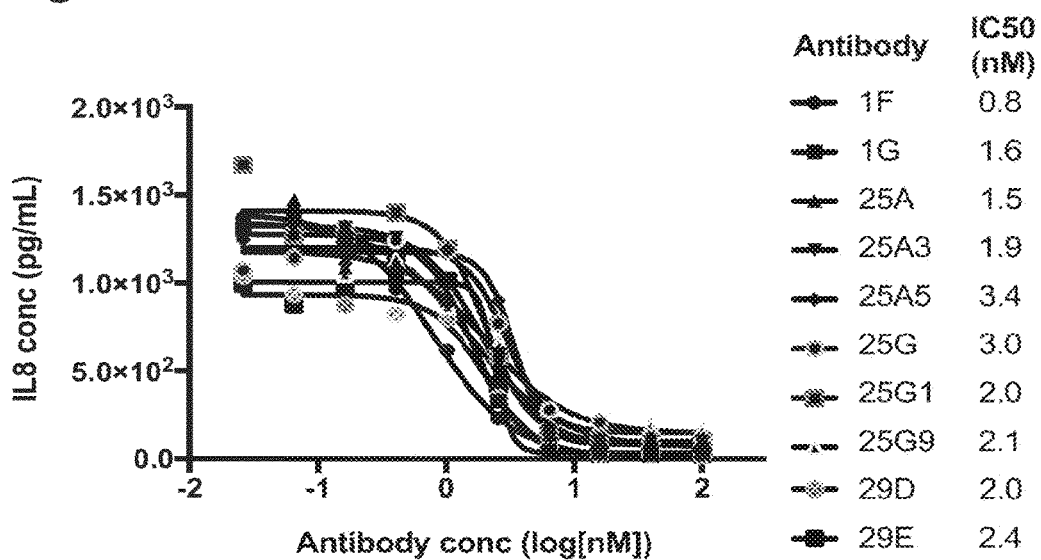
FIGS. 6A, 6B, 6C, and 6D show FVIIa-dependent TF signaling in the presence of anti-TF antibody.
Figure 6B:
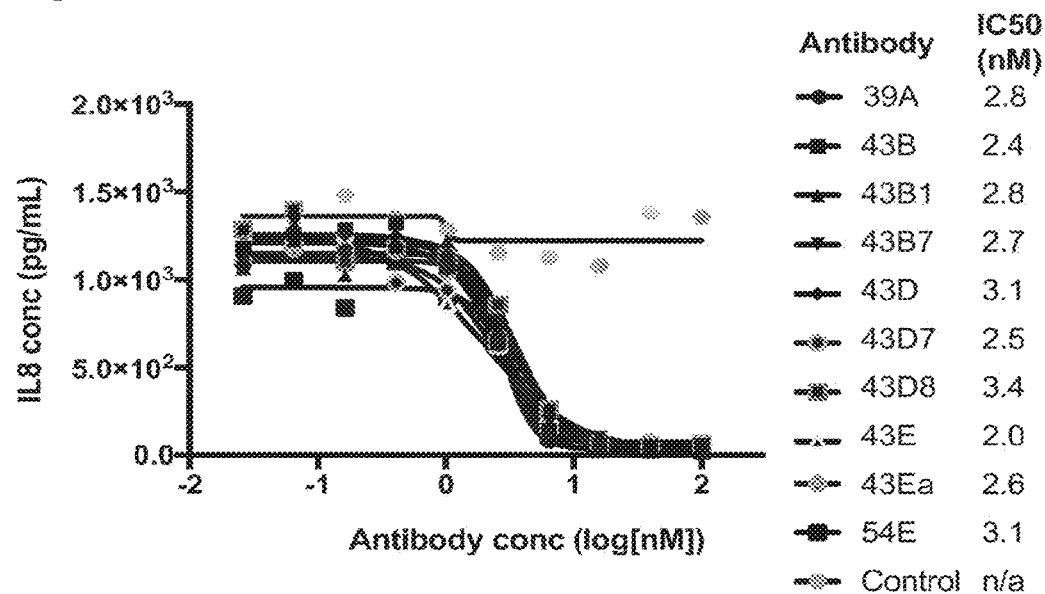
Figure 6C:
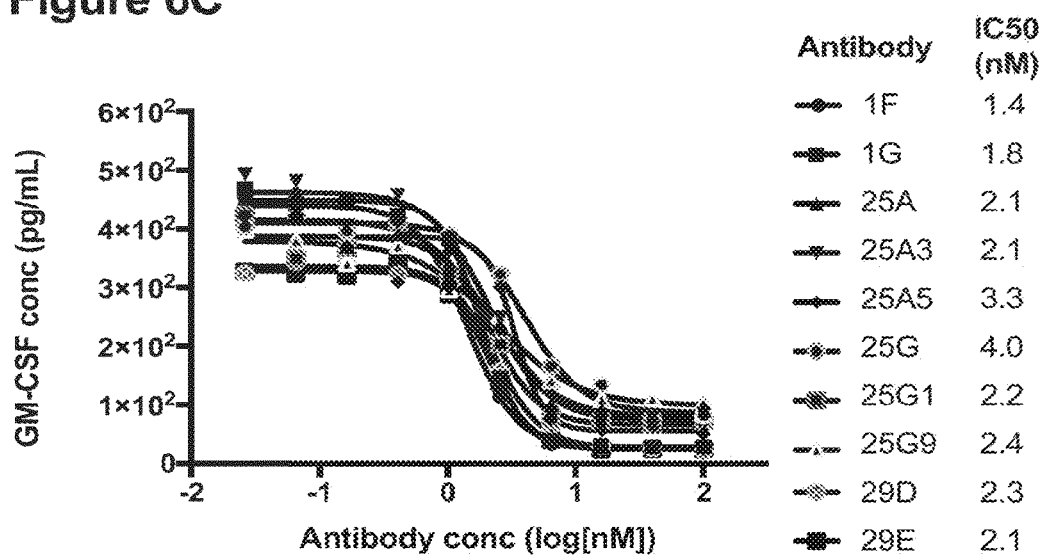
Figure 6D:
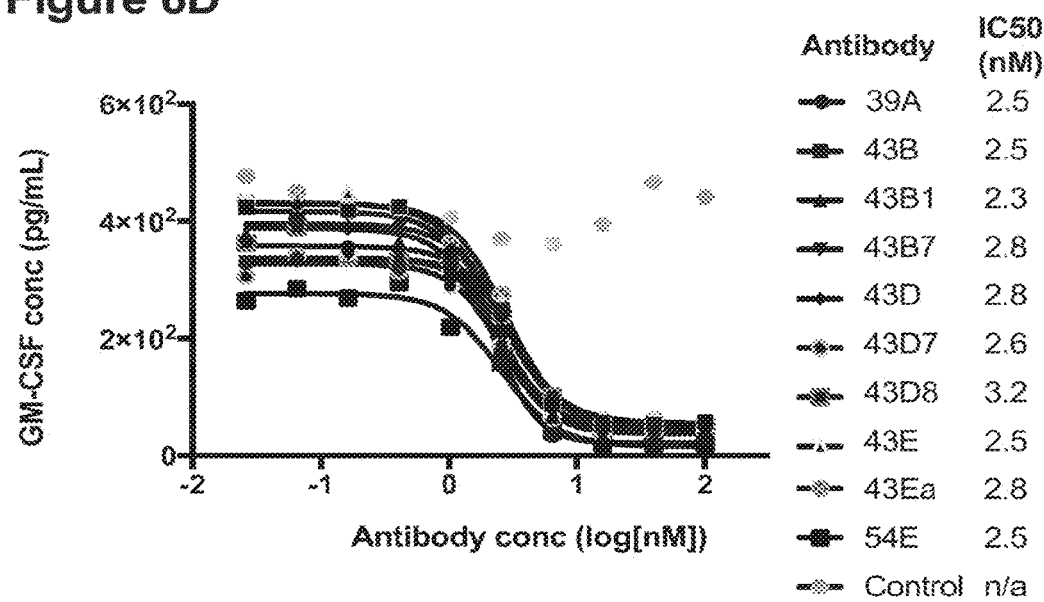

IL-8 and GM-CSF protein levels were measured as described previously in Hjortoe et al., *Blood*, 2004, 103: 3029-3037. TF-positive MDA-MB-231 cells (ATCC, Manassas, VA, USA) that underwent a 2 hr serum starvation with Leibovitz's L-15 medium were incubated with an 8-point 1:2.5 titration starting at 100 nM of anti-TF antibody. After 30 min at 37° C., FVIIa (NovoSeven RT, Novo Nordisk, Bagsvaerd, Denmark) was added to the cells at a final concentration of 20 nM. 5 hr later cell culture supernatants were harvested and analyzed by ELISA for IL8 or GM-CSF as recommended (R&D Biosystems, Minneapolis, MN, USA). A standard curve using recombinant IL8 or GM-CSF (R&D Biosystems, Minneapolis, MN, USA) was used in Prism to calculate cytokine concentration in the cell culture supernatants. Percent IL8 and GM-CSF (% IL8 and % GM-CSF) at reported antibody concentration were calculated relative to a no antibody control. The concentration of IL8 with the anti-TF antibody titration is plotted in FIGS. 6A and 6B and the % IL8 at different antibodies concentrations are shown in Table 10. The concentration of GM-CSF with the anti-TF antibody titration is plotted in FIGS. 6C and 6D and the % IL8 at different antibodies concentrations are shown in Table 11.

IL8 concentrations were reduced by more than 75% in the presence of the anti-TF antibodies at concentrations greater than or equal to 6.4 nM. GM-CSF concentrations were reduced by more than 60% in the presence of the anti-TF antibodies at concentrations greater than or equal to 6.4 nM.

This data indicates that all tested anti-TF antibodies inhibit FVIIa-dependent TF signaling.

TABLE 10

Inhibition of IL8

| Antibody | % IL8 | | | | |
|---|---|---|---|---|---|
| | 100 nM | 40 nM | 16 nM | 6.4 nM | 2.56 nM |
| 1F | 2 | 2 | 2 | 3 | 18 |
| 1G | 2 | 2 | 3 | 4 | 26 |
| 25A | 9 | 8 | 10 | 11 | 43 |
| 25A3 | 8 | 8 | 8 | 9 | 47 |
| 25A5 | 6 | 7 | 7 | 14 | 70 |
| 25G | 9 | 10 | 16 | 22 | 60 |
| 25G1 | 9 | 8 | 9 | 12 | 46 |
| 25G9 | 13 | 14 | 15 | 22 | 51 |
| 29D | 1 | 2 | 2 | 6 | 27 |
| 29E | 2 | 2 | 2 | 5 | 33 |
| 39A | 3 | 2 | 2 | 6 | 52 |
| 43B | 4 | 4 | 5 | 11 | 50 |
| 43B1 | 5 | 5 | 6 | 12 | 56 |
| 43B7 | 4 | 4 | 8 | 15 | 55 |
| 43D | 5 | 5 | 7 | 21 | 58 |
| 43D7 | 5 | 4 | 5 | 11 | 48 |
| 43D8 | 5 | 5 | 5 | 21 | 67 |
| 43E | 5 | 5 | 6 | 15 | 49 |
| 43Ea | 6 | 6 | 6 | 14 | 52 |
| 54E | 2 | 2 | 3 | 8 | 48 |
| Control | 106 | 108 | 84 | 88 | 90 |

TABLE 11

Inhibition of GM-CSF

| Antibody | % GM-CSF | | | | |
|---|---|---|---|---|---|
| | 100 nM | 40 nM | 16 nM | 6.4 nM | 2.56 nM |
| 1F | 6 | 6 | 6 | 8 | 27 |
| 1G | 7 | 7 | 7 | 9 | 34 |
| 25A | 22 | 19 | 22 | 24 | 57 |
| 25A3 | 20 | 19 | 19 | 20 | 59 |
| 25A5 | 12 | 15 | 14 | 18 | 72 |
| 25G | 19 | 18 | 32 | 39 | 77 |
| 25G1 | 17 | 16 | 17 | 18 | 48 |
| 25G9 | 25 | 26 | 26 | 34 | 60 |
| 29D | 5 | 6 | 7 | 15 | 38 |
| 29E | 6 | 6 | 5 | 9 | 33 |
| 39A | 7 | 5 | 5 | 8 | 42 |
| 43B | 14 | 13 | 12 | 21 | 59 |
| 43B1 | 11 | 11 | 13 | 16 | 50 |
| 43B7 | 11 | 11 | 13 | 17 | 50 |
| 43D | 12 | 11 | 13 | 24 | 56 |
| 43D7 | 10 | 10 | 9 | 15 | 45 |
| 43D8 | 12 | 11 | 11 | 24 | 57 |
| 43E | 14 | 15 | 15 | 21 | 61 |
| 43Ea | 14 | 15 | 14 | 21 | 65 |
| 54E | 5 | 5 | 5 | 10 | 38 |
| Control | 105 | 111 | 94 | 86 | 88 |

Example 8: Antibody Competition Assay

Alexa Fluor antibodies were generated using Alexa Fluor 488 5-sulfo-dichlorophenol esters (ThermoFisher Scientific). Excess Alexa Fluor dye was removed from the antibody dye conjugate preparations by gel filtration (ThermoFisher Scientific).

To evaluate competition between a first human antibody against TF and 25A, TF-positive A431 cells (ATCC, Manassas, VA, USA) were first incubated for 1 hr on ice with a titration of the first human antibody against TF. Subsequently, a final concentration of 20 nM of 25A conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 25A binding was summarized with % 25A binding=[$MFI_{antibody\ labeled\ cells}$−$MFI_{unstained\ cells}$]/[$MFI_{IgG1\ control\ labeled\ cells}$−$MFI_{unstained\ cells}$].

To evaluate competition between a first human antibody against TF and 43Ea, TF-positive A431 cells (ATCC, Manassas, VA, USA) were first incubated for 1 hr on ice with a titration of the first human antibody against TF. Subsequently, a final concentration of 20 nM of 43Ea conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 43Ea binding was summarized with % 43Ea binding= [$MFI_{antibody\ labeled\ cells}$−$MFI_{unstained\ cells}$]/[$MFI_{IgG1\ control\ labeled\ cells}$−$MFI_{unstained\ cells}$].

% 25A binding and % 43Ea binding are shown in Table 12. Antibodies from group 25 and group 43 reduced the % 25A binding and % 43Ea binding to less than 10%.

This data indicates that antibodies of group 25 and antibodies of group 43 compete with each other for binding to human TF, and may bind the same or an overlapping epitope of human TF.

TABLE 12

Competition of Anti-TF Antibody with Antibody Clone 25A or 43Ea

| Antibody (100 nM) | % 25A binding | % 43Ea binding |
|---|---|---|
| 1F | 95 | 77 |
| 1G | 75 | 58 |
| 25A | 3 | 1 |
| 25G | 7 | 3 |
| 29D | 70 | 64 |
| 29E | 96 | 85 |
| 39A | 99 | 96 |
| 43B | 0 | 0 |
| 43D | 0 | 0 |
| 43E | 0 | 0 |
| 54E | 99 | 96 |
| Isotype | 100 | 100 |

Example 9: Cell Viability Assay

To evaluate internalization of the anti-TF antibodies, a cytotoxicity assay was conducted. Briefly, cells were plated in 384-well plates (Greiner Bio-One, Monroe, NC, USA) at 4×10³ cells per well in 40 µl of media. Antibodies and secondary anti-human Fc antibodies conjugated to the tubulin inhibitor mono-methyl auristatin F (MMAF) (Moradec, San Diego, CA, USA) were serially diluted starting at 5 and 30 nM, respectively. Plates were incubated for 3 days, followed by lysis in CellTiter-Glo (CTG) assay reagent (Promega, Madison, WI, USA). CTG luminescence was measured on an Envision plate reader and the mean and standard deviation of 4 replicates graphed in Prism. For each anti-TF antibody, the $IC_{50}$ and its associated 95% confidence interval were calculated in Prism using a 4-parameter binding model.

Figure 7A:
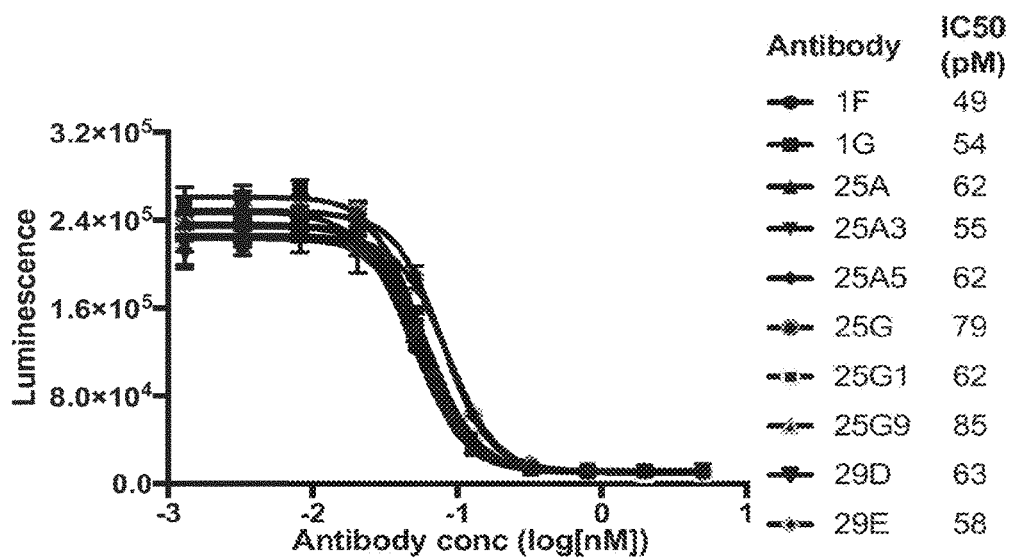
FIGS. 7A and 7B show internalization of anti-TF antibody by TF-positive cells.
Figure 7B:
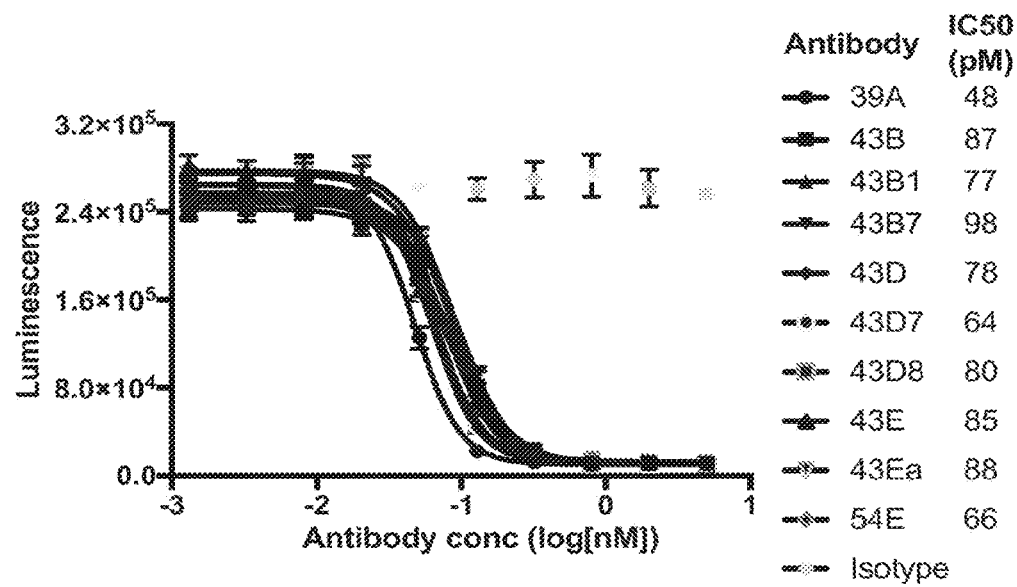

FIGS. 7A and 7B show the cell viability as indicated by the level of luminescence and the calculated $IC_{50}$.

This data indicates that all anti-TF antibodies tested from groups 1, 25, 29, 39, 43, and 54 were effective in reducing the viability of TF-positive A431 cells.

Example 10: Thrombin Generation Assay (TGA)

The TGA assay was performed using the calibrated-automated-thrombogram (CAT) instrument manufactured and distributed by STAGO. The test method design was equivalent to a standard CAT assay measurement, except that the plasma source was normal pooled plasma (NPP) in citrate supplemented with corn trypsin inhibitor (citrate/CTI). The anti-TF antibodies were titrated at 0, 10, 50 and 100 nM and mixed with normal pooled plasma (NPP) collected in 11 mM citrate supplemented with 100 microgram/mL of corn trypsin inhibitor (citrate/CTI). Relipidated TF was added to a 96-well assay plate, followed by addition of the antibody/NPP mixture. After a 10-min incubation or directly after combining the relipidated TF with antibody/NPP, thrombin generation was initiated by the addition of calcium and the thrombin substrate. The STAGO software was used to report the following parameters: Peak IIa (highest thrombin concentration generated [nM]); Lag Time (time to IIa generation [min]); ETP (endogenous thrombin potential, area under the curve [nM×min]); and ttPeak (time to Peak IIa [min]). Percent peak thrombin generation (% Peak IIa) and percent endogenous thrombin potential (% ETP) in the presence of each antibody relative to a no antibody plasma control on the same plate were also reported.

Figure 8A:
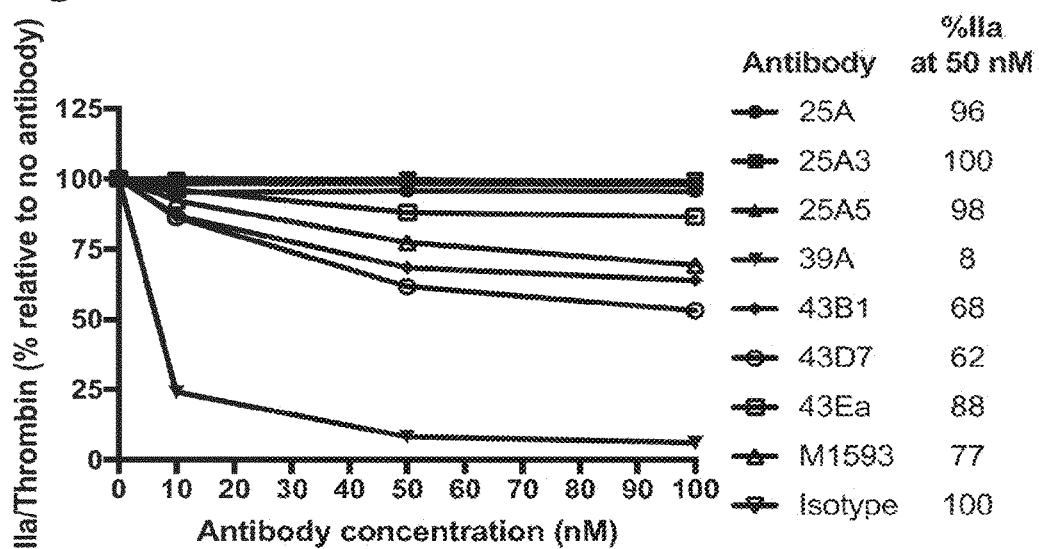
FIGS. 8A and 8B show thrombin generation in the presence of anti-TF antibody.
Figure 8B:
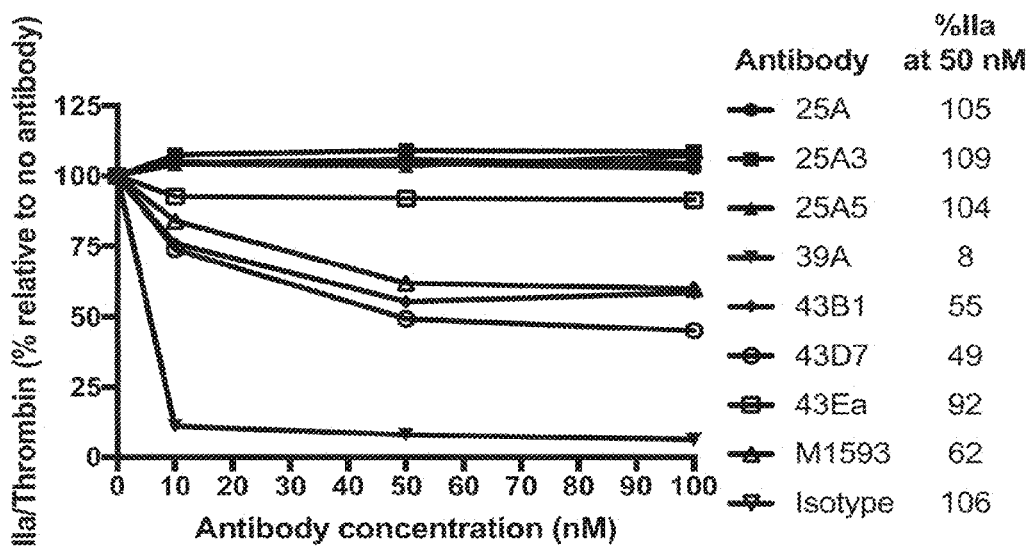

The Peak IIa, Lag Time, ETP, ttPeak, % Peak IIa, and % ETP in the presence of each antibody selected from 25A, 25A3, 25A5, 39A, 43B1, 43D7, 43Ea, and M1593 without antibody incubation prior to addition of calcium and thrombin substrate are shown in Table 37. The Peak IIa, Lag Time, ETP, ttPeak, % Peak IIa, and % ETP in the presence of each antibody selected from 25A, 25A3, 25A5, 39A, 43B1, 43D7, 43Ea, and M1593 with 10 min antibody incubation prior to addition of calcium and thrombin substrate are shown in Table 38. The % Peak IIa in the presence of titrations of anti-TF antibodies without antibody incubation prior to addition of calcium and thrombin substrate is plotted in FIG. 8A. The % Peak IIa in the presence of titrations of anti-TF antibodies with 10 min antibody incubation prior to addition of calcium and thrombin substrate is plotted in FIG. 8B. The M1593 antibody has a $V_H$ sequence of SEQ ID NO:821 and $V_L$ sequence of SEQ ID NO:822.

The % Peak IIa is 95% or greater in the presence of antibodies from group 25, including 25A, 25A3, and 25A5 without antibody pre-incubation. The % Peak IIa is 100% or greater in the presence of antibodies from group 25, including 25A, 25A3, and 25A5 with 10 min antibody pre-incubation. The % ETP is 99% or greater in the presence of the tested antibodies from group 25.

The % Peak IIa is greater than 50% but equal to or less than 96% in the presence of antibodies from group 43, including 43B1, 43D7, and 43Ea and anti-TF antibody M1593 without antibody pre-incubation. The % Peak IIa is greater than 40 but equal to or less than 93% in the presence of antibodies from group 43, including 43B1, 43D7, and 43Ea and anti-TF antibody M1593 with 10 m antibody pre-incubation. The % ETP is 92 or greater in the presence of the tested antibodies from group 43 and M1593 antibody.

This data indicates that antibodies from groups 25 and 43 allow normal thrombin generation, and therefore are not inhibitors of thrombin generation. The percent peak thrombin generation (% Peak IIa) is greater in the presence of antibodies of group 25 compared to antibodies of group 43 and M1593 antibody.

TABLE 37

Thrombin Generation Assay without Antibody Pre-Incubation

| Plate | Antibody | Ab conc. (nM) | Peak IIa (nM) | Lag Time (mm) | ETP (nM · min) | ttPeak (mm) | % Peak IIa | % ETP |
|---|---|---|---|---|---|---|---|---|
| 3 | 25A | 100 | 334 | 5.0 | 2390 | 8.7 | 96 | 105 |
|   |     | 50  | 335 | 5.0 | 2380 | 8.7 | 96 | 104 |
|   |     | 10  | 333 | 5.0 | 2387 | 8.6 | 95 | 104 |
| 3 | 25A3 | 100 | 343 | 5.0 | 2405 | 8.4 | 98 | 105 |
|   |      | 50  | 349 | 5.0 | 2433 | 8.4 | 100 | 106 |
|   |      | 10  | 350 | 5.0 | 2426 | 8.0 | 100 | 106 |
| 3 | 25A5 | 100 | 342 | 5.1 | 2393 | 8.5 | 98 | 105 |
|   |      | 50  | 344 | 4.8 | 2317 | 8.1 | 98 | 101 |
|   |      | 10  | 343 | 4.7 | 2270 | 8.0 | 98 | 99 |
| 3 | 39A | 100 | 22 | 38.1 | * | 48.3 | 6 | * |
|   |     | 50  | 29 | 33.1 | * | 43.2 | 8 | * |
|   |     | 10  | 84 | 12.4 | 1332 | 20.7 | 24 | 58 |
| 3 | 43B1 | 100 | 223 | 4.8 | 2111 | 10.0 | 64 | 92 |
|   |      | 50  | 239 | 4.9 | 2134 | 9.9 | 68 | 93 |
|   |      | 10  | 303 | 5.1 | 2318 | 9.1 | 87 | 101 |
| 3 | 43D7 | 100 | 186 | 5.6 | 2105 | 12.2 | 53 | 92 |
|   |      | 50  | 216 | 5.5 | 2183 | 11.3 | 62 | 96 |
|   |      | 10  | 301 | 5.4 | 2338 | 9.3 | 86 | 102 |
| 3 | 43Ea | 100 | 302 | 5.1 | 2347 | 9.1 | 87 | 103 |
|   |      | 50  | 308 | 5.1 | 2392 | 8.8 | 88 | 105 |
|   |      | 10  | 336 | 4.5 | 2305 | 7.8 | 96 | 101 |
| 3 | M1593 | 100 | 242 | 5.1 | 2235 | 10.4 | 69 | 98 |
|   |       | 50  | 270 | 5.1 | 2282 | 9.8 | 77 | 100 |
|   |       | 10  | 322 | 5.1 | 2368 | 8.8 | 92 | 104 |
| 3 | Isotype | 100 | 347 | 5.0 | 2319 | 8.1 | 99 | 101 |
|   |         | 50  | 348 | 5.0 | 2324 | 8.1 | 100 | 102 |
|   |         | 10  | 348 | 5.0 | 2326 | 8.3 | 100 | 102 |
| 3 | Plasma ctrl. | NA | 349 | 4.7 | 2285 | 7.7 | 100 | 100 |

* Groups with "No Tail Found" Errors when the software cannot calculate the ETP.

TABLE 38

Thrombin Generation Assay with 10 min Antibody Pre-Incubation

| Plate | Antibody | Ab conc. (nM) | Peak IIa (nM) | Lag Time (mm) | ETP (nM · min) | ttPeak (mm) | % Peak IIa | % ETP |
|---|---|---|---|---|---|---|---|---|
| 3 | 25A | 100 | 274 | 3.3 | 1879 | 7.0 | 103 | 106 |
|   |     | 50  | 279 | 3.3 | 1876 | 7.0 | 105 | 106 |
|   |     | 10  | 280 | 3.6 | 1872 | 7.0 | 105 | 106 |
| 3 | 25A3 | 100 | 290 | 3.4 | 1906 | 6.8 | 109 | 108 |
|   |      | 50  | 291 | 3.6 | 1925 | 6.8 | 109 | 109 |
|   |      | 10  | 287 | 3.3 | 1886 | 6.8 | 108 | 107 |
| 3 | 25A5 | 100 | 286 | 3.7 | 1883 | 7.0 | 107 | 107 |
|   |      | 50  | 277 | 3.7 | 1803 | 7.0 | 104 | 102 |
|   |      | 10  | 278 | 3.7 | 1808 | 7.0 | 104 | 102 |
| 3 | 39A | 100 | 17 | 32.1 | * | 43.2 | 6 | * |
|   |     | 50  | 21 | 29.0 | * | 39.7 | 8 | * |
|   |     | 10  | 30 | 20.9 | * | 30.8 | 11 | * |
| 3 | 43B1 | 100 | 156 | 3.6 | 1701 | 9.3 | 58 | 96 |
|   |      | 50  | 148 | 3.3 | 1667 | 9.6 | 55 | 94 |
|   |      | 10  | 203 | 3.7 | 1776 | 8.2 | 76 | 101 |
| 3 | 43D7 | 100 | 120 | 3.7 | 1633 | 10.8 | 45 | 92 |
|   |      | 50  | 131 | 3.7 | 1724 | 10.4 | 49 | 98 |
|   |      | 10  | 197 | 3.7 | 1784 | 8.8 | 74 | 101 |
| 3 | 43Ea | 100 | 244 | 3.3 | 1817 | 7.3 | 91 | 103 |
|   |      | 50  | 246 | 3.3 | 1833 | 7.3 | 92 | 104 |
|   |      | 10  | 247 | 3.3 | 1779 | 7.1 | 93 | 101 |
| 3 | M1593 | 100 | 160 | 3.7 | 1737 | 9.4 | 60 | 98 |
|   |       | 50  | 165 | 3.7 | 1739 | 9.3 | 62 | 99 |
|   |       | 10  | 224 | 3.7 | 1807 | 8.0 | 84 | 102 |

TABLE 38-continued

Thrombin Generation Assay with 10 min Antibody Pre-Incubation

| Plate | Antibody | Ab conc. (nM) | Peak IIa (nM) | Lag Time (min) | ETP (nM · min) | ttPeak (min) | % Peak IIa | % ETP |
|---|---|---|---|---|---|---|---|---|
| 3 | Isotype | 100 | 279 | 3.7 | 1829 | 7.2 | 105 | 104 |
|   |   | 50 | 283 | 3.7 | 1839 | 7.0 | 106 | 104 |
|   |   | 10 | 279 | 3.7 | 1814 | 7.1 | 105 | 103 |
| 3 | Plasma ctrl. | NA | 267 | 3.7 | 1766 | 7.2 | 100 | 100 |

* Groups with "No Tail Found" Errors when the software cannot calculate the ETP.

Example 11: Synthesis of Antibody-Drug Conjugates (ADCs)

Antibody-Drug Conjugates (ADCs) were synthesized as described in Behrens et al., *Mol Pharm*, 2015, 12:3986-98. 5 mg/mL of antibody in phosphate-buffered saline (PBS), pH 7.4 was reduced with 2.5 molar equivalents of Tris(2-carboxyehtyl)phosphine. After 2 hr at 37° C., the partially reduced antibody was cooled to room temperature and conjugated for 1 hr to 3 to 5 molar equivalents of MC-vc-PAB-MMAE (maleimidocaproyl-valine-citrulline-p-amino-benzoyloxycarbonyl-monomethyl auristatin E). The reaction was buffer exchanged into PBS to remove small molecular weight reagents. The drug-antibody ratio (DAR) of the resulting ADCs was 3-4. The DAR was determined with the following formula: Absorbance (248 nm)/Absorbance (280 nm)=$(n \times Ex_{PAB[248\ nm]} + Ex_{antibody[248\ nm]})/(n \times Ex_{PAB[280\ nm]} + Ex_{antibody[280\ nm]})$ with n as a variable for the DAR and Ex as the extinction coefficients of PAB and the antibody. Hydrophobic interaction chromatography and size exclusion chromatography were used to corroborate the absorbance-based DAR estimation and to ensure the ADC preparation was at least 95% monomeric, respectively.

Example 12: Cytotoxicity Assays of Antibody-Drug Conjugates (ADCs)

To evaluate cytotoxicity of ADCs, TF-positive A431 and HPAF-II cells were plated in 384-well plates (Greiner Bio-One, Monroe, NC, USA) at $4 \times 10^3$ cells per well in 40 µL of media. Anti-TF antibodies conjugated to MC-vc-PAB-MMAE were serially diluted starting at 5 nM. Plates were incubated for 3 to 4 days, followed by lysis in CellTiter-Glo (CTG) assay reagent (Promega, Madison, WI, USA). CTG luminescence was measured on an Envision plate reader and the mean and standard deviation of 4 replicates were graphed in Prism. For each ADC, the $IC_{50}$ and its associated 95% confidence interval were calculated in Prism using a 4-parameter binding model.

Figure 9A:
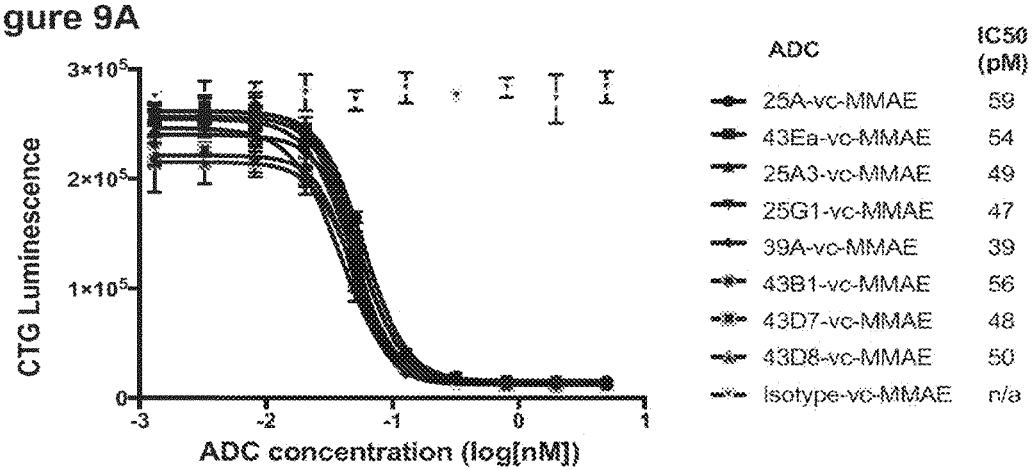
FIGS. 9A and 9B show anti-TF ADC-induced cell death in TF-positive cells.
Figure 9B:
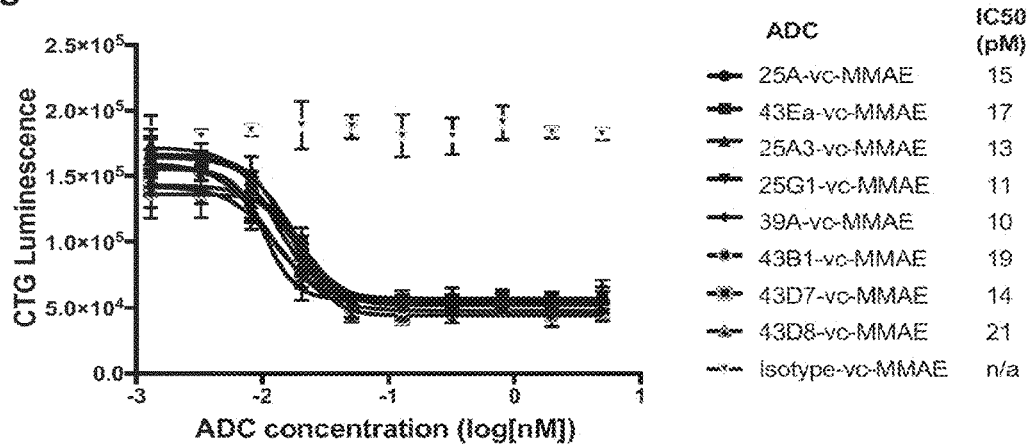

FIGS. 9A and 9B show the cell viability as indicated by CTG luminescence and the calculated $IC_{50}$ in TF-positive A431 and HPAF-II cells, respectively. ADCs comprising anti-TF antibodies from groups 25, 43, and 39 conjugated to MC-vc-PAB-MMAE resulted in cytotoxicity in TF-positive A431 and HPAF-II cells.

This data indicates that anti-TF antibody-drug conjugates reduced the viability of TF-positive cells in vitro.

Example 13: Xenograft Cell Line Studies

Xenograft studies in immune compromised mice were performed to evaluate the efficacy of the ADCs in vivo. The TF-positive A431 epidermoid carcinoma and the HPAF-II pancreatic carcinoma xenografts were implanted subcutaneously in the flank of athymic nude mice (Charles River Laboratories, Wilmington, MA). Animals were randomized when tumors reached an average size of 150-200 mm³ and treated with 5 mg/kg of the indicated ADC or vehicle (PBS) intraperitoneally (i.p.) once weekly for 3 weeks. Body weight and tumor size assessments were performed bi-weekly. Animals were removed from study and euthanized once tumor size reached 1200 mm³ or skin ulceration was evident.

Figure 10A:
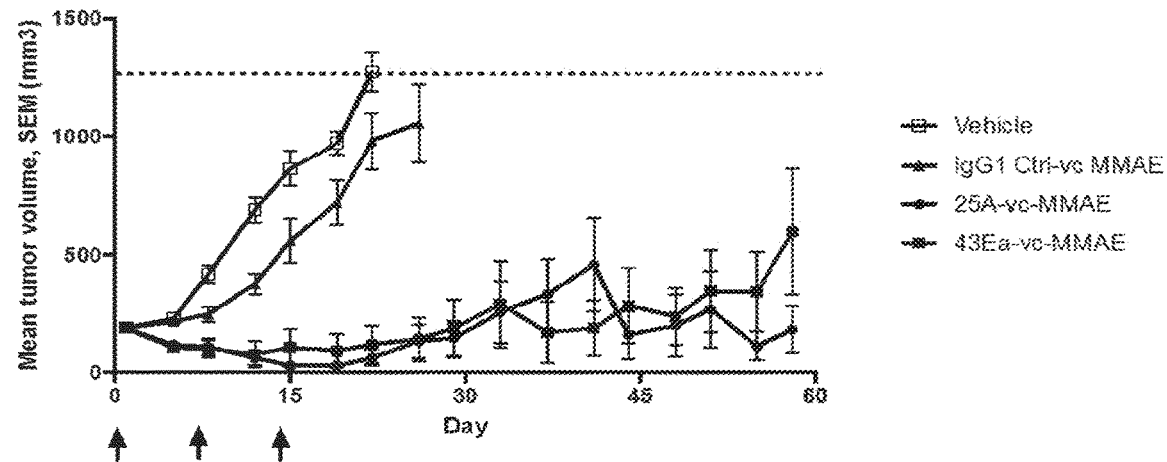
FIGS. 10A and 10B show the effect of anti-TF ADCs on tumor size in xenograft models.
Figure 10B:
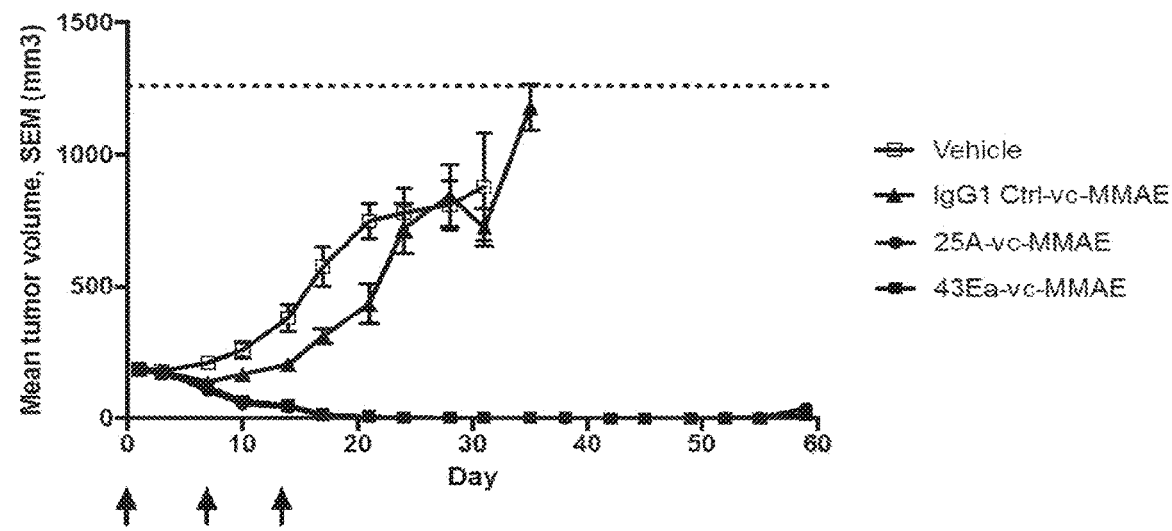

FIGS. 10A and 10B show the tumor size of vehicle-treated, IgG1 ADC-treated, and anti-TF ADC-treated groups in the TF-positive A431 epidermoid carcinoma and the HPAF-II pancreatic carcinoma xenograft models, respectively. ADCs comprising anti-TF antibodies 25A and 43Ea conjugated to MC-vc-PAB-MMAE decreased the tumor size in both xenograft models compared to the vehicle-treated or IgG1 ADC-treated groups.

This data indicates that anti-TF antibody-drug conjugates 25A-vc-MMAE and 43Ea-vc-MMAE were effective in reducing the tumor size in vivo.

Example 14: Studies of Patient-Derived Xenograft (PDX) Model

A TF-positive head and neck cancer patient-derived xenograft model was generated in athymic nude mice (Envigo, Indianapolis, IN) to further evaluate the efficacy of the ADCs in vivo. Tumors were passaged in stock animals and harvested for re-implantation. Study animals were implanted unilaterally on the left flank with tumor fragments and were randomized to treatment group when tumors reached an average size of 150-200 mm³. Animals were treated with 5 mg/kg of the indicated ADC intraperitoneally (i.p.) once weekly for 2 weeks. Body weight and tumor size assessments were performed bi-weekly. Animals were removed from study and euthanized once tumor size reached 1200 mm³ or skin ulceration was evident.

Figure 11:
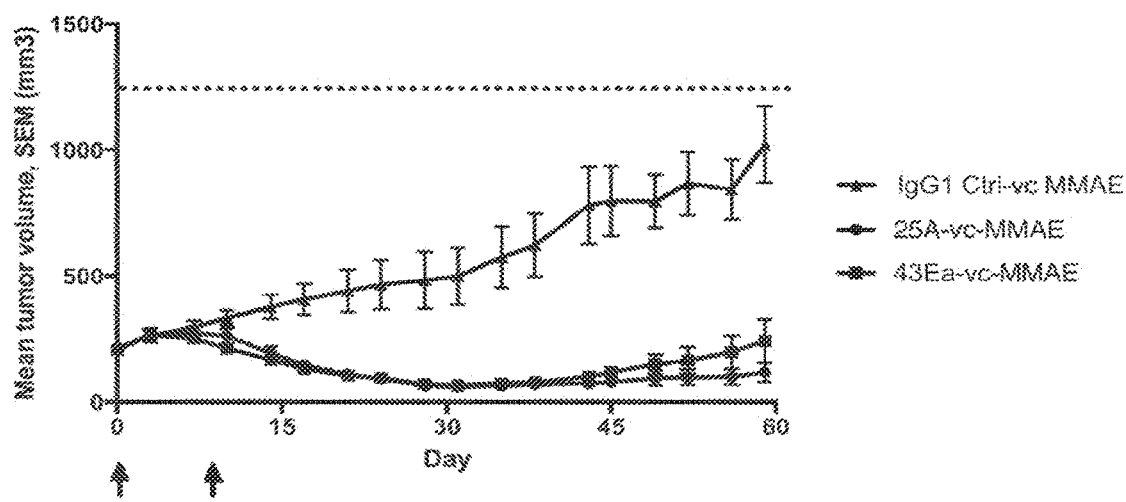
FIG. 11 shows the effect of anti-TF ADCs on tumor size in a head and neck cancer patient-derived xenograft model. The arrows indicate treatments with anti-TF ADC or IgG1 control ADC dosed at 5 mg/kg once per week for 2 weeks.

FIG. 11 shows the tumor size of IgG1 ADC-treated and anti-TF ADC-treated groups in the head and neck cancer patient-derived xenograft model. ADCs comprising anti-TF antibodies 25A and 43Ea conjugated to MC-vc-PAB-MMAE decreased the tumor size in the cancer patient-derived xenograft model compared to the IgG1 ADC-treated group.

This data indicates that anti-TF antibody-drug conjugates 25A-vc-MMAE and 43Ea-vc-MMAE were effective in reducing the tumor size in a cancer patient-derived xenograft model in vivo.

Example 15: Binding Affinity Assay For Pig TF

The ability of certain antibodies was tested for binding to pig TF. For pig TF Biacore-based measurements, a given anti-TF antibody was captured by an anti-human IgG antibody covalently coupled to a CM5 chip (GE Healthcare Bio-Sciences). Association between the anti-TF antibodies and a five-point three-fold titration of pig TF-His starting at 100 nM was measured for 180 to 240 sec. Subsequently, dissociation between the anti-TF antibody and TF-His was measured for 1800 sec. Kinetic data was analyzed and fitted globally using a 1:1 binding model. The $K_D$ values of the indicated TF antibodies measured by the Biacore-based experiments are shown in Table 40.

As shown in Table 40, anti-hTF antibodies from groups 25 and 43, 25G9 and 43D8, exhibit binding activity and cross-reactivity to pig TF.

TABLE 40

Antibody kinetics for pig TF

| Ab | Pig $K_D$ (nM) [standard deviation] |
|---|---|
| 1G | no binding* |
| 29D | no binding* |
| 25G9 | 3.31 [0.08] |
| 43D8 | 12.9 [0.03] | no binding*: no binding to weak binding, with no reportable $K_D$

Example 16: Cell-Based Binding Assay

Human TF-positive cancer cell lines A431 and MDA-MB-231 and *Macaca* mulatta TF-positive cell line RF/6A were obtained from the American Tissue Culture Collection (ATCC, Manassas, VA, USA) and were maintained as recommended.

Figure 12A:
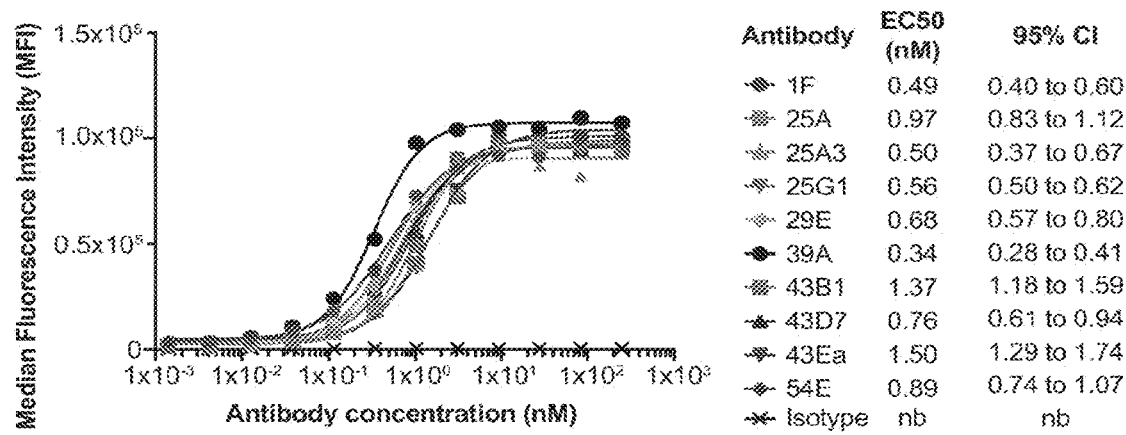
FIGS. 12A and 12B show binding of anti-TF antibodies to human TF-positive cancer cells.
Figure 12B:
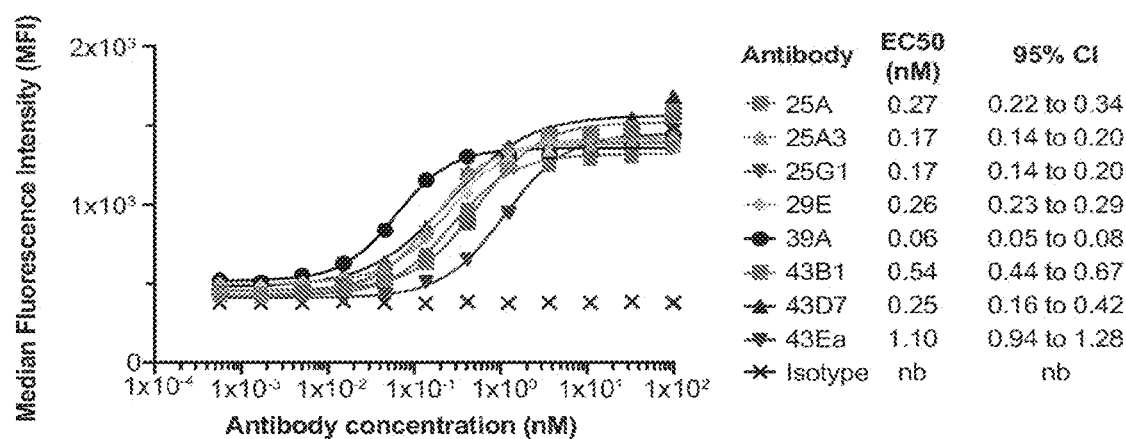

Cell-based antibody binding was assessed as previously described in Liao-Chan et al., *PLoS One*, 2015, 10:e0124708, which is incorporated by reference in its entirety. $1.2 \times 10^5$ cells collected with Cellstripper (Mediatech, Manassas, VA, USA) were incubated with a twelve-point 1:3 dilution titration of anti-human TF IgG1 antibody starting at 250 nM or 100 nM for 2 hr on ice. After 2 washes, cells labeled with IgG1 antibody were incubated for 30 min on ice with 150 nM of Goat Phycoerythrin (PE) F(ab')$_2$ fragment goat anti-human IgG, Fcγ fragment specific (Jackson ImmunoResearch, West Grove, PA, USA) or FITC-labeled F(ab')$_2$ fragment goat anti-human kappa (Southern-Biotech, Birmingham, AL, USA), respectively. After 2 washes, dead cells were labeled with TO-PRO-3 Iodide (ThermoFisher Scientific) and samples were analyzed on a CytoFLEX flow cytometer (Beckman Coulter, Brea, CA, USA) or Novocyte flow cytometer (ACEA Biosciences, San Diego, CA, USA). The median fluorescence intensities (MFIs) at each dilution were plotted and cell $EC_{50}$'s were derived using a 4-parameter binding model in Prism (GraphPad, La Jolla, CA, USA). Antibodies that does not substantially affect FX conversion (i.e. 25A, 25A3, 25G1, 43B1, 43D7 and 43Ea) and antibodies that inhibited FX conversion by more than 50% (i.e. 1F, 29E, 39A and 54E) were included in the assay. The results of binding of anti-TF antibodies to human TF-positive A431 cells are shown in FIG. 12A. The results of binding of anti-TF antibodies to human TF-positive MDA-MB-231 cells are shown in FIG. 12B.

All tested anti-hTF antibodies in FIG. 12A exhibit high affinity to human TF-positive A431 cells with an $EC_{50}$ ranging from about 1.50 nM to about 0.34 nM. An IgG1 isotype control did not bind A431 cells (no binding, nb). All tested anti-hTF antibodies in FIG. 12B exhibit high affinity to human TF-positive MDA-MB-231 cells with an $EC_{50}$ ranging from about 1.50 nM to about 0.06 nM. An IgG1 isotype control did not bind MDA-MB-231 cells (no binding, nb).

As described in Example 2 and shown in Table 5, the binding affinity of anti-hTF antibodies was evaluated on TF from cynomolgus monkey (*Macaca fascicularis*). The protein sequences of *Macaca fascicularis* TF and *Macaca mulatta* TF are identical. The binding of the TF-specific antibodies to cynomolgus monkey was confirmed using the *Macaca mulatta* RF/6A cell line as shown in Table 42. All tested anti-hTF antibodies exhibit high affinity to TF-positive *Macaca mulatta* RF/6A cells with an $EC_{50}$ ranging from about 1.28 nM to about 0.17 nM. The ability of the anti-TF antibodies to bind to cynomolgus monkey is advantageous for toxicology studies of these antibodies with nonhuman primate models.

TABLE 42

Binding of anti-TF antibodies to *Macaca mulatta* RF/6A cells

| Ab | RF/6A EC50 (nM) | RF/6A 95% CI |
|---|---|---|
| 1F | 0.17 | 0.14 to 0.21 |
| 25A | 0.43 | 0.37 to 0.50 |
| 25A3 | 0.27 | 0.24 to 0.30 |
| 25G1 | 0.27 | 0.23 to 0.32 |
| 29E | 0.53 | 0.46 to 0.61 |
| 39A | 0.27 | 0.23 to 0.32 |
| 43B1 | 0.47 | 0.40 to 0.55 |
| 43D7 | 0.41 | 0.35 to 0.49 |
| 43Ea | 0.92 | 0.83 to 1.01 |
| 54E | 1.28 | 1.16 to 1.41 |

Example 17: Binding Assay to *E. Coli*-Derived TF

*E. coli*-derived TF was expressed as a fusion between the OmpA signal sequence and TF ECD-His6, and purified by affinity and anion exchange chromatography. The binding of anti-TF antibodies 1F, 25A, 25A3, 25G1, 29E, 39A, 43B1, 43D7, 43Ea, and 54E to Expi293- or *E. coli*-derived TF was determined by protein ELISA studies. Plates coated with Expi293- or *E. coli*-derived TF-His were incubated with increasing concentrations of antibodies. After incubation with an HRP-conjugated secondary antibody (Jackson Immunoresearch), luminescence data were obtained and used to calculate an $EC_{50}$ with 95% confidence intervals using Prism. The $EC_{50}$'s and 95% confidence intervals of the antibodies are listed in Table 43.

TABLE 43

Binding of anti-TF antibodies to Expi293- or *E. coli*-derived TF

| Ab | Expi293-derived TF protein EC50 (nM) | Expi293-derived TF protein 95% CI | *E. coli*-derived TF protein EC50 (nM) | *E.coli*-derived TF protein 95% CI |
|---|---|---|---|---|
| 1F | 0.41 | 0.37 to 0.46 | 0.32 | 0.30 to 0.34 |
| 25A | 0.54 | 0.49 to 0.60 | 0.35 | 0.30 to 0.41 |
| 25A3 | 0.47 | 0.39 to 0.56 | 0.36 | 0.31 to 0.42 |
| 25G1 | 0.42 | 0.36 to 0.47 | 0.31 | 0.29 to 0.33 |
| 29E | 0.98 | 0.78 to 1.24 | 0.68 | 0.39 to 1.26 |
| 39A | 0.45 | 0.39 to 0.53 | 0.34 | 0.28 to 0.40 |
| 43B1 | 0.57 | 0.53 to 0.61 | 0.39 | 0.34 to 0.44 |
| 43D7 | 0.71 | 0.62 to 0.80 | 0.43 | 0.35 to 0.53 |
| 43Ea | 0.74 | 0.68 to 0.81 | 0.46 | 0.40 to 0.53 |
| 54E | 0.96 | 0.73 to 1.29 | 0.38 | 0.22 to 0.62 |

All tested anti-hTF antibodies exhibit high affinity to *E. coli*-derived TF with an $EC_{50}$ ranging from about 0.68 nM to about 0.31 nM, which is comparable to the binding affinity of the antibodies to Expi293-derived TF (about 0.98 nM to 0.41 nM). These results indicate that although the anti-TF antibodies were selected against glycosylated TF from a human cell line, the antibodies can bind to *E. coli*-derived TF with similar affinity when measured by protein ELISA.

Example 18: Thrombin Generation Assay (TGA)

TGA assay was performed using the calibrated-automated-thrombogram (CAT) instrument manufactured and distributed by STAGO (Diagnostica Stago SAS, Asnières sur Seine, France). See Samama et al., *Thromb Res*, 2012, 129:e77-82, which is incorporated by reference in its entirety. The test method design was equivalent to a standard CAT assay measurement, except that the plasma source was normal pooled plasma (NPP) collected in 11 mM citrate supplemented with 100 pg/mL of corn trypsin inhibitor (citrate/CTI). The anti-TF antibodies were titrated at 0, 10, 50 and 100 nM and mixed with NPP in citrate/CTI. Relipidated TF was added to a 96-well assay plate, followed by addition of the antibody/NPP mixture. After a 10-min incubation or directly after combining the relipidated TF with antibody/NPP, thrombin generation was initiated by the addition of calcium and the thrombin substrate. The STAGO software was used to report the following parameters: Peak IIa (highest thrombin concentration generated on the thrombin generation curve [nM]); Lag Time (time from assay start to the moment 10 nM of thrombin is formed [min]); ETP (endogenous thrombin potential, area under the curve [nM x min]); and ttPeak (time from assay start to Peak IIa [min]). Percent peak thrombin generation (% Peak IIa), percent endogenous thrombin potential (% ETP), and percent ttPeak (% ttPeak) in the presence of each antibody relative to a no-antibody plasma control on the same plate were also reported. As used herein, the term "thrombin generation assay" (TGA) refers to the TGA used in this example.

The Peak IIa, Lag Time, ETP, ttPeak, % Peak IIa, % ETP, and % ttPeak in the presence of each antibody selected from 1F, 25A, 25A3, 25G1, 29E, 39A, 43B1, 43D7, 43Ea, 54E, TF-011, 5G9, and 10H10 without antibody incubation prior to addition of calcium and thrombin substrate are shown in Table 44. The Peak IIa, Lag Time, ETP, ttPeak, % Peak IIa, % ETP, and % ttPeak in the presence of each antibody selected from 1F, 25A, 25A3, 25G1, 29E, 39A, 43B1, 43D7, 43Ea, 54E, TF-011, 5G9, and 10H10 with 10 min antibody incubation prior to addition of calcium and thrombin substrate are shown in Table 45. The thrombin generation curve in the presence of 100 nM anti-TF antibody without antibody pre-incubation is plotted in FIGS. 13A and 13B. The Peak thrombin concentration in the presence of titrations of anti-TF antibodies without antibody pre-incubation is plotted in FIG. 13C.

Figure 13A:
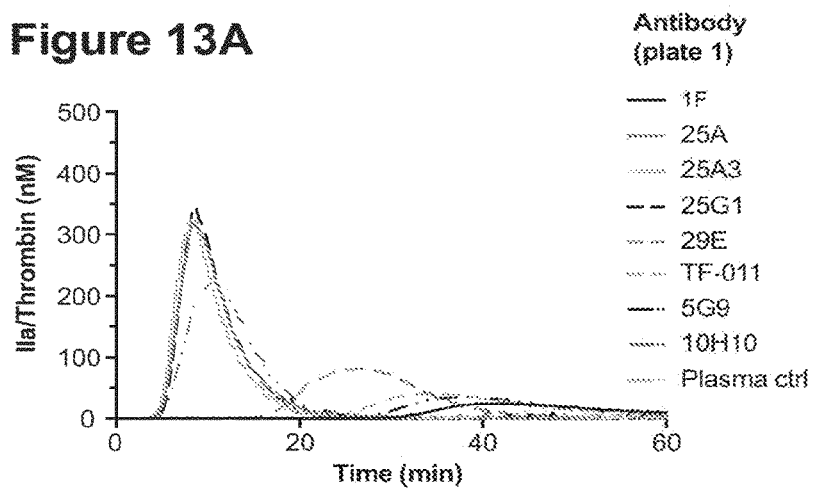
FIGS. 13A, 13B and 13C show thrombin generation in the presence of anti-TF antibody.
Figure 13B:
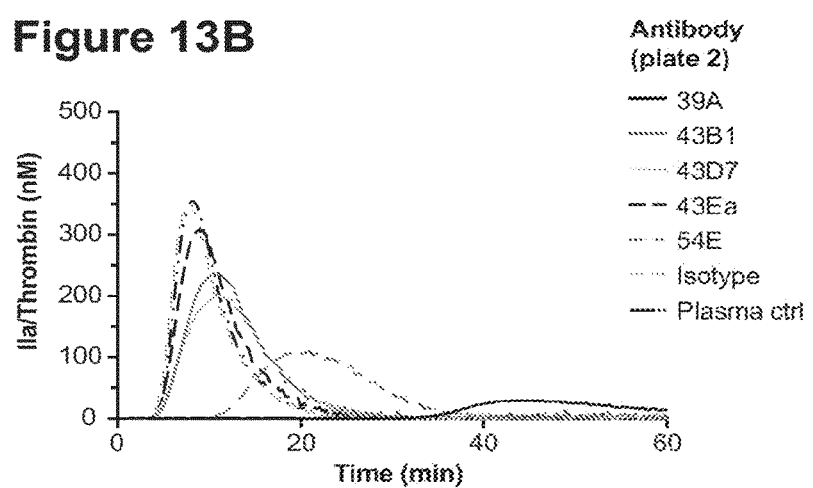
Figure 13C:
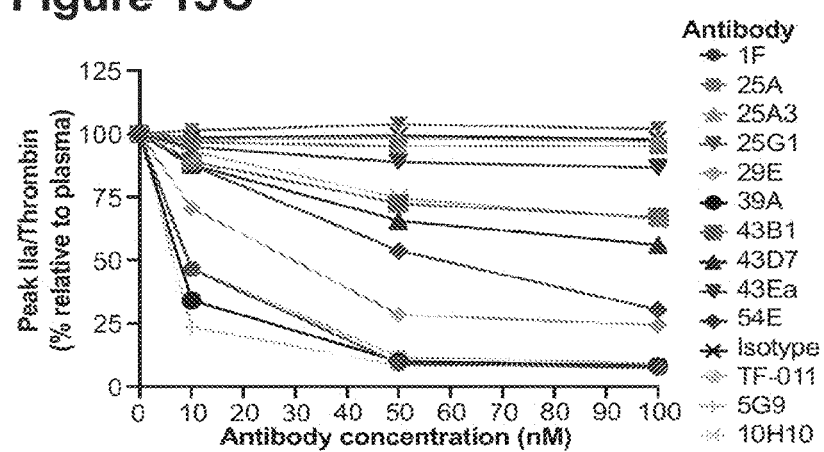

As shown in FIGS. 13A, 13B, and 13C and Table 44, under the conditions without antibody pre-incubation, at the 100 nM antibody concentration, 1F, 29E, 39A, 54E diminished the peak IIa concentration by 92, 76, 91 and 70%, respectively. Similarly, 100 nM of 5G9 and TF-011 inhibited peak IIa concentration by 92% and 91%, respectively. Severely reduced thrombin generation in the presence of the two highest concentrations of 1F, 39A, 5G9 and TF-011 hampered endogenous thrombin generation (ETP) calculations and increased time to Peak IIa/thrombin generation (ttPeak) by at least 284% and 353% at 50 nM and 100 nM respectively. In contrast, antibodies from group 25 did not impact the peak IIa concentration or ttPeak by more than 9%. Group 43 antibodies and 10H10 exhibited mild interference with the peak IIa concentration: 100 nM of 43B1, 43D7, 43Ea and 10H10 reduced the peak IIa concentration by 33, 44, 13 and 34%, respectively. In addition, 100 nM of 43B1, 43D7 and 10H10 showed at least a 29% increase in ttPeak. However, the observed decline in peak IIa concentration and delayed ttPeak for group 43 antibodies and 10H10 did not result in more than a 10% decline in the ETP.

Similar results are shown in Table 45 under the conditions with 10 min antibody pre-incubation. At the 100 nM antibody concentration, 1F, 29E, 39A, 54E diminished the peak IIa concentration by 93, 72, 93 and 87%, respectively. Similarly, 100 nM of 5G9 and TF-011 inhibited peak a concentration by 92% and 91%, respectively. Severely reduced thrombin generation in the presence of the two highest concentrations of 1F, 39A, 54E and TF-011 and all tested concentrations of 5G9 hampered endogenous thrombin generation (ETP) calculations and increased time to Peak IIa/thrombin generation (ttPeak) by at least 303% and 371% at 50 nM and 100 nM respectively. In contrast, antibodies from group 25 did not decrease the peak IIa concentration or increase ttPeak. Group 43 antibodies and 10H10 exhibited mild interference with the peak IIa concentration: 100 nM of 431B1, 43D7, 43Ea and 10H10 reduced the peak IIa concentration by 41, 56, 13 and 48% respectively. In addition, 100 nM of 43B1, 43D7 and 10H10 showed at least a 33% increase in ttPeak. However, the observed decline in peak IIa concentration and delayed ttPeak for group 43 antibodies and 10H10 did not result in more than an 11% decline in the ETP.

Overall, these results indicate that group 25 antibodies are completely inert in the penultimate step of the coagulation cascade when all three TGA parameters (ETP, Peak IIa concentration and ttPeak) are taken into consideration.

TABLE 44

Thrombin Generation Assay without Antibody Pre-Incubation

| Plate | Sample | Ab conc. (nM) | Peak IIa [nM] (SD) | Lag Time [min] (SD) | ETP [nM · min] (SD) | ttPeak [min] (SD) | % Peak IIa | % ETP | % ttPeak |
|---|---|---|---|---|---|---|---|---|---|
| 1 | 1F | 100 | 25 (1) | 31 (1) | * | 41 (0.7) | 8 | * | 419 |
|   |   | 50 | 31 (0) | 25.6 (0.3) | * | 35.3 (0.3) | 9 | * | 347 |
|   |   | 10 | 155 (1) | 8.2 (0.2) | 1738 (25) | 14.9 (0.2) | 47 | 86 | 89 |
| 1 | 25A | 100 | 317 (6) | 5.2 (0.2) | 2134 (28) | 8.6 (0.2) | 95 | 105 | 9 |
|   |   | 50 | 317 (2) | 5.2 (0.2) | 2122 (30) | 8.6 (0.2) | 95 | 105 | 9 |
|   |   | 10 | 322 (2) | 5 (0) | 2108 (29) | 8.2 (0.2) | 97 | 104 | 4 |

TABLE 44-continued

Thrombin Generation Assay without Antibody Pre-Incubation

| Plate | Sample | Ab conc. (nM) | Peak IIa [nM] (SD) | Lag Time [min] (SD) | ETP [nM · min] (SD) | ttPeak [min] (SD) | % Peak IIa | % ETP | % ttPeak |
|---|---|---|---|---|---|---|---|---|---|
| 1 | 25A3 | 100 | 323 (1) | 4.6 (0.2) | 2031 (19) | 7.9 (0.2) | 97 | 100 | 0 |
|  |  | 50 | 328 (2) | 4.7 (0) | 2080 (23) | 8 (0) | 98 | 103 | 1 |
|  |  | 10 | 326 (4) | 5.3 (0) | 2152 (14) | 8.4 (0.2) | 98 | 106 | 6 |
| 1 | 25G1 | 100 | 340 (3) | 5.3 (0) | 2160 (27) | 8.3 (0) | 102 | 107 | 5 |
|  |  | 50 | 346 (6) | 5.1 (0.2) | 2221 (40) | 8.2 (0.2) | 104 | 110 | 4 |
|  |  | 10 | 337 (1) | 4.7 (0) | 2061 (34) | 7.8 (0.2) | 101 | 102 | −1 |
| 1 | 29E | 100 | 81 (0) | 17.1 (0.2) | 1257 (18) | 26.2 (0.2) | 24 | 62 | 232 |
|  |  | 50 | 95 (1) | 14.1 (0.2) | 1365 (26) | 22.6 (0.4) | 29 | 67 | 186 |
|  |  | 10 | 235 (3) | 7 (0) | 1926 (9) | 11.7 (0) | 71 | 95 | 48 |
| 1 | Isotype | 100 | 326 (3) | 5.3 (0) | 2132 (13) | 8.6 (0.2) | 98 | 105 | 9 |
|  |  | 50 | 331 (3) | 5.3 (0) | 2177 (19) | 8.3 (0) | 99 | 108 | 5 |
|  |  | 10 | 328 (4) | 5.3 (0) | 2129 (26) | 8.4 (0.2) | 98 | 105 | 6 |
| 1 | TF-011 | 100 | 30 (1) | 26 (0.3) | * | 35.8 (0.2) | 9 | * | 353 |
|  |  | 50 | 39 (3) | 21.3 (0.5) | * | 30.3 (1.1) | 12 | * | 284 |
|  |  | 10 | 156 (7) | 8 (0) | 1714 (41) | 14.7 (0.5) | 47 | 85 | 86 |
| 1 | 5G9 | 100 | 27 (1) | 29.9 (0.4) | * | 39.6 (0.4) | 8 | * | 401 |
|  |  | 50 | 28 (0) | 25.1 (0.4) | * | 34.6 (0.2) | 8 | * | 338 |
|  |  | 10 | 79 (1) | 10.4 (0.2) | 1176 (16) | 18.6 (0.2) | 24 | 58 | 135 |
| 1 | 10H10 | 100 | 221 (4) | 5.2 (0.2) | 1945 (37) | 10.2 (0.2) | 66 | 96 | 29 |
|  |  | 50 | 248 (3) | 5.2 (0.2) | 1978 (32) | 9.8 (0.3) | 74 | 98 | 24 |
|  |  | 10 | 310 (2) | 5.2 (0.2) | 2036 (33) | 8.6 (0.2) | 93 | 101 | 9 |
| 1 | Plasma ctrl. | NA | 333 (0) | 4.7 (0) | 2023 (30) | 7.9 (0.2) | 100 | 100 | 0 |
| 2 | 39A | 100 | 29 (0) | 34.7 (0) | * | 44.6 (0.2) | 9 | * | 465 |
|  |  | 50 | 36 (1) | 29.8 (0.7) | * | 39.3 (0.7) | 11 | * | 397 |
|  |  | 10 | 122 (3) | 10.8 (0.3) | 1694 (57) | 18.6 (0.2) | 37 | 84 | 135 |
| 2 | 43B1 | 100 | 238 (4) | 5.3 (0) | 2300 (32) | 10.8 (0.2) | 67 | 99 | 37 |
|  |  | 50 | 258 (5) | 5.2 (0) | 2301 (29) | 10.2 (0.2) | 72 | 99 | 29 |
|  |  | 10 | 317 (1) | 5 (0) | 2341 (34) | 8.6 (0.2) | 89 | 101 | 9 |
| 2 | 43D7 | 100 | 199 (6) | 5.1 (0.2) | 2124 (27) | 11.2 (0.2) | 56 | 91 | 42 |
|  |  | 50 | 234 (1) | 5 (0) | 2190 (15) | 10.3 (0) | 66 | 94 | 30 |
|  |  | 10 | 312 (3) | 5 (0) | 2343 (49) | 8.9 (0.2) | 88 | 101 | 13 |
| 2 | 43Ea | 100 | 308 (2) | 5 (0) | 2349 (9) | 9 (0) | 87 | 101 | 14 |
|  |  | 50 | 316 (3) | 5 (0) | 2430 (69) | 8.7 (0) | 89 | 105 | 10 |
|  |  | 10 | 337 (4) | 5 (0) | 2416 (82) | 8.3 (0) | 95 | 104 | 5 |
| 2 | 54E | 100 | 108 (3) | 12.2 (0.2) | 1589 (13) | 20.2 (0.2) | 30 | 68 | 156 |
|  |  | 50 | 191 (2) | 8 (0) | 2109 (51) | 14.3 (0) | 54 | 91 | 81 |
|  |  | 10 | 311 (5) | 5 (0) | 2275 (41) | 8.8 (0.2) | 87 | 98 | 11 |
| 2 | Isotype | 100 | 351 (2) | 4.7 (0) | 2304 (14) | 7.9 (0.2) | 99 | 99 | 0 |
|  |  | 50 | 353 (1) | 5 (0) | 2391 (29) | 8.2 (0.2) | 99 | 103 | 4 |
|  |  | 10 | 348 (1) | 5 (0) | 2367 (9) | 8.3 (0) | 98 | 102 | 5 |
| 2 | Plasma ctrl. | NA | 356 (1) | 4.9 (0.2) | 2323 (76) | 8.11 (0.3) | 100 | 100 | 3 |

* Groups with "No Tail Found" Errors when the software cannot calculate the ETP.

TABLE 45

Thrombin Generation Assay with 10 min Antibody Pre-Incubation

| Plate | Sample | Ab conc. (nM) | Peak IIa [nM] (SD) | Lag Time [min] (SD) | ETP [nM · min] (SD) | ttPeak [min] (SD) | % Peak IIa | % ETP | % ttPeak |
|---|---|---|---|---|---|---|---|---|---|
| 1 | 1F | 100 | 20 (1) | 29.5 (0.2) | * | 40.8 (0.6) | 7 | * | 483 |
|  |  | 50 | 23 (0) | 26.5 (0.7) | * | 37.3 (0.4) | 8 | * | 433 |
|  |  | 10 | 44 (2) | 13.8 (0.5) | 742 (23) | 22.4 (0.4) | 16 | 41 | 220 |
| 1 | 25A | 100 | 291 (3) | 3.3 (0.1) | 1964 (36) | 6.7 (0.1) | 106 | 108 | −4 |
|  |  | 50 | 290 (0) | 3.3 (0.1) | 1972 (22) | 6.8 (0) | 106 | 108 | −3 |
|  |  | 10 | 284 (1) | 3.3 (0.1) | 1899 (21) | 6.8 (0) | 104 | 104 | −3 |
| 1 | 25A3 | 100 | 290 (3) | 3.1 (0) | 1893 (28) | 6.4 (0) | 106 | 104 | −9 |
|  |  | 50 | 284 (4) | 3.1 (0) | 1875 (16) | 6.4 (0) | 104 | 103 | −9 |
|  |  | 10 | 288 (3) | 3.1 (0) | 1901 (26) | 6.4 (0) | 105 | 105 | −9 |
| 1 | 25G1 | 100 | 311 (3) | 3.1 (0) | 1954 (20) | 6.3 (0.1) | 114 | 107 | −10 |
|  |  | 50 | 311 (1) | 3.1 (0) | 1951 (22) | 6.1 (0) | 114 | 107 | −13 |
|  |  | 10 | 302 (3) | 3.1 (0) | 1877 (33) | 6.1 (0) | 110 | 103 | −13 |
| 1 | 29E | 100 | 76 (1) | 14.7 (0.1) | 1201 (24) | 24.3 (0.3) | 28 | 66 | 247 |
|  |  | 50 | 83 (1) | 14.1 (0) | 1300 (17) | 23.6 (0.1) | 30 | 72 | 237 |
|  |  | 10 | 98 (1) | 9.4 (0) | 1408 (11) | 18.1 (0) | 36 | 77 | 159 |

TABLE 45-continued

Thrombin Generation Assay with 10 min Antibody Pre-Incubation

| Plate | Sample | Ab conc. (nM) | Peak IIa [nM] (SD) | Lag Time [min] (SD) | ETP [nM · min] (SD) | ttPeak [min] (SD) | % Peak IIa | % ETP | % ttPeak |
|---|---|---|---|---|---|---|---|---|---|
| 1 | Isotype | 100 | 288 (2) | 3.4 (0) | 1922 (28) | 6.8 (0) | 105 | 106 | −3 |
|   |         | 50  | 292 (2) | 3.4 (0) | 1921 (25) | 6.8 (0) | 107 | 106 | −3 |
|   |         | 10  | 290 (3) | 3.4 (0) | 1926 (38) | 6.8 (0) | 106 | 106 | −3 |
| 1 | TF-011  | 100 | 26 (0)  | 23.8 (1.1) | * | 34.2 (0.9) | 9 | * | 389 |
|   |         | 50  | 27 (1)  | 22.4 (0.1) | * | 33 (0.1)   | 10 | * | 371 |
|   |         | 10  | 46 (3)  | 13.5 (0.5) | 792 (55) | 22.5 (0.2) | 17 | 44 | 221 |
| 1 | 5G9     | 100 | 22 (0)  | 26.7 (0.3) | * | 37.5 (0.5) | 8 | * | 436 |
|   |         | 50  | 23 (3)  | 23.6 (2.2) | * | 34 (2.4)   | 8 | * | 386 |
|   |         | 10  | 30 (1)  | 19.3 (0.4) | * | 29 (0.8)   | 11 | * | 314 |
| 1 | 10H10   | 100 | 169 (3) | 3.4 (0) | 1795 (36) | 9.3 (0.1) | 62 | 99 | 33 |
|   |         | 50  | 175 (4) | 3.4 (0) | 1754 (20) | 9.2 (0.1) | 64 | 96 | 31 |
|   |         | 10  | 235 (8) | 3.4 (0) | 1807 (42) | 7.8 (0)   | 86 | 99 | 11 |
| 1 | Plasma ctrl. | NA | 274 (1) | 3.4 (0) | 1818 (24) | 7 (0.1) | 100 | 100 | 0 |
| 2 | 39A     | 100 | 19 (1)  | 33.6 (0.7) | * | 44.6 (0.9) | 7 | * | 537 |
|   |         | 50  | 22 (0)  | 30.7 (0.1) | * | 41.4 (0.1) | 8 | * | 491 |
|   |         | 10  | 36 (1)  | 19.6 (0.7) | * | 29.3 (0.8) | 13 | 0 | 319 |
| 2 | 43B1    | 100 | 167 (0) | 4 (0)   | 1806 (15) | 9.8 (0.1) | 59 | 98 | 40 |
|   |         | 50  | 174 (1) | 3.8 (0.1) | 1831 (22) | 9.6 (0) | 62 | 99 | 37 |
|   |         | 10  | 222 (5) | 3.7 (0.1) | 1841 (37) | 8.3 (0) | 79 | 100 | 19 |
| 2 | 43D7    | 100 | 123 (2) | 4 (0)   | 1673 (27) | 11.5 (0.1) | 44 | 91 | 64 |
|   |         | 50  | 122 (1) | 3.7 (0.1) | 1639 (29) | 11.3 (0) | 43 | 89 | 61 |
|   |         | 10  | 194 (5) | 4 (0)   | 1796 (35) | 8.8 (0.1) | 69 | 97 | 26 |
| 2 | 43Ea    | 100 | 244 (2) | 3.5 (0.1) | 1857 (42) | 7.5 (0.1) | 87 | 101 | 7 |
|   |         | 50  | 245 (0) | 3.6 (0) | 1851 (29) | 7.6 (0) | 87 | 100 | 9 |
|   |         | 10  | 262 (1) | 3.6 (0) | 1877 (15) | 7.3 (0) | 93 | 102 | 4 |
| 2 | 54E     | 100 | 37 (1)  | 22.3 (0.2) | * | 33 (0.5) | 13 | * | 371 |
|   |         | 50  | 44 (1)  | 18.3 (0.4) | * | 28.2 (1) | 16 | * | 303 |
|   |         | 10  | 121 (4) | 6.5 (0.1) | 1523 (20) | 13.7 (0.3) | 43 | 83 | 96 |
| 2 | Isotype | 100 | 275 (2) | 3.6 (0) | 1862 (23) | 7.3 (0) | 98 | 101 | 4 |
|   |         | 50  | 284 (0) | 3.6 (0) | 1899 (15) | 7.2 (0.1) | 101 | 103 | 3 |
|   |         | 10  | 281 (3) | 3.6 (0) | 1877 (13) | 7.3 (0) | 100 | 102 | 4 |
| 2 | Plasma ctrl. | NA | 282 (2) | 3.8 (0.1) | 1845 (22) | 7.3 (0) | 100 | 100 | 4 |

* Groups with "No Tail Found" Errors when the software cannot calculate the ETP.

Example 19: FXa Conversion Assay and FVIIa Competition Assay with Previously Described Anti-TF Antibodies The previously described TF-specific antibodies TF-011, 5G9 and 10H10 (Breij et al., Cancer Res, 2014, 74:1214-1226; Versteeg et al., Blood, 2008, 111:190-199; each of which is incorporated by reference in its entirety) were tested in FXa conversion assay and FVIIa competition assay.

To evaluate the ability of TF:FVIIa to convert FX into FXa in the presence of human antibodies against TF, a cell-based FX conversion assay was conducted as described in Larsen et al., J Biol Chem, 2010, 285:19959-19966, which is incorporated by reference in its entirety. Briefly, $5 \times 10^4$ MDA-MB-231 cells (ATCC, Manassas, VA, USA) were plated into tissue culture-treated black 96-well plates (Greiner Bio-One, Monroe, NC, USA) and cultured overnight. After removal of the cell culture media and addition of a final concentration of 200 nM of FX in a HEPES buffer with 1.5 mM $CaCl_2$), cells were incubated with a titration of the antibodies for 15 min at 37° C. Upon reconstitution of the binary TF:FVIIa complex with a final concentration of 20 nM of FVIIa, cells were incubated for 5 min at 37° C. After quenching the reaction with ethylenediaminetetraacetic acid (EDTA) in a black 94-well plate, generated FXa was measured with 50 pM of SN-7 6-amino-1-naphthalenesulfonamide-based fluorogenic substrate (Haematologic Technologies, Essex Junction, VT, USA) on an Envision plate reader equipped with an Umbelliferone 355 excitation filter, an Umbelliferone 460 emission filter, and a LANCE/DELFIA top mirror (Perkin Elmer, Waltham, MA, USA). FXa conversion percentages (% FXa) in the presence of an anti-TF antibody titration relative to a no antibody control are plotted in FIG. 14A.

To evaluate competition between FVIIa and the human antibodies against TF, TF-positive MDA-MB-231 cells (ATCC, Manassas, VA, USA) were first incubated for 1 hr on ice with a titration of the human antibodies against TF or an isotype control. Subsequently, FVII-Fc conjugated to Alexa488 was added to the antibody-cell mixture at a final concentration of 20 nM. After another 1 hr incubation on ice, cells were washed, stained with a viability dye, and analyzed by flow cytometry. The Alexa488 fluorescence data from viable cells was summarized using median fluorescence intensity (MFI). FVII-Fc binding was summarized with % FVII-Fc binding=[$MFI_{antibody\ labeled\ cells}$−$MFI_{unstained}$ cells]/ [$MFI_{IgG1\ control\ labeled\ cells}$−$MFI_{unstained}$ cells]. Percentage of FVIIa binding (% FVIIa) in the presence of an anti-TF antibody titration relative to an isotype control is plotted in FIG. 14B.

Figure 14A:
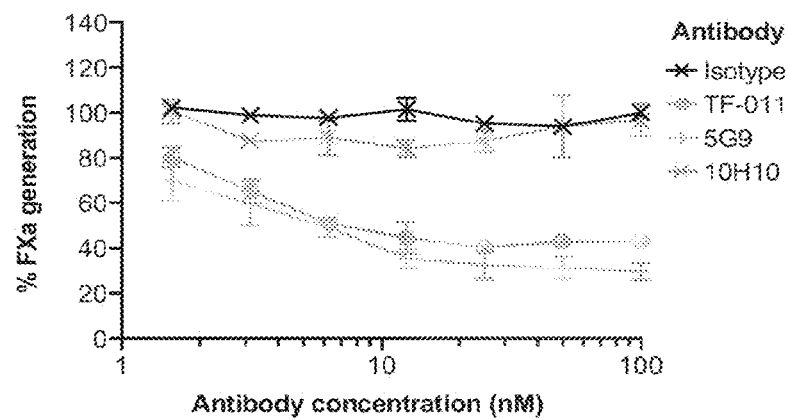
FIGS. 14A and 14B show TF:FVIIa-dependent FXa Conversion and FVII binding in the presence of anti-TF antibodies TF-011, 5G9, and 10H10.

As presented in FIG. 14A, TF-011 and 5G9 inhibited FX conversion by 57-59% and 67-70% at concentrations of 25, 50, and 100 nM. 10H10 did not significantly inhibit FX conversion at these three concentrations.

Figure 14B:
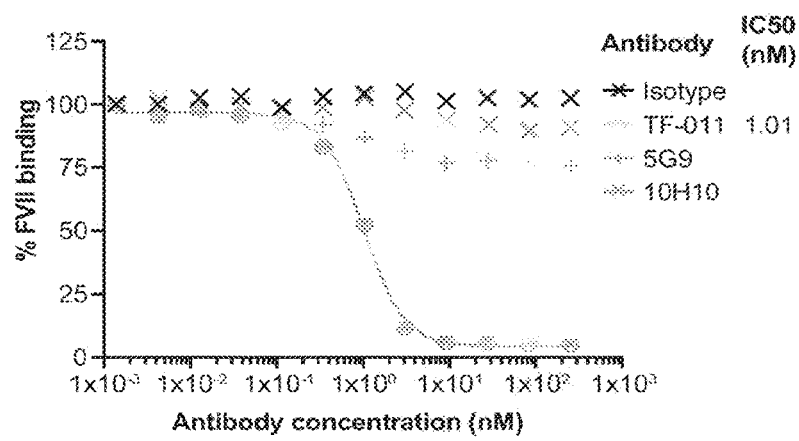
Figure 15A:
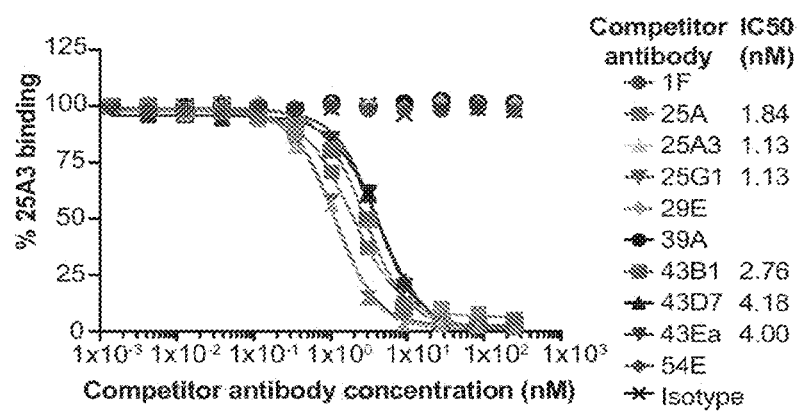
FIGS. 15A and 15B show percent binding (% Binding) of A488-conjugated 25A3 anti-TF antibody to MDA-MB-231 cells after pre-incubation of the cells with titrations of unlabeled competitor antibodies.
Figure 15B:
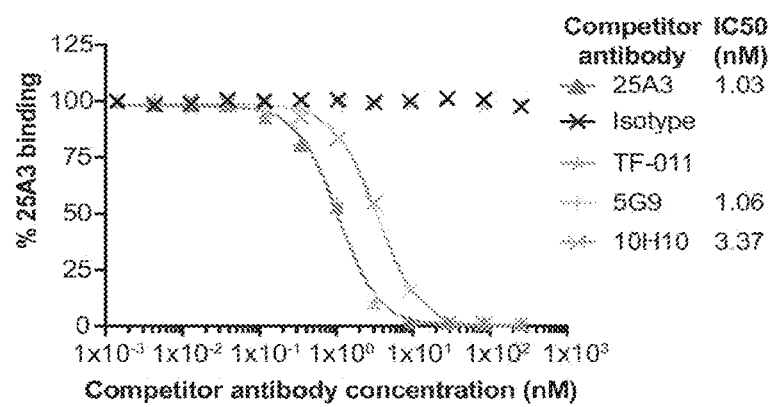
Figure 16A:
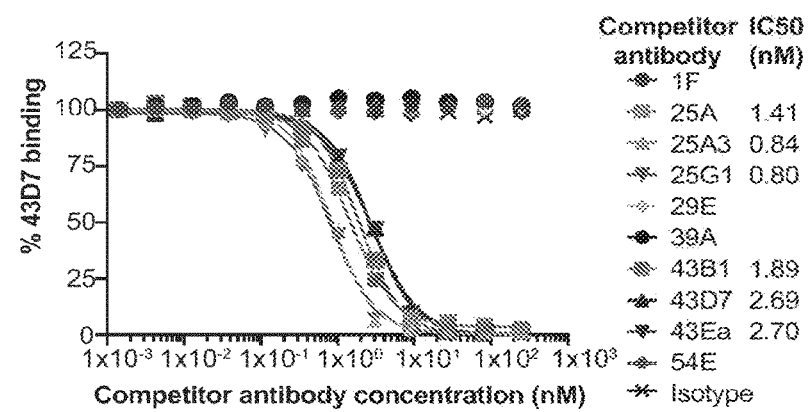
FIGS. 16A and 16B show percent binding (% Binding) of A488-conjugated 43D7 anti-TF antibody to MDA-MB-231 cells after pre-incubation of the cells with titrations of unlabeled competitor antibodies.
Figure 16B:
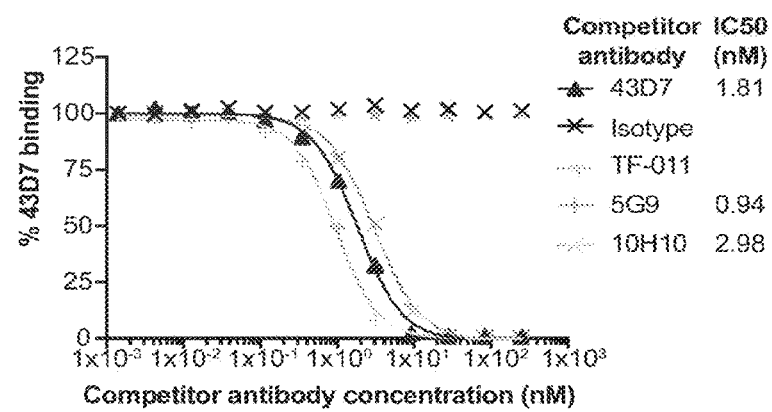
Figure 17A:
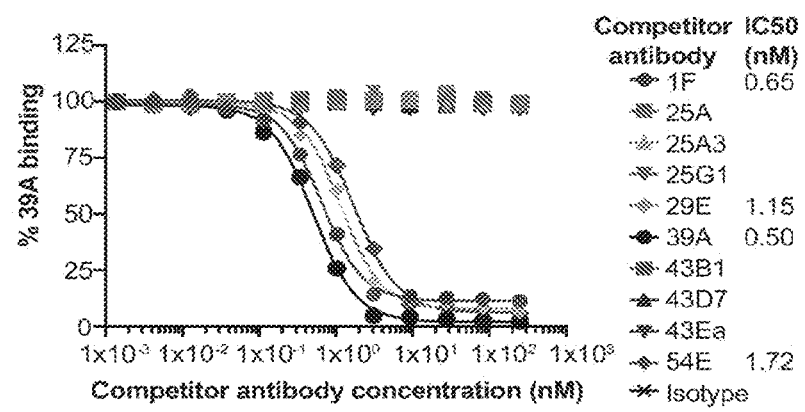
FIGS. 17A and 17B show percent binding (% Binding) of A488-conjugated 39A anti-TF antibody to MDA-MB-231 cells after pre-incubation of the cells with titrations of unlabeled competitor antibodies.
Figure 17B:
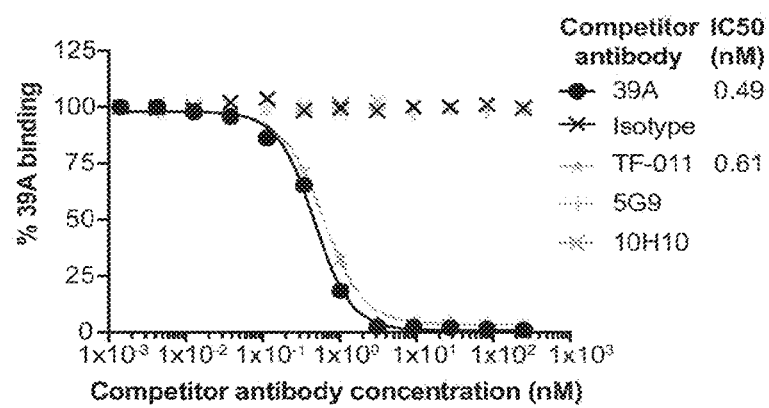

As presented in FIG. 14B, TF-011 effectively competed with FVII, whereas 5G9 and 10H10 showed less than 25% and 10% competition at the highest concentration of antibody, respectively.

These results indicate that 5G9 predominantly competes with substrate FX binding, resulting in the observed inhibition of FX conversion and thrombin generation. TF-011 inhibits thrombin generation by competing with FVIIa for binding to TF. However, 10H10 inhibits TF-FVIIa mediated signaling without substantially affecting binding of FVIIa to TF. These findings are consistent with previous observations described in Huang et al., *J Mol Biol,* 1998, 275:873-894; Ruf et al., *Biochem J,* 1991, 278:729-733; and Teplyakov et al., *Cell Signal,* 2017, 36:139-144; each of which is incorporated by reference in its entirety.

Example 20: Antibody Competition Assay

Alexa Fluor antibodies were generated using Alexa Fluor 488 5-sulfo-dichlorophenol esters (ThermoFisher Scientific) following manufacturer's protocol. Excess Alexa Fluor dye was removed from the antibody dye conjugate preparations by gel filtration (ThermoFisher Scientific).

To evaluate competition between a first human antibody against TF and 25A3, TF-positive MDA-MB-231 cells (ATCC, Manassas, VA, USA) were first incubated for 1 hr on ice with a titration of the first human antibody against TF. Subsequently, a final concentration of 20 nM of 25A3 conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 25A3 binding was summarized with % 25A3 binding= [$MFI_{antibody\ labeled\ cells}$−$MFI_{unstained}$ cells]/[$MFI_{IgG1\ control\ labeled\ cells}$−$MFI_{unstained}$ cells].

To evaluate competition between a first human antibody against TF and 43D7, TF-positive MDA-MB-231 cells (ATCC, Manassas, VA, USA) were first incubated for 1 hr on ice with a titration of the first human antibody against TF. Subsequently, a final concentration of 20 nM of 43D7 conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 43D7 binding was summarized with % 43D7 binding= [$MFI_{antibody\ labeled\ cells}$−$MFI_{unstained}$ cells]/[$MFI_{IgG1\ control\ labeled\ cells}$−$MFI_{unstained}$ cells].

To evaluate competition between a first human antibody against TF and 39A, TF-positive MDA-MB-231 cells (ATCC, Manassas, VA, USA) were first incubated for 1 hr on ice with a titration of the first human antibody against TF. Subsequently, a final concentration of 20 nM of 39A conjugated to Alexa488 was added to the antibody cell mixture. After another 1 hr incubation on ice, cells were washed, stained with a viability dye, and analyzed by flow cytometry. The Alexa488 fluorescence data from viable cells was summarized using median fluorescence intensity. 39A binding was summarized with % 39A binding= [$MFI_{antibody\ labeled\ cells}$−$MFI_{unstained}$ cells]/[$MFI_{IgG1\ control\ labeled\ cells}$−$MFI_{unstained}$ cells].

% 25A3 binding, % 43D7 binding, and % 39A binding are shown in FIGS. 15A and 15B, FIGS. 16A and 16B, and FIGS. 17A and 17B, respectively. Antibodies from groups 25 and 43, 5G9, and 10H10 reduced % 25A3 binding and % 43D7 binding and did not reduce % 39A binding. Antibodies from groups 1, 29, 39, and 54, and TF-011 reduced % 39A binding and did not reduce % 25A3 binding and % 43D7 binding.

While the antibody competition assay results indicate that groups 25 and 43 antibodies, 5G9, and 10H10 may bind to the same or an overlapping epitope of human TF or may affect the TF binding of each other through an allosteric mechanism, the chimeric TF construct mapping experiments as described elsewhere in this disclosure demonstrate that group 25 antibodies, group 43 antibodies, 5G9 and 10H10 bind distinct epitopes. In addition, while the antibody competition assay results indicate that antibodies of groups 1, 29, 39, and 54, and TF-011 may bind to the same or an overlapping epitope of human TF or may affect the TF binding of each other through an allosteric mechanism, the chimeric TF construct mapping experiments as described elsewhere in this disclosure demonstrate that the antibodies of groups 29, 39 and 54 bind epitopes distinct from TF-011's epitope.

Example 21: Anti-TF Antibody Internalization

Figure 18A:
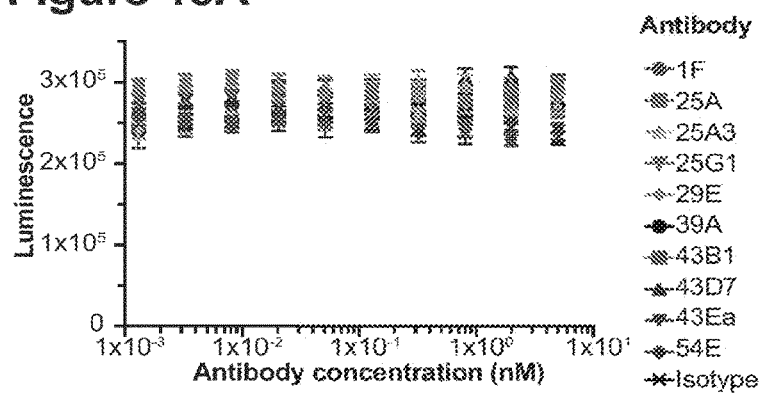
FIGS. 18A, 18B, and 18C show the internalization of anti-TF antibodies as measured by cell viability assay and internalization assay.
Figure 18B:
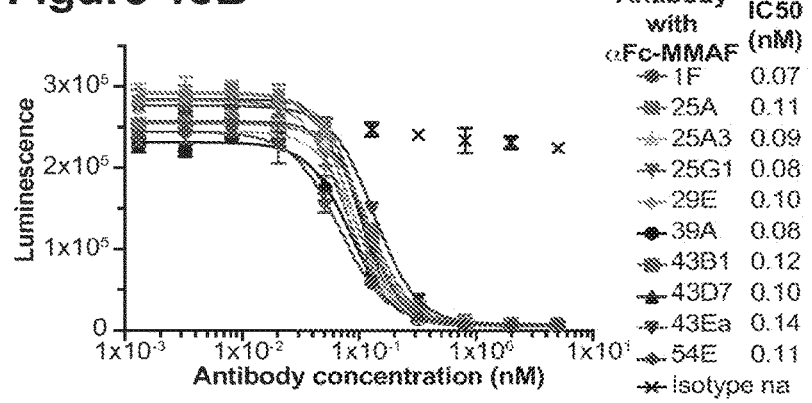

To evaluate internalization of the anti-TF antibodies, a cytotoxicity assay was conducted as described in Liao-Chan et al., *PLoS One,* 2015, 10:e0124708, which is incorporated by reference in its entirety. Briefly, cells were plated in 384-well plates (Greiner Bio-One, Monroe, NC, USA) at $4 \times 10^3$ cells per well in 40 µl of media. Antibodies and an anti-human Fc Fab conjugated to the tubulin inhibitor monomethyl auristatin F (MMAF) (Moradec, San Diego, CA, USA) were serially diluted starting at 5 and 30 nM, respectively. The anti-human Fc Fab conjugated to MMAF consisted of a polyclonal antibody specific to the Fc region of human IgGs with a DAR of 1.2 to 1.5. Plates were incubated for 3 days, followed by lysis in CellTiter-Glo (CTG) assay reagent (Promega, Madison, WI, USA). CTG luminescence was measured on an Envision plate reader and the mean and standard deviation of 4 replicates graphed in Prism (GraphPad, La Jolla, CA, USA). For each anti-TF antibody, the $IC_{50}$ and its associated 95% confidence interval were calculated in Prism using a 4-parameter binding model. The cell viability results after incubation with anti-TF antibodies and anti-TF antibody Fab:MMAF complexes are shown in FIGS. 18A and 18B. The 95% confidence intervals for the $IC_{50}$ values are shown in Table 46.

Figure 18C:
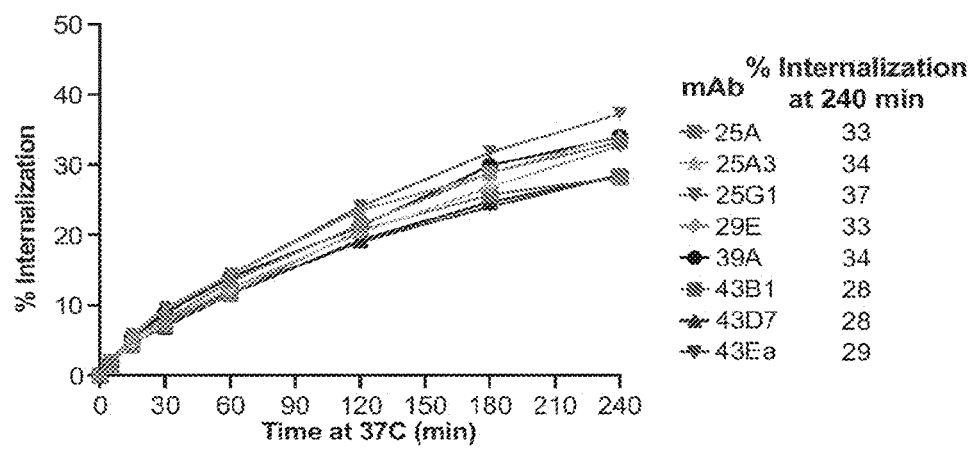

Internalization of the anti-TF antibodies was also evaluated by a quantitative assay based on internalized fluorescence and quenched surface-fluorescence. Cell surface fluorescence quenching was assessed as described in Liao-Chan et al., *PLoS One,* 2015, 10:e0124708. Briefly, $1.2 \times 10^5$ MDA-MB-231 cells were pre-incubated with 100 nM of A488-conjugated antibodies in media for 2 hr on ice. After 2 washes, cells were resuspended in cold media and pulsed for up to 4 hr at 37° C. Cells were rapidly chilled and incubated with or without 300 nM of anti-A488 antibody (clone 19A) for 30 min on ice. After 2 washes, dead cells were labeled with DAPI and samples were analyzed on a Novocyte flow cytometer (ACEA Biosciences). The median fluorescence intensities (MFIs) at each anti-A488 mAb concentration were normalized against the isotype control to obtain a normalized MFI percentage. Internalized fluorescence was calculated from quenched and non-quenched sample data by correcting for incomplete surface quenching: $1-(N_1-Q_1)/(N_1-(N_1Q_0/N_0))$ with $N_1$=unquenched MFI at each time point ($t_1$); $Q_1$=Quenched MFI at $t_1$; $Q_0$=Quenched MFI for the sample kept on ice ($t_0$); $N_0$=Unquenched MFI at $t_0$. Percent internalization of anti-TF antibodies conjugated to A488 is shown in FIG. 18C.

Because Fab:MMAF binds the Fc region of the TF-specific antibodies, cellular uptake of these complexes can trigger cell death. While the TF-specific antibodies alone had no impact on cell viability in three-day cultures of TF-positive A431 cells (FIG. 18A), the TF-specific antibodies in complex with Fab:MMAF showed dose-dependent cell killing with $IC_{50}$ values ranging between 0.07 and 0.14 nM (FIG. 18B).

Cellular uptake was corroborated with fluorescently labeled TF-specific antibodies. In a quantitative assay based on internalized fluorescence and quenched surface-fluorescence, the TF-specific antibodies showed between 28 and 37% internalization after a 4 h incubation (FIG. 18C).

These results indicate that the tested anti-TF antibodies can medicate internalization and toxin delivery into TF-positive cells.

TABLE 46

ADC Data With Ranking (Continuous Incubation)

| Antibody | Cell line: A431 ADC format: Secondary ADC Treatment: Continuous Figure: Figure 18B | | | Cell line: A431 ADC format: Primary ADC Treatment: Continuous Figure: Figure 20A | | | Cell line: MDA-MB-231 ADC format: Primary ADC Treatment: Continuous Figure: Figure 22D | | | Cell line: HPAF-II ADC format: Primary ADC Treatment: Continuous Figure: Figure 22E | | | Continuous Primary ADC RANK |
|---|---|---|---|---|---|---|---|---|---|---|---|---|---|
| | $IC_{50}$ (nM) | 95% CI | rank | $IC_{50}$ (nM) | 95% CI | rank | $IC_{50}$ (nM) | 95% CI | rank | $IC_{50}$ (nM) | 95% CI | rank | |
| 1F | 0.07 | 0.06 to 0.07 | Not tested | | Not tested | | | Not tested | | | Not tested | | Not included |
| 25A | 0.11 | 0.10 to 0.11 | 6 | 0.09 | 0.08 to 0.09 | 7 | 0.14 | 0.12 to 0.16 | 7 | 0.06 | 0.05 to 0.07 | 8 | 7 |
| 25A3 | 0.09 | 0.08 to 0.09 | 3 | 0.07 | 0.07 to 0.08 | 5 | 0.11 | 0.10 to 0.12 | 4 | 0.05 | 0.04 to 0.05 | 5 | 4 |
| 25G1 | 0.08 | 0.07 to 0.08 | 1 | 0.06 | 0.06 to 0.06 | 3 | 0.09 | 0.08 to 0.10 | 3 | 0.04 | 0.04 to 0.05 | 3 | 3 |
| 29E | 0.10 | 0.09 to 0.10 | 4 | 0.06 | 0.05 to 0.06 | 2 | 0.07 | 0.07 to 0.08 | 2 | 0.04 | 0.04 to 0.05 | 2 | 2 |
| 39A | 0.08 | 0.08 to 0.09 | 2 | 0.05 | 0.05 to 0.05 | 1 | 0.05 | 0.05 to 0.05 | 1 | 0.04 | 0.03 to 0.05 | 1 | 1 |
| 43B1 | 0.12 | 0.11 to 0.13 | 7 | 0.08 | 0.08 to 0.08 | 6 | 0.14 | 0.13 to 0.15 | 5 | 0.05 | 0.04 to 0.06 | 4 | 5 |
| 43D7 | 0.10 | 0.10 to 0.10 | 5 | 0.06 | 0.06 to 0.07 | 4 | 0.14 | 0.12 to 0.16 | 6 | 0.05 | 0.05 to 0.06 | 6 | 6 |
| 43Ea | 0.13 | 0.13 to 0.14 | 8 | 0.09 | 0.09 to 0.10 | 8 | 0.15 | 0.13 to 0.17 | 8 | 0.06 | 0.05 to 0.06 | 7 | 8 |
| 54E | 0.11 | 0.11 to 0.12 | Not tested | 0.07 | 0.07 to 0.07 | Not tested | | Not tested | | | Not tested | | Not included |
| Isotype | Not applicable | | | Not applicable | | | Not applicable | | | Not applicable | | | Not included |
| TF-011 | Not tested | | | 0.05 | 0.05 to 0.05 | | | Not tested | | | Not tested | | Not included |

TABLE 47

ADC Data With Ranking (4 h Incubation)

| Antibody | Cell line: A431 ADC format: Primary ADC Treatment: 4 hr, followed by washout Figure: Figure 20B Measurement: | | | Cell line: A431 ADC format: Primary ADC Treatment: 4 hr, followed by washout Figure: Figure 21A Measurement: | | | 4 hr Primary ADC RANK |
|---|---|---|---|---|---|---|---|
| | $IC_{50}$ (nM) | 95% CI | rank | $IC_{50}$ (nM) | 95% CI | rank | |
| 1F | Not tested | | | Not tested | | | Not included |
| 25A | 0.35 | 0.32 to 0.39 | 6 | 0.18 | 0.17 to 0.19 | 6 | 6 |
| 25A3 | 0.19 | 0.17 to 0.21 | 3 | 0.12 | 0.11 to 0.12 | 3 | 3 |
| 25G1 | 0.19 | 0.17 to 0.20 | 2 | 0.10 | 0.09 to 0.10 | 2 | 2 |
| 29E | 0.20 | 0.18 to 0.21 | 4 | 0.13 | 0.12 to 0.14 | 4 | 4 |
| 39A | 0.12 | 0.11 to 0.13 | 1 | 0.09 | 0.09 to 0.10 | 1 | 1 |
| 43B1 | 0.36 | 0.32 to 0.41 | 7 | 0.19 | 0.17 to 0.20 | 7 | 7 |
| 43D7 | 0.28 | 0.25 to 0.30 | 5 | 0.14 | 0.13 to 0.15 | 5 | 5 |
| 43Ea | 0.43 | 0.39 to 0.48 | 8 | 0.24 | 0.22 to 0.25 | 8 | 8 |

TABLE 47-continued

ADC Data With Ranking (4 h Incubation)

| | Cell line: | | | | | |
|---|---|---|---|---|---|---|
| | A431 | | | A431 | | |
| | ADC format: | | | | | |
| | Primary ADC | | | Primary ADC | | |
| | Treatment: | | | | | |
| | 4 hr, followed by washout | | | 4 hr, followed by washout | | |
| | Figure: | | | | | |
| | Figure 20B | | | Figure 21A | | 4 hr Primary |
| | Measurement: | | | | | |
| | $IC_{50}$ (nM) | 95% CI | rank | $IC_{50}$ (nM) | 95% CI | rank | ADC RANK |
| 54E | 0.26 | 0.24 to 0.29 | | 0.20 | 0.18 to 0.22 | | Not included |
| Isotype | | Not applicable | | | Not applicable | | Not included |
| TF-011 | 0.17 | 0.16 to 0.18 | | 0.09 | 0.09 to 0.10 | | Not included |

Example 22: Cell-Based Binding Assay of Antibody-Drug Conjugates (ADCs)

To evaluate the cell binding properties of ADCs, binding of anti-TF antibodies and anti-TF ADCs to endogenous human TF expressing HCT116 cells was assessed as previously described in Liao-Chan et al., *PLoS One*, 2015, 10:e0124708, which is incorporated by reference in its entirety. Briefly, $1.2 \times 10^5$ cells collected with Cellstripper (Mediatech, Manassas, VA, USA) were incubated with a twelve-point 1:3 dilution titration of anti-human TF antibody or ADC starting at 100 nM for 2 hr on ice. After 2 washes, cells labeled with antibody or ADC were incubated for 30 min on ice with 150 nM of Goat Phycoerythrin (PE) F(ab')$_2$ fragment goat anti-human IgG, Fcγ fragment specific (Jackson ImmunoResearch, West Grove, PA, USA) or FITC-labeled F(ab')$_2$ fragment goat anti-human kappa (SouthernBiotech, Birmingham, AL, USA), respectively. After 2 washes, dead cells were labeled with TO-PRO-3 Iodide (ThermoFisher Scientific) and samples were analyzed on a CytoFLEX flow cytometer (Beckman Coulter, Brea, CA, USA) or Novocyte flow cytometer (ACEA Biosciences, San Diego, CA, USA). The median fluorescence intensities (MFIs) at each dilution were plotted and cell $EC_{50}$'s were derived using a 4-parameter binding model in Prism (GraphPad, La Jolla, CA, USA). FIGS. 19A and 19B exhibit the binding curves of anti-TF antibodies and anti-TF ADCs, respectively. FIG. 19C lists the reportable cell $EC_{50}$'s and their 95% confidence intervals of the anti-TF antibodies and ADCs.

As shown in FIGS. 19A, 19B, and 19C, the cell binding properties of TF-specific ADCs are comparable to the cell binding properties of TF-specific antibodies, which indicates that the conjugation process of ADC did not alter the cell-binding properties of the TF-specific antibody moiety of the ADC.

Example 23: Cytotoxicity Assays of Antibody-Drug Conjugates (ADCs)

To evaluate ADC cytotoxicity, A431 cells were plated in 384-well plates (Greiner Bio-One). Anti-TF antibodies conjugated to MC-vc-PAB-MMAE were serially diluted as shown. The TF-specific ADCs were added to A431 cells, with either a 72 h incubation or a 4 h incubation followed by removal of excess ADC and culture for another 68 h. A431 cells were lysed in CTG assay reagent after treatment. CTG luminescence was measured and the mean and standard deviation of 4 replicates graphed in Prism. For each ADC, the $IC_{50}$ and its associated 95% confidence interval were calculated in Prism using a 4-parameter binding model.

FIG. 20A shows the cell viability after titrations of anti-TF ADCs with a continuous 72 h incubation. FIG. 20B shows the cell viability after titrations of anti-TF ADCs with a 4 h incubation followed by removal of excess ADC and culture for another 68 h. FIG. 20C shows the reportable $IC_{50}$ values of ADCs under both the continuous treatment and the pulse treatment. The 95% confidence intervals for the $IC_{50}$'s of the continuous treatment and the pulse treatment are listed in Table 46 and Table 47 respectively.

Both treatments resulted in efficacious cell killing, with a 2.4 to 4.7-fold increase in $IC_{50}$ when excess ADC was removed from the culture after the 4 h incubation compared to the 72 h incubation. Removal of excess 25A3 and 39A ADC had the smallest impact on $IC_{50}$, with a 2.7 and 2.4-fold increase from 0.07 and 0.05 nM, respectively.

These results indicate that similar to the TF-specific antibodies, the TF-specific ADCs undergo substantial cellular internalization.

Example 24: Cytotoxicity Assays in the Presence of FVIIa

To understand whether FVIIa interfered with the activity of the TF-specific ADC, we treated A431 cells for 4 h with the TF-specific ADCs (anti-TF antibodies conjugated to MC-vc-PAB-MMAE) in the absence or presence of FVIIa and measured cell viability 68 h later. A431 cells were pre-incubated for 30 min without or with 50 nM of FVIIa prior to the addition of an anti-TF ADC titration. Cell viability was determined by CTG assay. The mean and standard deviation of 4 replicates were graphed in Prism. For each ADC, the $IC_{50}$ were calculated in Prism using a 4-parameter binding model.

The cell viability after titrations of anti-TF ADCs in the absence or presence of FVIIa is shown in FIGS. 21A and 21B respectively. The reportable $IC_{50}$ values of ADCs in the absence or presence of FVIIa are listed in FIG. 21C.

While the ADCs that competed with FVIIa (29E, 39A, 54E and TF-011) were negatively affected by the presence of FVIIa by at least 2.3-fold, the ADCs that did not compete with FVIIa (group 25 and 43 antibodies) were equally efficacious in the absence or presence of FVIIa.

These results indicate that FVIIa does not interfere with the activity of anti-TF ADCs from groups 25 and 43.

Example 25: Cytotoxicity Assays on Additional Cancer Cell Lines

To evaluate TF copy number on the cell surface of different cell lines, $1.2 \times 10^5$ cells were harvested and incubated with 133 nM of anti-human TF antibody 5G9 on a mouse IgG2a backbone for 2 hr on ice. After 2 washes, QIFIKIT beads (Agilent) and cells labeled with anti-TF antibody were incubated for 30 min on ice with 150 nM of Goat Phycoerythrin (PE) F(ab')$_2$ fragment goat anti-mouse IgG, Fc-gamma fragment specific (Jackson ImmunoResearch). After 2 washes, dead cells were labeled with TO-PRO-3 Iodide (ThermoFisher Scientific) and samples were analyzed on a CytoFLEX flow cytometer (Beckman Coulter). After gating for single live cells, the MFI's were determined using FlowJo (Flowjo, Ashland, OR, USA). A standard curve using QIFIKIT beads was generated in Prism using a 5-parameter binding model to determine copy number. The lower limit of quantitation was $1.9 \times 10^3$ antibody binding sites (also referred to as copy number) and the upper limit of quantitation was $8.0 \times 10^5$ antibody binding sites.

The TF copy number on A431, CHO, HCT-116, HPAF-II, MDA-MB-231, and RF/6A is listed in FIG. 22A. The level of surface TF ranged from $1.9 \times 10^5$ to $5.7 \times 10^5$ copies in A431, MDA-MB-231 and HPAF-II cells. HCT-116 cells expressed $2.2 \times 10^4$ copies of surface TF and TF expression in CHO cells was below limit of quantitation (BLOQ). As 5G9 cross-reacts with *Macaca fascicularis* TF and the TF protein sequence between *M. fascicularis* and mulatta is identical, the level of surface TF in the *M. mulatta* cell line RF/6A was also qualified ($1.7 \times 10^4$ copies).

Cell viability of HCT-116, CHO, MDA-MB-231, and HPAF-II cells in the presence of titrations of anti-TF MMAE ADCs was shown in FIGS. 22B, 22C, 22D, and 22E respectively.

The TF-specific ADCs effectively reduced the viability of MDA-MB-231 and HPAF-II cancer cell lines (FIGS. 22D and 22E). Compared to the activity on MDA-MB-231 and HPAF-II cells, the ADCs were less efficacious on HCT-116 cells, with some activity at the highest concentration and no reportable IC$_{50}$ value (FIG. 22B). The TF-specific ADCs did not affect the viability of the CHO cultures (FIG. 22C).

These results indicate that the cytotoxicity of anti-TF ADCs is specific for TF positive cells.

When ranking the cell-killing efficacy of the ADCs on A431, HPAF-II and MDA-MB-231 cells, the top four ADCs in descending order were 39A, 29E, 25G1 and 25A3 (Table 46). When A431 cells were incubated for 4 h with the TF-specific ADCs followed by a washout, the top four ADCs in descending order were 39A, 25G1, 25A3 and 29E (Table 47). Thus, the top 2 ranking ADCs with no impact on coagulation were 25G1 and 25A3.

Example 26: Intracellular Microtubule Network in the Presence of Antibody-Drug Conjugates (ADCs)

Figure 23A:
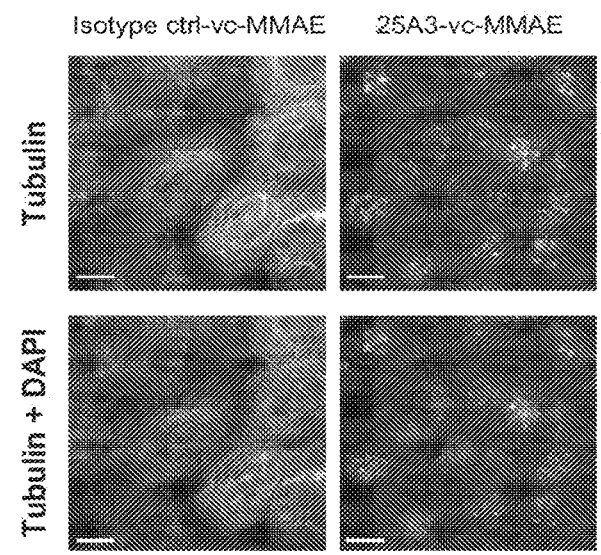
FIGS. 23A and 23B show staining of the microtubule network after treatment with anti-TF 25A3 MMAE ADC (25A3-vc-MMAE) or isotype control MMAE ADC (isotype ctrl-vc-MMAE).
Figure 23B:
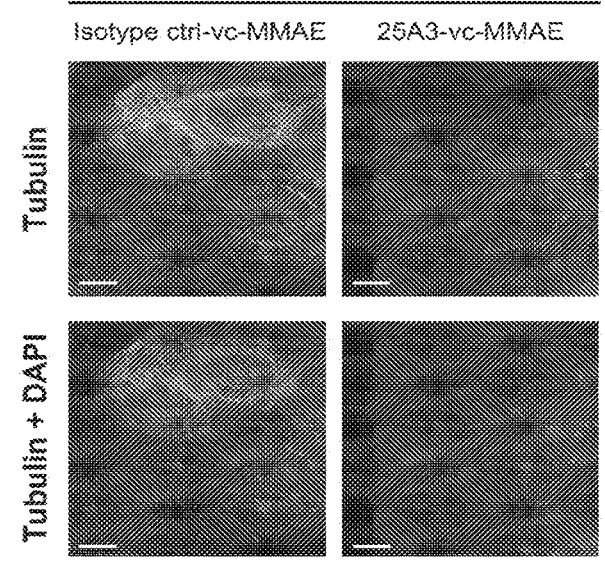

Immunofluorescence of the intracellular microtubule network of cells was conducted to illustrate the mechanism of action of the ADC. See Theunissen et al., *Methods Enzymol*, 2006, 409:251-284. Briefly, A431 or HPAF-II cells were seeded onto 8-well poly-D-lysine treated slides (Corning Inc, Corning, NY, USA). One day later, the culture medium was replaced with medium containing ADC at 5 nM. After twenty hours of ADC exposure, the cells were fixed for 15 min at room temperature with 4% paraformaldehyde (ThermoFisher Scientific). After three washes with PBS, the cells were permeabilized for 1 h with PBS containing 0.3% Triton X-100 and 5% normal goat serum. Next, the microtubule networks were stained for 3 h with anti-tubulin (11H10) rabbit mAb (Alexa Fluor 488 conjugate) (Cell Signaling Technology, Danvers, MA, USA) in PBS containing 1% BSA and 0.3% Triton X-100. After three washes, ProLong Gold Antifade reagent with DAPI (ThermoFisher Scientific) was added to the cells and the slide was mounted for microscopy by using a 0.17 mm coverslip. Image acquisition was conducted on a DMi8 fluorescence microscope (Leica Microsystems, Buffalo Grove, IL, USA) equipped with a sCMOS camera. The Leica LAS X software was used to acquire a system-optimized Z-stack of 6 to 7 microns. A sharp two-dimensional image from this Z-stack was created automatically with the extended depth of field (EDF) image feature. Representative images of tubulin staining of A431 or HPAF-II cells are shown in FIGS. 23A and 23B respectively.

While the isotype control ADC did not affect the microtubule network, the 25A3 ADC disrupted the microtubule network effectively in both A431 and HPAF-II cells.

These results indicate the MMAE-based anti-TF ADCs induce cytotoxicity in TF-positive cancer cells through disruption of the intracellular microtubule network.

Example 27: Cytotoxicity Assays and G$_2$/M Arrest in HUVECs

To evaluate TF copy number on the cell surface of human umbilical vein endothelial cells (HUVECs), $1.2 \times 10^5$ HUVECs were harvested and incubated with 133 nM of anti-human TF antibody 5G9 on a mouse IgG2a backbone for 2 hr on ice. After 2 washes, QIFIKIT beads (Agilent) and cells labeled with anti-TF antibody were incubated for 30 min on ice with 150 nM of Goat Phycoerythrin (PE) F(ab')$_2$ fragment goat anti-mouse IgG, Fc-gamma fragment specific (Jackson ImmunoResearch). After 2 washes, dead cells were labeled with TO-PRO-3 Iodide (ThermoFisher Scientific) and samples were analyzed on a CytoFLEX flow cytometer (Beckman Coulter). After gating for single live cells, the MFI's were determined using FlowJo (Flowjo, Ashland, OR, USA). A standard curve using QIFIKIT beads was generated in Prism using a 5-parameter binding model to determine copy number. The lower limit of quantitation was $1.9 \times 10^3$ antibody binding sites (also referred to as copy number) and the upper limit of quantitation was $8.0 \times 10^5$ antibody binding sites.

Figures 24A, 24B:
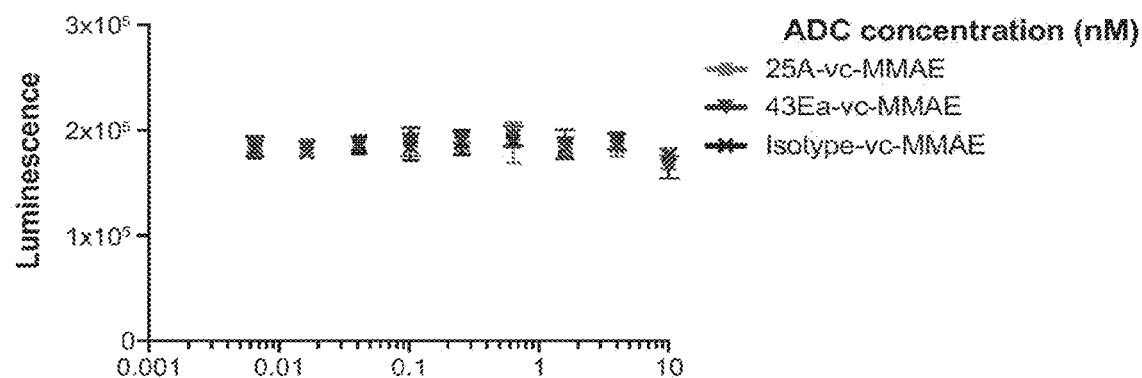
FIGS. 24A and 24B show the TF expression after cytokine treatment and the effect of anti-TF ADCs on the viability of cytokine-treated human umbilical vein endothelial cells (HUVECs).

In response to injury, inflammatory and angiogenic factors transiently increase expression of surface TF in the vasculature. See Holy et al., *Adv Pharmacol*, 2010, 59:259-592, which is incorporated by reference in its entirety. The transient upregulation of TF in cell culture was mimicked by treating HUVECs with a combination of inflammatory cytokines (5 ng/mL IL1-beta, 25 ng/mL TNF-alpha and 50 ng/mL VEGF). As shown in FIG. 24A, surface TF levels increased from $2.4 \times 10^3$ copies in the absence of inflammatory cytokines to $1.2 \times 10^4$ copies after 6 h of cytokine treatment. The surface TF was ~3-fold lower after 20 h of cytokine treatment relative to 6 h of treatment, which indicates that the cytokine-induced TF upregulation was transient.

For the ADC cytotoxicity assay, HUVEC cultures were seeded on half-area 96-well plates. The next day, the combination of inflammatory cytokines and a titration of ADCs was added to the cultures. Four days later viability of the cultures was assessed by lysis in CellTiter-Glo (CTG) assay reagent. As shown in FIG. 24B, the cell viability of inflammatory cytokine-treated HUVEC cultures was unaffected by the anti-TF ADCs, 25A-vc-MMAE and 43Ea-vc-MMAE. The results indicates that the inflammatory cytokine-treated endothelial cells are resistant to anti-TF ADCs.

To further understand the resistance of endothelial cells to anti-TF ADCs, cell cycle progression was evaluated 24 h after addition of the cytokines and TF-specific ADCs. Arrest at the G2/M phase of the cell cycle was analyzed as previously described in Theunissen et al, *Methods Enzymol,* 2006, 409:251-284. Briefly, low-passage HUVECs (Lifeline Cell Technologies, Frederick, MD, USA), propagated in VascuLife VEGF-Mv Endothelial media (Lifeline Cell Technologies), and HCT-116 cells were seeded on 12-well plates. The next day, media was removed and replaced with fresh media (no cytokines) or media containing 5 ng/mL IL1-beta, 25 ng/mL TNF-alpha and 50 ng/mL VEGF (with cytokines). A titration of MMAE-linked ADCs or free MMAE was added to the cells. After 24 h of treatment, cells were fixed in ice-cold 70% ethanol. Subsequently, the cells were washed with flow cytometry buffer (PBS, 1% FBS, 0.1% Triton) and stained for 1 h with a 1:100 dilution of phospho-Histone H3 (Ser10) (D2C8 PE Conjugate, Cell Signaling Technology). After 2 washes, the cells were treated for 20 min with 100 µg/mL PureLink RNAse A (ThermoFisher Scientific), followed by the addition of the viability dye TO-PRO-3 Iodide (ThermoFisher Scientific). 40,000 events were collected on a Novocyte flow cytometer. In the Flowjo data analysis software cell doublets and aneuploid cells were excluded. The pH3 signal was plotted against DNA content to determine the percentage of pH3-positive cells.

Figure 25A:
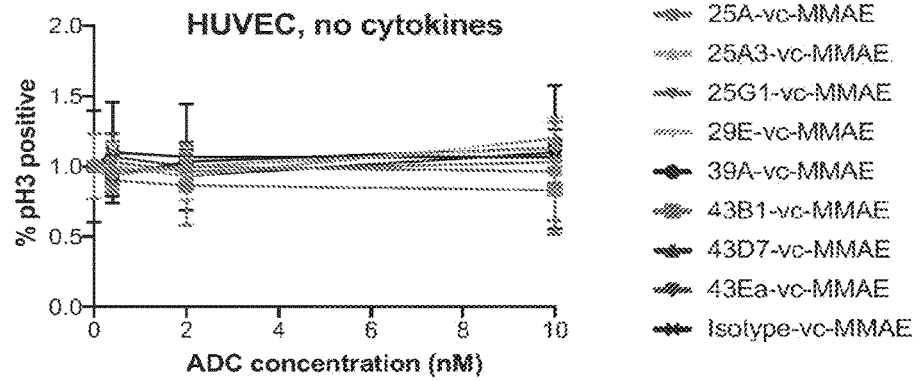
FIGS. 25A, 25B, and 25C show the quantitation of the G2/M arrest in HUVECs or HCT-116 cells treated for 24 h with titrations of anti-TF ADCs.
Figure 25B:
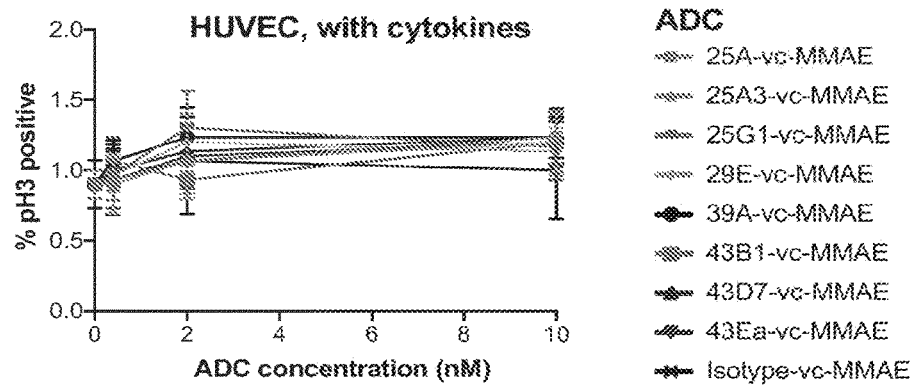
Figure 25C:
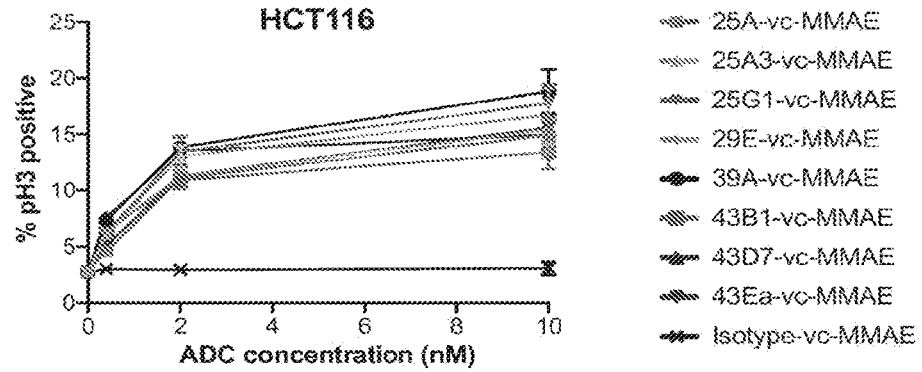

The percentage of pH3-positive cells (% pH3) with titrations of anti-TF ADCs on HUVECs in the absence or presence of inflammatory cytokines is shown in FIGS. 25A and 25B respectively. The percentage of pH3-positive cells (% pH3) with titrations of anti-TF ADCs on HCT-116 cells is shown in FIG. 25C.

Figure 26A:
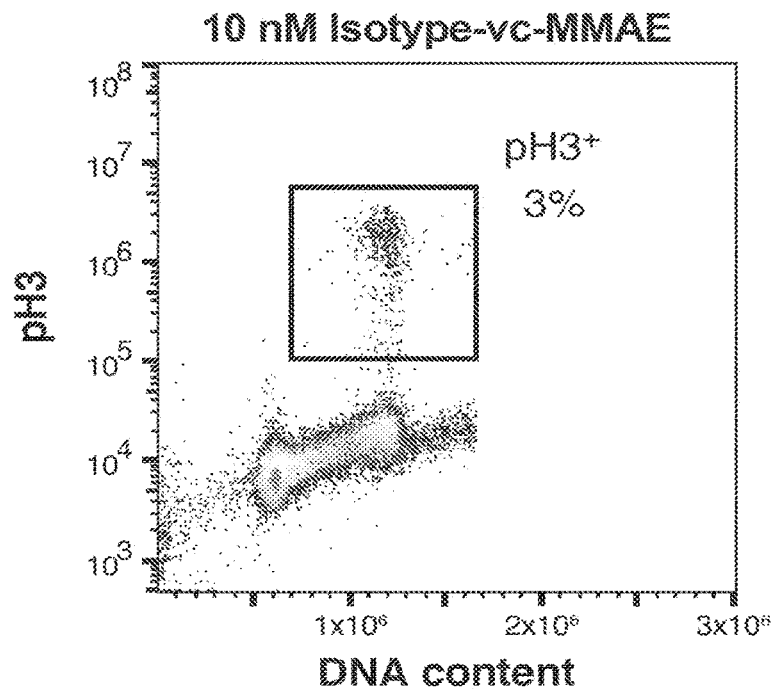
FIGS. 26A and 26B show the percentage of pH3-positive HCT-116 cells analyzed by flow cytometry with or without anti-TF ADC treatment.
Figure 26B:
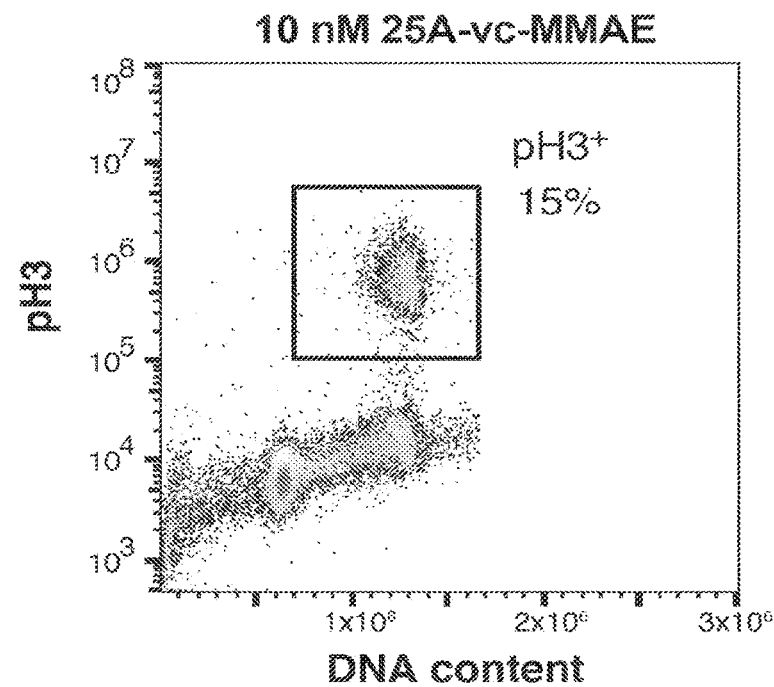

While the TF-specific ADCs induced an arrest at the G2/M phase of the cell cycle in HCT-116 cells, the ADCs did not impact cell cycle progression in HUVECs with or without inflammatory cytokine treatment. As shown in FIGS. 26A and 26B, the percentage of pH3-positive HCT-116 cells increased 5 times after treatment of 25A-vc-MMAE as compared to treatment of Isotype-vc-MMAE.

Figure 27A:
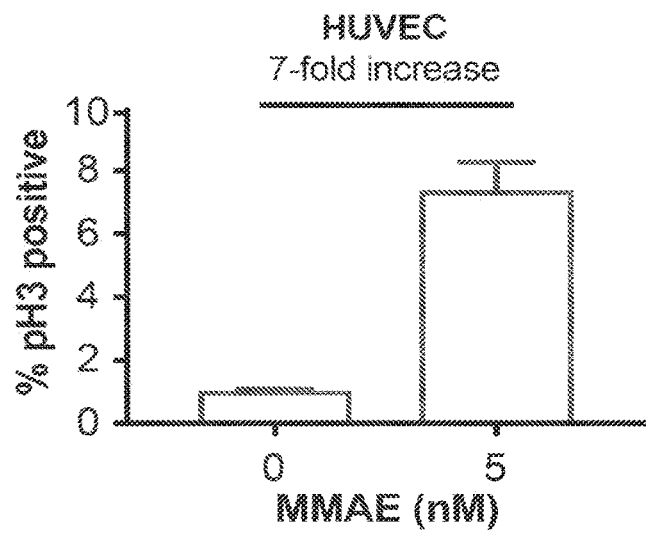
FIGS. 27A and 27B show the sensitivity of HUVECs and HCT-116 cells to MMAE.
Figure 27B:
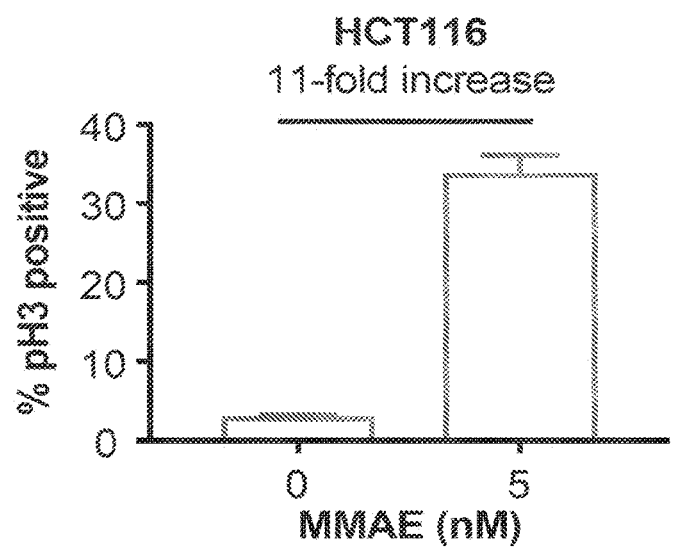

FIGS. 27A and 27B show that unconjugated MMAE increase the phosphorylation of histone H3 to a similar extent in both HCT-116 cells and HUVECs, indicating that the resistance in endothelial cells is specific for the MMAE-based ADC.

Taken together, these results indicate that the anti-TF ADCs do not affect the viability of HUVECs in the absence or presence of inflammatory cytokines.

Example 28: Erk Phosphorylation Assay

For assessment of Erk phosphorylation, A431 cells were plated in 6-well plates (Corning) in media overnight. The following day, cells were washed once and serum starved in serum-free media. After starvation, cells were preincubated with 100 nM of anti-TF antibodies for 30 min at 37° C. FVIIa was spiked into the wells at 50 nM and incubated for 20 min at 37° C. for p-ERK induction. After induction, cells were lysed with RIPA Lysis and Extraction Buffer with Halt™ Protease and Phosphatase Inhibitor Cocktail (ThermoFisher Scientific). Western blot was performed with 20 µg of cell lysate using Phospho-p44/42 MAPK (Erk1/2) (Thr202/Tyr204) and p44/42 MAPK (Erk1/2) (137F5) (Cell Signaling Technology) as primary antibodies and Peroxidase AffiniPure Donkey Anti-Rabbit IgG (H+L) (Jackson ImmunoResearch) as a secondary antibody. Non-saturating band intensities for pErk and Erk were measured on an Amersham AI600 (GE Healthcare). Each pErk intensity was normalized against its respective Erk intensity and the no-antibody no-FVIIa sample intensity.

Figure 28:
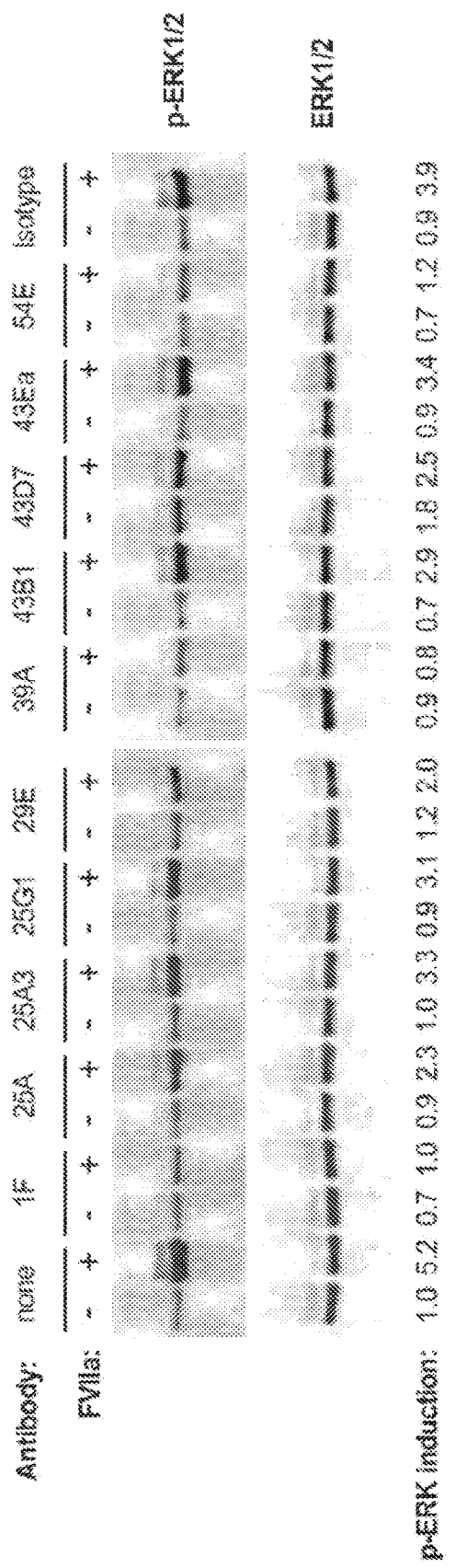
FIG. 28 shows the analysis of Erk phosphorylation by Western blotting with an anti-phospho-Erk1/2 antibody and an anti-Erk1/2 antibody. The values of pErk induction are listed.

The Western blot results of pErk and Erk are shown in FIG. 28. Treatment with FVIIa induced Erk phosphorylation by 5.2 fold in cell cultures without pretreatment of anti-TF antibodies. The indication of Erk phosphorylation was ablated by pretreatment with 1F, 39A and 54E (fold induction between 0.8 and 1.2) and attenuated by 29E and the members of groups 25 and 43 (fold induction between 2.0 and 3.4).

This data indicates that anti-TF antibodies inhibit FVIIa-dependent TF signaling when assessing Erk phosphorylation.

Example 29: Antibody-Dependent Cellular Cytotoxicity (ADCC) Assay

To evaluate ADCC activity, an ADCC Reporter Bioassay Core Kit (Promega) was used following the manufacturer's protocol. Briefly, A431 cells were plated on a microtiter plate (Corning). The following day, the cells were incubated with a ten-point 1:3 dilution titration of anti-TF antibodies or the ADCs starting at 50 nM. An ADCC effector-to-target cell ratio of 8:1 was added to each well and incubated for 6 h at 37° C. Bio-Glo™ Luciferase Assay Reagent was added to each well to measure luminescence on an Envision plate reader (PerkinElmer, Waltham, MA, USA). The mean and standard deviation of 4 replicates were graphed in Prism. For each antibody and ADC, the $EC_{50}$ and its associated 95% confidence interval were calculated in Prism using a 4-parameter binding model.

ADCC reporter luminescence after incubation with the reporter Jurkat cell line in the represece titrations of anti-TF antibodies or anti-TF ADCs is shown in FIGS. 29A and 29B respectively. The ADCC reporter luminescence $EC_{50}$ values for each anti-TF antibody or ADC are listed in FIG. 29C.

All the tested TF-specific antibodies and ADCs exerted induction of luciferase-dependent luminescence with $EC_{50}$ values ranging between 0.18 and 0.43 nM.

These data indicate that both the TF-specific antibodies and ADCs can induce antibody-dependent cellular cytotoxicity (ADCC) via the IgG1 Fc domain of the antibody.

Example 30: Studies in Cell Line-Derived Xenograft (CDX) Models

To evaluate the efficacy of the ADCs in vivo, xenograft studies in immune compromised mice were performed as described in Kim et al., *Blood Cancer J,* 2015, 5:e316, which is incorporated by reference in its entirety. Briefly, the A431 epidermoid carcinoma and the HPAF-II pancreatic carcinoma cell lines were implanted subcutaneously in the flank of athymic nude mice (Charles River Laboratories, Wilmington, MA). Animals were randomized and treated as indicated in the figures. Body weight and tumor size assessments were performed bi-weekly. Animals were removed from study and euthanized once tumor size reached 1200 mm³ or skin ulceration was evident. In addition, the MTV curve for the treatment group in question was no longer shown once an animal was removed from study due to size. The animals' care was in accordance with institutional guidelines. Mean tumor volume (MTV) with the standard error of the mean (SEM) was plotted over time. Treatment efficacy was determined by calculating tumor growth inhibition (% TGI=100% x [1-(final MTV-initial MTV of a treated group)/(final MTV-initial MTV of the control group)]) before any of the animals in the vehicle arm were euthanized due to a tumor size≥1200 mm$^3$. Statistical comparisons between the MTVs were conducted using one-way ANOVA followed by Tukey's multiple comparisons test comparing all groups. The P-values for each ADC compared to the vehicle control arm are reported. At the end of the study, efficacy was also determined in each treatment arm by counting the number of animals with a partial regression (PR) or a complete regression (CR) of the tumor. In a PR response, the tumor volume was 50% or less of its day 1 volume for 3 consecutive measurements during the course of study, and equal to or greater than 14 mm$^3$ for 1 or more of these measurements. In a CR response, the tumor volume was less than 14 mm$^3$ for 3 consecutive measurements. When an animal exhibited a CR response at the end of the study, it was classified as a tumor-free survivor (TFS) instead of a CR. Throughout the ADC studies no significant body weight changes due to ADC treatment were observed.

As shown in FIG. 30A, HPAF-II tumor-bearing mice were treated with 5 mg/kg of ADC on day 1, 8 and 15 after randomization. The effect of TF-011 ADC was compared with two representative clones from the two groups that did not impact coagulation (i.e. 25A and 43Ea). Twenty-one days after randomization the efficacy of the 25A, 43Ea and TF-011 ADCs was equivalent, with tumor growth inhibition ranging between 131 and 136%.

In the second HPAF-II study as shown in FIG. 30B, the highest affinity antibody that affected coagulation (i.e. 39A) and six antibodies with varying affinities from groups 25 and 43 (i.e. 25A, 25A3, 25G1, 43Ea, 43B1 and 43D7) were equally efficacious when dosed twice at 2 mg/kg. Tumor growth inhibition for the TF-specific ADCs ranged between 129 and 139% on day 21, and 6 to 9 out of 10 animals per treatment arm were classified as tumor-free survivors at the end of the study.

In the MDA-MB-231 xenograft model, the ADCs were administered on day 1 and 8 post-randomization at 4 or 2 mg/kg. As shown in FIG. 31A, all the TF-specific ADCs were active at 4 mg/kg, with tumor growth inhibition ranging between 69 and 100%, and a significant difference in mean tumor volume for each TF-specific ADC compared to the vehicle control arm. While a notable difference was observed in mean tumor volume between 25G1 and the other TF-specific ADCs, it was not statistically significant (P>0.05).

Figure 31B:
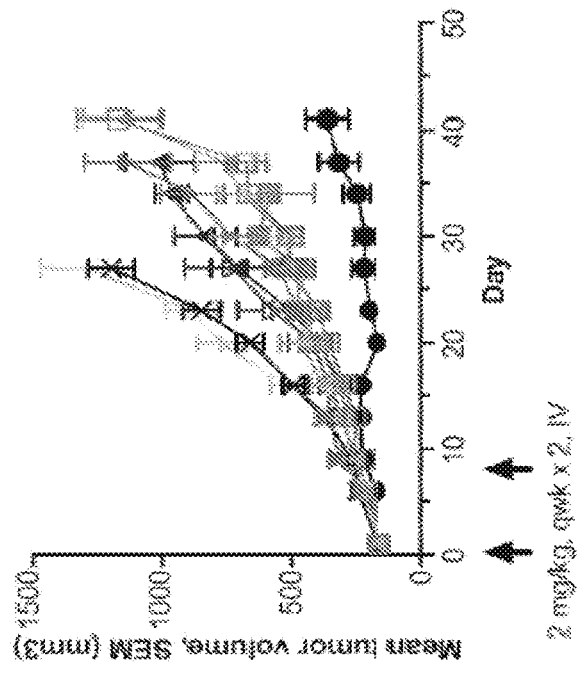
FIGS. 31A and 31B show in vivo efficacy of anti-TF ADCs in MDA-MB-231 xenograft model.
Figure 31A:
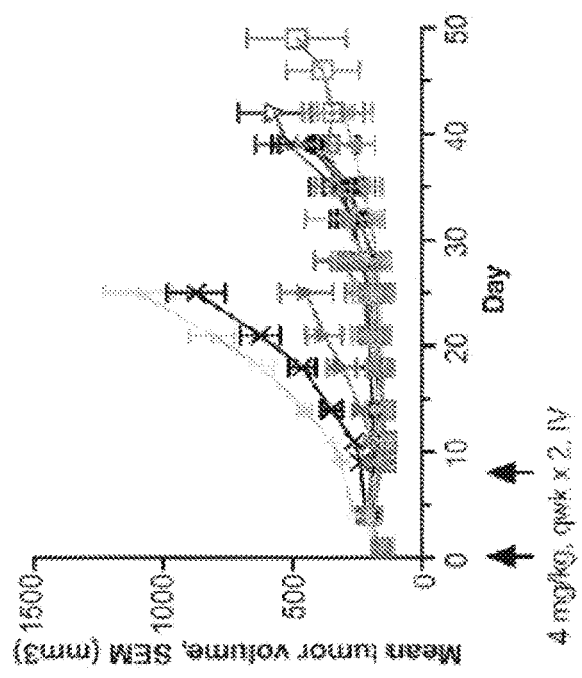

At 2 mg/kg of ADC as shown in FIG. 31B, all the TF-specific antibodies showed suboptimal activity with varying degrees of significance in mean tumor volume compared to the vehicle control arm. 25A3, 39A and 43B1 showed the greatest degree of significance in mean tumor volume compared to the vehicle control arm (P<1×10$^4$). The difference in mean tumor volume between 39A and the other antibodies was only significant for the comparison between 39A and 43Ea (P<0.05).

Figure 32:
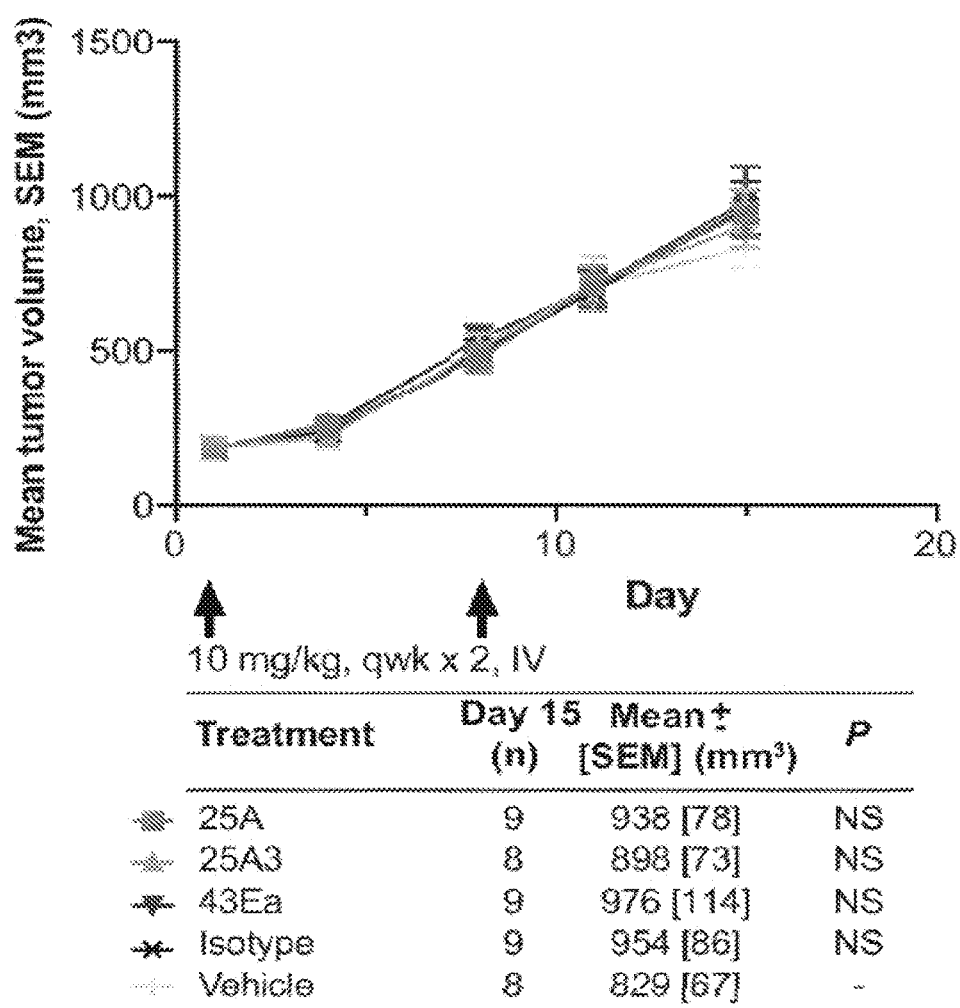
FIG. 32 shows the mean tumor volume after weekly treatment of unconjugated anti-TF antibodies at 10 mg/kg for 2 weeks in the HPAF-II xenograft model. The mean tumor volume on day 15 is listed.

In contrast, the unconjugated antibodies of 25A, 25A3 and 43Ea lacked substantial anticancer activity when dosed twice at 10 mg/kg in the HPAF-II xenograft model (FIG. 32).

There results indicate that the TF-specific ADCs are efficacious in the HPAF-II and MDA-MB-231 xenograft model under various dosing regimens. The activity of the ADCs are caused by the toxin delivery of the anti-TF antibodies.

Example 31: Studies in Patient-Derived Xenograft (PDX) Models

TF-positive PDX models were performed in athymic nude mice (Envigo, Indianapolis, IN) to evaluate the efficacy of the ADCs in vivo. The animals' care was in accordance with institutional guidelines. Study animals were implanted unilaterally on the left flank with tumor fragments.

For immunohistochemistry (IHC) analysis, tissues underwent pretreatment using Rip Tide (Mosaic Laboratories, Lake Forest, CA) for 40 min at 95-97° C. in a water bath, cooled for 10 min on the bench, rinsed 3 times with distilled water, and rinsed for 5 min with Splash-T Buffer (Mosaic Laboratories). Tissue sections were blocked in EnVision Peroxidase-Blocking Reagent (EnVision+Mouse HRP Detection Kit, Agilent, Carpinteria, CA) for 5 min, followed by 2 rinses in Splash-T Buffer for 5 min each. Next, the tissue sections were stained with an anti-TF antibody (mouse clone HTF-1) or a mouse negative control reagent for 30 min, followed by 2 rinses in Splash-T Buffer for 5 min each. The second staining step of the tissue sections was carried out for 30 min with EnVision+Mouse HRP (EnVision+Mouse HRP Detection Kit), followed by 2 rinses in Splash-T Buffer for 5 min each. To visualize the anti-TF staining, tissue sections were developed with DAB chromogen (EnVision+Mouse HRP Detection Kit) for 5 min, followed by 10 dips and a 5 min rinse in distilled water. Tissue sections were counterstained with Hematoxylin for 5 min followed by 3 rinses in distilled water.

Animals were randomized and treated as indicated in the figures. Animals were removed from study and euthanized once tumor size reached 1200 mm$^3$ or skin ulceration was evident. In addition, the MTV curve for the treatment group in question was no longer shown once an animal was removed from study due to size. TGI and statistical analyses were conducted in the same manner as for the CDX studies. The CR and PR response definitions were as follows for the PDX studies: a PR responder had a MTV≤30% of MTV at day 1 for 2 consecutive measurements; a CR responder had an undetectable MTV for 2 consecutive measurements. When an animal exhibited a CR response at the end of the study, it was classified as a TFS instead of a CR.

Figure 33B:
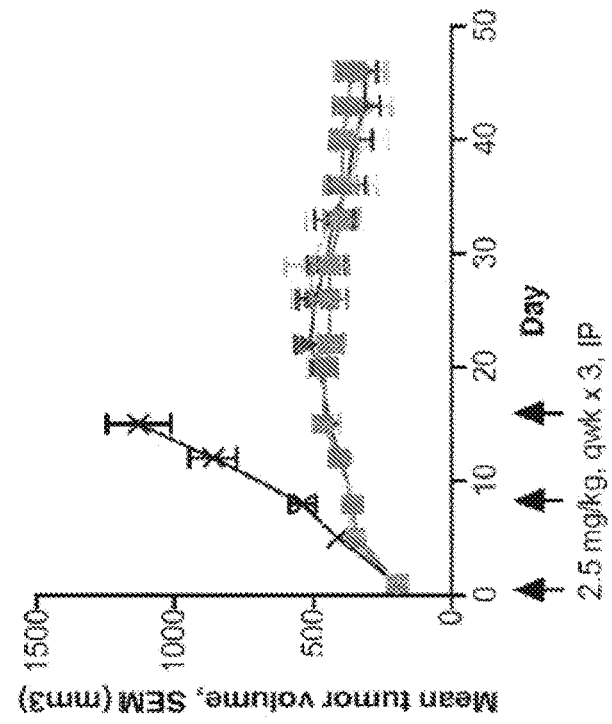
FIGS. 33A, 33B, and 33C show in vivo efficacy of anti-TF ADCs in patient-derived xenograft (PDX) models.
Figure 33A:
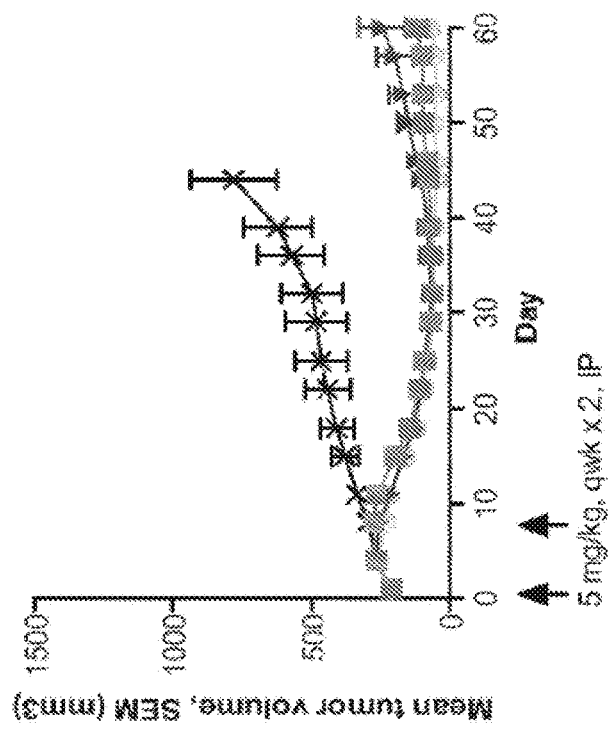
Figure 33C:
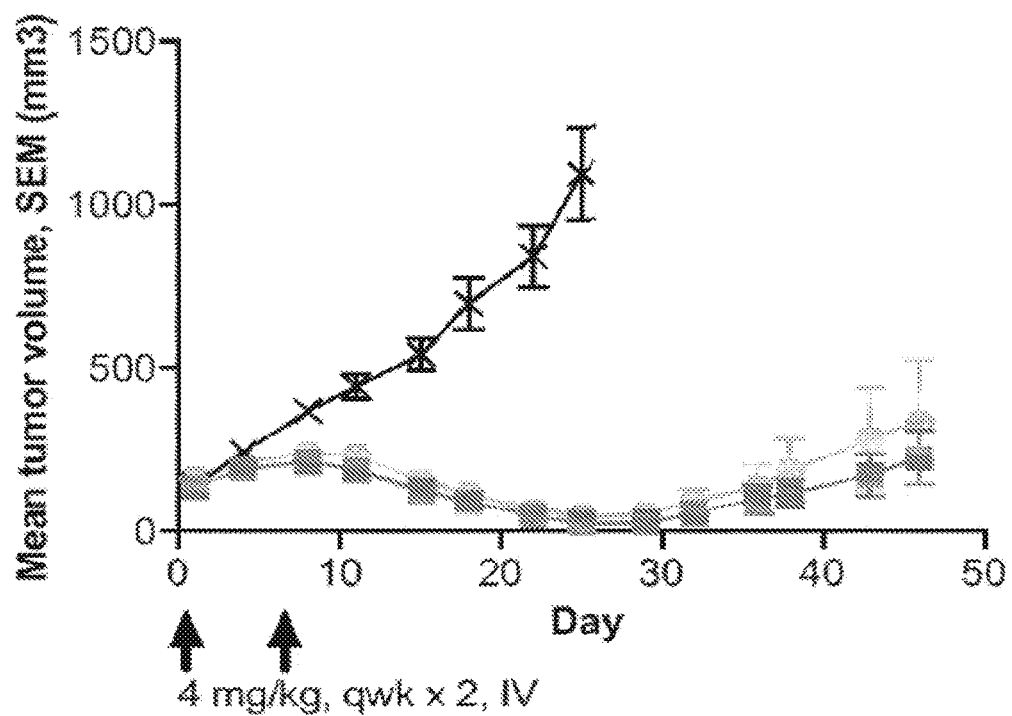

While the squamous cell carcinoma of the head and neck (SCCHN) and ovarian adenocarcinoma PDX had H-scores of 250 and 220, respectively, the gastric adenocarcinoma PDX had an H-score of 155 (data not shown). Upon randomization of tumor-bearing mice, treatment occurred on a weekly basis either twice or three times with the dose ranging between 2.5 and 5 mg/kg. As shown in FIGS. 33A, 33B, and 33C in all the PDX models a significant reduction in mean tumor volume was observed for each TF-specific ADC compared to the isotype control arm (P<1×10$^4$), with no significant difference between the various TF-specific ADCs (P>0.05). In the head and neck and ovarian PDX model, the number of complete responders and tumor-free survivors did not exceed 2 out of 10 animals at the end of the study in any of the treatment groups (FIGS. 33A and 33B). However, in the gastric PDX the 25A treatment arm had 2 partial responders, 2 complete responders and 3 tumor-free survivors, and the TF-011 arm contained 1 complete responder and 5 tumor-free survivors at the end of the study (FIG. 33C).

These data indicate that the anti-TF ADCs from groups 25 and 43 (i.e. 25A and 43Ea) were equally efficacious as tisotumab vedotin (TF-011) ADC.

Example 32: Efficacy Study in Swine CNV Model

An efficacy study in a swine choroidal neovascularization (CNV) model was performed to determine the effect 4 different anti-TF antibodies in reducing lesion size.

Figure 34A:
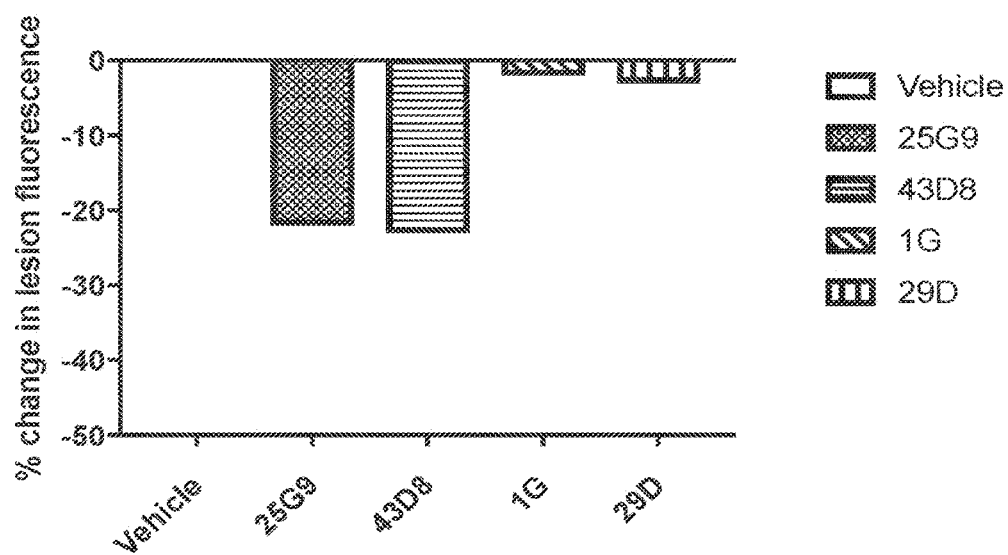
FIGS. 34A and 34B show the change in lesion size after administration of anti-TF antibody in a swine choroidal neovascularization (CNV) model.
Figure 34B:
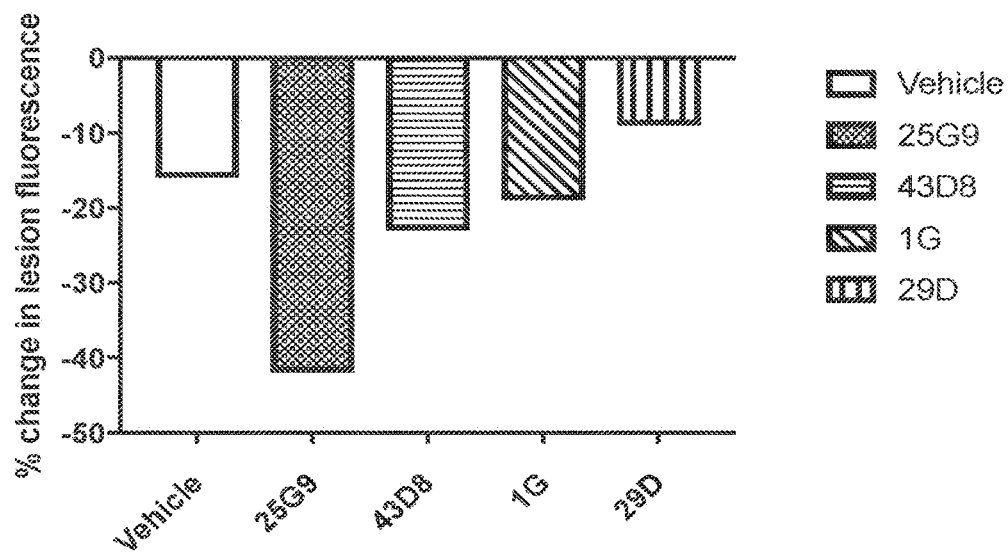

10-12 week old animals (Swine/Hampshire Cross) underwent bilateral laser using an 810 nm Diode laser delivered through an indirect ophthalmoscope to create approximately 6 single laser spots between retinal veins in each eye of each animal. For efficacy assessments, 2 mg of each anti-TF antibody, 25G9, 43D8, 1G, and 29D respectively, were administered intravitreally on day 7 post-laser treatment. A vehicle control group was also included in the study. Fluorescein Angiography (FA) to determine total lesion fluorescence was performed on day 7 (baseline), day 14 and day 28. FA was evaluated using a Corrected Total Lesion Fluorescence (CTLF) measurement for each individual lesion. The perimeter of the lesion was traced, and an integrated density value was obtained. CTLF was then calculated by subtracting the mean fluorescence background adjacent to the lesion from the integrated density measurement. Percent change in lesion size from day 7 to day 14 and from day 7 to day 28 are shown in FIG. 34A and FIG. 34B, respectively.

From day 7 to day 14, anti-hTF antibodies from groups 25 and 43, 25G9 and 43D8, reduced lesion size by greater than 20%. From day 7 to day 28, anti-hTF antibody 25G9 reduced lesion size by greater than 40%. Anti-hTF antibodies 1G and 29D did not reduce lesion size significantly as compared to the vehicle control group.

This data indicates that antibodies from groups 25 and 43, 25G9 and 43D8, were effective in reducing lesion size in a swine CNV model.

Example 33: Efficacy of 25G9 in Swine CNV Model

An efficacy study in a swine choroidal neovascularization (CNV) model was performed to compare different doses of anti-TF antibody 25G9 for their ability to reduce lesion size.

Figure 35:
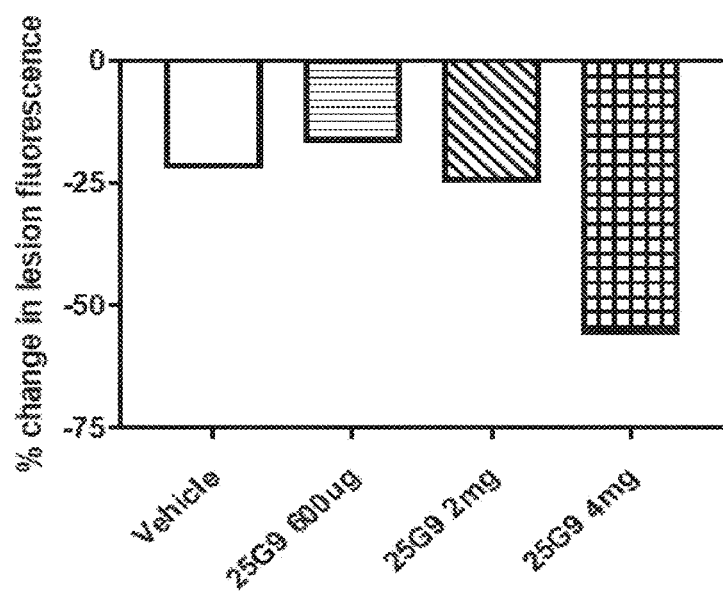
FIG. 35 shows the change in lesion size in a swine choroidal neovascularization (CNV) model from day 7 (baseline) to day 28 as measured by Fluorescein Angiography (FA) after intravitreal administration of anti-TF antibodies 25G9 at 600 ug, 2 mg and 4 mg respectively.

10-12 week old animals (Swine/Hampshire Cross) underwent bilateral laser using an 810 nm Diode laser delivered through an indirect ophthalmoscope to create approximately 6 single laser spots between retinal veins in each eye. For efficacy assessments 600 ug, 2 mg and 4 mg of anti-TF antibody 25G9 were administered intravitreally on Day 7 post-laser treatment. Fluorescein Angiography (FA) to determine total lesion fluorescence was performed on day 7 (baseline) and day 28. FA was evaluated using a Corrected Total Lesion Fluorescence (CTLF) measurement for each individual lesion. The perimeter of the lesion was traced, and an integrated density value was obtained. CTLF was then calculated by subtracting the mean fluorescence background adjacent to the lesion from the integrated density measurement. Percent changes in lesion size from day 7 to day 28 are shown in FIG. 35.

From day 7 to day 28, anti-hTF antibody 25G9 reduced lesion size in a dose-depenent matter. 25G9 reduced lesion size by greater than 50% at 4 mg. This data indicates that antibody 25G9 was effective in reducing lesion size in the swine CNV model in a dose-dependent matter.

Example 34: Binding Affinity Assay For Pig TF and Rabbit TF

The ability of certain antibodies was tested for binding to pig TF. For pig TF Biacore-based measurements, a given anti-TF antibody was captured by an anti-human IgG antibody covalently coupled to a CM5 chip (GE Healthcare Bio-Sciences). Association between the anti-TF antibodies and a five-point three-fold titration of pig TF-His starting at 100 nM was measured for 180 to 240 sec. Subsequently, dissociation between the anti-TF antibody and TF-His was measured for 1800 sec. Kinetic data was analyzed and fitted globally using a 1:1 binding model. The $K_D$ values of the indicated TF antibodies measured by the Biacore-based experiments are shown in Table 48.

The ability of certain antibodies was tested for binding to rabbit TF. For rabbit TF Biacore-based measurements, a given anti-TF antibody was captured by an anti-human IgG antibody covalently coupled to a CM5 chip (GE Healthcare Bio-Sciences). Association between the anti-TF antibodies and a five-point three-fold titration of rabbit TF-His starting at 100 nM was measured for 180 to 240 sec. Subsequently, dissociation between the anti-TF antibody and TF-His was measured for 1800 sec. Kinetic data was analyzed and fitted globally using a 1:1 binding model. The $K_D$ values of the indicated TF antibodies measured by the Biacore-based experiments are shown in Table 48.

As shown in Table 48, anti-hTF antibodies from groups 25 and 43 exhibit binding activity and cross-reactivity to pig TF and rabbit TF. In contrast, antibodies from groups 1 and 29 show no binding activity to pig TF or rabbit TF.

TABLE 48

Antibody kinetics for pig and rabbit TF

| Antibody | Pig $K_D$, nM | Rabbit $K_D$, nM |
| --- | --- | --- |
| 1G | no binding | no binding |
| 25A | 18.7 | 50.5 |
| 25A3 | 5.5 | 12.4 |
| 25A5 | 5.2 | 5.4 |
| 25A5-T | 4.5 | 5.4 |
| 25G | 26.0 | 75.5 |
| 25G1 | 2.6 | 3.6 |
| 25G9 | 3.3 | 4.2 |
| 29D | no binding | no binding |
| 43D7 | 8.8 | 6.8 |
| 43D8 | 19.2 | 7.7 | no binding*: no binding to weak binding, with no reportable $K_D$

Example 35: Immunohistochemistry (IHC) Assay

Tissues underwent pretreatment using Rip Tide (Mosaic Laboratories, Lake Forest, CA) for 40 min at 95-97° C. in a water bath, cooled for 10 min on the bench, rinsed 3 times with distilled water, and rinsed for 5 min with Splash-T Buffer (Mosaic Laboratories). Tissue sections were blocked in EnVision Peroxidase-Blocking Reagent (EnVision+ Mouse HRP Detection Kit, Agilent, Carpinteria, CA) for 5 min, followed by 2 rinses in Splash-T Buffer for 5 min each. The tissue sections were then stained with an anti-TF antibody (mouse clone HTF-1) or a mouse negative control reagent for 30 min, followed by 2 rinses in Splash-T Buffer for 5 min each. The second staining step of the tissue sections was carried out for 30 min with EnVision+Mouse HRP (EnVision+Mouse HRP Detection Kit), followed by 2 rinses in Splash-T Buffer for 5 min each. To visualize the anti-TF staining, tissue sections were developed with DAB chromogen (EnVision+Mouse HRP Detection Kit) for 5 min, followed by 10 dips and a 5 min rinse in distilled water. Tissue sections were counterstained with Hematoxylin for 5 min followed by 3 rinses in distilled water.

Staining intensity was scored on a semi-quantitative integer scale from 0 (negative) to 3 (or "3+") by a certified anatomic pathologist. The percentage of cells staining positively at each intensity level was recorded. Scoring was based on localization of TF to the cell membrane. The H score combines components of staining intensity with the percentage of positive cells. It has a value between 0 and 300 and is defined as: 1× (percentage of cells staining at 1+intensity)+2× (percentage of cells staining at 2+intensity)+3× (percentage of cells staining at 3+intensity)=H score.

Tissue sections from patients with kidney cancer, head & neck cancer, ovarian cancer, gastric cancer, prostate cancer, gastroesophageal junction cancer, cervical cancer, and glioblastoma were stained. The number of patients with scores within each H score range and the total number of patient for each cancer are shown in Table 50. These results indicate that TF is expressed in kidney cancer, head & neck cancer, ovarian cancer, gastric cancer, prostate cancer, gastroesophageal junction cancer, cervical cancer, and glioblastoma.

TABLE 50

Results of IHC assay

| Indication | H score 0 | H score 1-100 | H score 101-200 | H score 201-300 |
|---|---|---|---|---|
| Kidney | 19/28 | 6/28 | 1/28 | 2/28 |
| Head & Neck | 4/74 | 31/74 | 19/74 | 20/74 |
| Ovarian | 13/26 | 11/26 | 0/26 | 2/26 |
| Gastric | 1/20 | 9/20 | 4/20 | 6/20 |
| Prostate | 1/24 | 8/24 | 7/24 | 8/24 |
| Pancreatic | 14/37 | 18/37 | 5/37 | 0/37 |
| Gastroesophageal junction | 28/59 | 23/59 | 6/59 | 2/59 |
| Cervical | 31/60 | 21/60 | 7/60 | 1/60 |
| Glioblastoma | 2/41 | 7/41 | 23/41 | 9/41 |

Example 36: Epitope Binning of Anti-TF Antibodies

To establish epitope binding differences between the anti-human TF antibodies, chimeric TF construct mapping experiments were conducted. This mapping technique enables discrimination of antibody epitopes.

Because all the anti-human TF antibodies evaluated do not bind rat TF, the rat TF sequence was used for the construction of chimeric human-rat TF constructs. Chimeric human-rat construct design was guided by the N- and C-terminal domain of TF extracellular domain (amino acids 1-107 and 108-219 of the extracellular domain, respectively), with an alignment shown in FIG. 36. Based on the chimera mapping results using the constructs from FIG. 36, rat amino acid segment 141-194 was replaced by the human sequence (amino acid 136-189 of hTF extracelluar domain), with an alignment shown in FIG. 37. Design of three human TF constructs with either 1 or 2 human-rat substitutions (hTF_K68N, hTF_K149N and hTF_N171H_T197K) was based on reported contact residues K68, K149 and N171 and T197 for the 10H10 antibody (Teplyakov et al., *Cell Signal.*, 2017, 36:139-144), with an alignment shown in FIG. 38.

To establish binding of the anti-human TF antibodies to the various TF constructs, HEK293 cells were transfected with a DNA plasmid that co-expresses the TF construct and a green fluorescent protein marker. For a subset of the antibodies, an antibody titration (a 12-point 1:3 dilution series starting at 250 nM) was evaluated on select TF constructs (FIGS. 39A-F). These antibody titrations demonstrated that the antibody concentration of 15 µg/ml (100 nM) used in Tables 51 and 52 was appropriate to establish "Percentage antibody binding to TF construct relative to hTF". Two days after transfection, cells were collected from the tissue culture plate, stained with 15 µg/ml of the indicated anti-TF antibody, washed, stained with anti-human IgG-Fc Alexa Fluor 647 polyclonal antibody, washed, and stained with the viability dye 4',6-Diamidino-2-Phenylindole, Dihydrochloride. Upon acquisition of 80,000 live events on a flow cytometer, live cells marked with the fluorescent marker were analyzed for the degree of staining by the anti-TF antibody. The median fluorescence intensity values relative to an isotype control for each TF expression construct were divided by the median fluorescence intensity value relative to an isotype control for the hTF expression construct, and the resulting percentage listed as "Percentage antibody binding to TF construct relative to hTF" in Tables 51 and 52. As used herein, the term "live cell staining assay" refers to the antibody binding assay used in this example.

The assumption that all chimeric TF constructs were expressed on the cell surface at levels between 50% and 150% of the hTF control construct was met for all TF constructs for at least one anti-human TF antibody in the antibody collection, with the exception of the h1-107_r construct (human amino acid segment 1-107 replaced by rat sequence). Lack of binding of the anti-human TF antibodies to cell surface-expressed rat TF was expected. When "Percentage antibody binding to TF construct relative to hTF" in Tables 51 and 52 was less than 50%, the antibody was considered a non-binder (0) in Tables 53 and 54. When "Percentage antibody binding to TF construct relative to hTF" in Tables 51 and 52 was between 50% and 150%, the antibody was considered a binder (1) in Tables 53 and 54.

Each antibody was assigned to an epitope bin in Table 55 based on the combination of unbound constructs from Table 53. The antibodies from Lineage 25 (25A, 25A3, 25A5-T, 25G1 and 25G9) bind a unique epitope, referred to as Epitope Bin 6 in Table 55. The antibodies from Lineage 43 (43B1, 43D7, 43D8 and 43Ea) also bind a unique epitope, referred to as Epitope Bin 7 in Table 55. The antibody from Lineage 29 (29E) binds a unique epitope, referred to as Epitope Bin 2 in Table 55. The antibodies from Lineage 39 and 54 (39A and 54E) bind a unique epitope, referred to as Epitope Bin 3 in Table 55.

Figure 39A:
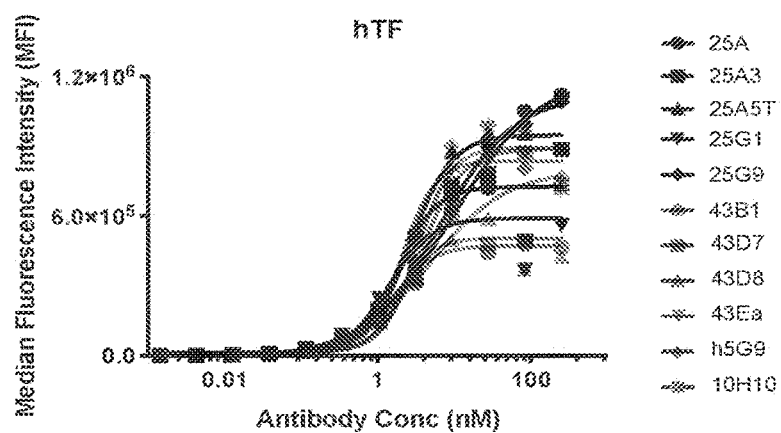
FIGS. 39A-F show the titration curves of anti-TF antibodies from lineages 25 and 43, h5G9, and 10H10 on select TF constructs.
Figure 39B:
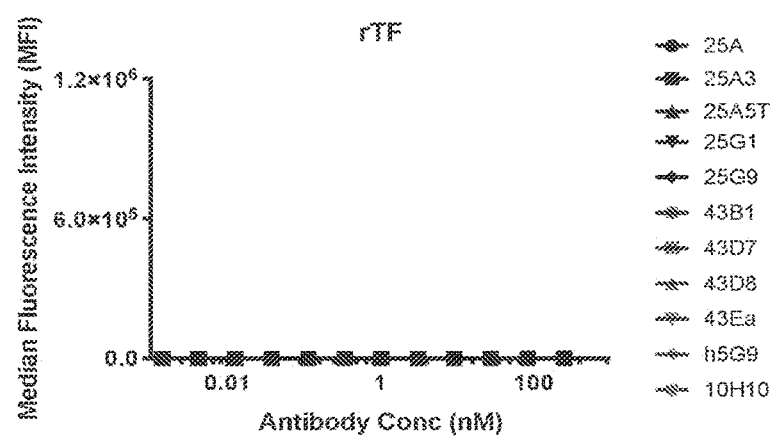
Figure 39C:
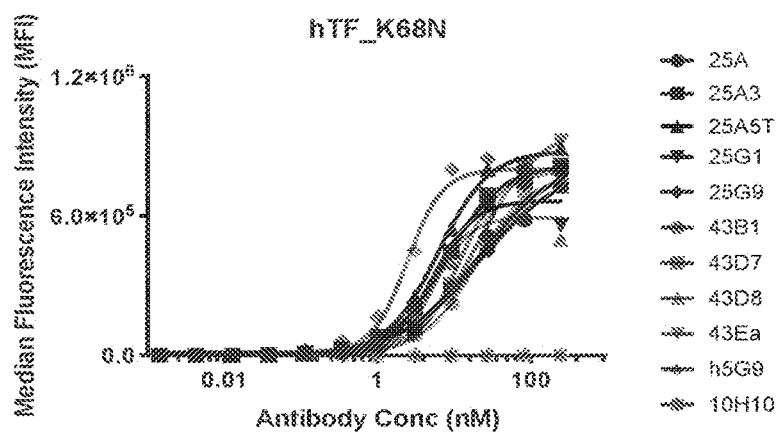
Figure 39D:
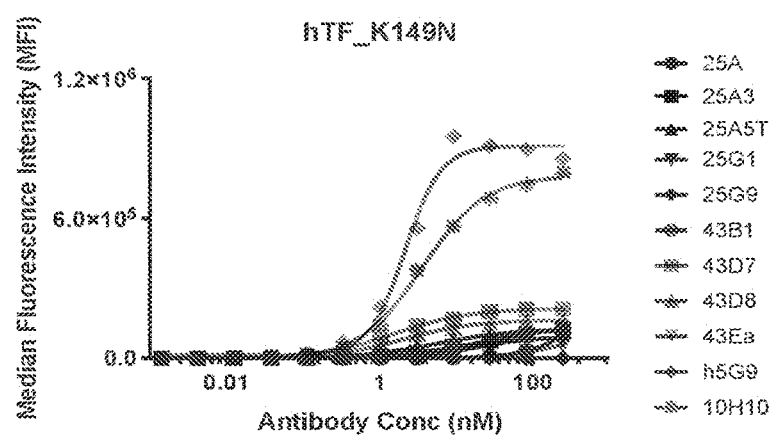
Figure 39E:
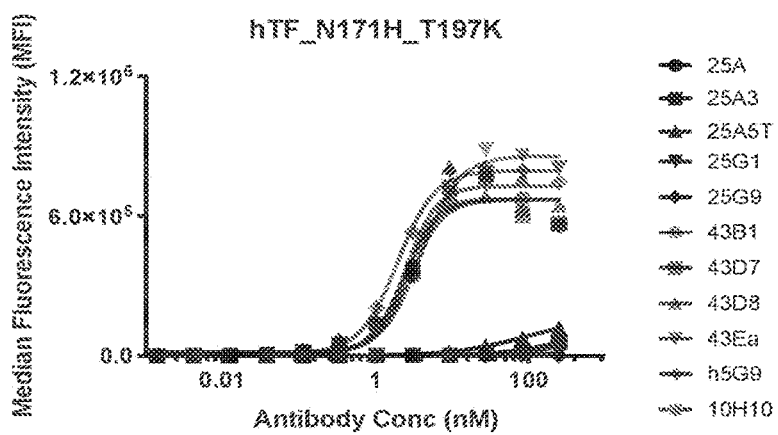
Figure 39F:
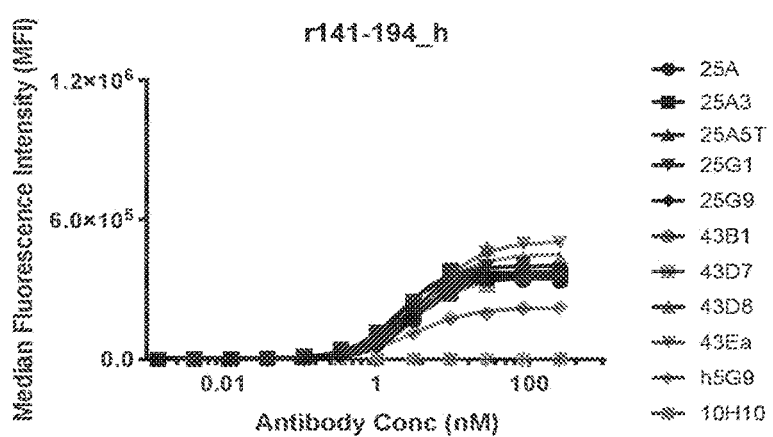

Lineage 25 and 43 antibodies are the only antibodies in the antibody panel that bind r141-194_h, the chimeric construct in which rat amino acids 141-194 were replaced by human sequence (FIG. 39F; Table 54). Furthermore, while M1593 cannot bind hTF_K68N, all the other antibodies in the antibody panel bind hTF_K68N (FIG. 39C; Table 54). Only Lineage 25 and 43 antibodies cannot bind hTF_K149N (FIG. 39D; Table 54). Only Lineage 25 antibodies cannot bind hTF_N171H_T197K (FIG. 39E; Table 54).

In summary, these results indicate that lineage 25 antibodies bind a unique epitope on human TF compared to all other antibodies tested. Lineage 43 antibodies bind a unique epitope on human TF compared to all other antibodies tested. Lineage 25 and lineage 43 antibodies bind a different epitope on human TF from M1593.

TABLE 51

Percent antibody binding to TF construct relative to hTF

| | Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|---|
| | hTF | 100 | 100 | 100 | 100 | 100 | 100 | 100 | 100 | 100 | 100 | 100 | 100 | 100 | 100 | 100 | 100 |
| | rTF | 0 | 0 | 0 | 0 | 0 | 0 | 0 | 0 | 0 | 0 | 0 | 0 | 0 | 0 | 0 | 0 |
| Human amino acid segment replaced by rat segment (in parentheses: number of amino acid changes relative to human TF) | h1-107r (52) | 0 | 0 | 0 | 0 | 0 | 41 | 0 | 32 | 36 | 36 | 37 | 28 | 33 | 35 | 31 | 37 |
| | h1-77_r (25) | 0 | 0 | 0 | 0 | 0 | 94 | 0 | 86 | 95 | 84 | 88 | 64 | 64 | 75 | 69 | 69 |
| | h1-38r (14) | 91 | 87 | 100 | 102 | 104 | 100 | 104 | 101 | 104 | 93 | 101 | 88 | 97 | 106 | 104 | 103 |
| | h39-77r (11) | 0 | 0 | 0 | 0 | 0 | 88 | 2 | 82 | 88 | 80 | 87 | 71 | 59 | 75 | 71 | 69 |
| | h78-107r (21) | 0 | 8 | 81 | 68 | 32 | 114 | 74 | 108 | 116 | 103 | 113 | 108 | 113 | 114 | 117 | 114 |
| | h78-107_r.v2 (27) | 0 | 0 | 76 | 62 | 23 | 101 | 59 | 95 | 96 | 91 | 94 | 93 | 97 | 100 | 101 | 101 |
| | h78-93r (18) | 102 | 0 | 77 | 91 | 110 | 102 | 104 | 106 | 105 | 92 | 101 | 98 | 101 | 104 | 102 | 103 |
| | h94-107r (9) | 1 | 82 | 85 | 89 | 27 | 91 | 46 | 82 | 86 | 78 | 83 | 77 | 84 | 92 | 89 | 91 |
| | h108-219r (46) | 119 | 118 | 118 | 122 | 128 | 0 | 0 | 0 | 0 | 0 | 0 | 0 | 0 | 0 | 0 | 0 |
| | h108-158r (19) | 98 | 101 | 107 | 108 | 108 | 63 | 4 | 1 | 0 | 0 | 11 | 22 | 0 | 1 | 0 | 0 |
| | h108-132r (10) | 105 | 108 | 109 | 107 | 124 | 125 | 124 | 112 | 112 | 106 | 111 | 118 | 122 | 126 | 122 | 124 |
| | h133-158r (9) | 113 | 122 | 119 | 130 | 134 | 91 | 0 | 0 | 0 | 0 | 2 | 3 | 0 | 4 | 1 | 0 |
| | h133-145r (4) | 84 | 95 | 96 | 104 | 104 | 108 | 100 | 77 | 80 | 80 | 87 | 100 | 99 | 104 | 103 | 106 |
| | h133-139r (2) | 82 | 90 | 95 | 103 | 102 | 104 | 103 | 88 | 89 | 88 | 91 | 86 | 94 | 101 | 97 | 101 |
| | h140-145r (2) | 89 | 100 | 101 | 110 | 109 | 113 | 97 | 80 | 87 | 86 | 89 | 105 | 101 | 104 | 104 | 109 |
| | h146-158r (5) | 115 | 122 | 125 | 134 | 134 | 91 | 133 | 2 | 17 | 18 | 17 | 0 | 3 | 20 | 10 | 0 |
| | h146-151r (1) | 122 | 133 | 139 | 142 | 143 | 141 | 118 | 3 | 14 | 17 | 7 | 0 | 11 | 39 | 23 | 2 |
| | h152-158r (4) | 110 | 121 | 128 | 127 | 136 | 82 | 132 | 110 | 116 | 112 | 116 | 111 | 119 | 134 | 129 | 134 |
| | h159-219r (27) | 132 | 134 | 141 | 142 | 155 | 0 | 137 | 0 | 0 | 0 | 0 | 0 | 132 | 130 | 130 | 76 |
| | h159-189r (11) | 94 | 101 | 104 | 110 | 112 | 0 | 105 | 0 | 0 | 0 | 0 | 0 | 100 | 106 | 104 | 94 |
| | h159-174r (6) | 96 | 98 | 101 | 118 | 120 | 0 | 98 | 0 | 0 | 0 | 0 | 0 | 103 | 115 | 112 | 101 |
| | h159-166r (3) | 89 | 93 | 96 | 100 | 98 | 104 | 100 | 93 | 95 | 87 | 91 | 88 | 99 | 106 | 105 | 110 |
| | h167-174r (3) | 96 | 112 | 96 | 122 | 128 | 0 | 118 | 0 | 0 | 0 | 0 | 0 | 109 | 121 | 112 | 104 |
| | h175-189r (5) | 97 | 113 | 112 | 118 | 123 | 119 | 114 | 86 | 95 | 99 | 100 | 86 | 109 | 118 | 114 | 122 |
| | h190-219r (16) | 111 | 138 | 149 | 141 | 145 | 12 | 143 | 125 | 124 | 119 | 127 | 144 | 133 | 140 | 136 | 147 |

TABLE 52

Percent antibody binding to TF construct relative to hTF

| Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|
| hTF | 100 | 100 | 100 | 100 | 100 | 100 | 100 | 100 | 100 | 100 | 100 | 100 | 100 | 100 | 100 | 100 |
| rTF | 0 | 0 | 0 | 0 | 0 | 0 | 0 | 0 | 0 | 0 | 0 | 0 | 0 | 0 | 0 | 0 |
| r141-194_h* | 0 | 0 | 0 | 0 | 0 | 32 | 0 | 65 | 89 | 88 | 83 | 108 | 90 | 102 | 95 | 81 |
| hTF_K68N | 105 | 115 | 119 | 118 | 111 | 132 | 0 | 93 | 124 | 126 | 115 | 103 | 107 | 116 | 119 | 118 |
| hTF_K149N | 115 | 117 | 131 | 127 | 132 | 145 | 111 | 2 | 12 | 13 | 7 | 0 | 10 | 29 | 20 | 1 |
| hTF_N171H_T197K | 83 | 98 | 94 | 89 | 109 | 102 | 113 | 1 | 4 | 7 | 1 | 0 | 98 | 101 | 103 | 118 |

*rat amino acid segment replaced by human segment, resulting in 20 amino acid changes

TABLE 53

Antibody binding to TF construct

| | Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|---|
| | hTF | 1 | 1 | 1 | 1 | 1 | 1 | 1 | 1 | 1 | 1 | 1 | 1 | 1 | 1 | 1 | 1 |
| | rTF | 0 | 0 | 0 | 0 | 0 | 0 | 0 | 0 | 0 | 0 | 0 | 0 | 0 | 0 | 0 | 0 |
| Human amino acid segment replaced by rat segment (in parentheses: number of amino acid changes relative to human TF) | h1-107_r (52) | 0 | 0 | 0 | 0 | 0 | 0 | 0 | 0 | 0 | 0 | 0 | 0 | 0 | 0 | 0 | 0 |
| | h1-77_r (25) | 0 | 0 | 0 | 0 | 0 | 1 | 0 | 1 | 1 | 1 | 1 | 1 | 1 | 1 | 1 | 1 |
| | h1-38_r (14) | 1 | 1 | 1 | 1 | 1 | 1 | 1 | 1 | 1 | 1 | 1 | 1 | 1 | 1 | 1 | 1 |
| | h39-77_r (11) | 0 | 0 | 0 | 0 | 0 | 1 | 0 | 1 | 1 | 1 | 1 | 1 | 1 | 1 | 1 | 1 |
| | h78-107_r (21) | 0 | 0 | 1 | 1 | 0 | 1 | 1 | 1 | 1 | 1 | 1 | 1 | 1 | 1 | 1 | 1 |
| | h78-107_r.v2 (27) | 0 | 0 | 1 | 1 | 0 | 1 | 1 | 1 | 1 | 1 | 1 | 1 | 1 | 1 | 1 | 1 |
| | h78-93_r (18) | 1 | 0 | 1 | 1 | 1 | 1 | 1 | 1 | 1 | 1 | 1 | 1 | 1 | 1 | 1 | 1 |
| | h94-107_r (9) | 0 | 1 | 1 | 1 | 0 | 1 | 0 | 1 | 1 | 1 | 1 | 1 | 1 | 1 | 1 | 1 |
| | h108-219_r (46) | 1 | 1 | 1 | 1 | 1 | 0 | 0 | 0 | 0 | 0 | 0 | 0 | 0 | 0 | 0 | 0 |

TABLE 53-continued

Antibody binding to TF construct

| Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|
| h108-158_r (19) | 1 | 1 | 1 | 1 | 1 | 1 | 0 | 0 | 0 | 0 | 0 | 0 | 0 | 0 | 0 | 0 |
| h108-132_r (10) | 1 | 1 | 1 | 1 | 1 | 1 | 1 | 1 | 1 | 1 | 1 | 1 | 1 | 1 | 1 | 1 |
| h133-158_r (9) | 1 | 1 | 1 | 1 | 1 | 1 | 0 | 0 | 0 | 0 | 0 | 0 | 0 | 0 | 0 | 0 |
| h133-145_r (4) | 1 | 1 | 1 | 1 | 1 | 1 | 1 | 1 | 1 | 1 | 1 | 1 | 1 | 1 | 1 | 1 |
| h133-139_r (2) | 1 | 1 | 1 | 1 | 1 | 1 | 1 | 1 | 1 | 1 | 1 | 1 | 1 | 1 | 1 | 1 |
| h140-145_r (2) | 1 | 1 | 1 | 1 | 1 | 1 | 1 | 1 | 1 | 1 | 1 | 1 | 1 | 1 | 1 | 1 |
| h146-158_r (5) | 1 | 1 | 1 | 1 | 1 | 1 | 1 | 0 | 0 | 0 | 0 | 0 | 0 | 0 | 0 | 0 |
| h146-151_r (1) | 1 | 1 | 1 | 1 | 1 | 1 | 1 | 0 | 0 | 0 | 0 | 0 | 0 | 0 | 0 | 0 |
| h152-158_r (4) | 1 | 1 | 1 | 1 | 1 | 1 | 1 | 1 | 1 | 1 | 1 | 1 | 1 | 1 | 1 | 1 |
| h159-219_r (27) | 1 | 1 | 1 | 1 | 1 | 0 | 1 | 0 | 0 | 0 | 0 | 0 | 1 | 1 | 1 | 1 |
| h159-189_r (11) | 1 | 1 | 1 | 1 | 1 | 0 | 1 | 0 | 0 | 0 | 0 | 0 | 1 | 1 | 1 | 1 |
| h159-174_r (6) | 1 | 1 | 1 | 1 | 1 | 0 | 1 | 0 | 0 | 0 | 0 | 0 | 1 | 1 | 1 | 1 |
| h159-166_r (3) | 1 | 1 | 1 | 1 | 1 | 1 | 1 | 1 | 1 | 1 | 1 | 1 | 1 | 1 | 1 | 1 |
| h167-174_r (3) | 1 | 1 | 1 | 1 | 1 | 0 | 1 | 0 | 0 | 0 | 0 | 0 | 1 | 1 | 1 | 1 |
| h175-189_r (5) | 1 | 1 | 1 | 1 | 1 | 1 | 1 | 1 | 1 | 1 | 1 | 1 | 1 | 1 | 1 | 1 |
| h190-219_r (16) | 1 | 1 | 1 | 1 | 1 | 0 | 1 | 1 | 1 | 1 | 1 | 1 | 1 | 1 | 1 | 1 |

TABLE 54

Antibody binding to TF construct

| Construct | 1F | 29E | 39A | 54E | TF-011 | 5G9 | M1593 | 25A | 25A3 | 25A5-T | 25G1 | 25G9 | 43B1 | 43D7 | 43D8 | 43Ea |
|---|---|---|---|---|---|---|---|---|---|---|---|---|---|---|---|---|
| hTF | 1 | 1 | 1 | 1 | 1 | 1 | 1 | 1 | 1 | 1 | 1 | 1 | 1 | 1 | 1 | 1 |
| rTF | 0 | 0 | 0 | 0 | 0 | 0 | 0 | 0 | 0 | 0 | 0 | 0 | 0 | 0 | 0 | 0 |
| r141-194_h* | 0 | 0 | 0 | 0 | 0 | 0 | 0 | 1 | 1 | 1 | 1 | 1 | 1 | 1 | 1 | 1 |
| hTF_K68N | 1 | 1 | 1 | 1 | 1 | 1 | 0 | 1 | 1 | 1 | 1 | 1 | 1 | 1 | 1 | 1 |
| hTF_K149N | 1 | 1 | 1 | 1 | 1 | 1 | 1 | 0 | 0 | 0 | 0 | 0 | 0 | 0 | 0 | 0 |
| hTF_N171H_T197K | 1 | 1 | 1 | 1 | 1 | 1 | 1 | 0 | 0 | 0 | 0 | 0 | 1 | 1 | 1 | 1 |

*rat amino acid segment replaced by human segment, resulting in 20 amino acid changes

TABLE 55

Epitope Bin assignment based on unbound chimeric constructs

| Antibody | Constructs not bound by antibody | Epitope Bin |
|---|---|---|
| 1F | rTF, h1-107_r, h1-77_r, h39-77_r, h78-107_r, h78-107_r.v2. h94-107_r | 1 |
| 29E | rTF, h1-107_r, h1-77_r, h39-77_r, h78-107_r, H78-107_r.v2, H78-93_r | 2 |
| 39A | rTF, h1-107_r, h1-77_r, h39-77_r | 3 |
| 54E | rTF, h1-107_r, h1-77_r, h39-77_r | 3 |
| TF-011 | rTF, h1-107_r, h1-77_r, h39-77_r, h78-107_r, h78-107_r.v2, h94-107_r | 1 |
| 5G9 | rTF, h1-107_r, h108-219_r, h159-219_r, h159-189_r, h159-174_r, h 167-174_r, h190-219_r | 4 |
| M1593 | rTF, h1-107_r, h1-77_r, h39-77_r, h94-107_r, h108-219_r, h 108-158_r, h133-158_r | 5 |
| 25A | rTF, h1-107_r, h108-219_r, h108-158_r, h133-158_r, h146-158_r, h146-151_r, h159-219_r, h159-189_r, h159-174_r, h167-174_r | 6 |
| 25A3 | rTF, h1-107_r, h108-219_r, h108-158_r, h133-158_r, h146-158_r, h146-151_r, h159-219 r, h159-189_r, h159-174_r, h167-174_r | 6 |
| 25A5-T | rTF, h1-107_r, h108-219_r, h108-158_r, h133-158_r, h146-158_r, h146-151_r, h159-219_r, h 159-189_r, h159-174_r, h167-174_r | 6 |
| 25G1 | rTF, h1-107_r, h108-219_r, h108-158_r, h133-158_r, h146-158_r, h146-151_r, h159-219_r, h159-189_r, h159-174_r, h167-174_r | 6 |
| 25G9 | rTF, h1-107_r, h108-219_r, h108-158_r, h133-158_r, h146-158_r, h146-151_r, h159-219_r, h159-189_r, h159-174 r, h167-174_r | 6 |
| 43B1 | rTF, h1-107_r, h108-219_r, h108-158_r, h133-158_r, h146-158_r, h146-151_r | 7 |
| 43D7 | rTF, h1-107_r, h108-219_r, h108-158_r, h133-158_r, h146-158_r, h146-151_r | 7 |
| 43D8 | rTF, h1-107_r, h108-219_r, h108-158_r, h133-158_r, h146-158_r, h146-151_r | 7 |
| 43Ea | rTF, h1-107_r, h108-219_r, h108-158_r, h133-158_r, h146-158_r, h146-151_r | 7 |

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

TABLE 13

| | Variable region sequences | |
|---|---|---|
| Clone | VH Domains (SEQ ID NO) | VL Domains (SEQ ID NO) |
| 1F | EVQLLESGGGLVQPGGSLRLSCAASG FTFSDYAMGWVRQAPGKGLEWVSTIS GSGGLTYYADSVKGRFTISRDNSKNT LYLQMNSLRAEDTAVYYCAKAPYGYY MDVWGKGTTVTVSS (SEQ ID NO: 37) | DIQMTQSPSTLSASVGDRVTITCRASQ SISSWLAWYQQKPGKAPKLLIYKASSL ESGVPSRFSGSGSGTEFTLTISSLQPD DFATYYCQQYKSYITFGGGTKVEIK (SEQ ID NO: 38) |
| 1G | EVQLLESGGGLVQPGGSLRLSCAASG FTFSSYAMAWVRQAPGKGLEWVSAIS GSGGLTYYADSVKGRFTISRDNSKNT LYLQMNSLRAEDTAVYYCAKAPYGYY MDVWGKGTTVTVSS (SEQ ID NO: 75) | DIQMTQSPSTLSASVGDRVTITCRASQ SISSWLAWYQQKPGKAPKLLIYKASSL ESGVPSRFSGSGSGTEFTLTISSLQPD DFATYYCQQYKSYITFGGGTKVEIK (SEQ ID NO: 76) |
| 25A | QVQLVQSGAEVKKPGASVKVSCKASG YTFDVYGISWVRQAPGQGLEWMGWIA PYNGNTNYAQKLQGRVTMTTDTSTST AYMELRSLRSDDTAVYYCARDAGTYS PFGYGMDVWGQGTTVTVSS (SEQ ID NO: 113) | DIQMTQSPSTLSASVGDRVTITCRASQ SISSWLAWYQQKPGKAPKLLIYKASSL ESGVPSRFSGSGSGTEFTLTISSLQPD DFATYYCQQFQSLPPFTFGGGTKVEIK (SEQ ID NO: 114) |
| 25A3 | QVQLVQSGAEVKKPGASVKVSCKASG YTFDVYGISWVRQAPGQGLEWMGWIA PYSGNTNYAQKLQGRVTMTTDTSTST AYMELRSLRSDDTAVYYCARDAGTYS PFGYGMDVWGQGTTVTVSS (SEQ ID NO: 151) | DIQMTQSPSTLSASVGDRVTITCQASQ SINNWLAWYQQKPGKAPKLLIYKAYNL ESGVPSRFSGSGSGTEFTLTISSLQPD DFATYYCQLFQSLPPFTFGGGTKVEIK (SEQ ID NO: 152) |
| 25A5 | QVQLVQSGAEVKKPGASVKVSCKASG YTFDVYGISWVRQAPGQGLEWMGWIA PYSGNTNYAQKLQGRVTMTTDTSTST AYMELRSLRSDDTAVYYCARDAGTYS PFGYGMDVWGQGTTVTVSS (SEQ ID NO: 189) | DIQMTQSPSTLSASVGDRVTITCRASE SISNWLAWYQQKPGKAPKLLIYKAYSL EYGVPSRFSGSGSGTEFTLTISSLQPD DFATYYCQQFQKLPPFTFGGGTKVEIK (SEQ ID NO: 190) |
| 25A5-T | QVQLVQSGAEVKKPGASVKVSCKASG YTFDAYGISWVRQAPGQGLEWMGWIA PYSGNTNYAQKLQGRVTMTTDTSTST AYMELRSLRSDDTAVYYCARDAGTYS PFGYGMDVWGQGTTVTVSS (SEQ ID NO: 836) | DIQMTQSPSTLSASVGDRVTITCRASE SISNWLAWYQQKPGKAPKLLIYKAYSL EYGVPSRFSGSGSGTEFTLTISSLQPD DFATYYCQQFQKLPPFTFGGGTKVEIK (SEQ ID NO: 837) |
| 25G | QVQLVQSGAEVKKPGASVKVSCKASG YTFRSYGISWVRQAPGQGLEWMGWVA PYNGNTNYAQKLQGRVTMTTDTSTST AYMELRSLRSDDTAVYYCARDAGTYS PYGYGMDVWGQGTTVTVSS (SEQ ID NO: 227) | DIQMTQSPSTLSASVGDRVTITCRASQ SISSWLAWYQQKPGKAPKLLIYKASSL ESGVPSRFSGSGSGTEFTLTISSLQPD DFATYYCQQFQSLPPFTFGGGTKVEIK (SEQ ID NO: 228) |
| 25G1 | QVQLVQSGAEVKKPGASVKVSCKASG YTFRSYGISWVRQAPGQGLEWMGWVA PYSGNTNYAQKLQGRVTMTTDTSTST AYMELRSLRSDDTAVYYCARDAGTYS PYGYGMDVWGQGTTVTVSS (SEQ ID NO: 265) | DIQMTQSPSTLSASVGDRVTITCRASH SIDSWLAWYQQKPGKAPKLLIYKASYL ESGVPSRFSGSGSGTEFTLTISSLQPD DFATYYCQLFQSLPPFTFGGGTKVEIK (SEQ ID NO: 266) |
| 25G9 | QVQLVQSGAEVKKPGASVKVSCKASG YTFRSYGISWVRQAPGQGLEWMGWVA PYSGNTNYAQKLQGRVTMTTDTSTST AYMELRSLRSDDTAVYYCARDAGTYS PYGYGMDVWGQGTTVTVSS (SEQ ID NO: 303) | DIQMTQSPSTLSASVGDRVTITCQASQ SIDSWLAWYQQKPGKAPKLLIYSASYL ESGVPSRFSGSGSGTEFTLTISSLQPD DFATYYCQRFQSLPPFTFGGGTKVEIK (SEQ ID NO: 304) |

TABLE 13-continued

Variable region sequences

| Clone | VH Domains (SEQ ID NO) | VL Domains (SEQ ID NO) |
|---|---|---|
| 29D | QVQLVESGGGVVQPGRSLRLSCAASG FTFHSRGMHWVRQAPGKGLEWVAVIT YDGINKYYADSVEGRFTISRDNSKNT LYLQMNSLRAEDTAVYYCARDGVYYG VYDYWGQGTLVTVSS(SEQ ID NO: 341) | DIVMTQSPDSLAVSLGERATINCKSSQ SVLFSSNNKNYLAWYQQKPGQPPKLLI YWASTRESGVPDRFSGSGSGTDFTLTI SSLQAEDVAVYYCQQFHSYPLTFGGGT KVEIK(SEQ ID NO: 342) |
| 29E | QVQLVESGGGVVQPGRSLRLSCAASG FTFRSYGMHWVRQAPGKGLEWVAVIT YDGINKYYADSVEGRFTISRDNSKNT LYLQMNSLRAEDTAVYYCARDGVYYG VYDYWGQGTLVTVSS(SEQ ID NO: 379) | DIVMTQSPDSLAVSLGERATINCKSSQ SVLFSSNNKNYLAWYQQKPGQPPKLLI YWASTRESGVPDRFSGSGSGTDFTLTI SSLQAEDVAVYYCQQFHSYPLTFGGGT KVEIK(SEQ ID NO: 380) |
| 39A | QVQLVQSGAEVKKPGSSVKVSCKASG GTFSSNAIGWVRQAPGQGLEWMGSII PIIGFANYAQKFQGRVTITADESTST AYMELSSLRSEDTAVYYCARDSGYYY GASSFGMDVWGQGTTVTVSS(SEQ ID NO: 417) | EIVMTQSPATLSVSPGERATLSCRASQ SVSSNLAWYQQKPGQAPRLLIYGASTR ATGIPARFSGSGSGTEFTLTISSLQSE DFAVYYCEQYNNLPLTFGGGTKVEIK (SEQ ID NO: 418) |
| 43B | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDAPYYY GGGYYYYMDVWGKGTTVTVSS(SEQ ID NO: 455) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 456) |
| 43B1 | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDAPYYY GGGYYYYMDVWGKGTTVTVSS(SEQ ID NO: 493) | EIVLTQSPGTLSLSPGERATLSCRASE SVDSSYLAWYQQKPGQAPRLLIYGAST RQTGIPDRFSGSGSGTDFTLTISRLEP EDFAVYYCQQAGVVPYTFGGGTKVEIK (SEQ ID NO: 494) |
| 43B7 | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDAPYYY GGGYYYYMDVWGKGTTVTVSS(SEQ ID NO: 531) | EIVLTQSPGTLSLSPGERATLSCRASE SVDSSYLAWYQQKPGQAPRLLIYGADS RATGIPDRFSGSGSGTDFTLTISRLEP EDFAVYYCQQDGVVPYTFGGGTKVEIK (SEQ ID NO: 532) |
| 43D | QVQLQQWGAGLLKPSETLSLTCAVYG GSLSGYYWSWIRQPPGKGLEWIGEIG ASGSTRYNPSLKSRVTISVDTSKNQF SLKLSSVTAADTAVYYCARDTPYYYE GGYYYYMDVWGKGTTVTVSS(SEQ ID NO: 569) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 570) |
| 43D7 | QVQLQQWGAGLLKPSETLSLTCAVYG GSLSGYYWSWIRQPPGKGLEWIGEIG ASGSTRYNPSLKSRVTISVDTSKNQF SLKLSSVTAADTAVYYCARDTPYYYE GGYYYYMDVWGKGTTVTVSS(SEQ ID NO: 607) | EIVLTQSPGTLSLSPGERATLSCRASD SVDSSYLAWYQQKPGQAPRLLIYGAFS RANGIPDRFSGSGSGTDFTLTISRLEP EDFAVYYCQQAGVVPYTFGGGTKVEIK (SEQ ID NO: 608) |
| 43D8 | QVQLQQWGAGLLKPSETLSLTCAVYG GSLSGYYWSWIRQPPGKGLEWIGEIG ASGSTRYNPSLKSRVTISVDTSKNQF SLKLSSVTAADTAVYYCARDTPYYYE GGYYYYMDVWGKGTTVTVSS(SEQ ID NO: 645) | EIVLTQSPGTLSLSPGERATLSCRASQ SVSSSFLAWYQQKPGQAPRLLIYGAYS RATGIPDRFSGSGSGTDFTLTISRLEP EDFAVYYCQQAGVVPYTFGGGTKVEIK (SEQ ID NO: 646) |
| 43E | QVQLQESGPGLVKPSQTLSLTCTVSG GSISSGQYWSWIRQHPGKGLEWIGEI YYSGSTRYNPSLKSRVTISVDTSKDQ FSLKLSSVTAADTAVYYCARDTPYYY DGGYYYYMDVWGKGTTVTVSS(SEQ ID NO: 683) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 684) |
| 43Ea | QVQLQESGPGLVKPSQTLSLTCTVSG GSISSGQYWSWIRQHPGKGLEWIGEI YYSGSTRYNPSLKSRVTISVDTSKNQ FSLKLSSVTAADTAVYYCARDTPYYY DGGYYYYMDVWGKGTTVTVSS(SEQ ID NO: 721) | EIVLTQSPGTLSLSPGERATLSCRASQ SVSSSYLAWYQQKPGQAPRLLIYGASS RATGIPDRFSGSGSGTDFTLTISRLEP EDFAVYYCQQVGVVPYTFGGGTKVEIK (SEQ ID NO: 722) |

TABLE 13-continued

Variable region sequences

| Clone | VH Domains (SEQ ID NO) | VL Domains (SEQ ID NO) |
|---|---|---|
| 54E | QVQLVQSGAEVKKPGASVKVSCKASG YTFANYYMHWVRQAPGQGLEWMGIIN PSGGITVYAQKFQGRVTMTRDTSTST VYMELSSLRSEDTAVYYCARGGSKVA ALAFDIWGQGTMVTVSS (SEQ ID NO: 759) | DIQMTQSPSSLSASVGDRVTITCQASQ DISNSLNWYQQKPGKAPKLLIYDASNL ETGVPSRFSGSRSGTDFTFTISSLQPE DIATYYCQQYNFHPLTFGGGTKVEIK (SEQ ID NO: 760) |

TABLE 14

Variable region sequence consensus

| Group | VH Domain Consensus (SEQ ID NO) | VL Domain Consensus (SEQ ID NO) |
|---|---|---|
| 1 | EVQLLESGGGLVQPGGSLR LSCAASGFTFSx[D/S]YA Mx[A/G]WVRQAPGKGLEW VSx[A/T]ISGSGGLTYYA DSVKGRFTISRDNSKNTLY LQMNSLRAEDTAVYYCAKA PYGYYMDVWGKGTTVTVSS (SEQ ID NO: 761) | DIQMTQSPSTLSASVGDRV TITCRASQSISSWLAWYQQ KPGKAPKLLIYKASSLESG VPSRFSGSGSGTEFTLTIS SLQPDDFATYYCQQYKSYI TFGGGTKVEIK (SEQ ID NO: 762) |
| 25 | QVQLVQSGAEVKKPGASVK VSCKASGYTFx[D/R]x[S/ V/A]YGISWVRQAPGQG LEWMGWx[I/V]APYx[S/ N]GNTNYAQKLQGRVTMTT DTSTSTAYMELRSLRSDDT AVYYCARDAGTYSPx[F/ Y]GYGMDVWGQGTTVTVSS (SEQ ID NO: 763) | DIQMTQSPSTLSASVGDRV TITCx[R/Q]ASx[Q/E/ H]SIx[S/D/N]x[S/N]W LAWYQQKPGKAPKLLIYx [K/S]Ax[S/Y]x[S/Y/N] LEx[S/Y]GVPSRFSGSGS GTEFTLTISSLQPDDFATY YCQx[Q/L/R]FQx[S/K] LPPFTFGGGTKVEIK (SEQ ID NO: 764) |
| 29 | QVQLVESGGGVVQPGRSLR LSCAASGFTFx[H/R]Sx [R/Y]GMHWVRQAPGKGLEW VAVITYDGINKYYADSVEG RFTISRDNSKNTLYLQMNS LRAEDTAVYYCARDGVYYG VYDYWGQGTLVTVSS (SEQ ID NO: 765) | DIVMTQSPDSLAVSLGERA TINCKSSQSVLFSSNNKNY LAWYQQKPGQPPKLLIYWA STRESGVPDRFSGSGSGTD FTLTISSLQAEDVAVYYCQ QFHSYPLTFGGGTKVEIK (SEQ ID NO: 766) |
| 39 | QVQLVQSGAEVKKPGSSVK VSCKASGGTFSSNAIGWVR QAPGQGLEWMGSIIPIIGF ANYAQKFQGRVTITADEST STAYMELSSLRSEDTAVYY CARDSGYYYGASSFGMDVW GQGTTVTVSS (SEQ ID NO: 767) | EIVMTQSPATLSVSPGERA TLSCRASQSVSSNLAWYQQ KPGQAPRLLIYGASTRATG IPARFSGSGSGTEFTLTIS SLQSEDFAVYYCEQYNNLP LTFGGGTKVEIK (SEQ ID NO: 768) |
| 43 | QVQLQx[E/Q]x[S/W]Gx [P/A]GLx[V/L]KPSx[Q/ E]TLSLTCx[T/A]Vx[S/ Y]GGSx[I/L]SSGx[Q/ Y]YWSWIRQx[H/P]PG KGLEWIGEIx[Y/G]x[Y/ A]SGSTRYNPSLKSRVTIS VDTSKx[N/D]QFSLKLSS VTAADTAVYYCARDx[T/ A]PYYYx[E/G/D]GGYYY YMDVWGKGTTVTVSS (SEQ ID NO: 769) | EIVLTQSPGTLSLSPGERA TLSCRASx[Q/E/D]SVx [S/D]SSx[Y/F]LAWYQQK PGQAPRLLIYGAx[S/D/ F/Y]x[S/T]Rx[A/Q]x [T/N]GIPDRFSGSGSGTDF TLTISRLEPEDFAVYYCQQ x[V/A/D]GVVPYTFGGGT KVEIK (SEQ ID NO: 770) |
| 54 | QVQLVQSGAEVKKPGASVK VSCKASGYTFANYYMHWVR QAPGQGLEWMGHNPSGGIT VYAQKFQGRVTMTRDTSTS TVYMELSSLRSEDTAVYYC ARGGSKVAALAFDIWGQGT MVTVSS (SEQ ID NO: 771) | DIQMTQSPSSLSASVGDRV TITCQASQDISNSLNWYQQ KPGKAPKLLIYDASNLETG VPSRFSGSRSGTDFTFTIS SLQPEDIATYYCQQYNFHP LTFGGGTKVEIK (SEQ ID NO: 772) |

TABLE 15

Antibody 1F-CDR Sequences

| | | Exemplary* | Kabat | Chothia | AbM | Contact | IMGT |
|---|---|---|---|---|---|---|---|
| VH CDR Seq. | VH CDR1 | GFTFSDYAMG (SEQ ID NO: 1) | DYAMG (SEQ ID NO: 7) | GFTFSDY (SEQ ID NO: 13) | GFTFSDYAMG (SEQ ID NO: 19) | SDYAMG (SEQ ID NO: 25) | GFTFSDYA (SEQ ID NO: 31) |
| | VH CDR2 | TISGSGGLTY YADSVKG (SEQ ID NO: 2) | TISGSGGLTYY ADSVKG (SEQ ID NO: 8) | GSGG (SEQ ID NO: 14) | TISGSGGLTY (SEQ ID NO: 20) | WVSTISG SGGLTY (SEQ ID NO: 26) | ISGSGGLT (SEQ ID NO: 32) |
| | VH CDR3 | APYGYYMDV (SEQ ID NO: 3) | APYGYYMDV (SEQ ID NO: 9) | PYGYYMD (SEQ ID NO: 15) | APYGYYMDV (SEQ ID NO: 21) | AKAPYGY YMD (SEQ ID NO: 27) | AKAPYGYY MDV (SEQ ID NO: 33) |
| VL CDR Seq. | VL CDR1 | RASQSISSWLA (SEQ ID NO: 4) | RASQSISSWLA (SEQ ID NO: 10) | SQSISSW (SEQ ID NO: 16) | RASQSISSWL A (SEQ ID NO: 22) | SSWLAWY (SEQ ID NO: 28) | QSISSW (SEQ ID NO: 34) |
| | VL CDR2 | KASSLES (SEQ ID NO: 5) | KASSLES (SEQ ID NO: 11) | KAS (SEQ ID NO: 17) | KASSLES (SEQ ID NO: 23) | LLIYKAS SLE (SEQ ID NO: 29) | KAS |

TABLE 15-continued

Antibody 1F-CDR Sequences

|  | Exemplary* | Kabat | Chothia | AbM | Contact | IMGT |
|---|---|---|---|---|---|---|
| VL CDR3 | QQYKSYIT (SEQ ID NO: 6) | QQYKSYIT) (SEQ ID NO: 12) | YKSYI (SEQ ID NO: 18) | QQYKSYIT (SEQ ID NO: 24) | QQYKSYI (SEQ ID NO: 30) | QQYKSYIT (SEQ ID NO: 36) |

VH Sequence*:
EVQLLESGGGLVQPGGSLRLSCAASGFTFSDYAMGWVRQAPGKGLEWVSTISGSGGLTYYADSVKGR
FTISRDNSKNTLYLQMNSLRAEDTAVYYCAKAPYGYYMDVWGKGTTVTVSS (SEQ ID NO: 37)

VL Sequence*:
DIQMTQSPSTLSASVGDRVTITCRASQSISSWLAWYQQKPGKAPKWYKASSLESGVPSRFSGSGSGT
EFTLTISSLQPDDFATYYCQQYKSYITFGGGTKVEIK (SEQ ID NO: 38)

*Exemplary CDR sequences encompass amino acids as determined by Kabat plus Chothia

TABLE 16

Antibody 1G-CDR Sequences

|  |  | Exemplary* | Kabat | Chothia | AbM | Contact | IMGT |
|---|---|---|---|---|---|---|---|
| VH CDR Seq. | VH CDR1 | GFTFSSYAMA (SEQ ID NO: 39) | SYAMA (SEQ ID NO: 45) | GFTFSSY (SEQ ID NO: 51) | GFTFSSYAMA (SEQ ID NO: 57) | SSYAMA (SEQ ID NO: 63) | GFTFSSYA (SEQ ID NO: 69) |
|  | VH CDR2 | AISGSGGLTYYADSVKG (SEQ ID NO: 40) | AISGSGGLTYYADSVKG (SEQ ID NO: 46) | GSGG (SEQ ID NO: 52) | AISGSGGLTY (SEQ ID NO: 58) | WVSAISGSGGLTY (SEQ ID NO: 64) | ISGSGGLT (SEQ ID NO: 70) |
|  | VH CDR3 | APYGYYMDV (SEQ ID NO: 41) | APYGYYMDV (SEQ ID NO: 47) | PYGYYMD (SEQ ID NO: 53) | APYGYYMDV (SEQ ID NO: 59) | AKAPYGYYMD (SEQ ID NO: 65) | AKAPYGYYMDV (SEQ ID NO: 71) |
| VL CDR Seq. | VL CDR1 | RASQSISSWLA (SEQ ID NO: 42) | RASQSISSWLA (SEQ ID NO: 48) | SQSISSW (SEQ ID NO: 54) | RASQSISSWLA (SEQ ID NO: 60) | SSWLAWY (SEQ ID NO: 66) | QSISSW (SEQ ID NO: 72) |
|  | VL CDR2 | KASSLES (SEQ ID NO: 43) | KASSLES (SEQ ID NO: 49) | KAS | KASSLES (SEQ ID NO: 61) | LLIYKASSLE (SEQ ID NO: 67) | KAS |
|  | VL CDR3 | QQYKSYIT (SEQ ID NO: 44) | QQYKSYIT (SEQ ID NO: 50) | YKSYI (SEQ ID NO: 56) | QQYKSYIT (SEQ ID NO: 62) | QQYKSYI (SEQ ID NO: 68) | QQYKSYIT (SEQ ID NO: 74) |

VH Sequence*:
EVQLLESGGGLVQPGGSLRLSCAASGFTFSSYAMAWVRQAPGKGLEWVSAISGSGGLTYYADSVKGRF
TISRDNSKNTLYLQMNSLRAEDTAVYYCAKAPYGYYMDVWGKGTTVTVSS (SEQ ID NO: 75)

VL Sequence*:
DIQMTQSPSTLSASVGDRVTITCRASQSISSWLAWYQQKPGKAPKLLIYKASSLESGVPSRFSGSGSG
TEFTLTISSLQPDDFATYYCQQYKSYITFGGGTKVEIK (SEQ ID NO: 76)

*Exemplary CDR sequences encompass amino acids as determined by Kabat plus Chothia

TABLE 17

Antibody 25A-CDR Sequences

|  |  | Exemplary* | Kabat | Chothia | AbM | Contact | IMGT |
|---|---|---|---|---|---|---|---|
| VH CDR Seq. | VH CDR1 | GYTFDVYGIS (SEQ ID NO: 77) | VYGIS (SEQ ID NO: 83) | GYTFDVY (SEQ ID NO: 89) | GYTFDVYGIS (SEQ ID NO: 95) | DVYGIS (SEQ ID NO: 101) | GYTFDVYG (SEQ ID NO: 107) |
|  | VH CDR2 | WIAPYNGNTNYAQKLQG (SEQ ID NO: 78) | WIAPYNGNTNYAQKLQG (SEQ ID NO: 84) | PYNG (SEQ ID NO: 90) | WIAPYNGNTN (SEQ ID NO: 96) | WMGWIAPYNGNTN (SEQ ID NO: 102) | IAPYNGNT (SEQ ID NO: 108) |
|  | VH CDR3 | DAGTYSPFGYGMDV (SEQ ID NO: 79) | DAGTYSPFGYGMDV (SEQ ID NO: 85) | AGTYSPFGYGMD (SEQ ID NO: 91) | DAGTYSPFGYGMDV (SEQ ID NO: 97) | ARDAGTYSPFGYGMD (SEQ ID NO: 103) | ARDAGTYSPFGTGMDV (SEQ ID NO: 109) |

TABLE 17-continued

Antibody 25A-CDR Sequences

|  |  | Exemplary* | Kabat | Chothia | AbM | Contact | IMGT |
|---|---|---|---|---|---|---|---|
| VL CDR Seq. | VL CDR1 | RASQSISSWLA (SEQ ID NO: 80) | RASQSISSWLA (SEQ ID NO: 86) | SQSISSW (SEQ ID NO: 92) | RASQSISSWLA (SEQ ID NO: 98) | SSWLAWY (SEQ ID NO: 104) | QSISSW (SEQ ID NO: 110) |
|  | VL CDR2 | KASSLES (SEQ ID NO: 81) | KASSLES (SEQ ID NO: 87) | KAS | KASSLES (SEQ ID NO: 99) | LLIYKASSLE (SEQ ID NO: 105) | KAS |
|  | VL CDR3 | QQFQSLPPFT (SEQ ID NO: 82) | QQFQSLPPFT (SEQ ID NO: 88) | FQSLPPF (SEQ ID NO: 94) | QQFQSLPPFT (SEQ ID NO: 100) | QQFQSLPPF (SEQ ID NO: 106) | QQFQSLPPFT (SEQ ID NO: 112) |

VH Sequence*:
QVQLVQSGAEVKKPGASVKVSCKASGYTFDVYGISWVRQAPGQGLEWMGWIAPYNGNTNYAQKLQGRVTMT
TDTSTSTAYMELRSLRSDDTAVYYCARDAGTYSPFGYGMDVWGQGTTVTVSS (SEQ ID NO: 113)

VL Sequence*:
DIQMTQSPSTLSASVGDRVTITCRASQSISSWLAWYQQKPGKAPKWYKASSLESGVPSRFSGSGSGTEFTL
TISSLQPDDFATYYCQQFQSLPPFTFGGGTKVEIK (SEQ ID NO: 114)

*Exemplary CDR sequences encompass amino acids as determined by Kabat plus Chothia

TABLE 18

Antibody 25A3-CDR Sequences

|  |  | Exemplary* | Kabat | Chothia | AbM | Contact | IMGT |
|---|---|---|---|---|---|---|---|
| VH CDR Seq. | VH CDR1 | GYTFDVYGIS (SEQ ID NO: 115) | VYGIS (SEQ ID NO: 121) | GYTFDVY (SEQ ID NO: 127) | GYTFDVYGIS (SEQ ID NO: 133) | DVYGIS (SEQ ID NO: 139) | GYTFDVYG (SEQ ID NO: 145) |
|  | VH CDR2 | WIAPYSGNTNY AQKLQG (SEQ ID NO: 116) | WIAPYSGNTNY AQKLQG (SEQ ID NO: 122) | PYSG (SEQ ID NO: 128) | WIAPYSGNTN (SEQ ID NO: 134) | WMGWIAPYSGN TN (SEQ ID NO: 140) | IAPYSGNT (SEQ ID NO: 146) |
|  | VH CDR3 | DAGTYSPFGYG MDV (SEQ ID NO: 117) | DAGTYSPFGYG MDV (SEQ ID NO: 123) | AGTYSPFG YGMD (SEQ ID NO: 129) | DAGTYSPFG MDV (SEQ ID NO: 135) | ARDAGTYSPFG YGMD (SEQ ID NO: 141) | ARDACTYS PFGTGMDV (SEQ ID NO: 147) |
| VL CDR Seq. | VL CDR1 | QASQSINNNWL A (SEQ ID NO: 118) | QASQSINNWLA (SEQ ID NO: 124) | SQSINNW (SEQ ID NO: 130) | QASQSINNWLA (SEQ ID NO: 136) | NNWLAWY (SEQ ID NO: 142) | QSINNW (SEQ ID NO: 148) |
|  | VL CDR2 | KAYNLES (SEQ ID NO: 119) | KAYNLES (SEQ ID NO: 125) | KAY | KAYNLES (SEQ ID NO: 137) | LLIYKAYNLE (SEQ ID NO: 143) | KAY |
|  | VL CDR3 | QLFQSLPPFT (SEQ ID NO: 120) | QLFQSLPPFT (SEQ ID NO: 126) | FQSLPPF (SEQ ID NO: 132) | QLFQSLPPFT (SEQ ID NO: 138) | QLFQSLPPF (SEQ ID NO: 144) | QLFQSLPPFT (SEQ ID NO: 150) |

VH Sequence*:
QVQLVQSGAEVKKPGASVKVSCKASGYTFDVYGISWVRQAPGQGLEWMGWIAPYSGNTNYAQKLQGRVTM
TTDTSTSTAYMELRSLRSDDTAVYYCARDAGTYSPFGYGMDVWGQGTTVTVSS (SEQ ID NO: 151)

VL Sequence*:
DIQMTQSPSTLSASVGDRVTITCQASQSINNWLAWYQQKPGKAPKLLIYKAYNLESGVPSRFSGSGSGTE
FTLTISSLQPDDFATYYCQLFQSLPPFTFGGGTKVEIK (SEQ ID NO: 152)

*Exemplary CDR sequences encompass amino acids as determined by Kabat plus Chothia TABLE 19a Antibody 25A5-CDR Sequences

|  |  | Exemplary* | Kabat | Chothia | AbM | Contact | IMGT |
|---|---|---|---|---|---|---|---|
| VH CDR Seq. | VH CDR1 | GYTFDVYGIS (SEQ ID NO: 153) | VYGIS (SEQ ID NO: 159) | GYTFDVY (SEQ ID NO: 165) | GYTFDVYGIS (SEQ ID NO: 171) | DVYGIS (SEQ ID NO: 177) | GYTFDVYG (SEQ ID NO: 183) |
|  | VH CDR2 | WIAPYSGNTNYAQKLQG (SEQ ID NO: 154) | WIAPYSGNTNYAQKLQG (SEQ ID NO: 160) | PYSG (SEQ ID NO: 166) | WIAPYSGNTNYAQKLQG (SEQ ID NO: 172) | WMGWIAPYSGNTN (SEQ ID NO: 178) | IAPYSGNT (SEQ ID NO: 184) |
|  | VH CDR3 | DAGTYSPFGYGMDV (SEQ ID NO: 155) | DAGTYSPFGYGMDV (SEQ ID NO: 161) | AGTYSPFGYGMD (SEQ ID NO: 167) | DAGTYSPFGYGMDV (SEQ ID NO: 173) | ARDAGTYSPFGYGMD (SEQ ID NO: 179) | ARDACTYSPFGTGMDV (SEQ ID NO: 185) |
| VL CDR Seq. | VL CDR1 | RASESISNWLA (SEQ ID NO: 156) | RASESISNWLA (SEQ ID NO: 162) | SESISNW (SEQ ID NO: 168) | RASESISNWLA (SEQ ID NO: 174) | SNWLAWY (SEQ ID NO: 180) | ESISNW (SEQ ID NO: 186) |
|  | VL CDR2 | KAYSLEY (SEQ ID NO: 157) | KAYSLEY (SEQ ID NO: 163) | KAY | KAYSLEY (SEQ ID NO: 175) | LLIYKAYSLE (SEQ ID NO: 181) | KAY |
|  | VL CDR3 | QQFQKLPPFT (SEQ ID NO: 158) | QQFQKLPPFT (SEQ ID NO: 164) | FQKLPPF (SEQ ID NO: 170) | QQFQKLPPFT (SEQ ID NO: 176) | QQFQKLPPF (SEQ ID NO: 182) | QQFQKLPPFT (SEQ ID NO: 188) |

VH Sequence*:
QVQLVQSGAEVKKPGASVKVSCKASGYTFDVYGISWVRQAPGQGLEWMGWIAPYSGNTNYAQKLQGRVTMTTDTSTAYMELRSLRSDDTAVYYCARDAGTYSPFGYGMDVWGQGTTVTVSS (SEQ ID NO: 189)

VL Sequence*:
DIQMTQSPSTLSASVGDRVTITCRASESISNWLAWYQQKPGKAPKWYKAYSLEYGVPSRFSGSGSGTEFTLTISSLQPDDFATYYCQQFQKLPPFTFGGGTKVEIK (SEQ ID NO: 190)

*Exemplary CDR sequences encompass amino acids as determined by Kabat plus Chothia TABLE 19b Antibody 25A5-T-CDR Sequences

|  |  | Exemplary* | Kabat | Chothia | AbM | Contact | IMGT |
|---|---|---|---|---|---|---|---|
| VH CDR Seq. | VH CDR1 | GYTFDAYGIS (SEQ ID NO: 884) | AYGIS (SEQ ID NO: 890) | GYTFDAY (SEQ ID NO: 896) | GYTFDAYGIS (SEQ ID NO: 902) | DAYGIS (SEQ ID NO: 908) | GYTFDAYG (SEQ ID NO: 914) |
|  | VH CDR2 | WIAPYSGNTNYAQKLQG (SEQ ID NO: 885) | WIAPYSGNTNYAQKLQG (SEQ ID NO: 891) | PYSG (SEQ ID NO: 897) | WIAPYSGNTN (SEQ ID NO: 903) | WMGWIAPYSGNTN (SEQ ID NO: 909) | IAPYSGNT (SEQ ID NO: 915) |
|  | VH CDR3 | DAGTYSPFGYGMDV (SEQ ID NO: 886) | DAGTYSPFGYGMDV (SEQ ID NO: 892) | AGTYSPFGYGMD (SEQ ID NO: 898) | DAGTYSPFGYGMDV (SEQ ID NO: 904) | ARDAGTYSPFGYGMD (SEQ ID NO: 910) | ARDACTYSPFGTGMDV (SEQ ID NO: 916) |
| VL CDR Seq. | VL CDR1 | RASESISNWLA (SEQ ID NO: 887) | RASESISNWLA (SEQ ID NO: 893) | SESISNW (SEQ ID NO: 899) | RASESISNWLA (SEQ ID NO: 905) | SNWLAWT (SEQ ID NO: 911) | ESISNW (SEQ ID NO: 917) |
|  | VL CDR2 | KAYSLEY (SEQ ID NO: 888) | KAYSLEY (SEQ ID NO: 894) | KAY | KAYSLEY (SEQ ID NO: 906) | LLIYKAYSLE (SEQ ID NO: 912) | KAY |
|  | VL CDR3 | QQFQKLPPFT (SEQ ID NO: 889) | QQFQKLPPFT (SEQ ID NO: 895) | FQKLPPF (SEQ ID NO: 901) | QQFQKLPPFT (SEQ ID NO: 907) | QQFQKLPPF (SEQ ID NO: 913) | QQFQKLPPFT (SEQ ID NO: 919) |

VH Sequence*:
QVQLVQSGAEVKKPGASVKVSCKASGYTFDAYGISWVRQAPGQGLEWMGWIAPYSGNTNYAQKLQGRVTMTTDTSTAYMELRSLRSDDTAVYYCARDAGTYSPFGYGMDVWGQGTTVTVSS (SEQ ID NO: 836)

VL Sequence*:
DIQMTQSPSTLSASVGDRVTITCRASESISNWLAWYQQKPGKAPKWYKAYSLEYGVPSRFSGSGSGTEFTLTISSLQPDDFATYYCQQFQKLPPFTFGGGTKVEIK (SEQ ID NO: 837)

*Exemplary CDR sequences encompass amino acids as determined by Kabat plus Chothia

TABLE 20

Antibody 25G-CDR Sequences

| | | Exemplary* | Kabat | Chothia | AbM | Contact | IMGT |
|---|---|---|---|---|---|---|---|
| VH CDR Seq. | VH CDR1 | GYTFRSYGIS (SEQ ID NO: 191) | SYGIS (SEQ ID NO: 197) | GYTFRSY (SEQ ID NO: 203) | GYTFRSYGIS (SEQ ID NO: 209) | RSYGIS (SEQ ID NO: 215) | GYTFRSYG (SEQ ID NO: 221) |
| | VH CDR2 | WVAPYNGNTNY AQKLQG (SEQ ID NO: 192) | WVAPYNGNTNY AQKLQG (SEQ ID NO: 198) | PYNG (SEQ ID NO: 204) | WVAPYNGNTN (SEQ ID NO: 210) | WMGWVAPY NGNTN (SEQ ID NO: 216) | VAPYNGNT (SEQ ID NO: 222) |
| | VH CDR3 | DAGTYSPYGYG MDV (SEQ ID NO: 193) | DAGTYSPYGYG MDV (SEQ ID NO: 199) | AGTYSPYG YGMD (SEQ ID NO: 205) | DAGTYSPYGYG MDV (SEQ ID NO: 211) | ARDAGTYS PYGYGMD (SEQ ID NO: 217) | ARDAGTYS PYGYGMDV (SEQ ID NO: 223) |
| VL CDR Seq. | VL CDR1 | RASQSISSWLA (SEQ ID NO: 194) | RASQSISSWLA (SEQ ID NO: 200) | SQSISSW (SEQ ID NO: 206) | RASQSISSWLA (SEQ ID NO: 212) | SSWLAWY (SEQ ID NO: 218) | QSISSW (SEQ ID NO: 224) |
| | VL CDR2 | KASSLES (SEQ ID NO: 195) | KASSLES (SEQ ID NO: 201) | KAS | KASSLES (SEQ ID NO: 213) | LLIYKASS LE (SEQ ID NO: 219) | KAS |
| | VL CDR3 | QQFQSLPPFT (SEQ ID NO: 196) | QQFQSLPPFT (SEQ ID NO: 202) | FQSLPPF (SEQ ID NO: 208) | QQFQSLPPFT (SEQ ID NO: 214) | QQFQSLPP F (SEQ ID NO: 220) | QQFQSLPP FT (SEQ ID NO: 226) |

VH Sequence*:
QVQLVQSGAEVKKPGASVKVSCKASGYTFRSYGISWVRQAPGQGLEWMGWVAPYNGNTNYAQKLQGRVTM
TTDTSTSTAYMELRSLRSDDTAVYYCARDAGTYSPYGYGMDVWGQGTTVTVSS (SEQ ID NO: 227)

VL Sequence*:
DIQMTQSPSTLSASVGDRVTITCRASQSISSWLAWYQQKPGKAPKWYKASSLESGVPSRFSGSGSGTEFT
LTISSLQPDDFATYYCQQFQSLPPFTFGGGTKVEIK (SEQ ID NO: 228)

*Exemplary CDR sequences encompass amino acids as determined by Kabat plus Chothia

TABLE 21

Antibody 25G1-CDR Sequences

| | | Exemplary* | Kabat | Chothia | AbM | Contact | IMGT |
|---|---|---|---|---|---|---|---|
| VH CDR Seq. | VH CDR1 | GYTFRSYGIS (SEQ ID NO: 229) | SYGIS (SEQ ID NO: 235) | GYTFRSY (SEQ ID NO: 241) | GYTFRSYGIS (SEQ ID NO: 247) | RSYGIS (SEQ ID NO: 253) | GYTFRSYG (SEQ ID NO: 259) |
| | VH CDR2 | WVAPYSGNTNY AQKLQG (SEQ ID NO: 230) | WVAPYSGNTNY AQKLQG (SEQ ID NO: 236) | PYSG (SEQ ID NO: 242) | WVAPYSGNTN (SEQ ID NO: 248) | WMGWVAPY SGNTN (SEQ ID NO: 254) | VAPYSGNT (SEQ ID NO: 260) |
| | VH CDR3 | DAGTYSPYGYG MDV (SEQ ID NO: 231) | DAGTYSPYGYG MDV (SEQ ID NO: 237) | AGTYSPYGY GMD (SEQ ID NO: 243) | DAGTYSPYGYG MDV (SEQ ID NO: 240) | ARDAGTYS PYGYGMD (SEQ ID NO: 255) | ARDAGTYS PYGYGMDV (SEQ ID NO: 261) |
| VL CDR Seq. | VL CDR1 | RASHSIDSWLA (SEQ ID NO: 232) | RASHSIDSWLA (SEQ ID NO: 238) | SHSIDSW (SEQ ID NO: 244) | RASHSIDSWLA (SEQ ID NO: 250) | DSWLAWY (SEQ ID NO: 256) | HSIDSW (SEQ ID NO: 262) |
| | VL CDR2 | KASYLES (SEQ ID NO: 233) | KASYLES (SEQ ID NO: 239) | KAS | KASYLES (SEQ ID NO: 251) | LLIYKASY LE (SEQ ID NO: 257) | KAS |
| | VL CDR3 | QLFQSLPPFT (SEQ ID NO: 234) | QLFQSLPPFT (SEQ ID NO: 240) | FQSLPPF (SEQ ID NO: 246) | QLFQSLPPFT (SEQ ID NO: 252) | QLFQSLPP F (SEQ ID NO: 258) | QLFQSLPP FT (SEQ ID NO: 264) |

VH Sequence*:
QVQLVQSGAEVKKPGASVKVSCKASGYTFRSYGISWVRQAPGQGLEWMGWVAPYSGNTNYAQKLQGRVTM
TTDTSTSTAYMELRSLRSDDTAVYYCARDAGTYSPYGYGMDVWGQGTTVTVSS (SEQ ID NO: 265)

VL Sequence*:
DIQMTQSPSTLSASVGDRVTITCRASHSIDSWLAWYQQKPGKAPKWYKASYLESGVPSRFSGSGSGTEFT
LTISSLQPDDFATYYCQLFQSLPPFTFGGGTKVEIK (SEQ ID NO: 266)

*Exemplary CDR sequences encompass amino acids as determined by Kabat plus Chothia

TABLE 22

Antibody 25G9-CDR Sequences

| | | Exemplary* | Kabat | Chothia | AbM | Contact | IMGT |
|---|---|---|---|---|---|---|---|
| VH CDR Seq. | VH CDR1 | GYTFRSYGIS (SEQ ID NO: 267) | SYGIS (SEQ ID NO: 273) | GYTFRSY (SEQ ID NO: 279) | GYTFRSYGIS (SEQ ID NO: 285) | RSYGIS (SEQ ID NO: 291) | GYTFRSYG (SEQ ID NO: 297) |
| | VH CDR2 | WVAPYSGNTNYAQKLQG (SEQ ID NO: 268) | WVAPYSGNTNYAQKLQG (SEQ ID NO: 274) | PYSG (SEQ ID NO: 280) | WVAPYSGNTN (SEQ ID NO: 286) | WMGWVAPYSGNTN (SEQ ID NO: 292) | VAPYSGNT (SEQ ID NO: 298) |
| | VH CDR3 | DAGTYSPYGYGMDV (SEQ ID NO: 269) | DAGTYSPYGYGMDV (SEQ ID NO: 275) | AGTYSPYGYGMD (SEQ ID NO: 281) | DAGTYSPYGYGMDV (SEQ ID NO: 287) | ARDAGTYSPYGYGMD (SEQ ID NO: 293) | ARDAGTYSPYGYGMDV (SEQ ID NO: 299) |
| VL CDR Seq. | VL CDR1 | QASQSIDSWLA (SEQ ID NO: 270) | QASQSIDSWLA (SEQ ID NO: 276) | SQSIDSW (SEQ ID NO: 282) | QASQSIDSWLA (SEQ ID NO: 288) | DSWLAWY (SEQ ID NO: 294) | QSIDSW (SEQ ID NO: 300) |
| | VL CDR2 | SASYLES (SEQ ID NO: 271) | SASYLES (SEQ ID NO: 277) | SAS | SASYLES (SEQ ID NO: 289) | LLIYSASYLE (SEQ ID NO: 295) | SAS |
| | VL CDR3 | QRFQSLPPFT (SEQ ID NO: 272) | QRFQSLPPFT (SEQ ID NO: 278) | FQSLPPF (SEQ ID NO: 284) | QRFQSLPPFT (SEQ ID NO: 290) | QRFQSLPPF (SEQ ID NO: 296) | QRFQSLPPFT (SEQ ID NO: 302) |

VH Sequence*:
QVQLVQSGAEVKKPGASVKVSCKASGYTFRSYGISWVRQAPGQGLEWMGWVAPYSGNTNYAQKLQGRVTM
TTDTSTSTAYMELRSLRSDDTAVYYCARDAGTYSPYGYGMDVWGQGTTVTVSS (SEQ ID NO: 303)

VL Sequence*:
DIQMTQSPSTLSASVGDRVTITCQASQSIDSWLAWYQQKPGKAPKWYSASYLESGVPSRFSGSGSGTEFT
LTISSLQPDDFATYYCQRFQSLPPFTFGGGTKVEIK (SEQ ID NO: 304)

*Exemplary CDR sequences encompass amino acids as determined by Kabat plus Chothia

TABLE 23

Antibody 29D-CDR Sequences

| | | Exemplary* | Kabat | Chothia | AbM | Contact | IMGT |
|---|---|---|---|---|---|---|---|
| VH CDR Seq. | VH CDR1 | GFTFHSRGMH (SEQ ID NO: 305) | SRGMH (SEQ ID NO: 311) | GFTFHSR (SEQ ID NO: 317) | GFTFHSRGMH (SEQ ID NO: 323) | HSRGMH (SEQ ID NO: 329) | GFTFHSRG (SEQ ID NO: 335) |
| | VH CDR2 | VITYDGINKYYADSVEG (SEQ ID NO: 306) | VITYDGINKYYADSVEG (SEQ ID NO: 312) | YDGI (SEQ ID NO: 318) | VITYDGINKY (SEQ ID NO: 324) | WVAVITYDGINKY (SEQ ID NO: 330) | ITYDGINK (SEQ ID NO: 336) |
| | VH CDR3 | DGVYYGVYDY (SEQ ID NO: 307) | DGVYYGVYDY (SEQ ID NO: 313) | GVYYGVYD (SEQ ID NO: 319) | DGVYYGVYDY (SEQ ID NO: 325) | ARDGVYYGVYD (SEQ ID NO: 331) | ARDGVYYGVYDY (SEQ ID NO: 337) |
| VL CDR Seq. | VL CDR1 | KSSQSVLFSSNNKNYLA (SEQ ID NO: 308) | KSSQSVLFSSNNKNYLA (SEQ ID NO: 314) | SQSVLFSSNNKNY (SEQ ID NO: 320) | KSSQSVLFSSNNKNY (SEQ ID NO: 326) | LFSSNNKNYLAWY (SEQ ID NO: 332) | QSVLFSSNNKNY (SEQ ID NO: 338) |
| | VL CDR2 | WASTRES (SEQ ID NO: 309) | WASTRES (SEQ ID NO: 315) | WAS | WASTRES (SEQ ID NO: 327) | LLIYWASTRE (SEQ ID NO: 333) | WAS |
| | VL CDR3 | QQFHSYPLT (SEQ ID NO: 310) | QQFHSYPLT (SEQ ID NO: 316) | FHSYPL (SEQ ID NO: 322) | QQFHSYPLT (SEQ ID NO: 328) | QQFHSYPL (SEQ ID NO: 334) | QQFHSYPLT (SEQ ID NO: 340) |

VH Sequence*:
QVQLVESGGGVVQPGRSLRLSCAASGFTFHSRGMHWVRQAPGKGLEWVAVITYDGINKYYADSVEGRFTIS
RDNSKNTLYLQMNSLRAEDTAVYYCARDGVYYGVYDYWGQGTLVTVSS (SEQ ID NO: 341)

VL Sequence*:
DIVMTQSPDSLAVSLGERATINCKSSQSVLFSSNNKNYLAWYQQKPGQPPKWYWASTRESGVPDRFSGSGS
GTDFTLTISSLQAEDVAVYYCQQFHSYPLTFGGGTKVEIK (SEQ ID NO: 342)

*Exemplary CDR sequences encompass amino acids as determined by Kabat plus Chothia

TABLE 24

Antibody 29E-CDR Sequences

|  |  | Exemplary* | Kabat | Chothia | AbM | Contact | IMGT |
|---|---|---|---|---|---|---|---|
| VH CDR Seq. | VH CDR1 | GFTFRSYGMH (SEQ ID NO: 343) | SYGMH (SEQ ID NO: 349) | GFTFRSY (SEQ ID NO: 355) | GFTFRSYGMH (SEQ ID NO: 361) | RSYGMH (SEQ ID NO: 367) | GFTFRSYG (SEQ ID NO: 373) |
|  | VH CDR2 | VITYDGINKYYADSVEG (SEQ ID NO: 344) | VITYDGINKYYADSVEG (SEQ ID NO: 350) | YDGI (SEQ ID NO: 356) | VITYDGINKY (SEQ ID NO: 362) | WVAVITYDGINKY (SEQ ID NO: 368) | ITYDGINK (SEQ ID NO: 374) |
|  | VH CDR3 | DGVYYGVYDY (SEQ ID NO: 345) | DGVYYGVYDY (SEQ ID NO: 351) | GVYYGVYD (SEQ ID NO: 357) | DGVYYGVYDY (SEQ ID NO: 363) | ARDGVYYGVYDY (SEQ ID NO: 369) | ARDGVYYGVYDY (SEQ ID NO: 375) |
| VL CDR Seq. | VL CDR1 | KSSQSVLFSSNNKNYLA (SEQ ID NO: 346) | KSSQSVLFSSNNKNYLA (SEQ ID NO: 352) | SQSVLFSSNNKNY (SEQ ID NO: 358) | KSSQSVLFSSNNKNYLA (SEQ ID NO: 364) | LFSSNNKNYLAWY (SEQ ID NO: 370) | QSVLFSSNNKNY (SEQ ID NO: 376) |
|  | VL CDR2 | WASTRES (SEQ ID NO: 347) | WASTRES (SEQ ID NO: 353) | WAS | WASTRES (SEQ ID NO: 365) | LLIYWASTRE (SEQ ID NO: 371) | WAS |
|  | VL CDR3 | QQFHSYPLT (SEQ ID NO: 348) | QQFHSYPLT (SEQ ID NO: 354) | FHSYPL (SEQ ID NO: 360) | QQFHSYPLT (SEQ ID NO: 366) | QQFHSYPL (SEQ ID NO: 372) | QQFHSYPLT (SEQ ID NO: 378) |

VH Sequence*:
QVQLVESGGGVVQPGRSLRLSCAASGFTFRSYGMHWVRQAPGKGLEWVAVITYDGINKYYADSVEGRF
TISRDNSKNTLYLQMNSLRAEDTAVYYCARDGVYYGVYDYWGQGTLVTVSS (SEQ ID NO: 379)

VL Sequence*:
DIVMTQSPDSLAVSLGERATINCKSSQSVLFSSNNICNYLAWYQQKPGQPPKWYWASTRESGVPDRFS
GSGSGTDFTLTISSLQAEDVAVYYCQQFHSYPLTFGGGTKVEIK (SEQ ID NO: 380)

*Exemplary CDR sequences encompass amino acids as determined by Kabat plus Chothia

TABLE 25

Antibody 39A-CDR Sequences

|  |  | Exemplary* | Kabat | Chothia | AbM | Contact | IMGT |
|---|---|---|---|---|---|---|---|
| VH CDR Seq. | VH CDR1 | GGTFSSNAIG (SEQ ID NO: 381) | SNAIG (SEQ ID NO: 387) | GGTFSSN (SEQ ID NO: 393) | GGTFSSNAIG (SEQ ID NO: 399) | SSNAIG (SEQ ID NO: 405) | GGTFSSNA (SEQ ID NO: 411) |
|  | VH CDR2 | SIIPIIGFANYAQKFQG (SEQ ID NO: 382) | SIIPIIGFANYAQKFQG (SEQ ID NO: 388) | PIIG (SEQ ID NO: 394) | SIIPIIGFAN (SEQ ID NO: 400) | WMGSIIPIIGFAN (SEQ ID NO: 406) | IIPIIGFA (SEQ ID NO: 412) |
|  | VH CDR3 | DSGYYYGASSFGMDV (SEQ ID NO: 383) | DSGYYYGASSFGMDV (SEQ ID NO: 389) | SGYYYGASSFGMD (SEQ ID NO: 395) | DSGYYYGASSFGMDV (SEQ ID NO: 401) | ARDSGYYYGASSFGMD (SEQ ID NO: 407) | ARDSGYYYGASSFGMDV (SEQ ID NO: 413) |
| VL CDR Seq. | VL CDR1 | RASQSVSSNLA (SEQ ID NO: 384) | RASQSVSSNLA (SEQ ID NO: 390) | SQSVSSN (SEQ ID NO: 396) | RASQSVSSNLA (SEQ ID NO: 402) | SSNLAWY (SEQ ID NO: 408) | QSVSSN (SEQ ID NO: 414) |
|  | VL CDR2 | GASTRAT (SEQ ID NO: 385) | GASTRAT (SEQ ID NO: 391) | GAS | GASTRAT (SEQ ID NO: 403) | LLIYGASTRA (SEQ ID NO: 409) | GAS |
|  | VL CDR3 | EQYNNLPLT (SEQ ID NO: 386) | EQYNNLPLT (SEQ ID NO: 392) | YNNLPL (SEQ ID NO: 398) | EQYNNLPLT (SEQ ID NO: 404) | EQYNNLPL (SEQ ID NO: 410) | EQYNNLPLT (SEQ ID NO: 416) |

VH Sequence*:
QVQLVQSGAEVKKPGSSVKVSCKASGGTFSSNAIGWVRQAPGQGLEWMGSIIPIIGFANYAQKFQGRVTIT
ADESTSTAYMELSSLRSEDTAVYYCARDSGYYYGASSFGMDVWGQGTTVTVSS (SEQ ID NO: 417)

VL Sequence*:
EIVMTQSPATLSVSPGERATLSCRASQSVSSNLAWYQQKPGQAPRLLIYGASTRATGIPARFSGSGSGTEF
TLTISSLQSEDFAVYYCEQYNNLPLTFGGGTKVEIK (SEQ ID NO: 418)

*Exemplary CDR sequences encompass amino acids as determined by Kabat plus Chothia

TABLE 26

Antibody 43B-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 419) | SGQYWS (SEQ ID NO: 425) | GGSISSGQ (SEQ ID NO: 431) | GGSISSGQYWS (SEQ ID NO: 437) | SSGQYWS (SEQ ID NO: 443) | GGSISSGQY (SEQ ID NO: 449) |
| | VH CDR2 | EIYYSGSTRYN PSLKS (SEQ ID NO: 420) | EIYYSGSTRYN PSLKS (SEQ ID NO: 426) | YSG (SEQ ID NO: 432) | EIYYSGSTR (SEQ ID NO: 438) | WIGEIYYSGST R (SEQ ID NO: 444) | IYYSGST (SEQ ID NO: 450) |
| | VH CDR3 | DAPYYYGGGYY YMDV (SEQ ID NO: 421) | DAPYYYGGGYY YMDV (SEQ ID NO: 427) | APYYYGGG YYYYMD (SEQ ID NO: 433) | DAPYYYGGGYY YMDV (SEQ ID NO: 439) | ARDAPYYYGGG YYYYMD (SEQ ID NO: 445) | ARDAPYYYG GGYYYYMDV (SEQ ID NO: 451) |
| VL CDR Seq. | VL CDR1 | RASQSVSSSYL A (SEQ ID NO: 422) | RASQSVSSSYL A (SEQ ID NO: 428) | SQSVSSSY (SEQ ID NO: 434) | RASQSVSSSYL A (SEQ ID NO: 440) | SSSYLAWY (SEQ ID NO: 446) | QSVSSSY (SEQ ID NO: 452) |
| | VL CDR2 | GASSRAT (SEQ ID NO: 423) | GASSRAT (SEQ ID NO: 429) | GAS | GASSRAT (SEQ ID NO: 441) | LLIYGASSRA (SEQ ID NO: 447) | GAS |
| | VL CDR3 | QQVGVVPYT (SEQ ID NO: 424) | QQVGVVPYT (SEQ ID NO: 430) | VGVVPY (SEQ ID NO: 436) | QQVGVVPYT (SEQ ID NO: 442) | QQVGVVPY (SEQ ID NO: 448) | QQVGVVPYT (SEQ ID NO: 454) |

VH Sequence*:
QVQLQESGPGLVKPSQTLSLTCTVSGGSISSGQYWSWIRQHPGKGLEWIGEIYYSGSTRYNPSLKSRVTIS
VDTSKNQFSLKLSSVTAADTAVYYCARDAPYYYGGGYYYYMDVWGKGTTVTVSS (SEQ ID NO: 455)

VL Sequence*:
EIVLTQSPGTLSLSPGERATLSCRASQSVSSSYLAWYQQKPGQAPRLLIYGASSRATGIPDRFSGSGSGTD
FTLTISRLEPEDFAVYYCQQVGVVPYTFGGGTKVEIK (SEQ ID NO: 456)

*Exemplary CDR sequences encompass amino acids as determined by Kabat & Chothia

TABLE 27

Antibody 43B1-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 457) | SGQYWS (SEQ ID NO: 463) | GGSISSGQ (SEQ ID NO: 469) | GGSISSGQYWS (SEQ ID NO: 475) | SSGQYWS (SEQ ID NO: 481) | GGSISSGQY (SEQ ID NO: 487) |
| | VH CDR2 | EIYYSGSTRYN PSLKS (SEQ ID NO: 458) | EIYYSGSTRYN PSLKS (SEQ ID NO: 464) | YSG (SEQ ID NO: 470) | EIYYSGSTR (SEQ ID NO: 476) | WIGEIYYS GSTR(SEQ ID NO: 482) | IYYSGST (SEQ ID NO: 488) |
| | VH CDR3 | DAPYYYGGGYY YMDV (SEQ ID NO: 459) | DAPYYYGGGYY YMDV (SEQ ID NO: 465) | APYYYGGG YYYYMD (SEQ ID NO: 471) | DAPYYYGGGYY YMDV (SEQ ID NO: 477) | ARDAPYYY GGGYYYYM D (SEQ ID NO: 483) | ARDAPYYYG GGYYYYMDV (SEQ ID NO: 489) |
| VL CDR Seq. | VL CDR1 | RASESVDSSYL A (SEQ ID NO: 460) | RASESVDSSYL A (SEQ ID NO: 466) | SESVDSSY (SEQ ID NO: 472) | RASESVDSSYL A (SEQ ID NO: 478) | DSSYLAWY (SEQ ID NO: 484) | ESVDSSY (SEQ ID NO: 490) |
| | VL CDR2 | GASTRQT (SEQ ID NO: 461) | GASTRQT (SEQ ID NO: 467) | GAS | GASTRQT (SEQ ID NO: 479) | LLIYGAST RQ (SEQ ID NO: 485) | GAS |
| | VL CDR3 | QQAGVVPYT (SEQ ID NO: 462) | QQAGVVPYT (SEQ ID NO: 468) | AGVVPY (SEQ ID NO: 474) | QQAGVVPYT (SEQ ID NO: 480) | QQAGVVPY (SEQ ID NO: 486) | QQAGVVPY T (SEQ ID NO: 492) |

VH Sequence*:
QVQLQESGPGLVKPSQTLSLTCTVSGGSISSGQYWSWIRQHPGKGLEWIGEIYYSGSTRYNPSLKSRVTIS
VDTSKNQFSLKLSSVTAADTAVYYCARDAPYYYGGGYYYYMDVWGKGTTVTVSS (SEQ ID NO: 493)

VL Sequence*:
EIVLTQSPGTLSLSPGERATLSCRASESVDSSYLAWYQQKPGQAPRLLIYGASTRQTGIPDRFSGSGSGTD
FTLTISRLEPEDFAVYYCQQAGVVPYTFGGGTKVEIK (SEQ ID NO: 494)

*Exemplary CDR sequences encompass amino acids as determined by Kabat & Chothia

TABLE 28

Antibody 43B7-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 495) | SGQYWS (SEQ ID NO: 501) | GGSISSGQ (SEQ ID NO: 507) | GGSISSGQYWS (SEQ ID NO: 513) | SSGQYWS (SEQ ID NO: 519) | GGSISSGQY (SEQ ID NO: 525) |
| | VH CDR2 | EIYYSGSTRYNPSLKS (SEQ ID NO: 496) | EIYYSGSTRYNPSLKS (SEQ ID NO: 502) | YSG | EIYYSGSTR (SEQ ID NO: 514) | WIGEIYYSGSTR (SEQ ID NO: 520) | IYYSGST (SEQ ID NO: 526) |
| | VH CDR3 | DAPYYYGGGYYYYMDV (SEQ ID NO: 497) | DAPYYYGGGYYYYMDV (SEQ ID NO: 503) | APYYYGGGYYYYMD (SEQ ID NO: 509) | DAPYYYGGGYYYYMDV (SEQ ID NO: 515) | ARDAPYYYGGGYYYYMD (SEQ ID NO: 521) | ARDAPYYYGGGYYYYMDV (SEQ ID NO: 527) |
| VL CDR Seq. | VL CDR1 | RASESVDSSYLA (SEQ ID NO: 498) | RASESVDSSYLA (SEQ ID NO: 504) | SESVDSSY (SEQ ID NO: 510) | RASESVDSSYLA (SEQ ID NO: 516) | DSSYLAWY (SEQ ID NO: 522) | ESVDSSY (SEQ ID NO: 528) |
| | VL CDR2 | GADSRAT (SEQ ID NO: 499) | GADSRAT (SEQ ID NO: 505) | GAD | GADSRAT (SEQ ID NO: 517) | LLIYGADSRA (SEQ ID NO: 523) | GAD |
| | VL CDR3 | QQDGVVPYT (SEQ ID NO: 500) | QQDGVVPYT (SEQ ID NO: 506) | DGVVPY (SEQ ID NO: 512) | QQDGVVPYT (SEQ ID NO: 518) | QQDGVVPYT (SEQ ID NO: 524) | QQDGVVPYT (SEQ ID NO: 530) |

VH Sequence*:
QVQLQESGPGLVKPSQTLSLTCTVSGGSISSGQYWSWIRQHPGKGLEWIGEIYYSGSTRYNPSLKSRVTISVDTSKNQFSLKLSSVTAADTAVYYCARDAPYYYGGGYYYYMDVWGKGTTVTVSS (SEQ ID NO: 531)

VL Sequence*:
EIVLTQSPGTLSLSPGERATLSCRASESVDSSYLAWYQQKPGQAPRLLIYGADSRATGIPDRFSGSGSGTDFTLTISRLEPEDFAVYYCQQDGVVPYTFGGGTKVEIK (SEQ ID NO: 532)

*Exemplary CDR sequences encompass amino acids as determined by Kabat & Chothia

TABLE 29

Antibody 43D-CDR Sequences

| | | Exemplary* | Kabat | Chothia | AbM | Contact | IMGT |
|---|---|---|---|---|---|---|---|
| VH CDR Seq. | VH CDR1 | GGSLSGYYWS (SEQ ID NO: 533) | GYYWS (SEQ ID NO: 539) | GGSLSGY (SEQ ID NO: 545) | GGSLSGYYWS (SEQ ID NO: 551) | SGYYWS (SEQ ID NO: 557) | GGSLSGYY (SEQ ID NO: 563) |
| | VH CDR2 | EIGASGSTRYNPSLKS (SEQ ID NO: 534) | EIGASGSTRYNPSLKS (SEQ ID NO: 540) | ASG | EIGASGSTR (SEQ ID NO: 552) | WIGEIGASGSTR (SEQ ID NO: 558) | IGASGST (SEQ ID NO: 564) |
| | VH CDR3 | DTPYYYEGGYYYYMDV (SEQ ID NO: 535) | DTPYYYEGGYYYYMDV (SEQ ID NO: 541) | TPYYYEGGYYY (SEQ ID NO: 547) | DTPYYYEGGYYYYMDV (SEQ ID NO: 553) | ARDTPYYYEGGYYYYMD (SEQ ID NO: 559) | ARDTPYYYEGGYYYYMDV (SEQ ID NO: 565) |
| VL CDR Seq. | VL CDR1 | RASQSVSSSYLA (SEQ ID NO: 536) | RASQSVSSSYLA (SEQ ID NO: 542) | SQSVSSSY (SEQ ID NO: 548) | RASQSVSSSYLA (SEQ ID NO: 554) | SSSYLAWY (SEQ ID NO: 560) | QSVSSSY (SEQ ID NO: 566) |
| | VL CDR2 | GASSRAT (SEQ ID NO: 537) | GASSRAT (SEQ ID NO: 543) | GAS | GASSRAT (SEQ ID NO: 555) | LLIYGASSRA (SEQ ID NO: 561) | GAS |
| | VL CDR3 | QQVGVVPYT (SEQ ID NO: 538) | QQVGVVPYT (SEQ ID NO: 544) | VGVVPY (SEQ ID NO: 550) | QQVGVVPYT (SEQ ID NO: 556) | QQVGVVPYT (SEQ ID NO: 562) | QQVGVVPYT (SEQ ID NO: 568) |

VH Sequence*:
QVQLQQWGAGLLKPSETLSLTCAVYGGSLSGYYWSWIRQPPGKGLEWIGEIGASGSTRYNPSLKSRVTISVDTSKNQFSLKLSSVTAADTAVYYCARDTPYYYEGGYYYYMDVWGKGTTVTVSS (SEQ ID NO: 569)

VL Sequence*:
EIVLTQSPGTLSLSPGERATLSCRASQSVSSSYLAWYQQKPGQAPRLLIYGASSRATGIPDRFSGSGSGTDFTLTISRLEPEDFAVYYCQQVGVVPYTFGGGTKVEIK (SEQ ID NO: 570)

*Exemplary CDR sequences encompass amino acids as determined by Kabat & Chothia

TABLE 30

Antibody 43D7-CDR Sequences

| | | Exemplary* | Kabat | Chothia | AbM | Contact | IMGT |
|---|---|---|---|---|---|---|---|
| VH CDR Seq. | VH CDR1 | GGSLSGYYWS (SEQ ID NO: 571) | GYYWS (SEQ ID NO: 577) | GGSLSGY (SEQ ID NO: 583) | GGSLSGYYWS (SEQ ID NO: 589) | SGYYWS (SEQ ID NO: 595) | GGSLSGYY (SEQ ID NO: 601) |
| | VH CDR2 | EIGASGSTRYNPSLKS (SEQ ID NO: 572) | EIGASGSTRYNPSLKS (SEQ ID NO: 578) | ASG | EIGASGSTR (SEQ ID NO: 590) | WIGEIGASGSTR (SEQ ID NO: 596) | IGASGST (SEQ ID NO: 602) |
| | VH CDR3 | DTPYYYEGGYYYYMDV (SEQ ID NO: 573) | DTPYYYEGGYYYYMDV (SEQ ID NO: 579) | TPYYYEGGYYYYMD (SEQ ID NO: 585) | DTPYYYEGGYYYYMD (SEQ ID NO: 591) | ARDTPYYYEGGYYYYMDV (SEQ ID NO: 597) | ARDTPYYYEGGYYYYMDV (SEQ ID NO: 603) |
| VL CDR Seq. | VL CDR1 | RASDSVDSYLA (SEQ ID NO: 574) | RASDSVDSYLA (SEQ ID NO: 580) | SDSVDSSY (SEQ ID NO: 586) | RASDSVDSYLA (SEQ ID NO: 592) | DSSYLAWY (SEQ ID NO: 598) | DSVDSSY (SEQ ID NO: 604) |
| | VL CDR2 | GAFSRAN (SEQ ID NO: 575) | GAFSRAN (SEQ ID NO: 581) | GAF | GAFSRAN (SEQ ID NO: 593) | LLIYGAFSRA (SEQ ID NO: 599) | GAF |
| | VL CDR3 | QQAGVVPYT (SEQ ID NO: 576) | QQAGVVPYT (SEQ ID NO: 582) | AGVVPY (SEQ ID NO: 588) | QQAGVVPYT (SEQ ID NO: 594) | QQAGVVPYT (SEQ ID NO: 600) | QQAGVVPYT (SEQ ID NO: 606) |

VH Sequence*:
QVQLQQWGAGLLKPSETLSLTCAVYGGSLSGYYWSWIRQPPGKGLEWIGEIGASGSTRYNPSLKSRVTISVDTSKNQFSLKLSSVTAADTAVYYCARDTPYYYEGGYYYYMDVWGKGTTVTVSS (SEQ ID NO: 607)

VL Sequence*:
EIVLTQSPGTLSLSPGERATLSCRASDSVDSYLAWYQQKPGQAPRLLIYGAFSRANGIPDRFSGSGSGTDFTLTISRLEPEDFAVYYCQQAGVVPYTFGGGTKVEIK (SEQ ID NO: 608)

*Exemplary CDR sequences encompass amino acids as determined by Kabat & Chothia

TABLE 31

Antibody 43D8-CDR Sequences

| | | Exemplary* | Kabat | Chothia | AbM | Contact | IMGT |
|---|---|---|---|---|---|---|---|
| VH CDR Seq. | VH CDR1 | GGSLSGYYWS (SEQ ID NO: 609) | GYYWS (SEQ ID NO: 615) | GGSLSGY (SEQ ID NO: 621) | GGSLSGYYWS (SEQ ID NO: 627) | SGYYWS (SEQ ID NO: 633) | GGSLSGYY (SEQ ID NO: 639) |
| | VH CDR2 | EIGASGSTRYNPSLKS (SEQ ID NO: 610) | EIGASGSTRYNPSLKS (SEQ ID NO: 616) | ASG | EIGASGSTR (SEQ ID NO: 628) | WIGEIGASGSTR (SEQ ID NO: 634) | IGASGST (SEQ ID NO: 640) |
| | VH CDR3 | DTPYYYEGGYYYYMDV (SEQ ID NO: 611) | DTPYYYEGGYYYYMDV (SEQ ID NO: 617) | TPYYYEGGYYYYMD (SEQ ID NO: 623) | DTPYYYEGGYYYYMDV (SEQ ID NO: 629) | ARDTPYYYEGGYYYYMDV (SEQ ID NO: 635) | ARDTPYYYEGGYYYYMDV (SEQ ID NO: 641) |
| VL CDR Seq. | VL CDR1 | RASQSVSSSFLA (SEQ ID NO: 612) | RASQSVSSSFLA (SEQ ID NO: 618) | SQSVSSSF (SEQ ID NO: 624) | RASQSVSSSFLA (SEQ ID NO: 630) | SSSFLAWY (SEQ ID NO: 636) | QSVSSSF (SEQ ID NO: 642) |
| | VL CDR2 | GAYSRAT (SEQ ID NO: 613) | GAYSRAT (SEQ ID NO: 619) | GAY | GAYSRAT (SEQ ID NO: 631) | LLIYGAYSRA (SEQ ID NO: 637) | GAY |
| | VL CDR3 | QQAGVVPYT (SEQ ID NO: 614) | QQAGVVPYT (SEQ ID NO: 620) | AGVVPY (SEQ ID NO: 626) | QQAGVVPYT (SEQ ID NO: 632) | QQAGVVPYT (SEQ ID NO: 638) | QQAGVVPYT (SEQ ID NO: 644) |

VH Sequence*:
QVQLQQWGAGLLKPSETLSLTCAVYGGSLSGYYWSWIRQPPGKGLEWIGEIGASGSTRYNPSLKSRVTISVDTSKNQFSLKLSSVTAADTAVYYCARDTPYYYEGGYYYYMDVWGKGTTVTVSS (SEQ ID NO: 645)

VL Sequence*:
EIVLTQSPGTLSLSPGERATLSCRASQSVSSSFLAWYQQKPGQAPRLLIYGAYSRATGIPDRFSGSGSGTDFTLTISRLEPEDFAVYYCQQAGVVPYTFGGGTKVEIK (SEQ ID NO: 646)

*Exemplary CDR sequences encompass amino acids as determined by Kabat & Chothia

TABLE 32

Antibody 43E-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 647) | SGQYWS (SEQ ID NO: 653) | GGSISSGQ (SEQ ID NO: 659) | GGSISSGQYWS (SEQ ID NO: 665) | SSGQYWS (SEQ ID NO: 671) | GGSISSGQY (SEQ ID NO: 677) |

TABLE 32-continued

Antibody 43E-CDR Sequences

| | | Exemplary* | Kabat | Chothia | AbM | Contact | IMGT |
|---|---|---|---|---|---|---|---|
| | VH CDR2 | EIYYSGSTRYNPSLKS (SEQ ID NO: 648) | EIYYSGSTRYNPSLKS (SEQ ID NO: 654) | YSG | EIYYSGSTR (SEQ ID NO: 666) | WIGEIYYSGSTR (SEQ ID NO: 672) | IYYSGST (SEQ ID NO: 678) |
| | VH CDR3 | DTPYYYDGGYYYYMDV (SEQ ID NO: 649) | DTPYYYDGGYYYYMDV (SEQ ID NO: 655) | TPYYYDGGYYYYMD (SEQ ID NO: 661) | DTPYYYDGGYYYYMDV (SEQ ID NO: 667) | ARDTPYYYDGGYYYYMD (SEQ ID NO: 673) | ARDTPYYYDGGYYYYMDV (SEQ ID NO: 679) |
| VL CDR Seq. | VL CDR1 | RASQSVSSSYLA (SEQ ID NO: 650) | RASQSVSSSYLA (SEQ ID NO: 656) | SQSVSSSY (SEQ ID NO: 662) | RASQSVSSSYLA (SEQ ID NO: 668) | SSSYLAWY (SEQ ID NO: 674) | QSVSSSY (SEQ ID NO: 680) |
| | VL CDR2 | GASSRAT (SEQ ID NO: 651) | GASSRAT (SEQ ID NO: 657) | GAS | GASSRAT (SEQ ID NO: 669) | LLIYGASSRA (SEQ ID NO: 675) | GAS |
| | VL CDR3 | QQVGVVPYT (SEQ ID NO: 652) | QQVGVVPYT (SEQ ID NO: 658) | VGVVPY (SEQ ID NO: 664) | QQVGVVPYT (SEQ ID NQ: 670) | QQVGVVPYT (SEQ ID NO: 676) | QQVGVVPYT (SEQ ID NO: 682) |

VH Sequence*:
QVQLQESGPGLVKPSQTLSLTCTVSGGSISSGQYWSWIRQHPGKGLEWIGEIYYSGSTRYNPSLKSRVTISVDTSKDQFSLKLSSVTAADTAVYYCARDTPYYYDGGYYYYMDVWGKGTTVTSS (SEQ ID NO: 683)

VL Sequence*:
EIVLTQSPGTLSLSPGERATLSCRASQSVSSSYLAWYQQKPGQAPRLLIYGASSRATGIPDRFSGSGSGTDFTLTISRLEPEDFAVYYCQQVGVVPYTFGGGTKVEIK (SEQ ID NO: 684)

*Exemplary CDR sequences encompass amino acids as determined by Kabat & Chothia

TABLE 33

Antibody 43Ea-CDR Sequences

| | | Exemplary* | Kabat | Chothia | AbM | Contact | IMGT |
|---|---|---|---|---|---|---|---|
| VH CDR Seq. | VH CDR1 | GGSISSGQYWS (SEQ ID NO: 685) | SGQYWS (SEQ ID NO: 691) | GGSISSGQYWS (SEQ ID NO: 697) | GGSISSGQYWS (SEQ ID NO: 703) | SSGQYWSY (SEQ ID NO: 709) | GGSISSGQY (SEQ ID NO: 715) |
| | VH CDR2 | EIYYSGSTRYNPSLKS (SEQ ID NO: 686) | EIYYSGSTRYNPSLKS (SEQ ID NO: 692) | YSG | EIYYSGSTR (SEQ ID NO: 704) | WIGEIYYSGSTR (SEQ ID NO: 710) | IYYSGST (SEQ ID NO: 716) |
| | VH CDR3 | DTPYYYDGGYYYYMDV (SEQ ID NO: 687) | DTPYYYDGGYYYYMDV (SEQ ID NO: 693) | TPYYYDGGYYYYMD (SEQ ID NO: 699) | DTPYYYDGGYYYYMDV (SEQ ID NO: 705) | ARDTPYYYDGGYYYYMD (SEQ ID NO: 711) | ARDTPYYYDGGYYYYMDV (SEQ ID NO: 717) |
| VL CDR Seq. | VL CDR1 | RASQSVSSSYLA (SEQ ID NO: 688) | RASQSVSSSYLA (SEQ ID NO: 694) | SQSVSSSY (SEQ ID NO: 700) | RASQSVSSSYLA (SEQ ID NO: 706) | SSSYLAWY (SEQ ID NO: 712) | QSVSSSY (SEQ ID NO: 718) |
| | VL CDR2 | GASSRAT (SEQ ID NO: 689) | GASSRAT (SEQ ID NO: 695) | GAS | GASSRAT (SEQ ID NO: 707) | LLIYGASSRA (SEQ ID NO: 713) | GAS |
| | VL CDR3 | QQVGVVPYT (SEQ ID NO: 690) | QQVGVVPYT (SEQ ID NO: 696) | VGVVPY (SEQ ID NO: 702) | QQVGVVPYT (SEQ ID NO: 714) | QQVGVVPYT (SEQ ID NO: 714) | QQVGVVPYT (SEQ ID NO: 720) |

VH Sequence*:
QVQLQESGPGLVKPSQTLSLTCTVSGGSISSGQYWSWIRQHPGKGLEWIGEIYYSGSTRYNPSLKSRVTISVDTSNQFSLKLSSVTAADTAVYYCARDTPYYYDGGYYYYMDVWGKGTTVTSS (SEQ ID NO: 721)

VL Sequence*:
EIVLTQSPGTLSLSPGERATLSCRASQSVSSSYLAWYQQKPGQAPRLLIYGASSRATGIPDRFSGSGSGTDFTLTISRLEPEDFAVYYCQQVGVVPYTFGGGTKVEIK (SEQ ID NO: 722)

*Exemplary CDR sequences encompass amino acids as determined by Kabat & Chothia

TABLE 34

Antibody 54E-CDR Sequences

| | | Exemplary* | Kabat | Chothia | AbM | Contact | IMGT |
|---|---|---|---|---|---|---|---|
| VH CDR Seq. | VH CDR1 | GYTFANYYMH (SEQ ID NO: 723) | NYYMH (SEQ ID NO: 729) | GYTFANY (SEQ ID NO: 735) | GYTFANYYMH (SEQ ID NO: 741) | ANYYMH (SEQ ID NO: 747) | GYTFANYY (SEQ ID NO: 753) |

TABLE 34-continued

Antibody 54E-CDR Sequences

| | | Exemplary* | Kabat | Chothia | AbM | Contact | IMGT |
|---|---|---|---|---|---|---|---|
| | VH CDR2 | IINP SGGI TVYA QKFQG (SEQ ID NO: 724) | IINP SGGI TVYA QKFQG (SEQ ID NO: 730) | PSGG (SEQ ID NO: 736) | IINP SGGI TV (SEQ ID NO: 742) | WMGI INPS GGIT V (SEQ ID NO: 748) | INPS GGIT (SEQ ID NO: 754) |
| | VH CDR3 | GGSK VAAL AFDI (SEQ ID NO: 725) | GGSK VAAL AFDI (SEQ ID NO: 731) | GSKV AALA FD (SEQ ID NO: 737) | GGSK VAAL AFDI (SEQ ID NO: 743) | ARGG SKVA ALA FD (SEQ ID NO: 749) | ARGG SKVA ALA FDI (SEQ ID NO: 755) |
| VL CDR Seq. | VL CDR1 | QASQ DISN SLN (SEQ ID NO: 726) | QASQ DISN SLN (SEQ ID NO: 732) | SQDI SNS (SEQ ID NO: 738) | QASQ DISN SLN (SEQ ID NO: 744) | SNSL NWY (SEQ ID NO: 750) | QDIS NS (SEQ ID NO: 756) |
| | VL CDR2 | DASN LET (SEQ ID NO: 727) | DASN LET (SEQ ID NO: 733) | DAS | DASN LET (SEQ ID NO: 745) | LLIY DASN LE (SEQ ID NO: 751) | DAS |
| | VL CDR3 | QQYN FHPL T (SEQ ID NO: 728) | QQYN FHPL T (SEQ ID NO: 734) | YNFH PL (SEQ ID NO: 740) | QQYN FHPL T (SEQ ID NO: 746) | QQYN FHPL T (SEQ ID NO: 752) | QQYN FHPL T (SEQ ID NO: 758) |

VH Sequence*:
QVQLVQSGAEVKKPGASVKVSCKASGYTFANYYMHWVRQAPGQGLEWMGI INPSGGITVYAQKFQGRVTMTRTDSTSTVYMELSSLRSEDTAVYYCARGG SKVAALAFDIWGQGTMVTVSS (SEQ ID NO: 759)

VL Sequence*:
DIQMTQSPSSLSASVGDRVTITCQASQDISNSLNWYQQKPGKAPKLLIY DASNLETGVPSRFSGSRSGTDFTFTISSLQPEDIATYYCQQYNFHPLTF GGGTKVEIK (SEQ ID NO: 760)

*Exemplary CDR sequences encompass amino acids as determined by Kabat plus Chothia

TABLE 35

Consensus CDRs

| | | Antibody Group | | | | | |
|---|---|---|---|---|---|---|---|
| | | 1 | 25 | 29 | 39 | 43 | 54 |
| VH CDR Seq.* | VH CDR1 | GFTFS x[D/S] YAMx [A/G] (SEQ ID NO: 773) | GYTF x[D/R] x[S/V] YGIS (SEQ ID NO: 779) | GFTF x[H/R] Sx[R/ Y]GMH (SEQ ID NO: 785) | GGTF SSNA IG (SEQ ID NO: 791) | GGSx [I/L] SSGx YWS (SEQ ID NO: 797) | GYTF ANYY MH (SEQ ID NO: 803) |
| | VH CDR2 | x[A/T] ISGS GGLT YYAD SVKG (SEQ ID NO: 774) | Wx[I/V] APYx [S/N] GNTNY AQKL QG (SEQ ID NO: 780) | VITY DGIN KYYA DSVE G (SEQ ID NO: 786) | SIIP IIGF ANYA QK FQG (SEQ ID NO: 792) | EIx [Y/G] x[Y/A] SGST RYNP SLKS (SEQ ID NO: 798) | IINP SGGI TVYA QKFQ G (SEQ ID NO: 804) |
| | VH CDR3 | APYG YYMD V (SEQ ID NO: 775) | DAGT YSPx [F/Y] GYG MDV (SEQ ID NO: 781) | DGVY YGVY DY (SEQ ID NO: 787) | DSGY YYGA SSFG MDV YMDV (SEQ ID NO: 793) | Dx[T/A] PYYYx [E/G/D] GGYYY (SEQ ID NO: 799) | GGSK VAAL AFDI (SEQ ID NO: 805) |
| VL CDR Seq.* | VL CDR1 | RASQ SISS WLA (SEQ ID NO: 776) | x[R/Q] Asx [Q/E/ H] SIx[S/ D/N] x[S/N] WLA (SEQ ID NO: 782) | KSSQ SVLF SS NN KNY LA (SEQ ID NO: 788) | RASQ SVLF SS NLA (SEQ ID NO: 794) | RASx [Q/ E/D] SVx [S/D] SSx [Y/F] LA (SEQ ID NO: 800) | QASQ DI SN SLN (SEQ ID NO: 806) |
| | VL CDR2 | KASS LES (SEQ ID NO: 777) | x[K/S] Ax [S/ Y] x[S/ Y/N] LEx [S/Y] | WAST RES | GAST RAT | GAx [S/D/ F/Y] x[S/T] Rx [A/Q] x[T/N] (SEQ ID NO: 795) | DASN LET (SEQ ID NO: 807) |
| | VL CDR3 | QQYK SYIT (SEQ ID NO: 778) | Qx[Q/ L/R] FQx [S/K] LPPF T (SEQ ID NO: 784) | QQFH SYPL T (SEQ ID NO: 790) | EQYN NLPL T (SEQ ID NO: 796) | QQx [V/A/ D]GV VPYT (SEQ ID NO: 802) | QQYN FHPL T (SEQ ID NO: 808) |

*Exemplary CDR sequences encompass amino acids as determined by Kabat plus Chothia

TABLE 36

Human, Cynomolgus Monkey, and Mouse TF Sequences

| | Species | | |
|---|---|---|---|
| | Human (Homo sapiens) | Cynomolgus Monkey (Macaca fascicularis) | Mouse (Mus musculus) |
| Full-length sequence [signal sequence underlined] | METPAWPRVP <u>RPETAVARTL LLGWVFAQVA GASGTTNTVA</u> AYNLTWKSTN FKTILEWEPK PVNQVYTVQI STKSGDWKSK | METPAWPRVP <u>RPETAVARTL LLGWVFAQVA GASGTTNTVA</u> AYNLTWKSTN FKTILEWEPK PINQVYTVQI STKSGDWKSK | MAILVRPRLL <u>AALAPTFLGC LLLQVTAGAG</u> IPEKAFNLTW ISTDFKTILE WQPKPTNYTY TVQISDRSRN WKNKCFSTTD |

TABLE 36-continued

Human, Cynomolgus Monkey, and Mouse TF Sequences

| | Species | | |
|---|---|---|---|
| | Human (Homo sapiens) | Cynomolgus Monkey (Macaca fascicularis) | Mouse (Mus musculus) |
| | CFYTTDTECD LTDEIVKDVK QTYLARVFSY PAGNVESTGS AGEPLYENSP EFTPYLETNL GQPTIQSFEQ VGTKVNVTVE DERTLVRRNN TFLSLRDVFG KDLIYTLYYW KSSSSGKKTA KTNTNEFLID VDKGENYCFS VQAVIPSRTV NRKSTDSPVE CMGQEKGEFR EIFYIIGAVV FVVIILVIIL AISLHKCRKA GVGQSWKENS PLNVS (SEQ ID NO: 809) | CFYTADTECD LTDEIVKDVK QTYLARVFSY PAGHVESTGS TEEPPYENSP EFTPYLETNL GQPTIQSFEQ VGTKVNVTVQ DEWTLVRRND TFLSLRDVFG KDLIYTLYYW KSSSSGKKTA KTNTNEFLID VDKGENYCFS VQAVIPSRRT ANRKSTDSPV ECMGHEKGES REIFYIIGAV VFVVIILVII LAISLHKCK KARVGRS WKENSPLNVA (SEQ ID NO: 813) | TECDLTDEIV KDVTWAYEAK VLSVPRRNSV HGDGDQLVIH GEEPPFTNAP KFLPYRDTNL GQPVIQQFEQ DGRKLNVVVK DSLTLVRKNG TFLTRQVFG KDLGYIITYR KGSSTGKKTN ITNTNEFSID VEEGVSYCFF VQAMIFSRKT NQNSPGSSTV CTEQWKSFLG ETLIIVGAVV LLATIFIILL SISLCKRRKN RAGQKGKNTP SRLA (SEQ ID NO: 817) |
| Extra-cellular domain (ECD) | SGTTNTVAAY NLTWKSTNFK TILEWEPKPV NQVYTVQIST KSGDWKSKCF YTTDTECDLT DEIVKDVKQT YLARVFSYPA GNVESTGSAG EPLYENSPEF TPYLETNLGQ PTIQSFEQVG TKVNVTVEDE RTLVRRNNTF LSLRDVFGKD LIYTLYYWKS SSSGKKTAKT NTNEFLIDVD KGENYCFSVQ AVIPSRTVNR KSTDSPVECM GQEKGEFRE (SEQ ID NO: 810) | SGTTNTVAAY NLTWKSTNFK TILEWEPKPI NQVYTVQIST KSGDWKSKCF YTADTECDLT DEIVKDVKQT YLARVFSYPA GHVESTGSTE EPPYENSPEF TPYLETNLGQ PTIQSFEQVG TKVNVTVQDE WTLVRRNDTF LSLRDVFGKD LIYTLYYWKS SSSGKKTAKT NTNEFLIDVD KGENYCFSVQ AVIPSRRTAN RKSTDSPVEC MGHEKGESRE (SEQ ID NO: 814) | AGIPEKAFNL TWISTDFKTI LEWQPKPTNY TYTVQISDRS RNWKNKCFST TDTECDLTDE IVKDVTWAYE AKVLSVPRRN SVHGDGDQLV IHGEEPPFTN APKFLPYRDT NLGQPVIQQF EQDGRKLNVV VKDSLTLVRK NGTFLTLRQV FGKDLGYIIT YRKGSSTGKK TNITNTNEFS IDVEEGVSYC FFVQAMIFSR KTNQNSPGSS TVCTEQWKSF LGE (SEQ ID NO: 818) |
| Sequence of TF ECD-His (TF-His) protein | SGTTNTVAAY NLTWKSTNFK TILEWEPKPV NQVYTVQIST KSGDWKSKCF YTTDTECDLT DEIVKDVKQT YLARVFSYPA GNVESTGSAG EPLYENSPEF TPYLETNLGQ PTIQSFEQVG TKVNVTVEDE RTLVRRNNTF LSLRDVFGKD LIYTLYYWKS SSSGKKTAKT NTNEFLIDVD KGENYCFSVQ AVIPSRTVNR | SGTTNTVAAY NLTWKSTNFK TILEWEPKPI NQVYTVQIST KSGDWKSKCF YTADTECDLT DEIVKDVKQT YLARVFSYPA GHVESTGSTE EPPYENSPEF TPYLETNLGQ PTIQSFEQVG TKVNVTVQDE WTLVRRNDTF LSLRDVFGKD LIYTLYYWKS SSSGKKTAKT NTNEFLIDVD KGENYCFSVQ AVIPSRRTAN | AGIPEKAFNL TWISTDFKTI LEWQPKPTNY TYTVQISDRS RNWKNKCFST TDTECDLTDE IVKDVTWAYE AKVLSVPRRN SVHGDGDQLV IHGEEPPFTN APKFLPYRDT NLGQPVIQQF EQDGRKLNVV VKDSLTLVRK NGTFLTLRQV FGKDLGYIIT YRKGSSTGKK TNITNTNEFS IDVEEGVSYC FFVQAMIFSR |

TABLE 36-continued

Human, Cynomolgus Monkey, and Mouse TF Sequences

| | Species | | |
|---|---|---|---|
| | Human (Homo sapiens) | Cynomolgus Monkey (Macaca fascicularis) | Mouse (Mus musculus) |
| | KSTDSPVECM GQEKGEFRET GHHHHHHH (SEQ ID NO: 811) | RKSTDSPVEC MGHEKGESRE TGHHHHHH (SEQ ID NO: 815) | KTNQNSPGSS TVCTEQWKSF LGETGHHHHH H (SEQ ID NO: 819) |
| Sequence of TF ECD-Fc (TF-Fc) fusion protein | SGTTNTVAAY NLTWKSTNFK TILEWEPKPV NQVYTVQIST KSGDWKSKCF YTTDTECDLT DEIVKDVKQT YLARVFSYPA GNVESTGSTE EPLYENSPEF TPYLETNLGQ PTIQSFEQVG TKVNVTVEDE RTLVRRNNTF LSLRDVFGKD LIYTLYYWKS SSSGKKTAKT NTNEFLIDVD KGENYCFSVQ AVIPSRTVNR KSTDSPVECM GQEKGEFRET GENLYFQGDK THTCPPCPAP ELLGGPSVFL FPPKPKDTLM ISRTPEVTCV VVDVSHEDPE VKFNWYVDGV EVHNAKTKP REEQYNSTYR VSVLTVLHQD WLNGKEYKCK VSNKALPAP EKTISKAKGQ PREPQVYTLP PSREEMTKNQ VSLTCLVKGF YPSDIAVEWE SNGQPENNYK TTPPVLDSDG SFFLYSKLTV DKSRWQQGNV FSCSVMHEAL HNHYTQKSLS LSPGK (SEQ ID NO: 812) | SGTTNTVAAY NLTWKSTNFK TILEWEPKPI NQVYTVQIST KSGDWKSKCF YTADTECDLT DEIVKDVKQT YLARVFSYPA GHVESTGSTE EPPYENSPEF TPYLETNLGQ PTIQSFEQVG TKVNVTVQDE WTLVRRNDTF LSLRDVFGKD LIYTLYYWKS SSSGKKTAKT NTNEFLIDVD KGENYCFSVQ AVIPSRRTAN RKSTDSPVEC MGHEKGESRE TGENLYFQGD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 816) | AGIPEKAFNL TWISTDFKTI LEWQPKPTNY TYTVQISDRS RNWKNKCFST TDTECDLTDE IVKDVTWAYE AKVLSVPRRN SVHGDGDQLV IHGEEPPFTN APKFLPYRDT NLGQPVIQQF EQDGRKLNVV VKDSLTLVRK NGTFLTLRQV FGKDLGYIIT YRKGSSTGKK TNITNTNEFS IDVEEGVSYC FFVQAMIFSR KTNQNSPGSS TVCTEQWKSF LGETGHHHHH QGDKTHTCPP CPAPELLGGP SVFLFPPKPK DTLMISRTPE VTCVVVDVSH EDPEVKFNWY VDGVEVHNAK TKPREEQYNS TYRVVSVLTV LHQDWLNGKE YKCKVSNKAL PAPIEKTISK AKGQPREPQV YTLPPSREEM TKNQVSLTCL VKGFYPSDIA VEWESNGQPE NNYKTTPPVL DSDGSFFLYS KLTVDKSRWQ QGNVFSCSVM HEALHNHYTQ KSLSLSPGK (SEQ ID NO: 820) |

TABLE 39

Sequences of Anti-TF Antibodies

| Antibody | VH domain | VL domain |
|---|---|---|
| 10H10 (M1593) | EVQLVQSGAEVKKPG ESLRISCKGSGYTFA PYWIEWVRQMPGKGL EWMGDILPGTFTTY SPSFQGHVTISADKS ISTAYLQWSSLKASD | DIVMTQTPLSLPVTP GEPASISCKSSQSLL SSGNQKNYLTWYLQK PGQSPQLLIYWASTR ESGVPDRFSGSGSGT DFTLKISRVEAEDVG |

TABLE 39-continued

Sequences of Anti-TF Antibodies

| Antibody | VH domain | VL domain |
|---|---|---|
| | TAMYYCARSGYYGNS GFAYWGQGTLVTVSS (SEQ ID NO: 821) | VYYCQNDYTYPLTFG QGTKLEIK (SEQ ID NO: 822) |
| TF-011 | EVQLLESGGGLVQPG GSLRLSCAASGFTFS NYAMSWVRQAPGKGL EWVSSISGSGDYTYY TDSVKGRFTISRDNS KNTLYLQMNSLRAED TAVYYCARSPWGYYL DSWGQGTLVTVSS (SEQ ID NO: 828) | DIQMTQSPPSLSASA GDRVTITCRASQGIS SRLAWYQQKPEKAPK SLIYAASSLQSGVPS RFSGSGSGTDFTLTI SSLQPEDFATYYCQQ YNSYPYTFGQGTKLE IK (SEQ ID NO: 829) |
| 5G9 (humanized TF8-5G9, CNTO 860) | QVQLVESGGGVVQPG RSLRLSCKASGFNIK DYYMHWVRQAPGKGL EWIGLIDPENGNTIY DPKFQGRFTISADNS KNTLFLQMDSLRPED TAVYYCARDNSYYFD YWGQGTPVTVSS (SEQ ID NO: 830) | DIQMTQSPSSLSASV GDRVTITCKASQDIR KYLNWYQQKPGKAPK LLIYYATSLADGVPS RFSGSGSGTDYTFTI SSLQPEDIATYYCLQ HGESPYTFGQGTKLE IT (SEQ ID NO: 831) |

TABLE 41

Pig TF sequences

| | |
|---|---|
| | Species Pig (*Sus scrofa*) |
| Full-length sequence [signal sequence underlined] | MATPTGPPVSCPKAAVARALLLGWV LVQVAGATGTTDVIVAYNLTWKSTN FKTILEWEPKPINYVYTQISPRLG DWKNKCFHTTDTECDVTDEIMRNVK ETYVARVLSYPADTVLTAQEPPFTN SPPFTPYLDTNLGQPVIQSFEQVGT KLNVTVEAARTLVRVNGTFLRLRDV FGKDLNYTLYYWRASSTGKKKATTN TNEFLIDVDKGENYCFSVQAVIPSR RVNQKSPESRIECTSQEKAVSRELF LIVGAVVFAVIVFVLVLSVSLYKCR KERAGPSGKENAPLNVA (SEQ ID NO: 824) |
| Extracellular domain (ECD) | TGTTDVIVAYNLTWKSTNFKTILEW EPKPINYVYTQISPRLGDWKNKCF HTTDTECDVTDEIMRNVKETYVARV LSYPADTVLTAQEPPFTNSPPFTPY LDTNLGQPVIQSFEQVGTKLNVTVE AARTLVRVNGTFLRLRDVFGKDLNY TLYYWRASSTGKKKATTNTNEFLID VDKGENYCFSVQAVIPSRRVNQKSP ESRIECTSQEKAVSRE (SEQ ID NO: 825) |
| Sequence of TF ECD-His (TF-His) protein | TGTTDVIVAYNLTWKSTNFKTILEW EPKPINYVYTQISPRLGDWKNKCF HTTDTECDVTDEIMRNVKETYVARV LSYPADTVLTAQEPPFTNSPPFTPY LDTNLGQPVIQSFEQVGTKLNVTVE AARTLVRVNGTFLRLRDVFGKDLNY TLYYWRASSTGKKKATTNTNEFLID VDKGENYCFSVQAVIPSRRVNQKSP ESRIECTSQEKAVSRETGHHHHHH (SEQ ID NO: 826) |
| Sequence of TF ECD-Fc (TF-Fc) fusion protein | TGTTDVIVAYNLTWKSTNFKTILEW EPKPINYVYTQISPRLGDWKNKCF HTTDTECDVTDEIMRNVKETYVARV LSYPADTVLTAQEPPFTNSPPFTPY LDTNLGQPVIQSFEQVGTKLNVTVE AARTLVRVNGTFLRLRDVFGKDLNY |

TABLE 41-continued

Pig TF sequences

| | |
|---|---|
| | Species Pig (*Sus scrofa*) |
| | TLYYWRASSTGKKKATTNTNEFLID VDKGENYCFSVQAVIPSRRVNQKSP ESRIECTSQEKAVSRETGENLYFQG DKTHTCPPCPAPELLGGPSVFLFPP KPKDTLMISRTPEVTCVVVDVSHED PEVKFNWYVDGVEVHNAKTKPREEQ YNSTYRVVSVLTVLHQDWLNGKEYK CKVSNKALPAPIEKTISKAKGQPRE PQVYTLPPSREEMTKNQVSLTCLVK GFYPSDIAVEWESNGQPENNYKTTP PVLDSDGSFFLYSKLTVDKSRWQQG NVFSCSVMHEALHNHYTQKSLSLSP GK (SEQ ID NO: 827) |

TABLE 49

Rabbit TF sequences

| | |
|---|---|
| | Species Rabbit (*Oryctolagus cuniculus*) |
| Full-length sequence [signal sequence underlined] | MAPPTRLQVPRPGTAVPYTV LLGWLLAQVARAADTTGRAY NLTWKSTNFKTILEWEPKSI DHVYTVQISTRLENWKSKCF LTAETECDLTDEVVKDVGQT YMARVLSYPARNGNTTGFPE EPPFRNSPEFTPYLDTNLGQ PTIQSFEQVGTKLNVTVQDA RTLVRRNGTFLSLRAVFGKD LNYTLYYWRASSTGKKTATT NTNEFLIDVDKGENYCFSVQ AVIPSRKRKQRSPESLTECT SREQGRAREMFFIIGAVVVV ALLIIVLSVTVYKCRKARAG PSGKESSPLNIA (SEQ ID NO: 832) |
| Extracellular domain (ECD) | ADTTGRAYNLTWKSTNFKTI LEWEPKSIDHVYTVQISTRL ENWKSKCFLTAETECDLTDE VVKDVGQTYMARVLSYPARN GNTTGFPEEPPFRNSPEFTP YLDTNLGQPTIQSFEQVGTK LNVTVQDARTLVRRNGTFLS LRAVFGKDLNYTLYYWRASS TGKKTATTNTNEFLIDVDKG ENYCFSVQAVIPSRKRKQRS PESLTECTSREQGRAREM (SEQ ID NO: 833) |
| Sequence of TF ECD-His (TF-His) protein | ADTTGRAYNLTWKSTNFKTI LEWEPKSIDHVYTVQISTRL ENWKSKCFLTAETECDLTDE VVKDVGQTYMARVLSYPARN GNTTGFPEEPPFRNSPEFTP YLDTNLGQPTIQSFEQVGTK LNVTVQDARTLVRRNGTFLS LRAVFGKDLNYTLYYWRASS TGKKTATTNTNEFLIDVDKG ENYCFSVQAVIPSRKRKQRS PESLTECTSREQGRAREMTG HHHHHH (SEQ ID NO: 834) |
| Sequence of TF ECD-Fc (TF-Fc) fusion protein | ADTTGRAYNLTWKSTNFKTI LEWEPKSIDHVYTVQISTRL ENWKSKCFLTAETECDLTDE VVKDVGQTYMARVLSYPARN GNTTGFPEEPPFRNSPEFTP YLDTNLGQPTIQSFEQVGTK |

TABLE 49-continued

Rabbit TF sequences

| Species Rabbit (*Oryctolagus cuniculus*) |
| --- |
| LNVTVQDARTLVRRNGTFLS LRAVFGKDLNYTLYYWRASS TGKKTATTNTNEFLIDVDKG ENYCFSVQAVIPSRKRKQRS PESLTECTSREQGRAREMEN LYFQGDKTHTCPPCPAPELL GGPSVFLFPPKPKDTLMISR TPEVTCVVVDVSHEDPEVKF NWYVDGVEVHNAKTKPREEQ YNSTYRVVSVLTVLHQDWLN GKEYKCKVSNKALPAPIEKT ISKAKGQPREPQVYTLPPSR EEMTKNQVSLTCLVKGFYPS DIAVEWESNGQPENNYKTTP PVLDSDGSFFLYSKLTVDKS RWQQGNVFSCSVMHEALHNH YTQKSLSLSPGK (SEQ ID NO: 835) |

TABLE 56

Rat TF ECD and chimeric construct ECD sequences

| Rat/Chimeric construct | Extracellular domain (ECD) sequence |
| --- | --- |
| rTF (rat TF) | AGTPPGKAFNLTWISTDFKTILEWQ PKPTNYTYTVQISDRSRNWKYKCTG TTDTECDLTDEIVKDVNWTYEARVL SVPWRNSTHGKETLFGTHGEEPPFT NARKFLPYRDTKIGQPVIQKYEQGG TKLKVTVKDSFTLVRKNGTFLTLRQ VFGNDLGYILTYRKDSSTGRKTNTT HTNEFLIDVEKGVSYCFFAQAVIFS RKTNHKSPESITKCTEQWKSVLGE (SEQ ID NO: 838) |
| h1-107_r | AGTPPGKAFNLTWISTDFKTILEWQ PKPTNYTYTVQISDRSRNWKYKCTG TTDTECDLTDEIVKDVNWTYEARVL SVPWRNSTHGKETLFGTHGEEPPFT NARKFLPYRDTKLGQPTIQSFEQVG TKVNVTVEDERTLVRRNNTFLSLRD VFGKDLIYTLYYWKSSSSGKKTAKT NTNEFLIDVDKGENYCFSVQAVIPS RTVNRKSTDSPVECMGQEKGEFRE (SEQ ID NO: 839) |
| h1-77_r | AGTPPGKAFNLTWISTDFKTILEWQ PKPTNYTYTVQISDRSRNWKYKCTG TTDTECDLTDEIVKDVNWTYEARVL SYPAGNVESTGSAGEPLYENSPEFT PYLETNLGQPTIQSFEQVGTKVNVT VEDERTLVRRNNTFLSLRDVFGKDL IYTLYYWKSSSSGKKTAKTNTNEFL IDVDKGENYCFSVQAVIPSRTVNRK STDSPVECMGQEKGEFRE (SEQ ID NO: 840) |
| h1-38_r | AGTPPGKAFNLTWISTDFKTILEWQ PKPTNYTYTVQISTKSGDWKSKCFY TTDTECDLTDEIVKDVKQTYLARVF SYPAGNVESTGSAGEPLYENSPEFT PYLETNLGQPTIQSFEQVGTKVNVT VEDERTLVRRNNTFLSLRDVFGKDL IYTLYYWKSSSSGKKTAKTNTNEFL IDVDKGENYCFSVQAVIPSRTVNRK STDSPVECMGQEKGEFRE (SEQ ID NO: 841) |

TABLE 56-continued

Rat TF ECD and chimeric construct ECD sequences

| Rat/Chimeric construct | Extracellular domain (ECD) sequence |
| --- | --- |
| h39-77_r | SGTTNTVAAYNLTWKSTNFKTILEW EPKPVNQVYTVQISDRSRNWKYKCT GTTDTECDLTDEIVKDVNWTYEARV LSYPAGNVESTGSAGEPLYENSPEF TPYLETNLGQPTIQSFEQVGTKVNV TVEDERTLVRRNNTFLSLRDVFGKD LIYTLYYWKSSSSGKKTAKTNTNEF LIDVDKGENYCFSVQAVIPSRTVNR KSTDSPVECMGOEKGEFRE (SEQ ID NO: 842) |
| h78-107_r | SGTTNTVAAYNLTWKSTNFKTILEW EPKPVNQVYTVQISTKSGDWKSKCF YTTDTECDLTDEIVKDVKQTYLARV FSVPWRNSTHGTHGEEPPFTNARKF LPYRDTKLGQPTIQSFEQVGTKVNV TVEDERTLVRRNNTFLSLRDVFGKD LIYTLYYWKSSSSGKKTAKTNTNEF LIDVDKGENYCFSVQAVIPSRTVNR KSTDSPVECMGQEKGEFRE (SEQ ID NO: 843) |
| h78-107_r.v2 | SGTTNTVAAYNLTWKSTNFKTILEW EPKPVNQVYTVQISTKSGDWKSKCF YTTDTECDLTDEIVKDVKQTYLARV FSVPWRNSTHGKETLFGTHGEEPPF TNARKFLPYRDTKLGQPTIQSFEQV GTKVNVTVEDERTLVRRNNTFLSLR DVFGKDLIYTLYYWKSSSSGKKTAK TNTNEFLIDVDKGENYCFSVQAVIP SRTVNRKSTDSPVECMGQEKGEF RE (SEQ ID NO: 844) |
| h78-93_r | SGTTNTVAAYNLTWKSTNFKTILEW EPKPVNQVYTVQISTKSGDWKSKCF YTTDTECDLTDEIVKDVKQTYLARV FSVPWRNSTHGKETLFGTHGEEPPY ENSPEFTPYLETNLGQPTIQSFEQV GTKVNVTVEDERTLVRRNNTFLSLR DVFGKDLIYTLYYWKSSSSGKKTAK TNTNEFLIDVDKGENYCFSVQAVIP SRTVNRKSTDSPVECMGQEKGEFRE (SEQ ID NO: 845) |
| h94-107_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLFTNARKF LPYRDTKLGQPTIQSFEQVGTKVNV TVEDERTLVRRNNTFLSLRDVFGKD LIYTLYYWKSSSSGKKTAKTNTNEF LIDVDKGENYCFSVQAVIPSRTVNR KSTDSPVECMGQEKGEFRE (SEQ ID NO: 846) |
| h108-219_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNIGQPVIQKYEQGGTKLKV TVKDSFTLVRKNGTFLTLRQVFGND LGYILTYRKDSSTGRKTNTTHTNEF LIDVEKGVSYCFFAQAVIFSRKTNH KSPESITKCTEQWKSVLGE (SEQ ID NO: 847) |
| h108-158_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNIGQPVIQKYEQGGTKLKV TVKDSFTLVRKNGTFLTLRQVFGND LGYILTYRKSSSSGKKTAKTNTNEF |

TABLE 56-continued

Rat TF ECD and chimeric construct ECD sequences

| Rat/Chimeric construct | Extracellular domain (ECD) sequence |
|---|---|
| | LIDVDKGENYCFSVQAVIPSRTVNR<br>KSTDSPVECMGQEKGEFRE<br>(SEQ ID NO: 848) |
| h108-132_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNIGQPVIQKYEQGGTKLKV<br>TVKDSFTLVRRNNTFLSLRDVFGKD<br>LIYTLYYWKSSSSGKKTAKTNTNEF<br>LIDVDKGENYCFSVQAVIPSRTVNR<br>KSTDSPVECMGQEKGEFRE<br>(SEQ ID NO: 849) |
| h133-158_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRKNGTFLTLRQVFGND<br>LGYILTYRKSSSGKKTAKTNTNEF<br>LIDVDKGENYCFSVQAVIPSRTVNR<br>KSTDSPVECMGQEKGEFRE<br>(SEQ ID NO: 850) |
| h133-145_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRKNGTFLTLRQVFGKD<br>LIYTLYYWKSSSSGKKTAKTNTNEF<br>LIDVDKGENYCFSVQAVIPSRTVNR<br>KSTDSPVECMGQEKGEFRE<br>(SEQ ID NO: 851) |
| h133-139_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRKNGTFLSLRDVFGKD<br>LIYTLYYWKSSSSGKKTAKTNTNEF<br>LIDVDKGENYCFSVQAVIPSRTVNR<br>KSTDSPVECMGQEKGEFRE<br>(SEQ ID NO: 852) |
| h140-145_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLTLRQVFGKD<br>LIYTLYYWKSSSSGKKTAKTNTNEF<br>LIDVDKGENYCFSVQAVIPSRTVNR<br>KSTDSPVECMGQEKGEFRE<br>(SEQ ID NO: 853) |
| h146-158_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLSLRDVFGND<br>LGYILTYRKSSSGKKTAKTNTNEF<br>LIDVDKGENYCFSVQAVIPSRTVNR<br>KSTDSPVECMGQEKGEFRE<br>(SEQ ID NO: 854) |
| h146-151_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF |

TABLE 56-continued

Rat TF ECD and chimeric construct ECD sequences

| Rat/Chimeric construct | Extracellular domain (ECD) sequence |
|---|---|
| | TPYLETNLGQPTIQSFEQVGTKVNV<br>TVEDERTLVRRNNTFLSLRDVFGND<br>LIYTLYYWKSSSGKKTAKTNTNEF<br>LIDVDKGENYCFSVQAVIPSRTVNR<br>KSTDSPVECMGQEKGEFRE<br>(SEQ ID NO: 855) |
| h152-158_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLSLRDVFGKD<br>LGYILTYRKSSSGKKTAKTNTNEF<br>LIDVDKGENYCFSVQAVIPSRTVNR<br>KSTDSPVECMGQEKGEFRE<br>(SEQ ID NO: 856) |
| h159-219_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLSLRDVFGKD<br>LIYTLYYWKDSSTGRKTNTTHTNEF<br>LIDVEKGVSYCFFAQAVIFSRKTNH<br>KSPESITKCTEQWKSVLGE<br>(SEQ ID NO: 857) |
| h159-189_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLSLRDVFGKD<br>LIYTLYYWKDSSTGRKTNTTHTNEF<br>LIDVEKGVSYCFFAQAVIPSRTVNR<br>KSTDSPVECMGQEKGEFRE<br>(SEQ ID NO: 858) |
| h159-174_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLSLRDVFGKD<br>LIYTLYYWKDSSTGRKTNTTHTNEF<br>LIDVDKGENYCFSVQAVIPSRTVNR<br>KSTDSPVECMGQEKGEFRE<br>(SEQ ID NO: 859) |
| h159-166_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLSLRDVFGKD<br>LIYTLYYWKDSSTGRKTAKTNTNEF<br>LIDVDKGENYCFSVQAVIPSRTVNR<br>KSTDSPVECMGQEKGEFRE<br>(SEQ ID NO: 860) |
| h167-174_r | SGTTNTVAAYNLTWKSTNFKTILEW<br>EPKPVNQVYTVQISTKSGDWKSKCF<br>YTTDTECDLTDEIVKDVKQTYLARV<br>FSYPAGNVESTGSAGEPLYENSPEF<br>TPYLETNLGQPTIQSFEQVGTKVNV<br>TVEDERTLVRRNNTFLSLRDVFGKD<br>LIYTLYYWKSSSSGKKTNTTHTNEF<br>LIDVDKGENYCFSVQAVIPSRTVNR<br>KSTDSPVECMGQEKGEFRE<br>(SEQ ID NO: 861) |

TABLE 56-continued

Rat TF ECD and chimeric construct ECD sequences

| Rat/Chimeric construct | Extracellular domain (ECD) sequence |
|---|---|
| h175-189_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKSSSGKKTAKTNTNEF LIDVEKGVSYCFFAQAVIPSRTVNR KSTDSPVECMGQEKGEFRE (SEQ ID NO: 862) |
| h190-219_r | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKSSSGKKTAKTNTNEF LIDVDKGENYCFSVQAVIPSRKTNH KSPESITKCTEQWKSVLGE (SEQ ID NO: 863) |
| hTF_K68N | SGTTNTVAAYNLTWKSTNFKTILEW EPKPVNQVYTVQISTKSGDWKSKCF YTTDTECDLTDEIVKDVNQTYLARV FSYPAGNVESTGSAGEPLYENSPEF TPYLETNLGQPTIQSFEQVGTKVNV TVEDERTLVRRNNTFLSLRDVFGKD LIYTLYYWKSSSGKKTAKTNTNEF LIDVDKGENYCFSVQAVIPSRTVNR KSTDSPVECMGQEKGEFRE (SEQ ID NO: 865) |
| hTF_K149N | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGND LIYTLYYWKSSSGKKTAKTNTNEF LIDVDKGENYCFSVQAVIPSRTVNR KSTDSPVECMGQEKGEFRE (SEQ ID NO: 866) |
| hTF_N171H_T197K | SGTTNTVAAYNLTWKSTNFKTILEW EPKPVNQVYTVQISTKSGDWKSKCF YTTDTECDLTDEIVKDVKQTYLARV FSYPAGNVESTGSAGEPLYENSPEF TPYLETNLGQPTIQSFEQVGTKVNV TVEDERTLVRRNNTFLSLRDVFGKD LIYTLYYWKSSSSGKKTAKTHTNEF LIDVDKGENYCFSVQAVIPSRKVNR KSTDSPVECMGQEKGEFRE (SEQ ID NO: 867) |
| r141-194_h | AGTPPGKAFNLTWISTDFKTILEWQ PKPTNYTYTVQISDRSRNWKYKCTG TTDTECDLTDEIVKDVNWTYEARVL SVPWRNSTHOKETLFGTHGEEPPFT NARKFLPYRDTKIGQPVIQKYEQGG TKLKVTVKDSFTLVRRNNTFLSRLD VFGKDLIYTLYYWKSSSGKKTAKT NTNEFLIDVDKGENYCFSVQAVIFS RKTNHKSPESITKCTEQWKSVLGE (SEQ ID NO: 864) |

TABLE 57

Variable region sequence consensus

| Group | VH Domain Consensus (SEQ ID NO) | VL Domain Consensus (SEQ ID NO) |
|---|---|---|
| Lineage 25A | QVQLVQSGAEVKKP GASVKVSCKASGYT FDx[V/A]YGISWV RQAPGQGLEWMGWI APYx[N/S]GNTNY AQKLQGRVTMTTDT STSTAYMELRSLRS DDTAVYYCARDAGT YSPFGYGMDVWGQG TTVTVSS (SEQ ID NO: 868) | DIQMTQSPSTLSAS VGDRVTITCx[R/Q] ASx[Q/E]SIx [S/N]x[S/N\|WLA WYQQKPGKAPKLLI YKAx[S/Y]x[S/N] LEx\|S/Y]GVPSRFS GSGSGTEFTLTISS LQPDDFATYYCQx [Q/L]FQx[S/K] LPPFTFGGGTKV EIK (SEQ ID NO: 869) |
| Lineage 25G | QVQLVQSGAEVKKP GASVKVSCKASGYT FRSYGISWVRQAPG QGLEWMGWVAPYx [N/S]GNTNYAQKL QGRVTMTT DTSTSTAYMELRSL RSDDTAVYYCARDA GTYSPYGYGMDVWG QGTTVTVSS (SEQ ID NO: 870) | DIQMTQSPSTLSAS VGDRVTITCx[R/Q] ASx[Q/H]SIx[S/D] SWLAWYQQKPGKA PKLLIYx\|K/S]ASx [S/Y]LESGVPSRFSG SGSGTEFTLTISSLQP DDFATYYCQx[Q/L/R] FQSLPPFTFGGGT KVEIK (SEQ ID NO: 871) |

TABLE 58

Consensus CDRs

| | | Antibody Group | |
|---|---|---|---|
| | | Lineage 25A | Lineage 25G |
| VH CDR Seq.* | VH CDR1 | GYTFDx[V/A]YGIS (SEQ ID NO: 872) | GYTFR SYGIS (SEQ ID NO: 878) |
| | VH CDR2 | WIAPYx[N/S] GNTNYA QKLQG (SEQ ID NO: 873) | WVAPYx [N/S]GN TNYAQK LQG (SEQ ID NO: 879) |
| | VH CDR3 | DAGTYSPF GYGMDV (SEQ ID NO: 874) | DAGTYSP YGYGMDV (SEQ ID NO: 880) |
| VL CDR Seq.* | VL CDR1 | x[R/Q]ASx [Q/E]SIx [S/N]x[S/ N]WLA (SEQ ID NO: 875) | x[R/Q]AS x[Q/H]S Ix[S/D] SWLA (SEQ ID NO: 881) |
| | VL CDR2 | KAx[S/Y] x[S/N]LE x[S/Y] (SEQ ID NO: 876) | x[K/S]AS x[S/Y]LES (SEQ ID NO: 882) |
| | VL CDR3 | Qx[Q/L]F Qx[S/K]L PPFT (SEQ ID NO: 877) | Qx[Q/L/R] FQSLPPFT (SEQ ID NO: 883) |

*Exemplary CDR sequences encompass amino acids as determined by Kabat & Chothia

The invention claimed is:

1. An antibody which binds to the extracellular domain of human Tissue Factor (TF), wherein the antibody comprises a VH-CDR1, a VH-CDR2, and a VH-CDR3 comprising the amino acid sequences of the VH-CDR1, the VH-CDR2, and the VH-CDR3, respectively, as set forth in a VH comprising the amino acid sequence of SEQ ID NO: 151, and a VL-CDR1, a VL-CDR2, and a VL-CDR3 comprising the amino acid sequences of the VL-CDR1, the VL-CDR2, and the VL-CDR3, respectively, as set forth in a VL comprising the amino acid sequence of SEQ ID NO: 152.

2. The antibody of claim 1, wherein
(i) the VH-CDR1 comprises the amino acid sequence of SEQ ID NO: 115, the VH-CDR2 comprises the amino acid sequence of SEQ ID NO: 116, the VH-CDR3 comprises the amino acid sequence of SEQ ID NO: 117, the VL-CDR1 comprises the amino acid sequence of SEQ ID NO: 118, the VL-CDR2 comprises the amino acid sequence of SEQ ID NO: 119, and the VL-CDR3 comprises the amino acid sequence of SEQ ID NO: 120;
(ii) the VH-CDR1 comprises the amino acid sequence of SEQ ID NO: 121, the VH-CDR2 comprises the amino acid sequence of SEQ ID NO: 122, the VH-CDR3 comprises the amino acid sequence of SEQ ID NO: 123, the VL-CDR1 comprises the amino acid sequence of SEQ ID NO: 124, the VL-CDR2 comprises the amino acid sequence of SEQ ID NO: 125, and the VL-CDR3 comprises the amino acid sequence of SEQ ID NO: 126;
(iii) the VH-CDR1 comprises the amino acid sequence of SEQ ID NO: 127, the VH-CDR2 comprises the amino acid sequence of SEQ ID NO: 128, the VH-CDR3 comprises the amino acid sequence of SEQ ID NO: 129, the VL-CDR1 comprises the amino acid sequence of SEQ ID NO: 130, the VL-CDR2 comprises the amino acid sequence KAY, and the VL-CDR3 comprises the amino acid sequence of SEQ ID NO: 132;
(iv) the VH-CDR1 comprises the amino acid sequence of SEQ ID NO: 133, the VH-CDR2 comprises the amino acid sequence of SEQ ID NO: 134, the VH-CDR3 comprises the amino acid sequence of SEQ ID NO: 135, the VL-CDR1 comprises the amino acid sequence of SEQ ID NO: 136, the VL-CDR2 comprises the amino acid sequence of SEQ ID NO: 137, and the VL-CDR3 comprises the amino acid sequence of SEQ ID NO: 138;
(v) the VH-CDR1 comprises the amino acid sequence of SEQ ID NO: 139, the VH-CDR2 comprises the amino acid sequence of SEQ ID NO: 140, the VH-CDR3 comprises the amino acid sequence of SEQ ID NO: 141, the VL-CDR1 comprises the amino acid sequence of SEQ ID NO: 142, the VL-CDR2 comprises the amino acid sequence of SEQ ID NO: 143, and the VL-CDR3 comprises the amino acid sequence of SEQ ID NO: 144; or
(vi) the VH-CDR1 comprises the amino acid sequence of SEQ ID NO: 145, the VH-CDR2 comprises the amino acid sequence of SEQ ID NO: 146, the VH-CDR3 comprises the amino acid sequence of SEQ ID NO: 147, the VL-CDR1 comprises the amino acid sequence of SEQ ID NO: 148, the VL-CDR2 comprises the amino acid sequence KAY, and the VL-CDR3 comprises the amino acid sequence of SEQ ID NO: 150.

3. The antibody of claim 1, wherein
the antibody comprises a VH sequence of SEQ ID NO:151 and a VL sequence of SEQ ID NO: 152.

4. A pharmaceutical composition comprising the antibody of claim 1 and a pharmaceutically acceptable excipient.

5. A kit comprising
(i) the antibody of claim 1; and
(ii) instructions for use.

6. The antibody of claim 1, wherein the VH-CDR1, the VH-CDR2, the VH-CDR3, the VL-CDR1, the VL-CDR2, and the VL-CDR3 are determined according to Kabat numbering scheme, Chothia numbering scheme, AbM numbering scheme, Contact numbering scheme, IMGT numbering scheme, or a combination thereof.

7. The antibody of claim 1, wherein the antibody is human, humanized, or chimeric.

8. The antibody of claim 1, wherein the antibody is a monoclonal antibody.

9. The antibody of claim 1, wherein the antibody is a Fab, Fab', F (ab')2, Fv, scFv, (scFv)2, single chain antibody molecule, dual variable domain antibody, linear antibody, or V domain antibody.

10. The antibody of claim 1, wherein the antibody comprises an Fc region.

11. The antibody of claim 1, wherein:
(i) the antibody comprises a heavy chain constant region of a class selected from IgG, IgA, IgD, IgE, and IgM, or
(ii) the antibody comprises a heavy chain constant region of the class IgG and a subclass selected from IgG1, IgG2, IgG3, and IgG4.

* * * * *

SEQUENCE LISTING

```
Sequence total quantity: 919
SEQ ID NO: 1                moltype = AA   length = 10
FEATURE                     Location/Qualifiers
source                      1..10
                            mol_type = protein
                            organism = synthetic construct
SEQUENCE: 1
GFTFSDYAMG                                                                10

SEQ ID NO: 2                moltype = AA   length = 17
FEATURE                     Location/Qualifiers
source                      1..17
                            mol_type = protein
                            organism = synthetic construct
SEQUENCE: 2
TISGSGGLTY YADSVKG                                                        17

SEQ ID NO: 3                moltype = AA   length = 9
FEATURE                     Location/Qualifiers
source                      1..9
                            mol_type = protein
                            organism = synthetic construct
SEQUENCE: 3
APYGYYMDV                                                                 9

SEQ ID NO: 4                moltype = AA   length = 11
FEATURE                     Location/Qualifiers
source                      1..11
                            mol_type = protein
                            organism = synthetic construct
SEQUENCE: 4
RASQSISSWL A                                                              11

SEQ ID NO: 5                moltype = AA   length = 7
FEATURE                     Location/Qualifiers
source                      1..7
                            mol_type = protein
                            organism = synthetic construct
SEQUENCE: 5
KASSLES                                                                   7

SEQ ID NO: 6                moltype = AA   length = 8
FEATURE                     Location/Qualifiers
source                      1..8
                            mol_type = protein
                            organism = synthetic construct
SEQUENCE: 6
QQYKSYIT                                                                  8

SEQ ID NO: 7                moltype = AA   length = 5
FEATURE                     Location/Qualifiers
source                      1..5
                            mol_type = protein
                            organism = synthetic construct
SEQUENCE: 7
DYAMG                                                                     5

SEQ ID NO: 8                moltype = AA   length = 17
FEATURE                     Location/Qualifiers
source                      1..17
                            mol_type = protein
                            organism = synthetic construct
SEQUENCE: 8
TISGSGGLTY YADSVKG                                                        17

SEQ ID NO: 9                moltype = AA   length = 9
FEATURE                     Location/Qualifiers
source                      1..9
                            mol_type = protein
                            organism = synthetic construct
SEQUENCE: 9
APYGYYMDV                                                                 9

SEQ ID NO: 10               moltype = AA   length = 11
FEATURE                     Location/Qualifiers
source                      1..11
                            mol_type = protein
                            organism = synthetic construct
```

```
SEQUENCE: 10
RASQSISSWL A                                                            11

SEQ ID NO: 11          moltype = AA  length = 7
FEATURE                Location/Qualifiers
source                 1..7
                       mol_type = protein
                       organism = synthetic construct
SEQUENCE: 11
KASSLES                                                                  7

SEQ ID NO: 12          moltype = AA  length = 8
FEATURE                Location/Qualifiers
source                 1..8
                       mol_type = protein
                       organism = synthetic construct
SEQUENCE: 12
QQYKSYIT                                                                 8

SEQ ID NO: 13          moltype = AA  length = 7
FEATURE                Location/Qualifiers
source                 1..7
                       mol_type = protein
                       organism = synthetic construct
SEQUENCE: 13
GFTFSDY                                                                  7

SEQ ID NO: 14          moltype = AA  length = 4
FEATURE                Location/Qualifiers
source                 1..4
                       mol_type = protein
                       organism = synthetic construct
SEQUENCE: 14
GSGG                                                                     4

SEQ ID NO: 15          moltype = AA  length = 7
FEATURE                Location/Qualifiers
source                 1..7
                       mol_type = protein
                       organism = synthetic construct
SEQUENCE: 15
PYGYYMD                                                                  7

SEQ ID NO: 16          moltype = AA  length = 7
FEATURE                Location/Qualifiers
source                 1..7
                       mol_type = protein
                       organism = synthetic construct
SEQUENCE: 16
SQSISSW                                                                  7

SEQ ID NO: 17          moltype =     length =
SEQUENCE: 17
000

SEQ ID NO: 18          moltype = AA  length = 5
FEATURE                Location/Qualifiers
source                 1..5
                       mol_type = protein
                       organism = synthetic construct
SEQUENCE: 18
YKSYI                                                                    5

SEQ ID NO: 19          moltype = AA  length = 10
FEATURE                Location/Qualifiers
source                 1..10
                       mol_type = protein
                       organism = synthetic construct
SEQUENCE: 19
GFTFSDYAMG                                                              10

SEQ ID NO: 20          moltype = AA  length = 10
FEATURE                Location/Qualifiers
source                 1..10
                       mol_type = protein
                       organism = synthetic construct
SEQUENCE: 20
TISGSGGLTY                                                              10
```

```
SEQ ID NO: 21              moltype = AA   length = 9
FEATURE                    Location/Qualifiers
source                     1..9
                           mol_type = protein
                           organism = synthetic construct
SEQUENCE: 21
APYGYYMDV                                                                 9

SEQ ID NO: 22              moltype = AA   length = 11
FEATURE                    Location/Qualifiers
source                     1..11
                           mol_type = protein
                           organism = synthetic construct
SEQUENCE: 22
RASQSISSWL A                                                             11

SEQ ID NO: 23              moltype = AA   length = 7
FEATURE                    Location/Qualifiers
source                     1..7
                           mol_type = protein
                           organism = synthetic construct
SEQUENCE: 23
KASSLES                                                                   7

SEQ ID NO: 24              moltype = AA   length = 8
FEATURE                    Location/Qualifiers
source                     1..8
                           mol_type = protein
                           organism = synthetic construct
SEQUENCE: 24
QQYKSYIT                                                                  8

SEQ ID NO: 25              moltype = AA   length = 6
FEATURE                    Location/Qualifiers
source                     1..6
                           mol_type = protein
                           organism = synthetic construct
SEQUENCE: 25
SDYAMG                                                                    6

SEQ ID NO: 26              moltype = AA   length = 13
FEATURE                    Location/Qualifiers
source                     1..13
                           mol_type = protein
                           organism = synthetic construct
SEQUENCE: 26
WVSTISGSGG LTY                                                           13

SEQ ID NO: 27              moltype = AA   length = 10
FEATURE                    Location/Qualifiers
source                     1..10
                           mol_type = protein
                           organism = synthetic construct
SEQUENCE: 27
AKAPYGYYMD                                                               10

SEQ ID NO: 28              moltype = AA   length = 7
FEATURE                    Location/Qualifiers
source                     1..7
                           mol_type = protein
                           organism = synthetic construct
SEQUENCE: 28
SSWLAWY                                                                   7

SEQ ID NO: 29              moltype = AA   length = 10
FEATURE                    Location/Qualifiers
source                     1..10
                           mol_type = protein
                           organism = synthetic construct
SEQUENCE: 29
LLIYKASSLE                                                               10

SEQ ID NO: 30              moltype = AA   length = 7
FEATURE                    Location/Qualifiers
source                     1..7
                           mol_type = protein
                           organism = synthetic construct
SEQUENCE: 30
QQYKSYI                                                                   7
```

```
SEQ ID NO: 31           moltype = AA  length = 8
FEATURE                 Location/Qualifiers
source                  1..8
                        mol_type = protein
                        organism = synthetic construct
SEQUENCE: 31
GFTFSDYA                                                                    8

SEQ ID NO: 32           moltype = AA  length = 8
FEATURE                 Location/Qualifiers
source                  1..8
                        mol_type = protein
                        organism = synthetic construct
SEQUENCE: 32
ISGSGGLT                                                                    8

SEQ ID NO: 33           moltype = AA  length = 11
FEATURE                 Location/Qualifiers
source                  1..11
                        mol_type = protein
                        organism = synthetic construct
SEQUENCE: 33
AKAPYGYYMD V                                                               11

SEQ ID NO: 34           moltype = AA  length = 6
FEATURE                 Location/Qualifiers
source                  1..6
                        mol_type = protein
                        organism = synthetic construct
SEQUENCE: 34
QSISSW                                                                      6

SEQ ID NO: 35           moltype =     length =
SEQUENCE: 35
000

SEQ ID NO: 36           moltype = AA  length = 8
FEATURE                 Location/Qualifiers
source                  1..8
                        mol_type = protein
                        organism = synthetic construct
SEQUENCE: 36
QQYKSYIT                                                                    8

SEQ ID NO: 37           moltype = AA  length = 118
FEATURE                 Location/Qualifiers
source                  1..118
                        mol_type = protein
                        organism = synthetic construct
SEQUENCE: 37
EVQLLESGGG LVQPGGSLRL SCAASGFTFS DYAMGWVRQA PGKGLEWVST ISGSGGLTYY           60
ADSVKGRFTI SRDNSKNTLY LQMNSLRAED TAVYYCAKAP YGYYMDVWGK GTTVTVSS            118

SEQ ID NO: 38           moltype = AA  length = 106
FEATURE                 Location/Qualifiers
source                  1..106
                        mol_type = protein
                        organism = synthetic construct
SEQUENCE: 38
DIQMTQSPST LSASVGDRVT ITCRASQSIS SWLAWYQQKP GKAPKLLIYK ASSLESGVPS           60
RFSGSGSGTE FTLTISSLQP DDFATYYCQQ YKSYITFGGG TKVEIK                        106

SEQ ID NO: 39           moltype = AA  length = 10
FEATURE                 Location/Qualifiers
source                  1..10
                        mol_type = protein
                        organism = synthetic construct
SEQUENCE: 39
GFTFSSYAMA                                                                 10

SEQ ID NO: 40           moltype = AA  length = 17
FEATURE                 Location/Qualifiers
source                  1..17
                        mol_type = protein
                        organism = synthetic construct
SEQUENCE: 40
AISGSGGLTY YADSVKG                                                         17
```

```
SEQ ID NO: 41         moltype = AA  length = 9
FEATURE               Location/Qualifiers
source                1..9
                      mol_type = protein
                      organism = synthetic construct
SEQUENCE: 41
APYGYYMDV                                                             9

SEQ ID NO: 42         moltype = AA  length = 11
FEATURE               Location/Qualifiers
source                1..11
                      mol_type = protein
                      organism = synthetic construct
SEQUENCE: 42
RASQSISSWL A                                                         11

SEQ ID NO: 43         moltype = AA  length = 7
FEATURE               Location/Qualifiers
source                1..7
                      mol_type = protein
                      organism = synthetic construct
SEQUENCE: 43
KASSLES                                                               7

SEQ ID NO: 44         moltype = AA  length = 8
FEATURE               Location/Qualifiers
source                1..8
                      mol_type = protein
                      organism = synthetic construct
SEQUENCE: 44
QQYKSYIT                                                              8

SEQ ID NO: 45         moltype = AA  length = 5
FEATURE               Location/Qualifiers
source                1..5
                      mol_type = protein
                      organism = synthetic construct
SEQUENCE: 45
SYAMA                                                                 5

SEQ ID NO: 46         moltype = AA  length = 17
FEATURE               Location/Qualifiers
source                1..17
                      mol_type = protein
                      organism = synthetic construct
SEQUENCE: 46
AISGSGGLTY YADSVKG                                                   17

SEQ ID NO: 47         moltype = AA  length = 9
FEATURE               Location/Qualifiers
source                1..9
                      mol_type = protein
                      organism = synthetic construct
SEQUENCE: 47
APYGYYMDV                                                             9

SEQ ID NO: 48         moltype = AA  length = 11
FEATURE               Location/Qualifiers
source                1..11
                      mol_type = protein
                      organism = synthetic construct
SEQUENCE: 48
RASQSISSWL A                                                         11

SEQ ID NO: 49         moltype = AA  length = 7
FEATURE               Location/Qualifiers
source                1..7
                      mol_type = protein
                      organism = synthetic construct
SEQUENCE: 49
KASSLES                                                               7

SEQ ID NO: 50         moltype = AA  length = 8
FEATURE               Location/Qualifiers
source                1..8
                      mol_type = protein
                      organism = synthetic construct
SEQUENCE: 50
QQYKSYIT                                                              8
```

```
SEQ ID NO: 51          moltype = AA  length = 7
FEATURE                Location/Qualifiers
source                 1..7
                       mol_type = protein
                       organism = synthetic construct
SEQUENCE: 51
GFTFSSY                                                                    7

SEQ ID NO: 52          moltype = AA  length = 4
FEATURE                Location/Qualifiers
source                 1..4
                       mol_type = protein
                       organism = synthetic construct
SEQUENCE: 52
GSGG                                                                       4

SEQ ID NO: 53          moltype = AA  length = 7
FEATURE                Location/Qualifiers
source                 1..7
                       mol_type = protein
                       organism = synthetic construct
SEQUENCE: 53
PYGYYMD                                                                    7

SEQ ID NO: 54          moltype = AA  length = 7
FEATURE                Location/Qualifiers
source                 1..7
                       mol_type = protein
                       organism = synthetic construct
SEQUENCE: 54
SQSISSW                                                                    7

SEQ ID NO: 55          moltype =     length =
SEQUENCE: 55
000

SEQ ID NO: 56          moltype = AA  length = 5
FEATURE                Location/Qualifiers
source                 1..5
                       mol_type = protein
                       organism = synthetic construct
SEQUENCE: 56
YKSYI                                                                      5

SEQ ID NO: 57          moltype = AA  length = 10
FEATURE                Location/Qualifiers
source                 1..10
                       mol_type = protein
                       organism = synthetic construct
SEQUENCE: 57
GFTFSSYAMA                                                                10

SEQ ID NO: 58          moltype = AA  length = 10
FEATURE                Location/Qualifiers
source                 1..10
                       mol_type = protein
                       organism = synthetic construct
SEQUENCE: 58
AISGSGGLTY                                                                10

SEQ ID NO: 59          moltype = AA  length = 9
FEATURE                Location/Qualifiers
source                 1..9
                       mol_type = protein
                       organism = synthetic construct
SEQUENCE: 59
APYGYYMDV                                                                  9

SEQ ID NO: 60          moltype = AA  length = 11
FEATURE                Location/Qualifiers
source                 1..11
                       mol_type = protein
                       organism = synthetic construct
SEQUENCE: 60
RASQSISSWL A                                                              11

SEQ ID NO: 61          moltype = AA  length = 7
FEATURE                Location/Qualifiers
```

```
source                    1..7
                          mol_type = protein
                          organism = synthetic construct
SEQUENCE: 61
KASSLES                                                                    7

SEQ ID NO: 62             moltype = AA   length = 8
FEATURE                   Location/Qualifiers
source                    1..8
                          mol_type = protein
                          organism = synthetic construct
SEQUENCE: 62
QQYKSYIT                                                                   8

SEQ ID NO: 63             moltype = AA   length = 6
FEATURE                   Location/Qualifiers
source                    1..6
                          mol_type = protein
                          organism = synthetic construct
SEQUENCE: 63
SSYAMA                                                                     6

SEQ ID NO: 64             moltype = AA   length = 13
FEATURE                   Location/Qualifiers
source                    1..13
                          mol_type = protein
                          organism = synthetic construct
SEQUENCE: 64
WVSAISGSGG LTY                                                            13

SEQ ID NO: 65             moltype = AA   length = 10
FEATURE                   Location/Qualifiers
source                    1..10
                          mol_type = protein
                          organism = synthetic construct
SEQUENCE: 65
AKAPYGYYMD                                                                10

SEQ ID NO: 66             moltype = AA   length = 7
FEATURE                   Location/Qualifiers
source                    1..7
                          mol_type = protein
                          organism = synthetic construct
SEQUENCE: 66
SSWLAWY                                                                    7

SEQ ID NO: 67             moltype = AA   length = 10
FEATURE                   Location/Qualifiers
source                    1..10
                          mol_type = protein
                          organism = synthetic construct
SEQUENCE: 67
LLIYKASSLE                                                                10

SEQ ID NO: 68             moltype = AA   length = 7
FEATURE                   Location/Qualifiers
source                    1..7
                          mol_type = protein
                          organism = synthetic construct
SEQUENCE: 68
QQYKSYI                                                                    7

SEQ ID NO: 69             moltype = AA   length = 8
FEATURE                   Location/Qualifiers
source                    1..8
                          mol_type = protein
                          organism = synthetic construct
SEQUENCE: 69
GFTFSSYA                                                                   8

SEQ ID NO: 70             moltype = AA   length = 8
FEATURE                   Location/Qualifiers
source                    1..8
                          mol_type = protein
                          organism = synthetic construct
SEQUENCE: 70
ISGSGGLT                                                                   8

SEQ ID NO: 71             moltype = AA   length = 11
```

```
FEATURE                Location/Qualifiers
source                 1..11
                       mol_type = protein
                       organism = synthetic construct
SEQUENCE: 71
AKAPYGYYMD V                                                              11

SEQ ID NO: 72          moltype = AA  length = 6
FEATURE                Location/Qualifiers
source                 1..6
                       mol_type = protein
                       organism = synthetic construct
SEQUENCE: 72
QSISSW                                                                    6

SEQ ID NO: 73          moltype =     length =
SEQUENCE: 73
000

SEQ ID NO: 74          moltype = AA  length = 8
FEATURE                Location/Qualifiers
source                 1..8
                       mol_type = protein
                       organism = synthetic construct
SEQUENCE: 74
QQYKSYIT                                                                  8

SEQ ID NO: 75          moltype = AA  length = 118
FEATURE                Location/Qualifiers
source                 1..118
                       mol_type = protein
                       organism = synthetic construct
SEQUENCE: 75
EVQLLESGGG LVQPGGSLRL SCAASGFTFS SYAMAWVRQA PGKGLEWVSA ISGSGGLTYY          60
ADSVKGRFTI SRDNSKNTLY LQMNSLRAED TAVYYCAKAP YGYYMDVWGK GTTVTVSS           118

SEQ ID NO: 76          moltype = AA  length = 106
FEATURE                Location/Qualifiers
source                 1..106
                       mol_type = protein
                       organism = synthetic construct
SEQUENCE: 76
DIQMTQSPST LSASVGDRVT ITCRASQSIS SWLAWYQQKP GKAPKLLIYK ASSLESGVPS          60
RFSGSGSGTE FTLTISSLQP DDFATYYCQQ YKSYITFGGG TKVEIK                        106

SEQ ID NO: 77          moltype = AA  length = 10
FEATURE                Location/Qualifiers
source                 1..10
                       mol_type = protein
                       organism = synthetic construct
SEQUENCE: 77
GYTFDVYGIS                                                                10

SEQ ID NO: 78          moltype = AA  length = 17
FEATURE                Location/Qualifiers
source                 1..17
                       mol_type = protein
                       organism = synthetic construct
SEQUENCE: 78
WIAPYNGNTN YAQKLQG                                                        17

SEQ ID NO: 79          moltype = AA  length = 14
FEATURE                Location/Qualifiers
source                 1..14
                       mol_type = protein
                       organism = synthetic construct
SEQUENCE: 79
DAGTYSPFGY GMDV                                                           14

SEQ ID NO: 80          moltype = AA  length = 11
FEATURE                Location/Qualifiers
source                 1..11
                       mol_type = protein
                       organism = synthetic construct
SEQUENCE: 80
RASQSISSWL A                                                              11

SEQ ID NO: 81          moltype = AA  length = 7
FEATURE                Location/Qualifiers
```

```
source                  1..7
                        mol_type = protein
                        organism = synthetic construct
SEQUENCE: 81
KASSLES                                                             7

SEQ ID NO: 82           moltype = AA  length = 10
FEATURE                 Location/Qualifiers
source                  1..10
                        mol_type = protein
                        organism = synthetic construct
SEQUENCE: 82
QQFQSLPPFT                                                         10

SEQ ID NO: 83           moltype = AA  length = 5
FEATURE                 Location/Qualifiers
source                  1..5
                        mol_type = protein
                        organism = synthetic construct
SEQUENCE: 83
VYGIS                                                               5

SEQ ID NO: 84           moltype = AA  length = 17
FEATURE                 Location/Qualifiers
source                  1..17
                        mol_type = protein
                        organism = synthetic construct
SEQUENCE: 84
WIAPYNGNTN YAQKLQG                                                 17

SEQ ID NO: 85           moltype = AA  length = 14
FEATURE                 Location/Qualifiers
source                  1..14
                        mol_type = protein
                        organism = synthetic construct
SEQUENCE: 85
DAGTYSPFGY GMDV                                                    14

SEQ ID NO: 86           moltype = AA  length = 11
FEATURE                 Location/Qualifiers
source                  1..11
                        mol_type = protein
                        organism = synthetic construct
SEQUENCE: 86
RASQSISSWL A                                                       11

SEQ ID NO: 87           moltype = AA  length = 7
FEATURE                 Location/Qualifiers
source                  1..7
                        mol_type = protein
                        organism = synthetic construct
SEQUENCE: 87
KASSLES                                                             7

SEQ ID NO: 88           moltype = AA  length = 10
FEATURE                 Location/Qualifiers
source                  1..10
                        mol_type = protein
                        organism = synthetic construct
SEQUENCE: 88
QQFQSLPPFT                                                         10

SEQ ID NO: 89           moltype = AA  length = 7
FEATURE                 Location/Qualifiers
source                  1..7
                        mol_type = protein
                        organism = synthetic construct
SEQUENCE: 89
GYTFDVY                                                             7

SEQ ID NO: 90           moltype = AA  length = 4
FEATURE                 Location/Qualifiers
source                  1..4
                        mol_type = protein
                        organism = synthetic construct
SEQUENCE: 90
PYNG                                                                4

SEQ ID NO: 91           moltype = AA  length = 12
```

```
FEATURE                 Location/Qualifiers
source                  1..12
                        mol_type = protein
                        organism = synthetic construct
SEQUENCE: 91
AGTYSPFGYG MD                                                           12

SEQ ID NO: 92           moltype = AA   length = 7
FEATURE                 Location/Qualifiers
source                  1..7
                        mol_type = protein
                        organism = synthetic construct
SEQUENCE: 92
SQSISSW                                                                 7

SEQ ID NO: 93           moltype =    length =
SEQUENCE: 93
000

SEQ ID NO: 94           moltype = AA   length = 7
FEATURE                 Location/Qualifiers
source                  1..7
                        mol_type = protein
                        organism = synthetic construct
SEQUENCE: 94
FQSLPPF                                                                 7

SEQ ID NO: 95           moltype = AA   length = 10
FEATURE                 Location/Qualifiers
source                  1..10
                        mol_type = protein
                        organism = synthetic construct
SEQUENCE: 95
GYTFDVYGIS                                                              10

SEQ ID NO: 96           moltype = AA   length = 10
FEATURE                 Location/Qualifiers
source                  1..10
                        mol_type = protein
                        organism = synthetic construct
SEQUENCE: 96
WIAPYNGNTN                                                              10

SEQ ID NO: 97           moltype = AA   length = 14
FEATURE                 Location/Qualifiers
source                  1..14
                        mol_type = protein
                        organism = synthetic construct
SEQUENCE: 97
DAGTYSPFGY GMDV                                                         14

SEQ ID NO: 98           moltype = AA   length = 11
FEATURE                 Location/Qualifiers
source                  1..11
                        mol_type = protein
                        organism = synthetic construct
SEQUENCE: 98
RASQSISSWL A                                                            11

SEQ ID NO: 99           moltype = AA   length = 7
FEATURE                 Location/Qualifiers
source                  1..7
                        mol_type = protein
                        organism = synthetic construct
SEQUENCE: 99
KASSLES                                                                 7

SEQ ID NO: 100          moltype = AA   length = 10
FEATURE                 Location/Qualifiers
source                  1..10
                        mol_type = protein
                        organism = synthetic construct
SEQUENCE: 100
QQFQSLPPFT                                                              10

SEQ ID NO: 101          moltype = AA   length = 6
FEATURE                 Location/Qualifiers
source                  1..6
                        mol_type = protein
```

```
SEQUENCE: 101
DVYGIS                                                                 6

SEQ ID NO: 102          moltype = AA  length = 13
FEATURE                 Location/Qualifiers
source                  1..13
                        mol_type = protein
                        organism = synthetic construct
SEQUENCE: 102
WMGWIAPYNG NTN                                                        13

SEQ ID NO: 103          moltype = AA  length = 15
FEATURE                 Location/Qualifiers
source                  1..15
                        mol_type = protein
                        organism = synthetic construct
SEQUENCE: 103
ARDAGTYSPF GYGMD                                                      15

SEQ ID NO: 104          moltype = AA  length = 7
FEATURE                 Location/Qualifiers
source                  1..7
                        mol_type = protein
                        organism = synthetic construct
SEQUENCE: 104
SSWLAWY                                                                7

SEQ ID NO: 105          moltype = AA  length = 10
FEATURE                 Location/Qualifiers
source                  1..10
                        mol_type = protein
                        organism = synthetic construct
SEQUENCE: 105
LLIYKASSLE                                                            10

SEQ ID NO: 106          moltype = AA  length = 9
FEATURE                 Location/Qualifiers
source                  1..9
                        mol_type = protein
                        organism = synthetic construct
SEQUENCE: 106
QQFQSLPPF                                                              9

SEQ ID NO: 107          moltype = AA  length = 8
FEATURE                 Location/Qualifiers
source                  1..8
                        mol_type = protein
                        organism = synthetic construct
SEQUENCE: 107
GYTFDVYG                                                               8

SEQ ID NO: 108          moltype = AA  length = 8
FEATURE                 Location/Qualifiers
source                  1..8
                        mol_type = protein
                        organism = synthetic construct
SEQUENCE: 108
IAPYNGNT                                                               8

SEQ ID NO: 109          moltype = AA  length = 16
FEATURE                 Location/Qualifiers
source                  1..16
                        mol_type = protein
                        organism = synthetic construct
SEQUENCE: 109
ARDAGTYSPF GTGMDV                                                     16

SEQ ID NO: 110          moltype = AA  length = 6
FEATURE                 Location/Qualifiers
source                  1..6
                        mol_type = protein
                        organism = synthetic construct
SEQUENCE: 110
QSISSW                                                                 6

SEQ ID NO: 111          moltype =     length =
SEQUENCE: 111
000
```

```
SEQ ID NO: 112          moltype = AA   length = 10
FEATURE                 Location/Qualifiers
source                  1..10
                        mol_type = protein
                        organism = synthetic construct
SEQUENCE: 112
QQFQSLPPFT                                                            10

SEQ ID NO: 113          moltype = AA   length = 123
FEATURE                 Location/Qualifiers
source                  1..123
                        mol_type = protein
                        organism = synthetic construct
SEQUENCE: 113
QVQLVQSGAE VKKPGASVKV SCKASGYTFD VYGISWVRQA PGQGLEWMGW IAPYNGNTNY      60
AQKLQGRVTM TTDTSTSTAY MELRSLRSDD TAVYYCARDA GTYSPFGYGM DVWGQGTTVT     120
VSS                                                                  123

SEQ ID NO: 114          moltype = AA   length = 108
FEATURE                 Location/Qualifiers
source                  1..108
                        mol_type = protein
                        organism = synthetic construct
SEQUENCE: 114
DIQMTQSPST LSASVGDRVT ITCRASQSIS SWLAWYQQKP GKAPKLLIYK ASSLESGVPS      60
RFSGSGSGTE FTLTISSLQP DDFATYYCQQ FQSLPPFTFG GGTKVEIK                 108

SEQ ID NO: 115          moltype = AA   length = 10
FEATURE                 Location/Qualifiers
source                  1..10
                        mol_type = protein
                        organism = synthetic construct
SEQUENCE: 115
GYTFDVYGIS                                                            10

SEQ ID NO: 116          moltype = AA   length = 17
FEATURE                 Location/Qualifiers
source                  1..17
                        mol_type = protein
                        organism = synthetic construct
SEQUENCE: 116
WIAPYSGNTN YAQKLQG                                                    17

SEQ ID NO: 117          moltype = AA   length = 14
FEATURE                 Location/Qualifiers
source                  1..14
                        mol_type = protein
                        organism = synthetic construct
SEQUENCE: 117
DAGTYSPFGY GMDV                                                       14

SEQ ID NO: 118          moltype = AA   length = 11
FEATURE                 Location/Qualifiers
source                  1..11
                        mol_type = protein
                        organism = synthetic construct
SEQUENCE: 118
QASQSINNWL A                                                          11

SEQ ID NO: 119          moltype = AA   length = 7
FEATURE                 Location/Qualifiers
source                  1..7
                        mol_type = protein
                        organism = synthetic construct
SEQUENCE: 119
KAYNLES                                                                7

SEQ ID NO: 120          moltype = AA   length = 10
FEATURE                 Location/Qualifiers
source                  1..10
                        mol_type = protein
                        organism = synthetic construct
SEQUENCE: 120
QLFQSLPPFT                                                            10

SEQ ID NO: 121          moltype = AA   length = 5
FEATURE                 Location/Qualifiers
source                  1..5
```

```
                            mol_type = protein
                            organism = synthetic construct
SEQUENCE: 121
VYGIS                                                                   5

SEQ ID NO: 122              moltype = AA  length = 17
FEATURE                     Location/Qualifiers
source                      1..17
                            mol_type = protein
                            organism = synthetic construct
SEQUENCE: 122
WIAPYSGNTN YAQKLQG                                                      17

SEQ ID NO: 123              moltype = AA  length = 14
FEATURE                     Location/Qualifiers
source                      1..14
                            mol_type = protein
                            organism = synthetic construct
SEQUENCE: 123
DAGTYSPFGY GMDV                                                         14

SEQ ID NO: 124              moltype = AA  length = 11
FEATURE                     Location/Qualifiers
source                      1..11
                            mol_type = protein
                            organism = synthetic construct
SEQUENCE: 124
QASQSINNWL A                                                            11

SEQ ID NO: 125              moltype = AA  length = 7
FEATURE                     Location/Qualifiers
source                      1..7
                            mol_type = protein
                            organism = synthetic construct
SEQUENCE: 125
KAYNLES                                                                 7

SEQ ID NO: 126              moltype = AA  length = 10
FEATURE                     Location/Qualifiers
source                      1..10
                            mol_type = protein
                            organism = synthetic construct
SEQUENCE: 126
QLFQSLPPFT                                                              10

SEQ ID NO: 127              moltype = AA  length = 7
FEATURE                     Location/Qualifiers
source                      1..7
                            mol_type = protein
                            organism = synthetic construct
SEQUENCE: 127
GYTFDVY                                                                 7

SEQ ID NO: 128              moltype = AA  length = 4
FEATURE                     Location/Qualifiers
source                      1..4
                            mol_type = protein
                            organism = synthetic construct
SEQUENCE: 128
PYSG                                                                    4

SEQ ID NO: 129              moltype = AA  length = 12
FEATURE                     Location/Qualifiers
source                      1..12
                            mol_type = protein
                            organism = synthetic construct
SEQUENCE: 129
AGTYSPFGYG MD                                                           12

SEQ ID NO: 130              moltype = AA  length = 7
FEATURE                     Location/Qualifiers
source                      1..7
                            mol_type = protein
                            organism = synthetic construct
SEQUENCE: 130
SQSINNW                                                                 7

SEQ ID NO: 131              moltype =    length =
SEQUENCE: 131
```

```
000

SEQ ID NO: 132          moltype = AA  length = 7
FEATURE                 Location/Qualifiers
source                  1..7
                        mol_type = protein
                        organism = synthetic construct SEQUENCE: 132
FQSLPPF                                                              7

SEQ ID NO: 133          moltype = AA  length = 10
FEATURE                 Location/Qualifiers
source                  1..10
                        mol_type = protein
                        organism = synthetic construct SEQUENCE: 133
GYTFDVYGIS                                                          10

SEQ ID NO: 134          moltype = AA  length = 10
FEATURE                 Location/Qualifiers
source                  1..10
                        mol_type = protein
                        organism = synthetic construct SEQUENCE: 134
WIAPYSGNTN                                                          10

SEQ ID NO: 135          moltype = AA  length = 14
FEATURE                 Location/Qualifiers
source                  1..14
                        mol_type = protein
                        organism = synthetic construct SEQUENCE: 135
DAGTYSPFGY GMDV                                                     14

SEQ ID NO: 136          moltype = AA  length = 11
FEATURE                 Location/Qualifiers
source                  1..11
                        mol_type = protein
                        organism = synthetic construct SEQUENCE: 136
QASQSINNWL A                                                        11

SEQ ID NO: 137          moltype = AA  length = 7
FEATURE                 Location/Qualifiers
source                  1..7
                        mol_type = protein
                        organism = synthetic construct SEQUENCE: 137
KAYNLES                                                              7

SEQ ID NO: 138          moltype = AA  length = 10
FEATURE                 Location/Qualifiers
source                  1..10
                        mol_type = protein
                        organism = synthetic construct SEQUENCE: 138
QLFQSLPPFT                                                          10

SEQ ID NO: 139          moltype = AA  length = 6
FEATURE                 Location/Qualifiers
source                  1..6
                        mol_type = protein
                        organism = synthetic construct SEQUENCE: 139
DVYGIS                                                               6

SEQ ID NO: 140          moltype = AA  length = 13
FEATURE                 Location/Qualifiers
source                  1..13
                        mol_type = protein
                        organism = synthetic construct SEQUENCE: 140
WMGWIAPYSG NTN                                                      13

SEQ ID NO: 141          moltype = AA  length = 15
FEATURE                 Location/Qualifiers
source                  1..15
                        mol_type = protein
                        organism = synthetic construct
```

```
SEQUENCE: 141
ARDAGTYSPF GYGMD                                                         15

SEQ ID NO: 142          moltype = AA  length = 7
FEATURE                 Location/Qualifiers
source                  1..7
                        mol_type = protein
                        organism = synthetic construct
SEQUENCE: 142
NNWLAWY                                                                   7

SEQ ID NO: 143          moltype = AA  length = 10
FEATURE                 Location/Qualifiers
source                  1..10
                        mol_type = protein
                        organism = synthetic construct
SEQUENCE: 143
LLIYKAYNLE                                                               10

SEQ ID NO: 144          moltype = AA  length = 9
FEATURE                 Location/Qualifiers
source                  1..9
                        mol_type = protein
                        organism = synthetic construct
SEQUENCE: 144
QLFQSLPPF                                                                 9

SEQ ID NO: 145          moltype = AA  length = 8
FEATURE                 Location/Qualifiers
source                  1..8
                        mol_type = protein
                        organism = synthetic construct
SEQUENCE: 145
GYTFDVYG                                                                  8

SEQ ID NO: 146          moltype = AA  length = 8
FEATURE                 Location/Qualifiers
source                  1..8
                        mol_type = protein
                        organism = synthetic construct
SEQUENCE: 146
IAPYSGNT                                                                  8

SEQ ID NO: 147          moltype = AA  length = 16
FEATURE                 Location/Qualifiers
source                  1..16
                        mol_type = protein
                        organism = synthetic construct
SEQUENCE: 147
ARDAGTYSPF GTGMDV                                                        16

SEQ ID NO: 148          moltype = AA  length = 6
FEATURE                 Location/Qualifiers
source                  1..6
                        mol_type = protein
                        organism = synthetic construct
SEQUENCE: 148
QSINNW                                                                    6

SEQ ID NO: 149          moltype =     length =
SEQUENCE: 149
000

SEQ ID NO: 150          moltype = AA  length = 10
FEATURE                 Location/Qualifiers
source                  1..10
                        mol_type = protein
                        organism = synthetic construct
SEQUENCE: 150
QLFQSLPPFT                                                               10

SEQ ID NO: 151          moltype = AA  length = 123
FEATURE                 Location/Qualifiers
source                  1..123
                        mol_type = protein
                        organism = synthetic construct
SEQUENCE: 151
QVQLVQSGAE VKKPGASVKV SCKASGYTFD VYGISWVRQA PGQGLEWMGW IAPYSGNTNY         60
AQKLQGRVTM TTDTSTSTAY MELRSLRSDD TAVYYCARDA GTYSPFGYGM DVWGQGTTVT        120
```

```
VSS                                                                      123

SEQ ID NO: 152          moltype = AA   length = 108
FEATURE                 Location/Qualifiers
source                  1..108
                        mol_type = protein
                        organism = synthetic construct
SEQUENCE: 152
DIQMTQSPST LSASVGDRVT ITCQASQSIN NWLAWYQQKP GKAPKLLIYK AYNLESGVPS          60
RFSGSGSGTE FTLTISSLQP DDFATYYCQL FQSLPPFTFG GGTKVEIK                      108

SEQ ID NO: 153          moltype = AA   length = 10
FEATURE                 Location/Qualifiers
source                  1..10
                        mol_type = protein
                        organism = synthetic construct
SEQUENCE: 153
GYTFDVYGIS                                                                10

SEQ ID NO: 154          moltype = AA   length = 17
FEATURE                 Location/Qualifiers
source                  1..17
                        mol_type = protein
                        organism = synthetic construct
SEQUENCE: 154
WIAPYSGNTN YAQKLQG                                                        17

SEQ ID NO: 155          moltype = AA   length = 14
FEATURE                 Location/Qualifiers
source                  1..14
                        mol_type = protein
                        organism = synthetic construct
SEQUENCE: 155
DAGTYSPFGY GMDV                                                           14

SEQ ID NO: 156          moltype = AA   length = 11
FEATURE                 Location/Qualifiers
source                  1..11
                        mol_type = protein
                        organism = synthetic construct
SEQUENCE: 156
RASESISNWL A                                                              11

SEQ ID NO: 157          moltype = AA   length = 7
FEATURE                 Location/Qualifiers
source                  1..7
                        mol_type = protein
                        organism = synthetic construct
SEQUENCE: 157
KAYSLEY                                                                   7

SEQ ID NO: 158          moltype = AA   length = 10
FEATURE                 Location/Qualifiers
source                  1..10
                        mol_type = protein
                        organism = synthetic construct
SEQUENCE: 158
QQFQKLPPFT                                                                10

SEQ ID NO: 159          moltype = AA   length = 5
FEATURE                 Location/Qualifiers
source                  1..5
                        mol_type = protein
                        organism = synthetic construct
SEQUENCE: 159
VYGIS                                                                     5

SEQ ID NO: 160          moltype = AA   length = 17
FEATURE                 Location/Qualifiers
source                  1..17
                        mol_type = protein
                        organism = synthetic construct
SEQUENCE: 160
WIAPYSGNTN YAQKLQG                                                        17

SEQ ID NO: 161          moltype = AA   length = 14
FEATURE                 Location/Qualifiers
source                  1..14
                        mol_type = protein
```

```
                         organism = synthetic construct
SEQUENCE: 161
DAGTYSPFGY GMDV                                                             14

SEQ ID NO: 162           moltype = AA  length = 11
FEATURE                  Location/Qualifiers
source                   1..11
                         mol_type = protein
                         organism = synthetic construct
SEQUENCE: 162
RASESISNWL A                                                                11

SEQ ID NO: 163           moltype = AA  length = 7
FEATURE                  Location/Qualifiers
source                   1..7
                         mol_type = protein
                         organism = synthetic construct
SEQUENCE: 163
KAYSLEY                                                                      7

SEQ ID NO: 164           moltype = AA  length = 10
FEATURE                  Location/Qualifiers
source                   1..10
                         mol_type = protein
                         organism = synthetic construct
SEQUENCE: 164
QQFQKLPPFT                                                                  10

SEQ ID NO: 165           moltype = AA  length = 7
FEATURE                  Location/Qualifiers
source                   1..7
                         mol_type = protein
                         organism = synthetic construct
SEQUENCE: 165
GYTFDVY                                                                      7

SEQ ID NO: 166           moltype = AA  length = 4
FEATURE                  Location/Qualifiers
source                   1..4
                         mol_type = protein
                         organism = synthetic construct
SEQUENCE: 166
PYSG                                                                         4

SEQ ID NO: 167           moltype = AA  length = 12
FEATURE                  Location/Qualifiers
source                   1..12
                         mol_type = protein
                         organism = synthetic construct
SEQUENCE: 167
AGTYSPFGYG MD                                                               12

SEQ ID NO: 168           moltype = AA  length = 7
FEATURE                  Location/Qualifiers
source                   1..7
                         mol_type = protein
                         organism = synthetic construct
SEQUENCE: 168
SESISNW                                                                      7

SEQ ID NO: 169           moltype =    length =
SEQUENCE: 169
000

SEQ ID NO: 170           moltype = AA  length = 7
FEATURE                  Location/Qualifiers
source                   1..7
                         mol_type = protein
                         organism = synthetic construct
SEQUENCE: 170
FQKLPPF                                                                      7

SEQ ID NO: 171           moltype = AA  length = 10
FEATURE                  Location/Qualifiers
source                   1..10
                         mol_type = protein
                         organism = synthetic construct
SEQUENCE: 171
GYTFDVYGIS                                                                  10
```

```
SEQ ID NO: 172           moltype = AA   length = 10
FEATURE                  Location/Qualifiers
source                   1..10
                         mol_type = protein
                         organism = synthetic construct
SEQUENCE: 172
WIAPYSGNTN                                                               10

SEQ ID NO: 173           moltype = AA   length = 14
FEATURE                  Location/Qualifiers
source                   1..14
                         mol_type = protein
                         organism = synthetic construct
SEQUENCE: 173
DAGTYSPFGY GMDV                                                          14

SEQ ID NO: 174           moltype = AA   length = 11
FEATURE                  Location/Qualifiers
source                   1..11
                         mol_type = protein
                         organism = synthetic construct
SEQUENCE: 174
RASESISNWL A                                                             11

SEQ ID NO: 175           moltype = AA   length = 7
FEATURE                  Location/Qualifiers
source                   1..7
                         mol_type = protein
                         organism = synthetic construct
SEQUENCE: 175
KAYSLEY                                                                  7

SEQ ID NO: 176           moltype = AA   length = 10
FEATURE                  Location/Qualifiers
source                   1..10
                         mol_type = protein
                         organism = synthetic construct
SEQUENCE: 176
QQFQKLPPFT                                                               10

SEQ ID NO: 177           moltype = AA   length = 6
FEATURE                  Location/Qualifiers
source                   1..6
                         mol_type = protein
                         organism = synthetic construct
SEQUENCE: 177
DVYGIS                                                                   6

SEQ ID NO: 178           moltype = AA   length = 13
FEATURE                  Location/Qualifiers
source                   1..13
                         mol_type = protein
                         organism = synthetic construct
SEQUENCE: 178
WMGWIAPYSG NTN                                                           13

SEQ ID NO: 179           moltype = AA   length = 15
FEATURE                  Location/Qualifiers
source                   1..15
                         mol_type = protein
                         organism = synthetic construct
SEQUENCE: 179
ARDAGTYSPF GYGMD                                                         15

SEQ ID NO: 180           moltype = AA   length = 7
FEATURE                  Location/Qualifiers
source                   1..7
                         mol_type = protein
                         organism = synthetic construct
SEQUENCE: 180
SNWLAWY                                                                  7

SEQ ID NO: 181           moltype = AA   length = 10
FEATURE                  Location/Qualifiers
source                   1..10
                         mol_type = protein
                         organism = synthetic construct
SEQUENCE: 181
```

```
LLIYKAYSLE                                                          10

SEQ ID NO: 182          moltype = AA  length = 9
FEATURE                 Location/Qualifiers
source                  1..9
                        mol_type = protein
                        organism = synthetic construct
SEQUENCE: 182
QQFQKLPPF                                                           9

SEQ ID NO: 183          moltype = AA  length = 8
FEATURE                 Location/Qualifiers
source                  1..8
                        mol_type = protein
                        organism = synthetic construct
SEQUENCE: 183
GYTFDVYG                                                            8

SEQ ID NO: 184          moltype = AA  length = 8
FEATURE                 Location/Qualifiers
source                  1..8
                        mol_type = protein
                        organism = synthetic construct
SEQUENCE: 184
IAPYSGNT                                                            8

SEQ ID NO: 185          moltype = AA  length = 16
FEATURE                 Location/Qualifiers
source                  1..16
                        mol_type = protein
                        organism = synthetic construct
SEQUENCE: 185
ARDAGTYSPF GTGMDV                                                   16

SEQ ID NO: 186          moltype = AA  length = 6
FEATURE                 Location/Qualifiers
source                  1..6
                        mol_type = protein
                        organism = synthetic construct
SEQUENCE: 186
ESISNW                                                              6

SEQ ID NO: 187          moltype =     length =
SEQUENCE: 187
000

SEQ ID NO: 188          moltype = AA  length = 10
FEATURE                 Location/Qualifiers
source                  1..10
                        mol_type = protein
                        organism = synthetic construct
SEQUENCE: 188
QQFQKLPPFT                                                          10

SEQ ID NO: 189          moltype = AA  length = 123
FEATURE                 Location/Qualifiers
source                  1..123
                        mol_type = protein
                        organism = synthetic construct
SEQUENCE: 189
QVQLVQSGAE VKKPGASVKV SCKASGYTFD VYGISWVRQA PGQGLEWMGW IAPYSGNTNY    60
AQKLQGRVTM TTDTSTSTAY MELRSLRSDD TAVYYCARDA GTYSPFGYGM DVWGQGTTVT    120
VSS                                                                 123

SEQ ID NO: 190          moltype = AA  length = 108
FEATURE                 Location/Qualifiers
source                  1..108
                        mol_type = protein
                        organism = synthetic construct
SEQUENCE: 190
DIQMTQSPST LSASVGDRVT ITCRASESIS NWLAWYQQKP GKAPKLLIYK AYSLEYGVPS    60
RFSGSGSGTE FTLTISSLQP DDFATYYCQQ FQKLPPFTFG GGTKVEIK                 108

SEQ ID NO: 191          moltype = AA  length = 10
FEATURE                 Location/Qualifiers
source                  1..10
                        mol_type = protein
                        organism = synthetic construct
SEQUENCE: 191
```

```
GYTFRSYGIS                                                                10

SEQ ID NO: 192           moltype = AA  length = 17
FEATURE                  Location/Qualifiers
source                   1..17
                         mol_type = protein
                         organism = synthetic construct SEQUENCE: 192
WVAPYNGNTN YAQKLQG                                                        17

SEQ ID NO: 193           moltype = AA  length = 14
FEATURE                  Location/Qualifiers
source                   1..14
                         mol_type = protein
                         organism = synthetic construct SEQUENCE: 193
DAGTYSPYGY GMDV                                                           14

SEQ ID NO: 194           moltype = AA  length = 11
FEATURE                  Location/Qualifiers
source                   1..11
                         mol_type = protein
                         organism = synthetic construct SEQUENCE: 194
RASQSISSWL A                                                              11

SEQ ID NO: 195           moltype = AA  length = 7
FEATURE                  Location/Qualifiers
source                   1..7
                         mol_type = protein
                         organism = synthetic construct SEQUENCE: 195
KASSLES                                                                   7

SEQ ID NO: 196           moltype = AA  length = 10
FEATURE                  Location/Qualifiers
source                   1..10
                         mol_type = protein
                         organism = synthetic construct SEQUENCE: 196
QQFQSLPPFT                                                                10

SEQ ID NO: 197           moltype = AA  length = 5
FEATURE                  Location/Qualifiers
source                   1..5
                         mol_type = protein
                         organism = synthetic construct SEQUENCE: 197
SYGIS                                                                     5

SEQ ID NO: 198           moltype = AA  length = 17
FEATURE                  Location/Qualifiers
source                   1..17
                         mol_type = protein
                         organism = synthetic construct SEQUENCE: 198
WVAPYNGNTN YAQKLQG                                                        17

SEQ ID NO: 199           moltype = AA  length = 14
FEATURE                  Location/Qualifiers
source                   1..14
                         mol_type = protein
                         organism = synthetic construct SEQUENCE: 199
DAGTYSPYGY GMDV                                                           14

SEQ ID NO: 200           moltype = AA  length = 11
FEATURE                  Location/Qualifiers
source                   1..11
                         mol_type = protein
                         organism = synthetic construct SEQUENCE: 200
RASQSISSWL A                                                              11

SEQ ID NO: 201           moltype = AA  length = 7
FEATURE                  Location/Qualifiers
source                   1..7
                         mol_type = protein
                         organism = synthetic construct
```

| | | |
|---|---|---|
| SEQUENCE: 201<br>KASSLES | | 7 |
| SEQ ID NO: 202<br>FEATURE<br>source | moltype = AA length = 10<br>Location/Qualifiers<br>1..10<br>mol_type = protein<br>organism = synthetic construct | |
| SEQUENCE: 202<br>QQFQSLPPFT | | 10 |
| SEQ ID NO: 203<br>FEATURE<br>source | moltype = AA length = 7<br>Location/Qualifiers<br>1..7<br>mol_type = protein<br>organism = synthetic construct | |
| SEQUENCE: 203<br>GYTFRSY | | 7 |
| SEQ ID NO: 204<br>FEATURE<br>source | moltype = AA length = 4<br>Location/Qualifiers<br>1..4<br>mol_type = protein<br>organism = synthetic construct | |
| SEQUENCE: 204<br>PYNG | | 4 |
| SEQ ID NO: 205<br>FEATURE<br>source | moltype = AA length = 12<br>Location/Qualifiers<br>1..12<br>mol_type = protein<br>organism = synthetic construct | |
| SEQUENCE: 205<br>AGTYSPYGYG MD | | 12 |
| SEQ ID NO: 206<br>FEATURE<br>source | moltype = AA length = 7<br>Location/Qualifiers<br>1..7<br>mol_type = protein<br>organism = synthetic construct | |
| SEQUENCE: 206<br>SQSISSW | | 7 |
| SEQ ID NO: 207<br>SEQUENCE: 207<br>000 | moltype = length = | |
| SEQ ID NO: 208<br>FEATURE<br>source | moltype = AA length = 7<br>Location/Qualifiers<br>1..7<br>mol_type = protein<br>organism = synthetic construct | |
| SEQUENCE: 208<br>FQSLPPF | | 7 |
| SEQ ID NO: 209<br>FEATURE<br>source | moltype = AA length = 10<br>Location/Qualifiers<br>1..10<br>mol_type = protein<br>organism = synthetic construct | |
| SEQUENCE: 209<br>GYTFRSYGIS | | 10 |
| SEQ ID NO: 210<br>FEATURE<br>source | moltype = AA length = 10<br>Location/Qualifiers<br>1..10<br>mol_type = protein<br>organism = synthetic construct | |
| SEQUENCE: 210<br>WVAPYNGNTN | | 10 |
| SEQ ID NO: 211<br>FEATURE<br>source | moltype = AA length = 14<br>Location/Qualifiers<br>1..14<br>mol_type = protein<br>organism = synthetic construct | |
| SEQUENCE: 211<br>DAGTYSPYGY GMDV | | 14 |

```
SEQ ID NO: 212           moltype = AA  length = 11
FEATURE                  Location/Qualifiers
source                   1..11
                         mol_type = protein
                         organism = synthetic construct
SEQUENCE: 212
RASQSISSWL A                                                          11

SEQ ID NO: 213           moltype = AA  length = 7
FEATURE                  Location/Qualifiers
source                   1..7
                         mol_type = protein
                         organism = synthetic construct
SEQUENCE: 213
KASSLES                                                               7

SEQ ID NO: 214           moltype = AA  length = 10
FEATURE                  Location/Qualifiers
source                   1..10
                         mol_type = protein
                         organism = synthetic construct
SEQUENCE: 214
QQFQSLPPFT                                                            10

SEQ ID NO: 215           moltype = AA  length = 6
FEATURE                  Location/Qualifiers
source                   1..6
                         mol_type = protein
                         organism = synthetic construct
SEQUENCE: 215
RSYGIS                                                                6

SEQ ID NO: 216           moltype = AA  length = 13
FEATURE                  Location/Qualifiers
source                   1..13
                         mol_type = protein
                         organism = synthetic construct
SEQUENCE: 216
WMGWVAPYNG NTN                                                        13

SEQ ID NO: 217           moltype = AA  length = 15
FEATURE                  Location/Qualifiers
source                   1..15
                         mol_type = protein
                         organism = synthetic construct
SEQUENCE: 217
ARDAGTYSPY GYGMD                                                      15

SEQ ID NO: 218           moltype = AA  length = 7
FEATURE                  Location/Qualifiers
source                   1..7
                         mol_type = protein
                         organism = synthetic construct
SEQUENCE: 218
SSWLAWY                                                               7

SEQ ID NO: 219           moltype = AA  length = 10
FEATURE                  Location/Qualifiers
source                   1..10
                         mol_type = protein
                         organism = synthetic construct
SEQUENCE: 219
LLIYKASSLE                                                            10

SEQ ID NO: 220           moltype = AA  length = 9
FEATURE                  Location/Qualifiers
source                   1..9
                         mol_type = protein
                         organism = synthetic construct
SEQUENCE: 220
QQFQSLPPF                                                             9

SEQ ID NO: 221           moltype = AA  length = 8
FEATURE                  Location/Qualifiers
source                   1..8
                         mol_type = protein
                         organism = synthetic construct
SEQUENCE: 221
GYTFRSYG                                                              8
```

| SEQ ID NO: 222 | moltype = AA length = 8 |
| --- | --- |
| FEATURE | Location/Qualifiers |
| source | 1..8 |
| | mol_type = protein |
| | organism = synthetic construct |

SEQUENCE: 222
VAPYNGNT                                                          8

| SEQ ID NO: 223 | moltype = AA length = 16 |
| --- | --- |
| FEATURE | Location/Qualifiers |
| source | 1..16 |
| | mol_type = protein |
| | organism = synthetic construct |

SEQUENCE: 223
ARDAGTYSPY GYGMDV                                                 16

| SEQ ID NO: 224 | moltype = AA length = 6 |
| --- | --- |
| FEATURE | Location/Qualifiers |
| source | 1..6 |
| | mol_type = protein |
| | organism = synthetic construct |

SEQUENCE: 224
QSISSW                                                            6

| SEQ ID NO: 225 | moltype = length = |
| --- | --- |

SEQUENCE: 225
000

| SEQ ID NO: 226 | moltype = AA length = 10 |
| --- | --- |
| FEATURE | Location/Qualifiers |
| source | 1..10 |
| | mol_type = protein |
| | organism = synthetic construct |

SEQUENCE: 226
QQFQSLPPFT                                                        10

| SEQ ID NO: 227 | moltype = AA length = 123 |
| --- | --- |
| FEATURE | Location/Qualifiers |
| source | 1..123 |
| | mol_type = protein |
| | organism = synthetic construct |

SEQUENCE: 227
QVQLVQSGAE VKKPGASVKV SCKASGYTFR SYGISWVRQA PGQGLEWMGW VAPYNGNTNY   60
AQKLQGRVTM TTDTSTSTAY MELRSLRSDD TAVYYCARDA GTYSPYGYGM DVWGQGTTVT  120
VSS                                                              123

| SEQ ID NO: 228 | moltype = AA length = 108 |
| --- | --- |
| FEATURE | Location/Qualifiers |
| source | 1..108 |
| | mol_type = protein |
| | organism = synthetic construct |

SEQUENCE: 228
DIQMTQSPST LSASVGDRVT ITCRASQSIS SWLAWYQQKP GKAPKLLIYK ASSLESGVPS   60
RFSGSGSGTE FTLTISSLQP DDFATYYCQQ FQSLPPFTFG GGTKVEIK              108

| SEQ ID NO: 229 | moltype = AA length = 10 |
| --- | --- |
| FEATURE | Location/Qualifiers |
| source | 1..10 |
| | mol_type = protein |
| | organism = synthetic construct |

SEQUENCE: 229
GYTFRSYGIS                                                        10

| SEQ ID NO: 230 | moltype = AA length = 17 |
| --- | --- |
| FEATURE | Location/Qualifiers |
| source | 1..17 |
| | mol_type = protein |
| | organism = synthetic construct |

SEQUENCE: 230
WVAPYSGNTN YAQKLQG                                                17

| SEQ ID NO: 231 | moltype = AA length = 14 |
| --- | --- |
| FEATURE | Location/Qualifiers |
| source | 1..14 |
| | mol_type = protein |
| | organism = synthetic construct |

SEQUENCE: 231
DAGTYSPYGY GMDV                                                   14

```
SEQ ID NO: 232              moltype = AA  length = 11
FEATURE                     Location/Qualifiers
source                      1..11
                            mol_type = protein
                            organism = synthetic construct
SEQUENCE: 232
RASHSIDSWL A                                                          11

SEQ ID NO: 233              moltype = AA  length = 7
FEATURE                     Location/Qualifiers
source                      1..7
                            mol_type = protein
                            organism = synthetic construct
SEQUENCE: 233
KASYLES                                                                7

SEQ ID NO: 234              moltype = AA  length = 10
FEATURE                     Location/Qualifiers
source                      1..10
                            mol_type = protein
                            organism = synthetic construct
SEQUENCE: 234
QLFQSLPPFT                                                            10

SEQ ID NO: 235              moltype = AA  length = 5
FEATURE                     Location/Qualifiers
source                      1..5
                            mol_type = protein
                            organism = synthetic construct
SEQUENCE: 235
SYGIS                                                                  5

SEQ ID NO: 236              moltype = AA  length = 17
FEATURE                     Location/Qualifiers
source                      1..17
                            mol_type = protein
                            organism = synthetic construct
SEQUENCE: 236
WVAPYSGNTN YAQKLQG                                                    17

SEQ ID NO: 237              moltype = AA  length = 14
FEATURE                     Location/Qualifiers
source                      1..14
                            mol_type = protein
                            organism = synthetic construct
SEQUENCE: 237
DAGTYSPYGY GMDV                                                       14

SEQ ID NO: 238              moltype = AA  length = 11
FEATURE                     Location/Qualifiers
source                      1..11
                            mol_type = protein
                            organism = synthetic construct
SEQUENCE: 238
RASHSIDSWL A                                                          11

SEQ ID NO: 239              moltype = AA  length = 7
FEATURE                     Location/Qualifiers
source                      1..7
                            mol_type = protein
                            organism = synthetic construct
SEQUENCE: 239
KASYLES                                                                7

SEQ ID NO: 240              moltype = AA  length = 10
FEATURE                     Location/Qualifiers
source                      1..10
                            mol_type = protein
                            organism = synthetic construct
SEQUENCE: 240
QLFQSLPPFT                                                            10

SEQ ID NO: 241              moltype = AA  length = 7
FEATURE                     Location/Qualifiers
source                      1..7
                            mol_type = protein
                            organism = synthetic construct
SEQUENCE: 241
```

```
GYTFRSY                                                                  7

SEQ ID NO: 242          moltype = AA  length = 4
FEATURE                 Location/Qualifiers
source                  1..4
                        mol_type = protein
                        organism = synthetic construct
SEQUENCE: 242
PYSG                                                                     4

SEQ ID NO: 243          moltype = AA  length = 12
FEATURE                 Location/Qualifiers
source                  1..12
                        mol_type = protein
                        organism = synthetic construct
SEQUENCE: 243
AGTYSPYGYG MD                                                           12

SEQ ID NO: 244          moltype = AA  length = 7
FEATURE                 Location/Qualifiers
source                  1..7
                        mol_type = protein
                        organism = synthetic construct
SEQUENCE: 244
SHSIDSW                                                                  7

SEQ ID NO: 245          moltype =     length =
SEQUENCE: 245
000

SEQ ID NO: 246          moltype = AA  length = 7
FEATURE                 Location/Qualifiers
source                  1..7
                        mol_type = protein
                        organism = synthetic construct
SEQUENCE: 246
FQSLPPF                                                                  7

SEQ ID NO: 247          moltype = AA  length = 10
FEATURE                 Location/Qualifiers
source                  1..10
                        mol_type = protein
                        organism = synthetic construct
SEQUENCE: 247
GYTFRSYGIS                                                              10

SEQ ID NO: 248          moltype = AA  length = 10
FEATURE                 Location/Qualifiers
source                  1..10
                        mol_type = protein
                        organism = synthetic construct
SEQUENCE: 248
WVAPYSGNTN                                                              10

SEQ ID NO: 249          moltype = AA  length = 14
FEATURE                 Location/Qualifiers
source                  1..14
                        mol_type = protein
                        organism = synthetic construct
SEQUENCE: 249
DAGTYSPYGY GMDV                                                         14

SEQ ID NO: 250          moltype = AA  length = 11
FEATURE                 Location/Qualifiers
source                  1..11
                        mol_type = protein
                        organism = synthetic construct
SEQUENCE: 250
RASHSIDSWL A                                                            11

SEQ ID NO: 251          moltype = AA  length = 7
FEATURE                 Location/Qualifiers
source                  1..7
                        mol_type = protein
                        organism = synthetic construct
SEQUENCE: 251
KASYLES                                                                  7

SEQ ID NO: 252          moltype = AA  length = 10
```

```
FEATURE             Location/Qualifiers
source              1..10
                    mol_type = protein
                    organism = synthetic construct
SEQUENCE: 252
QLFQSLPPFT                                                                      10

SEQ ID NO: 253      moltype = AA   length = 6
FEATURE             Location/Qualifiers
source              1..6
                    mol_type = protein
                    organism = synthetic construct
SEQUENCE: 253
RSYGIS                                                                          6

SEQ ID NO: 254      moltype = AA   length = 13
FEATURE             Location/Qualifiers
source              1..13
                    mol_type = protein
                    organism = synthetic construct
SEQUENCE: 254
WMGWVAPYSG NTN                                                                  13

SEQ ID NO: 255      moltype = AA   length = 15
FEATURE             Location/Qualifiers
source              1..15
                    mol_type = protein
                    organism = synthetic construct
SEQUENCE: 255
ARDAGTYSPY GYGMD                                                                15

SEQ ID NO: 256      moltype = AA   length = 7
FEATURE             Location/Qualifiers
source              1..7
                    mol_type = protein
                    organism = synthetic construct
SEQUENCE: 256
DSWLAWY                                                                         7

SEQ ID NO: 257      moltype = AA   length = 10
FEATURE             Location/Qualifiers
source              1..10
                    mol_type = protein
                    organism = synthetic construct
SEQUENCE: 257
LLIYKASYLE                                                                      10

SEQ ID NO: 258      moltype = AA   length = 9
FEATURE             Location/Qualifiers
source              1..9
                    mol_type = protein
                    organism = synthetic construct
SEQUENCE: 258
QLFQSLPPF                                                                       9

SEQ ID NO: 259      moltype = AA   length = 8
FEATURE             Location/Qualifiers
source              1..8
                    mol_type = protein
                    organism = synthetic construct
SEQUENCE: 259
GYTFRSYG                                                                        8

SEQ ID NO: 260      moltype = AA   length = 8
FEATURE             Location/Qualifiers
source              1..8
                    mol_type = protein
                    organism = synthetic construct
SEQUENCE: 260
VAPYSGNT                                                                        8

SEQ ID NO: 261      moltype = AA   length = 16
FEATURE             Location/Qualifiers
source              1..16
                    mol_type = protein
                    organism = synthetic construct
SEQUENCE: 261
ARDAGTYSPY GYGMDV                                                               16
```

| | | |
|---|---|---|
| SEQ ID NO: 262<br>FEATURE<br>source | moltype = AA length = 6<br>Location/Qualifiers<br>1..6<br>mol_type = protein<br>organism = synthetic construct | |
| SEQUENCE: 262<br>HSIDSW | | 6 |
| SEQ ID NO: 263<br>SEQUENCE: 263<br>000 | moltype =    length = | |
| SEQ ID NO: 264<br>FEATURE<br>source | moltype = AA length = 10<br>Location/Qualifiers<br>1..10<br>mol_type = protein<br>organism = synthetic construct | |
| SEQUENCE: 264<br>QLFQSLPPFT | | 10 |
| SEQ ID NO: 265<br>FEATURE<br>source | moltype = AA length = 123<br>Location/Qualifiers<br>1..123<br>mol_type = protein<br>organism = synthetic construct | |
| SEQUENCE: 265<br>QVQLVQSGAE VKKPGASVKV SCKASGYTFR SYGISWVRQA PGQGLEWMGW VAPYSGNTNY<br>AQKLQGRVTM TTDTSTSTAY MELRSLRSDD TAVYYCARDA GTYSPYGYGM DVWGQGTTVT<br>VSS | | 60<br>120<br>123 |
| SEQ ID NO: 266<br>FEATURE<br>source | moltype = AA length = 108<br>Location/Qualifiers<br>1..108<br>mol_type = protein<br>organism = synthetic construct | |
| SEQUENCE: 266<br>DIQMTQSPST LSASVGDRVT ITCRASHSID SWLAWYQQKP GKAPKLLIYK ASYLESGVPS<br>RFSGSGSGTE FTLTISSLQP DDFATYYCQL FQSLPPFTFG GGTKVEIK | | 60<br>108 |
| SEQ ID NO: 267<br>FEATURE<br>source | moltype = AA length = 10<br>Location/Qualifiers<br>1..10<br>mol_type = protein<br>organism = synthetic construct | |
| SEQUENCE: 267<br>GYTFRSYGIS | | 10 |
| SEQ ID NO: 268<br>FEATURE<br>source | moltype = AA length = 17<br>Location/Qualifiers<br>1..17<br>mol_type = protein<br>organism = synthetic construct | |
| SEQUENCE: 268<br>WVAPYSGNTN YAQKLQG | | 17 |
| SEQ ID NO: 269<br>FEATURE<br>source | moltype = AA length = 14<br>Location/Qualifiers<br>1..14<br>mol_type = protein<br>organism = synthetic construct | |
| SEQUENCE: 269<br>DAGTYSPYGY GMDV | | 14 |
| SEQ ID NO: 270<br>FEATURE<br>source | moltype = AA length = 11<br>Location/Qualifiers<br>1..11<br>mol_type = protein<br>organism = synthetic construct | |
| SEQUENCE: 270<br>QASQSIDSWL A | | 11 |
| SEQ ID NO: 271<br>FEATURE<br>source | moltype = AA length = 7<br>Location/Qualifiers<br>1..7<br>mol_type = protein<br>organism = synthetic construct | |
| SEQUENCE: 271<br>SASYLES | | 7 |

-continued

| | | |
|---|---|---|
| SEQ ID NO: 272<br>FEATURE<br>source | moltype = AA   length = 10<br>Location/Qualifiers<br>1..10<br>mol_type = protein<br>organism = synthetic construct | |
| SEQUENCE: 272<br>QRFQSLPPFT | | 10 |
| SEQ ID NO: 273<br>FEATURE<br>source | moltype = AA   length = 5<br>Location/Qualifiers<br>1..5<br>mol_type = protein<br>organism = synthetic construct | |
| SEQUENCE: 273<br>SYGIS | | 5 |
| SEQ ID NO: 274<br>FEATURE<br>source | moltype = AA   length = 17<br>Location/Qualifiers<br>1..17<br>mol_type = protein<br>organism = synthetic construct | |
| SEQUENCE: 274<br>WVAPYSGNTN YAQKLQG | | 17 |
| SEQ ID NO: 275<br>FEATURE<br>source | moltype = AA   length = 14<br>Location/Qualifiers<br>1..14<br>mol_type = protein<br>organism = synthetic construct | |
| SEQUENCE: 275<br>DAGTYSPYGY GMDV | | 14 |
| SEQ ID NO: 276<br>FEATURE<br>source | moltype = AA   length = 11<br>Location/Qualifiers<br>1..11<br>mol_type = protein<br>organism = synthetic construct | |
| SEQUENCE: 276<br>QASQSIDSWL A | | 11 |
| SEQ ID NO: 277<br>FEATURE<br>source | moltype = AA   length = 7<br>Location/Qualifiers<br>1..7<br>mol_type = protein<br>organism = synthetic construct | |
| SEQUENCE: 277<br>SASYLES | | 7 |
| SEQ ID NO: 278<br>FEATURE<br>source | moltype = AA   length = 10<br>Location/Qualifiers<br>1..10<br>mol_type = protein<br>organism = synthetic construct | |
| SEQUENCE: 278<br>QRFQSLPPFT | | 10 |
| SEQ ID NO: 279<br>FEATURE<br>source | moltype = AA   length = 7<br>Location/Qualifiers<br>1..7<br>mol_type = protein<br>organism = synthetic construct | |
| SEQUENCE: 279<br>GYTFRSY | | 7 |
| SEQ ID NO: 280<br>FEATURE<br>source | moltype = AA   length = 4<br>Location/Qualifiers<br>1..4<br>mol_type = protein<br>organism = synthetic construct | |
| SEQUENCE: 280<br>PYSG | | 4 |
| SEQ ID NO: 281<br>FEATURE<br>source | moltype = AA   length = 12<br>Location/Qualifiers<br>1..12<br>mol_type = protein<br>organism = synthetic construct | |
| SEQUENCE: 281<br>AGTYSPYGYG MD | | 12 |

```
SEQ ID NO: 282          moltype = AA  length = 7
FEATURE                 Location/Qualifiers
source                  1..7
                        mol_type = protein
                        organism = synthetic construct
SEQUENCE: 282
SQSIDSW                                                                    7

SEQ ID NO: 283          moltype =    length =
SEQUENCE: 283
000

SEQ ID NO: 284          moltype = AA  length = 7
FEATURE                 Location/Qualifiers
source                  1..7
                        mol_type = protein
                        organism = synthetic construct
SEQUENCE: 284
FQSLPPF                                                                    7

SEQ ID NO: 285          moltype = AA  length = 10
FEATURE                 Location/Qualifiers
source                  1..10
                        mol_type = protein
                        organism = synthetic construct
SEQUENCE: 285
GYTFRSYGIS                                                                10

SEQ ID NO: 286          moltype = AA  length = 10
FEATURE                 Location/Qualifiers
source                  1..10
                        mol_type = protein
                        organism = synthetic construct
SEQUENCE: 286
WVAPYSGNTN                                                                10

SEQ ID NO: 287          moltype = AA  length = 14
FEATURE                 Location/Qualifiers
source                  1..14
                        mol_type = protein
                        organism = synthetic construct
SEQUENCE: 287
DAGTYSPYGY GMDV                                                           14

SEQ ID NO: 288          moltype = AA  length = 11
FEATURE                 Location/Qualifiers
source                  1..11
                        mol_type = protein
                        organism = synthetic construct
SEQUENCE: 288
QASQSIDSWL A                                                              11

SEQ ID NO: 289          moltype = AA  length = 7
FEATURE                 Location/Qualifiers
source                  1..7
                        mol_type = protein
                        organism = synthetic construct
SEQUENCE: 289
SASYLES                                                                    7

SEQ ID NO: 290          moltype = AA  length = 10
FEATURE                 Location/Qualifiers
source                  1..10
                        mol_type = protein
                        organism = synthetic construct
SEQUENCE: 290
QRFQSLPPFT                                                                10

SEQ ID NO: 291          moltype = AA  length = 6
FEATURE                 Location/Qualifiers
source                  1..6
                        mol_type = protein
                        organism = synthetic construct
SEQUENCE: 291
RSYGIS                                                                     6

SEQ ID NO: 292          moltype = AA  length = 13
FEATURE                 Location/Qualifiers
```

```
source                   1..13
                         mol_type = protein
                         organism = synthetic construct
SEQUENCE: 292
WMGWVAPYSG NTN                                                         13

SEQ ID NO: 293           moltype = AA  length = 15
FEATURE                  Location/Qualifiers
source                   1..15
                         mol_type = protein
                         organism = synthetic construct
SEQUENCE: 293
ARDAGTYSPY GYGMD                                                       15

SEQ ID NO: 294           moltype = AA  length = 7
FEATURE                  Location/Qualifiers
source                   1..7
                         mol_type = protein
                         organism = synthetic construct
SEQUENCE: 294
DSWLAWY                                                                7

SEQ ID NO: 295           moltype = AA  length = 10
FEATURE                  Location/Qualifiers
source                   1..10
                         mol_type = protein
                         organism = synthetic construct
SEQUENCE: 295
LLIYSASYLE                                                             10

SEQ ID NO: 296           moltype = AA  length = 9
FEATURE                  Location/Qualifiers
source                   1..9
                         mol_type = protein
                         organism = synthetic construct
SEQUENCE: 296
QRFQSLPPF                                                              9

SEQ ID NO: 297           moltype = AA  length = 8
FEATURE                  Location/Qualifiers
source                   1..8
                         mol_type = protein
                         organism = synthetic construct
SEQUENCE: 297
GYTFRSYG                                                               8

SEQ ID NO: 298           moltype = AA  length = 8
FEATURE                  Location/Qualifiers
source                   1..8
                         mol_type = protein
                         organism = synthetic construct
SEQUENCE: 298
VAPYSGNT                                                               8

SEQ ID NO: 299           moltype = AA  length = 16
FEATURE                  Location/Qualifiers
source                   1..16
                         mol_type = protein
                         organism = synthetic construct
SEQUENCE: 299
ARDAGTYSPY GYGMDV                                                      16

SEQ ID NO: 300           moltype = AA  length = 6
FEATURE                  Location/Qualifiers
source                   1..6
                         mol_type = protein
                         organism = synthetic construct
SEQUENCE: 300
QSIDSW                                                                 6

SEQ ID NO: 301           moltype =   length =
SEQUENCE: 301
000

SEQ ID NO: 302           moltype = AA  length = 10
FEATURE                  Location/Qualifiers
source                   1..10
                         mol_type = protein
                         organism = synthetic construct
```

```
SEQUENCE: 302
QRFQSLPPFT                                                                          10

SEQ ID NO: 303           moltype = AA  length = 123
FEATURE                  Location/Qualifiers
source                   1..123
                         mol_type = protein
                         organism = synthetic construct
SEQUENCE: 303
QVQLVQSGAE VKKPGASVKV SCKASGYTFR SYGISWVRQA PGQGLEWMGW VAPYSGNTNY                    60
AQKLQGRVTM TTDTSTSTAY MELRSLRSDD TAVYYCARDA GTYSPYGYGM DVWGQGTTVT                   120
VSS                                                                                123

SEQ ID NO: 304           moltype = AA  length = 108
FEATURE                  Location/Qualifiers
source                   1..108
                         mol_type = protein
                         organism = synthetic construct
SEQUENCE: 304
DIQMTQSPST LSASVGDRVT ITCQASQSID SWLAWYQQKP GKAPKLLIYS ASYLESGVPS                    60
RFSGSGSGTE FTLTISSLQP DDFATYYCQR FQSLPPFTFG GGTKVEIK                                108

SEQ ID NO: 305           moltype = AA  length = 10
FEATURE                  Location/Qualifiers
source                   1..10
                         mol_type = protein
                         organism = synthetic construct
SEQUENCE: 305
GFTFHSRGMH                                                                          10

SEQ ID NO: 306           moltype = AA  length = 17
FEATURE                  Location/Qualifiers
source                   1..17
                         mol_type = protein
                         organism = synthetic construct
SEQUENCE: 306
VITYDGINKY YADSVEG                                                                  17

SEQ ID NO: 307           moltype = AA  length = 10
FEATURE                  Location/Qualifiers
source                   1..10
                         mol_type = protein
                         organism = synthetic construct
SEQUENCE: 307
DGVYYGVYDY                                                                          10

SEQ ID NO: 308           moltype = AA  length = 17
FEATURE                  Location/Qualifiers
source                   1..17
                         mol_type = protein
                         organism = synthetic construct
SEQUENCE: 308
KSSQSVLFSS NNKNYLA                                                                  17

SEQ ID NO: 309           moltype = AA  length = 7
FEATURE                  Location/Qualifiers
source                   1..7
                         mol_type = protein
                         organism = synthetic construct
SEQUENCE: 309
WASTRES                                                                              7

SEQ ID NO: 310           moltype = AA  length = 9
FEATURE                  Location/Qualifiers
source                   1..9
                         mol_type = protein
                         organism = synthetic construct
SEQUENCE: 310
QQFHSYPLT                                                                            9

SEQ ID NO: 311           moltype = AA  length = 5
FEATURE                  Location/Qualifiers
source                   1..5
                         mol_type = protein
                         organism = synthetic construct
SEQUENCE: 311
SRGMH                                                                                5

SEQ ID NO: 312           moltype = AA  length = 17
```

```
FEATURE                     Location/Qualifiers
source                      1..17
                            mol_type = protein
                            organism = synthetic construct
SEQUENCE: 312
VITYDGINKY YADSVEG                                                              17

SEQ ID NO: 313              moltype = AA  length = 10
FEATURE                     Location/Qualifiers
source                      1..10
                            mol_type = protein
                            organism = synthetic construct
SEQUENCE: 313
DGVYYGVYDY                                                                      10

SEQ ID NO: 314              moltype = AA  length = 17
FEATURE                     Location/Qualifiers
source                      1..17
                            mol_type = protein
                            organism = synthetic construct
SEQUENCE: 314
KSSQSVLFSS NNKNYLA                                                              17

SEQ ID NO: 315              moltype = AA  length = 7
FEATURE                     Location/Qualifiers
source                      1..7
                            mol_type = protein
                            organism = synthetic construct
SEQUENCE: 315
WASTRES                                                                          7

SEQ ID NO: 316              moltype = AA  length = 9
FEATURE                     Location/Qualifiers
source                      1..9
                            mol_type = protein
                            organism = synthetic construct
SEQUENCE: 316
QQFHSYPLT                                                                        9

SEQ ID NO: 317              moltype = AA  length = 7
FEATURE                     Location/Qualifiers
source                      1..7
                            mol_type = protein
                            organism = synthetic construct
SEQUENCE: 317
GFTFHSR                                                                          7

SEQ ID NO: 318              moltype = AA  length = 4
FEATURE                     Location/Qualifiers
source                      1..4
                            mol_type = protein
                            organism = synthetic construct
SEQUENCE: 318
YDGI                                                                             4

SEQ ID NO: 319              moltype = AA  length = 8
FEATURE                     Location/Qualifiers
source                      1..8
                            mol_type = protein
                            organism = synthetic construct
SEQUENCE: 319
GVYYGVYD                                                                         8

SEQ ID NO: 320              moltype = AA  length = 13
FEATURE                     Location/Qualifiers
source                      1..13
                            mol_type = protein
                            organism = synthetic construct
SEQUENCE: 320
SQSVLFSSNN KNY                                                                  13

SEQ ID NO: 321              moltype =     length =
SEQUENCE: 321
000

SEQ ID NO: 322              moltype = AA  length = 6
FEATURE                     Location/Qualifiers
source                      1..6
                            mol_type = protein
```

```
                             organism = synthetic construct
SEQUENCE: 322
FHSYPL                                                                          6

SEQ ID NO: 323           moltype = AA   length = 10
FEATURE                  Location/Qualifiers
source                   1..10
                         mol_type = protein
                         organism = synthetic construct
SEQUENCE: 323
GFTFHSRGMH                                                                     10

SEQ ID NO: 324           moltype = AA   length = 10
FEATURE                  Location/Qualifiers
source                   1..10
                         mol_type = protein
                         organism = synthetic construct
SEQUENCE: 324
VITYDGINKY                                                                     10

SEQ ID NO: 325           moltype = AA   length = 10
FEATURE                  Location/Qualifiers
source                   1..10
                         mol_type = protein
                         organism = synthetic construct
SEQUENCE: 325
DGVYYGVYDY                                                                     10

SEQ ID NO: 326           moltype = AA   length = 17
FEATURE                  Location/Qualifiers
source                   1..17
                         mol_type = protein
                         organism = synthetic construct
SEQUENCE: 326
KSSQSVLFSS NNKNYLA                                                             17

SEQ ID NO: 327           moltype = AA   length = 7
FEATURE                  Location/Qualifiers
source                   1..7
                         mol_type = protein
                         organism = synthetic construct
SEQUENCE: 327
WASTRES                                                                         7

SEQ ID NO: 328           moltype = AA   length = 9
FEATURE                  Location/Qualifiers
source                   1..9
                         mol_type = protein
                         organism = synthetic construct
SEQUENCE: 328
QQFHSYPLT                                                                       9

SEQ ID NO: 329           moltype = AA   length = 6
FEATURE                  Location/Qualifiers
source                   1..6
                         mol_type = protein
                         organism = synthetic construct
SEQUENCE: 329
HSRGMH                                                                          6

SEQ ID NO: 330           moltype = AA   length = 13
FEATURE                  Location/Qualifiers
source                   1..13
                         mol_type = protein
                         organism = synthetic construct
SEQUENCE: 330
WVAVITYDGI NKY                                                                 13

SEQ ID NO: 331           moltype = AA   length = 11
FEATURE                  Location/Qualifiers
source                   1..11
                         mol_type = protein
                         organism = synthetic construct
SEQUENCE: 331
ARDGVYYGVY D                                                                   11

SEQ ID NO: 332           moltype = AA   length = 13
FEATURE                  Location/Qualifiers
source                   1..13
```

```
                              mol_type = protein
                              organism = synthetic construct
SEQUENCE: 332
LFSSNNKNYL AWY                                                       13

SEQ ID NO: 333                moltype = AA  length = 10
FEATURE                       Location/Qualifiers
source                        1..10
                              mol_type = protein
                              organism = synthetic construct
SEQUENCE: 333
LLIYWASTRE                                                           10

SEQ ID NO: 334                moltype = AA  length = 8
FEATURE                       Location/Qualifiers
source                        1..8
                              mol_type = protein
                              organism = synthetic construct
SEQUENCE: 334
QQFHSYPL                                                              8

SEQ ID NO: 335                moltype = AA  length = 8
FEATURE                       Location/Qualifiers
source                        1..8
                              mol_type = protein
                              organism = synthetic construct
SEQUENCE: 335
GFTFHSRG                                                              8

SEQ ID NO: 336                moltype = AA  length = 8
FEATURE                       Location/Qualifiers
source                        1..8
                              mol_type = protein
                              organism = synthetic construct
SEQUENCE: 336
ITYDGINK                                                              8

SEQ ID NO: 337                moltype = AA  length = 12
FEATURE                       Location/Qualifiers
source                        1..12
                              mol_type = protein
                              organism = synthetic construct
SEQUENCE: 337
ARDGVYYGVY DY                                                        12

SEQ ID NO: 338                moltype = AA  length = 12
FEATURE                       Location/Qualifiers
source                        1..12
                              mol_type = protein
                              organism = synthetic construct
SEQUENCE: 338
QSVLFSSNNK NY                                                        12

SEQ ID NO: 339                moltype =     length =
SEQUENCE: 339
000

SEQ ID NO: 340                moltype = AA  length = 9
FEATURE                       Location/Qualifiers
source                        1..9
                              mol_type = protein
                              organism = synthetic construct
SEQUENCE: 340
QQFHSYPLT                                                             9

SEQ ID NO: 341                moltype = AA  length = 119
FEATURE                       Location/Qualifiers
source                        1..119
                              mol_type = protein
                              organism = synthetic construct
SEQUENCE: 341
QVQLVESGGG VVQPGRSLRL SCAASGFTFH SRGMHWVRQA PGKGLEWVAV ITYDGINKYY     60
ADSVEGRFTI SRDNSKNTLY LQMNSLRAED TAVYYCARDG VYYGVYDYWG QGTLVTVSS    119

SEQ ID NO: 342                moltype = AA  length = 113
FEATURE                       Location/Qualifiers
source                        1..113
                              mol_type = protein
                              organism = synthetic construct
```

```
SEQUENCE: 342
DIVMTQSPDS LAVSLGERAT INCKSSQSVL FSSNNKNYLA WYQQKPGQPP KLLIYWASTR    60
ESGVPDRFSG SGSGTDFTLT ISSLQAEDVA VYYCQQFHSY PLTFGGGTKV EIK          113

SEQ ID NO: 343          moltype = AA  length = 10
FEATURE                 Location/Qualifiers
source                  1..10
                        mol_type = protein
                        organism = synthetic construct
SEQUENCE: 343
GFTFRSYGMH                                                           10

SEQ ID NO: 344          moltype = AA  length = 17
FEATURE                 Location/Qualifiers
source                  1..17
                        mol_type = protein
                        organism = synthetic construct
SEQUENCE: 344
VITYDGINKY YADSVEG                                                   17

SEQ ID NO: 345          moltype = AA  length = 10
FEATURE                 Location/Qualifiers
source                  1..10
                        mol_type = protein
                        organism = synthetic construct
SEQUENCE: 345
DGVYYGVYDY                                                           10

SEQ ID NO: 346          moltype = AA  length = 17
FEATURE                 Location/Qualifiers
source                  1..17
                        mol_type = protein
                        organism = synthetic construct
SEQUENCE: 346
KSSQSVLFSS NNKNYLA                                                   17

SEQ ID NO: 347          moltype = AA  length = 7
FEATURE                 Location/Qualifiers
source                  1..7
                        mol_type = protein
                        organism = synthetic construct
SEQUENCE: 347
WASTRES                                                               7

SEQ ID NO: 348          moltype = AA  length = 9
FEATURE                 Location/Qualifiers
source                  1..9
                        mol_type = protein
                        organism = synthetic construct
SEQUENCE: 348
QQFHSYPLT                                                             9

SEQ ID NO: 349          moltype = AA  length = 5
FEATURE                 Location/Qualifiers
source                  1..5
                        mol_type = protein
                        organism = synthetic construct
SEQUENCE: 349
SYGMH                                                                 5

SEQ ID NO: 350          moltype = AA  length = 17
FEATURE                 Location/Qualifiers
source                  1..17
                        mol_type = protein
                        organism = synthetic construct
SEQUENCE: 350
VITYDGINKY YADSVEG                                                   17

SEQ ID NO: 351          moltype = AA  length = 10
FEATURE                 Location/Qualifiers
source                  1..10
                        mol_type = protein
                        organism = synthetic construct
SEQUENCE: 351
DGVYYGVYDY                                                           10

SEQ ID NO: 352          moltype = AA  length = 17
FEATURE                 Location/Qualifiers
source                  1..17
```

```
                        mol_type = protein
                        organism = synthetic construct
SEQUENCE: 352
KSSQSVLFSS NNKNYLA                                                      17

SEQ ID NO: 353          moltype = AA  length = 7
FEATURE                 Location/Qualifiers
source                  1..7
                        mol_type = protein
                        organism = synthetic construct
SEQUENCE: 353
WASTRES                                                                 7

SEQ ID NO: 354          moltype = AA  length = 9
FEATURE                 Location/Qualifiers
source                  1..9
                        mol_type = protein
                        organism = synthetic construct
SEQUENCE: 354
QQFHSYPLT                                                               9

SEQ ID NO: 355          moltype = AA  length = 7
FEATURE                 Location/Qualifiers
source                  1..7
                        mol_type = protein
                        organism = synthetic construct
SEQUENCE: 355
GFTFRSY                                                                 7

SEQ ID NO: 356          moltype = AA  length = 4
FEATURE                 Location/Qualifiers
source                  1..4
                        mol_type = protein
                        organism = synthetic construct
SEQUENCE: 356
YDGI                                                                    4

SEQ ID NO: 357          moltype = AA  length = 8
FEATURE                 Location/Qualifiers
source                  1..8
                        mol_type = protein
                        organism = synthetic construct
SEQUENCE: 357
GVYYGVYD                                                                8

SEQ ID NO: 358          moltype = AA  length = 13
FEATURE                 Location/Qualifiers
source                  1..13
                        mol_type = protein
                        organism = synthetic construct
SEQUENCE: 358
SQSVLFSSNN KNY                                                          13

SEQ ID NO: 359          moltype =     length =
SEQUENCE: 359
000

SEQ ID NO: 360          moltype = AA  length = 6
FEATURE                 Location/Qualifiers
source                  1..6
                        mol_type = protein
                        organism = synthetic construct
SEQUENCE: 360
FHSYPL                                                                  6

SEQ ID NO: 361          moltype = AA  length = 10
FEATURE                 Location/Qualifiers
source                  1..10
                        mol_type = protein
                        organism = synthetic construct
SEQUENCE: 361
GFTFRSYGMH                                                              10

SEQ ID NO: 362          moltype = AA  length = 10
FEATURE                 Location/Qualifiers
source                  1..10
                        mol_type = protein
                        organism = synthetic construct
SEQUENCE: 362
```

```
VITYDGINKY                                                                        10

SEQ ID NO: 363          moltype = AA  length = 10
FEATURE                 Location/Qualifiers
source                  1..10
                        mol_type = protein
                        organism = synthetic construct SEQUENCE: 363
DGVYYGVYDY                                                                        10

SEQ ID NO: 364          moltype = AA  length = 17
FEATURE                 Location/Qualifiers
source                  1..17
                        mol_type = protein
                        organism = synthetic construct SEQUENCE: 364
KSSQSVLFSS NNKNYLA                                                                17

SEQ ID NO: 365          moltype = AA  length = 7
FEATURE                 Location/Qualifiers
source                  1..7
                        mol_type = protein
                        organism = synthetic construct SEQUENCE: 365
WASTRES                                                                            7

SEQ ID NO: 366          moltype = AA  length = 9
FEATURE                 Location/Qualifiers
source                  1..9
                        mol_type = protein
                        organism = synthetic construct SEQUENCE: 366
QQFHSYPLT                                                                          9

SEQ ID NO: 367          moltype = AA  length = 6
FEATURE                 Location/Qualifiers
source                  1..6
                        mol_type = protein
                        organism = synthetic construct SEQUENCE: 367
RSYGMH                                                                             6

SEQ ID NO: 368          moltype = AA  length = 13
FEATURE                 Location/Qualifiers
source                  1..13
                        mol_type = protein
                        organism = synthetic construct SEQUENCE: 368
WVAVITYDGI NKY                                                                    13

SEQ ID NO: 369          moltype = AA  length = 11
FEATURE                 Location/Qualifiers
source                  1..11
                        mol_type = protein
                        organism = synthetic construct SEQUENCE: 369
ARDGVYYGVY D                                                                      11

SEQ ID NO: 370          moltype = AA  length = 13
FEATURE                 Location/Qualifiers
source                  1..13
                        mol_type = protein
                        organism = synthetic construct SEQUENCE: 370
LFSSNNKNYL AWY                                                                    13

SEQ ID NO: 371          moltype = AA  length = 10
FEATURE                 Location/Qualifiers
source                  1..10
                        mol_type = protein
                        organism = synthetic construct SEQUENCE: 371
LLIYWASTRE                                                                        10

SEQ ID NO: 372          moltype = AA  length = 8
FEATURE                 Location/Qualifiers
source                  1..8
                        mol_type = protein
                        organism = synthetic construct
```

```
SEQUENCE: 372
QQFHSYPL                                                                    8

SEQ ID NO: 373         moltype = AA  length = 8
FEATURE                Location/Qualifiers
source                 1..8
                       mol_type = protein
                       organism = synthetic construct
SEQUENCE: 373
GFTFRSYG                                                                    8

SEQ ID NO: 374         moltype = AA  length = 8
FEATURE                Location/Qualifiers
source                 1..8
                       mol_type = protein
                       organism = synthetic construct
SEQUENCE: 374
ITYDGINK                                                                    8

SEQ ID NO: 375         moltype = AA  length = 12
FEATURE                Location/Qualifiers
source                 1..12
                       mol_type = protein
                       organism = synthetic construct
SEQUENCE: 375
ARDGVYYGVY DY                                                              12

SEQ ID NO: 376         moltype = AA  length = 12
FEATURE                Location/Qualifiers
source                 1..12
                       mol_type = protein
                       organism = synthetic construct
SEQUENCE: 376
QSVLFSSNNK NY                                                              12

SEQ ID NO: 377         moltype =     length =
SEQUENCE: 377
000

SEQ ID NO: 378         moltype = AA  length = 9
FEATURE                Location/Qualifiers
source                 1..9
                       mol_type = protein
                       organism = synthetic construct
SEQUENCE: 378
QQFHSYPLT                                                                   9

SEQ ID NO: 379         moltype = AA  length = 119
FEATURE                Location/Qualifiers
source                 1..119
                       mol_type = protein
                       organism = synthetic construct
SEQUENCE: 379
QVQLVESGGG VVQPGRSLRL SCAASGFTFR SYGMHWVRQA PGKGLEWVAV ITYDGINKYY          60
ADSVEGRFTI SRDNSKNTLY LQMNSLRAED TAVYYCARDG VYYGVYDYWG QGTLVTVSS          119

SEQ ID NO: 380         moltype = AA  length = 113
FEATURE                Location/Qualifiers
source                 1..113
                       mol_type = protein
                       organism = synthetic construct
SEQUENCE: 380
DIVMTQSPDS LAVSLGERAT INCKSSQSVL FSSNNKNYLA WYQQKPGQPP KLLIYWASTR          60
ESGVPDRFSG SGSGTDFTLT ISSLQAEDVA VYYCQQFHSY PLTFGGGTKV EIK                113

SEQ ID NO: 381         moltype = AA  length = 10
FEATURE                Location/Qualifiers
source                 1..10
                       mol_type = protein
                       organism = synthetic construct
SEQUENCE: 381
GGTFSSNAIG                                                                 10

SEQ ID NO: 382         moltype = AA  length = 17
FEATURE                Location/Qualifiers
source                 1..17
                       mol_type = protein
                       organism = synthetic construct
SEQUENCE: 382
```

SIIPIIGFAN YAQKFQG                                                               17

SEQ ID NO: 383          moltype = AA  length = 15
FEATURE                 Location/Qualifiers
source                  1..15
                        mol_type = protein
                        organism = synthetic construct SEQUENCE: 383
DSGYYYGASS FGMDV                                                                 15

SEQ ID NO: 384          moltype = AA  length = 11
FEATURE                 Location/Qualifiers
source                  1..11
                        mol_type = protein
                        organism = synthetic construct SEQUENCE: 384
RASQSVSSNL A                                                                     11

SEQ ID NO: 385          moltype = AA  length = 7
FEATURE                 Location/Qualifiers
source                  1..7
                        mol_type = protein
                        organism = synthetic construct SEQUENCE: 385
GASTRAT                                                                          7

SEQ ID NO: 386          moltype = AA  length = 9
FEATURE                 Location/Qualifiers
source                  1..9
                        mol_type = protein
                        organism = synthetic construct SEQUENCE: 386
EQYNNLPLT                                                                        9

SEQ ID NO: 387          moltype = AA  length = 5
FEATURE                 Location/Qualifiers
source                  1..5
                        mol_type = protein
                        organism = synthetic construct SEQUENCE: 387
SNAIG                                                                            5

SEQ ID NO: 388          moltype = AA  length = 17
FEATURE                 Location/Qualifiers
source                  1..17
                        mol_type = protein
                        organism = synthetic construct SEQUENCE: 388
SIIPIIGFAN YAQKFQG                                                               17

SEQ ID NO: 389          moltype = AA  length = 15
FEATURE                 Location/Qualifiers
source                  1..15
                        mol_type = protein
                        organism = synthetic construct SEQUENCE: 389
DSGYYYGASS FGMDV                                                                 15

SEQ ID NO: 390          moltype = AA  length = 11
FEATURE                 Location/Qualifiers
source                  1..11
                        mol_type = protein
                        organism = synthetic construct SEQUENCE: 390
RASQSVSSNL A                                                                     11

SEQ ID NO: 391          moltype = AA  length = 7
FEATURE                 Location/Qualifiers
source                  1..7
                        mol_type = protein
                        organism = synthetic construct SEQUENCE: 391
GASTRAT                                                                          7

SEQ ID NO: 392          moltype = AA  length = 9
FEATURE                 Location/Qualifiers
source                  1..9
                        mol_type = protein
                        organism = synthetic construct

```
SEQUENCE: 392
EQYNNLPLT                                                                     9

SEQ ID NO: 393          moltype = AA  length = 7
FEATURE                 Location/Qualifiers
source                  1..7
                        mol_type = protein
                        organism = synthetic construct
SEQUENCE: 393
GGTFSSN                                                                       7

SEQ ID NO: 394          moltype = AA  length = 4
FEATURE                 Location/Qualifiers
source                  1..4
                        mol_type = protein
                        organism = synthetic construct
SEQUENCE: 394
PIIG                                                                          4

SEQ ID NO: 395          moltype = AA  length = 13
FEATURE                 Location/Qualifiers
source                  1..13
                        mol_type = protein
                        organism = synthetic construct
SEQUENCE: 395
SGYYYGASSF GMD                                                               13

SEQ ID NO: 396          moltype = AA  length = 7
FEATURE                 Location/Qualifiers
source                  1..7
                        mol_type = protein
                        organism = synthetic construct
SEQUENCE: 396
SQSVSSN                                                                       7

SEQ ID NO: 397          moltype =     length =
SEQUENCE: 397
000

SEQ ID NO: 398          moltype = AA  length = 6
FEATURE                 Location/Qualifiers
source                  1..6
                        mol_type = protein
                        organism = synthetic construct
SEQUENCE: 398
YNNLPL                                                                        6

SEQ ID NO: 399          moltype = AA  length = 10
FEATURE                 Location/Qualifiers
source                  1..10
                        mol_type = protein
                        organism = synthetic construct
SEQUENCE: 399
GGTFSSNAIG                                                                   10

SEQ ID NO: 400          moltype = AA  length = 10
FEATURE                 Location/Qualifiers
source                  1..10
                        mol_type = protein
                        organism = synthetic construct
SEQUENCE: 400
SIIPIIGFAN                                                                   10

SEQ ID NO: 401          moltype = AA  length = 15
FEATURE                 Location/Qualifiers
source                  1..15
                        mol_type = protein
                        organism = synthetic construct
SEQUENCE: 401
DSGYYYGASS FGMDV                                                             15

SEQ ID NO: 402          moltype = AA  length = 11
FEATURE                 Location/Qualifiers
source                  1..11
                        mol_type = protein
                        organism = synthetic construct
SEQUENCE: 402
RASQSVSSNL A                                                                 11
```

```
SEQ ID NO: 403              moltype = AA   length = 7
FEATURE                     Location/Qualifiers
source                      1..7
                            mol_type = protein
                            organism = synthetic construct
SEQUENCE: 403
GASTRAT                                                                  7

SEQ ID NO: 404              moltype = AA   length = 9
FEATURE                     Location/Qualifiers
source                      1..9
                            mol_type = protein
                            organism = synthetic construct
SEQUENCE: 404
EQYNNLPLT                                                                9

SEQ ID NO: 405              moltype = AA   length = 6
FEATURE                     Location/Qualifiers
source                      1..6
                            mol_type = protein
                            organism = synthetic construct
SEQUENCE: 405
SSNAIG                                                                   6

SEQ ID NO: 406              moltype = AA   length = 13
FEATURE                     Location/Qualifiers
source                      1..13
                            mol_type = protein
                            organism = synthetic construct
SEQUENCE: 406
WMGSIIPIIG FAN                                                           13

SEQ ID NO: 407              moltype = AA   length = 16
FEATURE                     Location/Qualifiers
source                      1..16
                            mol_type = protein
                            organism = synthetic construct
SEQUENCE: 407
ARDSGYYYGA SSFGMD                                                        16

SEQ ID NO: 408              moltype = AA   length = 7
FEATURE                     Location/Qualifiers
source                      1..7
                            mol_type = protein
                            organism = synthetic construct
SEQUENCE: 408
SSNLAWY                                                                  7

SEQ ID NO: 409              moltype = AA   length = 10
FEATURE                     Location/Qualifiers
source                      1..10
                            mol_type = protein
                            organism = synthetic construct
SEQUENCE: 409
LLIYGASTRA                                                               10

SEQ ID NO: 410              moltype = AA   length = 8
FEATURE                     Location/Qualifiers
source                      1..8
                            mol_type = protein
                            organism = synthetic construct
SEQUENCE: 410
EQYNNLPL                                                                 8

SEQ ID NO: 411              moltype = AA   length = 8
FEATURE                     Location/Qualifiers
source                      1..8
                            mol_type = protein
                            organism = synthetic construct
SEQUENCE: 411
GGTFSSNA                                                                 8

SEQ ID NO: 412              moltype = AA   length = 8
FEATURE                     Location/Qualifiers
source                      1..8
                            mol_type = protein
                            organism = synthetic construct
SEQUENCE: 412
IIPIIGFA                                                                 8
```

```
SEQ ID NO: 413            moltype = AA   length = 17
FEATURE                   Location/Qualifiers
source                    1..17
                          mol_type = protein
                          organism = synthetic construct
SEQUENCE: 413
ARDSGYYYGA SSFGMDV                                                        17

SEQ ID NO: 414            moltype = AA   length = 6
FEATURE                   Location/Qualifiers
source                    1..6
                          mol_type = protein
                          organism = synthetic construct
SEQUENCE: 414
QSVSSN                                                                     6

SEQ ID NO: 415            moltype =      length =
SEQUENCE: 415
000

SEQ ID NO: 416            moltype = AA   length = 9
FEATURE                   Location/Qualifiers
source                    1..9
                          mol_type = protein
                          organism = synthetic construct
SEQUENCE: 416
EQYNNLPLT                                                                  9

SEQ ID NO: 417            moltype = AA   length = 124
FEATURE                   Location/Qualifiers
source                    1..124
                          mol_type = protein
                          organism = synthetic construct
SEQUENCE: 417
QVQLVQSGAE VKKPGSSVKV SCKASGGTFS SNAIGWVRQA PGQGLEWMGS IIPIIGFANY          60
AQKFQGRVTI TADESTSTAY MELSSLRSED TAVYYCARDS GYYYGASSFG MDVWGQGTTV         120
TVSS                                                                     124

SEQ ID NO: 418            moltype = AA   length = 107
FEATURE                   Location/Qualifiers
source                    1..107
                          mol_type = protein
                          organism = synthetic construct
SEQUENCE: 418
EIVMTQSPAT LSVSPGERAT LSCRASQSVS SNLAWYQQKP GQAPRLLIYG ASTRATGIPA          60
RFSGSGSGTE FTLTISSLQS EDFAVYYCEQ YNNLPLTFGG GTKVEIK                      107

SEQ ID NO: 419            moltype = AA   length = 11
FEATURE                   Location/Qualifiers
source                    1..11
                          mol_type = protein
                          organism = synthetic construct
SEQUENCE: 419
GGSISSGQYW S                                                              11

SEQ ID NO: 420            moltype = AA   length = 16
FEATURE                   Location/Qualifiers
source                    1..16
                          mol_type = protein
                          organism = synthetic construct
SEQUENCE: 420
EIYYSGSTRY NPSLKS                                                         16

SEQ ID NO: 421            moltype = AA   length = 16
FEATURE                   Location/Qualifiers
source                    1..16
                          mol_type = protein
                          organism = synthetic construct
SEQUENCE: 421
DAPYYYGGGY YYYMDV                                                         16

SEQ ID NO: 422            moltype = AA   length = 12
FEATURE                   Location/Qualifiers
source                    1..12
                          mol_type = protein
                          organism = synthetic construct
SEQUENCE: 422
RASQSVSSSY LA                                                             12
```

```
SEQ ID NO: 423            moltype = AA  length = 7
FEATURE                   Location/Qualifiers
source                    1..7
                          mol_type = protein
                          organism = synthetic construct
SEQUENCE: 423
GASSRAT                                                              7

SEQ ID NO: 424            moltype = AA  length = 9
FEATURE                   Location/Qualifiers
source                    1..9
                          mol_type = protein
                          organism = synthetic construct
SEQUENCE: 424
QQVGVVPYT                                                            9

SEQ ID NO: 425            moltype = AA  length = 6
FEATURE                   Location/Qualifiers
source                    1..6
                          mol_type = protein
                          organism = synthetic construct
SEQUENCE: 425
SGQYWS                                                               6

SEQ ID NO: 426            moltype = AA  length = 16
FEATURE                   Location/Qualifiers
source                    1..16
                          mol_type = protein
                          organism = synthetic construct
SEQUENCE: 426
EIYYSGSTRY NPSLKS                                                   16

SEQ ID NO: 427            moltype = AA  length = 16
FEATURE                   Location/Qualifiers
source                    1..16
                          mol_type = protein
                          organism = synthetic construct
SEQUENCE: 427
DAPYYYGGGY YYYMDV                                                   16

SEQ ID NO: 428            moltype = AA  length = 12
FEATURE                   Location/Qualifiers
source                    1..12
                          mol_type = protein
                          organism = synthetic construct
SEQUENCE: 428
RASQSVSSSY LA                                                       12

SEQ ID NO: 429            moltype = AA  length = 7
FEATURE                   Location/Qualifiers
source                    1..7
                          mol_type = protein
                          organism = synthetic construct
SEQUENCE: 429
GASSRAT                                                              7

SEQ ID NO: 430            moltype = AA  length = 9
FEATURE                   Location/Qualifiers
source                    1..9
                          mol_type = protein
                          organism = synthetic construct
SEQUENCE: 430
QQVGVVPYT                                                            9

SEQ ID NO: 431            moltype = AA  length = 8
FEATURE                   Location/Qualifiers
source                    1..8
                          mol_type = protein
                          organism = synthetic construct
SEQUENCE: 431
GGSISSGQ                                                             8

SEQ ID NO: 432            moltype =     length =
SEQUENCE: 432
000

SEQ ID NO: 433            moltype = AA  length = 14
FEATURE                   Location/Qualifiers
```

| | | |
|---|---|---|
| source | 1..14<br>mol_type = protein<br>organism = synthetic construct | |
| SEQUENCE: 433<br>APYYYGGGYY YYMD | | 14 |
| SEQ ID NO: 434<br>FEATURE<br>source | moltype = AA  length = 8<br>Location/Qualifiers<br>1..8<br>mol_type = protein<br>organism = synthetic construct | |
| SEQUENCE: 434<br>SQSVSSSY | | 8 |
| SEQ ID NO: 435<br>SEQUENCE: 435<br>000 | moltype =   length = | |
| SEQ ID NO: 436<br>FEATURE<br>source | moltype = AA  length = 6<br>Location/Qualifiers<br>1..6<br>mol_type = protein<br>organism = synthetic construct | |
| SEQUENCE: 436<br>VGVVPY | | 6 |
| SEQ ID NO: 437<br>FEATURE<br>source | moltype = AA  length = 11<br>Location/Qualifiers<br>1..11<br>mol_type = protein<br>organism = synthetic construct | |
| SEQUENCE: 437<br>GGSISSGQYW S | | 11 |
| SEQ ID NO: 438<br>FEATURE<br>source | moltype = AA  length = 9<br>Location/Qualifiers<br>1..9<br>mol_type = protein<br>organism = synthetic construct | |
| SEQUENCE: 438<br>EIYYSGSTR | | 9 |
| SEQ ID NO: 439<br>FEATURE<br>source | moltype = AA  length = 16<br>Location/Qualifiers<br>1..16<br>mol_type = protein<br>organism = synthetic construct | |
| SEQUENCE: 439<br>DAPYYYGGGY YYYMDV | | 16 |
| SEQ ID NO: 440<br>FEATURE<br>source | moltype = AA  length = 12<br>Location/Qualifiers<br>1..12<br>mol_type = protein<br>organism = synthetic construct | |
| SEQUENCE: 440<br>RASQSVSSSY LA | | 12 |
| SEQ ID NO: 441<br>FEATURE<br>source | moltype = AA  length = 7<br>Location/Qualifiers<br>1..7<br>mol_type = protein<br>organism = synthetic construct | |
| SEQUENCE: 441<br>GASSRAT | | 7 |
| SEQ ID NO: 442<br>FEATURE<br>source | moltype = AA  length = 9<br>Location/Qualifiers<br>1..9<br>mol_type = protein<br>organism = synthetic construct | |
| SEQUENCE: 442<br>QQVGVVPYT | | 9 |
| SEQ ID NO: 443<br>FEATURE<br>source | moltype = AA  length = 7<br>Location/Qualifiers<br>1..7<br>mol_type = protein<br>organism = synthetic construct | |

```
SEQUENCE: 443
SSGQYWS                                                                        7

SEQ ID NO: 444         moltype = AA  length = 12
FEATURE                Location/Qualifiers
source                 1..12
                       mol_type = protein
                       organism = synthetic construct
SEQUENCE: 444
WIGEIYYSGS TR                                                                  12

SEQ ID NO: 445         moltype = AA  length = 17
FEATURE                Location/Qualifiers
source                 1..17
                       mol_type = protein
                       organism = synthetic construct
SEQUENCE: 445
ARDAPYYYGG GYYYYMD                                                             17

SEQ ID NO: 446         moltype = AA  length = 8
FEATURE                Location/Qualifiers
source                 1..8
                       mol_type = protein
                       organism = synthetic construct
SEQUENCE: 446
SSSYLAWY                                                                       8

SEQ ID NO: 447         moltype = AA  length = 10
FEATURE                Location/Qualifiers
source                 1..10
                       mol_type = protein
                       organism = synthetic construct
SEQUENCE: 447
LLIYGASSRA                                                                     10

SEQ ID NO: 448         moltype = AA  length = 8
FEATURE                Location/Qualifiers
source                 1..8
                       mol_type = protein
                       organism = synthetic construct
SEQUENCE: 448
QQVGVVPY                                                                       8

SEQ ID NO: 449         moltype = AA  length = 9
FEATURE                Location/Qualifiers
source                 1..9
                       mol_type = protein
                       organism = synthetic construct
SEQUENCE: 449
GGSISSGQY                                                                      9

SEQ ID NO: 450         moltype = AA  length = 7
FEATURE                Location/Qualifiers
source                 1..7
                       mol_type = protein
                       organism = synthetic construct
SEQUENCE: 450
IYYSGST                                                                        7

SEQ ID NO: 451         moltype = AA  length = 18
FEATURE                Location/Qualifiers
source                 1..18
                       mol_type = protein
                       organism = synthetic construct
SEQUENCE: 451
ARDAPYYYGG GYYYYMDV                                                            18

SEQ ID NO: 452         moltype = AA  length = 7
FEATURE                Location/Qualifiers
source                 1..7
                       mol_type = protein
                       organism = synthetic construct
SEQUENCE: 452
QSVSSSY                                                                        7

SEQ ID NO: 453         moltype =     length =
SEQUENCE: 453
000
```

```
SEQ ID NO: 454          moltype = AA   length = 9
FEATURE                 Location/Qualifiers
source                  1..9
                        mol_type = protein
                        organism = synthetic construct
SEQUENCE: 454
QQVGVVPYT                                                                  9

SEQ ID NO: 455          moltype = AA   length = 125
FEATURE                 Location/Qualifiers
source                  1..125
                        mol_type = protein
                        organism = synthetic construct
SEQUENCE: 455
QVQLQESGPG LVKPSQTLSL TCTVSGGSIS SGQYWSWIRQ HPGKGLEWIG EIYYSGSTRY          60
NPSLKSRVTI SVDTSKNQFS LKLSSVTAAD TAVYYCARDA PYYYGGGYYY YMDVWGKGTT         120
VTVSS                                                                    125

SEQ ID NO: 456          moltype = AA   length = 108
FEATURE                 Location/Qualifiers
source                  1..108
                        mol_type = protein
                        organism = synthetic construct
SEQUENCE: 456
EIVLTQSPGT LSLSPGERAT LSCRASQSVS SSYLAWYQQK PGQAPRLLIY GASSRATGIP          60
DRFSGSGSGT DFTLTISRLE PEDFAVYYCQ QVGVVPYTFG GGTKVEIK                     108

SEQ ID NO: 457          moltype = AA   length = 11
FEATURE                 Location/Qualifiers
source                  1..11
                        mol_type = protein
                        organism = synthetic construct
SEQUENCE: 457
GGSISSGQYW S                                                              11

SEQ ID NO: 458          moltype = AA   length = 16
FEATURE                 Location/Qualifiers
source                  1..16
                        mol_type = protein
                        organism = synthetic construct
SEQUENCE: 458
EIYYSGSTRY NPSLKS                                                         16

SEQ ID NO: 459          moltype = AA   length = 16
FEATURE                 Location/Qualifiers
source                  1..16
                        mol_type = protein
                        organism = synthetic construct
SEQUENCE: 459
DAPYYYGGGY YYYMDV                                                         16

SEQ ID NO: 460          moltype = AA   length = 12
FEATURE                 Location/Qualifiers
source                  1..12
                        mol_type = protein
                        organism = synthetic construct
SEQUENCE: 460
RASESVDSSY LA                                                             12

SEQ ID NO: 461          moltype = AA   length = 7
FEATURE                 Location/Qualifiers
source                  1..7
                        mol_type = protein
                        organism = synthetic construct
SEQUENCE: 461
GASTRQT                                                                    7

SEQ ID NO: 462          moltype = AA   length = 9
FEATURE                 Location/Qualifiers
source                  1..9
                        mol_type = protein
                        organism = synthetic construct
SEQUENCE: 462
QQAGVVPYT                                                                  9

SEQ ID NO: 463          moltype = AA   length = 6
FEATURE                 Location/Qualifiers
source                  1..6
                        mol_type = protein
```

```
SEQUENCE: 463
SGQYWS                                                                              6

SEQ ID NO: 464          moltype = AA  length = 16
FEATURE                 Location/Qualifiers
source                  1..16
                        mol_type = protein
                        organism = synthetic construct
SEQUENCE: 464
EIYYSGSTRY NPSLKS                                                                  16

SEQ ID NO: 465          moltype = AA  length = 16
FEATURE                 Location/Qualifiers
source                  1..16
                        mol_type = protein
                        organism = synthetic construct
SEQUENCE: 465
DAPYYYGGGY YYYMDV                                                                  16

SEQ ID NO: 466          moltype = AA  length = 12
FEATURE                 Location/Qualifiers
source                  1..12
                        mol_type = protein
                        organism = synthetic construct
SEQUENCE: 466
RASESVDSSY LA                                                                      12

SEQ ID NO: 467          moltype = AA  length = 7
FEATURE                 Location/Qualifiers
source                  1..7
                        mol_type = protein
                        organism = synthetic construct
SEQUENCE: 467
GASTRQT                                                                             7

SEQ ID NO: 468          moltype = AA  length = 9
FEATURE                 Location/Qualifiers
source                  1..9
                        mol_type = protein
                        organism = synthetic construct
SEQUENCE: 468
QQAGVVPYT                                                                           9

SEQ ID NO: 469          moltype = AA  length = 8
FEATURE                 Location/Qualifiers
source                  1..8
                        mol_type = protein
                        organism = synthetic construct
SEQUENCE: 469
GGSISSGQ                                                                            8

SEQ ID NO: 470          moltype =     length =
SEQUENCE: 470
000

SEQ ID NO: 471          moltype = AA  length = 14
FEATURE                 Location/Qualifiers
source                  1..14
                        mol_type = protein
                        organism = synthetic construct
SEQUENCE: 471
APYYYGGGYY YYMD                                                                    14

SEQ ID NO: 472          moltype = AA  length = 8
FEATURE                 Location/Qualifiers
source                  1..8
                        mol_type = protein
                        organism = synthetic construct
SEQUENCE: 472
SESVDSSY                                                                            8

SEQ ID NO: 473          moltype =     length =
SEQUENCE: 473
000

SEQ ID NO: 474          moltype = AA  length = 6
FEATURE                 Location/Qualifiers
source                  1..6
```

```
                                mol_type = protein
                                organism = synthetic construct
SEQUENCE: 474
AGVVPY                                                                              6

SEQ ID NO: 475                  moltype = AA   length = 11
FEATURE                         Location/Qualifiers
source                          1..11
                                mol_type = protein
                                organism = synthetic construct
SEQUENCE: 475
GGSISSGQYW S                                                                       11

SEQ ID NO: 476                  moltype = AA   length = 9
FEATURE                         Location/Qualifiers
source                          1..9
                                mol_type = protein
                                organism = synthetic construct
SEQUENCE: 476
EIYYSGSTR                                                                           9

SEQ ID NO: 477                  moltype = AA   length = 16
FEATURE                         Location/Qualifiers
source                          1..16
                                mol_type = protein
                                organism = synthetic construct
SEQUENCE: 477
DAPYYYGGGY YYYMDV                                                                  16

SEQ ID NO: 478                  moltype = AA   length = 12
FEATURE                         Location/Qualifiers
source                          1..12
                                mol_type = protein
                                organism = synthetic construct
SEQUENCE: 478
RASESVDSSY LA                                                                      12

SEQ ID NO: 479                  moltype = AA   length = 7
FEATURE                         Location/Qualifiers
source                          1..7
                                mol_type = protein
                                organism = synthetic construct
SEQUENCE: 479
GASTRQT                                                                             7

SEQ ID NO: 480                  moltype = AA   length = 9
FEATURE                         Location/Qualifiers
source                          1..9
                                mol_type = protein
                                organism = synthetic construct
SEQUENCE: 480
QQAGVVPYT                                                                           9

SEQ ID NO: 481                  moltype = AA   length = 7
FEATURE                         Location/Qualifiers
source                          1..7
                                mol_type = protein
                                organism = synthetic construct
SEQUENCE: 481
SSGQYWS                                                                             7

SEQ ID NO: 482                  moltype = AA   length = 12
FEATURE                         Location/Qualifiers
source                          1..12
                                mol_type = protein
                                organism = synthetic construct
SEQUENCE: 482
WIGEIYYSGS TR                                                                      12

SEQ ID NO: 483                  moltype = AA   length = 17
FEATURE                         Location/Qualifiers
source                          1..17
                                mol_type = protein
                                organism = synthetic construct
SEQUENCE: 483
ARDAPYYYGG GYYYYMD                                                                 17

SEQ ID NO: 484                  moltype = AA   length = 8
FEATURE                         Location/Qualifiers
```

```
source                     1..8
                           mol_type = protein
                           organism = synthetic construct
SEQUENCE: 484
DSSYLAWY                                                                    8

SEQ ID NO: 485             moltype = AA  length = 10
FEATURE                    Location/Qualifiers
source                     1..10
                           mol_type = protein
                           organism = synthetic construct
SEQUENCE: 485
LLIYGASTRQ                                                                 10

SEQ ID NO: 486             moltype = AA  length = 8
FEATURE                    Location/Qualifiers
source                     1..8
                           mol_type = protein
                           organism = synthetic construct
SEQUENCE: 486
QQAGVVPY                                                                    8

SEQ ID NO: 487             moltype = AA  length = 9
FEATURE                    Location/Qualifiers
source                     1..9
                           mol_type = protein
                           organism = synthetic construct
SEQUENCE: 487
GGSISSGQY                                                                   9

SEQ ID NO: 488             moltype = AA  length = 7
FEATURE                    Location/Qualifiers
source                     1..7
                           mol_type = protein
                           organism = synthetic construct
SEQUENCE: 488
IYYSGST                                                                     7

SEQ ID NO: 489             moltype = AA  length = 18
FEATURE                    Location/Qualifiers
source                     1..18
                           mol_type = protein
                           organism = synthetic construct
SEQUENCE: 489
ARDAPYYYGG GYYYYMDV                                                        18

SEQ ID NO: 490             moltype = AA  length = 7
FEATURE                    Location/Qualifiers
source                     1..7
                           mol_type = protein
                           organism = synthetic construct
SEQUENCE: 490
ESVDSSY                                                                     7

SEQ ID NO: 491             moltype =    length =
SEQUENCE: 491
000

SEQ ID NO: 492             moltype = AA  length = 9
FEATURE                    Location/Qualifiers
source                     1..9
                           mol_type = protein
                           organism = synthetic construct
SEQUENCE: 492
QQAGVVPYT                                                                   9

SEQ ID NO: 493             moltype = AA  length = 125
FEATURE                    Location/Qualifiers
source                     1..125
                           mol_type = protein
                           organism = synthetic construct
SEQUENCE: 493
QVQLQESGPG LVKPSQTLSL TCTVSGGSIS SGQYWSWIRQ HPGKGLEWIG EIYYSGSTRY           60
NPSLKSRVTI SVDTSKNQFS LKLSSVTAAD TAVYYCARDA PYYYGGGYYY YMDVWGKGTT          120
VTVSS                                                                     125

SEQ ID NO: 494             moltype = AA  length = 108
FEATURE                    Location/Qualifiers
source                     1..108
```

```
                        mol_type = protein
                        organism = synthetic construct
SEQUENCE: 494
EIVLTQSPGT LSLSPGERAT LSCRASESVD SSYLAWYQQK PGQAPRLLIY GASTRQTGIP     60
DRFSGSGSGT DFTLTISRLE PEDFAVYYCQ QAGVVPYTFG GGTKVEIK                  108

SEQ ID NO: 495          moltype = AA   length = 11
FEATURE                 Location/Qualifiers
source                  1..11
                        mol_type = protein
                        organism = synthetic construct
SEQUENCE: 495
GGSISSGQYW S                                                          11

SEQ ID NO: 496          moltype = AA   length = 16
FEATURE                 Location/Qualifiers
source                  1..16
                        mol_type = protein
                        organism = synthetic construct
SEQUENCE: 496
EIYYSGSTRY NPSLKS                                                     16

SEQ ID NO: 497          moltype = AA   length = 16
FEATURE                 Location/Qualifiers
source                  1..16
                        mol_type = protein
                        organism = synthetic construct
SEQUENCE: 497
DAPYYYGGGY YYYMDV                                                     16

SEQ ID NO: 498          moltype = AA   length = 12
FEATURE                 Location/Qualifiers
source                  1..12
                        mol_type = protein
                        organism = synthetic construct
SEQUENCE: 498
RASESVDSSY LA                                                         12

SEQ ID NO: 499          moltype = AA   length = 7
FEATURE                 Location/Qualifiers
source                  1..7
                        mol_type = protein
                        organism = synthetic construct
SEQUENCE: 499
GADSRAT                                                               7

SEQ ID NO: 500          moltype = AA   length = 9
FEATURE                 Location/Qualifiers
source                  1..9
                        mol_type = protein
                        organism = synthetic construct
SEQUENCE: 500
QQDGVVPYT                                                             9

SEQ ID NO: 501          moltype = AA   length = 6
FEATURE                 Location/Qualifiers
source                  1..6
                        mol_type = protein
                        organism = synthetic construct
SEQUENCE: 501
SGQYWS                                                                6

SEQ ID NO: 502          moltype = AA   length = 16
FEATURE                 Location/Qualifiers
source                  1..16
                        mol_type = protein
                        organism = synthetic construct
SEQUENCE: 502
EIYYSGSTRY NPSLKS                                                     16

SEQ ID NO: 503          moltype = AA   length = 16
FEATURE                 Location/Qualifiers
source                  1..16
                        mol_type = protein
                        organism = synthetic construct
SEQUENCE: 503
DAPYYYGGGY YYYMDV                                                     16

SEQ ID NO: 504          moltype = AA   length = 12
```

-continued

```
FEATURE              Location/Qualifiers
source               1..12
                     mol_type = protein
                     organism = synthetic construct
SEQUENCE: 504
RASESVDSSY LA                                                          12

SEQ ID NO: 505       moltype = AA  length = 7
FEATURE              Location/Qualifiers
source               1..7
                     mol_type = protein
                     organism = synthetic construct
SEQUENCE: 505
GADSRAT                                                                7

SEQ ID NO: 506       moltype = AA  length = 9
FEATURE              Location/Qualifiers
source               1..9
                     mol_type = protein
                     organism = synthetic construct
SEQUENCE: 506
QQDGVVPYT                                                              9

SEQ ID NO: 507       moltype = AA  length = 8
FEATURE              Location/Qualifiers
source               1..8
                     mol_type = protein
                     organism = synthetic construct
SEQUENCE: 507
GGSISSGQ                                                               8

SEQ ID NO: 508       moltype =     length =
SEQUENCE: 508
000

SEQ ID NO: 509       moltype = AA  length = 14
FEATURE              Location/Qualifiers
source               1..14
                     mol_type = protein
                     organism = synthetic construct
SEQUENCE: 509
APYYYGGGYY YYMD                                                        14

SEQ ID NO: 510       moltype = AA  length = 8
FEATURE              Location/Qualifiers
source               1..8
                     mol_type = protein
                     organism = synthetic construct
SEQUENCE: 510
SESVDSSY                                                               8

SEQ ID NO: 511       moltype =     length =
SEQUENCE: 511
000

SEQ ID NO: 512       moltype = AA  length = 6
FEATURE              Location/Qualifiers
source               1..6
                     mol_type = protein
                     organism = synthetic construct
SEQUENCE: 512
DGVVPY                                                                 6

SEQ ID NO: 513       moltype = AA  length = 11
FEATURE              Location/Qualifiers
source               1..11
                     mol_type = protein
                     organism = synthetic construct
SEQUENCE: 513
GGSISSGQYW S                                                           11

SEQ ID NO: 514       moltype = AA  length = 9
FEATURE              Location/Qualifiers
source               1..9
                     mol_type = protein
                     organism = synthetic construct
SEQUENCE: 514
EIYYSGSTR                                                              9
```

```
SEQ ID NO: 515              moltype = AA   length = 16
FEATURE                     Location/Qualifiers
source                      1..16
                            mol_type = protein
                            organism = synthetic construct
SEQUENCE: 515
DAPYYYGGGY YYYMDV                                                               16

SEQ ID NO: 516              moltype = AA   length = 12
FEATURE                     Location/Qualifiers
source                      1..12
                            mol_type = protein
                            organism = synthetic construct
SEQUENCE: 516
RASESVDSSY LA                                                                   12

SEQ ID NO: 517              moltype = AA   length = 7
FEATURE                     Location/Qualifiers
source                      1..7
                            mol_type = protein
                            organism = synthetic construct
SEQUENCE: 517
GADSRAT                                                                         7

SEQ ID NO: 518              moltype = AA   length = 9
FEATURE                     Location/Qualifiers
source                      1..9
                            mol_type = protein
                            organism = synthetic construct
SEQUENCE: 518
QQDGVVPYT                                                                       9

SEQ ID NO: 519              moltype = AA   length = 7
FEATURE                     Location/Qualifiers
source                      1..7
                            mol_type = protein
                            organism = synthetic construct
SEQUENCE: 519
SSGQYWS                                                                         7

SEQ ID NO: 520              moltype = AA   length = 12
FEATURE                     Location/Qualifiers
source                      1..12
                            mol_type = protein
                            organism = synthetic construct
SEQUENCE: 520
WIGEIYYSGS TR                                                                   12

SEQ ID NO: 521              moltype = AA   length = 17
FEATURE                     Location/Qualifiers
source                      1..17
                            mol_type = protein
                            organism = synthetic construct
SEQUENCE: 521
ARDAPYYYGG GYYYYMD                                                              17

SEQ ID NO: 522              moltype = AA   length = 8
FEATURE                     Location/Qualifiers
source                      1..8
                            mol_type = protein
                            organism = synthetic construct
SEQUENCE: 522
DSSYLAWY                                                                        8

SEQ ID NO: 523              moltype = AA   length = 10
FEATURE                     Location/Qualifiers
source                      1..10
                            mol_type = protein
                            organism = synthetic construct
SEQUENCE: 523
LLIYGADSRA                                                                      10

SEQ ID NO: 524              moltype = AA   length = 8
FEATURE                     Location/Qualifiers
source                      1..8
                            mol_type = protein
                            organism = synthetic construct
SEQUENCE: 524
QQDGVVPY                                                                        8
```

```
SEQ ID NO: 525          moltype = AA  length = 9
FEATURE                 Location/Qualifiers
source                  1..9
                        mol_type = protein
                        organism = synthetic construct
SEQUENCE: 525
GGSISSGQY                                                                 9

SEQ ID NO: 526          moltype = AA  length = 7
FEATURE                 Location/Qualifiers
source                  1..7
                        mol_type = protein
                        organism = synthetic construct
SEQUENCE: 526
IYYSGST                                                                   7

SEQ ID NO: 527          moltype = AA  length = 18
FEATURE                 Location/Qualifiers
source                  1..18
                        mol_type = protein
                        organism = synthetic construct
SEQUENCE: 527
ARDAPYYYGG GYYYYMDV                                                       18

SEQ ID NO: 528          moltype = AA  length = 7
FEATURE                 Location/Qualifiers
source                  1..7
                        mol_type = protein
                        organism = synthetic construct
SEQUENCE: 528
ESVDSSY                                                                   7

SEQ ID NO: 529          moltype =     length =
SEQUENCE: 529
000

SEQ ID NO: 530          moltype = AA  length = 9
FEATURE                 Location/Qualifiers
source                  1..9
                        mol_type = protein
                        organism = synthetic construct
SEQUENCE: 530
QQDGVVPYT                                                                 9

SEQ ID NO: 531          moltype = AA  length = 125
FEATURE                 Location/Qualifiers
source                  1..125
                        mol_type = protein
                        organism = synthetic construct
SEQUENCE: 531
QVQLQESGPG LVKPSQTLSL TCTVSGGSIS SGQYWSWIRQ HPGKGLEWIG EIYYSGSTRY         60
NPSLKSRVTI SVDTSKNQFS LKLSSVTAAD TAVYYCARDA PYYYGGGYYY YMDVWGKGTT         120
VTVSS                                                                     125

SEQ ID NO: 532          moltype = AA  length = 108
FEATURE                 Location/Qualifiers
source                  1..108
                        mol_type = protein
                        organism = synthetic construct
SEQUENCE: 532
EIVLTQSPGT LSLSPGERAT LSCRASESVD SSYLAWYQQK PGQAPRLLIY GADSRATGIP         60
DRFSGSGSGT DFTLTISRLE PEDFAVYYCQ QDGVVPYTFG GGTKVEIK                     108

SEQ ID NO: 533          moltype = AA  length = 10
FEATURE                 Location/Qualifiers
source                  1..10
                        mol_type = protein
                        organism = synthetic construct
SEQUENCE: 533
GGSLSGYYWS                                                                10

SEQ ID NO: 534          moltype = AA  length = 16
FEATURE                 Location/Qualifiers
source                  1..16
                        mol_type = protein
                        organism = synthetic construct
SEQUENCE: 534
EIGASGSTRY NPSLKS                                                         16
```

```
SEQ ID NO: 535          moltype = AA  length = 16
FEATURE                 Location/Qualifiers
source                  1..16
                        mol_type = protein
                        organism = synthetic construct
SEQUENCE: 535
DTPYYYEGGY YYYMDV                                                       16

SEQ ID NO: 536          moltype = AA  length = 12
FEATURE                 Location/Qualifiers
source                  1..12
                        mol_type = protein
                        organism = synthetic construct
SEQUENCE: 536
RASQSVSSSY LA                                                           12

SEQ ID NO: 537          moltype = AA  length = 7
FEATURE                 Location/Qualifiers
source                  1..7
                        mol_type = protein
                        organism = synthetic construct
SEQUENCE: 537
GASSRAT                                                                  7

SEQ ID NO: 538          moltype = AA  length = 9
FEATURE                 Location/Qualifiers
source                  1..9
                        mol_type = protein
                        organism = synthetic construct
SEQUENCE: 538
QQVGVVPYT                                                                9

SEQ ID NO: 539          moltype = AA  length = 5
FEATURE                 Location/Qualifiers
source                  1..5
                        mol_type = protein
                        organism = synthetic construct
SEQUENCE: 539
GYYWS                                                                    5

SEQ ID NO: 540          moltype = AA  length = 16
FEATURE                 Location/Qualifiers
source                  1..16
                        mol_type = protein
                        organism = synthetic construct
SEQUENCE: 540
EIGASGSTRY NPSLKS                                                       16

SEQ ID NO: 541          moltype = AA  length = 16
FEATURE                 Location/Qualifiers
source                  1..16
                        mol_type = protein
                        organism = synthetic construct
SEQUENCE: 541
DTPYYYEGGY YYYMDV                                                       16

SEQ ID NO: 542          moltype = AA  length = 12
FEATURE                 Location/Qualifiers
source                  1..12
                        mol_type = protein
                        organism = synthetic construct
SEQUENCE: 542
RASQSVSSSY LA                                                           12

SEQ ID NO: 543          moltype = AA  length = 7
FEATURE                 Location/Qualifiers
source                  1..7
                        mol_type = protein
                        organism = synthetic construct
SEQUENCE: 543
GASSRAT                                                                  7

SEQ ID NO: 544          moltype = AA  length = 9
FEATURE                 Location/Qualifiers
source                  1..9
                        mol_type = protein
                        organism = synthetic construct
SEQUENCE: 544
```

```
QQVGVVPYT                                                                        9

SEQ ID NO: 545         moltype = AA  length = 7
FEATURE                Location/Qualifiers
source                 1..7
                       mol_type = protein
                       organism = synthetic construct
SEQUENCE: 545
GGSLSGY                                                                          7

SEQ ID NO: 546         moltype =     length =
SEQUENCE: 546
000

SEQ ID NO: 547         moltype = AA  length = 14
FEATURE                Location/Qualifiers
source                 1..14
                       mol_type = protein
                       organism = synthetic construct
SEQUENCE: 547
TPYYYEGGYY YYMD                                                                 14

SEQ ID NO: 548         moltype = AA  length = 8
FEATURE                Location/Qualifiers
source                 1..8
                       mol_type = protein
                       organism = synthetic construct
SEQUENCE: 548
SQSVSSSY                                                                         8

SEQ ID NO: 549         moltype =     length =
SEQUENCE: 549
000

SEQ ID NO: 550         moltype = AA  length = 6
FEATURE                Location/Qualifiers
source                 1..6
                       mol_type = protein
                       organism = synthetic construct
SEQUENCE: 550
VGVVPY                                                                           6

SEQ ID NO: 551         moltype = AA  length = 10
FEATURE                Location/Qualifiers
source                 1..10
                       mol_type = protein
                       organism = synthetic construct
SEQUENCE: 551
GGSLSGYYWS                                                                      10

SEQ ID NO: 552         moltype = AA  length = 9
FEATURE                Location/Qualifiers
source                 1..9
                       mol_type = protein
                       organism = synthetic construct
SEQUENCE: 552
EIGASGSTR                                                                        9

SEQ ID NO: 553         moltype = AA  length = 16
FEATURE                Location/Qualifiers
source                 1..16
                       mol_type = protein
                       organism = synthetic construct
SEQUENCE: 553
DTPYYYEGGY YYYMDV                                                               16

SEQ ID NO: 554         moltype = AA  length = 12
FEATURE                Location/Qualifiers
source                 1..12
                       mol_type = protein
                       organism = synthetic construct
SEQUENCE: 554
RASQSVSSSY LA                                                                   12

SEQ ID NO: 555         moltype = AA  length = 7
FEATURE                Location/Qualifiers
source                 1..7
                       mol_type = protein
                       organism = synthetic construct
```

```
SEQUENCE: 555
GASSRAT                                                                    7

SEQ ID NO: 556          moltype = AA  length = 9
FEATURE                 Location/Qualifiers
source                  1..9
                        mol_type = protein
                        organism = synthetic construct
SEQUENCE: 556
QQVGVVPYT                                                                  9

SEQ ID NO: 557          moltype = AA  length = 6
FEATURE                 Location/Qualifiers
source                  1..6
                        mol_type = protein
                        organism = synthetic construct
SEQUENCE: 557
SGYYWS                                                                     6

SEQ ID NO: 558          moltype = AA  length = 12
FEATURE                 Location/Qualifiers
source                  1..12
                        mol_type = protein
                        organism = synthetic construct
SEQUENCE: 558
WIGEIGASGS TR                                                             12

SEQ ID NO: 559          moltype = AA  length = 17
FEATURE                 Location/Qualifiers
source                  1..17
                        mol_type = protein
                        organism = synthetic construct
SEQUENCE: 559
ARDTPYYYEG GYYYYMD                                                        17

SEQ ID NO: 560          moltype = AA  length = 8
FEATURE                 Location/Qualifiers
source                  1..8
                        mol_type = protein
                        organism = synthetic construct
SEQUENCE: 560
SSSYLAWY                                                                   8

SEQ ID NO: 561          moltype = AA  length = 10
FEATURE                 Location/Qualifiers
source                  1..10
                        mol_type = protein
                        organism = synthetic construct
SEQUENCE: 561
LLIYGASSRA                                                                10

SEQ ID NO: 562          moltype = AA  length = 8
FEATURE                 Location/Qualifiers
source                  1..8
                        mol_type = protein
                        organism = synthetic construct
SEQUENCE: 562
QQVGVVPY                                                                   8

SEQ ID NO: 563          moltype = AA  length = 8
FEATURE                 Location/Qualifiers
source                  1..8
                        mol_type = protein
                        organism = synthetic construct
SEQUENCE: 563
GGSLSGYY                                                                   8

SEQ ID NO: 564          moltype = AA  length = 7
FEATURE                 Location/Qualifiers
source                  1..7
                        mol_type = protein
                        organism = synthetic construct
SEQUENCE: 564
IGASGST                                                                    7

SEQ ID NO: 565          moltype = AA  length = 18
FEATURE                 Location/Qualifiers
source                  1..18
                        mol_type = protein
```

```
                                 -continued organism = synthetic construct
SEQUENCE: 565
ARDTPYYYEG GYYYYMDV                                                   18

SEQ ID NO: 566           moltype = AA  length = 7
FEATURE                  Location/Qualifiers
source                   1..7
                         mol_type = protein
                         organism = synthetic construct
SEQUENCE: 566
QSVSSSY                                                               7

SEQ ID NO: 567           moltype =    length =
SEQUENCE: 567
000

SEQ ID NO: 568           moltype = AA  length = 9
FEATURE                  Location/Qualifiers
source                   1..9
                         mol_type = protein
                         organism = synthetic construct
SEQUENCE: 568
QQVGVVPYT                                                             9

SEQ ID NO: 569           moltype = AA  length = 124
FEATURE                  Location/Qualifiers
source                   1..124
                         mol_type = protein
                         organism = synthetic construct
SEQUENCE: 569
QVQLQQWGAG LLKPSETLSL TCAVYGGSLS GYYWSWIRQP PGKGLEWIGE IGASGSTRYN     60
PSLKSRVTIS VDTSKNQFSL KLSSVTAADT AVYYCARDTP YYYEGGYYYY MDVWGKGTTV    120
TVSS                                                                 124

SEQ ID NO: 570           moltype = AA  length = 108
FEATURE                  Location/Qualifiers
source                   1..108
                         mol_type = protein
                         organism = synthetic construct
SEQUENCE: 570
EIVLTQSPGT LSLSPGERAT LSCRASQSVS SSYLAWYQQK PGQAPRLLIY GASSRATGIP     60
DRFSGSGSGT DFTLTISRLE PEDFAVYYCQ QVGVVPYTFG GGTKVEIK                 108

SEQ ID NO: 571           moltype = AA  length = 10
FEATURE                  Location/Qualifiers
source                   1..10
                         mol_type = protein
                         organism = synthetic construct
SEQUENCE: 571
GGSLSGYYWS                                                            10

SEQ ID NO: 572           moltype = AA  length = 16
FEATURE                  Location/Qualifiers
source                   1..16
                         mol_type = protein
                         organism = synthetic construct
SEQUENCE: 572
EIGASGSTRY NPSLKS                                                     16

SEQ ID NO: 573           moltype = AA  length = 16
FEATURE                  Location/Qualifiers
source                   1..16
                         mol_type = protein
                         organism = synthetic construct
SEQUENCE: 573
DTPYYYEGGY YYYMDV                                                     16

SEQ ID NO: 574           moltype = AA  length = 12
FEATURE                  Location/Qualifiers
source                   1..12
                         mol_type = protein
                         organism = synthetic construct
SEQUENCE: 574
RASDSVDSSY LA                                                         12

SEQ ID NO: 575           moltype = AA  length = 7
FEATURE                  Location/Qualifiers
source                   1..7
                         mol_type = protein
```

```
                                    -continued

SEQUENCE: 575                                                          organism = synthetic construct
GAFSRAN                                                                                            7

SEQ ID NO: 576          moltype = AA  length = 9
FEATURE                 Location/Qualifiers
source                  1..9
                        mol_type = protein
                        organism = synthetic construct
SEQUENCE: 576
QQAGVVPYT                                                                                          9

SEQ ID NO: 577          moltype = AA  length = 5
FEATURE                 Location/Qualifiers
source                  1..5
                        mol_type = protein
                        organism = synthetic construct
SEQUENCE: 577
GYYWS                                                                                              5

SEQ ID NO: 578          moltype = AA  length = 16
FEATURE                 Location/Qualifiers
source                  1..16
                        mol_type = protein
                        organism = synthetic construct
SEQUENCE: 578
EIGASGSTRY NPSLKS                                                                                 16

SEQ ID NO: 579          moltype = AA  length = 16
FEATURE                 Location/Qualifiers
source                  1..16
                        mol_type = protein
                        organism = synthetic construct
SEQUENCE: 579
DTPYYYEGGY YYYMDV                                                                                 16

SEQ ID NO: 580          moltype = AA  length = 12
FEATURE                 Location/Qualifiers
source                  1..12
                        mol_type = protein
                        organism = synthetic construct
SEQUENCE: 580
RASDSVDSSY LA                                                                                     12

SEQ ID NO: 581          moltype = AA  length = 7
FEATURE                 Location/Qualifiers
source                  1..7
                        mol_type = protein
                        organism = synthetic construct
SEQUENCE: 581
GAFSRAN                                                                                            7

SEQ ID NO: 582          moltype = AA  length = 9
FEATURE                 Location/Qualifiers
source                  1..9
                        mol_type = protein
                        organism = synthetic construct
SEQUENCE: 582
QQAGVVPYT                                                                                          9

SEQ ID NO: 583          moltype = AA  length = 7
FEATURE                 Location/Qualifiers
source                  1..7
                        mol_type = protein
                        organism = synthetic construct
SEQUENCE: 583
GGSLSGY                                                                                            7

SEQ ID NO: 584          moltype =     length =
SEQUENCE: 584
000

SEQ ID NO: 585          moltype = AA  length = 14
FEATURE                 Location/Qualifiers
source                  1..14
                        mol_type = protein
                        organism = synthetic construct
SEQUENCE: 585
TPYYYEGGYY YYMD                                                                                   14
```

```
SEQ ID NO: 586         moltype = AA  length = 8
FEATURE                Location/Qualifiers
source                 1..8
                       mol_type = protein
                       organism = synthetic construct
SEQUENCE: 586
SDSVDSSY                                                                 8

SEQ ID NO: 587         moltype =     length =
SEQUENCE: 587
000

SEQ ID NO: 588         moltype = AA  length = 6
FEATURE                Location/Qualifiers
source                 1..6
                       mol_type = protein
                       organism = synthetic construct
SEQUENCE: 588
AGVVPY                                                                   6

SEQ ID NO: 589         moltype = AA  length = 10
FEATURE                Location/Qualifiers
source                 1..10
                       mol_type = protein
                       organism = synthetic construct
SEQUENCE: 589
GGSLSGYYWS                                                              10

SEQ ID NO: 590         moltype = AA  length = 9
FEATURE                Location/Qualifiers
source                 1..9
                       mol_type = protein
                       organism = synthetic construct
SEQUENCE: 590
EIGASGSTR                                                                9

SEQ ID NO: 591         moltype = AA  length = 16
FEATURE                Location/Qualifiers
source                 1..16
                       mol_type = protein
                       organism = synthetic construct
SEQUENCE: 591
DTPYYYEGGY YYYMDV                                                       16

SEQ ID NO: 592         moltype = AA  length = 12
FEATURE                Location/Qualifiers
source                 1..12
                       mol_type = protein
                       organism = synthetic construct
SEQUENCE: 592
RASDSVDSSY LA                                                           12

SEQ ID NO: 593         moltype = AA  length = 7
FEATURE                Location/Qualifiers
source                 1..7
                       mol_type = protein
                       organism = synthetic construct
SEQUENCE: 593
GAFSRAN                                                                  7

SEQ ID NO: 594         moltype = AA  length = 9
FEATURE                Location/Qualifiers
source                 1..9
                       mol_type = protein
                       organism = synthetic construct
SEQUENCE: 594
QQAGVVPYT                                                                9

SEQ ID NO: 595         moltype = AA  length = 6
FEATURE                Location/Qualifiers
source                 1..6
                       mol_type = protein
                       organism = synthetic construct
SEQUENCE: 595
SGYYWS                                                                   6

SEQ ID NO: 596         moltype = AA  length = 12
FEATURE                Location/Qualifiers
```

```
source                  1..12
                        mol_type = protein
                        organism = synthetic construct
SEQUENCE: 596
WIGEIGASGS TR                                                        12

SEQ ID NO: 597          moltype = AA  length = 17
FEATURE                 Location/Qualifiers
source                  1..17
                        mol_type = protein
                        organism = synthetic construct
SEQUENCE: 597
ARDTPYYYEG GYYYYMD                                                   17

SEQ ID NO: 598          moltype = AA  length = 8
FEATURE                 Location/Qualifiers
source                  1..8
                        mol_type = protein
                        organism = synthetic construct
SEQUENCE: 598
DSSYLAWY                                                              8

SEQ ID NO: 599          moltype = AA  length = 10
FEATURE                 Location/Qualifiers
source                  1..10
                        mol_type = protein
                        organism = synthetic construct
SEQUENCE: 599
LLIYGAFSRA                                                           10

SEQ ID NO: 600          moltype = AA  length = 8
FEATURE                 Location/Qualifiers
source                  1..8
                        mol_type = protein
                        organism = synthetic construct
SEQUENCE: 600
QQAGVVPY                                                              8

SEQ ID NO: 601          moltype = AA  length = 8
FEATURE                 Location/Qualifiers
source                  1..8
                        mol_type = protein
                        organism = synthetic construct
SEQUENCE: 601
GGSLSGYY                                                              8

SEQ ID NO: 602          moltype = AA  length = 7
FEATURE                 Location/Qualifiers
source                  1..7
                        mol_type = protein
                        organism = synthetic construct
SEQUENCE: 602
IGASGST                                                               7

SEQ ID NO: 603          moltype = AA  length = 18
FEATURE                 Location/Qualifiers
source                  1..18
                        mol_type = protein
                        organism = synthetic construct
SEQUENCE: 603
ARDTPYYYEG GYYYYMDV                                                  18

SEQ ID NO: 604          moltype = AA  length = 7
FEATURE                 Location/Qualifiers
source                  1..7
                        mol_type = protein
                        organism = synthetic construct
SEQUENCE: 604
DSVDSSY                                                               7

SEQ ID NO: 605          moltype =     length =
SEQUENCE: 605
000

SEQ ID NO: 606          moltype = AA  length = 9
FEATURE                 Location/Qualifiers
source                  1..9
                        mol_type = protein
                        organism = synthetic construct
```

```
SEQUENCE: 606
QQAGVVPYT                                                                       9

SEQ ID NO: 607           moltype = AA  length = 124
FEATURE                  Location/Qualifiers
source                   1..124
                         mol_type = protein
                         organism = synthetic construct
SEQUENCE: 607
QVQLQQWGAG LLKPSETLSL TCAVYGGSLS GYYWSIRQP  PGKGLEWIGE IGASGSTRYN               60
PSLKSRVTIS VDTSKNQFSL KLSSVTAADT AVYYCARDTP YYYEGGYYYY MDVWGKGTTV              120
TVSS                                                                          124

SEQ ID NO: 608           moltype = AA  length = 108
FEATURE                  Location/Qualifiers
source                   1..108
                         mol_type = protein
                         organism = synthetic construct
SEQUENCE: 608
EIVLTQSPGT LSLSPGERAT LSCRASDSVD SSYLAWYQQK PGQAPRLLIY GAFSRANGIP               60
DRFSGSGSGT DFTLTISRLE PEDFAVYYCQ QAGVVPYTFG GGTKVEIK                           108

SEQ ID NO: 609           moltype = AA  length = 10
FEATURE                  Location/Qualifiers
source                   1..10
                         mol_type = protein
                         organism = synthetic construct
SEQUENCE: 609
GGSLSGYYWS                                                                     10

SEQ ID NO: 610           moltype = AA  length = 16
FEATURE                  Location/Qualifiers
source                   1..16
                         mol_type = protein
                         organism = synthetic construct
SEQUENCE: 610
EIGASGSTRY NPSLKS                                                              16

SEQ ID NO: 611           moltype = AA  length = 16
FEATURE                  Location/Qualifiers
source                   1..16
                         mol_type = protein
                         organism = synthetic construct
SEQUENCE: 611
DTPYYYEGGY YYYMDV                                                              16

SEQ ID NO: 612           moltype = AA  length = 12
FEATURE                  Location/Qualifiers
source                   1..12
                         mol_type = protein
                         organism = synthetic construct
SEQUENCE: 612
RASQSVSSSF LA                                                                  12

SEQ ID NO: 613           moltype = AA  length = 7
FEATURE                  Location/Qualifiers
source                   1..7
                         mol_type = protein
                         organism = synthetic construct
SEQUENCE: 613
GAYSRAT                                                                         7

SEQ ID NO: 614           moltype = AA  length = 9
FEATURE                  Location/Qualifiers
source                   1..9
                         mol_type = protein
                         organism = synthetic construct
SEQUENCE: 614
QQAGVVPYT                                                                       9

SEQ ID NO: 615           moltype = AA  length = 5
FEATURE                  Location/Qualifiers
source                   1..5
                         mol_type = protein
                         organism = synthetic construct
SEQUENCE: 615
GYYWS                                                                           5

SEQ ID NO: 616           moltype = AA  length = 16
```

```
                        -continued

FEATURE                 Location/Qualifiers
source                  1..16
                        mol_type = protein
                        organism = synthetic construct
SEQUENCE: 616
EIGASGSTRY NPSLKS                                                               16

SEQ ID NO: 617          moltype = AA   length = 16
FEATURE                 Location/Qualifiers
source                  1..16
                        mol_type = protein
                        organism = synthetic construct
SEQUENCE: 617
DTPYYYEGGY YYYMDV                                                               16

SEQ ID NO: 618          moltype = AA   length = 12
FEATURE                 Location/Qualifiers
source                  1..12
                        mol_type = protein
                        organism = synthetic construct
SEQUENCE: 618
RASQSVSSSF LA                                                                   12

SEQ ID NO: 619          moltype = AA   length = 7
FEATURE                 Location/Qualifiers
source                  1..7
                        mol_type = protein
                        organism = synthetic construct
SEQUENCE: 619
GAYSRAT                                                                          7

SEQ ID NO: 620          moltype = AA   length = 9
FEATURE                 Location/Qualifiers
source                  1..9
                        mol_type = protein
                        organism = synthetic construct
SEQUENCE: 620
QQAGVVPYT                                                                        9

SEQ ID NO: 621          moltype = AA   length = 7
FEATURE                 Location/Qualifiers
source                  1..7
                        mol_type = protein
                        organism = synthetic construct
SEQUENCE: 621
GGSLSGY                                                                          7

SEQ ID NO: 622          moltype =    length =
SEQUENCE: 622
000

SEQ ID NO: 623          moltype = AA   length = 14
FEATURE                 Location/Qualifiers
source                  1..14
                        mol_type = protein
                        organism = synthetic construct
SEQUENCE: 623
TPYYYEGGYY YYMD                                                                 14

SEQ ID NO: 624          moltype = AA   length = 8
FEATURE                 Location/Qualifiers
source                  1..8
                        mol_type = protein
                        organism = synthetic construct
SEQUENCE: 624
SQSVSSSF                                                                         8

SEQ ID NO: 625          moltype =    length =
SEQUENCE: 625
000

SEQ ID NO: 626          moltype = AA   length = 6
FEATURE                 Location/Qualifiers
source                  1..6
                        mol_type = protein
                        organism = synthetic construct
SEQUENCE: 626
AGVVPY                                                                           6
```

```
SEQ ID NO: 627              moltype = AA  length = 10
FEATURE                     Location/Qualifiers
source                      1..10
                            mol_type = protein
                            organism = synthetic construct
SEQUENCE: 627
GGSLSGYYWS                                                                 10

SEQ ID NO: 628              moltype = AA  length = 9
FEATURE                     Location/Qualifiers
source                      1..9
                            mol_type = protein
                            organism = synthetic construct
SEQUENCE: 628
EIGASGSTR                                                                   9

SEQ ID NO: 629              moltype = AA  length = 16
FEATURE                     Location/Qualifiers
source                      1..16
                            mol_type = protein
                            organism = synthetic construct
SEQUENCE: 629
DTPYYYEGGY YYYMDV                                                          16

SEQ ID NO: 630              moltype = AA  length = 12
FEATURE                     Location/Qualifiers
source                      1..12
                            mol_type = protein
                            organism = synthetic construct
SEQUENCE: 630
RASQSVSSSF LA                                                              12

SEQ ID NO: 631              moltype = AA  length = 7
FEATURE                     Location/Qualifiers
source                      1..7
                            mol_type = protein
                            organism = synthetic construct
SEQUENCE: 631
GAYSRAT                                                                     7

SEQ ID NO: 632              moltype = AA  length = 9
FEATURE                     Location/Qualifiers
source                      1..9
                            mol_type = protein
                            organism = synthetic construct
SEQUENCE: 632
QQAGVVPYT                                                                   9

SEQ ID NO: 633              moltype = AA  length = 6
FEATURE                     Location/Qualifiers
source                      1..6
                            mol_type = protein
                            organism = synthetic construct
SEQUENCE: 633
SGYYWS                                                                      6

SEQ ID NO: 634              moltype = AA  length = 12
FEATURE                     Location/Qualifiers
source                      1..12
                            mol_type = protein
                            organism = synthetic construct
SEQUENCE: 634
WIGEIGASGS TR                                                              12

SEQ ID NO: 635              moltype = AA  length = 17
FEATURE                     Location/Qualifiers
source                      1..17
                            mol_type = protein
                            organism = synthetic construct
SEQUENCE: 635
ARDTPYYYEG GYYYYMD                                                         17

SEQ ID NO: 636              moltype = AA  length = 8
FEATURE                     Location/Qualifiers
source                      1..8
                            mol_type = protein
                            organism = synthetic construct
SEQUENCE: 636
SSSFLAWY                                                                    8
```

```
SEQ ID NO: 637            moltype = AA   length = 10
FEATURE                   Location/Qualifiers
source                    1..10
                          mol_type = protein
                          organism = synthetic construct
SEQUENCE: 637
LLIYGAYSRA                                                                10

SEQ ID NO: 638            moltype = AA   length = 8
FEATURE                   Location/Qualifiers
source                    1..8
                          mol_type = protein
                          organism = synthetic construct
SEQUENCE: 638
QQAGVVPY                                                                   8

SEQ ID NO: 639            moltype = AA   length = 8
FEATURE                   Location/Qualifiers
source                    1..8
                          mol_type = protein
                          organism = synthetic construct
SEQUENCE: 639
GGSLSGYY                                                                   8

SEQ ID NO: 640            moltype = AA   length = 7
FEATURE                   Location/Qualifiers
source                    1..7
                          mol_type = protein
                          organism = synthetic construct
SEQUENCE: 640
IGASGST                                                                    7

SEQ ID NO: 641            moltype = AA   length = 18
FEATURE                   Location/Qualifiers
source                    1..18
                          mol_type = protein
                          organism = synthetic construct
SEQUENCE: 641
ARDTPYYYEG GYYYYMDV                                                       18

SEQ ID NO: 642            moltype = AA   length = 7
FEATURE                   Location/Qualifiers
source                    1..7
                          mol_type = protein
                          organism = synthetic construct
SEQUENCE: 642
QSVSSSF                                                                    7

SEQ ID NO: 643            moltype =    length =
SEQUENCE: 643
000

SEQ ID NO: 644            moltype = AA   length = 9
FEATURE                   Location/Qualifiers
source                    1..9
                          mol_type = protein
                          organism = synthetic construct
SEQUENCE: 644
QQAGVVPYT                                                                  9

SEQ ID NO: 645            moltype = AA   length = 124
FEATURE                   Location/Qualifiers
source                    1..124
                          mol_type = protein
                          organism = synthetic construct
SEQUENCE: 645
QVQLQQWGAG LLKPSETLSL TCAVYGGSLS GYYWSWIRQP PGKGLEWIGE IGASGSTRYN          60
PSLKSRVTIS VDTSKNQFSL KLSSVTAADT AVYYCARDTP YYYEGGYYYY MDVWGKGTTV         120
TVSS                                                                     124

SEQ ID NO: 646            moltype = AA   length = 108
FEATURE                   Location/Qualifiers
source                    1..108
                          mol_type = protein
                          organism = synthetic construct
SEQUENCE: 646
EIVLTQSPGT LSLSPGERAT LSCRASQSVS SSFLAWYQQK PGQAPRLLIY GAYSRATGIP          60
DRFSGSGSGT DFTLTISRLE PEDFAVYYCQ QAGVVPYTFG GGTKVEIK                     108
```

```
SEQ ID NO: 647           moltype = AA  length = 11
FEATURE                  Location/Qualifiers
source                   1..11
                         mol_type = protein
                         organism = synthetic construct
SEQUENCE: 647
GGSISSGQYW S                                                              11

SEQ ID NO: 648           moltype = AA  length = 16
FEATURE                  Location/Qualifiers
source                   1..16
                         mol_type = protein
                         organism = synthetic construct
SEQUENCE: 648
EIYYSGSTRY NPSLKS                                                         16

SEQ ID NO: 649           moltype = AA  length = 16
FEATURE                  Location/Qualifiers
source                   1..16
                         mol_type = protein
                         organism = synthetic construct
SEQUENCE: 649
DTPYYYDGGY YYYMDV                                                         16

SEQ ID NO: 650           moltype = AA  length = 12
FEATURE                  Location/Qualifiers
source                   1..12
                         mol_type = protein
                         organism = synthetic construct
SEQUENCE: 650
RASQSVSSSY LA                                                             12

SEQ ID NO: 651           moltype = AA  length = 7
FEATURE                  Location/Qualifiers
source                   1..7
                         mol_type = protein
                         organism = synthetic construct
SEQUENCE: 651
GASSRAT                                                                   7

SEQ ID NO: 652           moltype = AA  length = 9
FEATURE                  Location/Qualifiers
source                   1..9
                         mol_type = protein
                         organism = synthetic construct
SEQUENCE: 652
QQVGVVPYT                                                                 9

SEQ ID NO: 653           moltype = AA  length = 6
FEATURE                  Location/Qualifiers
source                   1..6
                         mol_type = protein
                         organism = synthetic construct
SEQUENCE: 653
SGQYWS                                                                    6

SEQ ID NO: 654           moltype = AA  length = 16
FEATURE                  Location/Qualifiers
source                   1..16
                         mol_type = protein
                         organism = synthetic construct
SEQUENCE: 654
EIYYSGSTRY NPSLKS                                                         16

SEQ ID NO: 655           moltype = AA  length = 16
FEATURE                  Location/Qualifiers
source                   1..16
                         mol_type = protein
                         organism = synthetic construct
SEQUENCE: 655
DTPYYYDGGY YYYMDV                                                         16

SEQ ID NO: 656           moltype = AA  length = 12
FEATURE                  Location/Qualifiers
source                   1..12
                         mol_type = protein
                         organism = synthetic construct
SEQUENCE: 656
```

RASQSVSSSY LA                                                                              12

SEQ ID NO: 657        moltype = AA   length = 7
FEATURE               Location/Qualifiers
source                1..7
                      mol_type = protein
                      organism = synthetic construct SEQUENCE: 657
GASSRAT                                                                                     7

SEQ ID NO: 658        moltype = AA   length = 9
FEATURE               Location/Qualifiers
source                1..9
                      mol_type = protein
                      organism = synthetic construct SEQUENCE: 658
QQVGVVPYT                                                                                   9

SEQ ID NO: 659        moltype = AA   length = 8
FEATURE               Location/Qualifiers
source                1..8
                      mol_type = protein
                      organism = synthetic construct SEQUENCE: 659
GGSISSGQ                                                                                    8

SEQ ID NO: 660        moltype =      length =
SEQUENCE: 660
000

SEQ ID NO: 661        moltype = AA   length = 14
FEATURE               Location/Qualifiers
source                1..14
                      mol_type = protein
                      organism = synthetic construct SEQUENCE: 661
TPYYYDGGYY YYMD                                                                            14

SEQ ID NO: 662        moltype = AA   length = 8
FEATURE               Location/Qualifiers
source                1..8
                      mol_type = protein
                      organism = synthetic construct SEQUENCE: 662
SQSVSSSY                                                                                    8

SEQ ID NO: 663        moltype =      length =
SEQUENCE: 663
000

SEQ ID NO: 664        moltype = AA   length = 6
FEATURE               Location/Qualifiers
source                1..6
                      mol_type = protein
                      organism = synthetic construct SEQUENCE: 664
VGVVPY                                                                                      6

SEQ ID NO: 665        moltype = AA   length = 11
FEATURE               Location/Qualifiers
source                1..11
                      mol_type = protein
                      organism = synthetic construct SEQUENCE: 665
GGSISSGQYW S                                                                               11

SEQ ID NO: 666        moltype = AA   length = 9
FEATURE               Location/Qualifiers
source                1..9
                      mol_type = protein
                      organism = synthetic construct SEQUENCE: 666
EIYYSGSTR                                                                                   9

SEQ ID NO: 667        moltype = AA   length = 16
FEATURE               Location/Qualifiers
source                1..16
                      mol_type = protein
                      organism = synthetic construct

```
SEQUENCE: 667
DTPYYYDGGY YYYMDV                                                              16

SEQ ID NO: 668          moltype = AA  length = 12
FEATURE                 Location/Qualifiers
source                  1..12
                        mol_type = protein
                        organism = synthetic construct
SEQUENCE: 668
RASQSVSSSY LA                                                                  12

SEQ ID NO: 669          moltype = AA  length = 7
FEATURE                 Location/Qualifiers
source                  1..7
                        mol_type = protein
                        organism = synthetic construct
SEQUENCE: 669
GASSRAT                                                                         7

SEQ ID NO: 670          moltype = AA  length = 9
FEATURE                 Location/Qualifiers
source                  1..9
                        mol_type = protein
                        organism = synthetic construct
SEQUENCE: 670
QQVGVVPYT                                                                       9

SEQ ID NO: 671          moltype = AA  length = 7
FEATURE                 Location/Qualifiers
source                  1..7
                        mol_type = protein
                        organism = synthetic construct
SEQUENCE: 671
SSGQYWS                                                                         7

SEQ ID NO: 672          moltype = AA  length = 12
FEATURE                 Location/Qualifiers
source                  1..12
                        mol_type = protein
                        organism = synthetic construct
SEQUENCE: 672
WIGEIYYSGS TR                                                                  12

SEQ ID NO: 673          moltype = AA  length = 17
FEATURE                 Location/Qualifiers
source                  1..17
                        mol_type = protein
                        organism = synthetic construct
SEQUENCE: 673
ARDTPYYYDG GYYYYMD                                                             17

SEQ ID NO: 674          moltype = AA  length = 8
FEATURE                 Location/Qualifiers
source                  1..8
                        mol_type = protein
                        organism = synthetic construct
SEQUENCE: 674
SSSYLAWY                                                                        8

SEQ ID NO: 675          moltype = AA  length = 10
FEATURE                 Location/Qualifiers
source                  1..10
                        mol_type = protein
                        organism = synthetic construct
SEQUENCE: 675
LLIYGASSRA                                                                     10

SEQ ID NO: 676          moltype = AA  length = 8
FEATURE                 Location/Qualifiers
source                  1..8
                        mol_type = protein
                        organism = synthetic construct
SEQUENCE: 676
QQVGVVPY                                                                        8

SEQ ID NO: 677          moltype = AA  length = 9
FEATURE                 Location/Qualifiers
source                  1..9
                        mol_type = protein
```

```
                        organism = synthetic construct
SEQUENCE: 677
GGSISSGQY                                                                    9

SEQ ID NO: 678          moltype = AA   length = 7
FEATURE                 Location/Qualifiers
source                  1..7
                        mol_type = protein
                        organism = synthetic construct
SEQUENCE: 678
IYYSGST                                                                      7

SEQ ID NO: 679          moltype = AA   length = 18
FEATURE                 Location/Qualifiers
source                  1..18
                        mol_type = protein
                        organism = synthetic construct
SEQUENCE: 679
ARDTPYYYDG GYYYYMDV                                                          18

SEQ ID NO: 680          moltype = AA   length = 7
FEATURE                 Location/Qualifiers
source                  1..7
                        mol_type = protein
                        organism = synthetic construct
SEQUENCE: 680
QSVSSSY                                                                      7

SEQ ID NO: 681          moltype =    length =
SEQUENCE: 681
000

SEQ ID NO: 682          moltype = AA   length = 9
FEATURE                 Location/Qualifiers
source                  1..9
                        mol_type = protein
                        organism = synthetic construct
SEQUENCE: 682
QQVGVVPYT                                                                    9

SEQ ID NO: 683          moltype = AA   length = 125
FEATURE                 Location/Qualifiers
source                  1..125
                        mol_type = protein
                        organism = synthetic construct
SEQUENCE: 683
QVQLQESGPG LVKPSQTLSL TCTVSGGSIS SGQYWSWIRQ HPGKGLEWIG EIYYSGSTRY            60
NPSLKSRVTI SVDTSKDQFS LKLSSVTAAD TAVYYCARDT PYYYDGGYYY YMDVWGKGTT           120
VTVSS                                                                      125

SEQ ID NO: 684          moltype = AA   length = 108
FEATURE                 Location/Qualifiers
source                  1..108
                        mol_type = protein
                        organism = synthetic construct
SEQUENCE: 684
EIVLTQSPGT LSLSPGERAT LSCRASQSVS SSYLAWYQQK PGQAPRLLIY GASSRATGIP            60
DRFSGSGSGT DFTLTISRLE PEDFAVYYCQ QVGVVPYTFG GGTKVEIK                       108

SEQ ID NO: 685          moltype = AA   length = 11
FEATURE                 Location/Qualifiers
source                  1..11
                        mol_type = protein
                        organism = synthetic construct
SEQUENCE: 685
GGSISSGQYW S                                                                11

SEQ ID NO: 686          moltype = AA   length = 16
FEATURE                 Location/Qualifiers
source                  1..16
                        mol_type = protein
                        organism = synthetic construct
SEQUENCE: 686
EIYYSGSTRY NPSLKS                                                           16

SEQ ID NO: 687          moltype = AA   length = 16
FEATURE                 Location/Qualifiers
source                  1..16
                        mol_type = protein
```

```
SEQUENCE: 687
DTPYYYDGGY YYYMDV                                                    16

SEQ ID NO: 688          moltype = AA   length = 12
FEATURE                 Location/Qualifiers
source                  1..12
                        mol_type = protein
                        organism = synthetic construct
SEQUENCE: 688
RASQSVSSSY LA                                                        12

SEQ ID NO: 689          moltype = AA   length = 7
FEATURE                 Location/Qualifiers
source                  1..7
                        mol_type = protein
                        organism = synthetic construct
SEQUENCE: 689
GASSRAT                                                              7

SEQ ID NO: 690          moltype = AA   length = 9
FEATURE                 Location/Qualifiers
source                  1..9
                        mol_type = protein
                        organism = synthetic construct
SEQUENCE: 690
QQVGVVPYT                                                            9

SEQ ID NO: 691          moltype = AA   length = 6
FEATURE                 Location/Qualifiers
source                  1..6
                        mol_type = protein
                        organism = synthetic construct
SEQUENCE: 691
SGQYWS                                                               6

SEQ ID NO: 692          moltype = AA   length = 16
FEATURE                 Location/Qualifiers
source                  1..16
                        mol_type = protein
                        organism = synthetic construct
SEQUENCE: 692
EIYYSGSTRY NPSLKS                                                    16

SEQ ID NO: 693          moltype = AA   length = 16
FEATURE                 Location/Qualifiers
source                  1..16
                        mol_type = protein
                        organism = synthetic construct
SEQUENCE: 693
DTPYYYDGGY YYYMDV                                                    16

SEQ ID NO: 694          moltype = AA   length = 12
FEATURE                 Location/Qualifiers
source                  1..12
                        mol_type = protein
                        organism = synthetic construct
SEQUENCE: 694
RASQSVSSSY LA                                                        12

SEQ ID NO: 695          moltype = AA   length = 7
FEATURE                 Location/Qualifiers
source                  1..7
                        mol_type = protein
                        organism = synthetic construct
SEQUENCE: 695
GASSRAT                                                              7

SEQ ID NO: 696          moltype = AA   length = 9
FEATURE                 Location/Qualifiers
source                  1..9
                        mol_type = protein
                        organism = synthetic construct
SEQUENCE: 696
QQVGVVPYT                                                            9

SEQ ID NO: 697          moltype = AA   length = 8
FEATURE                 Location/Qualifiers
source                  1..8
```

```
                         mol_type = protein
                         organism = synthetic construct
SEQUENCE: 697
GGSISSGQ                                                                8

SEQ ID NO: 698           moltype =    length =
SEQUENCE: 698
000

SEQ ID NO: 699           moltype = AA   length = 14
FEATURE                  Location/Qualifiers
source                   1..14
                         mol_type = protein
                         organism = synthetic construct
SEQUENCE: 699
TPYYYDGGYY YYMD                                                        14

SEQ ID NO: 700           moltype = AA   length = 8
FEATURE                  Location/Qualifiers
source                   1..8
                         mol_type = protein
                         organism = synthetic construct
SEQUENCE: 700
SQSVSSSY                                                                8

SEQ ID NO: 701           moltype =    length =
SEQUENCE: 701
000

SEQ ID NO: 702           moltype = AA   length = 6
FEATURE                  Location/Qualifiers
source                   1..6
                         mol_type = protein
                         organism = synthetic construct
SEQUENCE: 702
VGVVPY                                                                  6

SEQ ID NO: 703           moltype = AA   length = 11
FEATURE                  Location/Qualifiers
source                   1..11
                         mol_type = protein
                         organism = synthetic construct
SEQUENCE: 703
GGSISSGQYW S                                                           11

SEQ ID NO: 704           moltype = AA   length = 9
FEATURE                  Location/Qualifiers
source                   1..9
                         mol_type = protein
                         organism = synthetic construct
SEQUENCE: 704
EIYYSGSTR                                                               9

SEQ ID NO: 705           moltype = AA   length = 16
FEATURE                  Location/Qualifiers
source                   1..16
                         mol_type = protein
                         organism = synthetic construct
SEQUENCE: 705
DTPYYYDGGY YYYMDV                                                      16

SEQ ID NO: 706           moltype = AA   length = 12
FEATURE                  Location/Qualifiers
source                   1..12
                         mol_type = protein
                         organism = synthetic construct
SEQUENCE: 706
RASQSVSSSY LA                                                          12

SEQ ID NO: 707           moltype = AA   length = 7
FEATURE                  Location/Qualifiers
source                   1..7
                         mol_type = protein
                         organism = synthetic construct
SEQUENCE: 707
GASSRAT                                                                 7

SEQ ID NO: 708           moltype = AA   length = 9
FEATURE                  Location/Qualifiers
```

```
source                          1..9
                                mol_type = protein
                                organism = synthetic construct
SEQUENCE: 708
QQVGVVPYT                                                                         9

SEQ ID NO: 709                  moltype = AA   length = 7
FEATURE                         Location/Qualifiers
source                          1..7
                                mol_type = protein
                                organism = synthetic construct
SEQUENCE: 709
SSGQYWS                                                                           7

SEQ ID NO: 710                  moltype = AA   length = 12
FEATURE                         Location/Qualifiers
source                          1..12
                                mol_type = protein
                                organism = synthetic construct
SEQUENCE: 710
WIGEIYYSGS TR                                                                    12

SEQ ID NO: 711                  moltype = AA   length = 17
FEATURE                         Location/Qualifiers
source                          1..17
                                mol_type = protein
                                organism = synthetic construct
SEQUENCE: 711
ARDTPYYYDG GYYYYMD                                                               17

SEQ ID NO: 712                  moltype = AA   length = 8
FEATURE                         Location/Qualifiers
source                          1..8
                                mol_type = protein
                                organism = synthetic construct
SEQUENCE: 712
SSSYLAWY                                                                          8

SEQ ID NO: 713                  moltype = AA   length = 10
FEATURE                         Location/Qualifiers
source                          1..10
                                mol_type = protein
                                organism = synthetic construct
SEQUENCE: 713
LLIYGASSRA                                                                       10

SEQ ID NO: 714                  moltype = AA   length = 8
FEATURE                         Location/Qualifiers
source                          1..8
                                mol_type = protein
                                organism = synthetic construct
SEQUENCE: 714
QQVGVVPY                                                                          8

SEQ ID NO: 715                  moltype = AA   length = 9
FEATURE                         Location/Qualifiers
source                          1..9
                                mol_type = protein
                                organism = synthetic construct
SEQUENCE: 715
GGSISSGQY                                                                         9

SEQ ID NO: 716                  moltype = AA   length = 7
FEATURE                         Location/Qualifiers
source                          1..7
                                mol_type = protein
                                organism = synthetic construct
SEQUENCE: 716
IYYSGST                                                                           7

SEQ ID NO: 717                  moltype = AA   length = 18
FEATURE                         Location/Qualifiers
source                          1..18
                                mol_type = protein
                                organism = synthetic construct
SEQUENCE: 717
ARDTPYYYDG GYYYYMDV                                                              18

SEQ ID NO: 718                  moltype = AA   length = 7
```

```
FEATURE              Location/Qualifiers
source               1..7
                     mol_type = protein
                     organism = synthetic construct
SEQUENCE: 718
QSVSSSY                                                                          7

SEQ ID NO: 719       moltype =    length =
SEQUENCE: 719
000

SEQ ID NO: 720       moltype = AA   length = 9
FEATURE              Location/Qualifiers
source               1..9
                     mol_type = protein
                     organism = synthetic construct
SEQUENCE: 720
QQVGVVPYT                                                                        9

SEQ ID NO: 721       moltype = AA   length = 125
FEATURE              Location/Qualifiers
source               1..125
                     mol_type = protein
                     organism = synthetic construct
SEQUENCE: 721
QVQLQESGPG LVKPSQTLSL TCTVSGGSIS SGQYWSWIRQ HPGKGLEWIG EIYYSGSTRY                 60
NPSLKSRVTI SVDTSKNQFS LKLSSVTAAD TAVYYCARDT PYYYDGGYYY YMDVWGKGTT                120
VTVSS                                                                          125

SEQ ID NO: 722       moltype = AA   length = 108
FEATURE              Location/Qualifiers
source               1..108
                     mol_type = protein
                     organism = synthetic construct
SEQUENCE: 722
EIVLTQSPGT LSLSPGERAT LSCRASQSVS SSYLAWYQQK PGQAPRLLIY GASSRATGIP                 60
DRFSGSGSGT DFTLTISRLE PEDFAVYYCQ QVGVVPYTFG GGTKVEIK                            108

SEQ ID NO: 723       moltype = AA   length = 10
FEATURE              Location/Qualifiers
source               1..10
                     mol_type = protein
                     organism = synthetic construct
SEQUENCE: 723
GYTFANYYMH                                                                      10

SEQ ID NO: 724       moltype = AA   length = 17
FEATURE              Location/Qualifiers
source               1..17
                     mol_type = protein
                     organism = synthetic construct
SEQUENCE: 724
IINPSGGITV YAQKFQG                                                              17

SEQ ID NO: 725       moltype = AA   length = 12
FEATURE              Location/Qualifiers
source               1..12
                     mol_type = protein
                     organism = synthetic construct
SEQUENCE: 725
GGSKVAALAF DI                                                                   12

SEQ ID NO: 726       moltype = AA   length = 11
FEATURE              Location/Qualifiers
source               1..11
                     mol_type = protein
                     organism = synthetic construct
SEQUENCE: 726
QASQDISNSL N                                                                    11

SEQ ID NO: 727       moltype = AA   length = 7
FEATURE              Location/Qualifiers
source               1..7
                     mol_type = protein
                     organism = synthetic construct
SEQUENCE: 727
DASNLET                                                                          7

SEQ ID NO: 728       moltype = AA   length = 9
```

```
FEATURE                 Location/Qualifiers
source                  1..9
                        mol_type = protein
                        organism = synthetic construct
SEQUENCE: 728
QQYNFHPLT                                                                    9

SEQ ID NO: 729          moltype = AA  length = 5
FEATURE                 Location/Qualifiers
source                  1..5
                        mol_type = protein
                        organism = synthetic construct
SEQUENCE: 729
NYYMH                                                                        5

SEQ ID NO: 730          moltype = AA  length = 17
FEATURE                 Location/Qualifiers
source                  1..17
                        mol_type = protein
                        organism = synthetic construct
SEQUENCE: 730
IINPSGGITV YAQKFQG                                                          17

SEQ ID NO: 731          moltype = AA  length = 12
FEATURE                 Location/Qualifiers
source                  1..12
                        mol_type = protein
                        organism = synthetic construct
SEQUENCE: 731
GGSKVAALAF DI                                                               12

SEQ ID NO: 732          moltype = AA  length = 11
FEATURE                 Location/Qualifiers
source                  1..11
                        mol_type = protein
                        organism = synthetic construct
SEQUENCE: 732
QASQDISNSL N                                                                11

SEQ ID NO: 733          moltype = AA  length = 7
FEATURE                 Location/Qualifiers
source                  1..7
                        mol_type = protein
                        organism = synthetic construct
SEQUENCE: 733
DASNLET                                                                      7

SEQ ID NO: 734          moltype = AA  length = 9
FEATURE                 Location/Qualifiers
source                  1..9
                        mol_type = protein
                        organism = synthetic construct
SEQUENCE: 734
QQYNFHPLT                                                                    9

SEQ ID NO: 735          moltype = AA  length = 7
FEATURE                 Location/Qualifiers
source                  1..7
                        mol_type = protein
                        organism = synthetic construct
SEQUENCE: 735
GYTFANY                                                                      7

SEQ ID NO: 736          moltype = AA  length = 4
FEATURE                 Location/Qualifiers
source                  1..4
                        mol_type = protein
                        organism = synthetic construct
SEQUENCE: 736
PSGG                                                                         4

SEQ ID NO: 737          moltype = AA  length = 10
FEATURE                 Location/Qualifiers
source                  1..10
                        mol_type = protein
                        organism = synthetic construct
SEQUENCE: 737
GSKVAALAFD                                                                  10
```

```
SEQ ID NO: 738          moltype = AA  length = 7
FEATURE                 Location/Qualifiers
source                  1..7
                        mol_type = protein
                        organism = synthetic construct
SEQUENCE: 738
SQDISNS                                                                    7

SEQ ID NO: 739          moltype =     length =
SEQUENCE: 739
000

SEQ ID NO: 740          moltype = AA  length = 6
FEATURE                 Location/Qualifiers
source                  1..6
                        mol_type = protein
                        organism = synthetic construct
SEQUENCE: 740
YNFHPL                                                                     6

SEQ ID NO: 741          moltype = AA  length = 10
FEATURE                 Location/Qualifiers
source                  1..10
                        mol_type = protein
                        organism = synthetic construct
SEQUENCE: 741
GYTFANYYMH                                                                10

SEQ ID NO: 742          moltype = AA  length = 10
FEATURE                 Location/Qualifiers
source                  1..10
                        mol_type = protein
                        organism = synthetic construct
SEQUENCE: 742
IINPSGGITV                                                                10

SEQ ID NO: 743          moltype = AA  length = 12
FEATURE                 Location/Qualifiers
source                  1..12
                        mol_type = protein
                        organism = synthetic construct
SEQUENCE: 743
GGSKVAALAF DI                                                             12

SEQ ID NO: 744          moltype = AA  length = 11
FEATURE                 Location/Qualifiers
source                  1..11
                        mol_type = protein
                        organism = synthetic construct
SEQUENCE: 744
QASQDISNSL N                                                              11

SEQ ID NO: 745          moltype = AA  length = 7
FEATURE                 Location/Qualifiers
source                  1..7
                        mol_type = protein
                        organism = synthetic construct
SEQUENCE: 745
DASNLET                                                                    7

SEQ ID NO: 746          moltype = AA  length = 9
FEATURE                 Location/Qualifiers
source                  1..9
                        mol_type = protein
                        organism = synthetic construct
SEQUENCE: 746
QQYNFHPLT                                                                  9

SEQ ID NO: 747          moltype = AA  length = 6
FEATURE                 Location/Qualifiers
source                  1..6
                        mol_type = protein
                        organism = synthetic construct
SEQUENCE: 747
ANYYMH                                                                     6

SEQ ID NO: 748          moltype = AA  length = 13
FEATURE                 Location/Qualifiers
source                  1..13
```

```
SEQUENCE: 748
WMGIINPSGG ITV                                                        13

SEQ ID NO: 749          moltype = AA  length = 13
FEATURE                 Location/Qualifiers
source                  1..13
                        mol_type = protein
                        organism = synthetic construct
SEQUENCE: 749
ARGGSKVAAL AFD                                                        13

SEQ ID NO: 750          moltype = AA  length = 7
FEATURE                 Location/Qualifiers
source                  1..7
                        mol_type = protein
                        organism = synthetic construct
SEQUENCE: 750
SNSLNWY                                                                7

SEQ ID NO: 751          moltype = AA  length = 10
FEATURE                 Location/Qualifiers
source                  1..10
                        mol_type = protein
                        organism = synthetic construct
SEQUENCE: 751
LLIYDASNLE                                                            10

SEQ ID NO: 752          moltype = AA  length = 8
FEATURE                 Location/Qualifiers
source                  1..8
                        mol_type = protein
                        organism = synthetic construct
SEQUENCE: 752
QQYNFHPL                                                               8

SEQ ID NO: 753          moltype = AA  length = 8
FEATURE                 Location/Qualifiers
source                  1..8
                        mol_type = protein
                        organism = synthetic construct
SEQUENCE: 753
GYTFANYY                                                               8

SEQ ID NO: 754          moltype = AA  length = 8
FEATURE                 Location/Qualifiers
source                  1..8
                        mol_type = protein
                        organism = synthetic construct
SEQUENCE: 754
INPSGGIT                                                               8

SEQ ID NO: 755          moltype = AA  length = 14
FEATURE                 Location/Qualifiers
source                  1..14
                        mol_type = protein
                        organism = synthetic construct
SEQUENCE: 755
ARGGSKVAAL AFDI                                                       14

SEQ ID NO: 756          moltype = AA  length = 6
FEATURE                 Location/Qualifiers
source                  1..6
                        mol_type = protein
                        organism = synthetic construct
SEQUENCE: 756
QDISNS                                                                 6

SEQ ID NO: 757          moltype =    length =
SEQUENCE: 757
000

SEQ ID NO: 758          moltype = AA  length = 9
FEATURE                 Location/Qualifiers
source                  1..9
                        mol_type = protein
                        organism = synthetic construct
SEQUENCE: 758
```

QQYNFHPLT                                                                        9

SEQ ID NO: 759          moltype = AA  length = 121
FEATURE                 Location/Qualifiers
source                  1..121
                        mol_type = protein
                        organism = synthetic construct
SEQUENCE: 759
QVQLVQSGAE VKKPGASVKV SCKASGYTFA NYYMHWVRQA PGQGLEWMGI INPSGGITVY   60
AQKFQGRVTM TRDTSTSTVY MELSSLRSED TAVYYCARGG SKVAALAFDI WGQGTMVTVS  120
S                                                                 121

SEQ ID NO: 760          moltype = AA  length = 107
FEATURE                 Location/Qualifiers
source                  1..107
                        mol_type = protein
                        organism = synthetic construct
SEQUENCE: 760
DIQMTQSPSS LSASVGDRVT ITCQASQDIS NSLNWYQQKP GKAPKLLIYD ASNLETGVPS   60
RFSGSRSGTD FTFTISSLQP EDIATYYCQQ YNFHPLTFGG GTKVEIK               107

SEQ ID NO: 761          moltype = AA  length = 118
FEATURE                 Location/Qualifiers
source                  1..118
                        mol_type = protein
                        organism = synthetic construct
VARIANT                 31
                        note = D or S
VARIANT                 35
                        note = A or G
VARIANT                 50
                        note = A or T
SEQUENCE: 761
EVQLLESGGG LVQPGGSLRL SCAASGFTFS XYAMXWVRQA PGKGLEWVSX ISGSGGLTYY   60
ADSVKGRFTI SRDNSKNTLY LQMNSLRAED TAVYYCAKAP YGYYMDVWGK GTTVTVSS   118

SEQ ID NO: 762          moltype = AA  length = 106
FEATURE                 Location/Qualifiers
source                  1..106
                        mol_type = protein
                        organism = synthetic construct
SEQUENCE: 762
DIQMTQSPST LSASVGDRVT ITCRASQSIS SWLAWYQQKP GKAPKLLIYK ASSLESGVPS   60
RFSGSGSGTE FTLTISSLQP DDFATYYCQQ YKSYITFGGG TKVEIK                106

SEQ ID NO: 763          moltype = AA  length = 123
FEATURE                 Location/Qualifiers
source                  1..123
                        mol_type = protein
                        organism = synthetic construct
VARIANT                 30
                        note = D or R
VARIANT                 31
                        note = S or V or A
VARIANT                 51
                        note = I or V
VARIANT                 55
                        note = S or N
VARIANT                 106
                        note = F or Y
SEQUENCE: 763
QVQLVQSGAE VKKPGASVKV SCKASGYTFX XYGISWVRQA PGQGLEWMGW XAPYXGNTNY   60
AQKLQGRVTM TTDTSTSTAY MELRSLRSDD TAVYYCARDA GTYSPXGYGM DVWGQGTTVT  120
VSS                                                               123

SEQ ID NO: 764          moltype = AA  length = 108
FEATURE                 Location/Qualifiers
source                  1..108
                        mol_type = protein
                        organism = synthetic construct
VARIANT                 24
                        note = R or Q
VARIANT                 27
                        note = Q or E or H
VARIANT                 30
                        note = S or D or N
VARIANT                 31
                        note = S or N
VARIANT                 50

```
VARIANT          note = K or S
                 52
                 note = S or Y
VARIANT          53
                 note = S or Y or N
VARIANT          56
                 note = S or Y
VARIANT          90
                 note = Q or L or R
VARIANT          93
                 note = S or K
SEQUENCE: 764
DIQMTQSPST LSASVGDRVT ITCXASXSIX XWLAWYQQKP GKAPKLLIYX AXXLEXGVPS    60
RFSGSGSGTE FTLTISSLQP DDFATYYCQX FQXLPPFTFG GGTKVEIK                108

SEQ ID NO: 765           moltype = AA  length = 119
FEATURE                  Location/Qualifiers
source                   1..119
                         mol_type = protein
                         organism = synthetic construct
VARIANT                  30
                         note = H or R
VARIANT                  32
                         note = R or Y
SEQUENCE: 765
QVQLVESGGG VVQPGRSLRL SCAASGFTFX SXGMHWVRQA PGKGLEWVAV ITYDGINKYY    60
ADSVEGRFTI SRDNSKNTLY LQMNSLRAED TAVYYCARDG VYYGVYDYWG QGTLVTVSS    119

SEQ ID NO: 766           moltype = AA  length = 113
FEATURE                  Location/Qualifiers
source                   1..113
                         mol_type = protein
                         organism = synthetic construct
SEQUENCE: 766
DIVMTQSPDS LAVSLGERAT INCKSSQSVL FSSNNKNYLA WYQQKPGQPP KLLIYWASTR    60
ESGVPDRFSG SGSGTDFTLT ISSLQAEDVA VYYCQQFHSY PLTFGGGTKV EIK          113

SEQ ID NO: 767           moltype = AA  length = 124
FEATURE                  Location/Qualifiers
source                   1..124
                         mol_type = protein
                         organism = synthetic construct
SEQUENCE: 767
QVQLVQSGAE VKKPGSSVKV SCKASGGTFS SNAIGWVRQA PGQGLEWMGS IIPIIGFANY    60
AQKFQGRVTI TADESTSTAY MELSSLRSED TAVYYCARDS GYYYGASSFG MDWGQGTTV    120
TVSS                                                                124

SEQ ID NO: 768           moltype = AA  length = 107
FEATURE                  Location/Qualifiers
source                   1..107
                         mol_type = protein
                         organism = synthetic construct
SEQUENCE: 768
EIVMTQSPAT LSVSPGERAT LSCRASQSVS SNLAWYQQKP GQAPRLLIYG ASTRATGIPA    60
RFSGSGSGTE FTLTISSLQS EDFAVYYCEQ YNNLPLTFGG GTKVEIK                 107

SEQ ID NO: 769           moltype = AA  length = 125
FEATURE                  Location/Qualifiers
source                   1..125
                         mol_type = protein
                         organism = synthetic construct
VARIANT                  6
                         note = E or Q
VARIANT                  7
                         note = S or W
VARIANT                  9
                         note = P or A
VARIANT                  12
                         note = V or L
VARIANT                  16
                         note = Q or E
VARIANT                  23
                         note = T or A
VARIANT                  25
                         note = S or Y
VARIANT                  29
                         note = I or L
VARIANT                  33
                         note = Q or Y
```

| | |
|---|---|
| VARIANT | 41 |
| | note = H or P |
| VARIANT | 53 |
| | note = Y or G |
| VARIANT | 54 |
| | note = Y or A |
| VARIANT | 77 |
| | note = N or D |
| VARIANT | 100 |
| | note = T or A |
| VARIANT | 105 |
| | note = E or G or D |
| SEQUENCE: 769 | |
| QVQLQXXGXG LXKPSXTLSL TCXVXGGSXS SGXYWSWIRQ XPGKGLEWIG EIXXSGSTRY | 60 |
| NPSLKSRVTI SVDTSKXQFS LKLSSVTAAD TAVYYCARDX PYYYXGGYYY YMDVWGKGTT | 120 |
| VTVSS | 125 |
| | |
| SEQ ID NO: 770 | moltype = AA   length = 108 |
| FEATURE | Location/Qualifiers |
| source | 1..108 |
| | mol_type = protein |
| | organism = synthetic construct |
| VARIANT | 27 |
| | note = Q or E or D |
| VARIANT | 30 |
| | note = S or D |
| VARIANT | 33 |
| | note = Y or F |
| VARIANT | 53 |
| | note = S or D or F or Y |
| VARIANT | 54 |
| | note = S or T |
| VARIANT | 56 |
| | note = A or Q |
| VARIANT | 57 |
| | note = T or N |
| VARIANT | 92 |
| | note = V or A or D |
| SEQUENCE: 770 | |
| EIVLTQSPGT LSLSPGERAT LSCRASXSVX SSXLAWYQQK PGQAPRLLIY GAXXRXXGIP | 60 |
| DRFSGSGSGT DFTLTISRLE PEDFAVYYCQ QXGVVPYTFG GGTKVEIK | 108 |
| | |
| SEQ ID NO: 771 | moltype = AA   length = 121 |
| FEATURE | Location/Qualifiers |
| source | 1..121 |
| | mol_type = protein |
| | organism = synthetic construct |
| SEQUENCE: 771 | |
| QVQLVQSGAE VKKPGASVKV SCKASGYTFA NYYMHWVRQA PGQGLEWMGI INPSGGITVY | 60 |
| AQKFQGRVTM TRDTSTSTVY MELSSLRSED TAVYYCARGG SKVAALAFDI WGQGTMVTVS | 120 |
| S | 121 |
| | |
| SEQ ID NO: 772 | moltype = AA   length = 107 |
| FEATURE | Location/Qualifiers |
| source | 1..107 |
| | mol_type = protein |
| | organism = synthetic construct |
| SEQUENCE: 772 | |
| DIQMTQSPSS LSASVGDRVT ITCQASQDIS NSLNWYQQKP GKAPKLLIYD ASNLETGVPS | 60 |
| RFSGSRSGTD FTFTISSLQP EDIATYYCQQ YNFHPLTFGG GTKVEIK | 107 |
| | |
| SEQ ID NO: 773 | moltype = AA   length = 10 |
| FEATURE | Location/Qualifiers |
| source | 1..10 |
| | mol_type = protein |
| | organism = synthetic construct |
| VARIANT | 6 |
| | note = D or S |
| VARIANT | 10 |
| | note = A or G |
| SEQUENCE: 773 | |
| GFTFSXYAMX | 10 |
| | |
| SEQ ID NO: 774 | moltype = AA   length = 17 |
| FEATURE | Location/Qualifiers |
| source | 1..17 |
| | mol_type = protein |
| | organism = synthetic construct |
| VARIANT | 1 |

```
                                 -continued note = A or T
SEQUENCE: 774
XISGSGGLTY YADSVKG                                                 17

SEQ ID NO: 775          moltype = AA   length = 9
FEATURE                 Location/Qualifiers
source                  1..9
                        mol_type = protein
                        organism = synthetic construct
SEQUENCE: 775
APYGYYMDV                                                           9

SEQ ID NO: 776          moltype = AA   length = 11
FEATURE                 Location/Qualifiers
source                  1..11
                        mol_type = protein
                        organism = synthetic construct
SEQUENCE: 776
RASQSISSWL A                                                       11

SEQ ID NO: 777          moltype = AA   length = 7
FEATURE                 Location/Qualifiers
source                  1..7
                        mol_type = protein
                        organism = synthetic construct
SEQUENCE: 777
KASSLES                                                             7

SEQ ID NO: 778          moltype = AA   length = 8
FEATURE                 Location/Qualifiers
source                  1..8
                        mol_type = protein
                        organism = synthetic construct
SEQUENCE: 778
QQYKSYIT                                                            8

SEQ ID NO: 779          moltype = AA   length = 10
FEATURE                 Location/Qualifiers
source                  1..10
                        mol_type = protein
                        organism = synthetic construct
VARIANT                 5
                        note = D or R
VARIANT                 6
                        note = S or V
SEQUENCE: 779
GYTFXXYGIS                                                         10

SEQ ID NO: 780          moltype = AA   length = 17
FEATURE                 Location/Qualifiers
source                  1..17
                        mol_type = protein
                        organism = synthetic construct
VARIANT                 2
                        note = I or V
VARIANT                 6
                        note = S or N
SEQUENCE: 780
WXAPYXGNTN YAQKLQG                                                 17

SEQ ID NO: 781          moltype = AA   length = 14
FEATURE                 Location/Qualifiers
source                  1..14
                        mol_type = protein
                        organism = synthetic construct
VARIANT                 8
                        note = F or Y
SEQUENCE: 781
DAGTYSPXGY GMDV                                                    14

SEQ ID NO: 782          moltype = AA   length = 11
FEATURE                 Location/Qualifiers
source                  1..11
                        mol_type = protein
                        organism = synthetic construct
VARIANT                 1
                        note = R or Q
VARIANT                 4
                        note = Q or E or H
```

```
VARIANT            7
                   note = S or D or N
VARIANT            8
                   note = S or N
SEQUENCE: 782
XASXSIXXWL A                                                                11

SEQ ID NO: 783     moltype =   length =
SEQUENCE: 783
000

SEQ ID NO: 784     moltype = AA  length = 10
FEATURE            Location/Qualifiers
source             1..10
                   mol_type = protein
                   organism = synthetic construct
VARIANT            2
                   note = Q or L or R
VARIANT            5
                   note = S or K
SEQUENCE: 784
QXFQXLPPFT                                                                  10

SEQ ID NO: 785     moltype = AA  length = 10
FEATURE            Location/Qualifiers
source             1..10
                   mol_type = protein
                   organism = synthetic construct
VARIANT            5
                   note = H or R
VARIANT            7
                   note = R or Y
SEQUENCE: 785
GFTFXSXGMH                                                                  10

SEQ ID NO: 786     moltype = AA  length = 17
FEATURE            Location/Qualifiers
source             1..17
                   mol_type = protein
                   organism = synthetic construct
SEQUENCE: 786
VITYDGINKY YADSVEG                                                          17

SEQ ID NO: 787     moltype = AA  length = 10
FEATURE            Location/Qualifiers
source             1..10
                   mol_type = protein
                   organism = synthetic construct
SEQUENCE: 787
DGVYYGVYDY                                                                  10

SEQ ID NO: 788     moltype = AA  length = 17
FEATURE            Location/Qualifiers
source             1..17
                   mol_type = protein
                   organism = synthetic construct
SEQUENCE: 788
KSSQSVLFSS NNKNYLA                                                          17

SEQ ID NO: 789     moltype = AA  length = 7
FEATURE            Location/Qualifiers
source             1..7
                   mol_type = protein
                   organism = synthetic construct
SEQUENCE: 789
WASTRES                                                                     7

SEQ ID NO: 790     moltype = AA  length = 9
FEATURE            Location/Qualifiers
source             1..9
                   mol_type = protein
                   organism = synthetic construct
SEQUENCE: 790
QQFHSYPLT                                                                   9

SEQ ID NO: 791     moltype = AA  length = 10
FEATURE            Location/Qualifiers
source             1..10
                   mol_type = protein
```

```
                              organism = synthetic construct
SEQUENCE: 791
GGTFSSNAIG                                                              10

SEQ ID NO: 792           moltype = AA  length = 17
FEATURE                  Location/Qualifiers
source                   1..17
                         mol_type = protein
                         organism = synthetic construct
SEQUENCE: 792
SIIPIIGFAN YAQKFQG                                                      17

SEQ ID NO: 793           moltype = AA  length = 15
FEATURE                  Location/Qualifiers
source                   1..15
                         mol_type = protein
                         organism = synthetic construct
SEQUENCE: 793
DSGYYYGASS FGMDV                                                        15

SEQ ID NO: 794           moltype = AA  length = 11
FEATURE                  Location/Qualifiers
source                   1..11
                         mol_type = protein
                         organism = synthetic construct
SEQUENCE: 794
RASQSVSSNL A                                                            11

SEQ ID NO: 795           moltype = AA  length = 7
FEATURE                  Location/Qualifiers
source                   1..7
                         mol_type = protein
                         organism = synthetic construct
SEQUENCE: 795
GASTRAT                                                                 7

SEQ ID NO: 796           moltype = AA  length = 9
FEATURE                  Location/Qualifiers
source                   1..9
                         mol_type = protein
                         organism = synthetic construct
SEQUENCE: 796
EQYNNLPLT                                                               9

SEQ ID NO: 797           moltype = AA  length = 11
FEATURE                  Location/Qualifiers
source                   1..11
                         mol_type = protein
                         organism = synthetic construct
VARIANT                  4
                         note = I or L
VARIANT                  8
                         note = Q or Y
SEQUENCE: 797
GGSXSSGXYW S                                                            11

SEQ ID NO: 798           moltype = AA  length = 16
FEATURE                  Location/Qualifiers
source                   1..16
                         mol_type = protein
                         organism = synthetic construct
VARIANT                  3
                         note = Y or G
VARIANT                  4
                         note = Y or A
SEQUENCE: 798
EIXXSGSTRY NPSLKS                                                       16

SEQ ID NO: 799           moltype = AA  length = 16
FEATURE                  Location/Qualifiers
source                   1..16
                         mol_type = protein
                         organism = synthetic construct
VARIANT                  2
                         note = T or A
VARIANT                  7
                         note = E or G or D
SEQUENCE: 799
DXPYYYXGGY YYYMDV                                                       16
```

```
SEQ ID NO: 800           moltype = AA   length = 12
FEATURE                  Location/Qualifiers
source                   1..12
                         mol_type = protein
                         organism = synthetic construct
VARIANT                  4
                         note = Q or E or D
VARIANT                  7
                         note = S or D
VARIANT                  10
                         note = Y or F
SEQUENCE: 800
RASXSVXSSX LA                                                           12

SEQ ID NO: 801           moltype =    length =
SEQUENCE: 801
000

SEQ ID NO: 802           moltype = AA   length = 9
FEATURE                  Location/Qualifiers
source                   1..9
                         mol_type = protein
                         organism = synthetic construct
VARIANT                  3
                         note = V or A or D
SEQUENCE: 802
QQXGVVPYT                                                                9

SEQ ID NO: 803           moltype = AA   length = 10
FEATURE                  Location/Qualifiers
source                   1..10
                         mol_type = protein
                         organism = synthetic construct
SEQUENCE: 803
GYTFANYYMH                                                              10

SEQ ID NO: 804           moltype = AA   length = 17
FEATURE                  Location/Qualifiers
source                   1..17
                         mol_type = protein
                         organism = synthetic construct
SEQUENCE: 804
IINPSGGITV YAQKFQG                                                      17

SEQ ID NO: 805           moltype = AA   length = 12
FEATURE                  Location/Qualifiers
source                   1..12
                         mol_type = protein
                         organism = synthetic construct
SEQUENCE: 805
GGSKVAALAF DI                                                           12

SEQ ID NO: 806           moltype = AA   length = 11
FEATURE                  Location/Qualifiers
source                   1..11
                         mol_type = protein
                         organism = synthetic construct
SEQUENCE: 806
QASQDISNSL N                                                            11

SEQ ID NO: 807           moltype = AA   length = 7
FEATURE                  Location/Qualifiers
source                   1..7
                         mol_type = protein
                         organism = synthetic construct
SEQUENCE: 807
DASNLET                                                                  7

SEQ ID NO: 808           moltype = AA   length = 9
FEATURE                  Location/Qualifiers
source                   1..9
                         mol_type = protein
                         organism = synthetic construct
SEQUENCE: 808
QQYNFHPLT                                                                9

SEQ ID NO: 809           moltype = AA   length = 295
FEATURE                  Location/Qualifiers
```

```
source                      1..295
                            mol_type = protein
                            organism = Homo sapiens
SEQUENCE: 809
METPAWPRVP RPETAVARTL LLGWVFAQVA GASGTTNTVA AYNLTWKSTN FKTILEWEPK    60
PVNQVYTVQI STKSGDWKSK CFYTTDTECD LTDEIVKDVK QTYLARVFSY PAGNVESTGS   120
AGEPLYENSP EFTPYLETNL GQPTIQSFEQ VGTKVNVTVE DERTLVRRNN TFLSLRDVFG   180
KDLIYTLYYW KSSSSGKKTA KTNTNEFLID VDKGENYCFS VQAVIPSRTV NRKSTDSPVE   240
CMGQEKGEFR EIFYIIGAVV FVVIILVIIL AISLHKCRKA GVGQSWKENS PLNVS         295

SEQ ID NO: 810              moltype = AA  length = 219
FEATURE                     Location/Qualifiers
source                      1..219
                            mol_type = protein
                            organism = Homo sapiens
SEQUENCE: 810
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG   120
TKVNVTVEDE RTLVRRNNTF LSLRDVFGKD LIYTLYYWKS SSSGKKTAKT NTNEFLIDVD   180
KGENYCFSVQ AVIPSRTVNR KSTDSPVECM GQEKGEFRE                          219

SEQ ID NO: 811              moltype = AA  length = 227
FEATURE                     Location/Qualifiers
source                      1..227
                            mol_type = protein
                            organism = synthetic construct
SEQUENCE: 811
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG   120
TKVNVTVEDE RTLVRRNNTF LSLRDVFGKD LIYTLYYWKS SSSGKKTAKT NTNEFLIDVD   180
KGENYCFSVQ AVIPSRTVNR KSTDSPVECM GQEKGEFRET GHHHHHH                 227

SEQ ID NO: 812              moltype = AA  length = 455
FEATURE                     Location/Qualifiers
source                      1..455
                            mol_type = protein
                            organism = synthetic construct
SEQUENCE: 812
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG   120
TKVNVTVEDE RTLVRRNNTF LSLRDVFGKD LIYTLYYWKS SSSGKKTAKT NTNEFLIDVD   180
KGENYCFSVQ AVIPSRTVNR KSTDSPVECM GQEKGEFRET GENLYFQGDK THTCPPCPAP   240
ELLGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 813              moltype = AA  length = 296
FEATURE                     Location/Qualifiers
source                      1..296
                            mol_type = protein
                            organism = Macaca fascicularis
SEQUENCE: 813
METPAWPRVP RPETAVARTL LLGWVFAQVA GASGTTNTVA AYNLTWKSTN FKTILEWEPK    60
PINQVYTVQI STKSGDWKSK CFYTADTECD LTDEIVKDVK QTYLARVFSY PAGHVESTGS   120
TEEPPYENSP EFTPYLETNL GQPTIQSFEQ VGTKVNVTVQ DEWTLVRRND TFLSLRDVFG   180
KDLIYTLYYW KSSSSGKKTA KTNTNEFLID VDKGENYCFS VQAVIPSRRT ANRKSTDSPV   240
ECMGHEKGES REIFYIIGAV VFVVIILVII LAISLHKCKK ARVGRSWKEN SPLNVA        296

SEQ ID NO: 814              moltype = AA  length = 220
FEATURE                     Location/Qualifiers
source                      1..220
                            mol_type = protein
                            organism = Macaca fascicularis
SEQUENCE: 814
SGTTNTVAAY NLTWKSTNFK TILEWEPKPI NQVYTVQIST KSGDWKSKCF YTADTECDLT    60
DEIVKDVKQT YLARVFSYPA GHVESTGSTE EPPYENSPEF TPYLETNLGQ PTIQSFEQVG   120
TKVNVTVQDE WTLVRRNDTF LSLRDVFGKD LIYTLYYWKS SSSGKKTAKT NTNEFLIDVD   180
KGENYCFSVQ AVIPSRRTAN RKSTDSPVEC MGHEKGESRE                         220

SEQ ID NO: 815              moltype = AA  length = 228
FEATURE                     Location/Qualifiers
source                      1..228
                            mol_type = protein
                            organism = synthetic construct
SEQUENCE: 815
SGTTNTVAAY NLTWKSTNFK TILEWEPKPI NQVYTVQIST KSGDWKSKCF YTADTECDLT    60
DEIVKDVKQT YLARVFSYPA GHVESTGSTE EPPYENSPEF TPYLETNLGQ PTIQSFEQVG   120
TKVNVTVQDE WTLVRRNDTF LSLRDVFGKD LIYTLYYWKS SSSGKKTAKT NTNEFLIDVD   180
```

```
KGENYCFSVQ AVIPSRRTAN RKSTDSPVEC MGHEKGESRE TGHHHHHH              228

SEQ ID NO: 816            moltype = AA   length = 456
FEATURE                   Location/Qualifiers
source                    1..456
                          mol_type = protein
                          organism = synthetic construct
SEQUENCE: 816
SGTTNTVAAY NLTWKSTNFK TILEWEPKPI NQVYTVQIST KSGDWKSKCF YTADTECDLT   60
DEIVKDVKQT YLARVFSYPA GHVESTGSTE EPPYENSPEF TPYLETNLGQ PTIQSFEQVG  120
TKVNVTVQDE WTLVRRNDTF LSLRDVFGKD LIYTLYYWKS SSSGKKTAKT NTNEFLIDVD  180
KGENYCFSVQ AVIPSRRTAN RKSTDSPVEC MGHEKGESRE TGENLYFQGD KTHTCPPCPA  240
PELLGGPSVF LFPPKPKDTL MISRTPEVTC VVVDVSHEDP EVKFNWYVDG VEVHNAKTKP  300
REEQYNSTYR VVSVLTVLHQ DWLNGKEYKC KVSNKALPAP IEKTISKAKG QPREPQVYTL  360
PPSREEMTKN QVSLTCLVKG FYPSDIAVEW ESNGQPENNY KTTPPVLDSD GSFFLYSKLT  420
VDKSRWQQGN VFSCSVMHEA LHNHYTQKSL SLSPGK                           456

SEQ ID NO: 817            moltype = AA   length = 294
FEATURE                   Location/Qualifiers
source                    1..294
                          mol_type = protein
                          organism = Mus musculus
SEQUENCE: 817
MAILVRPRLL AALAPTFLGC LLLQVTAGAG IPEKAFNLTW ISTDFKTILE WQPKPTNYTY   60
TVQISDRSRN WKNKCFSTTD TECDLTDEIV KDVTWAYEAK VLSVPRRNSV HGDGDQLVIH  120
GEEPPFTNAP KFLPYRDTNL GQPVIQQFEQ DGRKLNVVVK DSLTLVRKNG TFLTLRQVFG  180
KDLGYIITYR KGSSTGKKTN ITNTNEFSID VEEGVSYCFF VQAMIFSRKT NQNSPGSSTV  240
CTEQWKSFLG ETLIIVGAVV LLATIFIILL SISLCKRRKN RAGQKGKNTP SRLA        294

SEQ ID NO: 818            moltype = AA   length = 223
FEATURE                   Location/Qualifiers
source                    1..223
                          mol_type = protein
                          organism = Mus musculus
SEQUENCE: 818
AGIPEKAFNL TWISTDFKTI LEWQPKPTNY TYTVQISDRS RNWKNKCFST TDTECDLTDE   60
IVKDVTWAYE AKVLSVPRRN SVHGDGDQLV IHGEEPPFTN APKFLPYRDT NLGQPVIQQF  120
EQDGRKLNVV VKDSLTLVRK NGTFLTLRQV FGKDLGYIIT YRKGSSTGKK TNITNTNEFS  180
IDVEEGVSYC FFVQAMIFSR KTNQNSPGSS TVCTEQWKSF LGE                   223

SEQ ID NO: 819            moltype = AA   length = 231
FEATURE                   Location/Qualifiers
source                    1..231
                          mol_type = protein
                          organism = synthetic construct
SEQUENCE: 819
AGIPEKAFNL TWISTDFKTI LEWQPKPTNY TYTVQISDRS RNWKNKCFST TDTECDLTDE   60
IVKDVTWAYE AKVLSVPRRN SVHGDGDQLV IHGEEPPFTN APKFLPYRDT NLGQPVIQQF  120
EQDGRKLNVV VKDSLTLVRK NGTFLTLRQV FGKDLGYIIT YRKGSSTGKK TNITNTNEFS  180
IDVEEGVSYC FFVQAMIFSR KTNQNSPGSS TVCTEQWKSF LGETGHHHHH H          231

SEQ ID NO: 820            moltype = AA   length = 459
FEATURE                   Location/Qualifiers
source                    1..459
                          mol_type = protein
                          organism = synthetic construct
SEQUENCE: 820
AGIPEKAFNL TWISTDFKTI LEWQPKPTNY TYTVQISDRS RNWKNKCFST TDTECDLTDE   60
IVKDVTWAYE AKVLSVPRRN SVHGDGDQLV IHGEEPPFTN APKFLPYRDT NLGQPVIQQF  120
EQDGRKLNVV VKDSLTLVRK NGTFLTLRQV FGKDLGYIIT YRKGSSTGKK TNITNTNEFS  180
IDVEEGVSYC FFVQAMIFSR KTNQNSPGSS TVCTEQWKSF LGETGENLYF QGDKTHTCPP  240
CPAPELLGGP SVFLFPPKPK DTLMISRTPE VTCVVVDVSH EDPEVKFNWY VDGVEVHNAK  300
TKPREEQYNS TYRVVSVLTV LHQDWLNGKE YKCKVSNKAL PAPIEKTISK AKGQPREPQV  360
YTLPPSREEM TKNQVSLTCL VKGFYPSDIA VEWESNGQPE NNYKTTPPVL DSDGSFFLYS  420
KLTVDKSRWQ QGNVFSCSVM HEALHNHYTQ KSLSLSPGK                        459

SEQ ID NO: 821            moltype = AA   length = 120
FEATURE                   Location/Qualifiers
source                    1..120
                          mol_type = protein
                          organism = synthetic construct
SEQUENCE: 821
EVQLVQSGAE VKKPGESLRI SCKGSGYTFA PYWIEWVRQM PGKGLEWMGD ILPGTGFTTY   60
SPSFQGHVTI SADKSISTAY LQWSSLKASD TAMYYCARSG YYGNSGFAYW GQGTLVTVSS  120

SEQ ID NO: 822            moltype = AA   length = 113
FEATURE                   Location/Qualifiers
source                    1..113
                          mol_type = protein
```

```
                            organism = synthetic construct
SEQUENCE: 822
DIVMTQTPLS LPVTPGEPAS ISCKSSQSLL SSGNQKNYLT WYLQKPGQSP QLLIYWASTR    60
ESGVPDRFSG SGSGTDFTLK ISRVEAEDVG VYYCQNDYTY PLTFGQGTKL EIK          113

SEQ ID NO: 823              moltype = AA   length = 5
FEATURE                     Location/Qualifiers
source                      1..5
                            mol_type = protein
                            organism = synthetic construct
SEQUENCE: 823
GGGGS                                                                 5

SEQ ID NO: 824              moltype = AA   length = 292
FEATURE                     Location/Qualifiers
source                      1..292
                            mol_type = protein
                            organism = Sus scrofa
SEQUENCE: 824
MATPTGPPVS CPKAAVARAL LLGWVLVQVA GATGTTDVIV AYNLTWKSTN FKTILEWEPK    60
PINYVYTVQI SPRLGDWKNK CFHTTDTECD VTDEIMRNVK ETYVARVLSY PADTVLTAQE   120
PPFTNSPPFT PYLDTNLGQP VIQSFEQVGT KLNVTVEAAR TLVRVNGTFL RLRDVFGKDL   180
NYTLYYWRAS STGKKKATTN TNEFLIDVDK GENYCFSVQA VIPSRRVNQK SPESRIECTS   240
QEKAVSRELF LIVGAVVFAV IVFVLVLSVS LYKCRKERAG PSGKENAPLN VA           292

SEQ ID NO: 825              moltype = AA   length = 216
FEATURE                     Location/Qualifiers
source                      1..216
                            mol_type = protein
                            organism = Sus scrofa
SEQUENCE: 825
TGTTDVIVAY NLTWKSTNFK TILEWEPKPI NYVYTVQISP RLGDWKNKCF HTTDTECDVT    60
DEIMRNVKET YVARVLSYPA DTVLTAQEPP FTNSPPFTPY LDTNLGQPVI QSFEQVGTKL   120
NVTVEAARTL VRVNGTFLRL RDVFGKDLNY TLYYWRASST GKKKATTNTN EFLIDVDKGE   180
NYCFSVQAVI PSRRVNQKSP ESRIECTSQE KAVSRE                             216

SEQ ID NO: 826              moltype = AA   length = 224
FEATURE                     Location/Qualifiers
source                      1..224
                            mol_type = protein
                            organism = synthetic construct
SEQUENCE: 826
TGTTDVIVAY NLTWKSTNFK TILEWEPKPI NYVYTVQISP RLGDWKNKCF HTTDTECDVT    60
DEIMRNVKET YVARVLSYPA DTVLTAQEPP FTNSPPFTPY LDTNLGQPVI QSFEQVGTKL   120
NVTVEAARTL VRVNGTFLRL RDVFGKDLNY TLYYWRASST GKKKATTNTN EFLIDVDKGE   180
NYCFSVQAVI PSRRVNQKSP ESRIECTSQE KAVSRETGHH HHHH                    224

SEQ ID NO: 827              moltype = AA   length = 452
FEATURE                     Location/Qualifiers
source                      1..452
                            mol_type = protein
                            organism = synthetic construct
SEQUENCE: 827
TGTTDVIVAY NLTWKSTNFK TILEWEPKPI NYVYTVQISP RLGDWKNKCF HTTDTECDVT    60
DEIMRNVKET YVARVLSYPA DTVLTAQEPP FTNSPPFTPY LDTNLGQPVI QSFEQVGTKL   120
NVTVEAARTL VRVNGTFLRL RDVFGKDLNY TLYYWRASST GKKKATTNTN EFLIDVDKGE   180
NYCFSVQAVI PSRRVNQKSP ESRIECTSQE KAVSRETGEN LYFQGDKTHT CPPCPAPELL   240
GGPSVFLFPP KPKDTLMISR TPEVTCVVVD VSHEDPEVKF NWYVDGVEVH NAKTKPREEQ   300
YNSTYRVVSV LTVLHQDWLN GKEYKCKVSN KALPAPIEKT ISKAKGQPRE PQVYTLPPSR   360
EEMTKNQVSL TCLVKGFYPS DIAVEWESNG QPENNYKTTP PVLDSDGSFF LYSKLTVDKS   420
RWQQGNVFSC SVMHEALHNH YTQKSLSLSP GK                                 452

SEQ ID NO: 828              moltype = AA   length = 118
FEATURE                     Location/Qualifiers
source                      1..118
                            mol_type = protein
                            organism = synthetic construct
SEQUENCE: 828
EVQLLESGGG LVQPGGSLRL SCAASGFTFS NYAMSWVRQA PGKGLEWVSS ISGSGDYTYY    60
TDSVKGRFTI SRDNSKNTLY LQMNSLRAED TAVYYCARSP WGYYLDSWGQ GTLVTVSS    118

SEQ ID NO: 829              moltype = AA   length = 107
FEATURE                     Location/Qualifiers
source                      1..107
                            mol_type = protein
                            organism = synthetic construct
SEQUENCE: 829
DIQMTQSPPS LSASAGDRVT ITCRASQGIS SRLAWYQQKP EKAPKSLIYA ASSLQSGVPS    60
RFSGSGSGTD FTLTISSLQP EDFATYYCQQ YNSYPYTFGQ GTKLEIK                 107
```

```
SEQ ID NO: 830          moltype = AA  length = 117
FEATURE                 Location/Qualifiers
source                  1..117
                        mol_type = protein
                        organism = synthetic construct
SEQUENCE: 830
QVQLVESGGG VVQPGRSLRL SCKASGFNIK DYYMHWVRQA PGKGLEWIGL IDPENGNTIY     60
DPKFQGRFTI SADNSKNTLF LQMDSLRPED TAVYYCARDN SYYFDYWGQG TPVTVSS       117

SEQ ID NO: 831          moltype = AA  length = 107
FEATURE                 Location/Qualifiers
source                  1..107
                        mol_type = protein
                        organism = synthetic construct
SEQUENCE: 831
DIQMTQSPSS LSASVGDRVT ITCKASQDIR KYLNWYQQKP GKAPKLLIYY ATSLADGVPS     60
RFSGSGSGTD YTFTISSLQP EDIATYYCLQ HGESPYTFGQ GTKLEIT                  107

SEQ ID NO: 832          moltype = AA  length = 292
FEATURE                 Location/Qualifiers
source                  1..292
                        mol_type = protein
                        organism = Oryctolagus cuniculus
SEQUENCE: 832
MAPPTRLQVP RPGTAVPYTV LLGWLLAQVA RAADTTGRAY NLTWKSTNFK TILEWEPKSI     60
DHVYTVQIST RLENWKSKCF LTAETECDLT DEVVKDVGQT YMARVLSYPA RNGNTTGFPE    120
EPPFRNSPEF TPYLDTNLGQ PTIQSFEQVG TKLNVTVQDA RTLVRRNGTF LSLRAVFGKD    180
LNYTLYYWRA SSTGKKTATT NTNEFLIDVD KGENYCFSVQ AVIPSRKRKQ RSPESLTECT    240
SREQGRAREM FFIIGAVVVV ALLIIVLSVT VYKCRKARAG PSGKESSPLN IA            292

SEQ ID NO: 833          moltype = AA  length = 218
FEATURE                 Location/Qualifiers
source                  1..218
                        mol_type = protein
                        organism = Oryctolagus cuniculus
SEQUENCE: 833
ADTTGRAYNL TWKSTNFKTI LEWEPKSIDH VYTVQISTRL ENWKSKCFLT AETECDLTDE     60
VVKDVGQTYM ARVLSYPARN GNTTGFPEEP PFRNSPEFTP YLDTNLGQPT IQSFEQVGTK    120
LNVTVQDART LVRRNGTFLS LRAVFGKDLN YTLYYWRASS TGKKTATTNT NEFLIDVDKG    180
ENYCFSVQAV IPSRKRKQRS PESLTECTSR EQGRAREM                           218

SEQ ID NO: 834          moltype = AA  length = 226
FEATURE                 Location/Qualifiers
source                  1..226
                        mol_type = protein
                        organism = synthetic construct
SEQUENCE: 834
ADTTGRAYNL TWKSTNFKTI LEWEPKSIDH VYTVQISTRL ENWKSKCFLT AETECDLTDE     60
VVKDVGQTYM ARVLSYPARN GNTTGFPEEP PFRNSPEFTP YLDTNLGQPT IQSFEQVGTK    120
LNVTVQDART LVRRNGTFLS LRAVFGKDLN YTLYYWRASS TGKKTATTNT NEFLIDVDKG    180
ENYCFSVQAV IPSRKRKQRS PESLTECTSR EQGRAREMTG HHHHHH                  226

SEQ ID NO: 835          moltype = AA  length = 452
FEATURE                 Location/Qualifiers
source                  1..452
                        mol_type = protein
                        organism = synthetic construct
SEQUENCE: 835
ADTTGRAYNL TWKSTNFKTI LEWEPKSIDH VYTVQISTRL ENWKSKCFLT AETECDLTDE     60
VVKDVGQTYM ARVLSYPARN GNTTGFPEEP PFRNSPEFTP YLDTNLGQPT IQSFEQVGTK    120
LNVTVQDART LVRRNGTFLS LRAVFGKDLN YTLYYWRASS TGKKTATTNT NEFLIDVDKG    180
ENYCFSVQAV IPSRKRKQRS PESLTECTSR EQGRAREMEN LYFQGDKTHT CPPCPAPELL    240
GGPSVFLFPP KPKDTLMISR TPEVTCVVVD VSHEDPEVKF NWYVDGVEVH NAKTKPREEQ    300
YNSTYRVVSV LTVLHQDWLN GKEYKCKVSN KALPAPIEKT ISKAKGQPRE PQVYTLPPSR    360
EEMTKNQVSL TCLVKGFYPS DIAVEWESNG QPENNYKTTP PVLDSDGSFF LYSKLTVDKS    420
RWQQGNVFSC SVMHEALHNH YTQKSLSLSP GK                                 452

SEQ ID NO: 836          moltype = AA  length = 123
FEATURE                 Location/Qualifiers
source                  1..123
                        mol_type = protein
                        organism = synthetic construct
SEQUENCE: 836
QVQLVQSGAE VKKPGASVKV SCKASGYTFD AYGISWVRQA PGQGLEWMGW IAPYSGNTNY     60
AQKLQGRVTM TTDTSTSTAY MELRSLRSDD TAVYYCARDA GTYSPFGYGM DVWGQGTTVT    120
VSS                                                                 123

SEQ ID NO: 837          moltype = AA  length = 108
```

```
FEATURE              Location/Qualifiers
source               1..108
                     mol_type = protein
                     organism = synthetic construct
SEQUENCE: 837
DIQMTQSPST LSASVGDRVT ITCRASESIS NWLAWYQQKP GKAPKLLIYK AYSLEYGVPS   60
RFSGSGSGTE FTLTISSLQP DDFATYYCQQ FQKLPPFTFG GGTKVEIK              108

SEQ ID NO: 838       moltype = AA  length = 224
FEATURE              Location/Qualifiers
source               1..224
                     mol_type = protein
                     organism = Rattus norvegicus
SEQUENCE: 838
AGTPPGKAFN LTWISTDFKT ILEWQPKPTN YTYTVQISDR SRNWKYKCTG TTDTECDLTD   60
EIVKDVNWTY EARVLSVPWR NSTHGKETLF GTHGEEPPFT NARKFLPYRD TKIGQPVIQK  120
YEQGGTKLKV TVKDSFTLVR KNGTFLTLRQ VFGNDLGYIL TYRKDSSTGR KTNTTHTNEF  180
LIDVEKGVSY CFFAQAVIFS RKTNHKSPES ITKCTEQWKS VLGE                  224

SEQ ID NO: 839       moltype = AA  length = 224
FEATURE              Location/Qualifiers
source               1..224
                     mol_type = protein
                     organism = synthetic construct
SEQUENCE: 839
AGTPPGKAFN LTWISTDFKT ILEWQPKPTN YTYTVQISDR SRNWKYKCTG TTDTECDLTD   60
EIVKDVNWTY EARVLSVPWR NSTHGKETLF GTHGEEPPFT NARKFLPYRD TKLGQPTIQS  120
FEQVGTKVNV TVEDERTLVR RNNTFLSLRD VFGKDLIYTL YYWKSSSSGK KTAKTNTNEF  180
LIDVDKGENY CFSVQAVIPS RTVNRKSTDS PVECMGQEKG EFRE                  224

SEQ ID NO: 840       moltype = AA  length = 218
FEATURE              Location/Qualifiers
source               1..218
                     mol_type = protein
                     organism = synthetic construct
SEQUENCE: 840
AGTPPGKAFN LTWISTDFKT ILEWQPKPTN YTYTVQISDR SRNWKYKCTG TTDTECDLTD   60
EIVKDVNWTY EARVLSYPAG NVESTGSAGE PLYENSPEFT PYLETNLGQP TIQSFEQVGT  120
KVNVTVEDER TLVRRNNTFL SLRDVFGKDL IYTLYYWKSS SSGKKTAKTN TNEFLIDVDK  180
GENYCFSVQA VIPSRTVNRK STDSPVECMG QEKGEFRE                         218

SEQ ID NO: 841       moltype = AA  length = 218
FEATURE              Location/Qualifiers
source               1..218
                     mol_type = protein
                     organism = synthetic construct
SEQUENCE: 841
AGTPPGKAFN LTWISTDFKT ILEWQPKPTN YTYTVQISTK SGDWKSKCFY TTDTECDLTD   60
EIVKDVKQTY LARVFSYPAG NVESTGSAGE PLYENSPEFT PYLETNLGQP TIQSFEQVGT  120
KVNVTVEDER TLVRRNNTFL SLRDVFGKDL IYTLYYWKSS SSGKKTAKTN TNEFLIDVDK  180
GENYCFSVQA VIPSRTVNRK STDSPVECMG QEKGEFRE                         218

SEQ ID NO: 842       moltype = AA  length = 219
FEATURE              Location/Qualifiers
source               1..219
                     mol_type = protein
                     organism = synthetic construct
SEQUENCE: 842
SGTTNTVAAY NLTWKSTNFK TILEWEPKPV NQVYTVQISD RSRNWKYKCT GTTDTECDLT   60
DEIVKDVNWT YEARVLSYPA GNVESTGSAG EPLYENSPEF TPYLETNLGQ PTIQSFEQVG  120
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                        219

SEQ ID NO: 843       moltype = AA  length = 219
FEATURE              Location/Qualifiers
source               1..219
                     mol_type = protein
                     organism = synthetic construct
SEQUENCE: 843
SGTTNTVAAY NLTWKSTNFK TILEWEPKPV NQVYTVQIST KSGDWKSKCF YTTDTECDLT   60
DEIVKDVKQT YLARVFSVPW RNSTHGTHGE EPPFTNARKF LPYRDTKLGQ PTIQSFEQVG  120
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                        219

SEQ ID NO: 844       moltype = AA  length = 225
FEATURE              Location/Qualifiers
source               1..225
                     mol_type = protein
                     organism = synthetic construct
```

```
SEQUENCE: 844
SGTTNTVAAY NLTWKSTNFK TILEWEPKPV NQVYTVQIST KSGDWKSKCF YTTDTECDLT    60
DEIVKDVKQT YLARVFSVPW RNSTHGKETL FGTHGEEPPF TNARKFLPYR DTKLGQPTIQ   120
SFEQVGTKVN VTVEDERTLV RRNNTFLSLR DVFGKDLIYT LYYWKSSSSG KKTAKTNTNE   180
FLIDVDKGEN YCFSVQAVIP SRTVNRKSTD SPVECMGQEK GEFRE                   225

SEQ ID NO: 845         moltype = AA  length = 225
FEATURE                Location/Qualifiers
source                 1..225
                       mol_type = protein
                       organism = synthetic construct
SEQUENCE: 845
SGTTNTVAAY NLTWKSTNFK TILEWEPKPV NQVYTVQIST KSGDWKSKCF YTTDTECDLT    60
DEIVKDVKQT YLARVFSVPW RNSTHGKETL FGTHGEEPPY ENSPEFTPYL ETNLGQPTIQ   120
SFEQVGTKVN VTVEDERTLV RRNNTFLSLR DVFGKDLIYT LYYWKSSSSG KKTAKTNTNE   180
FLIDVDKGEN YCFSVQAVIP SRTVNRKSTD SPVECMGQEK GEFRE                   225

SEQ ID NO: 846         moltype = AA  length = 219
FEATURE                Location/Qualifiers
source                 1..219
                       mol_type = protein
                       organism = synthetic construct
SEQUENCE: 846
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLFTNARKF LPYRDTKLGQ PTIQSFEQVG   120
TKVNVTVEDE RTLVRRNNTF LSLRDVFGKD LIYTLYYWKS SSSGKKTAKT NTNEFLIDVD   180
KGENYCFSVQ AVIPSRTVNR KSTDSPVECM GQEKGEFRE                          219

SEQ ID NO: 847         moltype = AA  length = 219
FEATURE                Location/Qualifiers
source                 1..219
                       mol_type = protein
                       organism = synthetic construct
SEQUENCE: 847
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNIGQ PVIQKYEQGG   120
TKLKVTVKDS FTLVRKNGTF LTLRQVFGND LGYILTYRKD SSTGRKTNTT HTNEFLIDVE   180
KGVSYCFFAQ AVIFSRKTNH KSPESITKCT EQWKSVLGE                          219

SEQ ID NO: 848         moltype = AA  length = 219
FEATURE                Location/Qualifiers
source                 1..219
                       mol_type = protein
                       organism = synthetic construct
SEQUENCE: 848
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNIGQ PVIQKYEQGG   120
TKLKVTVKDS FTLVRKNGTF LTLRQVFGND LGYILTYRKS SSSGKKTAKT NTNEFLIDVD   180
KGENYCFSVQ AVIPSRTVNR KSTDSPVECM GQEKGEFRE                          219

SEQ ID NO: 849         moltype = AA  length = 219
FEATURE                Location/Qualifiers
source                 1..219
                       mol_type = protein
                       organism = synthetic construct
SEQUENCE: 849
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNIGQ PVIQKYEQGG   120
TKLKVTVKDS FTLVRRNNTF LSLRDVFGKD LIYTLYYWKS SSSGKKTAKT NTNEFLIDVD   180
KGENYCFSVQ AVIPSRTVNR KSTDSPVECM GQEKGEFRE                          219

SEQ ID NO: 850         moltype = AA  length = 219
FEATURE                Location/Qualifiers
source                 1..219
                       mol_type = protein
                       organism = synthetic construct
SEQUENCE: 850
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG   120
TKVNVTVEDE RTLVRKNGTF LTLRQVFGND LGYILTYRKS SSSGKKTAKT NTNEFLIDVD   180
KGENYCFSVQ AVIPSRTVNR KSTDSPVECM GQEKGEFRE                          219

SEQ ID NO: 851         moltype = AA  length = 219
FEATURE                Location/Qualifiers
source                 1..219
                       mol_type = protein
                       organism = synthetic construct
SEQUENCE: 851
SGTTNTVAAY NLTWKSTNFK TILEWEPKPV NQVYTVQIST KSGDWKSKCF YTTDTECDLT    60
```

```
DEIVKDVKQT YLARVFSYPA GNVESTGSAG EPLYENSPEF TPYLETNLGQ PTIQSFEQVG    120
TKVNVTVEDE RTLVRKNGTF LTLRQVFGKD LIYTLYYWKS SSSGKKTAKT NTNEFLIDVD    180
KGENYCFSVQ AVIPSRTVNR KSTDSPVECM GQEKGEFRE                          219

SEQ ID NO: 852          moltype = AA   length = 219
FEATURE                 Location/Qualifiers
source                  1..219
                        mol_type = protein
                        organism = synthetic construct
SEQUENCE: 852
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG    120
TKVNVTVEDE RTLVRKNGTF LSLRDVFGKD LIYTLYYWKS SSSGKKTAKT NTNEFLIDVD    180
KGENYCFSVQ AVIPSRTVNR KSTDSPVECM GQEKGEFRE                          219

SEQ ID NO: 853          moltype = AA   length = 219
FEATURE                 Location/Qualifiers
source                  1..219
                        mol_type = protein
                        organism = synthetic construct
SEQUENCE: 853
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG    120
TKVNVTVEDE RTLVRRNNTF LTLRQVFGKD LIYTLYYWKS SSSGKKTAKT NTNEFLIDVD    180
KGENYCFSVQ AVIPSRTVNR KSTDSPVECM GQEKGEFRE                          219

SEQ ID NO: 854          moltype = AA   length = 219
FEATURE                 Location/Qualifiers
source                  1..219
                        mol_type = protein
                        organism = synthetic construct
SEQUENCE: 854
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG    120
TKVNVTVEDE RTLVRRNNTF LSLRDVFGND LGYILTYRKS SSSGKKTAKT NTNEFLIDVD    180
KGENYCFSVQ AVIPSRTVNR KSTDSPVECM GQEKGEFRE                          219

SEQ ID NO: 855          moltype = AA   length = 219
FEATURE                 Location/Qualifiers
source                  1..219
                        mol_type = protein
                        organism = synthetic construct
SEQUENCE: 855
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG    120
TKVNVTVEDE RTLVRRNNTF LSLRDVFGND LIYTLYYWKS SSSGKKTAKT NTNEFLIDVD    180
KGENYCFSVQ AVIPSRTVNR KSTDSPVECM GQEKGEFRE                          219

SEQ ID NO: 856          moltype = AA   length = 219
FEATURE                 Location/Qualifiers
source                  1..219
                        mol_type = protein
                        organism = synthetic construct
SEQUENCE: 856
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG    120
TKVNVTVEDE RTLVRRNNTF LSLRDVFGKD LGYILTYRKS SSSGKKTAKT NTNEFLIDVD    180
KGENYCFSVQ AVIPSRTVNR KSTDSPVECM GQEKGEFRE                          219

SEQ ID NO: 857          moltype = AA   length = 219
FEATURE                 Location/Qualifiers
source                  1..219
                        mol_type = protein
                        organism = synthetic construct
SEQUENCE: 857
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG    120
TKVNVTVEDE RTLVRRNNTF LSLRDVFGKD LIYTLYYWKD SSTGRKTNTT HTNEFLIDVE    180
KGVSYCFFAQ AVIFSRKTNH KSPESITKCT EQWKSVLGE                          219

SEQ ID NO: 858          moltype = AA   length = 219
FEATURE                 Location/Qualifiers
source                  1..219
                        mol_type = protein
                        organism = synthetic construct
SEQUENCE: 858
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG    120
TKVNVTVEDE RTLVRRNNTF LSLRDVFGKD LIYTLYYWKD SSTGRKTNTT HTNEFLIDVE    180
```

```
KGVSYCFFAQ AVIPSRTVNR KSTDSPVECM GQEKGEFRE                                  219

SEQ ID NO: 859          moltype = AA   length = 219
FEATURE                 Location/Qualifiers
source                  1..219
                        mol_type = protein
                        organism = synthetic construct
SEQUENCE: 859
SGTTNTVAAY NLTWKSTNFK TILEWEPKPV NQVYTVQIST KSGDWKSKCF YTTDTECDLT            60
DEIVKDVKQT YLARVFSYPA GNVESTGSAG EPLYENSPEF TPYLETNLGQ PTIQSFEQVG           120
TKVNVTVEDE RTLVRRNNTF LSLRDVFGKD LIYTLYYWKD SSTGRKTNTT HTNEFLIDVD           180
KGENYCFSVQ AVIPSRTVNR KSTDSPVECM GQEKGEFRE                                  219

SEQ ID NO: 860          moltype = AA   length = 219
FEATURE                 Location/Qualifiers
source                  1..219
                        mol_type = protein
                        organism = synthetic construct
SEQUENCE: 860
SGTTNTVAAY NLTWKSTNFK TILEWEPKPV NQVYTVQIST KSGDWKSKCF YTTDTECDLT            60
DEIVKDVKQT YLARVFSYPA GNVESTGSAG EPLYENSPEF TPYLETNLGQ PTIQSFEQVG           120
TKVNVTVEDE RTLVRRNNTF LSLRDVFGKD LIYTLYYWKD SSTGRKTAKT NTNEFLIDVD           180
KGENYCFSVQ AVIPSRTVNR KSTDSPVECM GQEKGEFRE                                  219

SEQ ID NO: 861          moltype = AA   length = 219
FEATURE                 Location/Qualifiers
source                  1..219
                        mol_type = protein
                        organism = synthetic construct
SEQUENCE: 861
SGTTNTVAAY NLTWKSTNFK TILEWEPKPV NQVYTVQIST KSGDWKSKCF YTTDTECDLT            60
DEIVKDVKQT YLARVFSYPA GNVESTGSAG EPLYENSPEF TPYLETNLGQ PTIQSFEQVG           120
TKVNVTVEDE RTLVRRNNTF LSLRDVFGKD LIYTLYYWKS SSSGKKTNTT HTNEFLIDVD           180
KGENYCFSVQ AVIPSRTVNR KSTDSPVECM GQEKGEFRE                                  219

SEQ ID NO: 862          moltype = AA   length = 219
FEATURE                 Location/Qualifiers
source                  1..219
                        mol_type = protein
                        organism = synthetic construct
SEQUENCE: 862
SGTTNTVAAY NLTWKSTNFK TILEWEPKPV NQVYTVQIST KSGDWKSKCF YTTDTECDLT            60
DEIVKDVKQT YLARVFSYPA GNVESTGSAG EPLYENSPEF TPYLETNLGQ PTIQSFEQVG           120
TKVNVTVEDE RTLVRRNNTF LSLRDVFGKD LIYTLYYWKS SSSGKKTAKT NTNEFLIDVE           180
KGVSYCFFAQ AVIPSRTVNR KSTDSPVECM GQEKGEFRE                                  219

SEQ ID NO: 863          moltype = AA   length = 219
FEATURE                 Location/Qualifiers
source                  1..219
                        mol_type = protein
                        organism = synthetic construct
SEQUENCE: 863
SGTTNTVAAY NLTWKSTNFK TILEWEPKPV NQVYTVQIST KSGDWKSKCF YTTDTECDLT            60
DEIVKDVKQT YLARVFSYPA GNVESTGSAG EPLYENSPEF TPYLETNLGQ PTIQSFEQVG           120
TKVNVTVEDE RTLVRRNNTF LSLRDVFGKD LIYTLYYWKS SSSGKKTAKT NTNEFLIDVD           180
KGENYCFSVQ AVIFSRKTNH KSPESITKCT EQWKSVLGE                                  219

SEQ ID NO: 864          moltype = AA   length = 224
FEATURE                 Location/Qualifiers
source                  1..224
                        mol_type = protein
                        organism = synthetic construct
SEQUENCE: 864
AGTPPGKAFN LTWISTDFKT ILEWQPKPTN YTYTVQISDR SRNWKYKCTG TTDTECDLTD            60
EIVKDVNWTY EARVLSVPWR NSTHGKETLF GTHGEEPPPT NARKFLPYRD TKIGQPVIQK           120
YEQGGTKLKV TVKDSFTLVR RNNTFLSLRD VFGKDLIYTL YYWKSSSSGK KTAKTNTNEF           180
LIDVDKGENY CFSVQAVIFS RKTNHKSPES ITKCTEQWKS VLGE                            224

SEQ ID NO: 865          moltype = AA   length = 219
FEATURE                 Location/Qualifiers
source                  1..219
                        mol_type = protein
                        organism = synthetic construct
SEQUENCE: 865
SGTTNTVAAY NLTWKSTNFK TILEWEPKPV NQVYTVQIST KSGDWKSKCF YTTDTECDLT            60
DEIVKDVNQT YLARVFSYPA GNVESTGSAG EPLYENSPEF TPYLETNLGQ PTIQSFEQVG           120
TKVNVTVEDE RTLVRRNNTF LSLRDVFGKD LIYTLYYWKS SSSGKKTAKT NTNEFLIDVD           180
KGENYCFSVQ AVIPSRTVNR KSTDSPVECM GQEKGEFRE                                  219
```

| SEQ ID NO: 866 | moltype = AA length = 219 |
| --- | --- |
| FEATURE | Location/Qualifiers |
| source | 1..219 |
| | mol_type = protein |
| | organism = synthetic construct |

SEQUENCE: 866
```
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG   120
TKVNVTVEDE RTLVRRNNTF LSLRDVFGND LIYTLYYWKS SSSGKKTAKT NTNEFLIDVD   180
KGENYCFSVQ AVIPSRTVNR KSTDSPVECM GQEKGEFRE                         219
```

| SEQ ID NO: 867 | moltype = AA length = 219 |
| --- | --- |
| FEATURE | Location/Qualifiers |
| source | 1..219 |
| | mol_type = protein |
| | organism = synthetic construct |

SEQUENCE: 867
```
SGTTNTVAAY NLTWKSTNFK TILEWEPKPV NQVYTVQIST KSGDWKSKCF YTTDTECDLT    60
DEIVKDVKQT YLARVFSYPA GNVESTGSAG EPLYENSPEF TPYLETNLGQ PTIQSFEQVG   120
TKVNVTVEDE RTLVRRNNTF LSLRDVFGKD LIYTLYYWKS SSSGKKTAKT HTNEFLIDVD   180
KGENYCFSVQ AVIPSRKVNR KSTDSPVECM GQEKGEFRE                         219
```

| SEQ ID NO: 868 | moltype = AA length = 123 |
| --- | --- |
| FEATURE | Location/Qualifiers |
| source | 1..123 |
| | mol_type = protein |
| | organism = synthetic construct |
| VARIANT | 31 |
| | note = V or A |
| VARIANT | 55 |
| | note = N or S |

SEQUENCE: 868
```
QVQLVQSGAE VKKPGASVKV SCKASGYTFD XYGISWVRQA PGQGLEWMGW IAPYXGNTNY    60
AQKLQGRVTM TTDTSTSTAY MELRSLRSDD TAVYYCARDA GTYSPFGYGM DVWGQGTTVT   120
VSS                                                                123
```

| SEQ ID NO: 869 | moltype = AA length = 108 |
| --- | --- |
| FEATURE | Location/Qualifiers |
| source | 1..108 |
| | mol_type = protein |
| | organism = synthetic construct |
| VARIANT | 24 |
| | note = R or Q |
| VARIANT | 27 |
| | note = Q or E |
| VARIANT | 30 |
| | note = S or N |
| VARIANT | 31 |
| | note = S or N |
| VARIANT | 52 |
| | note = S or Y |
| VARIANT | 53 |
| | note = S or N |
| VARIANT | 56 |
| | note = S or Y |
| VARIANT | 90 |
| | note = Q or L |
| VARIANT | 93 |
| | note = S or K |

SEQUENCE: 869
```
DIQMTQSPST LSASVGDRVT ITCXASXSIX XWLAWYQQKP GKAPKLLIYK AXXLEXGVPS    60
RFSGSGSGTE FTLTISSLQP DDFATYYCQX FQXLPPFTFG GGTKVEIK                108
```

| SEQ ID NO: 870 | moltype = AA length = 123 |
| --- | --- |
| FEATURE | Location/Qualifiers |
| source | 1..123 |
| | mol_type = protein |
| | organism = synthetic construct |
| VARIANT | 55 |
| | note = N or S |

SEQUENCE: 870
```
QVQLVQSGAE VKKPGASVKV SCKASGYTFR SYGISWVRQA PGQGLEWMGW VAPYXGNTNY    60
AQKLQGRVTM TTDTSTSTAY MELRSLRSDD TAVYYCARDA GTYSPYGYGM DVWGQGTTVT   120
VSS                                                                123
```

| SEQ ID NO: 871 | moltype = AA length = 108 |
| --- | --- |
| FEATURE | Location/Qualifiers |
| source | 1..108 |
| | mol_type = protein |

```
                              organism = synthetic construct
VARIANT                       24
                              note = Q or R
VARIANT                       27
                              note = Q or H
VARIANT                       30
                              note = S or D
VARIANT                       50
                              note = K or S
VARIANT                       53
                              note = S or Y
VARIANT                       90
                              note = Q or L or R
SEQUENCE: 871
DIQMTQSPST LSASVGDRVT ITCXASXSIX SWLAWYQQKP GKAPKLLIYX ASXLESGVPS    60
RFSGSGSGTE FTLTISSLQP DDFATYYCQX FQSLPPFTFG GGTKVEIK                108

SEQ ID NO: 872                moltype = AA  length = 10
FEATURE                       Location/Qualifiers
source                        1..10
                              mol_type = protein
                              organism = synthetic construct
VARIANT                       6
                              note = V or A
SEQUENCE: 872
GYTFDXYGIS                                                          10

SEQ ID NO: 873                moltype = AA  length = 17
FEATURE                       Location/Qualifiers
source                        1..17
                              mol_type = protein
                              organism = synthetic construct
VARIANT                       6
                              note = N or S
SEQUENCE: 873
WIAPYXGNTN YAQKLQG                                                  17

SEQ ID NO: 874                moltype = AA  length = 14
FEATURE                       Location/Qualifiers
source                        1..14
                              mol_type = protein
                              organism = synthetic construct
SEQUENCE: 874
DAGTYSPFGY GMDV                                                     14

SEQ ID NO: 875                moltype = AA  length = 11
FEATURE                       Location/Qualifiers
source                        1..11
                              mol_type = protein
                              organism = synthetic construct
VARIANT                       1
                              note = R or Q
VARIANT                       4
                              note = Q or E
VARIANT                       7
                              note = S or N
VARIANT                       8
                              note = S or N
SEQUENCE: 875
XASXSIXXWL A                                                        11

SEQ ID NO: 876                moltype = AA  length = 7
FEATURE                       Location/Qualifiers
source                        1..7
                              mol_type = protein
                              organism = synthetic construct
VARIANT                       3
                              note = S or Y
VARIANT                       4
                              note = S or N
VARIANT                       7
                              note = S or Y
SEQUENCE: 876
KAXXLEX                                                              7

SEQ ID NO: 877                moltype = AA  length = 10
FEATURE                       Location/Qualifiers
source                        1..10
                              mol_type = protein
```

```
                            -continued organism = synthetic construct
VARIANT                     2
                            note = Q or L
VARIANT                     5
                            note = S or K
SEQUENCE: 877
QXFQXLPPFT                                                              10

SEQ ID NO: 878              moltype = AA  length = 10
FEATURE                     Location/Qualifiers
source                      1..10
                            mol_type = protein
                            organism = synthetic construct
SEQUENCE: 878
GYTFRSYGIS                                                              10

SEQ ID NO: 879              moltype = AA  length = 17
FEATURE                     Location/Qualifiers
source                      1..17
                            mol_type = protein
                            organism = synthetic construct
VARIANT                     6
                            note = N or S
SEQUENCE: 879
WVAPYXGNTN YAQKLQG                                                      17

SEQ ID NO: 880              moltype = AA  length = 14
FEATURE                     Location/Qualifiers
source                      1..14
                            mol_type = protein
                            organism = synthetic construct
SEQUENCE: 880
DAGTYSPYGY GMDV                                                         14

SEQ ID NO: 881              moltype = AA  length = 11
FEATURE                     Location/Qualifiers
source                      1..11
                            mol_type = protein
                            organism = synthetic construct
VARIANT                     1
                            note = R or Q
VARIANT                     4
                            note = Q or H
VARIANT                     7
                            note = S or D
SEQUENCE: 881
XASXSIXSWL A                                                            11

SEQ ID NO: 882              moltype = AA  length = 7
FEATURE                     Location/Qualifiers
source                      1..7
                            mol_type = protein
                            organism = synthetic construct
VARIANT                     1
                            note = K or S
VARIANT                     4
                            note = S or Y
SEQUENCE: 882
XASXLES                                                                 7

SEQ ID NO: 883              moltype = AA  length = 10
FEATURE                     Location/Qualifiers
source                      1..10
                            mol_type = protein
                            organism = synthetic construct
VARIANT                     2
                            note = Q or L or R
SEQUENCE: 883
QXFQSLPPFT                                                              10

SEQ ID NO: 884              moltype = AA  length = 10
FEATURE                     Location/Qualifiers
source                      1..10
                            mol_type = protein
                            organism = synthetic construct
SEQUENCE: 884
GYTFDAYGIS                                                              10

SEQ ID NO: 885              moltype = AA  length = 17
```

```
FEATURE                 Location/Qualifiers
source                  1..17
                        mol_type = protein
                        organism = synthetic construct
SEQUENCE: 885
WIAPYSGNTN YAQKLQG                                                      17

SEQ ID NO: 886          moltype = AA   length = 14
FEATURE                 Location/Qualifiers
source                  1..14
                        mol_type = protein
                        organism = synthetic construct
SEQUENCE: 886
DAGTYSPFGY GMDV                                                         14

SEQ ID NO: 887          moltype = AA   length = 11
FEATURE                 Location/Qualifiers
source                  1..11
                        mol_type = protein
                        organism = synthetic construct
SEQUENCE: 887
RASESISNWL A                                                            11

SEQ ID NO: 888          moltype = AA   length = 7
FEATURE                 Location/Qualifiers
source                  1..7
                        mol_type = protein
                        organism = synthetic construct
SEQUENCE: 888
KAYSLEY                                                                 7

SEQ ID NO: 889          moltype = AA   length = 10
FEATURE                 Location/Qualifiers
source                  1..10
                        mol_type = protein
                        organism = synthetic construct
SEQUENCE: 889
QQFQKLPPFT                                                              10

SEQ ID NO: 890          moltype = AA   length = 5
FEATURE                 Location/Qualifiers
source                  1..5
                        mol_type = protein
                        organism = synthetic construct
SEQUENCE: 890
AYGIS                                                                   5

SEQ ID NO: 891          moltype = AA   length = 17
FEATURE                 Location/Qualifiers
source                  1..17
                        mol_type = protein
                        organism = synthetic construct
SEQUENCE: 891
WIAPYSGNTN YAQKLQG                                                      17

SEQ ID NO: 892          moltype = AA   length = 14
FEATURE                 Location/Qualifiers
source                  1..14
                        mol_type = protein
                        organism = synthetic construct
SEQUENCE: 892
DAGTYSPFGY GMDV                                                         14

SEQ ID NO: 893          moltype = AA   length = 11
FEATURE                 Location/Qualifiers
source                  1..11
                        mol_type = protein
                        organism = synthetic construct
SEQUENCE: 893
RASESISNWL A                                                            11

SEQ ID NO: 894          moltype = AA   length = 7
FEATURE                 Location/Qualifiers
source                  1..7
                        mol_type = protein
                        organism = synthetic construct
SEQUENCE: 894
KAYSLEY                                                                 7
```

```
SEQ ID NO: 895           moltype = AA  length = 10
FEATURE                  Location/Qualifiers
source                   1..10
                         mol_type = protein
                         organism = synthetic construct
SEQUENCE: 895
QQFQKLPPFT                                                                10

SEQ ID NO: 896           moltype = AA  length = 7
FEATURE                  Location/Qualifiers
source                   1..7
                         mol_type = protein
                         organism = synthetic construct
SEQUENCE: 896
GYTFDAY                                                                   7

SEQ ID NO: 897           moltype = AA  length = 4
FEATURE                  Location/Qualifiers
source                   1..4
                         mol_type = protein
                         organism = synthetic construct
SEQUENCE: 897
PYSG                                                                      4

SEQ ID NO: 898           moltype = AA  length = 12
FEATURE                  Location/Qualifiers
source                   1..12
                         mol_type = protein
                         organism = synthetic construct
SEQUENCE: 898
AGTYSPFGYG MD                                                            12

SEQ ID NO: 899           moltype = AA  length = 7
FEATURE                  Location/Qualifiers
source                   1..7
                         mol_type = protein
                         organism = synthetic construct
SEQUENCE: 899
SESISNW                                                                   7

SEQ ID NO: 900           moltype =     length =
SEQUENCE: 900
000

SEQ ID NO: 901           moltype = AA  length = 7
FEATURE                  Location/Qualifiers
source                   1..7
                         mol_type = protein
                         organism = synthetic construct
SEQUENCE: 901
FQKLPPF                                                                   7

SEQ ID NO: 902           moltype = AA  length = 10
FEATURE                  Location/Qualifiers
source                   1..10
                         mol_type = protein
                         organism = synthetic construct
SEQUENCE: 902
GYTFDAYGIS                                                               10

SEQ ID NO: 903           moltype = AA  length = 10
FEATURE                  Location/Qualifiers
source                   1..10
                         mol_type = protein
                         organism = synthetic construct
SEQUENCE: 903
WIAPYSGNTN                                                               10

SEQ ID NO: 904           moltype = AA  length = 14
FEATURE                  Location/Qualifiers
source                   1..14
                         mol_type = protein
                         organism = synthetic construct
SEQUENCE: 904
DAGTYSPFGY GMDV                                                          14

SEQ ID NO: 905           moltype = AA  length = 11
FEATURE                  Location/Qualifiers
source                   1..11
```

```
SEQUENCE: 905
RASESISNWL A                                                    11

SEQ ID NO: 906        moltype = AA   length = 7
FEATURE               Location/Qualifiers
source                1..7
                      mol_type = protein
                      organism = synthetic construct
SEQUENCE: 906
KAYSLEY                                                          7

SEQ ID NO: 907        moltype = AA   length = 10
FEATURE               Location/Qualifiers
source                1..10
                      mol_type = protein
                      organism = synthetic construct
SEQUENCE: 907
QQFQKLPPFT                                                      10

SEQ ID NO: 908        moltype = AA   length = 6
FEATURE               Location/Qualifiers
source                1..6
                      mol_type = protein
                      organism = synthetic construct
SEQUENCE: 908
DAYGIS                                                           6

SEQ ID NO: 909        moltype = AA   length = 13
FEATURE               Location/Qualifiers
source                1..13
                      mol_type = protein
                      organism = synthetic construct
SEQUENCE: 909
WMGWIAPYSG NTN                                                  13

SEQ ID NO: 910        moltype = AA   length = 15
FEATURE               Location/Qualifiers
source                1..15
                      mol_type = protein
                      organism = synthetic construct
SEQUENCE: 910
ARDAGTYSPF GYGMD                                                15

SEQ ID NO: 911        moltype = AA   length = 7
FEATURE               Location/Qualifiers
source                1..7
                      mol_type = protein
                      organism = synthetic construct
SEQUENCE: 911
SNWLAWY                                                          7

SEQ ID NO: 912        moltype = AA   length = 10
FEATURE               Location/Qualifiers
source                1..10
                      mol_type = protein
                      organism = synthetic construct
SEQUENCE: 912
LLIYKAYSLE                                                      10

SEQ ID NO: 913        moltype = AA   length = 9
FEATURE               Location/Qualifiers
source                1..9
                      mol_type = protein
                      organism = synthetic construct
SEQUENCE: 913
QQFQKLPPF                                                        9

SEQ ID NO: 914        moltype = AA   length = 8
FEATURE               Location/Qualifiers
source                1..8
                      mol_type = protein
                      organism = synthetic construct
SEQUENCE: 914
GYTFDAYG                                                         8

SEQ ID NO: 915        moltype = AA   length = 8
FEATURE               Location/Qualifiers
```

```
source                  1..8
                        mol_type = protein
                        organism = synthetic construct
SEQUENCE: 915
IAPYSGNT                                                                            8

SEQ ID NO: 916          moltype = AA  length = 16
FEATURE                 Location/Qualifiers
source                  1..16
                        mol_type = protein
                        organism = synthetic construct
SEQUENCE: 916
ARDAGTYSPF GTGMDV                                                                  16

SEQ ID NO: 917          moltype = AA  length = 6
FEATURE                 Location/Qualifiers
source                  1..6
                        mol_type = protein
                        organism = synthetic construct
SEQUENCE: 917
ESISNW                                                                              6

SEQ ID NO: 918          moltype =    length =
SEQUENCE: 918
000

SEQ ID NO: 919          moltype = AA  length = 10
FEATURE                 Location/Qualifiers
source                  1..10
                        mol_type = protein
                        organism = synthetic construct
SEQUENCE: 919
QQFQKLPPFT                                                                         10
```